United States Patent
Iikura et al.

(10) Patent No.: US 8,278,465 B2
(45) Date of Patent: Oct. 2, 2012

(54) COUMARIN DERIVATIVE HAVING ANTITUMOR ACTIVITY

(75) Inventors: Hitoshi Iikura, Kamakura (JP); Ikumi Hyoudoh, Kamakura (JP); Toshihiro Aoki, Kamakura (JP); Noriyuki Furuichi, Kamakura (JP); Masayuki Matsushita, Kamakura (JP); Fumio Watanabe, Kamakura (JP); Sawako Ozawa, Kamakura (JP); Masahiro Sakaitani, Kamakura (JP); Pil-Su Ho, Kyunggi-do (KR); Yasushi Tomii, Kamakura (JP); Kenji Takanashi, Kamakura (JP); Naoki Harada, Kamakura (JP)

(73) Assignees: Chugai Seiyaku Kabushiki Kaisha, Tokyo (JP); Sakai Toshiyuki, Kyoto (JP)

( * ) Notice: Subject to any disclaimer, the term of this patent is extended or adjusted under 35 U.S.C. 154(b) by 0 days.

(21) Appl. No.: 12/960,134

(22) Filed: Dec. 3, 2010

(65) Prior Publication Data

US 2011/0092700 A1   Apr. 21, 2011

Related U.S. Application Data

(62) Division of application No. 12/161,256, filed as application No. PCT/JP2007/052800 on Feb. 9, 2007, now Pat. No. 7,897,792.

(30) Foreign Application Priority Data

Feb. 9, 2006   (JP) ................ P2006-032903

(51) Int. Cl.
*C07D 311/00*   (2006.01)
(52) U.S. Cl. .................................... 549/289
(58) Field of Classification Search ............ 549/289
See application file for complete search history.

(56) References Cited

U.S. PATENT DOCUMENTS

| | | | |
|---|---|---|---|
| 5,550,129 | A | 8/1996 | Noldner |
| 5,686,486 | A | 11/1997 | Tomich |
| 6,331,562 | B1 | 12/2001 | Bhagwat |
| 6,355,658 | B1 | 3/2002 | Reboud-Ravaux |
| 7,026,491 | B2 | 4/2006 | Cheng |
| 2005/0014705 | A1 | 1/2005 | Cheng |
| 2005/0020634 | A1 | 1/2005 | Terashita |
| 2005/0054717 | A1 | 3/2005 | Muto |
| 2007/0183995 | A1 | 8/2007 | Nip |
| 2007/0238710 | A1 | 10/2007 | Yan |
| 2009/0181996 | A1 | 7/2009 | Fuerstner |

FOREIGN PATENT DOCUMENTS

| | | |
|---|---|---|
| JP | 2002-533456 | 10/2002 |
| JP | 2004-509855 | 4/2004 |
| JP | 2005-002133 | 1/2005 |
| JP | 2005-162727 | 6/2005 |
| WO | WO 93/16064 | 8/1993 |
| WO | WO 94/05649 | 3/1994 |
| WO | WO 94/18188 | 8/1994 |
| WO | WO 99/21550 | 5/1999 |
| WO | WO 00/39120 | 7/2000 |
| WO | WO 02/08217 | 1/2002 |
| WO | WO 02/085882 | 10/2002 |
| WO | WO 03/024950 | 3/2003 |
| WO | WO 03/028652 | 4/2003 |
| WO | WO 2004/069820 | 8/2004 |
| WO | WO 2005/004859 | 1/2005 |
| WO | WO 2006/078833 | 7/2006 |
| WO | WO 2007/014011 | 2/2007 |

OTHER PUBLICATIONS

Dorwald, Side Reactions in Organic Synthesis, 2005, Wiley: VCH, Weinheim p. IX of Preface p. 1-15.*
Venkatesh et al., J. Pharm. Sci. 89, 145-54 (2000) (p. 146, left column).*
Madari et al., "Dicoumarol: a unique microtubule stabilizing natural product that is synergistic with taxol." Cancer Research 63: 1214-1220, 2003.
Reddy et al., "Synthesis of new coumarin 3-(N-aryl)sulfonamides and their anticancer activity." Bioorganic & Medicinal Chem. Lett. 14: 4093-4097, 2004.
Reddy et al., "Novel coumarin 3(N-aryl)carboxamides arrest breast cancer cell growth by inhibiting ErbB-2 and ERK1." Bioorganic & Medicinal Chem. 13: 3141-3147, 2005.
Kempen et al., "3-Bromophenyl 6-acetoxymethyl-2-oxo-2H-1-benzopyran-3-carboxylate inhibits cancer cell invasion in vivo and tumor growth in vitro." Br. J. Cancer 88: 1111-1118, 2003.
Han et al., "Identification of coumarin derivatives as a novel class of allosteric MEK-1 inhibitors." Bioorganic & Medicinal Chem. Lett. 15: 5467-5473, 2005.
Cheng et al., "Discovery and structure-activity relationship of coumarin derivatives as TNF-alpha inhibitors." Bioorganic & Medicinal Chem. Lett. 14: 2411-2415, 2004.

* cited by examiner

*Primary Examiner* — Nizal Chandrakumar
(74) *Attorney, Agent, or Firm* — Morgan, Lewis & Bockius, LLP

(57) ABSTRACT

The present invention provides a compound represented by general formula (1) below or a pharmaceutically acceptable salt thereof:

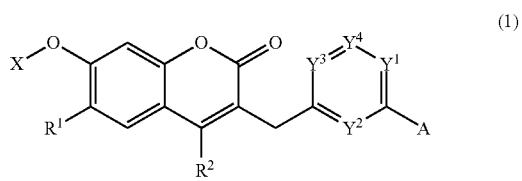

(1)

wherein: X is selected from heteroaryl etc., $Y^1$ and $Y^2$ are selected from —N= etc., $Y^3$ and $Y^4$ are selected from —CH= etc., A is selected from sulfamide etc., $R^1$ is selected from hydrogen etc., and $R^2$ is selected from $C_{1-6}$ alkyl etc. The compound or salt has sufficiently high antitumor activity, and is useful in the treatment of cell proliferative disorders, particularly cancers. The present invention also provides a pharmaceutical composition containing the compound or salt as an active ingredient.

9 Claims, No Drawings

COUMARIN DERIVATIVE HAVING ANTITUMOR ACTIVITY

CROSS-REFERENCE TO RELATED APPLICATIONS

The present application is divisional of U.S. patent application Ser. No. 12/161,256, filed Mar. 2, 2009 now U.S. Pat. No. 7,897,792, which is a U.S. National Phase Application of International Application PCT/JP2007/052800, filed Feb. 9, 2007, which claims the benefit of Japanese Patent Application No. 2006-032903 (filed on Feb. 9, 2006) all of which are hereby incorporated by reference in their entirety.

TECHNICAL FIELD

The present invention relates to a novel coumarin derivative having antitumor activity, and to a pharmaceutical composition containing the same as an active ingredient, particularly to a therapeutic agent for a cell proliferative disorder.

BACKGROUND ART

It has already been revealed that coumarin derivatives, i.e., compounds which have a coumarin skeleton as a core structure, and in which the skeleton is derivatized at various positions, have different pharmacological effects depending on the position at which a chemical modification occurs (Non-patent document 31). For example, warfarin, which has anti-thrombogenic activity, is well known as a drug having a coumarin skeleton (Non-patent document 1). Furthermore, coumarin derivatives which exert antitumor activity by acting on various different target proteins, or coumarin derivatives which inhibit proteins associated with antitumor activity have been obtained by chemical modification at different positions of the core structure.

A coumarin derivative that exerts antitumor activity by inhibiting steroid sulfatase has been reported (Non-patent documents 2 to 6). This is currently in clinical testing. This compound forms a cycloalkyl group at the 3- and 4-positions of the coumarin skeleton, and has a sulfamate group at the 7-position. Its application to breast cancer is being considered from the viewpoint of pharmacological action.

Furthermore, as for coumarin derivatives which exert antitumor activity through binding to the estrogen receptor, a group of compounds having a characteristic substituent at the 4-position have been reported. Specifically, there have been reported a group of compounds having an arylalkyl group at the 4-position and having substituents at the 3- and 7-positions (Patent document 1), and a group of compounds in which a phenyl group is directly bound to the skeleton at the 4-position, and which have a phenoxy group at the 3-position (Patent document 2).

Also, as for a coumarin derivative exhibiting Raf inhibitory activity and exhibiting antitumor activity in cells, a compound having a 6-pyrazinyloxy group at the 7-position has been reported (Patent document 5).

In addition, known are several coumarin derivatives whose target proteins are unknown, and which are reported to exhibit antitumor activity. These include a group of compounds derived from natural sources (Non-patent documents 7 to 12), and a group of new compounds obtained by chemical synthesis (Non-patent documents 13 to 23, 32 to 34). As for the new compounds obtained by chemical synthesis, there have been reported, for example: a compound having alkoxy groups at the 5-, 6- and 7-positions of the coumarin skeleton (Non-patent document 13); a compound having an alkoxy group only at the 7-position of the coumarin skeleton (Non-patent document 14); a compound having an enone functional group at the 6- or 7-position of the coumarin skeleton (Non-patent document 15); a compound having a methyl group at the 4-position of the coumarin skeleton, and substituents at the 7- and 8-positions (Non-patent document 16); a compound having substituents at all of the 4-, 5-, 6-, 7- and 8-positions of the coumarin skeleton (Non-patent document 17); a compound in which an amide group, ester group or sulfonamide group is directly bound to the coumarin skeleton at the 3-position, and which has a substituent at the 6- or 8-position (Non-patent documents 18 and 19); a compound in which an amide group is directly bound to the coumarin skeleton at the 3-position, and which has a substituent at the 7-position (Patent document 3 and Non-patent document 20); a compound having substituents at the 6- and 7-positions of the coumarin skeleton (Non-patent document 21); a compound having a hydroxy group at the 7-position of the coumarin skeleton, and a nitro group at an appropriate position of the 3-, 6- and 8-positions (Non-patent documents 22 and 23); and a compound having a methoxy or hydroxy group at the 7-position of the coumarin skeleton, a phenyl group at the 3-position, and a substituent at the 4-position.

There have also been reported: a compound having a substituent with a nitrogen atom (diethylamino group, etc.) at the 7-position, a cyano group at the 4-position, and a heteroaryl group at the 3-position (optionally with no substituent at the 4-position) (Non-patent document 32); and a compound having a heteroaryl group at the 3-position, and a methyl group, halogen atom, nitro group, etc. at the 6-, 7- or 8-position (Non-patent document 33). There have also been reported examples of using a compound with a coumarin structure as a ligand for a Pd compound having antitumor activity in cells (Non-patent document 34).

As for compounds which exhibit target protein inhibitory activity, and which are likely to have antitumor activity despite the absence of a report dealing with their antitumor activity, there have been reported coumarin derivatives exhibiting TNFα inhibitory activity (Patent document 4 and Non-patent documents 24 to 28), aromatase inhibitory activity (Non-patent document 29), MEK inhibitory activity (Non-patent document 30), or the like. In compounds mentioned in these reports, the substituents are located at the 3-, 4-, 6- or 7-position of the coumarin skeleton.

As described above, although several coumarin derivatives having antitumor activity are known, few of the compounds exhibit a sufficiently high antitumor activity to put it to practical use as an anticancer drug. Therefore, more practical compounds having sufficiently high antitumor activity are still strongly sought.

Patent document 1: International Publication WO 2000/039120
Patent document 2: International Publication WO 2004/069820
Patent document 3: International Publication WO 2003/024950
Patent document 4: International Publication WO 2002/008217
Patent document 5: International Publication WO 2006/067466
Non-patent document 1: Ansell, J.; Bergqvist, D; Drugs 2004, 64, 1-5
Non-patent document 2: Purohit, A.; Woo, L. W. L.; Chander, S. K.; Newman, S. P.; Ireson, C.; Ho, Y.; Grasso, A.; Leese, M. P.; Potter, B. V. L.; Reed, M. J.; J. Steroid Biochem. Mol. Biol. 2003, 86, 423-432

Non-patent document 3: Lloyd, M. D.; Pederick, R. L.; Natesh, R.; Woo, L. W. L.; Purohit, A.; Reed, M. J.; Acharya, K. R.; Potter, B. V. L.; Biochem. J. 2005, 385, 715-720

Non-patent document 4: Purohit, A.; Woo, L. W. L.; Potter, B. V. L.; Reed, M. J.; Cancer Research 2000, 60, 3394-3396

Non-patent document 5: Woo, L. W. L.; Howarth, N. M.; Purohit, A.; Hejaz, A. M.; Reed, M. J.; Potter, B. V. L.; J. Med. Chem. 1998, 41, 1068-1083

Non-patent document 6: Woo, L. W. L.; Purohit, A.; Reed, M. J.; Potter, B. V. L.; J. Med. Chem. 1996, 39, 1349-1351

Non-patent document 7: Lopez-Perez, J. L.; Olmedo, D. A.; Olmo, E. D.; Vasquez, Y.; Solis, P. N.; Gupta, M. P.; Feliciano, A. S.; J. Nat. Prod. 2005, 68, 369-373

Non-patent document 8: Ito, C.; Itoigawa, M.; Mishina, Y.; Filho, V. C.; Enjo, F.; Tokuda, H.; Nishino, H.; Furukawa, H.; J. Nat. Prod. 2003, 66, 368-371

Non-patent document 9: Chen, Y-C.; Cheng, M-J.; Lee, S-J.; Dixit, A-K.; Ishikawa, T.; Tsai, I-L.; Chen, I-S.; Helv. Chim. Acta 2004, 87, 2805-2811

Non-patent document 10: Lee, K-H.; Chai, H-B.; Tamez, P. A.; Pezzuto, J. M.; Cordell, G. A.; Win, K. K.; Tin-Wa, M.; Phytochemistry 2003, 64, 535-541

Non-patent document 11: Chaturvedula, V. S. P.; Schilling, J. K.; Kingston, D. G. I.; J. Nat. Prod. 2002, 65, 965-972

Non-patent document 12: Madari, H.; Panda, D.; Wilson, L.; Jacobs, R. S.; Cancer Research 2003, 63, 1214-1220

Non-patent document 13: Riveiro, M. E.; Shayo, C.; Monczor, F.; Fernandez, N.; Baldi, A.; De Kimpe, N.; Rossi, J.; Debenedetti, S.; Davio, C.; Cancer Letters 2004, 210, 179-188

Non-patent document 14: Baba, M.; Jin, Y.; Mizuno, A.; Suzuki, H.; Okada, Y.; Takasuka, N.; Tokuda, H.; Nishino, H.; Okuyama, T.; Biol. Pharm. Bull. 2002, 25, 244-246

Non-patent document 15: Chen, Y-L.; Wang, T-C.; Tzeng, C-C.; Helv. Chim. Acta 1999, 82, 191-197

Non-patent document 16: Mazzei, M.; Miele, M.; Nieddu, E.; Barbieri, F.; Bruzzo, C.; Alama, A.; Eur. J. Med. Chem. 2001, 36, 915-923

Non-patent document 17: Kimura, S.; Ito, C.; Jyoko, N.; Segawa, H.; Kuroda, J.; Okada, M.; Adachi, S.; Nakahata, T.; Yuasa, T.; Filho, V. C.; Furukawa, H.; Maekawa, T.; Int. J. Cancer 2005, 113, 158-165

Non-patent document 18: Reddy, N. S.; Mallireddigari, M. R.; Cosenza, S. C.; Gumireddy, K.; Bell, S. C.; Reddy, E. P.; Reddy, M. V. R.; Bioorg. Med. Chem. Lett. 2004, 14, 4093-4097

Non-patent document 19: Reddy, N. S.; Gumireddy, K.; Mallireddigari, M. R.; Cosenza, S. C.; Venkatapuram, P.; Bell, S. C.; Reddy, E. P.; Reddy, M. V. R.; Bioorg. Med. Chem. 2005, 13, 3141-3147

Non-patent document 20: Kempen, I.; Papapostolou, D.; Thierry, N.; Pochet, L; Counerotte, S.; Masereel, B.; Foidart, J. M.; Ravaux, M. R.; Noeul, A.; Pirotte, B.; Br. J. Cancer 2003, 88, 1111-1118

Non-patent document 21: Kim, H. H.; Bang, S. S.; Ghoi, J. S.; Han, H.; Kim, I-H.; Cancer Letters 2005, 223, 191-201

Non-patent document 22: Finn, G. J.; Creaven, B. S.; Egan, D. A.; Cancer Letters 2004, 214, 43-54

Non-patent document 23: Firm, G. J.; Creaven, B. S.; Egan, D. A.; Euro. J. Pharmacol. 2003, 481, 159-167

Non-patent document 24: Cheng, J. F.; Chen, M.; Wallace, D.; Tith, S.; Arrhenius, T.; Kashiwagi, H.; Ono, Y.; Ishikawa, A.; Sato, H.; Kozono, T.; Sato, H.; Nadzan, A. M.; Bioorg. Med. Chem. Lett. 2004, 14, 2411-2415

Non-patent document 25: Fries, W.; Mazzon, E.; Sturiale, S.; Giofre, M. R.; Lo Presti, M. A.; Cuzzocrea, S.; Campo, G. M.; Caputi, A. P.; Longo, G.; Sturniolo, G. C.; Life Sci. 2004, 74, 2749-2756

Non-patent document 26: Corsini, E.; Lucchi, L.; Binaglia, M.; Viviani, B.; Bevilacqua, C.; Monastra, G.; Marinovich, M.; Galli, C. L.; Eur. J. Pharmacol. 2001, 418, 231-237

Non-patent document 27: Cuzzocrea, S.; Mazzon, E.; Bevilaqua, C.; Costanitino, G.; Britti, D.; Mazzullo, G.; De Sarro, A.; Caputi, A. P.; Br. J. Pharmacol. 2000, 131, 1399-1407

Non-patent document 28: Tada, Y.; Shikishima, Y.; Takaishi, Y.; Shibata, H.; Higuti, T.; Honda, G.; Ito, M.; Takeda, Y.; Kodzhimatov, O. K.; Ashurmetov, O.; Ohmoto, Y.; Phytochemistry 2002, 59, 649-654

Non-patent document 29: Chen, S.; Cho, M.; Karlsberg, K.; Zhou, D.; Yuan, Y. C.; J. Biol. Chem. 2004, 279, 48071-48078

Non-patent document 30: Han, S.; Zhou, V.; Pan, S.; Liu, Y.; Hornsby, M.; McMullan, D.; Klock, H. E.; Haugen, J.; Lesley, S. A.; Gray, N.; Caldwell, J.; Gu, X-J.; Bioorg. Med. Chem. Lett. 2005, 15, 5467-5473

Non-patent document 31: Kulkarni, M. V.; Kulkarni, G. M.; Lin, C-H.; Sun, C-M; Current Medicinal Chemistry 2006, 13, 2795-2818

Non-patent document 32: Lee, S.; Sivakumar, K.; Shin, W-S.; Xie, F.; Wang, Q.; Bioorganic & Medicinal Chemistry Letters 2006, 16, 4596-4599

Non-patent document 33: Vijaya, K. P.; Rajeswar, R. V.; Indian Journal of Chemistry, Section B: Organic Chemistry Including Medicinal Chemistry 2005, 44B, 2120-2125

Non-patent document 34: Budzisz, E.; Malecka, M.; Lorenz, I-P.; Mayer, P.; Kwiecien, R. A.; Paneth, P.; Krajewska, U.; Rozalski, M.; Inorganic Chemistry 2006, 45, 9688-9695

DISCLOSURE OF THE INVENTION

The object of the present invention is to provide a compound which has sufficiently high antitumor activity and which is useful as a therapeutic agent for a cell proliferative disorder, particularly cancer, and a pharmaceutical composition containing the compound as an active ingredient.

The inventors of the present invention conducted intensive research for the purpose of providing a novel compound effective for treatment of a cell proliferative disorder, particularly cancer, and found that a coumarin derivative which has substituents at the 3-, 4- and 7-positions of the coumarin skeleton, which may have a substituent at the 6-position, and which has a sulfamide group or α-amidomethylene sulfonamide group, is a compound which has high antitumor activity, or which has high antitumor activity and exhibits high systemic exposure. The present invention was completed on the basis of this finding.

The present invention provides a compound represented by general formula (11) below or a pharmaceutically acceptable salt thereof:

[Chemical Formula 1]

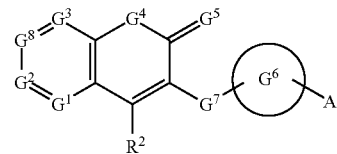

(11)

wherein:

$G^1$, $G^2$, $G^3$ and $G^8$ are each independently —N=, —CR$^1$= or —C(-G$^9$-X)=;

one from among $G^1$, $G^2$, $G^3$ and $G^8$ is —C(-G$^9$-X)=;

X is a $C_{1-6}$ alkyl group (where the $C_{1-6}$ alkyl group may optionally be substituted with a group selected from a halogen atom, a hydroxy group, a cyano group and —NR$^{56}$R$^{57}$), an aryl group, a heterocyclic group, R$^{31}$CS—, R$^{31}$CO—, R$^{33}$R$^{34}$NCS—, R$^{33}$R$^{34}$NC=NH—, R$^3$R$^4$NCO— or R$^{33}$R$^{34}$NCO$_2$—;

$G^9$ is a single bond, an oxygen atom, a sulfur atom, —(CR$^{35}$R$^{36}$)$_l$— (where l represents an integer of 1 to 3) or —NR$^{37}$—;

Ring $G^6$ is a divalent aryl group or a divalent heterocyclic group,

A is a group represented by general formula (2) below or a group represented by general formula (3) below:

[Chemical Formula 2]

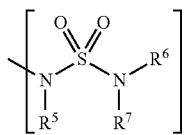

(2)

[Chemical Formula 3]

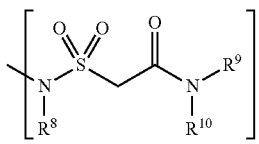

(3)

$G^4$ is an oxygen atom, a sulfur atom, —NR$^{38}$— or —CR$^{40}$R$^{41}$—;

$G^5$ is two hydrogen atoms, or an oxygen atom, a sulfur atom or =CH$_2$;

$G^7$ is an oxygen atom, —CR$^{42}$R$^{43}$—, —CR$^{42}$R$^{43}$—O—, —O—CR$^{42}$R$^{43}$—, —CONR$^{44}$—, —NR$^{44}$CO—, —NR$^{45}$—, —NR$^{45}$CR$^{42}$R$^{43}$—, —CR$^{42}$R$^{43}$NR$^{45}$—, —S(=O)$_n$—, —NR$^{44}$S(=O)$_n$—, —S(=O)$_n$NR$^{44}$— (where n represents an integer of 0 to 2), —N=CR$^{42}$—, —CR$^{42}$=N—, —CR$^{42}$=CR$^{43}$—, =C—, —NR$^{44}$—O—, —O—NR$^{44}$—, —C(=O)—O— or —O—C(=O)—;

R$^1$ is a hydrogen atom, a halogen atom, a cyano group, a $C_{1-6}$ alkyl group (where the $C_{1-6}$ alkyl group may optionally be substituted with a group selected from a halogen atom, a hydroxy group and —NR$^{46}$R$^{47}$), a $C_{2-7}$ alkenyl group, a carbamoyl group or a $C_{2-7}$ alkynyl group (where the $C_{2-7}$ alkynyl group may optionally be substituted with a $C_{1-4}$ acyl group);

when $G^2$ or $G^3$ is —CR$^1$=, $G^8$ is —C(-G$^9$-X)=, and X is R$^3$R$^4$NCO—, R$^{33}$R$^{34}$NC=NH— or R$^{33}$R$^{34}$NCS—; when $G^8$ is —CR$^1$=, $G^3$ is —C(-G$^9$-X)=, and X is R$^3$R$^4$NCO—, R$^{33}$R$^{34}$NC=NH— or R$^{33}$R$^{34}$NCS—; when $G^1$ or $G^8$ is —CR$^1$=, $G^2$ is —C(-G$^9$-X)=, and X is R$^3$R$^4$NCO—, R$^{33}$R$^{34}$NC=NH— or R$^{33}$R$^{34}$NCS—; or when $G^2$ is —CR$^1$=, $G^1$ is —C(-G$^9$-X)=, and X is R$^3$R$^4$NCO—, R$^{33}$R$^{34}$NC=NH— or R$^{33}$R$^{34}$NCS—, R$^1$ may form a single bond or —CH$_2$— together with R$^4$ or R$^{34}$;

R$^2$ is a hydroxy group, a $C_{1-6}$ alkoxy group, —NR$^{48}$R$^{49}$ or a $C_{1-6}$ alkyl group (where the $C_{1-6}$ alkyl group may optionally be substituted with a group selected from a halogen atom, a hydroxy group, a $C_{1-6}$ alkoxy group, a formyl group, —CO$_2$R$^{50}$ and —CO$_2$NR$^{51}$R$^{52}$);

R$^3$, R$^4$, R$^6$, R$^7$, R$^9$, R$^{10}$, R$^{31}$, R$^{46}$ and R$^{47}$ are each independently a hydrogen atom, a $C_{1-6}$ alkoxy group, a $C_{3-8}$ cycloalkyl group or a $C_{1-6}$ alkyl group (where the $C_{1-6}$ alkyl group may optionally be substituted with a group selected from a cyano group, a halogen atom, a hydroxy group, a $C_{1-6}$ alkoxy group, —NR$^{13}$R$^{14}$, —CONR$^{28}$R$^{29}$ and an aryl group);

R$^{33}$ and R$^{34}$ are each independently a hydrogen atom, a $C_{1-6}$ alkyl group or an aryl group;

the combination of R$^3$ and R$^4$, combination of R$^6$ and R$^7$, combination of R$^9$ and R$^{10}$, combination of R$^{33}$ and R$^{34}$, and combination of R$^{46}$ and R$^{47}$ may form, together with the nitrogen atom to which they are bonded, a 4- to 6-membered heterocyclic group having at least one nitrogen atom (where the heterocyclic group may optionally be fused with a benzene ring);

one R$^{35}$ group and one R$^{36}$ group are each independently a hydrogen atom, a halogen atom or a $C_{1-6}$ alkyl group;

R$^{45}$ is a hydrogen atom, a $C_{1-6}$ alkyl group or —S(=O)$_m$NR$^{54}$R$^{55}$ (where m represents an integer of 0 to 2);

R$^{13}$, R$^{14}$, R$^{56}$ and R$^{57}$ are each independently a hydrogen atom, a $C_{1-6}$ alkyl group, —COR$^{32}$ or —CO$_2$R$^{32}$; and R$^5$, R$^8$, R$^{28}$, R$^{29}$, R$^{32}$, R$^{37}$, R$^{38}$, R$^{40}$, R$^{41}$, R$^{42}$, R$^{43}$, R$^{44}$, R$^{48}$, R$^{49}$, R$^{50}$, R$^{51}$, R$^{52}$, R$^{54}$ and R$^{55}$ are each independently a hydrogen atom or a $C_{1-6}$ alkyl group.

$G^1$, $G^2$ and $G^3$ are each independently preferably —CR$^1$=, and $G^1$ and $G^3$ are more preferably —CH=.

$G^8$ is preferably —C(-G$^9$-X)=. The following groups may be mentioned as examples of X-G$^9$-:

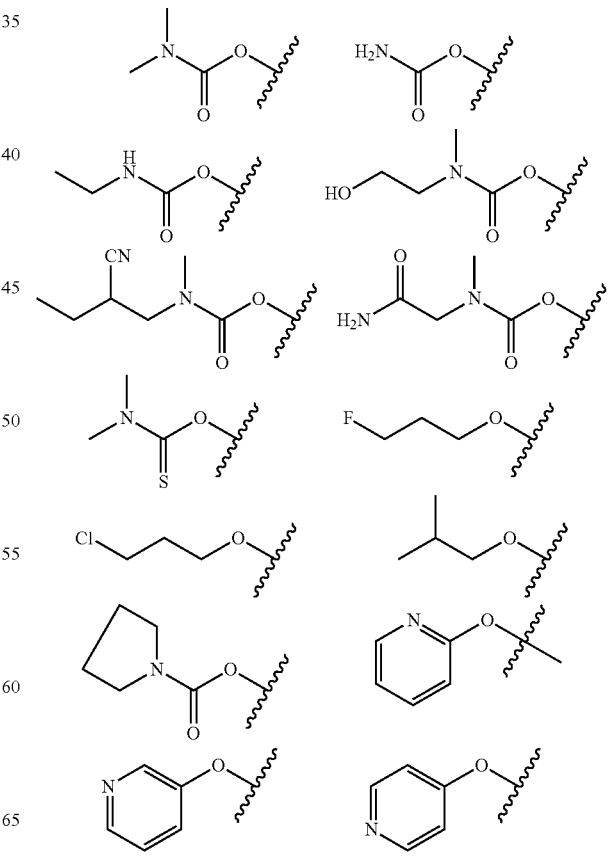

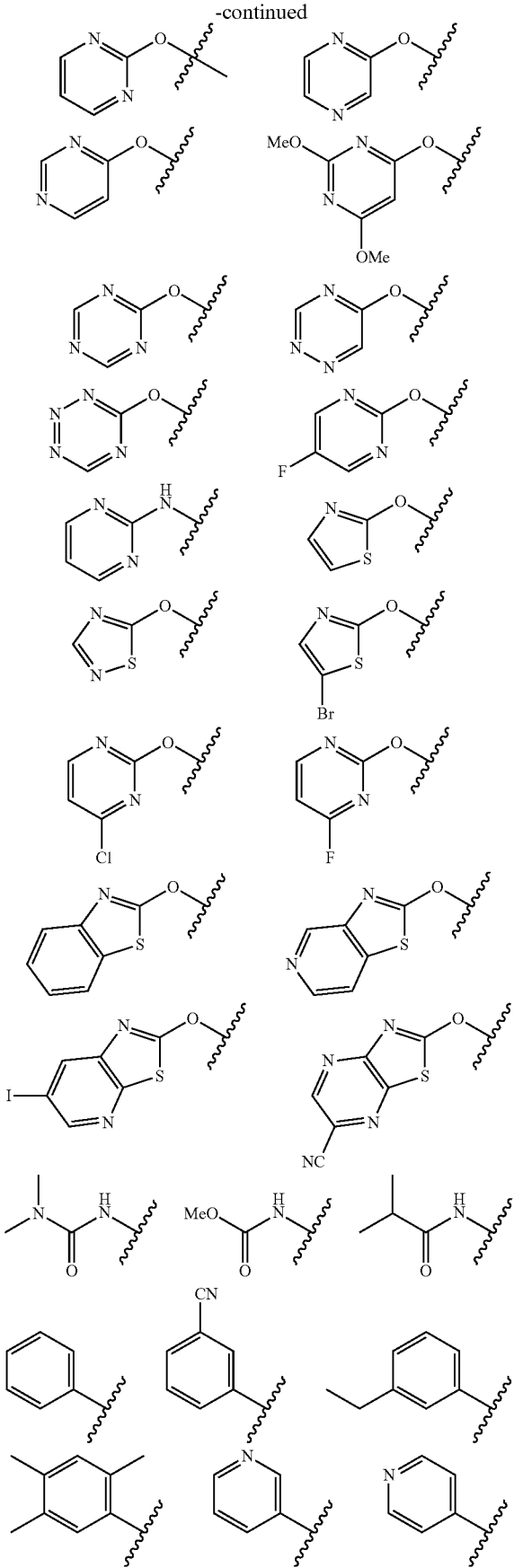
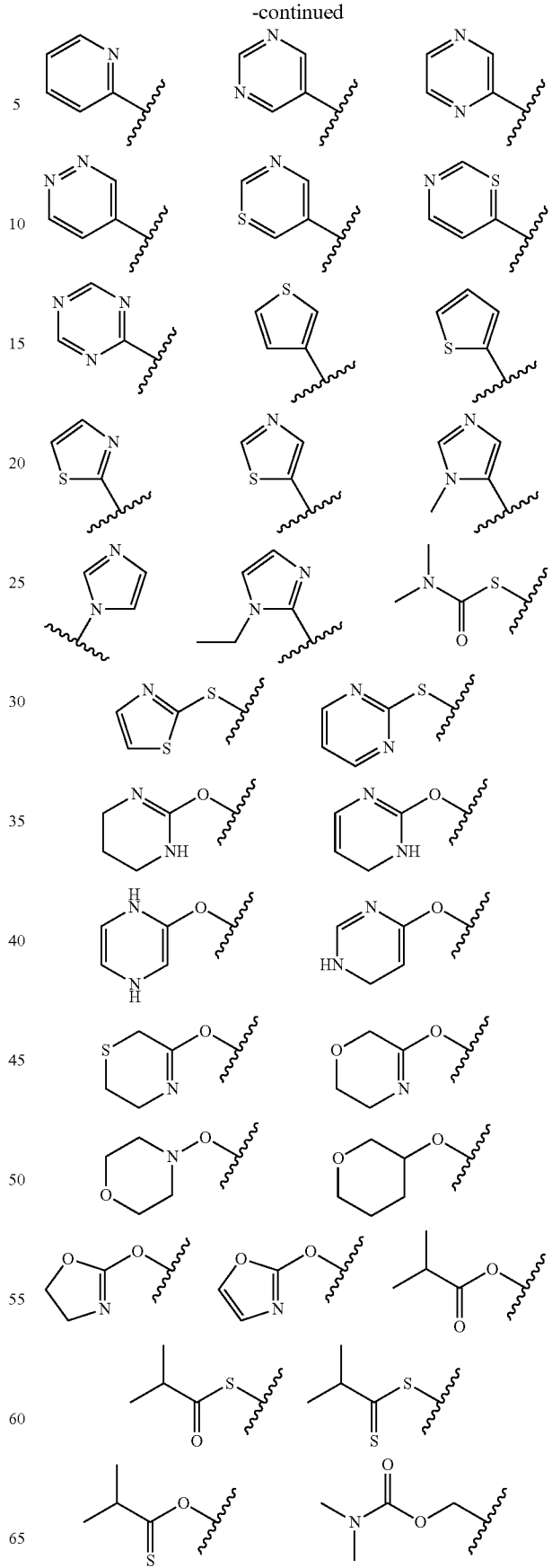

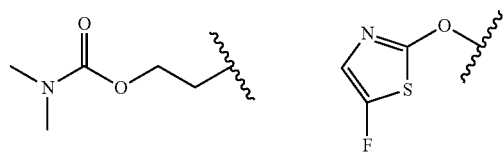

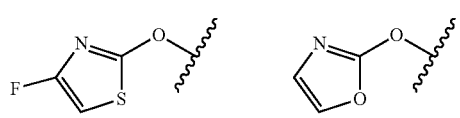

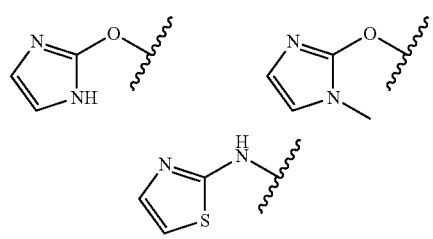

When $G^2$ or $G^3$ is —$CR^1$=, $G^8$ is —C(-$G^9$-X)=, and X is $R^3R^4NCO$—, $R^{33}R^{34}NC$=NH— or $R^{33}R^{34}NCS$—; when $G^8$ is —$CR^1$=, $G^3$ is —C(-$G^9$-X)=, and X is $R^3R^4NCO$—, $R^{33}R^{34}NC$=NH— or $R^{33}R^{34}NCS$—; when $G^1$ or $G^8$ is —$CR^1$=, $G^2$ is —C(-$G^9$-X)=, and X is $R^3R^4NCO$—, $R^{33}R^{34}NC$=NH— or $R^{33}R^{34}NCS$—; or when $G^2$ is —$CR^1$=, $G^1$ is —C(-$G^9$-X)=, and X is $R^3R^4NCO$—, $R^{33}R^{34}NC$=NH— or $R^{33}R^{34}NCS$—, $R^1$ may form a single bond or —$CH_2$— together with $R^4$ or $R^{34}$.

The following partial structures may be mentioned as examples of partial structures formed when $R^1$ and $R^4$ are linked:

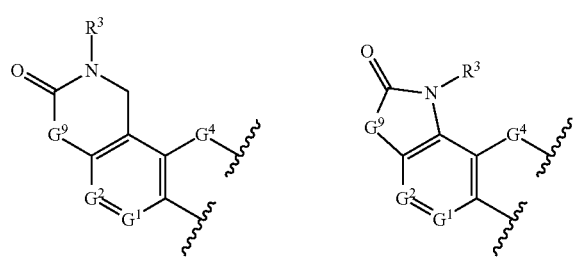

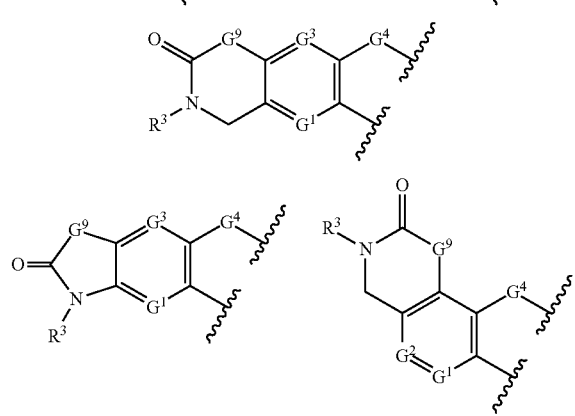

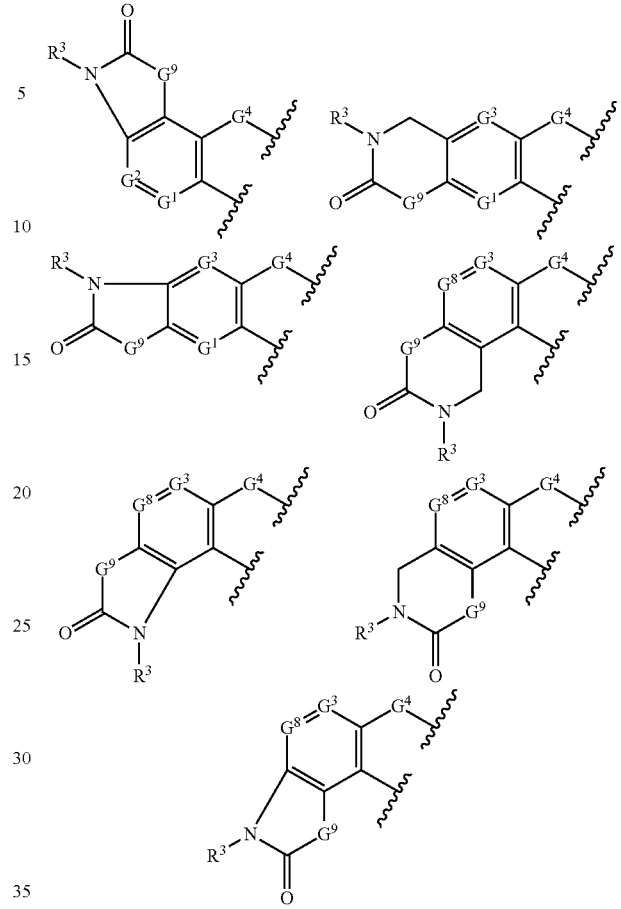

More specifically, the following partial structures may be mentioned:

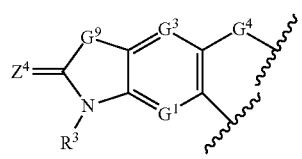

[where the combinations of $G^9$, $Z^4$, $R^3$, $G^1$ and $G^3$ are as listed in the table below.]

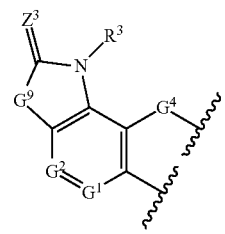

| $G^9$ | $Z^4$ | $R^3$ | $G^1$ | $G^3$ |
|---|---|---|---|---|
| O | O | $CH_3$ | CH | CH |
| O | O | H | CH | CH |
| S | O | $CH_3$ | CH | CH |

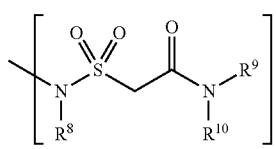

| $G^9$ | $Z^4$ | $R^3$ | $G^1$ | $G^3$ |
|---|---|---|---|---|
| O | S | $CH_3$ | CH | CH |
| NH | O | $CH_3$ | CH | CH |
| O | O | $CH_3$ | N | CH |

[where the combinations of $G^9$, $Z^3$, $R^3$, $G^1$ and $G^2$ are as listed in the table below.]

| $G^9$ | $Z^3$ | $R^3$ | $G^1$ | $G^2$ |
|---|---|---|---|---|
| O | O | $CH_3$ | CH | CH |
| O | O | H | CH | CH |
| S | O | $CH_3$ | CH | $CCH_3$ |
| O | S | $CH_3$ | CH | CH |
| NH | O | $CH_3$ | CH | CF |
| O | O | $CH_3$ | N | CH |
| O | O | $CH_3$ | CH | N |

When $G^9$ is —$(CR^{35}R^{36})_l$— (where l represents an integer of 1 to 3), X is preferably $R^{33}R^{34}NCO_2$—.

When X is a $C_{1-6}$ alkyl group (where the $C_{1-6}$ alkyl group may optionally be substituted with a group selected from a halogen atom, a hydroxy group, a cyano group and —$NR^{56}R^{57}$) and $G^9$ is a single bond, $R^1$ is preferably a hydrogen atom, a halogen atom, a cyano group, a $C_{2-7}$ alkenyl group, a carbamoyl group or a $C_{2-7}$ alkynyl group (where the $C_{2-7}$ alkynyl group may optionally be substituted with a $C_{1-4}$ acyl group).

The compound represented by general formula (11) is preferably a compound represented by general formula (1) below:

[Chemical Formula 1]

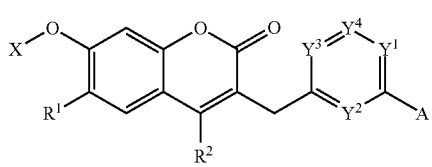

(1)

wherein:

X is a heteroaryl group or $R^3R^4NCO$—;

$Y^1$ and $Y^2$ are each independently —N= or —$CR^1$=;

$Y^3$ and $Y^4$ may be the same or different, and are each —$CR^{12}$=;

A is a group represented by general formula (2) below or a group represented by general formula (3) below:

[Chemical Formula 2]

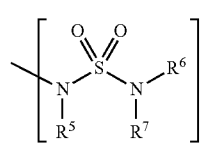

(2)

[Chemical Formula 3]

$$\left[ \begin{array}{c} O\ O \\ \| \| \\ -N-S-N-R^9 \\ | \quad \| \quad | \\ R^8 \quad O \quad R^{10} \end{array} \right]$$ (3)

$R^1$ is a hydrogen atom, a halogen atom, a cyano group, a $C_{1-6}$ alkyl group, a $C_{2-7}$ alkenyl group, a carbamoyl group or a $C_{2-7}$ alkynyl group (where the $C_{2-7}$ alkynyl group may optionally be substituted with a $C_{1-4}$ acyl group);

$R^2$ is a $C_{1-6}$ alkyl group optionally substituted with a halogen atom;

$R^3$, $R^4$, $R^6$, $R^7$, $R^9$ and $R^{10}$ are each independently a hydrogen atom, a $C_{1-6}$ alkoxy group, a $C_{3-8}$ cycloalkyl group or a $C_{1-6}$ alkyl group (where the $C_{1-6}$ alkyl group may optionally be substituted with a group selected from a cyano group, a halogen atom, a hydroxy group, a $C_{1-6}$ alkoxy group and —$NR^{13}R^{14}$);

the combination of $R^3$ and $R^4$, combination of $R^6$ and $R^7$, and combination of $R^9$ and $R^{10}$ may form, together with the nitrogen atom to which they are bonded, a 4- to 6-membered heterocyclic group having at least one nitrogen atom;

$R^5$, $R^8$, $R^{13}$ and $R^{14}$ are each independently a hydrogen atom or a $C_{1-6}$ alkyl group;

$R^{11}$ is a hydrogen atom, a halogen atom, a $C_{1-6}$ alkyl group, a $C_{1-4}$ acyl group, a $C_{1-4}$ acloxy group or —$NR^{15}R^{16}$;

$R^{12}$ is a hydrogen atom, a halogen atom or a $C_{1-6}$ alkyl group; and $R^{15}$ and $R^{16}$ are each independently a hydrogen atom or a $C_{1-4}$ acyl group.

The above described compound or a pharmaceutically acceptable salt thereof has more excellent properties as an anticancer drug than conventional coumarin compounds, because it has markedly high antitumor activity compared to conventional compounds, or because it has sufficiently high antitumor activity that is equivalent to those of conventional compounds, and exhibits higher systemic exposure than conventional compounds.

The above described compound or a pharmaceutically acceptable salt thereof having such properties can be used as an active ingredient of a pharmaceutical composition. Therefore, the present invention also provides a pharmaceutical composition comprising a compound represented by general formula (11), preferably general formula (1), or a pharmaceutically acceptable salt thereof as an active ingredient.

Further, the above described compound or a pharmaceutically acceptable salt thereof can be used as an active ingredient of a therapeutic agent for a cell proliferative disorder, particularly cancer. Therefore, the present invention also provides a therapeutic agent for a cell proliferative disorder, particularly cancer, comprising a compound represented by general formula (11), preferably general formula (1), or a pharmaceutically acceptable salt thereof as an active ingredient.

According to the present invention, there are provided a compound which has sufficiently high antitumor activity, and is useful in the treatment of cell proliferative disorders, particularly cancers, and a pharmaceutical composition comprising the compound as an active ingredient.

BEST MODES FOR CARRYING OUT THE INVENTION

Preferred embodiments of the present invention will now be described below.

The compound of the present invention is represented by general formula (11) above, preferably general formula (1) above.

In general formulas (11) and (1), the heteroaryl group means a 5- to 10-membered aromatic heterocyclic group having one or more heteroatoms selected from oxygen, nitrogen and sulfur atoms. As specific examples, there may be mentioned furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidinyl, pyrazinyl, pyridazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, indolizinyl and imidazopyridyl, among which thiazolyl, pyrimidinyl, pyridyl and the like are preferred, and thiazol-2-yl, pyrimidin-2-yl, 2-pyridyl and the like are further preferred.

The heteroaryl group may be optionally substituted with halogen, $C_{1-6}$ alkyl, $C_{1-6}$ alkoxy, cyano, amino, carbamoyl, nitro, carboxy, $C_{2-7}$ alkenyl, $C_{2-7}$ alkynyl or the like on an atom of the ring, but it is preferably unsubstituted.

The aryl group means an aromatic hydrocarbon group having 6 to 10 carbon atoms. As specific examples, there may be mentioned phenyl, 1-naphthyl and 2-naphthyl. The aryl group may be optionally substituted with halogen, $C_{1-6}$ alkyl, $C_{1-6}$ alkoxy, cyano, amino, carbamoyl, nitro, carboxy, $C_{2-7}$ alkenyl, $C_{2-7}$ alkynyl or the like on a carbon atom.

The divalent aryl group means a group obtained by removing any one of the hydrogen atoms on the atoms of the aforementioned aryl group. The divalent aryl group may be substituted with $G^7$ and A in any manner, and when the divalent aryl group is a phenylene group, for example, they may be 1,2-substituted, 1,3-substituted or 1,4-substituted.

The halogen atom means a fluorine, chlorine, bromine or iodine atom.

The $C_{1-6}$ alkyl group means a straight- or branched-chain alkyl group having 1 to 6 carbon atoms. As specific examples, there may be mentioned methyl, ethyl, n-propyl, i-propyl, n-butyl, sec-butyl, t-butyl, 1-methylpropyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl and 2-ethylbutyl.

The $C_{2-7}$ alkenyl group means a straight- or branched-chain alkenyl group having 2 to 7 carbon atoms. As specific examples, there may be mentioned vinyl, allyl, 1-butenyl, 2-butenyl, 3-butenyl, pentenyl, pentadienyl, hexenyl, hexadienyl, heptenyl, heptadienyl and heptatrienyl.

The $C_{2-7}$ alkynyl group means a straight- or branched-chain alkynyl group having 2 to 7 carbon atoms. As specific examples, there may be mentioned ethynyl, 1-propynyl, 2-propynyl, 1-butynyl, 2-butyryl, 3-butynyl, pentynyl, pentadiynyl, hexynyl, hexadiynyl, heptynyl, heptadiynyl and heptatriynyl.

The $C_{1-4}$ acyl group means an acyl group having 1 to 4 carbon atoms. As specific examples, there may be mentioned formyl, acetyl, n-propionyl, i-propionyl, butyryl and sec-butyryl (isobutyryl).

The $C_{1-6}$ alkoxy group means an alkyloxy group having, as an alkyl moiety, a straight- or branched-chain alkyl group having 1 to 6 carbon atoms. As specific examples, there may be mentioned methoxy, ethoxy, n-propoxy, i-propoxy, n-butoxy, s-butoxy, t-butoxy, pentoxy and hexoxy.

The $C_{3-8}$ cycloalkyl group means a 3- to 8-membered cyclic alkyl group which has 3 to 8 total carbon atoms (where the cyclic alkyl group may optionally be substituted with a straight- or branched-chain alkyl group having 1 to 3 carbon atoms). As specific examples, there may be mentioned: nonsubstituted cycloalkyl groups such as cyclopropyl, cyclobutyl, cyclopentyl, cyclohexyl, cycloheptyl and cyclooctyl; and substituted cycloalkyl groups such as methylcyclopropyl, ethylcyclopropyl, dimethylcyclopropyl, trimethylcyclopropyl, diethylcyclopropyl, ethylmethylcyclopropyl, dimethylethylcyclopropyl, diethylmethylcyclopropyl, methylcyclobutyl, ethylcyclobutyl, dimethylcyclobutyl, trimethylcyclobutyl, tetramethylcyclobutyl, diethylcyclobutyl, ethylmethylcyclobutyl, dimethylethylcyclobutyl, methylcyclopentyl, ethylcyclopentyl, dimethylcyclopentyl, trimethylcyclopentyl, ethylmethylcyclopentyl, methylcyclohexyl, ethylcyclohexyl, dimethylcyclohexyl and methylheptyl, among which nonsubstituted cycloalkyl groups are preferred, and cyclopropyl is further preferred.

The 4- to 6-membered heterocyclic group having at least one nitrogen atom means a saturated or unsaturated heterocyclic group which has 4 to 6 ring atoms and which may have, in addition to one or more nitrogen atoms, one or more heteroatoms selected from oxygen and sulfur atoms (where the heterocyclic group may optionally be fused with a benzene ring). As specific examples, there may be mentioned azetidinyl, pyrrolidinyl, piperidinyl, piperazinyl, pyrrolyl, dihydropyrrolyl, imidazolyl, imidazolynyl, imidazolidinyl, pyrazolyl, pyrazolynyl, pyridazolidinyl, oxazolynyl, oxazolidinyl, morpholinyl, thiomorpholinyl, pyridinyl, dihydropyridinyl, pyrazinyl, pyrimidinyl, and pyridazinyl.

The 4- to 6-membered heterocyclic group having at least one nitrogen atom may be optionally substituted with halogen, $C_{1-6}$ alkyl, $C_{1-6}$ alkoxy, cyano, amino, carbamoyl, nitro, carboxy, $C_{2-7}$ alkenyl, $C_{2-7}$ alkynyl or the like on an atom of the ring.

The heterocyclic group means a 4- to 12-membered, preferably 5- to 7-membered, saturated or unsaturated cyclic group having one or more heteroatoms selected from nitrogen, oxygen and sulfur atoms. The heterocycle may be a monocycle or fused ring, and examples thereof include the aforementioned heteroaryl groups as well as the aforementioned 4- to 6-membered heterocyclic groups having one or more nitrogen atoms.

As specific examples of the heterocyclic group, there may be mentioned: furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridyl, pyrimidinyl, pyrazinyl, pyridazinyl, triazinyl, benzofuranyl, benzothienyl, benzothiadiazolyl, benzothiazolyl, benzoxazolyl, benzoxadiazolyl, benzimidazolyl, indolyl, isoindolyl, indazolyl, quinolyl, isoquinolyl, cinnolinyl, quinazolinyl, quinoxalinyl, indolizinyl, imidazopyridyl, azetidinyl, pyrrolidinyl, piperidinyl, piperazinyl, pyrrolyl, dihydropyrrolyl, imidazolyl, imidazolinyl, imidazolidinyl, pyrazolyl, pyrazolynyl, pyridazolidinyl, oxazolinyl, oxazolidinyl, morpholinyl, thiomorpholinyl, pyridinyl, dihydropyridinyl, pyrimidinyl, pyridazinyl, tetrahydrofuryl, tetrahydrothienyl, dioxolanyl, oxathiolanyl, dioxanyl, isobenzofuranyl, chromenyl, indolizinyl, indolyl, isoindolyl, indazolyl, puryl, quinolidinyl, isoquinolinyl, quinolinyl, phthalazinyl, naphthylidinyl, quinoxalinyl, quinazolinyl, cinnolinyl, pteridinyl, isochromanyl, chromanyl, quinuclidinyl, oxacycloheptyl, dioxacycloheptyl, thiacycloheptyl and diazacycloheptyl.

The heterocyclic group may be optionally substituted with halogen, $C_{1-6}$ alkyl, $C_{1-6}$ alkoxy, cyano, amino, carbamoyl, nitro, carboxy, $C_{2-7}$ alkenyl, $C_{2-7}$ alkynyl or the like on an atom of the ring.

The divalent heterocyclic group means a group obtained by removing any one of the hydrogen atoms on the atoms of the aforementioned heterocyclic group. The divalent heterocyclic group may be substituted with $G^7$ and A in any manner, and when the divalent heterocyclic group is pyridinediyl, for example, they may be 2,3-substituted, 2,4-substituted, 2,5-substituted, 2,6-substituted, 3,4-substituted, 3,5-substituted, 3,6-substituted, 4,5-substituted, 4,6-substituted or 5,6-substituted.

The $C_{1-4}$ acyloxy group means an acyloxy group having, as an acyl moiety, an acyl group having 1 to 4 carbon atoms. As specific examples, there may be mentioned formyloxy, acetyloxy, n-propionyloxy, i-propionyloxy, butyryloxy and sec-butyryloxy (isobutyryloxy).

As specific examples of the $C_{1-6}$ alkyl group substituted with a halogen atom, there may be mentioned fluoromethyl, difluoromethyl, trifluoromethyl, fluoroethyl, difluoroethyl, trifluoroethyl, pentafluoroethyl, fluoropropyl, difluoropropyl, trifluoropropyl, heptafluoropropyl, fluorobutyl, difluorobutyl, trifluorobutyl, fluoropentyl, difluoropentyl, trifluoropentyl, tetrafluoropentyl, fluoroheptyl, difluoroheptyl, trifluoroheptyl, tetrafluoroheptyl, pentafluoroheptyl, chloromethyl, dichloromethyl, trichloromethyl, chloroethyl, dichloroethyl, trichloroethyl, pentachloroethyl, chloropropyl, dichloropropyl, trichloropropyl, heptachloropropyl, chlorobutyl, dichlorobutyl, trichlorobutyl, chloropentyl, dichloropentyl, trichloropentyl, tetrachloropentyl, chloroheptyl, dichloroheptyl, trichloroheptyl, tetrachloroheptyl, pentachloroheptyl, bromomethyl, dibromomethyl, tribromomethyl, bromoethyl, dibromoethyl, tribromoethyl, pentabromoethyl, bromopropyl, dibromopropyl, tribromopropyl, heptabromopropyl, bromobutyl, dibromobutyl, tribromobutyl, bromopentyl, dibromopentyl, tribromopentyl, tetrabromopentyl, bromoheptyl, dibromoheptyl, tribromoheptyl, tetrabromoheptyl, pentabromoheptyl, iodomethyl, diiodomethyl, triiodomethyl, iodoethyl, diiodoethyl, triiodoethyl, pentaiodoethyl, iodopropyl, diiodopropyl, triiodopropyl, heptaiodopropyl, iodobutyl, diiodobutyl, triiodobutyl, iodopentyl, diiodopentyl, triiodopentyl, tetraiodopentyl, iodoheptyl, diiodoheptyl, triiodoheptyl, tetraiodoheptyl and pentaiodoheptyl.

As for $R^1$, hydrogen, halogen, cyano, $C_{1-6}$ alkyl, carbamoyl, and $C_{2-7}$ alkynyl (where the $C_{2-7}$ alkynyl may optionally be substituted with $C_{1-4}$ acyl) are preferred; hydrogen, halogen, cyano, methyl, ethenyl and acetylethenyl are particularly preferred; hydrogen, halogen and methyl are further preferred; and hydrogen, fluorine, chlorine and methyl are still further preferred.

As for $R^2$, $C_{1-6}$ alkyl optionally substituted with fluorine is preferred; methyl, ethyl, n-propyl, fluoromethyl, 1-fluoroethyl, 2-fluoroethyl, 2,2-difluoroethyl, 1-fluoro-n-propyl, 2-fluoro-n-propyl and 2,2-difluoro-n-propyl are particularly preferred; and —$CH_3$, —$CH_2F$ and —$CH_2CH_3$ are further preferred.

$R^3$, $R^4$, $R^6$, $R^7$, $R^9$ and $R^{10}$ are each preferably hydrogen or $C_{1-6}$ alkyl. As for the $C_{1-6}$ alkyl, methyl, ethyl, n-propyl and i-propyl are preferred, and methyl, ethyl and i-propyl are particularly preferred.

$R^3$ and $R^4$ are each preferably a $C_{1-6}$ alkyl group. It is further preferred that both $R^3$ and $R^4$ are the same $C_{1-6}$ alkyl group, particularly a methyl group.

$R^6$ and $R^7$ are each preferably hydrogen, $C_{1-6}$ alkoxy, $C_{3-8}$ cycloalkyl, or $C_{1-6}$ alkyl (where the $C_{1-6}$ alkyl may optionally be substituted with a group selected from cyano, halogen, hydroxy, $C_{1-6}$ alkoxy and —$NR^{13}R^{14}$). As for the $C_{1-6}$ alkoxy represented by $R^6$ or $R^7$, methoxy and ethoxy are preferred, and methoxy is particularly preferred. As for the $C_{3-8}$ cycloalkyl represented by $R^6$ or $R^7$, nonsubstituted cycloalkyl is preferred, and cyclopropyl is particularly preferred. As for the $C_{1-6}$ alkyl represented by $R^6$ or $R^7$, methyl, ethyl and n-propyl are preferred, while ethyl is particularly preferred when the $C_{1-6}$ alkyl is substituted, and methyl is particularly preferred when the $C_{1-6}$ alkyl is unsubstituted. The halogen atom to be selected as a substituent of the $C_{1-6}$ alkyl is preferably fluorine. The $C_{1-6}$ alkoxy to be selected as a substituent of the $C_{1-6}$ alkyl is preferably methoxy.

As for $R^6$ and $R^7$, each one is more preferably hydrogen, nonsubstituted cycloalkyl or nonsubstituted $C_{1-6}$ alkyl. As for the combination of $R^6$ and $R^7$, combinations of: hydrogen atoms; hydrogen and methyl; hydrogen and cyclopropyl; methyl groups; hydrogen and cyanoethyl; hydrogen and methoxyethyl; hydrogen and aminoethyl; hydrogen and trifluoroethyl; hydrogen and methoxy; hydrogen and hydroxyethyl; and hydrogen and methylaminoethyl are preferred, and combinations of: hydrogen atoms; hydrogen and cyclopropyl; and hydrogen and methyl are particularly preferred.

$R^9$ and $R^{10}$ are each preferably hydrogen, $C_{1-6}$ alkyl or $C_{1-6}$ alkoxy. As for the $C_{1-6}$ alkyl, methyl, ethyl, n-propyl and i-propyl are preferred, and methyl, ethyl and i-propyl are particularly preferred. As for the $C_{1-6}$ alkoxy, methoxy, ethoxy, n-propoxy and i-propoxy are preferred, and methoxy is particularly preferred.

As for the combination of $R^9$ and $R^{10}$, combinations of: hydrogen atoms; hydrogen and methyl; methyl groups; hydrogen and ethyl; ethyl groups; hydrogen and i-propyl; methyl and i-propyl; ethyl and i-propyl; i-propyl groups; hydrogen and methoxy; methyl and methoxy; ethyl and methoxy; and i-propyl and methoxy are preferred, and combinations of: hydrogen atoms; hydrogen and methyl; methyl groups; hydrogen and ethyl; hydrogen and i-propyl; and hydrogen and methoxy are particularly preferred.

$R^5$ and $R^8$ are preferably a hydrogen atom.

As for the $C_{1-4}$ acyl represented by $R^{15}$ or $R^{16}$, formyl, acetyl and propionyl are preferred, and acetyl is particularly preferred. As for the combination of $R^{15}$ and $R^{16}$, combinations of: hydrogen atoms; and hydrogen and acetyl are preferred, and a combination of hydrogen and acetyl is particularly preferred.

As for the $C_{1-6}$ alkyl represented by $R^{11}$, methyl, ethyl and n-propyl are preferred, and methyl is particularly preferred. As the $C_{1-4}$ acyl represented by $R^{11}$, formyl, acetyl and n-propionyl are preferred, and acetyl is particularly preferred. As the $C_{1-4}$ acyloxy represented by $R^{11}$, formyloxy, acetyloxy and n-propionyloxy are preferred, and acetyloxy is particularly preferred. As for $R^{11}$, hydrogen and halogen are preferred, and hydrogen and fluorine are particularly preferred.

As for $Y^1$, —N=, —CH=, —CF= and —CCl= are preferred; —N=, —CH= and —CF= are particularly preferred; and —N= and —CH= are further preferred.

As for $R^{11}$ of —$CR^{11}$= represented by $Y^2$, hydrogen, halogen, $C_{1-4}$ acyl and —$NR^{15}R^{16}$ are preferred, and hydrogen, fluorine and chlorine, acetyl and —$NHCOCH_3$ are particularly preferred. As for $Y^2$, —N=, —CH= and —CF= are preferred, and —CH= and —CF= are particularly preferred.

As for $R^{12}$, hydrogen, fluorine and methyl are preferred; hydrogen and fluorine are particularly preferred; and hydrogen is further preferred.

$R^{13}$ and $R^{14}$ are each preferably hydrogen, methyl or ethyl, and more preferably hydrogen or methyl. As for the combination of $R^{13}$ and $R^{14}$, combinations of hydrogen atoms; and hydrogen and methyl are preferred.

As for X, thiazol-2-yl, pyrimidin-2-yl, 2-pyridyl and $R^3R^4NCO$— (where $R^3$ and $R^4$ have the same definitions as above) are preferred. It is particularly preferred that both $R^3$ and $R^4$ are a methyl group.

A is preferably a group represented by general formula (2).

When X is a thiazol-2-yl group, it is preferred that: $Y^1$ is —N= or —CH=; $Y^2$ is —CH=, —CF= or —CCl=; $R^1$ is hydrogen, chlorine or methyl; and $R^2$ is methyl, ethyl or fluoromethyl. Then, if A is a group represented by general formula (2), the combination of $R^6$ and $R^7$ is preferably a combination of: hydrogen atoms; or hydrogen and methyl, and if A is a group represented by general formula (3), the combination of $R^9$ and $R^{10}$ is preferably a combination of: hydrogen and methyl; or hydrogen and cyclopropyl.

When X is a pyrimidin-2-yl group, it is preferred that: $Y^1$ is —N= or —CH=; $Y^2$ is —N=, —CH= or —CF=; $R^1$ is hydrogen, fluorine, chlorine or methyl; $R^2$ is methyl, ethyl or fluoromethyl; A is a group represented by general formula (2); and the combination of $R^6$ and $R^7$ is a combination of hydrogen atoms, a combination of methyl groups, a combination of hydrogen and methyl, or a combination of hydrogen and cyclopropyl.

When X is $(H_3C)_2NCO$—, it is preferred that: $Y^1$ is —N= or —CH=; $Y^2$ is —CH=, —CF= or —CCl=; $R^1$ is hydrogen, fluorine, chlorine, iodine, cyano or methyl; and $R^2$ is methyl or fluoromethyl. Then, if A is a group represented by general formula (2), the combination of $R^6$ and $R^7$ is preferably a combination of: hydrogen atoms; hydrogen and methyl; or methyl groups, and if A is a group represented by general formula (3), the combination of $R^9$ and $R^{10}$ is preferably a combination of: hydrogen and methyl; hydrogen and methoxyethyl; or hydrogen and cyanoethyl.

When $Y^1$ is —N=, it is preferred that: X is thiazol-2-yl, pyrimidin-2-yl or $(H_3C)_2NCO$—; $Y^2$ is —CH=, —CF= or —CCl=; $R^1$ is hydrogen, fluorine, chlorine or methyl; $R^2$ is methyl or ethyl; A is a group represented by general formula (2); and the combination of $R^6$ and $R^7$ is a combination of hydrogen atoms, a combination of methyl groups, a combination of hydrogen and methyl, or a combination of hydrogen and cyclopropyl.

When $Y^1$ is —CH=, it is preferred that: X is thiazol-2-yl, pyrimidin-2-yl or $(H_3C)_2NCO$—; $Y^2$ is —N=, —CH= or —CF=; $R^1$ is hydrogen, fluorine, chlorine, iodine, methyl or cyano; and $R^2$ is methyl or fluoromethyl. Then, if A is a group represented by general formula (2), the combination of $R^6$ and $R^7$ is preferably a combination of: hydrogen atoms; methyl groups; or hydrogen and methyl, and if A is a group represented by general formula (3), the combination of $R^9$ and $R^{10}$ is preferably a combination of: hydrogen and methyl; hydrogen and methoxyethyl; or hydrogen and cyanoethyl.

When $Y^2$ is —CH=, it is preferred that: X is thiazol-2-yl, pyrimidin-2-yl or $(H_3C)_2NCO$—; $Y^1$ is —N= or —CH=; $R^1$ is hydrogen, fluorine, chlorine, iodine, methyl or cyano; and $R^2$ is methyl, ethyl or fluoromethyl. Then, if A is a group represented by general formula (2), the combination of $R^6$ and $R^7$ is preferably a combination of: hydrogen atoms; methyl groups; or hydrogen and methyl, and if A is a group represented by general formula (3), the combination of $R^9$ and $R^{10}$ is preferably a combination of: hydrogen and methyl; hydrogen and methoxyethyl; or hydrogen and cyanoethyl.

When $Y^2$ is —CF=, it is preferred that: X is thiazol-2-yl, pyrimidin-2-yl or $(H_3C)_2NCO$—; $Y^1$ is —N= or —CH=; $R^1$ is hydrogen, fluorine, chlorine or methyl; $R^2$ is methyl, ethyl or fluoromethyl; A is a group represented by general formula (2); and the combination of $R^6$ and $R^7$ is a combination of hydrogen atoms, a combination of hydrogen and methyl, or a combination of hydrogen and cyclopropyl.

When $R^1$ is a hydrogen atom, it is preferred that: X is thiazol-2-yl, pyrimidin-2-yl or $(H_3C)_2NCO$—; $Y^1$ is —N= or —CH=; $Y^2$ is —N=, —CH= or —CF=; and $R^2$ is methyl or fluoromethyl. Then, if A is a group represented by general formula (2), the combination of $R^6$ and $R^7$ is preferably a combination of: hydrogen atoms; or hydrogen and methyl, and if A is a group represented by general formula (3), the combination of $R^9$ and $R^{10}$ is preferably a combination of hydrogen and methyl.

When $R^1$ is a fluorine atom, it is preferred that: X is thiazol-2-yl, pyrimidin-2-yl or $(H_3C)_2NCO$—; $Y^1$ is —N= or —CH=; $Y^2$ is —N=, —CH= or —CF=; $R^2$ is methyl; A is a group represented by general formula (2); and the combination of $R^6$ and $R^7$ is a combination of hydrogen atoms, a combination of methyl groups, a combination of hydrogen and methyl, a combination of hydrogen and cyclopropyl, a combination of hydrogen and methoxyethyl, or a combination of hydrogen and cyanoethyl.

When $R^1$ is a chlorine atom, it is preferred that: X is thiazol-2-yl, pyrimidin-2-yl or $(H_3C)_2NCO$—; $Y^1$ is —N= or —CH=; $Y^2$ is —CH= or —CF=; and $R^2$ is methyl or trifluoromethyl. Then, if A is a group represented by general formula (2), the combination of $R^6$ and $R^7$ is preferably a combination of: methyl groups; or hydrogen and methyl, and if A is a group represented by general formula (3), the combination of $R^9$ and $R^{10}$ is preferably a combination of: hydrogen and methyl; hydrogen and methoxyethyl; or hydrogen and cyanoethyl.

When $R^1$ is a methyl group, it is preferred that: X is thiazol-2-yl, pyrimidin-2-yl or $(H_3C)_2NCO$—; $Y^1$ is —N= or —CH=; $Y^2$ is —CH=, —CF= or —CCl=; $R^2$ is methyl, ethyl or trifluoromethyl; A is a group represented by general formula (2); and the combination of $R^6$ and $R^7$ is a combination of hydrogen and methyl.

When $R^2$ is a methyl group, it is preferred that: X is thiazol-2-yl, pyrimidin-2-yl or $(H_3C)_2NCO$—; $Y^1$ is —N= or —CH=; $Y^2$ is —N=, —CH=, —CF= or —CCl=; and $R^1$ is hydrogen, fluorine, chlorine, iodine, methyl or cyano. Then, if A is a group represented by general formula (2), the combination of $R^6$ and $R^7$ is preferably a combination of: hydrogen atoms; methyl groups; hydrogen and methyl; or hydrogen and cyclopropyl, and if A is a group represented by general formula (3), the combination of $R^9$ and $R^{10}$ is preferably a combination of: hydrogen and methyl; hydrogen and methoxyethyl; or hydrogen and cyanoethyl.

When $R^2$ is an ethyl group, it is preferred that: X is thiazol-2-yl or pyrimidin-2-yl; $Y^1$ is —N=; $Y^2$ is —CF=; $R^1$ is methyl; A is a group represented by general formula (2); and the combination of $R^6$ and $R^7$ is a combination of hydrogen and methyl.

When $R^2$ is a fluoromethyl group, it is preferred that: X is thiazol-2-yl, pyrimidin-2-yl or $(H_3C)_2NCO$—; $Y^1$ is —N= or —CH=; $Y^2$ is —N=, —CH= or —CF=; $R^1$ is hydrogen, fluorine, chlorine or methyl; A is a group represented by general formula (2); and the combination of $R^6$ and $R^7$ is a combination of hydrogen and methyl.

When the combination of $R^6$ and $R^7$ is a combination of hydrogen atoms, it is preferred that: X is thiazol-2-yl, pyrimidin-2-yl or $(H_3C)_2NCO$—; $Y^1$ is —N= or —CH=; $Y^2$ is —N=, —CH= or —CF=; $R^1$ is hydrogen, fluorine, chlorine or iodine; and $R^2$ is methyl, fluoromethyl, or ethyl.

When the combination of $R^6$ and $R^7$ is a combination of methyl groups, it is preferred that: X is thiazol-2-yl, pyrimidin-2-yl or $(H_3C)_2NCO$—; $Y^1$ is —N= or —CH=; $Y^2$ is —N═, —CH═, —CF═ or —CCl═; $R^1$ is hydrogen, fluorine, chlorine or methyl; and $R^2$ is methyl, fluoromethyl or ethyl.

When the combination of $R^6$ and $R^7$ is a combination of hydrogen and methyl, it is preferred that: X is thiazol-2-yl, pyrimidin-2-yl or $(H_3C)_2NCO$—; $Y^1$ is —N═ or —CH═; $Y^2$ is —N═, —CH═, —CF═ or —CCl═; $R^1$ is hydrogen, fluorine, chlorine, iodine, methyl or cyano; and $R^2$ is methyl, ethyl or fluoromethyl.

When the combination of $R^9$ and $R^{10}$ is a combination of hydrogen and methyl, it is preferred that: X is thiazol-2-yl, pyrimidin-2-yl or $(H_3C)_2NCO$—; $Y^1$ is —N═ or —CH═; $Y^2$ is —CH═ or —CF═; $R^1$ is hydrogen or chlorine; and $R^2$ is methyl.

As preferred examples of the compound represented by general formula (11), preferably general formula (1), or a pharmaceutically acceptable salt thereof, there may be mentioned, for example:

dimethylcarbamic acid 3-{3-(aminosulfonyl)aminobenzyl}-4-methyl-2-oxo-2H-1-benzopyran-7-yl ester, dimethylcarbamic acid 3-{3-(aminosulfonyl)aminobenzyl}-6-fluoro-4-methyl-2-oxo-2H-1-benzopyran-7-yl ester, dimethylcarbamic acid 3-{3-(aminosulfonyl)aminobenzyl}-6-chloro-4-methyl-2-oxo-2H-1-benzopyran-7-yl ester, dimethylcarbamic acid 3-(3-amino sulfonylamino-2-fluoro-benzyl)-4-methyl-2-oxo-2H-1-benzopyran-7-yl ester, dimethylcarbamic acid 3-{2-fluoro-3-(aminosulfonyl)aminobenzyl}-6-fluoro-4-methyl-2-oxo-2H-1-benzopyran-7-yl ester, dimethylcarbamic acid 3-{3-(aminosulfonyl)aminobenzyl}-6-iodo-4-methyl-2-oxo-2H-1-benzopyran-7-yl ester, dimethylcarbamic acid 3-{3-(aminosulfonyl)aminobenzyl}-6-methyl-4-methyl-2-oxo-2H-1-benzopyran-7-yl ester, dimethylcarbamic acid 3-{3-(aminosulfonyl)aminobenzyl}-6-cyano-4-methyl-2-oxo-2H-1-benzopyran-7-yl ester, dimethylcarbamic acid 3-{3-(aminosulfonyl)aminobenzyl}-4-fluoromethyl-2-oxo-2H-1-benzopyran-7-yl ester, dimethylcarbamic acid 3-{3-(aminosulfonyl)aminobenzyl}-6-fluoro-4-fluoromethyl-2-oxo-2H-1-benzopyran-7-yl ester, dimethylcarbamic acid 3-{3-(aminosulfonyl)aminobenzyl}-6-chloro-4-fluoromethyl-2-oxo-2H-1-benzopyran-7-yl ester, dimethylcarbamic acid 3-(3-aminosulfonylamino-2-fluoro-benzyl)-4-fluoromethyl-2-oxo-2H-1-benzopyran-7-yl ester, 3-{2-fluoro-3-(aminosulfonyl)aminobenzyl}-4-methyl-7-(pyrimidin-2-yloxy)-2-oxo-2H-1-benzopyran, 3-{3-(aminosulfonyl)aminobenzyl}-4-methyl-7-(thiazol-2-yloxy)-2-oxo-2H-1-benzopyran, 3-{3-(aminosulfonyl)aminobenzyl}-4-methyl-7-(thiazol-2-yloxy)-6-chloro-2-oxo-2H-1-benzopyran, 3-{2-fluoro-3-(aminosulfonyl)aminobenzyl}-4-methyl-7-(thiazol-2-yloxy)-2-oxo-2H-1-benzopyran, 3-{3-(aminosulfonyl)aminobenzyl}-4-methyl-7-(thiazol-2-yloxy)-6-methyl-2-oxo-2H-1-benzopyran, 3-{2-chloro-3-(aminosulfonyl)aminobenzyl}-4-methyl-7-(thiazol-2-yloxy)-2-oxo-2H-1-benzopyran, dimethylcarbamic acid 4-methyl-3-{3-(methylaminosulfonyl)aminobenzyl}-2-oxo-2H-1-benzopyran-7-yl ester, dimethylcarbamic acid 6-fluoro-4-methyl-3-{3-(methylaminosulfonyl)aminobenzyl}-2-oxo-2H-1-benzopyran-7-yl ester, dimethylcarbamic acid 3-(3-(N-methylsulfamoyl)aminobenzyl)-6-chloro-4-methyl-2-oxo-2H-1-benzopyran-7-yl ester, dimethylcarbamic acid 3-(3-methylaminosulfonylamino-2-fluoro-benzyl)-4-methyl-2-oxo-2H-1-benzopyran-7-yl ester, dimethylcarbamic acid 6-fluoro-4-methyl-3-{3-(methylaminosulfonyl)aminobenzyl}-2-oxo-2H-1-benzopyran-7-yl ester, dimethylcarbamic acid 6-iodo-4-methyl-3-{3-(methylaminosulfonyl)aminobenzyl}-2-oxo-2H-1-benzopyran-7-yl ester, dimethylcarbamic acid 6-methyl-4-methyl-3-{3-(methylaminosulfonyl)aminobenzyl}-2-oxo-2H-1-benzopyran-7-yl ester, dimethylcarbamic acid 6-cyano-4-methyl-3-{3-(methylaminosulfonyl)aminobenzyl}-2-oxo-2H-1-benzopyran-7-yl ester, dimethylcarbamic acid 4-methyl-3-{2-(methylaminosulfonyl)aminopyridin-4-ylmethyl}-2-oxo-2H-1-benzopyran-7-yl ester, dimethylcarbamic acid 4-methyl-3-{2-(methylaminosulfonyl)aminopyridin-4-ylmethyl}-6-fluoro-2-oxo-2H-1-benzopyran-7-yl ester, dimethylcarbamic acid 4-methyl-3-{2-(methylaminosulfonyl)aminopyridin-4-ylmethyl}-6-chloro-2-oxo-2H-1-benzopyran-7-yl ester, dimethylcarbamic acid 4-methyl-3-{6-(methylaminosulfonyl)aminopyridin-2-ylmethyl}-2-oxo-2H-1-benzopyran-7-yl ester, dimethylcarbamic acid 4-methyl-3-{6-(methylaminosulfonyl)aminopyridin-2-ylmethyl}-6-fluoro-2-oxo-2H-1-benzopyran-7-yl ester, dimethylcarbamic acid 4-methyl-3-{6-(methylaminosulfonyl)aminopyridin-2-ylmethyl}-6-chloro-2-oxo-2H-1-benzopyran-7-yl ester, dimethylcarbamic acid 3-(3-methylamino sulfonylamino-2-fluoro-benzyl)-4-fluoromethyl-2-oxo-2H-1-benzopyran-7-yl ester, dimethylcarbamic acid 3-(3-methylaminosulfonylaminobenzyl)-4-fluoromethyl-2-oxo-2H-1-benzopyran-7-yl ester, dimethylcarbamic acid 3-(3-methylaminosulfonylaminobenzyl)-6-fluoro-4-fluoromethyl-2-oxo-2H-1-benzopyran-7-yl ester, dimethylcarbamic acid 6-chloro-4-fluoromethyl-3-{3-(methylaminosulfonyl)aminobenzyl}-2-oxo-2H-1-benzopyran-7-yl ester, dimethylcarbamic acid 3-(3-methylaminosulfonylamino-2-fluoro-benzyl)-4-fluoromethyl-2-oxo-2H-1-benzopyran-7-yl ester, 3-{2-fluoro-3-(methylaminosulfonyl)aminobenzyl}-4-methyl-7-(pyrimidin-2-yloxy)-2-oxo-2H-1-benzopyran, 3-{2-fluoro-3-(methylaminosulfonyl)aminobenzyl}-4-methyl-7-(pyrimidin-2-yloxy)-6-fluoro-2-oxo-2H-1-benzopyran, 3-{2-fluoro-3-(methylaminosulfonyl)aminobenzyl}-4-fluoromethyl-7-(pyrimidin-2-yloxy)-2-oxo-2H-1-benzopyran, 3-{2-(methylaminosulfonyl)aminopyridin-4-ylmethyl}-4-methyl-7-(pyrimidin-2-yloxy)-2-oxo-2H-1-benzopyran, 3-{2-(methylaminosulfonyl)aminopyridin-4-ylmethyl}-4-methyl-7-(pyrimidin-2-yloxy)-6-chloro-2-oxo-2H-1-benzopyran, 3-{3-(methylaminosulfonyl)aminobenzyl}-4-methyl-7-(thiazol-2-yloxy)-2-oxo-2H-1-benzopyran, 3-{3-(methylaminosulfonyl)aminobenzyl}-4-methyl-7-(thiazol-2-yloxy)-6-chloro-2-oxo-2H-1-benzopyran, 3-{2-fluoro-3-(methylaminosulfonyl)aminobenzyl}-4-methyl-7-(thiazol-2-yloxy)-2-oxo-2H-1-benzopyran, 3-{3-(methylaminosulfonyl)aminobenzyl}-4-methyl-7-(thiazol-2-yloxy)-6-methyl-2-oxo-2H-1-benzopyran,
dimethylcarbamic acid 6-chloro-4-methyl-3-{3-(dimethylaminosulfonyl)aminobenzyl}-2-oxo-2H-1-benzopyran-7-yl ester,
3-{2-fluoro-3-(dimethylaminosulfonyl)aminobenzyl}-4-methyl-7-(pyrimidin-2-yloxy)-2-oxo-2H-1-benzopyran,
dimethylcarbamic acid 3-(3-(N-(2-cyanoethyl)sulfamoyl)aminobenzyl)-6-chloro-4-methyl-2-oxo-2H-1-benzopyran-7-yl ester,
dimethylcarbamic acid 3-(3-(N-(2-hydroxyethyl)sulfamoyl)aminobenzyl)-6-chloro-4-methyl-2-oxo-2H-1-benzopyran-7-yl ester,
dimethylcarbamic acid 3-(3-(N-(2-methoxyethyl)sulfamoyl)aminobenzyl)-6-chloro-4-methyl-2-oxo-2H-1-benzopyran-7-yl ester,
dimethylcarbamic acid 3-(3-(N-(2-aminoethyl)sulfamoyl)aminobenzyl)-6-chloro-4-methyl-2-oxo-2H-1-benzopyran-7-yl ester hydrochloride,
dimethylcarbamic acid 3-(3-(N—(N'-methyl-2-aminoethyl)methylsulfamoyl)aminobenzyl)-6-chloro-4-methyl-2-oxo-2H-1-benzopyran-7-yl ester hydrochloride,
dimethylcarbamic acid 3-(3-(N-2,2,2-trifluoroethyl-sulfamoyl)aminobenzyl)-6-chloro-4-methyl-2-oxo-2H-1-benzopyran-7-yl ester,
dimethylcarbamic acid 3-(3-(N-methoxysulfamoyl)aminobenzyl)-6-chloro-4-methyl-2-oxo-2H-1-benzopyran-7-yl ester,
dimethylcarbamic acid 3-(3-carbamoylmethanesulfonylamino-benzyl)-6-chloro-4-methyl-2-oxo-2H-1-benzopyran-7-yl ester,
dimethylcarbamic acid 3-(3-methylcarbamoylmethanesulfonylamino-benzyl)-6-chloro-4-methyl-2-oxo-2H-1-benzopyran-7-yl ester,
2-{2-fluoro-3-[4-methyl-2-oxo-7-(pyrimidin-2-yloxy)-2H-1-benzopyran-3-ylmethyl]phenylsulfamoyl}-N-methylacetamide,
dimethylcarbamic acid 3-(3-dimethylcarbamoylmethanesulfonylamino-benzyl)-6-chloro-4-methyl-2-oxo-2H-1-benzopyran-7-yl ester,
2-{2-fluoro-3-[4-methyl-2-oxo-7-(thiazol-2-yloxy)-2H-1-benzopyran-3-ylmethyl]phenylsulfamoyl}-N-methyl-acetamide,
3-{2-methyl-3-(methylaminosulfonyl)aminobenzyl}-4-methyl-7-(pyrimidin-2-yloxy)-2-oxo-2H-1-benzopyran,
3-{2-(methylaminosulfonyl)amino-3-fluoropyridin-4-ylmethyl}-4-methyl-7-(pyrimidin-2-yloxy)-2-oxo-2H-1-benzopyran,
3-{2-(ethylaminosulfonyl)amino-3-fluoropyridin-4-ylmethyl}-4-methyl-7-(pyrimidin-2-yloxy)-2-oxo-2H-1-benzopyran,
3-{2-(isopropylaminosulfonyl)amino-3-fluoropyridin-4-ylmethyl}-4-methyl-7-(pyrimidin-2-yloxy)-2-oxo-2H-1-benzopyran,
3-{2-(methylaminosulfonyl)amino-3-fluoropyridin-4-ylmethyl}-4-methyl-6-fluoro-7-(pyrimidin-2-yloxy)-2-oxo-2H-1-benzopyran,
3-{2-(cyclopropylaminosulfonyl)amino-3-fluoropyridin-4-ylmethyl}-4-methyl-6-fluoro-7-(pyrimidin-2-yloxy)-2-oxo-2H-1-benzopyran,
3-{2-(methylaminosulfonyl)amino-3-fluoropyridin-4-ylmethyl}-4-methyl-6-chloro-7-(pyrimidin-2-yloxy)-2-oxo-2H-1-benzopyran,
3-{2-(methylaminosulfonyl)amino-3-fluoropyridin-4-ylmethyl}-4-methyl-6-methyl-7-(pyrimidin-2-yloxy)-2-oxo-2H-1-benzopyran,
3-{2-(methyl aminosulfonyl)amino-3-fluoropyridin-4-ylmethyl}-4-ethyl-6-methyl-7-(pyrimidin-2-yloxy)-2-oxo-2H-1-benzopyran,
3-{2-(cyclopropylaminosulfonyl)amino-3-fluoropyridin-4-ylmethyl}-4-methyl-6-methyl-7-(pyrimidin-2-yloxy)-2-oxo-2H-1-benzopyran,
3-{2-(cyclopropylaminosulfonyl)amino-3-fluoropyridin-4-ylmethyl}-4-methyl-7-(pyrimidin-2-yloxy)-2-oxo-2H-1-benzopyran,
3-{2-(methylaminosulfonyl)amino-3-chloropyridin-4-ylmethyl}-4-methyl-7-(pyrimidin-2-yloxy)-2-oxo-2H-1-benzopyran,
3-{2-(methylaminosulfonyl)aminopyridin-4-ylmethyl}-4-methyl-6-chloro-7-(thiazol-2-yloxy)-2-oxo-2H-1-benzopyran,
3-{2-(methylaminosulfonyl)amino-3-fluoropyridin-4-ylmethyl}-4-methyl-6-methyl-7-(thiazol-2-yloxy)-2-oxo-2H-1-benzopyran,
3-{2-(cyclopropylaminosulfonyl)amino-3-fluoropyridin-4-ylmethyl}-4-methyl-6-methyl-7-(thiazol-2-yloxy)-2-oxo-2H-1-benzopyran,
3-{2-(methylaminosulfonyl)aminopyridin-4-ylmethyl}-4-methyl-6-methyl-7-(thiazol-2-yloxy)-2-oxo-2H-1-benzopyran,
3-{2-(methylaminosulfonyl)amino-3-chloropyridin-4-ylmethyl}-4-methyl-6-methyl-7-(thiazol-2-yloxy)-2-oxo-2H-1-benzopyran,
3-{2-fluoro-3-(methylaminosulfonyl)aminobenzyl}-4-methyl-7-(5-fluoropyrimidin-2-yloxy)-2-oxo-2H-1-benzopyran,
3-{2-fluoro-3-(methylaminosulfonyl)aminobenzyl}-4-methyl-7-(4-chloropyrimidin-2-yloxy)-2-oxo-2H-1-benzopyran,
3-{2-fluoro-3-(methylaminosulfonyl)aminobenzyl}-4-methyl-7-(2,4-dimethoxypyrimidin-6-yloxy)-2-oxo-2H-1-benzopyran,
3-{2-fluoro-3-(methylaminosulfonyl)aminobenzyl}-4-methyl-7-(benzothiazol-2-yloxy)-2-oxo-2H-1-benzopyran,
3-{2-fluoro-3-(methylaminosulfonyl)aminobenzyl}-4-methyl-7-(5-bromothiazol-2-yloxy)-2-oxo-2H-1-benzopyran,
3-{2-(methylaminosulfonyl)amino-3-fluoropyridin-4-ylmethyl}-4-methyl-7-(5-fluoropyrimidin-2-yloxy)-2-oxo-2H-1-benzopyran,
3-{2-(methylaminosulfonyl)amino-3-fluoropyridin-4-ylmethyl}-4-methyl-7-(4-chloropyrimidin-2-yloxy)-2-oxo-2H-1-benzopyran,
3-{2-(methylaminosulfonyl)amino-3-fluoropyridin-4-ylmethyl}-4-methyl-7-(2,4-dimethoxypyrimidin-6-yloxy)-2-oxo-2H-1-benzopyran,
3-{2-(methylaminosulfonyl)amino-3-fluoropyridin-4-ylmethyl}-4-methyl-7-(benzothiazol-2-yloxy)-2-oxo-2H-1-benzopyran,
3-{2-(methylamino sulfonyl)amino-3-fluoropyridin-4-ylmethyl}-4-methyl-7-(5-bromothiazol-2-yloxy)-2-oxo-2H-1-benzopyran,
3-{2-(methylaminosulfonyl)amino-3-fluoropyridin-4-ylmethyl}-4-methyl-7-(pyrazin-2-yloxy)-2-oxo-2H-1-benzopyran, and
3-{2-(methylaminosulfonyl)amino-3-fluoropyridin-4-ylmethyl}-4-methyl-7-(pyridin-2-yloxy)-2-oxo-2H-1-benzopyran.

Preferred from the viewpoint of antitumor activity are compounds of general formula (1) wherein: X is a thiazol-2-yl group, a pyrimidin-2-yl group or $(H_3C)_2NCO-$; $Y^1$ is $-CH=$ or $-N=$; $Y^2$ is $-CH=$, $-CF=$ or $-CCl=$; $Y^3$ and $Y^4$ are $-CH=$; A is $-NHSO_2NR^{60}R^{70}$ or —NHSO$_2$CH$_2$CONCH$_3$R$^{90}$ (where R$^{60}$ and R$^{90}$ are each independently a hydrogen atom or a methyl group, and R$^{70}$ is a hydrogen atom, a methyl group, or an ethyl group (where the ethyl group may optionally be substituted with a substituent selected from methoxy and cyano)); R$^1$ is a hydrogen atom, a fluorine atom, a chlorine atom, an iodine atom, a methyl group or a cyano group; and R$^2$ is —CH$_3$, —CH$_2$F or —CH$_2$CH$_3$.

As examples preferred from the viewpoint of antitumor activity, there may be mentioned, for example:

dimethylcarbamic acid 3-(3-aminosulfonylamino-2-fluorobenzyl)-4-methyl-2-oxo-2H-1-benzopyran-7-yl ester, dimethylcarbamic acid 3-{2-fluoro-3-(aminosulfonyl)aminobenzyl}-6-fluoro-4-methyl-2-oxo-2H-1-benzopyran-7-yl ester, dimethylcarbamic acid 3-{3-(aminosulfonyl)aminobenzyl}-6-iodo-4-methyl-2-oxo-2H-1-benzopyran-7-yl ester, 3-{2-fluoro-3-(aminosulfonyl)aminobenzyl}-4-methyl-7-(thiazol-2-yloxy)-2-oxo-2H-1-benzopyran, dimethylcarbamic acid 6-fluoro-4-methyl-3-{2-fluoro-3-(methylaminosulfonyl)aminobenzyl}-2-oxo-2H-1-benzopyran-7-yl ester, dimethylcarbamic acid 3-(3-(N-methylsulfamoyl)aminobenzyl)-6-chloro-4-methyl-2-oxo-2H-1-benzopyran-7-yl ester, dimethylcarbamic acid 3-(3-methylaminosulfonylamino-2-fluoro-benzyl)-4-methyl-2-oxo-2H-1-benzopyran-7-yl ester, dimethylcarbamic acid 6-iodo-4-methyl-3-{3-(methylaminosulfonyl)aminobenzyl}-2-oxo-2H-1-benzopyran-7-yl ester, dimethylcarbamic acid 6-methyl-4-methyl-3-{3-(methylaminosulfonyl)aminobenzyl}-2-oxo-2H-1-benzopyran-7-yl ester, dimethylcarbamic acid 6-cyano-4-methyl-3-{3-(methylaminosulfonyl)aminobenzyl}-2-oxo-2H-1-benzopyran-7-yl ester, dimethylcarbamic acid 4-methyl-3-{2-(methylaminosulfonyl)aminopyridin-4-ylmethyl}-2-oxo-2H-1-benzopyran-7-yl ester, dimethylcarbamic acid 4-methyl-3-{2-(methylaminosulfonyl)aminopyridin-4-ylmethyl}-6-fluoro-2-oxo-2H-1-benzopyran-7-yl ester, dimethylcarbamic acid 4-methyl-3-{2-(methylaminosulfonyl)aminopyridin-4-ylmethyl}-6-chloro-2-oxo-2H-1-benzopyran-7-yl ester, dimethylcarbamic acid 3-(3-methylaminosulfonylamino-2-fluoro-benzyl)-4-fluoromethyl-2-oxo-2H-1-benzopyran-7-yl ester, dimethylcarbamic acid 6-chloro-4-fluoromethyl-3-{3-(methylaminosulfonyl)aminobenzyl}-2-oxo-2H-1-benzopyran-7-yl ester, 3-{2-(methylamino sulfonyl)amino-3-fluoropyridin-4-ylmethyl}-4-methyl-6-fluoro-7-(pyrimidin-2-yloxy)-2-oxo-2H-1-benzopyran, 3-{2-(methylaminosulfonyl)amino-3-fluoropyridin-4-ylmethyl}-4-methyl-6-chloro-7-(pyrimidin-2-yloxy)-2-oxo-2H-1-benzopyran, 3-{2-(methylaminosulfonyl)amino-3-fluoropyridin-4-ylmethyl}-4-methyl-6-methyl-7-(pyrimidin-2-yloxy)-2-oxo-2H-1-benzopyran, 3-{2-(methylaminosulfonyl)amino-3-fluoropyridin-4-ylmethyl}-4-ethyl-6-methyl-7-(pyrimidin-2-yloxy)-2-oxo-2H-1-benzopyran, 3-{2-fluoro-3-(methylaminosulfonyl)aminobenzyl}-4-methyl-7-(thiazol-2-yloxy)-2-oxo-2H-1-benzopyran, 3-{2-(methylaminosulfonyl)aminopyridin-4-ylmethyl}-4-methyl-6-chloro-7-(thiazol-2-yloxy)-2-oxo-2H-1-benzopyran, 3-{2-(methylaminosulfonyl)amino-3-fluoropyridin-4-ylmethyl}-4-methyl-6-methyl-7-(thiazol-2-yloxy)-2-oxo-2H-1-benzopyran, 3-{2-(methylaminosulfonyl)aminopyridin-4-ylmethyl}-4-methyl-6-methyl-7-(thiazol-2-yloxy)-2-oxo-2H-1-benzopyran, 3-{2-(methylaminosulfonyl)amino-3-chloropyridin-4-ylmethyl}-4-methyl-6-methyl-7-(thiazol-2-yloxy)-2-oxo-2H-1-benzopyran, dimethylcarbamic acid 6-chloro-4-methyl-3-{3-(dimethylaminosulfonyl)aminobenzyl}-2-oxo-2H-1-benzopyran-7-yl ester, dimethylcarbamic acid 3-(3-(N-(2-cyanoethyl)sulfamoyl)aminobenzyl)-6-chloro-4-methyl-2-oxo-2H-1-benzopyran-7-yl ester, dimethylcarbamic acid 3-(3-(N-(2-methoxyethyl)sulfamoyl)aminobenzyl)-6-chloro-4-methyl-2-oxo-2H-1-benzopyran-7-yl ester, dimethylcarbamic acid 3-(3-methylcarbamoylmethanesulfonylamino-benzyl)-6-chloro-4-methyl-2-oxo-2H-1-benzopyran-7-yl ester, and dimethylcarbamic acid 3-(3-dimethylcarbamoylmethanesulfonylamino-benzyl)-6-chloro-4-methyl-2-oxo-2H-1-benzopyran-7-yl ester.

Preferred from the viewpoint of systemic exposure are compounds of general formula (1) wherein: X is a thiazol-2-yl group or a pyrimidin-2-yl group; Y$^1$ is —CH= or —N=; Y$^2$ is —CH= or —CF=; Y$^3$ and Y$^4$ are —CH=; A is —NHSO$_2$NHR$^{60}$ or —NHSO$_2$CH$_2$CONHCH$_3$ (where R$^{60}$ is a hydrogen atom or a methyl group); R$^1$ is a hydrogen atom, a fluorine atom or a methyl group; and R$^2$ is —CH$_3$ or —CH$_2$F.

As examples preferred from the viewpoint of systemic exposure, there may be mentioned, for example:

3-{2-fluoro-3-(aminosulfonyl)aminobenzyl}-4-methyl-7-(pyrimidin-2-yloxy)-2-oxo-2H-1-benzopyran, dimethylcarbamic acid 4-methyl-3-{6-(methylaminosulfonyl)aminopyridin-2-ylmethyl}-2-oxo-2H-1-benzopyran-7-yl ester, 3-{2-fluoro-3-(methylaminosulfonyl)aminobenzyl}-4-methyl-7-(pyrimidin-2-yloxy)-2-oxo-2H-1-benzopyran, 3-{2-fluoro-3-(methylaminosulfonyl)aminobenzyl}-4-methyl-7-(pyrimidin-2-yloxy)-6-fluoro-2-oxo-2H-1-benzopyran, 3-{2-fluoro-3-(methylaminosulfonyl)aminobenzyl}-4-fluoromethyl-7-(pyrimidin-2-yloxy)-2-oxo-2H-1-benzopyran, 3-{2-(methylaminosulfonyl)aminopyridin-4-ylmethyl}-4-methyl-7-(pyrimidin-2-yloxy)-6-chloro-2-oxo-2H-1-benzopyran, 3-{2-(methylaminosulfonyl)amino-3-fluoropyridin-4-ylmethyl}-4-methyl-7-(pyrimidin-2-yloxy)-2-oxo-2H-1-benzopyran, 3-{3-(methylaminosulfonyl)aminobenzyl}-4-methyl-7-(thiazol-2-yloxy)-2-oxo-2H-1-benzopyran, 3-{3-(methylaminosulfonyl)aminobenzyl}-4-methyl-7-(thiazol-2-yloxy)-6-methyl-2-oxo-2H-1-benzopyran, and 2-{2-fluoro-3-[4-methyl-2-oxo-7-(thiazol-2-yloxy)-2H-1-benzopyran-3-ylmethyl]phenylsulfamoyl}-N-methyl-acetamide.

There also exist compounds, other than the compound represented by general formula (11), which, like the compound represented by general formula (11), have sufficiently high antitumor activity, and are useful as therapeutic agents for cell proliferative disorders, particularly cancers.

As examples of such compounds, there may be mentioned compounds having a structure similar to the compound of general formula (11), except that in place of the partial structure:

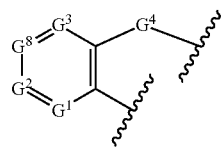

they have a structure below:

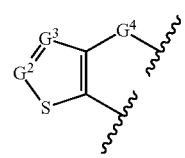
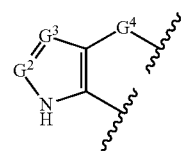
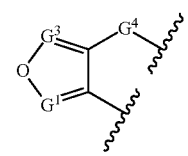
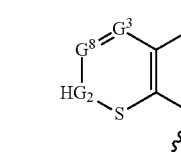
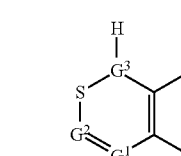
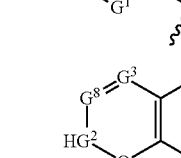
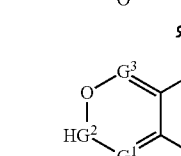
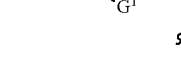

There may also be mentioned compounds having a structure similar to the compound of general formula (11), except that in place of the partial structure:

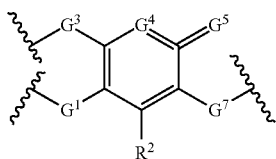

they have a structure below:

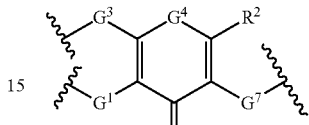
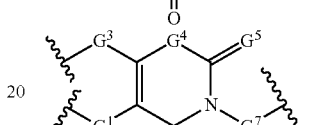
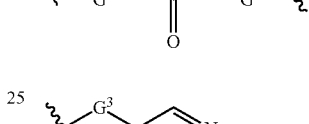
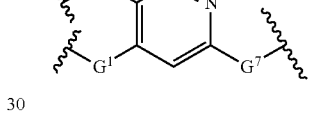
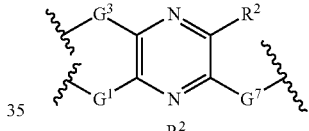
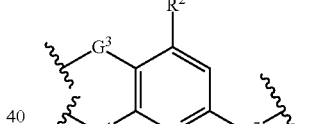
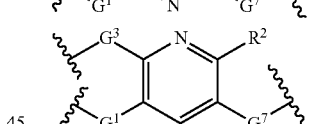
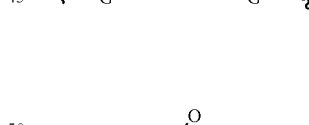
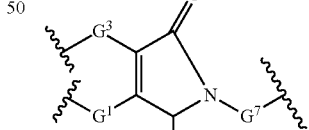
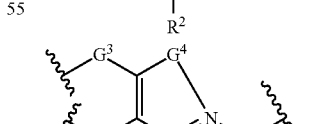
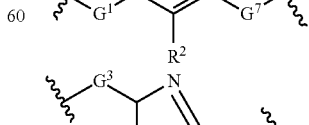
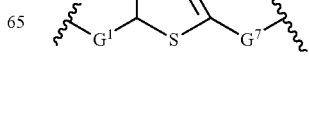

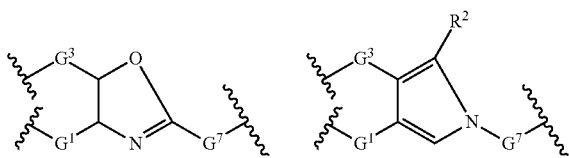
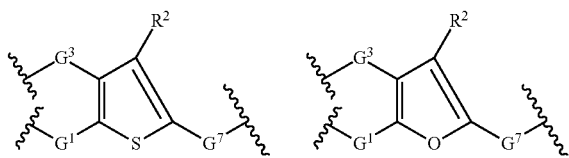
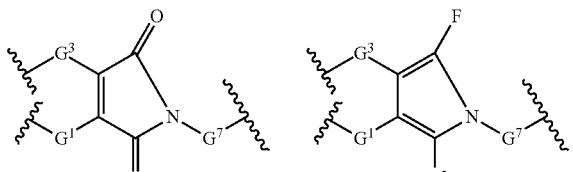
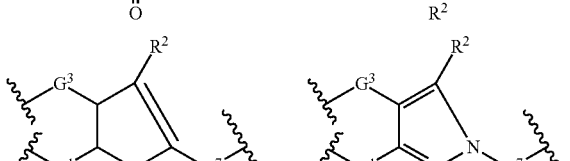
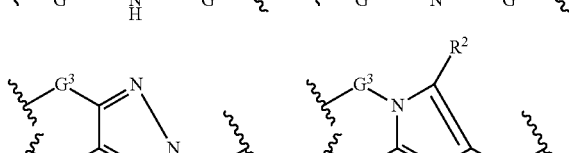
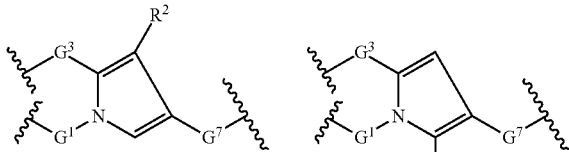
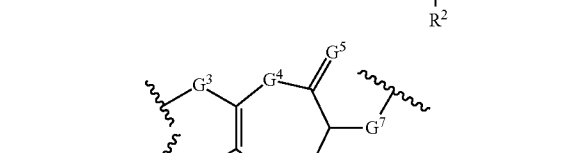
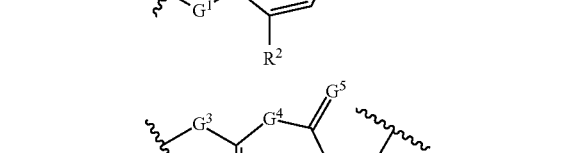

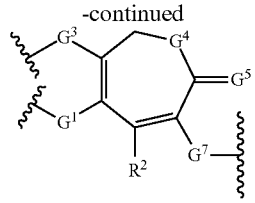

There may further be mentioned compounds having a structure similar to the compound of general formula (11), except that in place of the partial structure:

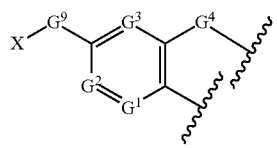

they have a structure below:

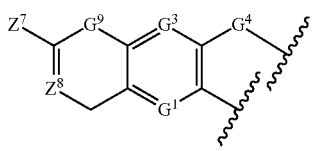

[where the combinations of $G^9$, $Z^7$, $Z^8$, $G^1$ and $G^3$ are as listed in the table below.]

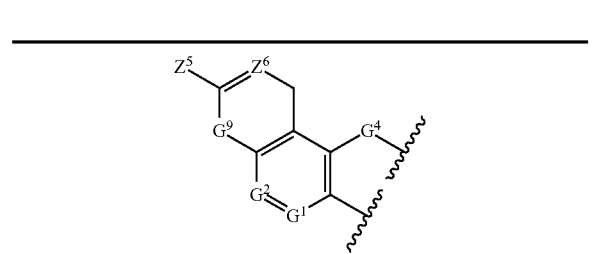

| $G^9$ | $Z^7$ | $Z^8$ | $G^1$ | $G^3$ |
|---|---|---|---|---|
| O | N(CH$_3$)$_2$ | N | CH | CH |
| S | N(CH$_3$)$_2$ | N | CH | CH |
| NH | N(CH$_3$)$_2$ | N | CH | CH |
| O | N(CH$_3$)$_2$ | CH | CH | CH |

[where the combinations of $G^9$, $Z^5$, $Z^6$, $G^1$ and $G^2$ are as listed in the table below.]

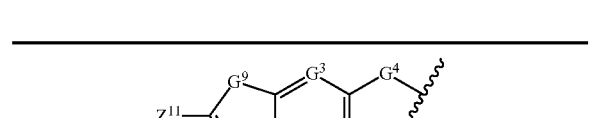

| $G^9$ | $Z^5$ | $Z^6$ | $G^1$ | $G^2$ |
|---|---|---|---|---|
| O | N(CH$_3$)$_2$ | N | CH | CCH$_3$ |
| S | N(CH$_3$)$_2$ | N | CH | CH |
| NH | N(CH$_3$)$_2$ | N | CH | CF |

-continued

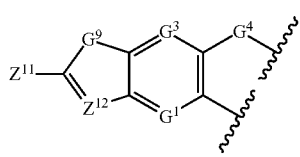

| $G^9$ | $Z^5$ | $Z^6$ | $G^1$ | $G^2$ |
|---|---|---|---|---|
| O | N(CH$_3$)$_2$ | CH | CH | CH |
| O | N(CH$_3$)$_2$ | N | CH | N |
| S | N(CH$_3$)$_2$ | N | N | CH |

[where the combinations of $G^9$, $Z^{11}$, $Z^{12}$, $G^1$ and $G^3$ are as listed in the table below.]

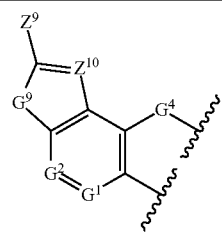

| $G^9$ | $Z^{11}$ | $Z^{12}$ | $G^1$ | $G^3$ |
|---|---|---|---|---|
| O | N(CH$_3$)$_2$ | N | CH | CH |
| S | N(CH$_3$)$_2$ | N | CH | CH |
| O | N(CH$_3$)$_2$ | CH | CH | CH |
| NH | N(CH$_3$)$_2$ | N | CH | CH |

[where the combinations of $G^9$, $Z^9$, $Z^{10}$, $G^1$ and $G^2$ are as listed in the table below.]

| $G^9$ | $Z^9$ | $Z^{10}$ | $G^1$ | $G^2$ |
|---|---|---|---|---|
| O | N(CH$_3$)$_2$ | N | CH | CH |
| S | N(CH$_3$)$_2$ | N | CH | CH |
| O | N(CH$_3$)$_2$ | CH | CH | CH |
| NH | N(CH$_3$)$_2$ | N | CH | CH |

A may be selected from groups represented by general formulas (2) and (3) above, as well as from groups represented by the following formulas:

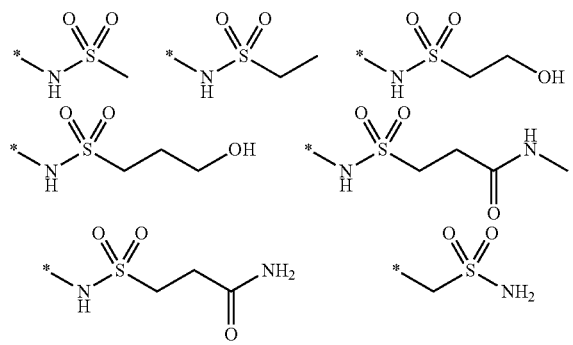

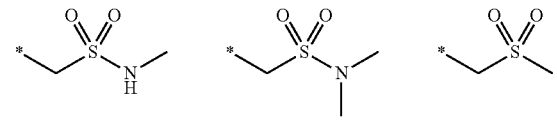
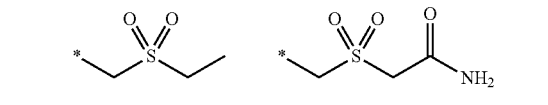
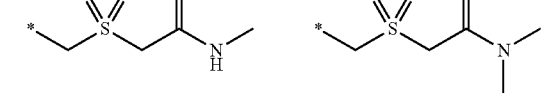
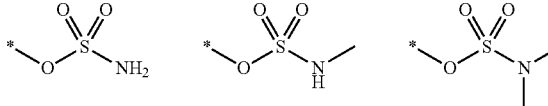
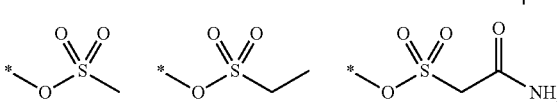
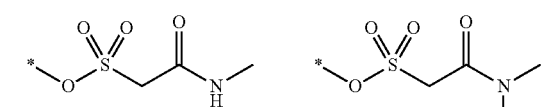
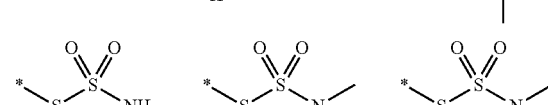
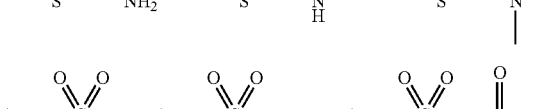
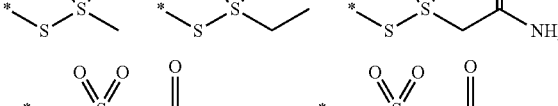

[where * represents the position at which $G^6$ is bonded.]

When A is a group represented by general formula (2), $R^7$ may form a ring together with atoms of ring $G^6$. As specific examples of partial structures formed in such cases, there may be mentioned partial structures represented by the following formulas:

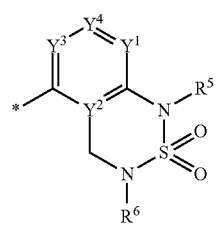
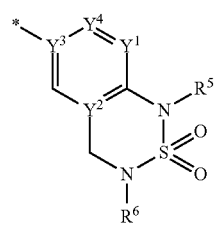

31
-continued
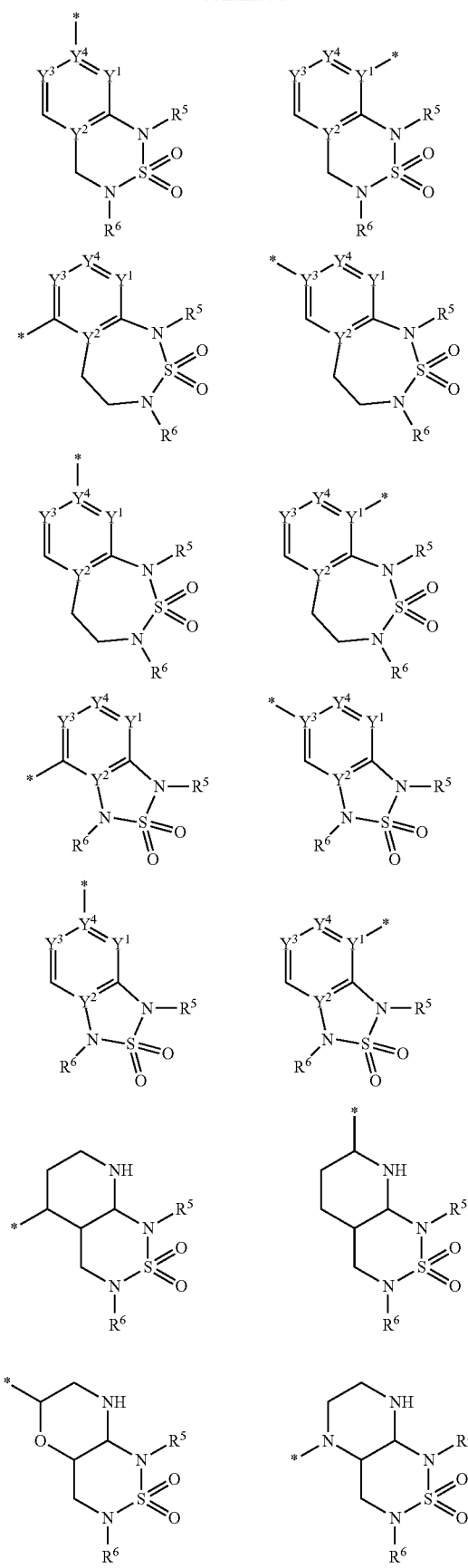
32
-continued
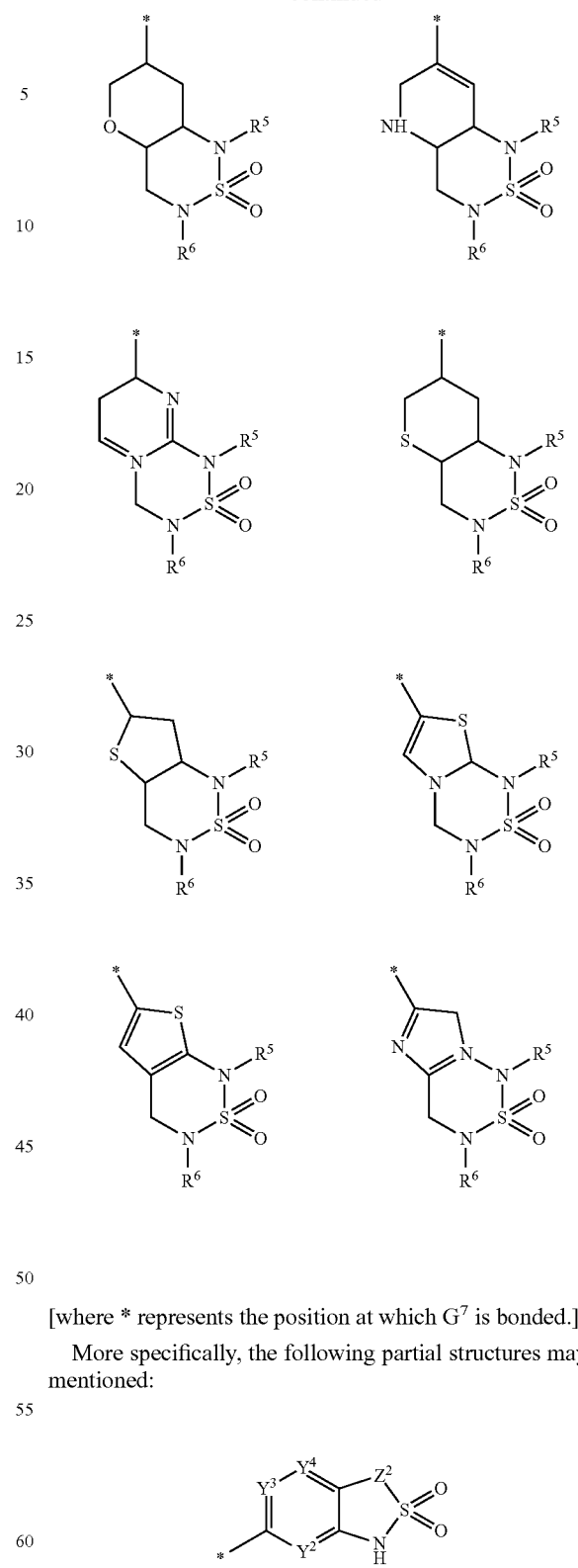
[where * represents the position at which $G^7$ is bonded.]
More specifically, the following partial structures may be mentioned:
[where * represents the position at which $G^7$ is bonded, and the combinations of $Y^1$, $Y^3$, $Y^4$ and $Z^2$ are as listed in the table below.]

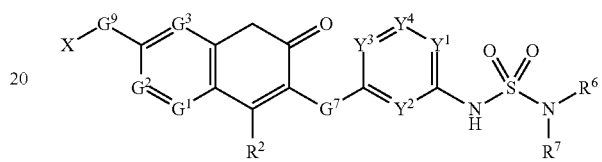

| Y¹ | Y³ | Y⁴ | Z² |
|---|---|---|---|
| CH | CH | CH | NH |
| CF | CH | CH | NCH₃ |
| CH | CH | CH | CH₂ |
| CF | CH | CH | N(CH₃)CH₂ |
| CH | CH | CH | N(CH₃)CH₂CH₂ |
| CH | CH | CH | CH₂CH₂ |
| CH | CH | CH | CH₂CH₂CH₂ |
| CF | CH | CH | NH |
| CH | CH | N | NCH₃ |

[where * represents the position at which $G^7$ is bonded, and the combinations of $Y^1$, $Y^3$, $Y^4$ and $Z^1$ are as listed in the table below.]

| Y¹ | Y³ | Y⁴ | Z¹ |
|---|---|---|---|
| CH | CH | CH | NH |
| N | CH | CH | NCH₃ |
| CH | CH | CH | CH₂ |
| N | CH | CH | N(CH₃)CH₂ |
| CH | CH | CH | N(CH₃)CH₂CH₂ |
| CH | CH | CH | CH₂CH₂ |
| CH | CH | CH | CH₂CH₂CH₂ |
| N | CH | CH | NH |
| N | CH | N | NCH₃ |

As specific examples of the compound represented by general formula (11), there may be mentioned compounds represented by the following formulas:

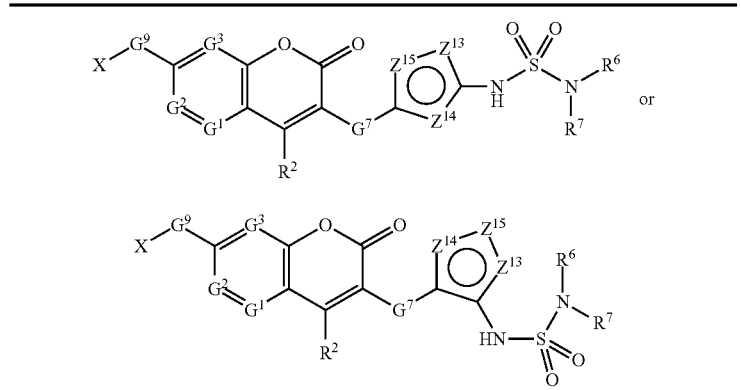

[where the combinations of $G^9$, $Y^1$, $Y^2$, $Y^3$, $Y^4$, $G^1$, $G^2$, $G^3$, $NR^6R^7$, $G^7$, and $R^2$ are as listed in the table below.]

| X | G⁹ | Y¹ | Y² | Y³ | Y⁴ | G¹ | G² | G³ | NR⁶R⁷ | G⁷ | R² |
|---|---|---|---|---|---|---|---|---|---|---|---|
| (CH₃)₂NCO | O | N | CF | CH | CH | CH | N | CH | N(CH₃)₂ | CH₂ | CH₃ |
| (CH₃)₂NCO | O | CH | CF | CH | CH | N | CH | CH | NH₂ | CH₂ | CH₃ |
| 2-N-Methyl imidazolyl | O | CH | CF | CH | CH | CH | N | CH | NH₂ | CH₂ | CH₃ |
| (CH₃)₂NCO | O | CH | CF | N | CH | CH | CH | CH | NHCH₃ | CH₂ | CH₃ |
| (CH₃)₂NCO | O | CH | CF | CH | N | CH | CH | CH | NHCH₃ | CH₂ | CH₃ |
| (CH₃)₂NCO | O | N | N | CH | CH | CH | CH | CH | NHCH₃ | CH₂ | CH₃ |
| (CH₃)₂NCO | O | CH | CF | CH | CH | N | CH | CH | NHCH₃ | CH₂ | CH₃ |
| (CH₃)₂NCO | O | CH | CF | CH | CH | CH | N | CH | NHCH₃ | CH₂ | CH₃ |
| (CH₃)₂NCO | O | N | CF | CH | CH | N | CH | CH | NHCH₃ | CH₂ | CH₃ |
| (CH₃)₂NCO | NH | N | CF | CH | CH | CH | CH | CH | NHCH₃ | CH₂ | CH₃ |
| 2-Pyrimidinyl | O | CH | CH | N | N | CH | CCH₃ | CH | NHCH₃ | CH₂ | CH₃ |
| 2-Pyrimidinyl | O | N | CF | CH | CH | N | CH | CH | NHCH₃ | CH₂ | CH₂CH₃ |
| 2-Pyrimidinyl | O | CH | CF | CH | CH | CH | N | CH | NHCH₃ | CH₂ | CH₃ |
| 2-Pyrimidinyl | O | N | N | CH | CH | CH | N | CH | NHCH₃ | CH₂ | CH₂F |
| 2-Pyrimidinyl | CH₂ | CH | CF | CH | CH | CH | CH | CH | NHCH₃ | CH₂ | CH₃ |
| 2-Thiazolyl | O | N | CF | CH | CH | CH | N | CH | NHCH₃ | CH₂ | CH₃ |
| 2-Thiazolyl | O | CH | CF | CH | CH | CH | CH | N | NHCH₃ | CH₂ | CH₃ |
| 2-Thiazolyl | O | CH | CH | N | CH | CH | CF | CH | NHCH₃ | CH₂ | CH₃ |
| 2-Thiazolyl | O | N | CF | CH | CH | CH | CH | CH | NHCH₃ | SO | CH₃ |
| 2-Thiazolyl | CF₂ | N | CF | CH | CH | N | CH | CH | NHCH₃ | SO | CH₃ |
| 2-N-Methyl imidazolyl | O | CH | CF | CH | CH | CH | CH | CH | NHCH₃ | CH₂ | CH₃ |

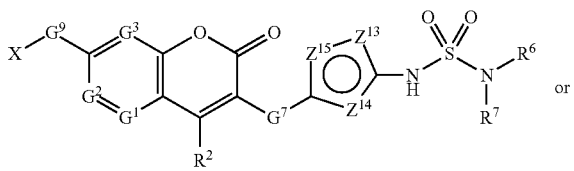

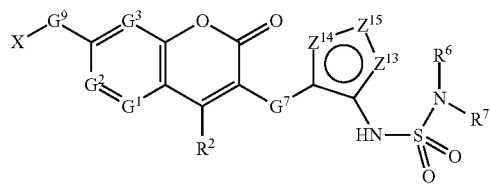

| X | G$^9$ | Y$^1$ | Y$^2$ | Y$^3$ | Y$^4$ | G$^1$ | G$^2$ | G$^3$ | NR$^6$R$^7$ | G$^7$ | R$^2$ |
|---|---|---|---|---|---|---|---|---|---|---|---|
| 2-N-Methyl imidazolyl | O | N | CF | CH | CH | CH | CH | CH | NHCH$_3$ | CH$_2$ | CH$_3$ |
| 2-N-Methyl imidazolyl | O | CH | CF | CH | CH | CH | CCH$_3$ | CH | NHCH$_3$ | CH$_2$ | CH$_3$ |
| 2-N-Methyl imidazolyl | O | CH | CF | CH | CH | CH | Cl | CH | NHCH$_3$ | CH$_2$ | CH$_3$ |

[where the combinations of G$^9$, Z$^{13}$, Z$^{14}$, Z$^{15}$, G$^1$, G$^2$, G$^3$, NR$^6$R$^7$, G$^7$ and R$^2$ are as listed in the table below.]

| X | G$^9$ | Z$^{13}$ | Z$^{14}$ | Z$^{15}$ | G$^1$ | G$^2$ | G$^3$ | NR$^6$R$^7$ | G$^7$ | R$^2$ |
|---|---|---|---|---|---|---|---|---|---|---|
| (CH$_3$)$_2$NCO | O | S | CH | CH | CH | CH | CH | NHCH$_3$ | CH$_2$ | CH$_3$ |
| (CH$_3$)$_2$NCO | O | CH | S | CH | CH | CH | CH | NHCH$_3$ | CH$_2$ | CH$_3$ |
| (CH$_3$)$_2$NCO | O | CH | CH | S | CH | CH | CH | NHCH$_3$ | CH$_2$ | CH$_3$ |
| (CH$_3$)$_2$NCO | O | NH | CH | CH | CH | CH | CH | NHCH$_3$ | CH$_2$ | CH$_3$ |
| (CH$_3$)$_2$NCO | O | CH | NH | CH | CH | CH | CH | NHCH$_3$ | CH$_2$ | CH$_3$ |
| (CH$_3$)$_2$NCO | O | CH | CH | NH | CH | CH | CH | NHCH$_3$ | CH$_2$ | CH$_3$ |
| (CH$_3$)$_2$NCO | O | O | CH | CH | CH | CH | CH | NHCH$_3$ | CH$_2$ | CH$_3$ |
| (CH$_3$)$_2$NCO | O | CH | O | CH | CH | CH | CH | NHCH$_3$ | CH$_2$ | CH$_3$ |
| (CH$_3$)$_2$NCO | O | CH | CH | O | CH | CH | CH | NHCH$_3$ | CH$_2$ | CH$_3$ |
| (CH$_3$)$_2$NCO | O | S | NH | CH | CH | CH | CH | NHCH$_3$ | CH$_2$ | CH$_3$ |
| (CH$_3$)$_2$NCO | O | N | CH | NH | CH | CH | CH | NHCH$_3$ | CH$_2$ | CH$_3$ |
| (CH$_3$)$_2$NCO | S | S | CH | CH | CH | CH | CH | NHCH$_3$ | CH$_2$ | CH$_3$ |
| (CH$_3$)$_2$NCO | CH$_2$ | S | CH | CH | CH | N | CH | NHCH$_3$ | S | CH$_3$ |
| (CH$_3$)$_2$NCO | CF$_2$ | CH | S | CH | CH | N | CH | NHCH$_3$ | SO | CH$_3$ |
| 2-Pyrimidinyl | O | S | CH | CH | CH | CH | CH | NHCH$_3$ | CH$_2$ | CH$_3$ |
| 2-Pyrimidinyl | O | CH | S | CH | CH | CH | CH | NHCH$_3$ | CH$_2$ | CH$_3$ |
| 2-Pyrimidinyl | O | CH | CH | S | CH | CH | CH | NHCH$_3$ | CH$_2$ | CH$_3$ |
| 2-Pyrimidinyl | O | S | CH | CH | CH | N | CH | NHCH$_3$ | CH$_2$ | CH$_3$ |
| 2-Pyrimidinyl | O | CH | S | CH | CH | CCH$_3$ | CH | NHCH$_3$ | CH$_2$ | CH$_3$ |
| 2-Pyrimidinyl | O | CH | CH | S | N | CH | CH | NHCH$_3$ | CH$_2$ | CH$_3$ |
| 2-Pyrimidinyl | O | S | CH | CH | CH | CH | CH | NHCH$_3$ | O | CH$_3$ |
| 2-Pyrimidinyl | O | CH | S | CH | CH | CH | CH | NHCH$_3$ | S | CH$_3$ |
| 2-Pyrimidinyl | O | CH | CH | S | CH | CH | CH | NHCH$_3$ | NH | CH$_3$ |
| 2-Thiazolyl | O | S | CH | CH | CH | CH | CH | NHCH$_3$ | CH$_2$ | CH$_3$ |
| 2-Thiazolyl | O | CH | S | CH | CH | CH | CH | NHCH$_3$ | CH$_2$ | CH$_3$ |
| 2-Thiazolyl | O | CH | CH | S | CH | CH | CH | NHCH$_3$ | CH$_2$ | CH$_3$ |
| 2-N-Methyl imidazolyl | O | S | CH | CH | CH | CH | CH | NHCH$_3$ | CH$_2$ | CH$_3$ |
| 2-N-Methyl imidazolyl | O | CH | CH | S | CH | CCH$_3$ | CH | NHCH$_3$ | CH$_2$ | CH$_3$ |
| 2-N-Methyl imidazolyl | O | N | S | CH | CH | CCH$_3$ | CH | NHCH$_3$ | S | CH$_3$ |

Examples of manufacturing processes for the compound or salt according to the present invention will now be explained. In each of the manufacturing processes explained hereafter, the order of steps may be changed as may be necessary. Furthermore, when a reactant in a certain step is subjected to an undesired chemical conversion under reaction conditions for the step, the manufacturing process may be carried out by, for example, performing protection and deprotection of a functional group. For selection of a protecting group and a method of protection and deprotection, there may be referred to, for example, T. W. Greene, P. G. M. Wuts, Protective Groups in Organic Synthesis, Second Edition, John Wiley and Sons, Inc., New York, 1991.

X, Y$^1$, Y$^2$, Y$^3$, Y$^4$, R$^1$, R$^5$, R$^6$, R$^7$, R$^8$, R$^9$ and R$^{10}$ have the same meanings as mentioned above, while Hal represents a halogen atom; R$^a$ represents a C$_{1-6}$ alkyl group (the C$_{1-6}$ alkyl group may be substituted with a substituent selected from the group consisting of a fluorine atom, an optionally protected hydroxy group, an optionally protected oxo group, and an optionally protected carboxy group); $R^b$ represents a leaving group, such as a halogen atom or 2-oxazolidinon-3-yl group; $R^c$ represents a protecting group for the carboxy group, such as a $C_{1-4}$ alkyl group; $R^d$ and $R^e$ are the same or different, and each independently or together represent a protecting group for the amino group; $R^f$ represents a $C_{1-4}$ alkyl group; $R^g$ represents a hydroxy group or halogen atom; $R^h$ represents a methyl group or $R^cOCO$—; $R^i$ represents a hydrogen atom or $C_{1-5}$ alkyl group; and B represents a nitro group or —$NR^dR^e$.

(General Process-1)

General process-1 is an example of a particularly preferred manufacturing process for a compound of general formula (1) wherein $R^2$ is $R^a$, and $Y^1$ and $Y^2$ are the same or different, and are each —$CR^{11}$=.

[Chemical Formula 4]

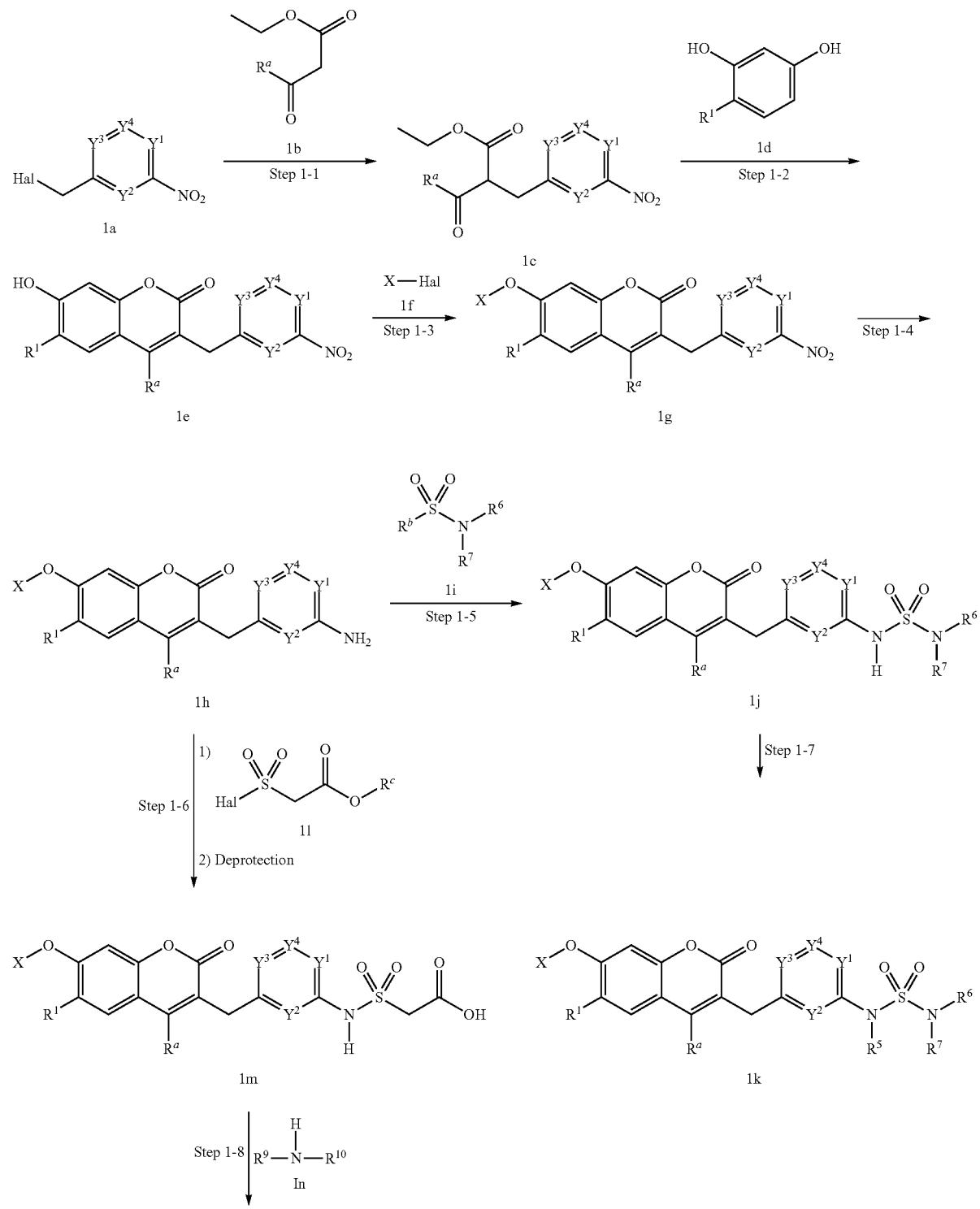

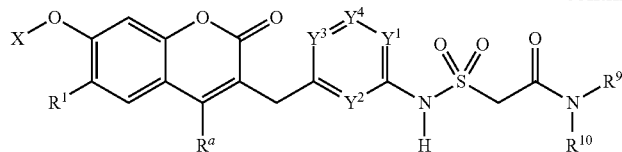

1o

Step 1-9 ↓

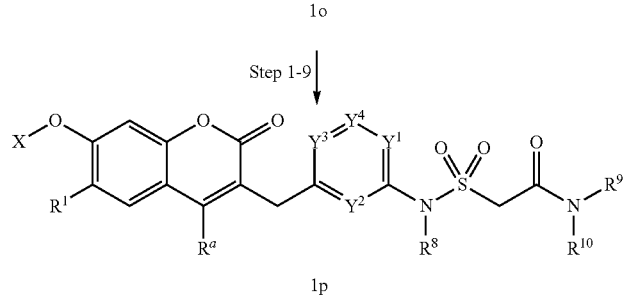

1p

Step 1-1

Compound 1c can be obtained by condensation between a deprotonated form of compound 1b, which is obtained by reaction of compound 1b with a base, and compound 1a.

As for the base, there may be mentioned, for example, sodium hydride, potassium hydride, lithium hexamethyldisilazide (also referred to as "LiHMDS" herein) and the like, among which sodium hydride and the like are preferred.

As for the reaction solvent, there may be mentioned: ether solvents such as tetrahydrofuran (also referred to as "THF" herein) and diethylether; and chlorine solvents such as methylene chloride, among which THF is preferred.

The reaction temperature may be appropriately determined depending on the type of reaction solvent and the like, while for the reaction between compound 1b and a base, it is generally −20° C. to 25° C., preferably 0° C. to 10° C., and for the condensation between the deprotonated form and compound 1a, it is generally 0° C. to 60° C., preferably 15° C. to 35° C.

The reaction time may be appropriately determined depending on the reaction temperature and the like, while for the reaction between compound 1b and a base, it is generally 10 minutes to 3 hours, preferably 20 minutes to 1 hour, and for the condensation between the deprotonated form and compound 1a, it is generally 2 hours to 20 hours, preferably 5 hours to 15 hours.

As for the method for subjecting the deprotonated form and compound 1a to the reaction, it is preferred to add dropwise a solution containing the deprotonated form to a solution containing compound 1a.

Step 1-2

Compound 1e can be obtained by reaction between compound 1c and compound 1d in the presence of acid.

As for the acid, there may be mentioned: Lewis acids such as zirconium chloride, samarium(II) chloride and aluminum chloride; inorganic acids such as sulfuric acid; and acidic resins such as zeolite, among which sulfuric acid is preferred.

As for the reaction solvent, solvents inactive for the reaction may be used, while solvent-free conditions are preferred. When sulfuric acid is used, the number of equivalents is generally 1 to 5, preferably 1 to 3, relative to compound 1d.

The reaction temperature is generally −20° C. to 50° C., preferably −10° C. to 30° C.

The reaction time may be appropriately determined depending on the reaction temperature and the like, while it is generally 2 hours to 20 hours, preferably 5 hours to 16 hours.

Step 1-3

Compound 1g can be obtained by reaction between compound 1e and compound 1f in the presence of base.

As for the base, there may be mentioned, for example: weakly basic inorganic salts such as sodium carbonate, potassium carbonate and cesium carbonate; and metal hydrides such as sodium hydride and potassium hydride, among which potassium carbonate, cesium carbonate and sodium hydride are preferred.

As for the reaction solvent, there may be mentioned: ether solvents such as tetrahydrofuran and diethylether; and N,N-dimethylformamide and the like, among which tetrahydrofuran and N,N-dimethylformamide are preferred.

The reaction temperature may be appropriately determined depending on the type of reaction solvent and the like, while for cases where X is an electron-deficient heteroaryl group such as a pyridyl or pyrimidinyl group, it is generally 60° C. to 150° C., preferably 70° C. to 100° C.; for cases where X is an electron-rich heteroaryl group such as a thiazolyl group, it is generally 90° C. to 200° C., preferably 100° C. to 120° C.; and for cases where X is a group represented by $R^3R^4NCO—$, it is generally 0° C. to 50° C., preferably 0° C. to 30° C.

The reaction time may be appropriately determined depending on the reaction temperature and the like, while it is generally 30 minutes to 5 hours, preferably 40 minutes to 2 hours.

Furthermore, when X is an electron-rich heteroaryl group such as a thiazolyl group, it is preferred to perform the reaction while irradiating microwave in the coexistence of a monovalent copper salt such as copper(I) iodide, $CuPF_6$ or Cu(I)OTf (copper(I) trifluoromethanesulfonate), preferably copper(I) iodide or the like.

Step 1-4

Compound 1h can be obtained by reduction of compound 1g.

As for the reducing agent, there may be mentioned tin(II) chloride, zinc and the like, among which tin(II) chloride is preferred.

As for the reaction solvent, there may be mentioned: alcohol solvents such as methanol and ethanol; acetic acid ester solvents such as ethyl acetate, n-propyl acetate and n-butyl acetate; and mixtures thereof, among which ethyl acetate, and a mixture of ethanol and ethyl acetate are preferred.

The reaction temperature is generally 50° C. to 150° C., preferably 60° C. to 90° C.

The reaction time is generally 30 minutes to 5 hours, preferably 1 hour to 3 hours.

Compound 1h can also be obtained by subjecting compound 1a to step 1-4, step 1-1, step 1-2 and step 1-3 in this order, or by subjecting compound 1c to step 1-4, step 1-2 and step 1-3 in this order.

Furthermore, compound 1h can also be obtained from a compound other than compound 1g by catalytic hydrogenation using palladium carbon or the like as the catalyst, referring to Bioorganic and Medicinal Chemistry Letters, 2004, 14, 2411-2415.

Step 1-5

Compound 1j can be obtained by reaction between compound 1h and compound 1i.

As for the reaction solvent, there may be mentioned methylene chloride, acetonitrile, N,N-dimethylformamide and the like, among which, from the viewpoint of solubility of compound 1h, acetonitrile, N,N-dimethylformamide and the like are preferred.

The reaction temperature is generally 15° C. to 120° C., preferably 20° C. to 85° C.

The reaction time is generally 1 hour to 2 days, preferably 2 hours to 24 hours.

Furthermore, it is preferred to perform the reaction in the coexistence of base. As for the base, organic amines such as pyridine, triethylamine and diisopropylethylamine are preferred.

Step 1-6

Compound 1m can be obtained by subjecting compound 1h to reaction with compound 1l in the presence of base, and then converting Rc to a hydrogen atom by deprotection.

In the reaction with compound 1l, as for the base, there may be mentioned organic amines such as pyridine, triethylamine and diisopropylethylamine, among which diisopropylethylamine and the like are preferred.

As for the reaction solvent, there may be mentioned ether solvents such as diethylether, THF and dioxane, among which THE is preferred.

The reaction temperature is generally 10° C. to 50° C., preferably 15° C. to 40° C.

The reaction time is generally 20 minutes to 2 hours, preferably 30 minutes to 1 hour.

As for the method for the deprotection, hydrolysis in the presence of base is preferred.

As for the base, there may be mentioned metal hydroxides such as sodium hydroxide and potassium hydroxide, among which sodium hydroxide and the like are preferred.

As for the reaction solvent, there may be mentioned: alcohol solvents such as methanol, ethanol and n-propanol; water; and mixtures thereof, among which a mixture of water and methanol is preferred.

The reaction temperature and reaction time are the same as those for compound 1l.

Step 1-8

Compound 1o can be obtained by condensation between compound 1m and compound 1n.

As for the condensing agent, there may be mentioned dicyclohexylcarbodiimide, carbonyldiimidazole, 1-ethyl-3-(3-dimethylaminopropyl)carbodiimide and the like, among which 1-ethyl-3-(3-dimethylaminopropyl)carbodiimide and the like are preferred. Furthermore, it is preferred to perform the condensation in the coexistence of an active esterifying agent such as N-hydroxysuccinimide, N-hydroxybenzotriazole or 3-hydroxy-3,4-dihydro-4-oxo-1,2,3-benzotriazole (preferably 3-hydroxy-3,4-dihydro-4-oxo-1,2,3-benzotriazole or the like).

As for the reaction solvent, there may be mentioned: ether solvents such as diethylether, THF and dimethoxyethane; halogen solvents such as methylene chloride, chloroform and carbon tetrachloride; and N,N-dimethylformamide, acetonitrile and the like, among which N,N-dimethyl formamide is preferred.

The reaction temperature is generally 10° C. to 50° C., preferably 15° C. to 40° C.

The reaction time is generally 5 hours to 40 hours, preferably 10 hours to 25 hours.

Step 1-7 and Step 1-9

Compound 1k and compound 1p can be obtained by introducing a $C_{1-6}$ alkyl group into compound 1j and compound 1o as necessary.

The introduction of $C_{1-6}$ alkyl can be performed referring to, for example, methods described in Bioorganic and Medicinal Chemistry 2005, 13, 1393-1402, Organic Preparations and Procedures International 2004, 36, 347-351, and Journal of Medicinal Chemistry 2004, 47, 6447-6450.

Compound 1k can also be obtained by subjecting compound 1h to step 1-7 and step 1-5 in this order. Compound 1p can also be obtained by subjecting compound 1h to step 1-9, step 1-6 and step 1-8 in this order.

Compound 1b is commercially available, and can be produced referring to, for example, methods described in common textbooks of organic chemistry (for example, Jerry March, WILEY INTERSCIENCE Advanced Organic Chemistry 4th edition). Compound 1d is commercially available, and can be produced referring to methods described in, for example, Journal of Fluorine Chemistry 2003, 120, 173-183, and Journal of Organic Chemistry 1986, 51, 3242-3244.

(General Process-2)

General process-2 is an example of a manufacturing process for compound 1a of general process-1.

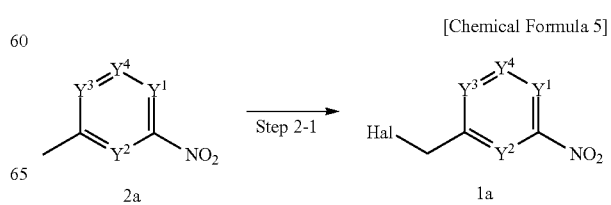

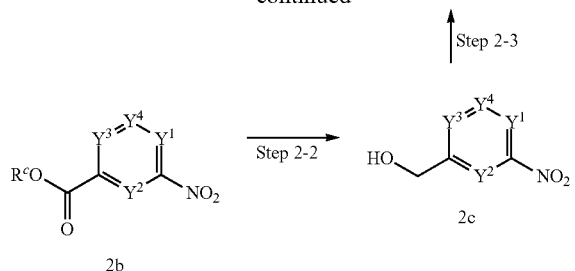

Step 2-1

Compound 1a can be obtained by halogenation, preferably bromination, of compound 2a.

As for the halogenating agent, there may be mentioned N-bromosuccinimide, N-chlorosuccinimide, N-iodosuccinimide and the like, among which N-bromosuccinimide is preferred.

As for the reaction solvent, inactive nonpolar solvents such as carbon tetrachloride are preferred.

The reaction temperature is generally 20° C. to 100° C., preferably 50° C. to 90° C.

The reaction time is generally 30 minutes to 10 hours, preferably 1 hour to 7 hours.

Step 2-2

Compound 2c can be obtained by reduction of compound 2b.

As for the reducing agent, there may be mentioned lithium aluminum hydride, diisobutylaluminum hydride (also referred to as "DIBAH" herein) and the like, among which DIBAH is preferred.

As for the reaction solvent, there may be mentioned: ether solvents such as diethylether, and THF; and benzene solvents such as benzene, toluene and xylene, among which, when DIBAH is used as the reducing agent, toluene and the like are preferred.

The reaction temperature is generally −100° C. to 10° C., preferably −85° C. to 0° C.

The reaction time is generally 10 minutes to 3 hours, preferably 30 minutes to 2 hours.

Compound 2c can also be obtained by converting the $R^cOCO-$ of compound 2b to a formyl group and subjecting the obtained compound to step 2-2.

Step 2-3

Compound 1a can be obtained by converting the hydroxy group of compound 2c to a halogen atom, preferably a bromine atom.

As for the halogenating agent, there may be mentioned diethylaminosulfur trifluoride (also referred to as "DAST" herein), thionyl chloride, phosphorus tribromide, a combination of triphenylphosphine and iodine, and a combination of paratoluenesulfonic acid chloride and sodium iodide, among which phosphorus tribromide is preferred.

As for the reaction solvent, there may be mentioned ether solvents such as diethylether, THF and dioxane, among which diethylether is preferred.

The reaction temperature is generally −10° C. to 10° C., preferably −5° C. to 5° C.

The reaction time is generally 10 minutes to 1 hour, preferably 20 minutes to 40 minutes.

Compound 2a and compound 2b are commercially available, and can be produced referring to, for example, methods described in common textbooks of organic chemistry (for example, Jerry March, WILEY INTERSCIENCE Advanced Organic Chemistry 4th edition). Compound 2b can also be produced by, for example, performing any one of the following (i) to (iii), regarding the corresponding halogenated aryl compound (i.e., a compound obtained by replacing the —CO-OR$^c$ of compound 2b by a halogen atom): (i) converting the halogen atom to a carboxy group; (ii) subjecting the halogenated compound to reaction with copper(I) cyanide in sulfuric acid (Journal of Antibiotics 1994, 47, 1456-1465; Liebigs Annalen Chemie 1979, 4, 554-563); and (iii) inserting carbon monoxide at the position at which the halogen atom is bound, using palladium catalyst (Journal of Organic Chemistry 1999, 64, 6921-6923).

(General Process-3)

General process-3 is an example of a particularly preferred manufacturing process for a compound 2a or 2b of general process-2 wherein $Y^2$ is —CF=.

[Chemical Formula 6]

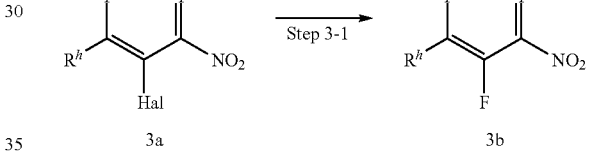

Step 3-1

Compound 3b can be obtained by subjecting compound 3a (wherein Hal is preferably a chlorine atom) to reaction with a fluorinating agent such as sodium fluoride, potassium fluoride and cesium fluoride (preferably cesium fluoride). A quaternary ammonium salt such as tetramethylammonium chloride may be added as necessary.

As for the reaction solvent, dimethylsulfoxide, sulforane and N,N-dimethylformamide and the like are preferred.

The reaction temperature is generally 100° C. to 200° C., preferably 120° C. to 160° C.

In cases where $R^h$ is a methyl group, the reaction time is generally 5 hours to 20 hours, preferably 7 hours to 15 hours; and in cases where $R^h$ is $R^cOCO-$, the reaction time is generally 20 minutes to 2 hours, preferably 30 minutes to 1 hour.

Compound 3b, particularly a compound wherein $Y^1$, $Y^3$ and $Y^4$ are each —CH=, is a novel compound, and is useful as a synthetic intermediate to a compound represented by general formula (1).

Compound 3a is commercially available, and can be produced referring to, for example, methods described in Yakugaku Zasshi 1955, 75, 292-296 and common textbooks of organic chemistry (for example, Jerry March, WILEY INTERSCIENCE Advanced Organic Chemistry 4th edition).

(General Process-4)

General process-4 is another manufacturing process for compound 1h.

[Chemical Formula 7]

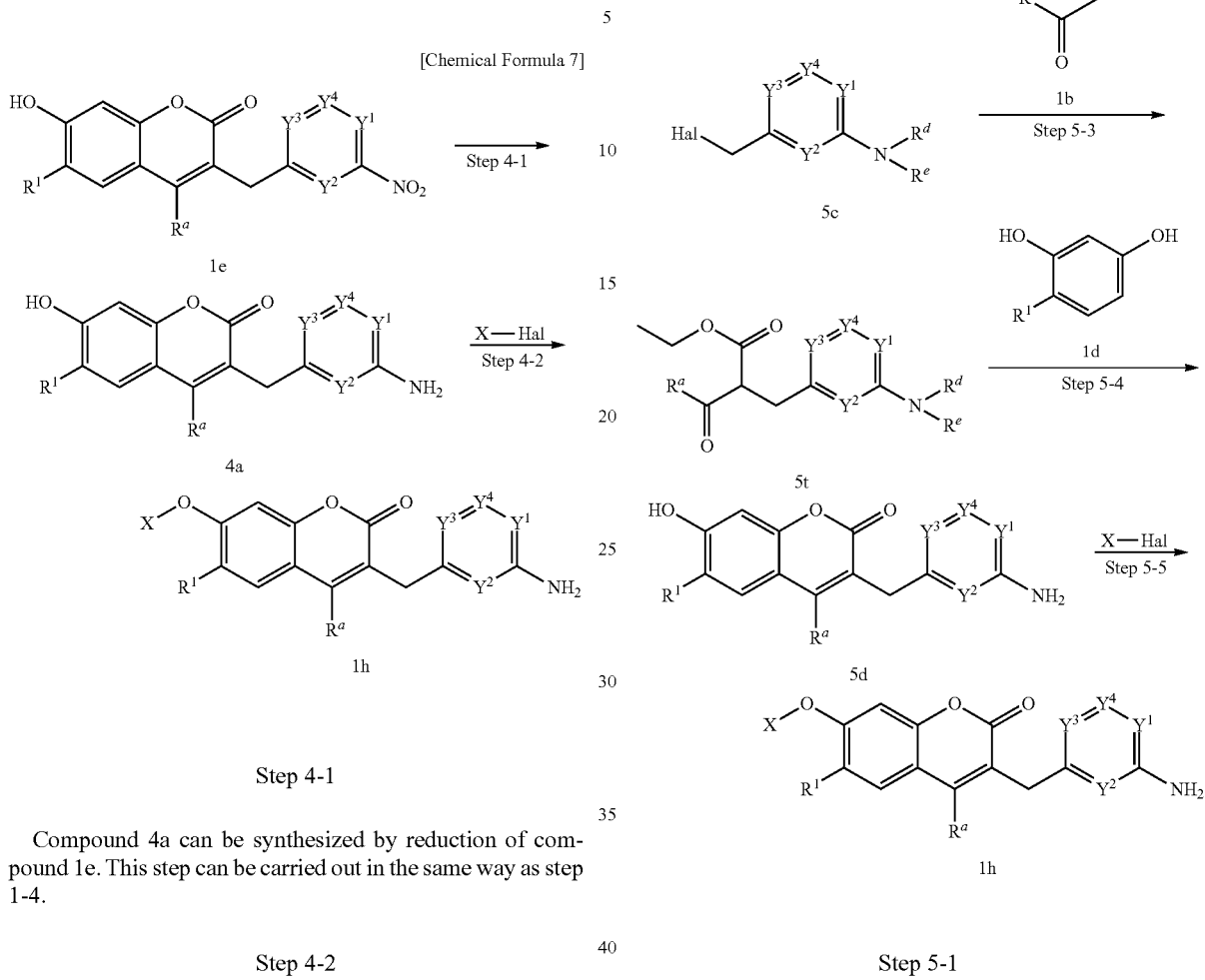

Step 4-1

Compound 4a can be synthesized by reduction of compound 1e. This step can be carried out in the same way as step 1-4.

Step 4-2

Compound 1h can be obtained by reaction between compound 4a and compound 1f in the presence of base. This step can be carried out in the same way as step 1-3.

(General Process-5)

General process-5 is still another manufacturing process for compound 1h. With this process, a compound 1h wherein $Y^1$ and $Y^2$ are each independently —N= or —CR$^{11}$= can be produced.

[Chemical Formula 8]

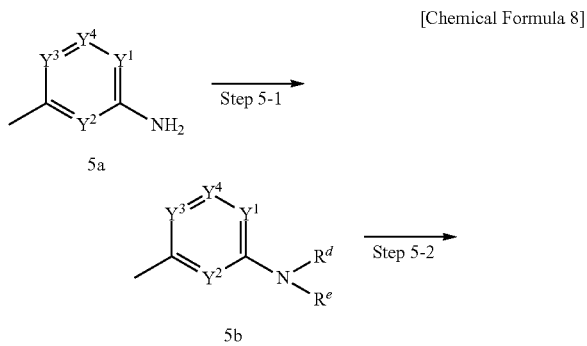

Step 5-1

Compound 5b can be obtained by protecting the amino group of compound 5a, preferably by converting $R^d$ and $R^e$ to a t-butoxycarbonyl group.

As for the protecting agent, Boc$_2$O (di-t-butylcarbonate) and the like are preferred.

As for the reaction solvent, there may be mentioned ether solvents such as diethylether and THF, among which THF and the like are preferred.

The reaction temperature may be appropriately determined depending on the type of reaction solvent and the like, while it is generally 0° C. to 90° C., preferably 20° C. to 70° C.

The reaction time is generally 2 hours to 2 days, preferably 3 hours to 20 hours.

Furthermore, it is preferred to perform the reaction in the coexistence of a reaction accelerator such as N,N-dimethylaminopyridine.

Step 5-2

Compound 5c can be obtained by halogenation, preferably bromination, of compound 5b.

As for the halogenating agent, there may be mentioned chlorine molecule, bromine molecule, iodine molecule, N-chlorosuccinimide, N-bromosuccinimide, N-iodosuccinimide and the like, among which N-bromosuccinimide is preferred. Furthermore, it is preferred to perform the halogenation in the coexistence of a radical initiator such as azoisobutylonitrile or benzoyl peroxide (preferably benzoyl peroxide or the like).

As for the reaction solvent, there may be mentioned halogen solvents such as carbon tetrachloride and chloroform; nonpolar hydrocarbon solvents such as cyclohexane and hexane, among which carbon tetrachloride is preferred.

The reaction temperature is generally 50° C. to 100° C., preferably 70° C. to 90° C.

The reaction time is generally 1 hour to 8 hours, preferably 2 hours to 6 hours.

Step 5-3

Compound 5t can be obtained by subjecting compound 5c to reaction with compound 1b in the presence of base.

As for the base, there may be mentioned, for example, metal hydrides such as sodium hydride, potassium hydride and LiHMDS, among which sodium hydride and the like are preferred.

As for the reaction solvent, there may be mentioned: ether solvents such as THF and diethylether; and chlorine solvents such as methylene chloride, among which THE is preferred.

The reaction temperature is generally −20° C. to 25° C., preferably 0° C. to 10° C.

The reaction time is generally 2 hours to 24 hours, preferably 6 hours to 15 hours.

Furthermore, compound 5t can be obtained by the condensation reaction described in International Publication WO 2002/08217 followed by catalytic hydrogenation.

Step 5-4

Compound 5d can be obtained by performing deprotection of the amino group at the same time as condensation reaction of compound 5t and compound 1d in the presence of acid.

As for the acid, there may be mentioned: Lewis acids such as zirconium chloride, samarium(H) chloride and aluminum chloride; inorganic acids such as sulfuric acid; and acidic resins such as zeolite, among which sulfuric acid is preferred.

As for the reaction solvent, solvents inactive for the reaction may be used, while solvent-free conditions are preferred. When sulfuric acid is used, the number of equivalents is generally 1 to 5, preferably 1 to 3, relative to compound 1d.

The reaction temperature is generally −20° C. to 50° C., preferably −10° C. to 30° C.

The reaction time may be appropriately determined depending on the reaction temperature and the like, while it is generally 2 hours to 20 hours, preferably 5 hours to 16 hours.

Step 5-5

Compound 1h can be obtained by subjecting compound 5d to reaction with compound 1f in the presence of base. This step can be carried out in the same way as step 1-3.

Compound 5a is commercially available, and can be produced referring to, for example, methods described in European Journal of Medicinal Chemistry 1999, 34, 1003-1008, Bioorganic and Medicinal Chemistry Letters 2004, 16, 1411-1416, Bioorganic and Medicinal Chemistry Letters 2002, 12, 2109-2112, Chemical and Pharmaceutical Bulletin 2004, 52, 818-829, and the like. Furthermore, compound 5a and compound 5b can also be produced by, for example, introducing a nitrogen atom into the corresponding halogenated aryl compound (i.e., a compound obtained by replacing the amino group or —NR$^d$R$^e$ of compound 5a or 5b by a halogen atom) at the position at which the halogen atom is bound, using palladium catalyst (Organic Letters 2002, 4, 4689-4692).

In general processes-1, -4, -5 and -8, from a compound wherein R$^a$ is a C$_{1-6}$ alkyl group (the C$_{1-6}$ alkyl group is substituted with a substituent selected from the group consisting of an optionally protected hydroxy group, an optionally protected oxo group, and an optionally protected carboxy group), it is possible to produce a compound of general formula (1) wherein R$^2$ is a C$_{1-6}$ alkyl group substituted with a halogen atom, by converting the optionally protected hydroxy group, the optionally protected oxo group or the optionally protected carboxy group to a halogen atom. Conversion to a fluorine atom can be performed at an appropriate step of general processes-1, -4, -5 and -8 using DAST or the like as a fluorinating agent, referring to Synthesis 2002, 17, 2561-2578 or the like. Conversion to a chlorine atom or bromine atom can be performed using compound 1j, compound 1o or the like and using thionyl chloride, PBr$_3$ or the like as a halogenating agent, referring to Larock, Comprehensive Organic Transformations or the like.

(General Process-6)

General process-6 is an example of a preferred manufacturing process for a compound of general formula (1) wherein R$^2$ is a C$_{1-6}$ alkyl group substituted with a fluorine atom.

[Chemical Formula 9]

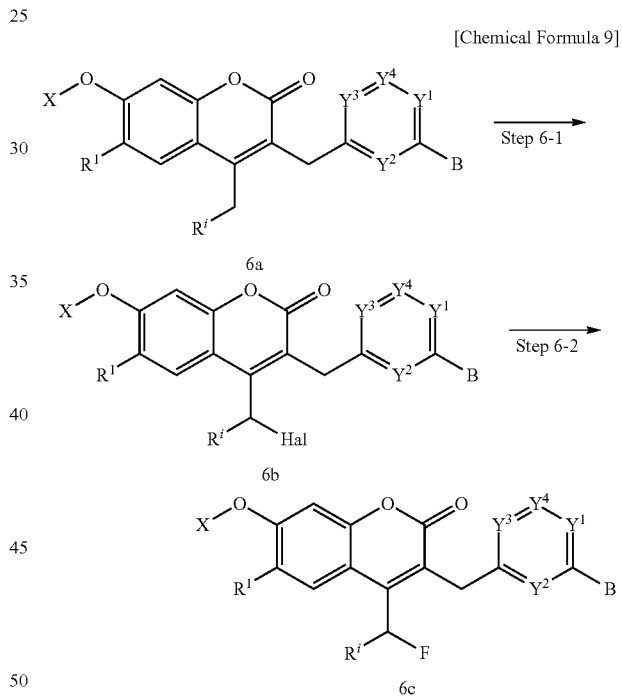

Step 6-1

Compound 6b can be obtained by introducing a halogen atom, preferably a bromine atom, into compound 6a.

As for the halogenating agent, there may be mentioned, for example, N-chloro succinimide, N-bromosuccinimide, N-iodosuccinimide and the like, among which N-bromosuccinimide is preferred.

As for the reaction solvent, there may be mentioned carbon tetrachloride, diethylether, THF and the like, among which THF and the like are preferred.

The reaction temperature is generally −50° C. to 10° C., preferably −20° C. to 5° C.

The reaction time is generally 20 minutes to 2 hours, preferably 30 minutes to 1 hour.

Step 6-2

Compound 6c can be obtained by further replacing the halogen atom of compound 6b by a fluorine atom.

(General Process-7)

General process-7 is an example of a preferred manufacturing process for a compound of general formula (1) wherein $R^2$ is a $C_{1-6}$ alkyl group substituted with a halogen atom.

[Chemical Formula 10]

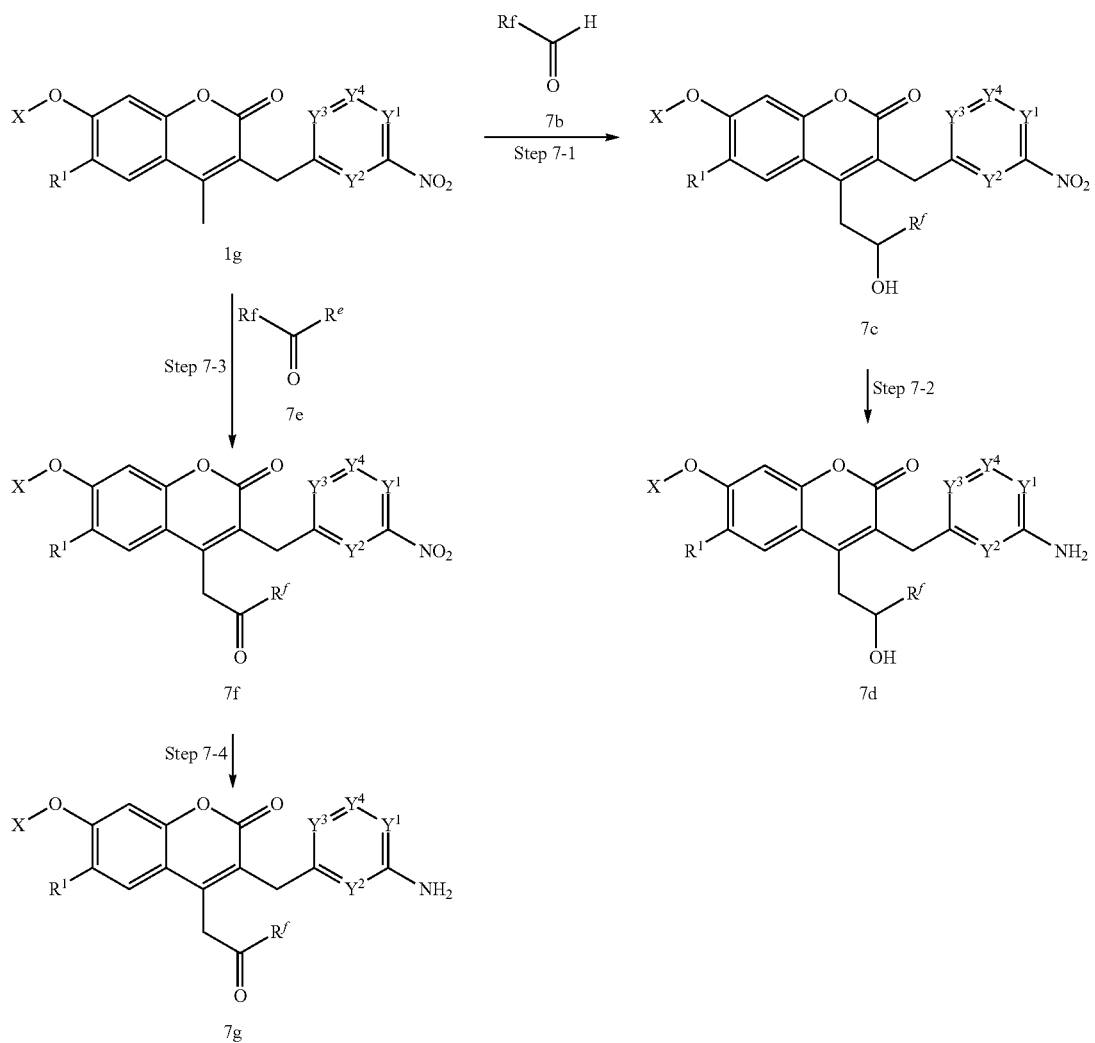

As for the fluorinating agent, there may be mentioned fluorinated metals such as potassium fluoride and sodium fluoride, among which potassium fluoride is preferred. It is preferred to perform the fluorination in the coexistence of a crown ether (for example, 18-crown-6) corresponding to a metal in the fluorinated metal to be used.

As for the reaction solvent, acetonitrile, for example, is preferred.

The reaction temperature is generally 20° C. to 100° C., preferably 20° C. to 80° C.

The reaction time is generally 1 hour to 6 hours, preferably 1.5 hours to 5 hours.

It is possible to produce a compound of general formula (1) wherein $R_2$ is a $C_{1-6}$ alkyl group substituted with a fluorine atom, by deprotecting compound 6c as necessary, and then subjecting it to step 1-4, step 1-5 or step 1-6, and the subsequent steps of general process-1.

Step 7-1

Compound 7c can be obtained by subjecting a deprotonated form of compound 1g, which is obtained by reaction between compound 1g and a base, to reaction with compound 7b.

As for the base, there may be mentioned sodium hydride, potassium hydride, LiHMDS and the like, among which LiHMDS is preferred.

As for the reaction solvent, there may be mentioned: ether solvents such as THF and diethylether; and chlorine solvents such as methylene chloride, among which THF is preferred.

The reaction temperature may be appropriately determined depending on the type of reaction solvent and the like, while for the reaction between compound 1g and a base, it is generally –100° C. to 10° C., preferably –85° C. to 5° C., and for the reaction between the deprotonated form and compound 7b, it is generally –5° C. to 40° C., preferably 0° C. to 30° C.

The reaction time may be appropriately determined depending on the reaction temperature and the like, while for the reaction between compound 1g and a base, it is generally 20 minutes to 3 hours, preferably 30 minutes to 1.5 hours, and for the reaction between the deprotonated form and compound 7b, it is generally 20 minutes to 20 hours, preferably 30 minutes to 15 hours.

Step 7-3

Compound 7f can be obtained by subjecting a deprotonated form of compound 1g, which is obtained by reaction between compound 1g and a base, to reaction with compound 7e. This step can be carried out in the same way as step 7-1.

Step 7-2 and Step 7-4

Compound 7d and compound 7g can be obtained by reduction of compound 7c and compound 7f, respectively. This step can be carried out in the same way as step 1-4.

It is possible to produce a compound of general formula (1) wherein $R^2$ is a $C_{1-6}$ alkyl group substituted with a halogen atom, by converting compound 7d or compound 7g by the same method as in general process-1.

A compound wherein $R^2$ is a $C_{1-6}$ alkyl group substituted with a fluorine atom can also be produced by converting the introduced hydroxy or oxo group of compound 7c or 7f to a fluorine atom, and then subjecting it to step 1-4 and the subsequent steps of general process-1. The conversion of the hydroxy or oxo group to a fluorine atom can be performed using DAST or the like as a fluorinating agent, referring to Synthesis 2002, 17, 2561-2578 or the like.

(General Process-8)

General process-8 is another manufacturing process for compound 5t, and is an example of a particularly preferred manufacturing process for a compound of general formula (1) wherein $Y^1$ is —N=.

[where $R^j$ represents a leaving group, such as a halogen atom, $C_{1-4}$ alkoxy group or di($C_{1-4}$ alkyl)amino group, or a hydrogen atom; and $R^k$ represents a leaving group, such as an acetyloxy group, trifluoroacetyloxy group, methanesulfonyloxy group, paratoluenesulfonyloxy group or halogen atom.]

Step 8-1

Compound 8b can be obtained by subjecting a deprotonated form of compound 8a, which is obtained by reaction between compound 8a and a strong base, to reaction with a compound represented by formula: $R^jCHO$ (hereinafter also referred to simply as "$R^jCHO$").

As for the strong base, there may be mentioned: metal amides such as lithium hexamethyldisilazide and lithium diisopropylamide; alkylmetals such as butyllithium and ethyllithium; and alkylmagnesium halide and the like, among which lithium hexamethyldisilazide, lithium diisopropylamide and the like are preferred. As for $R^jCHO$, there may be mentioned: formic acid derivatives such as formyl chloride and formic acid esters; formamides such as N,N-dimethylformamide (also referred to as "DMF" herein) and N,N-diethylformamide, among which DMF is preferred. By using formaldehyde as $R^jCHO$, it is possible to obtain compound 8c directly from compound 8a without producing compound 8b.

As for the reaction solvent, there may be mentioned: ether solvents such as THF and diethylether; and chlorine solvents such as methylene chloride and carbon tetrachloride, among which THF is preferred.

The reaction temperature may be appropriately determined depending on the type of reaction solvent and the like, while for the reaction between compound 8a and a strong base, it is generally −100° C. to 25° C., preferably −95° C. to −65° C., and for the reaction between the deprotonated form and $R^jCHO$, it is generally −100° C. to 35° C., preferably −30° C. to 10° C.

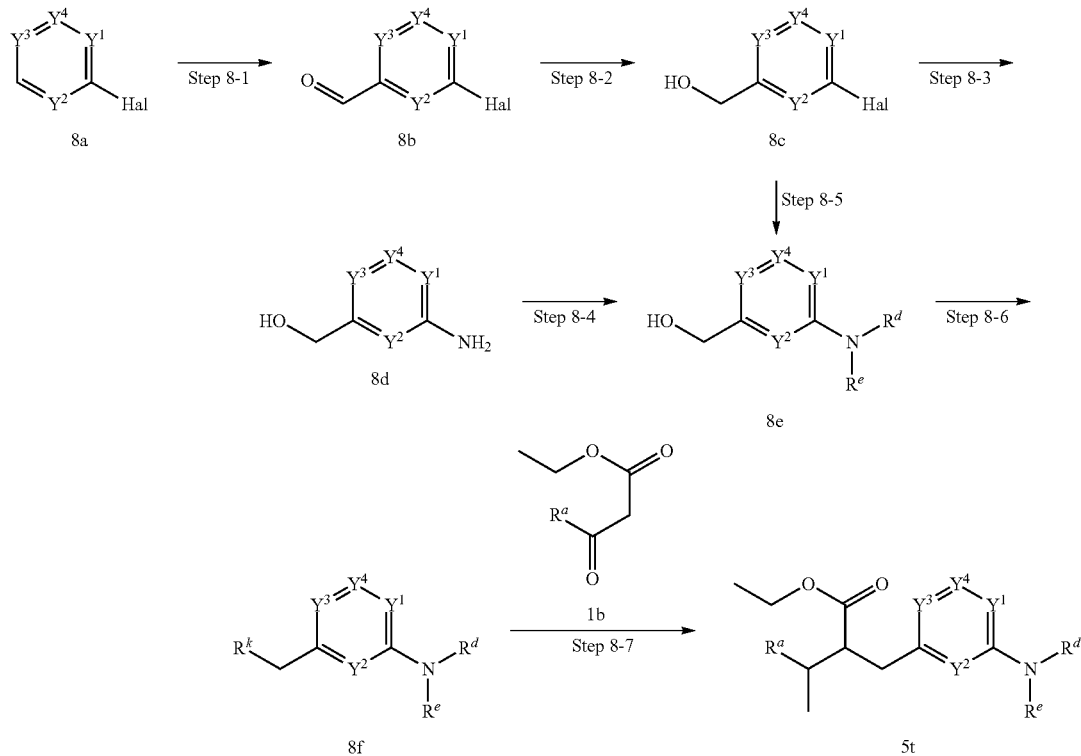

The reaction time may be appropriately determined depending on the reaction temperature and the like, while for the reaction between compound 8a and a strong base, it is generally 10 minutes to 10 hours, preferably 20 minutes to 5 hours, and for the reaction between the deprotonated form and R'CHO, it is generally 30 minutes to 40 hours, preferably 30 minutes to 4 hours.

Step 8-2

Compound 8c can be obtained by reaction between compound 8b and a reducing agent.

As for the reducing agent, there may be mentioned metal-hydrogen complex compounds (for example, metal borohydrides, such as sodium borohydride, sulfurated sodium borohydride, sodium cyanoborohydride, sodium trimethoxyborohydride, lithium borohydride, lithium cyanoborohydride, lithium triethylborohydride, lithium tri-s-butylborohydride, lithium tri-t-butylborohydride, calcium borohydride, potassium borohydride, potassium triisopropoxyborohydride, potassium tri-s-butylborohydride, zinc borohydride, and sodium triacetoxyborohydride; and metal aluminum hydrides, such as lithium aluminum hydride, lithium trimethoxyaluminum hydride, lithium tri-t-butoxyaluminum hydride, lithium aluminum hydride/trichloroaluminum, lithium aluminum hydride/boron trifluoride, chloromagnesium aluminum hydride, magnesium aluminum hydride, sodium aluminum hydride, sodium triethoxyaluminum hydride, and sodium bis(methoxyethoxy)aluminum hydride), among which metal borohydrides such as sodium borohydride are preferred.

As for the reaction solvent, there may be mentioned: ether solvents such as THF and diethyl ether; chlorine solvents such as methylene chloride and carbon tetrachloride; and alcohol solvents such as methanol and ethanol, among which THF is preferred.

The reaction temperature may be appropriately determined depending on the type of reaction solvent and the like, while it is generally −100° C. to 100° C., preferably −10° C. to 50° C.

The reaction time may be appropriately determined depending on the reaction temperature and the like, while it is generally 10 minutes to 30 hours, preferably 1 hour to 8 hours.

Step 8-3

Compound 8d can be obtained by reaction between compound 8c and an aminating agent.

As for the aminating agent, there may be mentioned: ammonia; aqueous ammonia; ammonium salts such as ammonium chloride and ammonium acetate; metal amides such as lithium hexamethyldisilazide, potassium hexamethyldisilazide, sodium hexamethyldisilazide, lithium amides, sodium amides and potassium amides; and silazanes such as hexamethyldisilazane, among which ammonia, and metal amides such as lithium hexamethyldisilazide are preferred.

When ammonia is used as the aminating agent, the reaction can be performed in the coexistence of an organic amine such as triethylamine, a base such as sodium hydroxide, or the like. When a metal amide such as lithium hexamethyldisilazide is used as the aminating agent, the reaction can be performed in the coexistence of palladium catalyst and phosphine ligand which can be used in step 8-5.

As for the reaction solvent, there may be mentioned: hydrocarbon solvents such as toluene and benzene; ether solvents such as THF, diethylether and dioxane; chlorine solvents such as methylene chloride; and non-proton polar solvents such as DMF, among which toluene, DMF and dioxane are particularly preferred.

The reaction temperature may be appropriately determined depending on the type of reaction solvent and the like, while it is generally 0° C. to 200° C., preferably 30° C. to 150° C.

The reaction time may be appropriately determined depending on the reaction temperature and the like, while it is generally 1 hour to 30 hours, preferably 2 hours to 10 hours.

Compound 8d can also be obtained by protecting the hydroxy group of compound 8c, then subjecting the compound to this step, and then deprotecting the hydroxy group.

For selection of a protecting group and a method of protection and deprotection, there may be referred to, for example, T. W. Greene, P. G. M. Wuts, Protective Groups in Organic Synthesis, Second Edition, John Wiley and Sons, Inc., New York, 1991. As preferred examples of the protecting group, there may be mentioned: trisubstituted silyl groups, such as a trimethylsilyl group, triethylsilyl group, triisopropylsilyl group, dimethylisopropylsilyl group, diethylisopropylsilyl group, dimethylthexylsilyl group, tert-butyldimethylsilyl group, tert-butyldiphenylsilyl group, tribenzylsilyi group, tri-p-xylylsilyl group, triphenylsilyl group, diphenylmethylsilyl group and tert-butylmethoxyphenylsilyl group; and substituted benzyl groups, such as a benzyl group, triphenylmethyl group, 2,4,6-trimethylbenzyl group, p-bromobenzyl group, o-nitrobenzyl group, p-nitrobenzyl group, p-methoxybenzyl group and 2,6-dimethoxybenzyl group, among which a tert-butyldimethylsilyl group (also referred to as "TBS group" herein) is preferred.

When the protecting group is a trisubstituted silyl group, the protection of the hydroxy group can be performed by subjecting compound 8c to reaction with a trisubstituted silyl halide in the presence of base.

As for the base, there may be mentioned amities such as triethylamine, pyridine, imidazole, triazole, benzimidazole and benzotriazole, among which imidazole is preferred.

As for the halide, there may be mentioned a chloride, bromide and iodide, among which a chloride is preferred.

As for the reaction solvent, there may be mentioned amide solvents such as N,N-dimethylacetamide, N,N-dimethylimidazolidinone (also referred to as "DMI" herein) and DMF, among which DMF is preferred.

The reaction temperature may be appropriately determined depending on the type of reaction solvent and the like, while it is generally 0° C. to 150° C., preferably 15° C. to 65° C.

The reaction time may be appropriately determined depending on the reaction temperature and the like, while it is generally 30 minutes to 30 hours, preferably 1 hour to 5 hours.

When the protecting group is a trisubstituted silyl group, the deprotection of the protected hydroxy group of compound 8d can be performed by, for example, subjecting the compound to reaction with an acid and a fluoride reagent.

As for the acid, there may be mentioned: inorganic acids such as hydrochloric acid, hydrobromic acid, sulfuric acid, nitric acid, phosphoric acid and perchloric acid; and organic acids such as trifluoroacetic acid, trichloroacetic acid, methanesulfonic acid, p-toluenesulfonic acid, benzenesulfonic acid, camphorsulfonic acid, oxalic acid and citric acid; and acidic ion-exchange resins may further be mentioned.

As for the fluoride reagent, there may be mentioned tetra-n-butylammonium fluoride, hydrogen fluoride/pyridine, hydrogen fluoride/triethylamine, hydrofluoric acid, lithium fluoride, sodium fluoride, potassium fluoride, cesium fluoride and the like, among which tetra-n-butylammonium fluoride and the like are preferred.

The reaction solvent may be appropriately determined, and there may be used, for example: alcohol solvents; ether solvents such as THF and diethylether; ester solvents such as ethyl acetate and methyl acetate; nitrile solvents such as acetonitrile, benzonitrile and benzyl cyanide; and amide solvents such as N,N-dimethylacetamide, DMI and DMF, among which ether solvents such as THF are preferred.

The reaction temperature may be appropriately determined depending on the type of reaction solvent and the like, while it is generally 0° C. to 150° C., preferably 15° C. to 65° C.

The reaction time may be appropriately determined depending on the reaction temperature and the like, while it is generally 5 minutes to 30 hours, preferably 10 minutes to 3 hours.

Step 8-4

Compound 8e can be obtained by protecting the amino group of compound 8d.

As for the method for protection of the amino group, methods using various protecting groups generally usable in organic chemistry are mentioned, while preferred are, for example, a method of forming a carbamate using a t-butoxycarbonyl group or the like, a method of forming an imine using a phenylmethylidenyl group, diphenylmethylidenyl group or the like, and a method of forming an amide by acetylation, trifluoroacetylation or the like, and particularly preferred are a method of forming a carbamate using a t-butoxycarbonyl group or the like, and a method of forming an imine using a diphenylmethylidenyl group or the like.

The method of forming a carbamate may be carried out in the same way as step 5-1.

The method of forming an imine may be carried out by heating compound 8d together with an aldehyde such as benzaldehyde, or a ketone such as benzophenone.

As for the reaction solvent, alcohol solvents such as methanol, ethanol, n-propanol and i-propanol are preferred, and methanol is particularly preferred.

The reaction temperature may be appropriately determined depending on the type of reaction solvent and the like, while it is generally 10° C. to 120° C., preferably 40° C. to 90° C.

The reaction time may be appropriately determined depending on the reaction temperature and the like, while it is generally 30 minutes to 20 hours, preferably 1 hour to 5 hours.

Step 8-5

Compound 8e can also be obtained by subjecting compound 8c to reaction with a compound represented by formula: $HNR^dR^e$ (hereinafter also referred to simply as "$HNR^dR^e$").

As for $HNR^dR^e$, there may be mentioned, for example: acetamides such as acetamide and bis(trimethylsilyl)acetamide; imines such as diphenylimine; and aralkylamines such as benzylamine, among which acetamide, bis(trimethylsilyl) acetamide and diphenylimine are preferred.

It is preferred to perform the reaction in the coexistence of palladium catalyst and phosphine ligand to accelerate it.

As for the palladium catalyst, there may be mentioned palladium acetate, palladium trifluoroacetate, palladium chloride, palladium carbon, allylpalladium chloride dimer, tetrakis(triphenylphosphine)palladium, bis(dibenzylideneacetone)palladium, tris(dibenzylideneacetone)dipalladium, tris(dibenzylideneacetone)dipalladium-chloroform adduct, dichlorobis(triphenylphosphine)palladium, bis(acetonitrile) dichloropalladium and the like, among which bis(dibenzylideneacetone)palladium, tris(dibenzylideneacetone)dipalladium and the like are preferred.

As for the phosphine ligand, there may be mentioned triphenylphosphine, tri-o-tolylphosphine, tri(2-furyl)phosphine, tri-t-butylphosphine, tricyclohexylphosphine, tri-n-butylphosphine, 1,2-bis(diphenylphosphino)ethane, 1,3-bis (diphenylphosphino)propane, 1,4-bis(diphenylphosphino) butane, 1,1'-bis(diphenylphosphino)ferrocene, 2,2'-bis (diphenylphosphino)-1,1'-binaphthyl, dicyclohexyl[2',4',6'-tris(1-methylethyl)-1,1'-biphenyl-2-yl]phosphine (X-Phos) and the like, among which 2,2'-bis(diphenylphosphino)-1,1'-binaphthyl and dicyclohexyl[2',4',6'-tris(1-methylethyl)-1,1'-biphenyl-2-yl]phosphine (X-Phos) are preferred.

As for the reaction solvent, there may be mentioned: hydrocarbon solvents such as hexane, heptane, octane, toluene, benzene and xylene; ether solvents such as THF, diethylether and dioxane; and non-proton polar solvents such as DMF and N,N-dimethylacetamide, among which aromatic hydrocarbon solvents such as toluene and benzene are preferred.

The reaction temperature may be appropriately determined depending on the type of reaction solvent and the like, while it is generally 20° C. to 140° C., preferably 45° C. to 80° C.

The reaction time may be appropriately determined depending on the reaction temperature and the like, while it is generally 1 hour to 30 hours, preferably 5 hours to 20 hours.

Compound 8e can also be obtained by protecting the hydroxy group of compound 8c, then subjecting the compound to this step, and then deprotecting the hydroxy group. This may be carried out in the same way as the process of protecting the hydroxy group of compound 8c, then subjecting the compound to step 8-3, and then deprotecting the hydroxy group to yield compound 8d.

Step 8-6

Compound 8f can be obtained by converting the hydroxy group of compound 8e to a leaving group, for example, by esterification (acetylation, mesylation, tosylation or the like) of the hydroxy group, or replacement of the hydroxy group by a halogen atom, preferably by sulfonate esterification (mesylation, tosylation or the like) of the hydroxy group.

The sulfonate esterification of compound 8e can be performed by subjecting compound 8e to reaction with methanesulfonyl chloride, para-toluenesulfonyl chloride or the like in the presence of base.

As for the base, there may be mentioned, for example: metal hydrides such as sodium hydride, potassium hydride and lithium hydride; and metal alkoxides such as potassium t-butoxide, sodium t-butoxide, lithium t-butoxide, potassium t-pentoxide, sodium t-pentoxide and lithium t-pentoxide, among which metal alkoxides such as lithium t-butoxide are preferred.

As for the reaction solvent, ether solvents such as THF, diethylether and dioxane are preferred, and THF is particularly preferred.

The reaction temperature may be appropriately determined depending on the type of reaction solvent and the like, while it is generally −90° C. to 30° C., preferably −50° C. to 10° C.

The reaction time may be appropriately determined depending on the reaction temperature and the like, while it is generally 5 minutes to 10 hours, preferably 15 minutes to 2 hours.

The acetate esterification (acetylation, trifluoroacetylation or the like) of compound 8e can be easily performed by a method generally used in organic chemistry. For example, it can be performed by subjecting compound 8e to reaction with the corresponding acid halide (acetyl chloride, trifluoroacetyl chloride or the like) or acid anhydride (acetic anhydride, trifluoroacetic anhydride or the like) in the presence of base.

The halogenation of compound 8e can be performed in the same way as step 2-3. Furthermore, it can also be carried out by performing an exchange reaction between the sulfonate ester obtained by the above-mentioned sulfonate esterification, and a halogen anion.

Step 8-7

Compound 5t can be obtained by subjecting compound 8f to reaction with compound 1b in the presence of base. This step can be carried out in the same way as step 5-3.

Compound 8a is commercially available, and can be produced referring to, for example, methods described in common textbooks of organic chemistry (for example, Jerry March, WILEY INTERSCIENCE Advanced Organic Chemistry 4th edition). As for Hal in compound 8a, a chlorine atom is preferred. Some examples of compounds 8b and 8c are known compounds which are readily available.

Based on general processes-1 to -8, and examples which will be described later, or referring thereto, the following compounds, for example, can also be synthesized:
- 3-{2-(methylaminosulfonyl)amino-3-fluoropyridin-4-ylmethyl}-4-methyl-7-(pyrimidin-2-yloxy)-2-oxo-2H-1-benzopyran,
- 3-{2-(aminosulfonyl)amino-3-fluoropyridin-4-ylmethyl}-4-methyl-7-(pyrimidin-2-yloxy)-2-oxo-2H-1-benzopyran,
- 3-{2-chloro-3-(methylaminosulfonyl)aminobenzyl}-4-methyl-7-(pyrimidin-2-yloxy)-2-oxo-2H-1-benzopyran,
- 3-{2-chloro-3-(aminosulfonyl)aminobenzyl}-4-methyl-7-(pyrimidin-2-yloxy)-2-oxo-2H-1-benzopyran,
- 3-{2-methyl-3-(methylaminosulfonyl)aminobenzyl}-4-methyl-7-(pyrimidin-2-yloxy)-2-oxo-2H-1-benzopyran,
- 3-{2-methyl-3-(aminosulfonyl)aminobenzyl}-4-methyl-7-(pyrimidin-2-yloxy)-2-oxo-2H-1-benzopyran,
- 3-{2-(methylaminosulfonyl)aminopyridin-4-ylmethyl}-4-methyl-6-fluoro-7-(thiazol-2-yloxy)-2-oxo-2H-1-benzopyran,
- 3-{2-(aminosulfonyl)aminopyridin-4-ylmethyl}-4-methyl-6-fluoro-7-(thiazol-2-yloxy)-2-oxo-2H-1-benzopyran,
- 3-{2-(methylaminosulfonyl)aminopyridin-4-ylmethyl}-4-methyl-6-chloro-7-(thiazol-2-yloxy)-2-oxo-2H-1-benzopyran,
- 3-{2-(aminosulfonyl)aminopyridin-4-ylmethyl}-4-methyl-6-chloro-7-(thiazol-2-yloxy)-2-oxo-2H-1-benzopyran,
- 3-{2-(methylaminosulfonyl)aminopyridin-4-ylmethyl}-4-methyl-6-methyl-7-(thiazol-2-yloxy)-2-oxo-2H-1-benzopyran,
- 3-{2-(aminosulfonyl)aminopyridin-4-ylmethyl}-4-methyl-6-methyl-7-(thiazol-2-yloxy)-2-oxo-2H-1-benzopyran,
- 3-{2-(methylaminosulfonyl)amino-3-fluoropyridin-4-ylmethyl}-4-methyl-7-(thiazol-2-yloxy)-2-oxo-2H-1-benzopyran,
- 3-{2-(aminosulfonyl)amino-3-fluoropyridin-4-ylmethyl}-4-methyl-7-(thiazol-2-yloxy)-2-oxo-2H-1-benzopyran,
- 3-{2-(methylaminosulfonyl)amino-3-fluoropyridin-4-ylmethyl}-4-methyl-6-fluoro-7-(thiazol-2-yloxy)-2-oxo-2H-1-benzopyran,
- 3-{2-(aminosulfonyl)amino-3-fluoropyridin-4-ylmethyl}-4-methyl-6-fluoro-7-(thiazol-2-yloxy)-2-oxo-2H-1-benzopyran,
- 3-{2-(methylaminosulfonyl)amino-3-fluoropyridin-4-ylmethyl}-4-methyl-6-chloro-7-(thiazol-2-yloxy)-2-oxo-2H-1-benzopyran,
- 3-{2-(aminosulfonyl)amino-3-fluoropyridin-4-ylmethyl}-4-methyl-6-chloro-7-(thiazol-2-yloxy)-2-oxo-2H-1-benzopyran,
- 3-{2-(methylaminosulfonyl)amino-3-fluoropyridin-4-ylmethyl}-4-methyl-6-methyl-7-(thiazol-2-yloxy)-2-oxo-2H-1-benzopyran,
- 3-{2-(aminosulfonyl)amino-3-fluoropyridin-4-ylmethyl}-4-methyl-6-methyl-7-(thiazol-2-yloxy)-2-oxo-2H-1-benzopyran,
- 3-{2-chloro-3-(methylaminosulfonyl)aminobenzyl}-4-methyl-7-(thiazol-2-yloxy)-2-oxo-2H-1-benzopyran,
- 3-{2-chloro-3-(aminosulfonyl)aminobenzyl}-4-methyl-7-(thiazol-2-yloxy)-2-oxo-2H-1-benzopyran,
- 3-{2-methyl-3-(methylaminosulfonyl)aminobenzyl}-4-methyl-7-(thiazol-2-yloxy)-2-oxo-2H-1-benzopyran,
- 3-{2-methyl-3-(aminosulfonyl)aminobenzyl}-4-methyl-7-(thiazol-2-yloxy)-2-oxo-2H-1-benzopyran,
- 3-{2-(methylaminosulfonyl)aminopyridin-4-ylmethyl}-4-methyl-6-fluoro-7-(N-methylimidazol-2-yloxy)-2-oxo-2H-1-benzopyran,
- 3-{2-(aminosulfonyl)aminopyridin-4-ylmethyl}-4-methyl-6-fluoro-7-(N-methylimidazol-2-yloxy)-2-oxo-2H-1-benzopyran,
- 3-{2-(methylaminosulfonyl)aminopyridin-4-ylmethyl}-4-methyl-6-chloro-7-(N-methylimidazol-2-yloxy)-2-oxo-2H-1-benzopyran,
- 3-{2-(aminosulfonyl)aminopyridin-4-ylmethyl}-4-methyl-6-chloro-7-(N-methylimidazol-2-yloxy)-2-oxo-2H-1-benzopyran,
- 3-{2-(methylaminosulfonyl)aminopyridin-4-ylmethyl}-4-methyl-6-methyl-7-(N-methylimidazol-2-yloxy)-2-oxo-2H-1-benzopyran,
- 3-{2-(aminosulfonyl)aminopyridin-4-ylmethyl}-4-methyl-6-methyl-7-(N-methylimidazol-2-yloxy)-2-oxo-2H-1-benzopyran,
- 3-{2-(methylaminosulfonyl)amino-3-fluoropyridin-4-ylmethyl}-4-methyl-7-(N-methylimidazol-2-yloxy)-2-oxo-2H-1-benzopyran,
- 3-{2-(amino sulfonyl)amino-3-fluoropyridin-4-ylmethyl}-4-methyl-7-(N-methylimidazol-2-yloxy)-2-oxo-2H-1-benzopyran,
- 3-{2-(methylaminosulfonyl)amino-3-fluoropyridin-4-ylmethyl}-4-methyl-6-fluoro-7-(N-methylimidazol-2-yloxy)-2-oxo-2H-1-benzopyran,
- 3-{2-(aminosulfonyl)amino-3-fluoropyridin-4-ylmethyl}-4-methyl-6-fluoro-7-(N-methylimidazol-2-yloxy)-2-oxo-2H-1-benzopyran,
- 3-{2-(methylaminosulfonyl)amino-3-fluoropyridin-4-ylmethyl}-4-methyl-6-chloro-7-(N-methylimidazol-2-yloxy)-2-oxo-2H-1-benzopyran,
- 3-{2-(aminosulfonyl)amino-3-fluoropyridin-4-ylmethyl}-4-methyl-6-chloro-7-(N-methylimidazol-2-yloxy)-2-oxo-2H-1-benzopyran,
- 3-{2-(methylaminosulfonyl)amino-3-fluoropyridin-4-ylmethyl}-4-methyl-6-methyl-7-(N-methylimidazol-2-yloxy)-2-oxo-2H-1-benzopyran,
- 3-{2-(aminosulfonyl)amino-3-fluoropyridin-4-ylmethyl}-4-methyl-6-methyl-7-(N-methylimidazol-2-yloxy)-2-oxo-2H-1-benzopyran,
- 3-{2-chloro-3-(methylaminosulfonyl)aminobenzyl}-4-methyl-7-(N-methylimidazol-2-yloxy)-2-oxo-2H-1-benzopyran,
- 3-{2-chloro-3-(aminosulfonyl)aminobenzyl}-4-methyl-7-(N-methylimidazol-2-yloxy)-2-oxo-2H-1-benzopyran,
- 3-{2-methyl-3-(methylaminosulfonyl)aminobenzyl}-4-methyl-7-(N-methylimidazol-2-yloxy)-2-oxo-2H-1-benzopyran, 3-{2-methyl-3-(aminosulfonyl)aminobenzyl}-4-methyl-7-(N-methylimidazol-2-yloxy)-2-oxo-2H-1-benzopyran, 3-{2-fluoro-3-(methylaminosulfonyl)aminobenzyl}-4-methyl-7-(N-methylimidazol-2-yloxy)-2-oxo-2H-1-benzopyran, and 3-{2-fluoro-3-(aminosulfonyl)aminobenzyl}-4-methyl-7-(N-methylimidazol-2-yloxy)-2-oxo-2H-1-benzopyran.

The present invention includes pharmaceutically acceptable salts of compounds represented by general formula (11), preferably general formula (1). These salts are produced by contacting the compound with an acid or base usable for production of pharmaceutical products. Examples of the salts include: inorganic acid salts such as hydrochlorides, hydrobromides, hydroiodides, sulfates and phosphates; sulfonates such as methanesulfonates, benzenesulfonates and toluenesulfonates; carboxylates such as formates, acetates, oxalates, maleates, fumarates, citrates, malates, succinates, malonates, gluconates, mandelates, benzoates, salicylates, fluoroacetates, trifluoroacetates, tartrates, propionates and glutarates; alkali metal salts such as lithium salts, sodium salts, potassium salts, cesium salts and rubidium salts; alkaline earth metal salts such as magnesium salts and calcium salts; and ammonium salts such as ammonium salts, alkylammonium salts, dialkylammonium salts, trialkyl ammonium salts and tetraalkylammonium salts. Among them, alkali metal salts such as lithium salts, sodium salts, potassium salts, cesium salts and rubidium salts are preferred, and sodium salts and potassium salts are particularly preferred.

The compound or pharmaceutically acceptable salt thereof according to the present invention can be used for treatment of a cell proliferative disorder, particularly cancer, by appropriately administering to the patient a pharmaceutically effective amount thereof by itself or in the form of a pharmaceutical composition. As for the administration route, there may be used: systemic administration such as oral administration, rectal administration, intravenous administration, intramuscular administration, subcutaneous administration, intracisternal administration, vaginal administration, intraperitoneal administration, intravesical administration or inhalation administration; or topical administration in the form of an ointment, gel, cream or the like.

When the compound or pharmaceutically acceptable salt thereof according to the present invention is used in the form of a pharmaceutical composition, it is generally prepared as a certain formulation (dosage form). As for the formulation, there may be mentioned, for example, a tablet, a capsule, a granule, a powder, a fine granule, a pill, and an aqueous or nonaqueous solution and suspension. Furthermore, the compound or salt may be used in the form of various controlled-release formulations, and as for the controlled-release formulation, there may be mentioned, for example, a formulation used implanted in the body, and a formulation applied to the oral or nasal mucosa. The solution or suspension may be stored filled in a container suited for the preparation of a single dose.

Various formulations as mentioned above may be produced by a known method, by mixing the compound or salt with a pharmaceutically acceptable additive. As for the additive, there may be mentioned an excipient, a lubricant (coating agent), a binder, a disintegrant, a stabilizer, a flavoring agent, a base, a dispersant, a diluent, a surfactant, an emulsifier, and the like.

As for the excipient, there may be mentioned, for example, starches (starch, potato starch, maize starch and the like), lactose, crystalline cellulose, and calcium hydrogen phosphate.

As for the lubricant (coating agent), there may be mentioned, for example, ethyl cellulose, hydroxypropyl cellulose, hydroxypropylmethyl cellulose, shellac, talc, carnauba wax, and paraffin.

As for the binder, there may be mentioned, for example, polyvinylpyrrolidone and macrogol, as well as the same compounds as mentioned for the excipient.

As for the disintegrant, there may be mentioned, for example, chemically modified starches and celluloses, such as croscarmellose sodium, sodium carboxymethyl starch, and crosslinked polyvinylpyrrolidone, as well as the same compounds as mentioned for the excipient.

As for the stabilizer, there may be mentioned, for example: paraoxybenzoic acid esters such as methylparaben and propylparaben; benzalkonium chloride; phenols such as phenol and cresol; thimerosal; dehydroacetic acid; and sorbic acid.

As for the flavoring agent, there may be mentioned, for example, sweeteners, acidulants and fragrances which are commonly used.

As for the base, there may be mentioned, for example: fats such as lard; vegetable oils such as olive oil and sesame oil; higher alcohols such as stearyl alcohol and cetanol; animal oils; lanolin acid; vaseline; paraffins; bentonite; glycerine; and glycol oils.

As for the dispersant, there may be mentioned, for example, cellulose derivatives (gum arabic, tragacanth, methyl cellulose and the like), stearic acid polyesters, sorbitan sesquioleate, aluminum monostearate, sodium alginate, polysorbates, and sorbitan fatty acid esters.

As for the solvent or diluent in a liquid formulation, there may be mentioned, for example, phenol, chlorocresol, purified water and distilled water.

As for the surfactant or emulsifier, there may be mentioned, for example, polysorbate 80, polyoxyl 40 stearate, and lauromacrogol.

The preferred content of the compound or pharmaceutically acceptable salt thereof according to the present invention in the formulation varies depending on the dosage form, and is generally 0.01% to 100% by weight.

When the compound or pharmaceutically acceptable salt thereof according to the present invention is used as a therapeutic agent for a cell proliferative disorder, the dose can be appropriately determined depending on the severity of symptom, age, body weight, relative health condition, presence or absence of concomitant drugs, administration route, and the like. For example, when the subject is a warm-blooded animal, particularly human, the dose per kilogram of body weight per day for oral administration is preferably 0.00001 to 5000 mg, more preferably 0.0001 to 10 mg. The dose for parenteral administration is also preferably 0.00001 to 5000 mg, more preferably 0.0001 to 10 mg. The dose as mentioned above may be given once every day to once every 3 weeks, or daily in 2 to 4 divided doses.

As described above, the compound or pharmaceutically acceptable salt thereof and pharmaceutical composition according to the present invention may be used as a therapeutic agent for a cell proliferative disorder, particularly cancer. As for the cancer, there may be mentioned, for example: blood cancers and lymphoid cancers, such as leukemias (acute myelocytic leukemia, acute lymphocytic leukemia, chronic myelocytic leukemia, chronic lymphocytic leukemia, and the like), malignant lymphomas (Hodgkin's disease, non-Hodgkin's lymphoma, and the like), multiple myeloma, and myelodysplastic syndrome; and solid cancers, such as brain tumor, glioma, head and neck cancers (pharyngeal cancer, laryngeal cancer, tongue cancer, and the like), esophageal cancer, gastric cancer, colorectal cancer, lung cancer (small cell lung cancer, non-small cell lung cancer, or the like), thyroid cancer, breast cancer, gallbladder cancer, pancreatic cancer, liver cancer, prostate cancer, ovarian cancer, uterine cancer, testicular cancer, renal cell carcinoma, bladder cancer, renal pelvic and ureteral cancer, malignant melanoma, and skin cancer.

As examples of the compound or pharmaceutically acceptable salt thereof according to the invention, there may be mentioned compounds represented by the following formulas and their pharmaceutically acceptable salts:

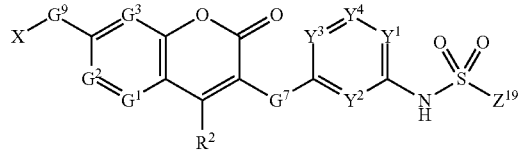

[where the combinations of $G^9$, $Y^1$, $Y^2$, $Y^3$, $Y^4$, $G^1$, $G^2$, $G^3$, $Z^{19}$, $G^7$ and $R^2$ are as listed in the table below.]

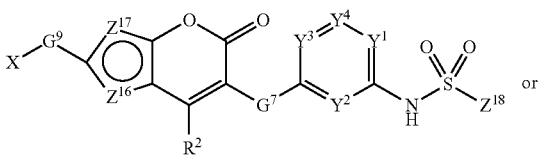

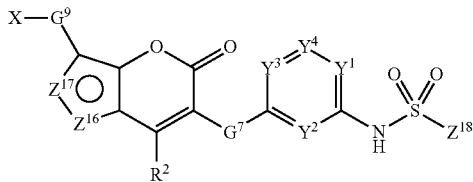

| X | $G^9$ | $Y^1$ | $Y^2$ | $Y^3$ | $Y^4$ | $G^1$ | $G^2$ | $G^3$ | $Z^{19}$ | $G^7$ | $R^2$ |
|---|---|---|---|---|---|---|---|---|---|---|---|
| $(CH_3)_2NCO$ | O | N | N | CH | CH | CH | CH | CH | $CH_2CH_2CH_3$ | $CH_2$ | $CH_3$ |
| $(CH_3)_2NCO$ | O | N | CH | CH | CH | CH | CH | CH | $CH_2CH_3$ | $CH_2$ | $CH_3$ |
| $(CH_3)_2NCO$ | O | N | CF | CH | CH | CH | N | CH | $CH_2CH_3$ | $CH_2$ | $CH_3$ |
| 2-Pyrimidinyl | O | N | CF | CH | CH | CH | CH | CH | $CH_2CH_3$ | $CH_2$ | $CH_3$ |
| 2-Pyrimidinyl | O | N | CF | CH | CH | CH | CF | CH | $CH_2CH_3$ | $CH_2$ | $CH_3$ |
| 2-Pyrimidinyl | O | N | CF | CH | CH | CH | $CCH_3$ | CH | $CH_2CH_3$ | $CH_2$ | $CH_3$ |
| 2-Pyrimidinyl | O | CH | CF | CH | CH | N | $CCH_3$ | CH | $CH_2CH_3$ | $CH_2$ | $CH_3$ |
| 2-Pyrimidinyl | O | CH | CF | CH | CH | CH | N | CH | $CH_2CH_3$ | $CH_2$ | $CH_3$ |
| 2-Pyrimidinyl | O | CH | CF | CH | CH | CH | N | N | $CH_2CH_3$ | $CH_2$ | $CH_3$ |
| 2-Pyrimidinyl | S | N | CH | CH | CH | CH | CH | CH | $CH_2CH_3$ | $CH_2$ | $CH_3$ |
| 2-Pyrimidinyl | NH | N | CH | CH | CH | CH | CH | CH | $CH_2CH_3$ | $CH_2$ | $CH_3$ |
| 2-Pyrimidinyl | $CF_2$ | N | CH | CH | CH | CH | CH | CH | $CH_2CH_3$ | $CH_2$ | $CH_3$ |
| 2-Thiazolyl | O | N | CF | CH | CH | CH | $CCH_3$ | CH | $CH_2CH_3$ | $CH_2$ | $CH_3$ |
| 2-Thiazolyl | O | N | N | CH | CH | CH | $CCH_3$ | CH | $CH_2CH_3$ | $CH_2$ | $CH_3$ |
| 2-Thiazolyl | O | CH | CF | CH | CH | N | CH | CH | $CH_2CH_3$ | $CH_2$ | $CH_3$ |
| 2-Thiazolyl | O | CH | CH | N | CH | CH | $CCH_3$ | CH | $CH_2CH_3$ | $CH_2$ | $CH_3$ |
| 2-Thiazolyl | O | CH | CF | CH | N | CH | $CCH_3$ | CH | $CH_2CH_3$ | $CH_2$ | $CH_3$ |
| 2-Thiazolyl | O | N | CF | CH | CH | CH | CH | CH | $CH_2CH_3$ | S | $CH_3$ |
| 2-N-Methyl imidazolyl | O | CH | CF | CH | CH | CH | N | CH | $CH_2CH_3$ | $CH_2$ | $CH_3$ |
| $(CH_3)_2NCO$ | O | N | CF | CH | CH | CH | $CCH_3$ | CH | $CH_2CONHCH_3$ | $CH_2$ | $CH_3$ |
| $(CH_3)_2NCO$ | O | N | CF | CH | CH | CH | $CCH_3$ | CH | $CH_3$ | $CH_2$ | $CH_3$ |
| $(CH_3)_2NCO$ | O | CH | CF | CH | N | CH | $CCH_3$ | CH | $CH_3$ | $CH_2$ | $CH_3$ |
| $(CH_3)_2NCO$ | O | CH | CF | CH | N | CH | CH | CH | $CH_3$ | $CH_2$ | $CH_2CH_3$ |
| $(CH_3)_2NCO$ | O | CH | CF | CH | CH | CH | N | CH | $CH_3$ | $CH_2$ | $CH_3$ |
| $(CH_3)_2NCO$ | S | N | CF | CH | CH | CH | CH | CH | $CH_3$ | $CH_2$ | $CH_3$ |
| $(CH_3)_2NCO$ | S | N | CF | CH | CH | CH | CH | CH | $CH_3$ | S | $CH_3$ |
| $(CH_3)_2NCO$ | NH | CH | CF | CH | CH | CH | CH | CH | $CH_3$ | O | $CH_3$ |
| 2-Thiazolyl | S | N | CF | CH | CH | CH | CH | CH | $CH_3$ | NH | $CH_3$ |
| 2-N-Methyl imidazolyl | O | N | CF | CH | CH | CH | CH | CH | $CH_3$ | $CH_2$ | $CH_3$ |

[where the combinations of $G^9, Y^1, Y^2, Y^3, Y^4, Z^{16}, Z^{17}, Z^{18}, G^7$ and $R^2$ are as listed in the table below.]

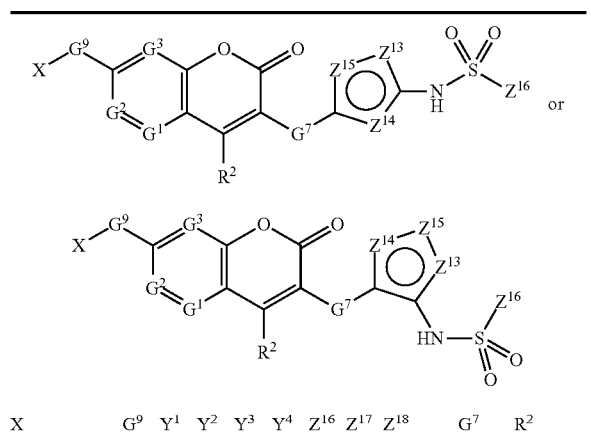

| X | $G^9$ | $Y^1$ | $Y^2$ | $Y^3$ | $Y^4$ | $Z^{16}$ | $Z^{17}$ | $Z^{18}$ | $G^7$ | $R^2$ |
|---|---|---|---|---|---|---|---|---|---|---|
| 2-Pyrimidinyl | O | CH | CH | CH | CH | CH | S | $CH_2CH_3$ | $CH_2$ | $CH_3$ |
| 2-Thiazolyl | O | CH | CH | CH | CH | CH | S | $CH_2CH_3$ | $CH_2$ | $CH_3$ |
| 2-Thiazolyl | O | N | CF | CH | CH | CH | S | $CH_2CH_3$ | $CH_2$ | $CH_3$ |
| 2-Thiazolyl | O | N | N | CH | CH | CH | S | $CH_2CH_3$ | $CH_2$ | $CH_3$ |
| $(CH_3)_2NCO$ | O | N | CF | CH | CH | CH | S | $CH_3$ | $CH_2$ | $CH_3$ |
| 2-Pyrimidinyl | O | CH | CF | CH | CH | S | CH | $CH_3$ | $CH_2$ | $CH_3$ |

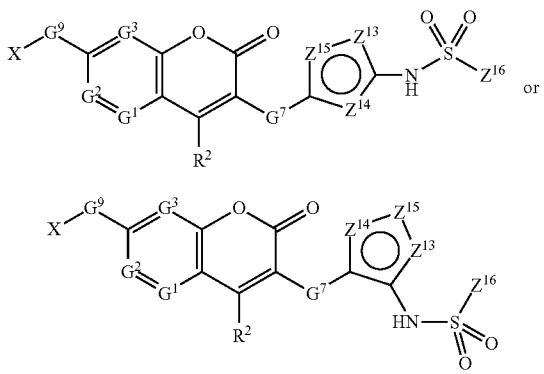

| X | $G^9$ | $Y^1$ | $Y^2$ | $Y^3$ | $Y^4$ | $Z^{16}$ | $Z^{17}$ | $Z^{18}$ | $G^7$ | $R^2$ |
|---|---|---|---|---|---|---|---|---|---|---|
| 2-Thiazolyl | O | CH | CH | CH | CH | S | CH | $CH_3$ | $CH_2$ | $CH_3$ |
| 2-Thiazolyl | O | N | CF | CH | CH | S | CH | $CH_3$ | $CH_2$ | $CH_3$ |
| 2-N-Methyl imidazolyl | O | CH | CF | CH | CH | NH | CH | $CH_3$ | $CH_2$ | $CH_3$ |
| 2-N-Methyl imidazolyl | O | N | CF | N | CH | CH | O | $CH_3$ | $CH_2$ | $CH_2CH_3$ |

[where the combinations of $G^9, Z^{13}, Z^{14}, Z^{15}, G^1, G^2, G^3, Z^{16}, G^7$ and $R^2$ are as listed in the table below.]

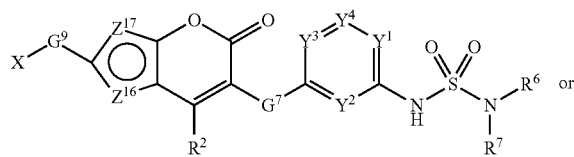

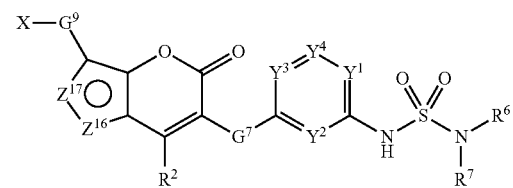

| X | $G^9$ | $Z^{13}$ | $Z^{14}$ | $Z^{15}$ | $G^1$ | $G^2$ | $G^3$ | $Z^{16}$ | $G^7$ | $R^2$ |
|---|---|---|---|---|---|---|---|---|---|---|
| $(CH_3)_2NCO$ | O | CH | S | CH | CH | CH | CH | $CH_2CH_3$ | $CH_2$ | $CH_3$ |
| $(CH_3)_2NCO$ | O | N | CH | NH | CH | CH | CH | $CH_2CH_3$ | $CH_2$ | $CH_3$ |
| 2-Thiazolyl | O | CH | S | CH | CH | CH | CH | $CH_2CH_3$ | O | $CH_3$ |
| 2-Thiazolyl | O | CH | S | CH | N | CH | CH | $CH_2CH_3$ | $CH_2$ | $CH_3$ |
| $(CH_3)_2NCO$ | O | S | CH | CH | CH | N | CH | $CH_3$ | $CH_2$ | $CH_3$ |
| $(CH_3)_2NCO$ | NH | CH | S | CH | CH | N | CH | $CH_3$ | $CH_2$ | $CH_3$ |
| 2-Pyrimidinyl | O | S | CH | CH | CH | CH | CH | $CH_3$ | $CH_2$ | $CH_3$ |
| 2-Pyrimidinyl | O | CH | O | CH | CH | CH | CH | $CH_3$ | $CH_2$ | $CH_3$ |
| 2-Pyrimidinyl | O | CH | CH | NH | CH | CH | CH | $CH_3$ | $CH_2$ | $CH_3$ |
| 2-Thiazolyl | O | S | CH | CH | CH | CH | CH | $CH_3$ | $CH_2$ | $CH_2CH_3$ |
| 2-Thiazolyl | O | CH | CH | S | CH | CH | CH | $CH_3$ | $CH_2$ | $CH_3$ |
| 2-Thiazolyl | O | S | CH | CH | CH | N | CH | $CH_3$ | S | $CH_2CH_3$ |
| 2-N-Methyl imidazolyl | O | CH | S | CH | CH | N | CH | $CH_3$ | $CH_2$ | $CH_3$ |

[where the combinations of $G^9$, $Y^1$, $Y^2$, $Y^3$, $Y^4$, $Z^{16}$, $Z^{17}$, $NR^6R^7$, $G^7$ and $R^2$ are as listed in the table below.]

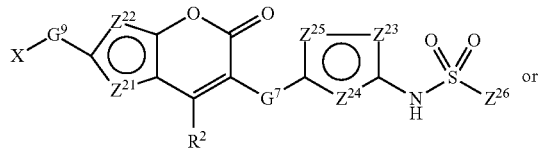

or

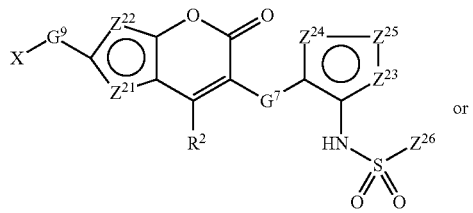

or

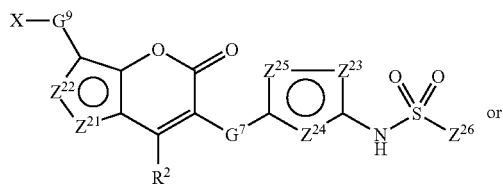

or

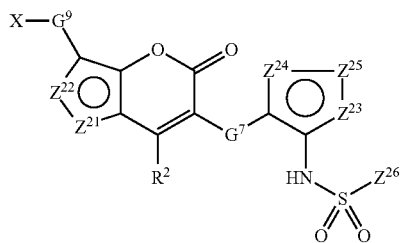

| X | $G^9$ | $Y^1$ | $Y^2$ | $Y^3$ | $Y^4$ | $Z^{16}$ | $Z^{17}$ | $NR^6R^7$ | $G^7$ | $R^2$ |
|---|---|---|---|---|---|---|---|---|---|---|
| 2-Thiazolyl | O | CH | CH | CH | CH | S | CH | $N(CH_3)_2$ | $CH_2$ | $CH_3$ |
| 2-Thiazolyl | O | CH | CH | CH | CH | CH | S | $NH_2$ | $CH_2$ | $CH_3$ |
| $(CH_3)_2NCO$ | O | CH | CH | CH | CH | S | CH | $NHCH_3$ | $CH_2$ | $CH_3$ |
| $(CH_3)_2NCO$ | O | CH | CH | CH | CH | CH | S | $NHCH_3$ | $CH_2$ | $CH_3$ |
| $(CH_3)_2NCO$ | O | N | CF | CH | CH | CH | S | $NHCH_3$ | $CH_2$ | $CH_3$ |
| $(CH_3)_2NCO$ | O | N | CH | CH | CH | NH | CH | $NHCH_3$ | $CH_2$ | $CH_3$ |
| $(CH_3)_2NCO$ | O | CH | CH | CH | CH | CH | NH | $NHCH_3$ | $CH_2$ | $CH_3$ |
| $(CH_3)_2NCO$ | O | CH | CH | CH | CH | O | CH | $NHCH_3$ | $CH_2$ | $CH_3$ |
| $(CH_3)_2NCO$ | O | N | CF | CH | CH | CH | O | $NHCH_3$ | $CH_2$ | $CH_3$ |
| $(CH_3)_2NCO$ | S | CH | CH | CH | CH | S | CH | $NHCH_3$ | $CH_2$ | $CH_3$ |
| $(CH_3)_2NCO$ | S | CH | CH | CH | CH | CH | S | $NHCH_3$ | $CH_2$ | $CH_3$ |
| $(CH_3)_2NCO$ | NH | CH | CH | CH | CH | S | CH | $NHCH_3$ | $CH_2$ | $CH_2CH_3$ |
| $(CH_3)_2NCO$ | NH | CH | CF | CH | CH | CH | S | $NHCH_3$ | $CH_2$ | $CH_3$ |
| $(CH_3)_2NCO$ | O | CH | CH | CH | CH | S | N | $NHCH_3$ | $CH_2$ | $CH_3$ |
| $(CH_3)_2NCO$ | O | CH | CH | CH | CH | N | S | $NHCH_3$ | $CH_2$ | $CH_3$ |
| $(CH_3)_2NCO$ | O | CH | CH | CH | CH | N | N | $NHCH_3$ | $CH_2$ | $CH_2CH_3$ |
| $(CH_3)_2NCO$ | O | CH | CH | CH | N | N | N | $NHCH_3$ | $CH_2$ | $CH_3$ |
| 2-Pyrimidinyl | O | CH | CF | CH | CH | S | CH | $NHCH_3$ | $CH_2$ | $CH_3$ |
| 2-Pyrimidinyl | O | CH | CH | CH | CH | CH | S | $NHCH_3$ | $CH_2$ | $CH_3$ |
| 2-Pyrimidinyl | O | CH | CH | CH | CH | S | CH | $NHCH_3$ | O | $CH_3$ |
| 2-Pyrimidinyl | O | CH | CH | CH | CH | CH | S | $NHCH_3$ | S | $CH_3$ |
| 2-Pyrimidinyl | O | N | CH | CH | CH | S | CH | $NHCH_3$ | $CH_2$ | $CH_3$ |
| 2-Pyrimidinyl | O | N | CF | CH | CH | CH | S | $NHCH_3$ | $CH_2$ | $CH_3$ |
| 2-Pyrimidinyl | S | CH | CH | CH | CH | $NCH_3$ | CH | $NHCH_3$ | $CH_2$ | $CH_2CH_3$ |
| 2-Pyrimidinyl | NH | CH | CH | CH | CH | CH | $NCH_3$ | $NHCH_3$ | $CH_2$ | $CH_3$ |
| 2-Thiazolyl | O | N | CF | CH | CH | O | CH | $NHCH_3$ | $CH_2$ | $CH_3$ |
| 2-Thiazolyl | O | N | N | CH | CH | CH | O | $NHCH_3$ | $CH_2$ | $CH_2CH_3$ |
| 2-Thiazolyl | O | N | N | N | CH | CH | S | $NHCH_3$ | $CH_2$ | $CH_3$ |
| 2-N-Methyl imidazolyl | O | N | CF | CH | CH | CH | S | $NHCH_3$ | $CH_2$ | $CH_3$ |
| 2-N-Methyl imidazolyl | O | N | CF | CH | CH | CH | S | $NHCH_3$ | O | $CH_3$ |

[where the combinations of $G^9$, $Z^{23}$, $Z^{24}$, $Z^{25}$, $Z^{21}$, $Z^{22}$, $Z^{26}$, $Z^7$ and $R^2$ are as listed in the table below.]

| X | $G^9$ | $Z^{23}$ | $Z^{24}$ | $Z^{25}$ | $Z^{21}$ | $Z^{22}$ | $Z^{26}$ | $G^7$ | $R^2$ |
|---|---|---|---|---|---|---|---|---|---|
| $(CH_3)_2NCO$ | O | S | CH | CH | S | CH | $NHCH_3$ | $CH_2$ | $CH_3$ |
| $(CH_3)_2NCO$ | O | S | CH | CH | S | CH | $CH_2CONHCH_3$ | $CH_2$ | $CH_3$ |
| $(CH_3)_2NCO$ | O | S | CH | CH | S | CH | $CH_2CH_3$ | $CH_2$ | $CH_3$ |
| $(CH_3)_2NCO$ | O | S | CH | CH | S | CH | $CH_2CH_2OH$ | $CH_2$ | $CH_3$ |
| $(CH_3)_2NCO$ | O | S | CH | CH | CH | S | $NHCH_3$ | $CH_2$ | $CH_3$ |
| $(CH_3)_2NCO$ | O | CH | S | CH | S | CH | $NHCH_3$ | $CH_2$ | $CH_3$ |
| $(CH_3)_2NCO$ | O | CH | S | CH | CH | S | $NHCH_3$ | $CH_2$ | $CH_3$ |
| $(CH_3)_2NCO$ | O | CH | CH | S | S | CH | $NHCH_3$ | $CH_2$ | $CH_3$ |
| $(CH_3)_2NCO$ | O | CH | CH | S | CH | S | $NHCH_3$ | $CH_2$ | $CH_3$ |
| $(CH_3)_2NCO$ | O | NH | CH | CH | S | CH | $NHCH_3$ | $CH_2$ | $CH_3$ |
| $(CH_3)_2NCO$ | O | NH | CH | CH | S | CH | $CH_2CONHCH_3$ | $CH_2$ | $CH_3$ |
| $(CH_3)_2NCO$ | O | $NCH_3$ | CH | CH | S | CH | $CH_2CH_3$ | $CH_2$ | $CH_3$ |
| $(CH_3)_2NCO$ | O | NH | CH | CH | S | CH | $CH_2CH_2OH$ | $CH_2$ | $CH_3$ |
| $(CH_3)_2NCO$ | O | NH | CH | CH | CH | S | $NHCH_3$ | $CH_2$ | $CH_3$ |
| $(CH_3)_2NCO$ | O | NH | CH | CH | CH | S | $CH_3$ | $CH_2$ | $CH_3$ |
| $(CH_3)_2NCO$ | O | CH | NH | CH | S | CH | $NHCH_3$ | $CH_2$ | $CH_3$ |
| $(CH_3)_2NCO$ | O | CH | NH | CH | S | CH | $CH_2CH_3$ | $CH_2$ | $CH_3$ |
| $(CH_3)_2NCO$ | O | CH | NH | CH | CH | S | $NHCH_3$ | $CH_2$ | $CH_3$ |
| $(CH_3)_2NCO$ | O | CH | NH | CH | CH | S | $CH_2CONHCH_3$ | $CH_2$ | $CH_3$ |
| $(CH_3)_2NCO$ | O | CH | CH | NH | S | CH | $NHCH_3$ | $CH_2$ | $CH_3$ |
| $(CH_3)_2NCO$ | O | CH | CH | NH | S | CH | $CH_2CH_3$ | $CH_2$ | $CH_3$ |
| $(CH_3)_2NCO$ | O | CH | CH | NH | CH | S | $NHCH_3$ | $CH_2$ | $CH_3$ |
| 2-Pyrimidinyl | O | S | CH | CH | S | CH | $NHCH_3$ | $CH_2$ | $CH_3$ |
| 2-Pyrimidinyl | O | S | CH | CH | CH | S | $NHCH_3$ | $CH_2$ | $CH_3$ |
| 2-Pyrimidinyl | O | S | NH | CH | S | CH | $NHCH_3$ | $CH_2$ | $CH_3$ |
| 2-Pyrimidinyl | O | S | NH | CH | CH | S | $NHCH_3$ | $CH_2$ | $CH_3$ |
| 2-Pyrimidinyl | O | S | CH | CH | S | N | $NHCH_3$ | $CH_2$ | $CH_3$ |
| 2-Pyrimidinyl | O | S | CH | CH | N | S | $NHCH_3$ | $CH_2$ | $CH_3$ |
| 2-Pyrimidinyl | O | NH | S | CH | S | CH | $NHCH_3$ | $CH_2$ | $CH_3$ |
| 2-Pyrimidinyl | O | NH | S | CH | CH | S | $NHCH_3$ | $CH_2$ | $CH_3$ |
| 2-Pyrimidinyl | O | N | CH | NH | S | CH | $NHCH_3$ | $CH_2$ | $CH_3$ |
| 2-Pyrimidinyl | O | N | CH | $NCH_3$ | CH | S | $NHCH_3$ | $CH_2$ | $CH_3$ |
| 2-Pyrimidinyl | O | S | CH | CH | S | CH | $CH_3$ | $CH_2$ | $CH_3$ |
| 2-Pyrimidinyl | O | S | CH | CH | CH | S | $CH_2CH_3$ | $CH_2$ | $CH_3$ |
| 2-Pyrimidinyl | O | S | NH | CH | S | CH | $CH_2CH_2OH$ | $CH_2$ | $CH_3$ |
| 2-Pyrimidinyl | O | S | NH | CH | CH | S | $CH_2CONHCH_3$ | $CH_2$ | $CH_3$ |
| 2-Pyrimidinyl | O | S | CH | CH | S | N | $CH_2CH_3$ | $CH_2$ | $CH_3$ |
| 2-Pyrimidinyl | O | S | CH | CH | N | S | $CH_2CH_3$ | $CH_2$ | $CH_3$ |
| 2-Pyrimidinyl | O | NH | S | CH | S | CH | $CH_2CH_3$ | $CH_2$ | $CH_3$ |
| 2-Pyrimidinyl | O | NH | S | CH | CH | S | $CH_2CH_3$ | $CH_2$ | $CH_3$ |
| 2-Pyrimidinyl | O | N | CH | NH | S | CH | $CH_2CH_3$ | $CH_2$ | $CH_3$ |
| 2-Pyrimidinyl | O | N | CH | $NCH_3$ | CH | S | $CH_2CH_3$ | $CH_2$ | $CH_3$ |
| 2-Thiazolyl | O | CH | O | CH | S | CH | $NHCH_3$ | $CH_2$ | $CH_3$ |
| 2-Thiazolyl | O | CH | O | CH | S | CH | $NHCH_3$ | $CH_2$ | $CH_3$ |
| 2-Thiazolyl | O | NH | O | CH | S | CH | $NHCH_3$ | $CH_2$ | $CH_3$ |
| 2-Thiazolyl | O | NH | O | CH | S | CH | $NHCH_3$ | $CH_2$ | $CH_3$ |
| 2-Thiazolyl | O | N | CH | NH | S | CH | $NHCH_3$ | $CH_2$ | $CH_3$ |
| 2-Thiazolyl | O | N | CH | NH | S | CH | $NHCH_3$ | $CH_2$ | $CH_3$ |
| 2-Thiazolyl | O | CH | O | CH | NH | CH | $NHCH_3$ | $CH_2$ | $CH_3$ |
| 2-Thiazolyl | O | CH | O | CH | $NCH_3$ | CH | $NHCH_3$ | $CH_2$ | $CH_3$ |
| 2-Thiazolyl | S | CH | O | CH | S | CH | $NHCH_3$ | $CH_2$ | $CH_3$ |
| 2-Thiazolyl | NH | CH | O | CH | S | CH | $NHCH_3$ | $CH_2$ | $CH_3$ |
| 2-Thiazolyl | $CH_2$ | NH | O | CH | S | CH | $NHCH_3$ | $CH_2$ | $CH_3$ |
| 2-Thiazolyl | $CF_2$ | NH | O | CH | S | CH | $NHCH_3$ | $CH_2$ | $CH_3$ |
| 2-Thiazolyl | S | N | CH | NH | S | CH | $NHCH_3$ | $CH_2$ | $CH_3$ |
| 2-Thiazolyl | S | N | CH | NH | S | CH | $NHCH_3$ | $CH_2$ | $CH_3$ |
| 2-Thiazolyl | NH | CH | O | CH | NH | CH | $NHCH_3$ | $CH_2$ | $CH_3$ |
| 2-Thiazolyl | SO | CH | O | CH | $NCH_3$ | CH | $NHCH_3$ | $CH_2$ | $CH_3$ |
| 2-Thiazolyl | O | CH | O | CH | S | CH | $NHCH_3$ | S | $CH_3$ |
| 2-Thiazolyl | O | CH | O | CH | S | CH | $NHCH_3$ | NH | $CH_3$ |
| 2-Thiazolyl | O | NH | O | CH | S | CH | $NHCH_3$ | O | $CH_3$ |
| 2-Thiazolyl | O | NH | O | CH | S | CH | $CH_3$ | $CH_2$ | $CH_3$ |
| 2-Thiazolyl | O | N | CH | NH | S | CH | $CH_2CH_3$ | $CH_2$ | $CH_3$ |
| 2-Thiazolyl | O | N | CH | NH | S | CH | $CH_2CH_2OH$ | $CH_2$ | $CH_3$ |
| 2-Thiazolyl | O | CH | O | CH | NH | CH | $CH_2CONHCH_3$ | $CH_2$ | $CH_3$ |

-continued

| X | $G^9$ | $Z^{23}$ | $Z^{24}$ | $Z^{25}$ | $Z^{21}$ | $Z^{22}$ | $Z^{26}$ | $G^7$ | $R^2$ |
|---|---|---|---|---|---|---|---|---|---|
| 2-Thiazolyl | O | CH | O | CH | $NCH_3$ | CH | $CH_2CH_3$ | $CH_2$ | $CH_3$ |
| 2-N-Methyl imidazolyl | O | NH | CH | CH | CH | S | $NHCH_3$ | $CH_2$ | $CH_3$ |
| 2-N-Methyl imidazolyl | O | S | CH | CH | CH | NH | $NHCH_3$ | $CH_2$ | $CH_3$ |
| 2-N-Methyl imidazolyl | O | CH | S | CH | CH | NH | $NHCH_3$ | $CH_2$ | $CH_3$ |
| 2-N-Methyl imidazolyl | O | CH | CH | S | CH | NH | $NHCH_3$ | $CH_2$ | $CH_3$ |
| 2-N-Methyl imidazolyl | O | S | CH | CH | N | NH | $NHCH_3$ | $CH_2$ | $CH_3$ |
| 2-N-Methyl imidazolyl | O | CH | S | CH | N | NH | $NHCH_3$ | $CH_2$ | $CH_3$ |
| 2-N-Methyl imidazolyl | O | CH | CH | S | N | NH | $NHCH_3$ | $CH_2$ | $CH_3$ |
| 2-N-Methyl imidazolyl | O | NH | CH | CH | CH | S | $CH_3$ | $CH_2$ | $CH_3$ |
| 2-N-Methyl imidazolyl | O | S | CH | CH | CH | NH | $CH_2CH_3$ | $CH_2$ | $CH_3$ |
| 2-N-Methyl imidazolyl | O | CH | S | CH | CH | NH | $CH_2CH_2OH$ | $CH_2$ | $CH_3$ |
| 2-N-Methyl imidazolyl | O | CH | CH | S | CH | NH | $CH_2CONHCH_3$ | $CH_2$ | $CH_3$ |
| 2-N-Methyl imidazolyl | O | S | CH | CH | N | NH | $CH_2CH_3$ | $CH_2$ | $CH_3$ |
| 2-N-Methyl imidazolyl | O | N | S | CH | N | NH | $NHCH_3$ | $CH_2$ | $CH_3$ |

Exemplified embodiments of the present invention will now be described more specifically based on examples (manufacturing examples and testing examples).

MANUFACTURING EXAMPLES

In the following manufacturing examples (synthetic examples), NMR analysis was performed using JNM-EX270 (270 MHz) manufactured by JEOL, JNM-GSX400 (400 MHz) manufactured by the same, or ARX-300 (300 MHz) manufactured by Broker, NMR data were shown in ppm (parts per million, δ), and the deuterium lock signal from the sample solvent was used as a reference.

Further, mass spectral data were obtained using JMS-DX303 manufactured by JEOL, or IMS-SX/SX102A manufactured by the same, or using Micromass (Navigator manufactured by Finningan) equipped with gradient high performance liquid chromatograph Agilent 1100 manufactured by Agilent Technologies.

When reagents available on the market were used, they were used directly in the reaction without pretreatment such as distillation or recrystallization. The used reaction solvents were anhydrous when they are available on the market.

In the meantime, all chemical reactions were performed under nitrogen atmosphere.

As used herein, "solvent was distilled away" means that solvent was distilled under reduced pressure using a rotary evaporator.

When a compound of sufficiently high purity cannot be obtained by standard synthesis protocols, separation and purification by silica gel chromatography, alumina gel chromatography or the like may be carried out as necessary to obtain a compound of higher purity.

(General Process-1)

First, manufacturing examples associated with General process-1 previously mentioned will be explained.

Compound 1c-2

2-(2-Fluoro-3-nitrobenzyl)-3-oxobutanoic acid ethyl ester

[Chemical Formula 11]

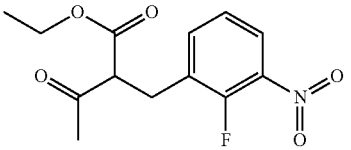

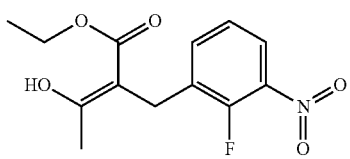

Ethyl acetoacetate (37.4 mL, 294 mmol) was added at 0° C. to a suspension of sodium hydride (65%, 10.8 g) in THF (600 mL), and the mixture was stirred at 0° C. for 30 minutes. It was added dropwise at 0° C. to a solution of 1-bromomethyl-2-fluoro-3-nitrobenzene (compound 1a-1) (68.7 g, 294 mmol) in THF (400 mL), and the reaction mixture was stirred at room temperature overnight. The reaction mixture was then poured into 0.5N hydrochloric acid and extracted with ethyl acetate. The organic extract was washed with saturated saline and dried over magnesium sulfate. A crude product was obtained by vacuum concentration, and purified by column chromatography (ethyl acetate:hexane=1:3) to yield the title compound (52.2 g, 63%) as a yellow oil.

$^1$H NMR (DMSO-$d_6$, 270 MHz) (ketone body) δ (ppm): 8.01 (td, J=7.6, 1.9 Hz, 1H), 7.72 (td, J=7.2, 1.9 Hz, 1H), 7.37

(td, J=7.5, 1.1 Hz, 1H), 4.11 (m, 1H), 4.07 (qd, J=7.0, 1.0 Hz, 2H), 3.16 (t, J=7.3 Hz, 2H), 2.23 (s, 3H), 1.10 (t, J=7.0 Hz, 3H).

ESIMS m/z: 284 (M+H).

Compound 1c-1

2-(3-Nitrobenzyl)-3-oxobutanoic acid ethyl ester

[Chemical Formula 12]

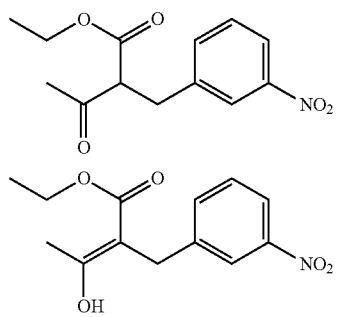

The title compound was synthesized under the same conditions as in the manufacturing example for compound 1c-2, except that 1-bromomethyl-3-nitrobenzene was used instead of 1-bromomethyl-2-fluoro-3-nitrobenzene.

$^1$H NMR (DMSO-$d_6$, 270 MHz) δ (ppm): 1.08 (3H, t, J=6.8 Hz), 2.25 (3H, s), 3.17 (2H, m), 4.05 (2H, qd, J=6.8, 2.7 Hz), 4.16 (1H, m), 7.58 (1H, dd, J=8.1 Hz), 7.71 (1H, d, J=8.1 Hz), 8.08 (1H, d, J=8.1 Hz), 8.14 (1H, s).

ESI (LC/MS positive mode) m/z: 266 (M+H).

Compound 1c-3

2-(2-Methyl-3-nitrobenzyl)-3-oxobutanoic acid ethyl ester

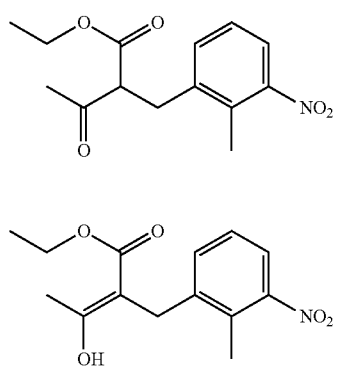

The title compound was synthesized under the same conditions as in the manufacturing example for compound 1c-2, except that 1-chloromethyl-2-methyl-3-nitrobenzene was used instead of 1-bromomethyl-2-fluoro-3-nitrobenzene.

$^1$H NMR (Bruker, 300 MHz, CDCl$_3$) δ (ppm): 7.62 (1H, d, J=8.0 Hz), 7.37 (1H, d, J=7.2 Hz), 7.23 (1H, m), 4.16 (2H, q), 3.73 (1H, t, J=7.4 Hz), 3.28 (2H, m), 2.43 (3H, s), 2.24 (3H, s), 1.21 (3H, t, J=7.1 Hz).

Compound 1c-46

2-(4-Nitrobenzyl)-3-oxobutanoic acid ethyl ester

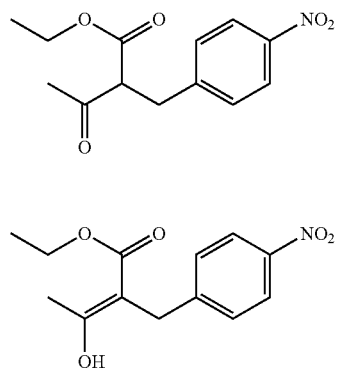

The title compound was synthesized under the same conditions as in the manufacturing example for compound 1c-2, except that 1-bromomethyl-4-nitrobenzene was used instead of 1-bromomethyl-2-fluoro-3-nitrobenzene.

$^1$H-NMR (Bruker, 300 MHz, CDCl$_3$) δ (ppm): 8.14 (2H, d, J=8.7 Hz), 7.36 (2H, d, J=8.7 Hz), 4.17 (2H, m), 3.79 (1H, t, J=7.6 Hz), 3.25 (2H, m), 2.24 (3H, s), 1.22 (3H, m).

Compound 1c-45

2-(2-Nitrobenzyl)-3-oxobutanoic acid ethyl ester

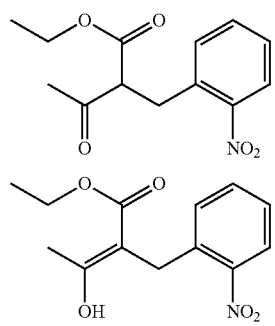

The title compound was synthesized under the same conditions as in the manufacturing example for compound 1c-2, except that 1-bromomethyl-2-nitrobenzene was used instead of 1-bromomethyl-2-fluoro-3-nitrobenzene.

$^1$H-NMR (Bruker, 300 MHz, CDCl$_3$) δ (ppm): 8.00 (1H, d, J=8.4 Hz), 7.52-7.42 (3H, m), 4.22-4.09 (2H, m), 4.01 (1H, q), 3.54-3.32 (2H, m), 2.28 (3H, s), 1.20 (3H, t, J=7.1 Hz).

Compound 1c-36

2-(4-Fluoro-3-nitrobenzyl)-3-oxobutanoic acid ethyl ester

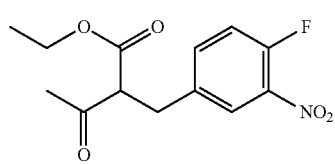

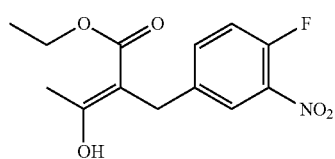

The title compound was synthesized under the same conditions as in the manufacturing example for compound 1c-2, except that 1-bromomethyl-3-nitro-4-fluorobenzene was used instead of 1-bromomethyl-2-fluoro-3-nitrobenzene.

$^1$H NMR (270 MHz, DMSO-d$_6$) δ (ppm): 8.07 (dd, 1H, J=7.1, 2.2 Hz), 7.67 (m, 1H), 7.52 (dd, 1H, J=10.7, 8.6 Hz), 4.11 (m, 1H), 4.07 (q, 2H, J=7.0 Hz), 3.20 (m, 2H), 2.21 (s, 3H), 1.13 (t, 3H, J=7.0 Hz).

ESIMS m/z: 284 (M+H).

Compound 1c-51a 3-(Methoxycarbonylhydrazono)-2-(3-nitrophenylamino)butanoic acid ethyl ester

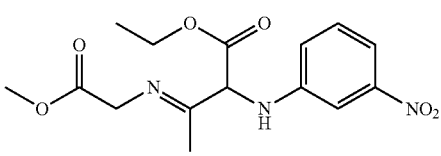

3-Nitroaniline (2.92 g, 21.27 mmol) was added to a solution of ethyl 3-carbomethoxyazocrotonate (4.2 g, 21.13 mmol) (which is known in the literature) in THF (40 mL), and the mixture was stirred at 70° C. for a day and a night. After cooling to room temperature, hexane was added thereto, and the deposited precipitate was filtered out to yield the title compound (5.08 g, 71%).

$^1$H NMR (270 MHz, DMSO-d$_6$) δ (ppm): 10.10 (s, 1H), 7.55 (s, 1H), 7.46-7.31 (m, 2H), 7.11 (d, 1H, J=8.1 Hz), 6.96 (d, 1H, J=7.4 Hz), 4.94 (d, 1H, J=7.7 Hz), 4.18 (q, 2H, J=7.1 Hz), 3.67 (s, 3H), 1.83 (s, 3H), 1.21 (t, 3H, J=7.1 Hz).

ESIMS m/z: 339 (M+H).

Compound 1c-51

2-(3-Nitrophenylamino)-3-oxobutanoic acid ethyl ester

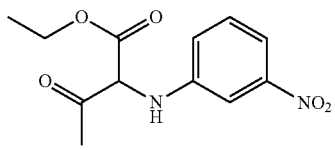

Titanium trichloride (10% solution in 20-30% HCl) was added to a solution of 3-(methoxycarbonylhydrazono)-2-(3-nitrophenylamino)butyric acid ethyl ester (compound 1c-51a) (5.0 g, 14.78 mmol) in acetone (50 mL), and the mixture was stirred at room temperature for 1 hour. Water was then added to the reaction mixture, extraction was performed with ethyl acetate, and the organic extract was washed with water and saturated saline. After drying over magnesium sulfate, it was concentrated under reduced pressure to yield a crude product, which was then purified by column chromatography to yield the title compound (3.75 g, 95%) as a yellow oil.

$^1$H NMR (270 MHz, DMSO-d$_6$) (2:1 mixture of keto and enol forms) δ (ppm): 12.37 (s, 1/3H), 7.53 (t, 2/3H, J=2.2 Hz), 7.47-7.37 (m, 10/3H), 7.27 (t, 1/3H, J=2.2 Hz), 7.13 (m, 2/3H), 7.05 (d, 2/3H, J=8.6 Hz), 6.92 (d, 1/3H, J=9.1 Hz), 5.35 (d, 2/3H, J=8.6 Hz), 4.25-4.11 (m, 6/3H), 2.31 (s, 6/3H), 1.99 (s, 3/3H), 1.21 (t, 6/3H, J=7.1 Hz), 1.08 (t, 3/3H, J=7.1 Hz).

ESIMS m/z: 267 (M+H).

Compound 1c-59

2-(2-Nitrobenzoylamino)-3-oxobutanoic acid ethyl ester (Known Compound)

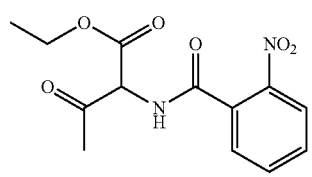

Rh$_2$(OAc)$_4$ (30 mg, 0.063 mmol) was added to a solution of ethyl diazoacetoacetate (1.0 g, 6.32 mmol) and 2-nitrobenzamide (1.05 g, 6.32 mmol) in methylene chloride (15 mL), and the mixture was stirred at 40° C. for a day and a night. Water was then added to the reaction mixture, extraction was performed with ethyl acetate, and the organic extract was washed with water and saturated saline. After drying over magnesium sulfate, it was concentrated under reduced pressure to yield a crude product, which was then purified by column chromatography to yield the title compound (1.42 g, 77%) as a yellow oil.

$^1$H NMR (270 MHz, DMSO-d$_6$) δ (ppm): 9.58 (d, 1H, J=7.4 Hz), 8.09 (d, 1H, J=7.9 Hz), 7.84 (td, 1H, J=7.5, 0.5 Hz), 7.73 (td, 1H, J=7.8, 1.2 Hz), 7.63 (dd, 1H, J=7.4, 1.5 Hz), 5.39 (d, 1H, J=7.6 Hz), 4.21 (m, 2H), 2.30 (s, 3H), 1.24 (t, 3H, J=7.3 Hz).

ESIMS m/z: 295 (M+H).

Compound 1c-73

2-(5-Nitro-thiophen-2-ylmethyl)-3-oxobutanoic acid ethyl ester

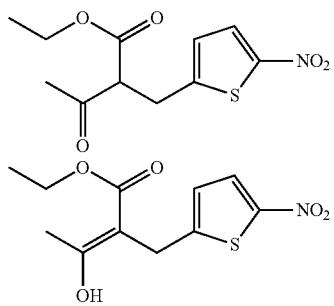

Ethyl acetoacetate (0.64 mL, 5.06 mmol) was added to a mixture of sodium iodide (379 mg, 2.53 mmol) with tetrahydrofuran. A solution of 1 M LiOtBu in THF (3.03 mL, 3.03 mmol) was added thereto at 4° C., and the mixture was stirred for 30 minutes. A solution of compound 1a-73 (600 mg, 2.53 mmol) in tetrahydrofuran (2.0 mL) was then added at 4° C., and the mixture was raised to room temperature and stirred for 22 hours. Water (20 mL) was added, and the organic layer was extracted with ethyl acetate. It was then purified by silica gel chromatography (hexane:ethyl acetate=6:1) to yield the title compound (623 mg, 91%).

$^1$H-NMR (Bruker (ARX300), 300 MHz, CDCl$_3$) δ (ppm): 7.79 (1H, d, J=4.20 Hz), 6.85 (1H, d, J=4.20 Hz), 4.27 (2H, q), 3.84 (1H, t, J=6.87 Hz), 3.41 (2H, dd, J=6.87, 7.25 Hz), 2.34 (3H, s), 1.32 (3H, t, J=6.87 Hz).

Compound 1e-0-4

3-(2-Fluoro-3-nitrobenzyl)-7-hydroxy-4-methyl-2-oxo-2H-1-benzopyran

[Chemical Formula 13]

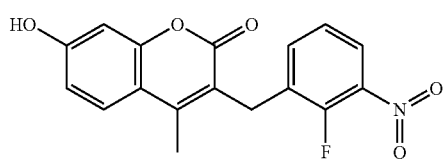

Concentrated sulfuric acid (21.5 mL) was added at 0° C. to a mixture of resorcinol (14.8 g, 135 mmol) and 2-(2-fluoro-3-nitrobenzyl)-3-oxobutanoic acid ethyl ester (38.2 g, 135 mmol), and the reaction mixture was stirred at room temperature overnight. The reaction mixture was then poured into water, and the solid was filtered off. It was washed with water and methanol to yield the title compound (28.3 g, 64%) as a pale yellow powder.

$^1$H NMR (DMSO-d$_6$, 270 MHz) δ (ppm): 7.98 (td, J=8.9, 1.6 Hz, 1H), 7.69 (d, J=8.9 Hz, 1H), 7.58 (td, J=6.2, 4.3 Hz, 1H), 7.32 (td, J=8.9, 1.1 Hz, 1H), 6.83 (dd, J=8.9, 2.4 Hz, 1H), 6.72 (d, J=2.4 Hz, 1H), 4.02 (s, 2H), 2.43 (s, 3H).

ESIMS m/z: 330 (M+H).

Compound 1e-0-1

3-(3-Nitrobenzyl)-7-hydroxy-4-methyl-2-oxo-2H-1-benzopyran

[Chemical Formula 14]

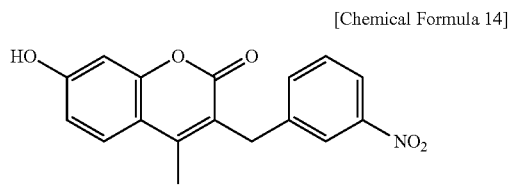

The title compound was synthesized using resorcinol and compound 1c-1 under the same conditions as in the manufacturing example for compound 1e-0-4.

$^1$H NMR (DMSO-d$_6$, 270 MHz) δ (ppm): 2.44 (3H, s), 4.08 (2H, s), 6.72 (1H, d, J=1.9 Hz), 6.82 (1H, dd, J=1.9, 8.6 Hz), 7.58 (1H, dd, J=7.8, 7.8 Hz), 7.66-7.72 (2H, m), 8.05-8.08 (2H, m).

ESI (LC/MS positive mode) m/z: 312 (M+H).

Compound 1e-0-2

3-(3-Nitrobenzyl)-7-hydroxy-4-methyl-6-fluoro-2-oxo-2H-1-benzopyran

[Chemical Formula 15]

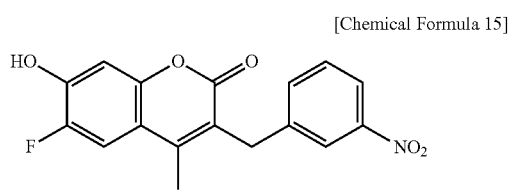

The title compound was synthesized using 4-fluororesorcinol and compound 1c-1 under the same conditions as in the manufacturing example for compound 1e-0-4.

$^1$H NMR (DMSO-d$_6$, 270 MHz) δ (ppm): 2.43 (3H, s), 4.13 (2H, s), 6.71 (2H, d, J=7.6 Hz), 7.55-7.71 (3H, m), 8.05-8.07 (2H, m), 10.51 (1H, s).

ESI (LC/MS positive mode) m/z: 330 (M+H).

Compound 1e-0-3

3-(3-Nitrobenzyl)-7-hydroxy-4-methyl-6-chloro-2-oxo-2H-1-benzopyran

[Chemical Formula 16]

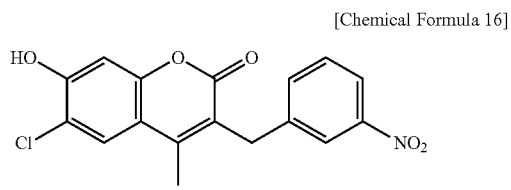

The title compound was synthesized using 4-chlororesorcinol and compound 1c-1 under the same conditions as in the manufacturing example for compound 1e-0-4.

$^1$H NMR (DMSO-d$_6$, 270 MHz) δ (ppm): 2.48 (3H, s), 4.09 (2H, s), 6.90 (1H, s), 7.55 (1H, t, J=7.7 Hz), 7.70 (1H, d, J=7.7 Hz), 7.81 (1H, s), 8.05 (1H, d, J=7.7 Hz), 8.06 (1H, s).

ESI (LC/MS positive mode) m/z: 346 (M+H).

Compound 1e-0-5

3-(2-Fluoro-3-nitrobenzyl)-7-hydroxy-4-methyl-6-fluoro-2-oxo-2H-1-benzopyran

[Chemical Formula 17]

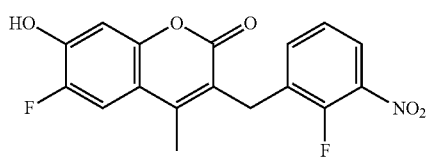

The title compound was synthesized using 4-fluororesorcinol and compound 1c-2 under the same conditions as in the manufacturing example for compound 1e-0-4.

$^1$H NMR (DMSO-$d_6$, 270 MHz) δ (ppm): 2.42 (3H, s), 4.03 (2H, s), 6.92 (1H, d, J=7.6 Hz), 7.32 (1H, dd, J=7.7, 8.6 Hz), 7.57 (1H, dd, J=7.7, 6.3 Hz), 7.69 (1H, d, J=12.0 Hz), 7.99 (1H, dd, J=6.9, 8.6 Hz), 11.07 (1H, brs).

ESI (LC/MS positive mode) m/z: 347 (M+H).

Compound 1e-0-6

3-(2-Methyl-3-nitrobenzyl)-7-hydroxy-4-methyl-2-oxo-2H-1-benzopyran

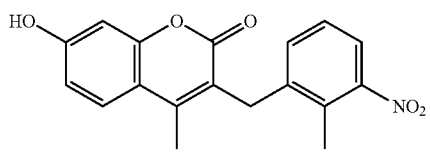

The title compound was synthesized using resorcinol and compound 1c-3 under the same conditions as in the manufacturing example for compound 1e-0-4.

$^1$H NMR (Bruker, 300 MHz, DMSO-$d_6$) δ (ppm): 10.51 (1H, s), 7.69 (1H, d, J=8.8 Hz), 7.65 (1H, d, J=8.0 Hz), 7.27 (1H, t, J=8.0 Hz), 7.12 (1H, d, J=7.6 Hz), 6.84 (1H, dd, J=2.3, 8.8 Hz), 6.74 (1H, d, J=2.3 Hz), 3.95 (2H, s), 2.42 (3H, s), 2.33 (3H, s).

Compound 1e-0-7

3-(3-Nitrobenzyl)-7-hydroxy-4-methyl-6-iodo-2-oxo-2H-1-benzopyran

[Chemical Formula 18]

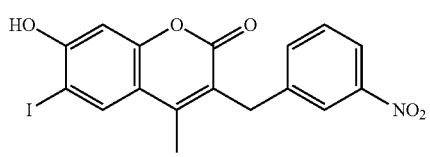

The title compound was synthesized using 4-iodoresorcinol and compound 1c-1 under the same conditions as in the manufacturing example for compound 1e-0-4.

$^1$H NMR (DMSO-$d_6$, 270 MHz) δ (ppm): 2.44 (3H, s), 4.07 (2H, s), 6.82 (1H, s), 7.57 (1H, dd, J=5.4, 5.4 Hz), 7.69 (1H, d, J=2.7 Hz), 8.05-8.10 (3H, m), 11.39 (1H, s).

ESI (LC/MS positive mode) m/z: 437 (M+H).

Compound 1e-0-8

3-(3-Nitrobenzyl)-7-hydroxy-4-methyl-6-methyl-2-oxo-2H-1-benzopyran

[Chemical Formula 19]

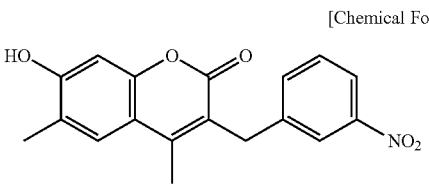

The title compound was synthesized using 4-methylresorcinol and compound 1c-1 under the same conditions as in the manufacturing example for compound 1e-0-4.

$^1$H NMR (DMSO-$d_6$, 270 MHz) δ (ppm): 2.19 (3H, s), 2.44 (3H, s), 4.07 (2H, s), 6.74 (1H, s), 7.53-7.61 (2H, m), 7.69 (1H, d, J=7.9 Hz), 8.02-8.09 (2H, m), 10.50 (1H, s).

ESI (LC/MS positive mode) m/z: 326 (M+H).

Compound 1e-0-36

3-(4-Fluoro-3-nitrobenzyl)-7-hydroxy-4-methyl-2-oxo-2H-1-benzopyran

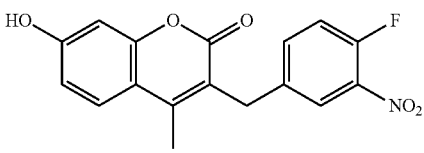

The title compound was synthesized under the same conditions as in the manufacturing example for compound 1e-0-4, except that compound 1c-36 was used instead of compound 1c-2.

$^1$H NMR (270 MHz, DMSO-$d_6$) δ (ppm): 7.98 (dd, 1H, J=7.1, 2.2 Hz), 7.69-7.61 (m, 2H), 7.49 (dd, 1H, J=10.7, 8.6 Hz), 6.82 (dd, 1H, J=8.9, 2.4 Hz), 6.72 (d, 1H, J=2.4 Hz), 4.07 (s, 2H), 2.38 (s, 3H).

ESIMS m/z: 371 (M+H).

Compound 1e-0-46

3-(4-Nitrobenzyl)-7-hydroxy-4-methyl-2H-1-benzopyran

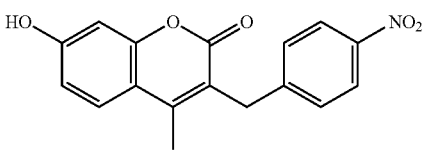

The title compound was synthesized using resorcinol and compound 1c-46 under the same conditions as in the manufacturing example for compound 1e-0-4.

¹H-NMR (Bruker, 300 MHz, DMSO-$d_6$) δ (ppm): 10.48 (1H, s), 8.13 (2H, d, J=8.4 Hz), 7.66 (1H, d, J=8.8 Hz), 7.50 (2H, d, J=8.4 Hz), 6.82 (1H, dd, J=2.3, 8.8 Hz), 6.72 (1H, d, J=2.3 Hz), 4.06 (2H, s), 2.41 (3H, s).

Compound 1e-0-45

3-(2-Nitrobenzyl)-7-hydroxy-4-methyl-2-oxo-2H-1-benzopyran

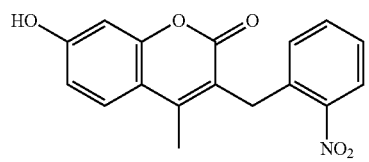

The title compound was synthesized using resorcinol and compound 1c-45 under the same conditions as in the manufacturing example for compound 1e-0-4.

¹H-NMR (Bruker, 300 MHz, DMSO-$d_6$) δ (ppm): 10.55 (1H, s), 7.97 (1H, d, J=8.0 Hz), 7.69 (1H, d, J=8.8 Hz), 7.56 (1H, d, J=7.6 Hz), 7.46 (1H, t, J=7.6 Hz), 7.20 (1H, d, J=7.6 Hz), 6.83 (1H, dd, J=2.3, 8.8 Hz), 6.72 (1H, d, J=2.3 Hz), 4.17 (2H, s), 2.37 (3H, s).

MS (Micromass, Quattromicro, ESI+) m/z: 311.76 (M+H).

Compound 1e-0-47

4,7-Dihydroxy-3-(3-nitrobenzyl)-2-oxo-2H-1-benzopyran

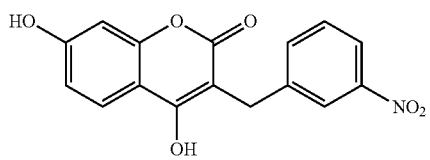

4,7-Dihydroxy-2-oxo-2H-1-benzopyran (500 mg, 2.81 mmol) and 3-nitrobenzaldehyde (424 mg, 2.81 mmol) were added to a mixture of triethylamine (1.57 mL, 11.23 mmol) and formic acid (1.07 mL, 28.07 mmol), and the obtained mixture was stirred at 100° C. for 2 hours. A 5N hydrochloric acid aqueous solution was added to the reaction mixture, and extraction was performed with ethyl acetate. The organic extract was washed with saturated saline and dried over magnesium sulfate, and then concentrated under reduced pressure to yield the title compound (300 mg, 34%) as a pale yellow solid.

¹H NMR (270 MHz, DMSO-$d_6$) δ (ppm): 10.52 (s, 1H), 8.09-8.04 (m, 2H), 7.83 (d, 1H, J=8.7 Hz), 7.71 (d, 1H, J=7.6 Hz), 7.57 (t, 1H, J=7.7 Hz), 6.80 (dd, 1H, J=9.0, 2.4 Hz), 6.69 (d, 1H, J=2.0 Hz), 3.95 (s, 2H).

ESIMS m/z: 314 (M+H).

Compound 1e-0-51

7-Hydroxy-4-methyl-3-(3-nitrophenylamino)-2-oxo-2H-1-benzopyran

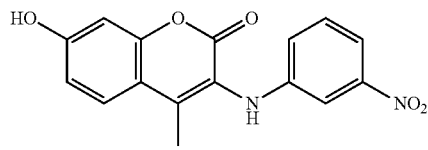

The title compound was synthesized under the same conditions as in the manufacturing example for compound 1e-0-4, except that 2-(3-nitrophenylamino)-3-oxobutanoic acid ethyl ester (compound 1c-51) was used instead of compound 1c-2.

¹H NMR (270 MHz, DMSO-$d_6$) δ (ppm): 10.50 (s, 1H), 8.13 (s, 1H), 7.65 (d, 1H, J=8.7 Hz), 7.51 (d, 1H, J=9.1 Hz), 7.42-7.34 (m, 2H), 7.01 (d, 1H, J=7.3 Hz), 6.86 (dd, 1H, J=8.7, 2.3 Hz), 6.77 (d, 1H, J=2.3 Hz), 2.29 (s, 3H).

ESIMS m/z: 313 (M+H).

Compound 1e-0-59

2-Nitro-N-(7-hydroxy-4-methyl-2-oxo-2H-1-benzopyran-3-yl)benzamide

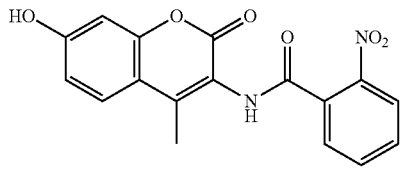

The title compound was synthesized under the same conditions as in the manufacturing example for compound 1e-0-4, except that compound 1c-59 was used instead of compound 1c-2.

¹H NMR (270 MHz, DMSO-$d_6$) δ (ppm): 10.68 (s, 1H), 10.26 (s, 1H), 8.12 (d, 1H, J=7.7 Hz), 7.89 (t, 1H, J=6.3 Hz), 7.80-7.74 (m, 3H), 7.71 (d, 1H, J=8.7 Hz), 6.88 (dd, 1H, J=8.4, 2.3 Hz), 6.77 (d, 1H, J=2.3 Hz), 2.40 (s, 3H).

ESIMS m/z: 341 (M+H).

Compound 1e-0-72

7-Hydroxy-4-methyl-3-(3-nitrobenzyl)-pyrano[2,3-b]pyridin-2-one

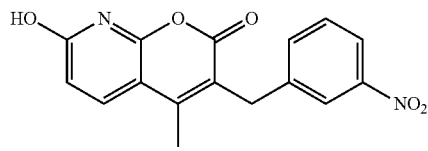

Zn(OTf)$_2$ (669 mg, 1.84 mmol) was added to a suspension of pyridine-2,6-diol (204 mg, 1.84 mmol) and 2-(3-nitrobenzyl)-3-oxobutyric acid ethyl ester (488 mg, 1.84 mmol) in methanol (10 mL), and the mixture was stirred at 75° C. for 30 hours. The reaction mixture was then poured into water and extracted with ethyl acetate. The organic extract was washed with saturated saline and dried over magnesium sulfate. It was then concentrated under reduced pressure to yield a crude product, which was then purified by column chromatography to yield the title compound (330 mg, 57%).

$^1$H-NMR (DMSO-d$_6$, 270 MHz) δ (ppm): 2.44 (3H, s), 4.07 (2H, s), 6.67 (1H, d, J=8.6 Hz), 7.57 (1H, dd, J=7.7, 7.9 Hz), 7.71 (1H, d, J=7.7 Hz), 8.05-8.14 (3H, m).

ESI (LC/MS positive mode) m/z: 313 (M+H).

Compound 1e-0-73

3-(5-Nitro-thiophen-2-ylmethyl)-7-hydroxy-4-methyl-2-oxo-2H-1-benzopyran

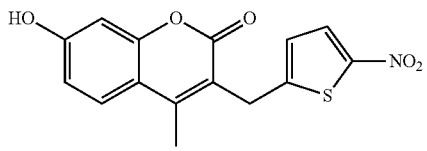

The title compound was synthesized using compound 1c-73 under the same conditions as in the manufacturing example for compound 1e-0-4.

$^1$H-NMR (Bruker (ARX-300), 300 MHz, DMSO-d$_6$) δ (ppm): 10.58 (1H, s), 7.98 (1H, d, J=4.20), 7.68 (1H, d, J=8.77 Hz), 7.11 (1H, d, J=4.20 Hz), 6.82 (1H, dd, J=8.77 Hz), J=1.91 Hz), 6.72 (1H, d, J=2.29 Hz), 4.17 (2H, s), 2.47 (3H, s).

MS (Micromass, Quattromicro, ESI−) m/z: 315.83 (M−1).

Compound 1g-1-5

Dimethylcarbamic acid 2-oxo-2H-3-(2-fluoro-3-nytrobenzyl)-4-methyl-6-fluoro-1-benzopyran-7-yl ester

[Chemical Formula 20]

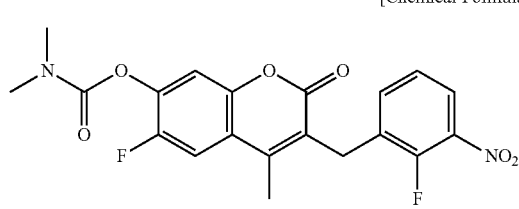

Sodium hydride (60%, 46.2 mg, 1.16 mmol) was added to a solution of compound 1e-0-5 (364.9 mg, 1.05 mmol) in THF (4 mL), and the mixture was stirred at room temperature for 5 minutes. N,N-dimethylcarbamoyl chloride (116 μL, 1.26 mmol) was added thereto, and the mixture was stirred at room temperature for 1 hour. Aqueous saturated ammonium chloride solution (2 mL) was then added to the reaction solution, and precipitates were recovered by filtration. The precipitates were then washed with water to yield the title compound (407.8 mg, 93%) as a white solid.

$^1$H NMR (DMSO-d$_6$, 270 MHz) δ (ppm): 2.42 (3H, s), 2.94 (3H, s), 3.09 (3H, s), 4.07 (2H, s), 7.31-7.34 (1H, m), 7.49 (1H, d, J=6.8 Hz), 7.59-7.63 (1H, m), 7.89 (1H, d, J=11.4 Hz), 7.99 (1H, dd, J=6.9, 8.24 Hz).

ESI (LC/MS positive mode) m/z: 419 (M+H).

Compound 1g-1-1

Dimethylcarbamic acid 4-methyl-3-(3-nitrobenzyl)-2-oxo-2H-1-benzopyran-7-yl ester

[Chemical Formula 21]

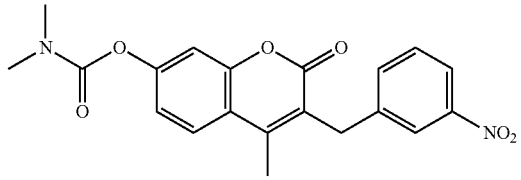

The title compound was synthesized under the same conditions as in the manufacturing example for compound 1g-1-5, except that compound 1e-0-1 was used instead of compound 1e-0-5.

$^1$H NMR (DMSO-d$_6$, 270 MHz) δ (ppm): 8.12 (s, 1H), 8.07 (d, J=8.2 Hz, 1H), 7.86 (d, J=8.7 Hz, 1H), 7.72 (d, J=7.7 Hz, 1H), 7.58 (t, J=7.9 Hz, 1H), 7.26 (d, J=2.3 Hz, 1H), 7.19 (dd, J=8.7, 2.5 Hz, 1H), 4.14 (s, 2H), 3.07 (s, 3H), 2.93 (s, 3H), 2.51 (s, 3H).

ESIMS m/z: 383 (M+H).

Compound 1g-1-2

Dimethylcarbamic acid 2-oxo-2H-3-(3-nitrobenzyl)-4-methyl-6-fluoro-1-benzopyran-7-yl ester

[Chemical Formula 22]

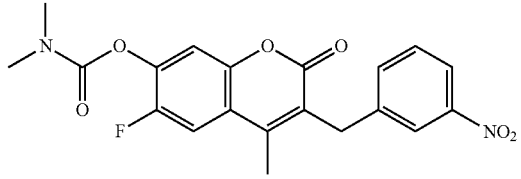

The title compound was synthesized under the same conditions as in the manufacturing example for compound 1g-1-5, except that compound 1e-0-2 was used instead of compound 1e-0-5.

$^1$H NMR (DMSO-d$_6$, 270 MHz) δ (ppm): 2.50 (3H, s), 2.94 (3H, s), 3.08 (3H, s), 4.14 (2H, s), 7.49 (1H, d, J=6.8 Hz), 7.58 (1H, dd, J=7.9, 7.9 Hz), 7.72 (1H, d, J=7.9 Hz), 7.86 (1H, d, J=11.1 Hz), 8.08 (1H, m), 8.12 (1H, s).

ESI (LC/MS positive mode) m/z: 419 (M+H).

Compound 1g-1-3

Dimethylcarbamic acid 2-oxo-2H-3-(3-nitrobenzyl)-4-methyl-6-chloro-1-benzopyran-7-yl ester

[Chemical Formula 23]

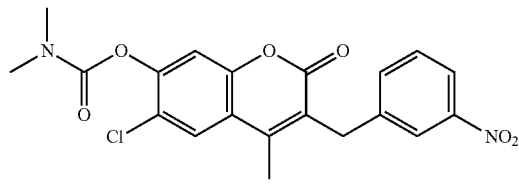

The title compound was synthesized under the same conditions as in the manufacturing example for compound 1g-1-5, except that compound 1e-0-3 was used instead of compound 1e-0-5.

$^1$H NMR (DMSO-$d_6$, 270 MHz) δ (ppm): 8.12 (s, 1H), 8.08 (d, J=8.2 Hz, 1H), 8.02 (s, 1H), 7.72 (d, J=8.2 Hz, 1H), 7.58 (t, J=8.2 Hz, 1H), 7.50 (s, 1H), 4.14 (s, 2H), 3.11 (s, 3H), 2.95 (s, 3H), 2.51 (s, 3H).

ESIMS m/z: 417 (M+H).

Compound 1g-1-4

Dimethylcarbamic acid 2-oxo-2H-3-(2-fluoro-3-nitrobenzyl)-4-methyl-1-benzopyran-7-yl ester

[Chemical Formula 24]

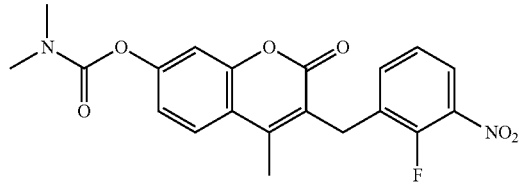

The title compound was synthesized under the same conditions as in the manufacturing example for compound 1g-1-5, except that compound 1e-0-4 was used instead of compound 1e-0-5.

$^1$H NMR (270 MHz, DMSO-$d_6$) δ (ppm): 2.93 (3H, s), 3.07 (3H, s), 4.08 (2H, s), 7.20 (1H, dd, J=8.7, 2.3 Hz), 7.26 (1H, d, J=2.3 Hz), 7.31 (1H, td, J=8.3, 2.3 Hz), 7.60 (1H, ddd, J=8.3, 6.5, 1.8 Hz), 7.88 (1H, d, J=8.7 Hz), 7.99 (1H, ddd, J=8.3, 6.5, 1.8 Hz).

ESI (LC/MS positive mode) m/z: 401 (M+1H)

Compound 1g-1-7

Dimethylcarbamic acid 2-oxo-2H-3-(3-nitrobenzyl)-4-methyl-6-iodo-1-benzopyran-7-yl ester

[Chemical Formula 25]

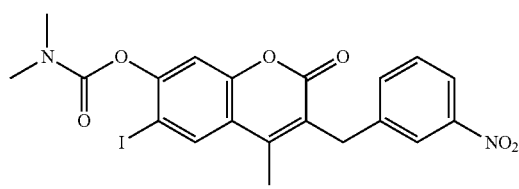

The title compound was synthesized under the same conditions as in the manufacturing example for compound 1g-1-5, except that compound 1e-0-7 was used instead of compound 1e-0-5.

$^1$H NMR (DMSO-$d_6$, 270 MHz) δ (ppm): 2.96 (3H, s), 3.13 (3H, s), 4.13 (2H, s), 7.38 (1H, s), 7.57 (1H, dd, J=7.7, 8.1 Hz), 7.71 (1H, d, J=7.7 Hz), 8.08 (1H, d, J=8.1 Hz), 8.11 (1H, s), 8.24 (1H, s).

One of the $CH_3$ peaks was overlapped with the DMSO peak.

ESI (LC/MS positive mode) m/z: 509 (M+H).

Compound 1g-1-8

Dimethylcarbamic acid 2-oxo-2H-3-(3-nitrobenzyl)-4-methyl-6-methyl-1-benzopyran-7-yl ester

[Chemical Formula 26]

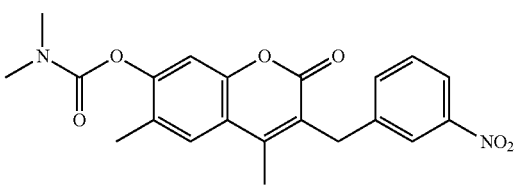

The title compound was synthesized under the same conditions as in the manufacturing example for compound 1g-1-5, except that compound 1e-0-8 was used instead of compound 1e-0-5.

$^1$H NMR (DMSO-$d_6$, 270 MHz) δ (ppm): 2.23 (3H, s), 2.94 (3H, s), 3.09 (3H, s), 4.13 (2H, s), 7.22 (1H, s), 7.57 (1H, dd, J=7.4, 8.1 Hz), 7.71 (1H, d, J=7.4 Hz), 7.76 (1H, s), 8.08 (1H, d, J=8.1 Hz), 8.10 (1H, s).

One of the $CH_3$ peaks was overlapped with the DMSO peak.

ESI (LC/MS positive mode) m/z: 397 (M+H).

Compound 1g-1-9

Dimethylcarbamic acid 2-oxo-2H-3-(3-nitrobenzyl)-4-methyl-6-cyano-1-benzopyran-7-yl ester

[Chemical Formula 27]

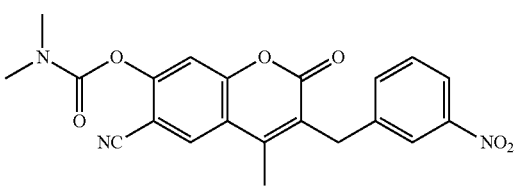

The title compound was synthesized under the same conditions as in the manufacturing example for compound 1g-1-5, except that compound 1e-0-9 was used instead of compound 1e-0-5.

$^1$H NMR (DMSO-$d_6$, 270 MHz) δ (ppm): 2.99 (3H, s), 3.14 (3H, s), 4.12 (2H, s), 7.38 (1H, s), 7.57 (1H, dd, J=7.7, 8.1 Hz), 7.71 (1H, d, J=7.7 Hz), 8.08 (1H, d, J=8.1 Hz), 8.11 (1H, s), 8.24 (1H, s).

One of the $CH_3$ peaks was overlapped with the DMSO peak.

ESI (LC/MS positive mode) m/z: 408 (M+H).

Compound 1g-1-38

Dimethylcarbamic acid 6-carbamoyl-4-methyl-3-(3-nitrobenzyl)-2-oxo-2H-1-benzopyran-7-yl ester

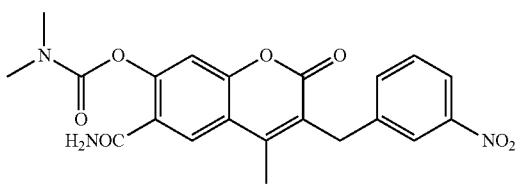

Acetic acid (5 mL) and concentrated sulfuric acid (5 mL) were added to compound 1g-1-9 (1.2 g, 2.95 mmol), and the mixture was stirred at room temperature for 1.5 hours. The reaction mixture was poured into sodium hydrogen carbonate solution and extracted with ethyl acetate. The organic extract was washed with saturated saline and dried over magnesium sulfate. It was then concentrated under reduced pressure to yield a crude product, which was then purified by column chromatography to yield the title compound (1.1 g, 90%).

$^1$H-NMR (DMSO-$d_6$, 270 MHz) δ (ppm): 2.90 (3H, s), 3.06 (3H, s), 4.15 (2H, s), 7.29 (1H, s), 7.50 (1H, brs), 7.55-7.61 (2H, m), 7.70-7.73 (2H, m), 7.80 (1H, brs), 8.01 (1H, s).

One of the methyl peaks was overlapped with the DMSO peak.

ESI (LC/MS positive mode) m/z: 426 (M+H).

Compound 1g-1-39

Dimethylcarbamic acid 3-(3-nitrobenzyl)-4-methyl-2-oxo-6-trimethylsilanylethynyl-2H-1-benzopyran-7-yl ester

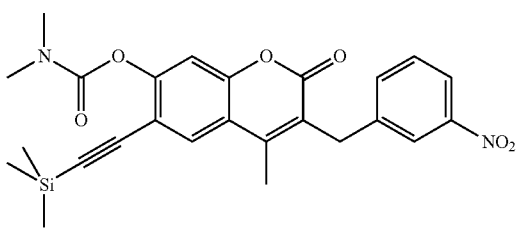

Compound 1g-1-7 (1.45 g, 2.85 mmol), bis(triphenylphosphine)palladium(II) dichloride (100 mg, 0.143 mmol), copper(I) iodide (55 mg, 0.29 mmol), trimethylsilylacetylene (1.4 g, 14.3 mmol) and diisopropylethylamine (550 μL, 3.2 mmol) were mixed with 10 mL of anhydrous tetrahydrofuran, and the mixture was heated and stirred at 45 to 55° C. for 10 hours. It was then purified by silica gel chromatography (elution with methylene chloride) to yield 1.06 g of the title compound.

$^1$H-NMR (DMSO-$d_6$, 270 MHz) δ (ppm): 0.21 (9H, s), 2.94 (3H, s), 3.08 (3H, s), 4.13 (2H, s), 7.39 (1H, s), 7.57 (1H, t, J=8.0 Hz), 7.70 (1H, d, J=8.0 Hz), 7.94 (1H, s), 8.06 (1H, d, J=8.0 Hz), 8.12 (1H, s).

One of the methyl peaks was overlapped with the DMSO peak.

ESI (LC/MS positive mode) m/z: 449 (M+H).

Compound 1g-1-59

Dimethylcarbamic acid 3-(2-nitrobenzoylamino)-4-methyl-2-oxo-2H-1-benzopyran-7-yl ester

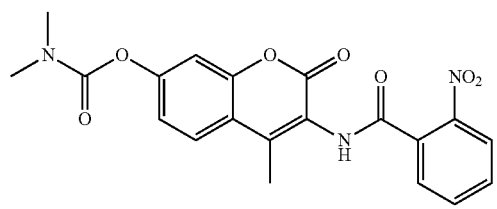

The title compound was synthesized under the same conditions as in the manufacturing example for compound 1g-1-5, except that compound 1e-0-59 was used instead of compound 1e-0-5.

$^1$H NMR (270 MHz, DMSO-$d_6$) δ (ppm): 10.44 (s, 1H), 8.13 (d, 1H, J=7.7 Hz), 7.92-7.88 (m, 2H), 7.80-7.76 (m, 2H), 7.33 (d, 1H, J=2.1 Hz), 7.25 (dd, 1H, J=8.7, 2.3 Hz), 3.08 (s, 3H), 2.92 (s, 3H), 2.46 (s, 3H).

ESIMS m/z: 412 (M+H).

Compound 1g-1-72

Dimethylcarbamic acid 4-methyl-3-(3-nitrobenzyl)-2-oxo-2H-pyrano[2,3-b]pyridin-7-yl ester

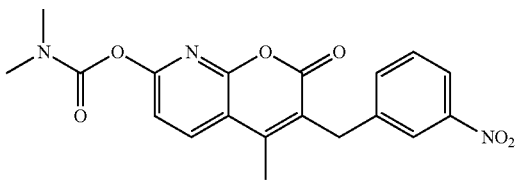

The title compound was synthesized under the same conditions as in the manufacturing example for compound 1g-1-5, except that compound 1e-0-72 was used instead of compound 1e-0-5.

$^1$H-NMR (DMSO-$d_6$, 270 MHz) δ (ppm): 2.95 (3H, s), 3.07 (3H, s), 4.14 (2H, s), 7.28 (1H, d, J=8.4 Hz), 7.58 (1H, dd, J=7.7, 8.1 Hz), 7.73 (1H, d, J=7.7 Hz), 8.05-8.14 (2H, m), 8.43 (1H, d, J=8.4 Hz).

The CH$_3$ peak was overlapped with the DMSO peak.

ESI (LC/MS positive mode) m/z: 384 (M+H).

Compound 1g-1b-1

7-Isobutoxy-4-methyl-3-(3-nitrobenzyl)-2-oxo-2H-1-benzopyran

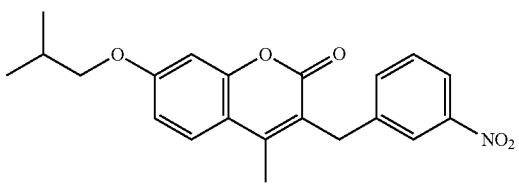

The title compound was synthesized under the same conditions as in the manufacturing example for compound 1g-2-4, except that compound 1e-0-1 was used instead of compound 1e-0-4, and that isopropyl bromide was used instead of bromopyrimidine.

¹H-NMR (270 MHz, DMSO-d₆) δ (ppm): 0.98 (3H, s), 1.00 (3H, s), 1.95-2.11 (1H, m), 2.47 (3H, s), 3.86 (2H, d, J=6.5 Hz), 4.10 (2H, s), 6.93-7.06 (2H, m), 7.58 (1H, dd, J=8.1, 7.8 Hz), 7.64-7.79 (2H, m), 8.00-8.11 (2H, m).

ESI (LC-MS positive mode) m/z: 368 (M+H).

p-Toluenesulfonic acid 2-fluoroethyl ester

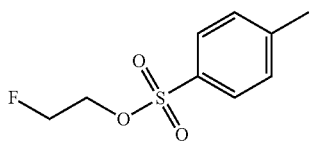

1 g (15.6 mmol) of 2-fluoroethanol was dissolved in pyridine (15 mL), and 6.5 g (34.1 mmol) of p-toluenesulfonic acid was added thereto over a period of 30 minutes while stirring on ice. The mixture was stirred at 0° C. under nitrogen atmosphere for 3 hours, and after adding 35 mL of ice water to the reaction mixture, extraction was performed with 30 mL of ethyl acetate. The obtained organic layer was washed three times with 30 mL of 1 N hydrochloric acid, and then further washed with sodium carbonate solution and saturated saline. The obtained organic layer was dried over anhydrous sodium sulfate, and the solvent was distilled away under reduced pressure to yield the title compound (3.19 g, 94%) as a colorless oil.

¹H-NMR (270 MHz, CDCl₃) δ (ppm): 2.46 (3H, s), 4.14-4.25 (1H, m), 4.25-4.36 (1H, m), 4.43-4.36 (1H, m), 4.61-4.71 (1H, m), 7.36 (2H, d, J=8.1 Hz), 7.81 (2H, d, J=8.1 Hz).

Compound 1g-1c-1

7-(2-Fluoroethoxy)-4-methyl-3-(3-nitrobenzyl)-2-oxo-2H-1-benzopyran

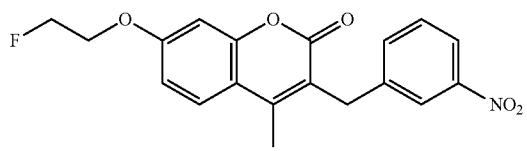

The title compound was synthesized under the same conditions as in the manufacturing example for compound 1g-2-4, except that compound 1e-0-1 was used instead of compound 1e-0-4, and that p-toluenesulfonic acid 2-fluoroethyl ester was used instead of bromopyrimidine.

¹H-NMR (270 MHz, DMSO-d₆) δ (ppm): 2.43 (3H, s), 4.10 (2H, s), 4.29-4.36 (1H, m), 4.39-4.46 (1H, m), 4.64-4.71 (1H, m), 4.82-4.89 (1H, m), 6.96-7.07 (2H, m), 7.58 (1H, dd, J=8.1, 7.6 Hz), 7.71 (1H, d, J=8.1 Hz), 7.78 (1H, d, J=8.6 Hz), 8.01-8.11 (2H, m).

Compound 1g-1c-3

6-Chloro-7-(2-fluoroethoxy)-4-methyl-3-(3-nitrobenzyl)-2-oxo-2H-1-benzopyran

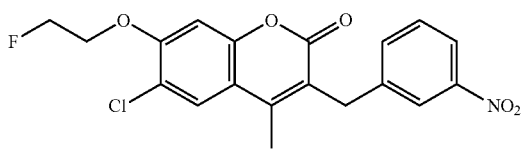

The title compound was synthesized under the same conditions as in the manufacturing example for compound 1g-2-4, except that compound 1e-0-3 was used instead of compound 1e-0-4, and that p-toluenesulfonic acid 2-fluoroethyl ester was used instead of bromopyrimidine.

¹H-NMR (270 MHz, DMSO-d₆) δ (ppm): 2.43 (3H, s), 4.11 (2H, s), 4.36-4.43 (1H, m), 4.46-4.54 (1H, m), 4.68-4.73 (1H, m), 4.86-4.91 (1H, m), 7.30 (1H, s), 7.58 (1H, dd, J=8.1, 7.8 Hz), 7.71 (1H, d, J=8.1 Hz), 7.93 (1H, s), 8.04-8.11 (2H, m).

Compound 1g-1d-1

Pyrrolidine-1-carboxylic acid 4-methyl-3-(3-nitrobenzyl)-2-oxo-2H-1-benzopyran-7-yl ester

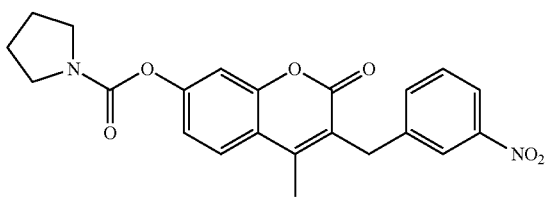

The title compound was synthesized under the same conditions as in the manufacturing example for compound 1g-1-5, except that 1e-0-1 was used instead of compound 1e-0-5, and that pyrrolidine-1-carbonyl chloride was used instead of N,N-carbamic acid chloride.

¹H-NMR (CDCl₃, 270 MHz) δ (ppm): 1.93-2.02 (4H, m), 2.49 (3H, s), 3.50 (2H, t, J=6.6 Hz), 3.59 (2H, t, J=6.6 Hz), 4.15 (2H, s), 7.14-7.19 (2H, m), 7.45 (1H, t, J=7.8 Hz), 7.61-7.65 (2H, m), 8.06-8.10 (2H, m)

ESI (LC/MS positive mode) m/z: 409 (M+H).

Compound 1g-2-4

4-Methyl-3-(2-fluoro-3-nitrobenzyl)-7-(pyrimidin-2-yloxy)-2-oxo-2H-1-benzopyran

[Chemical Formula 28]

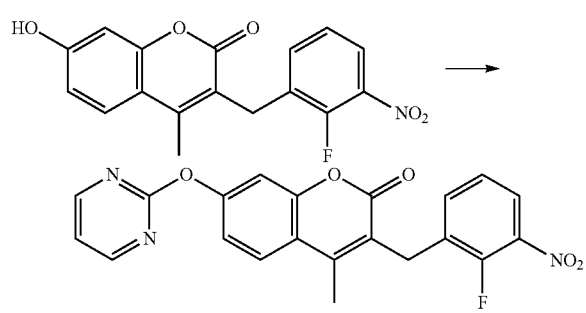

Compound 1e-0-4 (15 g, 45.6 mmol) and 2-bromopyrimidine (72.4 g, 455 mmol) were dissolved in N,N-dimethylformamide (300 mL), and potassium carbonate (12.6 g, 91.2 mmol) was added thereto. The mixture was stirred at 80° C. under nitrogen atmosphere for 1 hour. Ethyl acetate was then added to the reaction solution, and the solution was washed with sodium hydrogen carbonate solution, water and saturated saline. The organic layer was dried over anhydrous sodium sulfate, and the solvent was distilled away under reduced pressure. The resultant residue was purified by silica gel column chromatography (hexane:ethyl acetate=1:2) to yield the title compound (10.57 g, 57%) as a pale yellow powder.

$^1$H NMR (270 MHz, DMSO-$d_6$) δ (ppm): 2.52 (3H, s), 4.10 (2H, s), 7.28 (1H, dd, J=8.8, 2.4 Hz), 7.30-7.36 (2H, m), 7.38 (1H, d, J=2.4 Hz), 7.59-7.64 (1H, m), 7.93 (1H, d, J=8.8 Hz), 7.97-8.03 (1H, m), 8.69 (2H, d, J=4.4 Hz).

ESI (LC/MS positive mode) m/z: 408 (M+H).

Compound 1g-2-1

4-Methyl-3-(3-nitrobenzyl)-7-(pyrimidin-2-yloxy)-2-oxo-2H-1-benzopyran

[Chemical Formula 29]

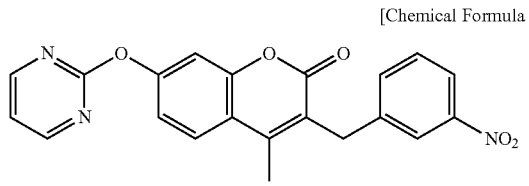

The title compound was synthesized under the same conditions as in the manufacturing example for compound 1g-2-4, except that compound 1e-0-1 was used instead of compound 1e-0-4.

$^1$H NMR (CDCl$_3$, 270 MHz) δ (ppm): 2.52 (3H, s), 4.17 (2H, s), 7.12 (1H, t, J=4.8 Hz), 7.20 (1H, dd, J=2.1, 8.7 Hz), 7.20-7.40 (1H, m), 7.46 (1H, dd, J=7.7, 7.7 Hz), 7.64 (1H, d, J=7.7 Hz), 7.72 (1H, d, J=8.7 Hz), 8.07-8.10 (2H, m), 8.59 (2H, d, J=4.8 Hz).

ESI (LC/MS positive mode) m/z: 390 (M+H).

Compound 1g-2-3

4-Methyl-3-(3-nitrobenzyl)-7-(pyrimidin-2-yloxy)-6-chloro-2-oxo-2H-1-benzopyran

[Chemical Formula 30]

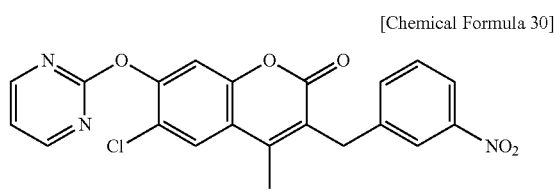

The title compound was synthesized under the same conditions as in the manufacturing example for compound 1g-2-4, except that compound 1e-0-3 was used instead of compound 1e-0-4.

$^1$H NMR (CDCl$_3$, 270 MHz) δ (ppm): 2.51 (3H, s), 4.16 (2H, s), 7.13 (1H, t, J=4.8 Hz), 7.29 (1H, s), 7.45 (1H, t, J=7.7 Hz), 7.62 (1H, d, J=7.7 Hz), 7.75 (1H, s), 8.06 (1H, d, J=7.7 Hz), 8.07 (1H, brs), 8.60 (2H, d, J=4.8 Hz).

ESI (LC/MS positive mode) m/z: 424 (M+H).

Compound 1g-2-47

4-Hydroxy-3-(3-nitrobenzyl)-7-(pyrimidin-2-yloxy)-2-oxo-2H-1-benzopyran

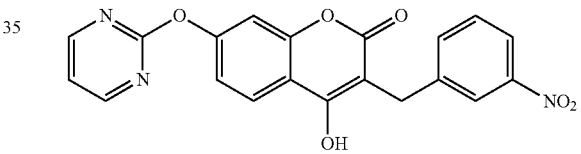

The title compound was synthesized under the same conditions as in the manufacturing example for compound 1g-2-4, except that compound 1e-0-47 was used instead of compound 1e-0-4.

$^1$H NMR (270 MHz, DMSO-$d_6$) δ (ppm): 8.69 (d, 2H, J=4.8 Hz), 8.12 (m, 1H), 8.09-8.03 (dd, 2H), 7.73 (d, 1H, J=7.7 Hz), 7.57 (t, 1H, J=7.9 Hz), 7.35-7.32 (m, 2H), 7.25 (dd, 1H, J=9.0, 2.2 Hz), 4.00 (s, 2H).

ESIMS m/z: 392 (M+H).

Compound 1g-3-3

4-Methyl-3-(3-nitrobenzyl)-7-(thiazol-2-yloxy)-6-chloro-2-oxo-2H-1-benzopyran

[Chemical Formula 31]

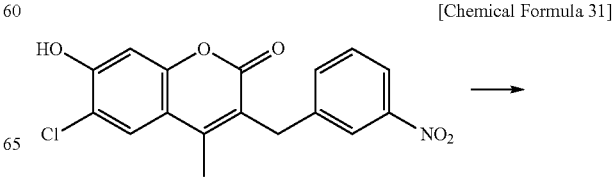

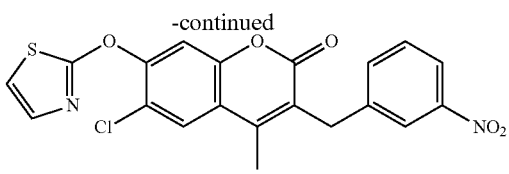

Compound 1e-0-3 (2.0 g, 5.78 mmol) was dissolved in N,N-dimethylformamide (10 mL), and 2-bromothiazole (2.1 mL, 23.1 mmol), cesium carbonate (3.8 g, 11.6 mmol) and copper(I) iodide (220 mg, 1.16 mmol) were added thereto. The mixture was stirred at 110° C. for 1 hour while irradiating microwave (100 W). Ethyl acetate was then added to the reaction solution, and the solution was washed with water and saturated saline. The organic layer was dried over anhydrous magnesium sulfate, and the solvent was distilled away under reduced pressure. The resultant residue was purified by silica gel column chromatography (dichloromethane:methanol=20:1) to yield the title compound (496 mg, 20%) as a pale yellow powder.

$^1$H NMR (CDCl$_3$, 270 MHz) δ (ppm): 2.50 (3H, s), 4.15 (2H, s), 6.94 (1H, d, J=3.8 Hz), 7.23 (1H, d, J=3.8 Hz), 7.44-7.50 (2H, m), 7.60-7.63 (1H, m), 7.75 (1H, s), 8.07-8.10 (2H, m).

ESI (LC/MS positive mode) m/z: 429 (M+H).

Compound 1g-3-1

4-Methyl-3-(3-nitrobenzyl)-7-(thiazol-2-yloxy)-2-oxo-2H-1-benzopyran

[Chemical Formula 32]

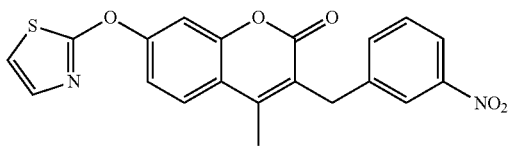

The title compound was synthesized under the same conditions as in the manufacturing example for compound 1g-3-3, except that compound 1e-0-1 was used instead of compound 1e-0-3.

$^1$H NMR (CDCl$_3$, 270 MHz) δ (ppm): 2.50 (3H, s), 4.15 (2H, s), 6.93 (1H, d, J=3.8 Hz), 7.26-7.34 (3H, m), 7.43-7.50 (1H, m), 7.61-7.66 (1H, m), 7.68 (1H, d, J=8.8 Hz), 8.05-8.10 (2H, m).

ESI (LC/MS positive mode) m/z: 395 (M+H).

Compound 1g-3-8

4-Methyl-3-(3-nitrobenzyl)-7-(thiazol-2-yloxy)-6-methyl-2-oxo-2H-1-benzopyran

[Chemical Formula 33]

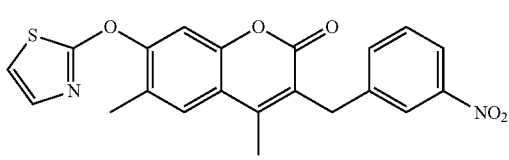

The title compound was synthesized under the same conditions as in the manufacturing example for compound 1g-3-3, except that compound 1e-0-8 was used instead of compound 1e-0-3.

$^1$H NMR (DMSO-d$_6$, 270 MHz) δ (ppm): 2.28 (3H, s), 4.14 (2H, s), 7.29 (2H, s), 7.45 (1H, s), 7.58 (1H, dd, J=7.4, 8.2 Hz), 7.72 (1H, d, J=7.4 Hz), 7.87 (1H, s), 8.08 (1H, d, J=8.2 Hz), 8.11 (1H, s).

One of the CH$_3$ peaks was overlapped with the DMSO peak.

ESI (LC/MS positive mode) m/z: 409 (M+H).

Compound 1g-11-3

4-Methyl-3-(3-nitrobenzyl)-7-(thiophen-3-yl)-6-chloro-2-oxo-2H-1-benzopyran

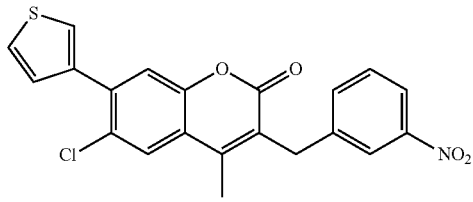

The compound trifluorosulfonic acid 2-oxo-2H-3-(3-nitrobenzyl)-4-methyl-6-chloro-1-benzopyran-7-yl ester (compound 1g-1e-3) was synthesized under the same conditions as in the manufacturing example for compound 1g-1-5, except that compound 1e-0-3 was used instead of compound 1e-0-5, and that trifluorosulfonic anhydride was used instead of dimethylcarbamoyl chloride.

Compound 1g-1e-3 (200 mg, 0.419 mmol) was added to tetrahydrofuran (6 mL), thiophene-3-boronic acid (160 mg, 1.25 mmol), tetrakis(triphenylphosphine)palladium (72 mg, 0.084 mmol) and K$_3$PO$_4$ (412 mg, 2.51 mmol), and the mixture was stirred at 80° C. for 12 hours. It was then purified by silica gel chromatography (hexane:ethyl acetate=4:1) to yield the title compound (121 mg).

$^1$H-NMR (Bruker (ARX-300), 300 MHz, CDCl$_3$) δ (ppm): 8.10 (1H, s), 8.08 (1H, d, J=6.49 Hz), 7.73 (1H, s), 7.65 (1H, d, J=8.01 Hz), 7.59 (1H, dd, J=3.05, 1.53 Hz), 7.50-7.42 (3H, m), 7.36 (1H, dd, J=5.34, 1.53 Hz), 4.17 (2H, s), 2.51 (3H, s).

Compound 1g-12-1

4-Methyl-3-(3-nitrobenzyl)-7-(pyridin-4-yl)-2-oxo-2H-1-benzopyran

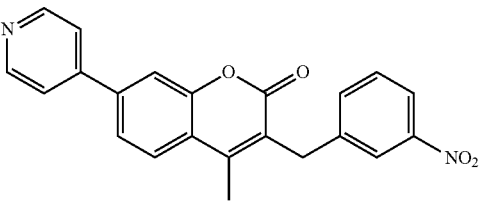

The compound trifluorosulfonic acid 2-oxo-2H-3-(3-nitrobenzyl)-4-methyl-6-chloro-1-benzopyran-7-yl ester (compound 1g-1e-1) was synthesized under the same conditions as in the manufacturing example for compound 1g-1-5, except that compound 1e-0-1 was used instead of compound 1e-0-5, and that trifluoroacetic anhydride was used instead of dimethylcarbamoyl chloride.

The title compound was synthesized under the same conditions as in the manufacturing example for compound 1g-11-3, except that compound 1g-1e-1 was used instead of compound 1g-1e-3, and that pyridine-4-boronic acid was used instead of thiophene-3-boronic acid.

¹H-NMR (Bruker (ARX-300), 300 MHz, CDCl₃) δ (ppm): 8.73 (2H, d, J=6.49 Hz), 8.10 (1H, s), 8.08 (1H, d, J=9.16 Hz), 7.78 (1H, d, J=9.16 Hz), 7.71-7.44 (6H, m), 4.19 (2H, s), 2.56 (3H, s).

Compound 1g-13-1

4-Methyl-3-(3-nitrobenzyl)-7-(dibenzhydrylidene-amino)-2-oxo-2H-1-benzopyran

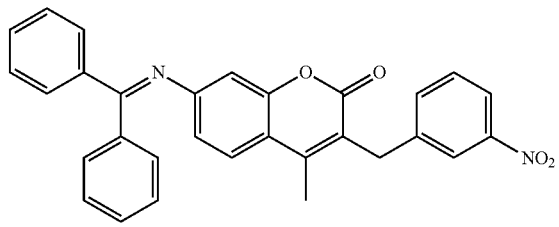

Compound 1g-1e-1 (88 mg, 0.2 mmol), BINAP (11 mg, 0.02 mmol), palladium(II) acetate (3 mg, 0.013 mmol), cesium carbonate (164 mg, 0.5 mmol) and benzophenoneimine (154 mg, 0.24 mmol) were mixed, and the mixture was heated under reflux under nitrogen atmosphere for 3.5 hours. It was then purified by silica gel chromatography (ethyl acetate:hexane=8:1 to 4:1) to yield the title compound (49 mg, 52%).

¹H-NMR (Bruker (ARX-300), 300 MHz, CDCl₃) δ (ppm): 8.08 (1H, d, J=1.91 Hz), 8.06 (1H, d, J=9.54 Hz), 7.76 (2H, d, J=7.25 Hz), 7.64 (1H, d, J=7.63 Hz), 7.55-7.41 (5H, m), 7.29 (3H, m), 7.13 (2H, d, J=4.96 Hz), 6.70 (1H, dd, J=8.39, 2.29 Hz), 6.67 (1H, d, J=1.91 Hz), 4.10 (2H, s), 2.42 (3H, s).

Compound 1g-14-1

4-Methyl-3-(3-nitrobenzyl)-7-amino-2-oxo-2H-1-benzopyran

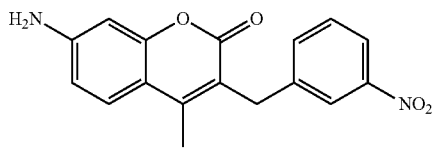

2.5 mL of 2N hydrochloric acid was added to a mixture of compound 1g-13-1 (6.2 g) in THF (50 mL), and the obtained mixture was stirred at room temperature for 20 minutes. A 1N sodium hydroxide aqueous solution was further added, and extraction was performed with methylene chloride. After distilling away the solvent, a product (3.9 g, 96%) was obtained by solidification using a mixture of hexane and ethyl acetate (2:1).

¹H-NMR (Bruker (ARX-300), 300 MHz, DMSO-d₆) δ (ppm): 8.05 (1H, s), 8.04 (1H, d, J=6.49 Hz), 7.68 (1H, d, J=7.63 Hz), 7.56 (1H, t, J=7.63 Hz), 7.47 (1H, d, J=8.78 Hz), 6.58 (1H, d, J=8.39 Hz), 6.42 (1H, s), 6.06 (2H, s), 4.02 (2H, s), 2.36 (3H, s).
MS (Micromass, Quattromicro, ESI+) m/z: 311.35 (M+1).

Compound 1g-15-1

4-Methyl-3-(3-nitrobenzyl)-7-iodo-2-oxo-2H-1-benzopyran

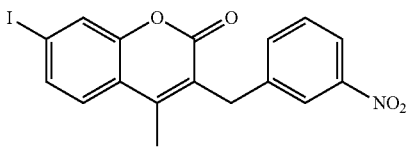

To a mixture of compound 1g-14-1 (620 mg, 0.064 mmol), 0.013 mL of concentrated sulfuric acid and 0.13 mL of water, there was added an aqueous solution (0.013 mL) of NaNO₂ (4.6 mg, 0.068 mmol) at 0° C. over a period of 1 hour. An aqueous solution (0.09 mL) of potassium iodide (32 mg, 0.192 mmol) was then added dropwise at 0° C. over a period of 30 minutes, and the mixture was stirred at room temperature for 1 hour. It was then purified by silica gel chromatography (hexane:ethyl acetate=2:1) to yield the title compound (25 mg, 92%).

¹H-NMR (Bruker (ARX-300), 300 MHz, CDCl₃) δ (ppm): 8.08 (1H, s), 8.07 (1H, d, J=6.49 Hz), 7.72 (1H, d, J=0.53 Hz), 7.65 (2H, dd, J=8.39, 1.91 Hz), 7.46 (1H, t, J=7.63 Hz), 7.35 (1H, d, J=8.39 Hz), 4.14 (2H, s), 2.48 (3H, s).
MS (Micromass, Quattromicro, ESI−) m/z: 420.43 (M−1).

5-Tributylstannylthiazole

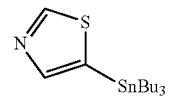

A hexane solution of n-BuLi (4.14 mL, 10 mmol) was added dropwise to an anhydrous tetrahydrofuran solution of 5-bromothiazole (0.46 mL, 5.0 mmol) at −78° C. under nitrogen atmosphere over a period of 30 minutes, and the mixture was stirred for 1 hour. A solution of n-Bu₃SnCl (1.41 mL, 5.0 mmol) in THF was then added dropwise over a period of 30 minutes at −78° C., and after stirring for 2 hours, the mixture was raised to room temperature and stirred for another hour. Three drops of a 1N HCl solution were added, and the organic layer was extracted from the aqueous layer twice with 10 mL of ether. The solvent was distilled away to yield the title compound (650 mg, 35 mL).

¹H-NMR (Bruker (ARX-300), 300 MHz, CDCl₃) δ (ppm): 9.09 (1H, s), 7.88 (1H, s), 1.61-0.87 (27H, m).
MS (Micromass, Quattromicro, ESI+) m/z: 376.07 (M+1).

Compound 1g-16-1

4-Methyl-3-(3-nitrobenzyl)-7-(thiazol-5-yl-2-oxo-2H-1-benzopyran

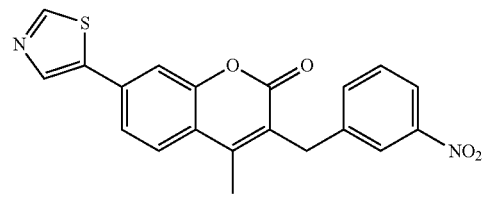

Compound 1g-15-1 (150 mg, 0.36 mmol), 5-tributylstannylthiazole (173 mg, 0.46 mmol), bis(triphenylphosphine)palladium dichloride (6.5 mg, 0.009 mmol), tri(2-furyl)phosphine (4.3 mg, 0.02 mmol) and acetonitrile (4.5 mL) were mixed, and the mixture was heated under reflux under argon atmosphere overnight. It was then purified by silica gel chromatography (hexane:ethyl acetate=2:1; methylene chloride:hexane:ethyl acetate=1:1:1) to yield the title compound (126 mg, 70%).

$^1$H-NMR (Bruker (ARX-300), 300 MHz, CDCl$_3$) δ (ppm): 8.84 (1H, s), 8.20 (1H, s), 8.10 (1H, s), 8.09 (1H, d, J=8.39 Hz), 7.68 (2H, t, J=6.87 Hz), 7.54 (2H, m), 7.47 (1H, t, J=7.63 Hz), 4.17 (2H, s), 2.53 Hz (3H, s).

MS (Micromass, Quattromicro, ESI+) m/z: 397.04 (M+1).

2-Tributylstannylthiazole

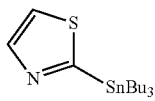

To a mixture of 2-bromothiazole (4.6 mL, 50 mmol) and anhydrous ether (50 mL), there was added an n-BuLi hexane solution (22 mL, 55 mmol) dropwise at −70° C. under nitrogen atmosphere, and the mixture was stirred for 30 minutes. A solution of n-Bu$_3$SnCl (14 mL, 50 mmol) in ether (20 mL) was then added at −70° C., and after stirring for 4 hours, the mixture was raised to room temperature and stirred for another hour. After adding water (50 mL), the organic layer was extracted three times with ether (50 mL), and the solvent was distilled away. It was then purified by silica gel chromatography (hexane:ethyl acetate=20:1) to yield the title compound (17 g, 90%).

$^1$H-NMR (Bruker (ARX-300), 300 MHz, CDCl$_3$) δ (ppm): 8.17 (1H, d, J=3.05 Hz), 7.54 (1H, d, J=3.05 Hz), 1.65-1.55 (6H, m), 1.38-1.19 (12H, m), 0.89 (9H, t, J=7.25 Hz).

Compound 1g-17-1

4-Methyl-3-(3-nitrobenzyl)-7-(thiazol-2-yl)-2-oxo-2H-1-benzopyran

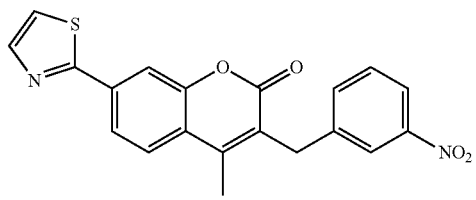

The title compound was synthesized under the same conditions as in the manufacturing example for compound 1g-16-1, except that 2-tributylstannylthiazole was used instead of 5-tributylstannylthiazole.

$^1$H-NMR (Bruker (ARX-300), 300 MHz, CDCl$_3$) δ (ppm): 8.12 (1H, s), 8.08 (1H, d, J=8.01 Hz), 7.94 (3H, m), 7.72 (1H, d, J=8.01 Hz), 7.67 (1H, d, J=7.63 Hz), 7.48 (1H, d, J=8.01 Hz), 7.44 (1H, d, J=3.43 Hz), 4.18 (2H, s), 2.54 (3H, s).

MS (Micromass, Quattromicro, ESI+) m/z: 397.04 (M+1).

Compound 1g-18-1

4-Methyl-3-(3-nitrobenzyl)-7-(pyridin-3-yl)-2-oxo-2H-1-benzopyran

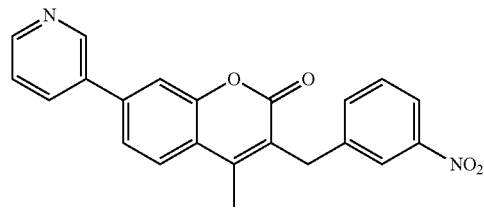

The compound trifluorosulfonic acid 2-oxo-2H-3-(3-nitrobenzyl)-4-methyl-1-benzopyran-7-yl ester (compound 1g-1e-1) was synthesized under the same conditions as in the manufacturing example for compound 1g-1-5, except that compound 1e-0-1 was used instead of compound 1e-0-5, and that trifluorosulfonic anhydride was used instead of dimethylcarbamoyl chloride.

The title compound was synthesized under the same conditions as in the manufacturing example for compound 1g-11-3, except that compound 1g-1e-1 was used instead of compound 1g-1e-3, and that pyridine-3-boronic acid was used instead of thiophene-3-boronic acid.

$^1$H-NMR (Bruker (ARX-300), 300 MHz, CDCl$_3$) δ (ppm): 8.91 (1H, d, J=1.91 Hz), 8.67 (1H, dd, J=4.58, 1.53 Hz), 8.11 (1H, s), 8.08 (1H, dd, J=8.77, 1.91 Hz), 7.92 (1H, dt, J=8.01, 2.29 Hz), 7.78-7.42 (6H, m), 4.19 (2H, s), 2.56 (3H, s).

Compound 1g-19-3

4-Methyl-3-(3-nitrobenzyl)-6-chloro-7-(3-methoxyphenyl)-2-oxo-2H-1-benzopyran

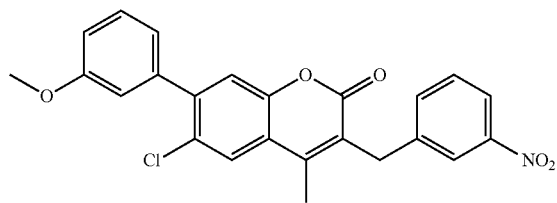

The title compound was synthesized under the same conditions as in the manufacturing example for compound 1g-11-3, except that 3-phenoxyboronic acid was used instead of thiophene-3-boronic acid.

$^1$H-NMR (Bruker (ARX-300), 300 MHz, CDCl$_3$) δ (ppm): 8.09 (1H, s), 8.08 (1H, d, J=6.49 Hz), 7.74 (1H, s), 7.65 (1H, d, J=7.63 Hz), 7.49 (1H, t, J=8.01 Hz), 7.39 (1H, t, J=8.77 Hz), 7.35 (1H, s), 7.03 (1H, dd, J=7.63, 1.14 Hz), 6.99-6.97 (2H, m), 4.18 (2H, s), 3.86 (3H, s), 2.52 (3H, s).

1-Methyl-2-tributylstannyl-1H-imidazole

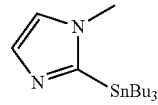

n-BuLi (7.6 mL, 18.9 mmol) was added dropwise at −10° C. under nitrogen atmosphere over a period of 30 minutes to an anhydrous tetrahydrofuran solution (20 mL) of 1-methyl-1H-imidazole (1.6 mL, 18.8 mmol), and the mixture was stirred for 2.5 hours. Next, a tetrahydrofuran solution (12 mL) of Bu₃SnCl (5.1 mL, 18.8 mmol) was added dropwise over a period of one hour at −78° C., and then the mixture was raised to room temperature and stirred overnight. The title compound (5.48 g, 79%) was obtained by vacuum distillation (140-142° C., 0.5 mmHg).

¹H-NMR (Bruker (ARX-300), 300 MHz, CDCl₃) δ (ppm): 7.20 (1H, s), 7.01 (1H, s), 3.68 (3H, s), 1.56 (6H, m), 1.37-1.15 (12H, m), 0.88 (9H, t, J=7.2 Hz).

Compound 1g-20-1

4-Methyl-3-(3-nitrobenzyl)-7-(1-methyl-1H-imidazol-2-yl)-2-oxo-2H-1-benzopyran

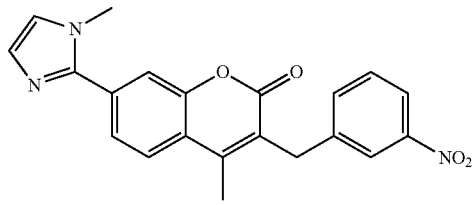

The title compound was synthesized under the same conditions as in the manufacturing example for compound 1g-16-1, except that 1-methyl-2-tributylstannyl-1H-imidazole was used instead of 5-tributylstannylthiazole.

¹H-NMR (Bruker (ARX-300), 300 MHz, CDCl₃) δ (ppm): 8.10 (1H, s), 8.08 (1H, d, J=8.01 Hz), 7.74 (2H, s), 7.67 (1H, d, J=7.25 Hz), 7.58 (1H, s), 7.47 (1H, t, J=7.63 Hz), 7.18 (1H, d, J=1.14 Hz), 7.04 (1H, d, J=0.76 Hz), 4.19 (2H, s), 3.85 (3H, s), 2.55 (3H, s).

Compound 1g-21-3

4-Methyl-3-(3-nitrobenzyl)-6-chloro-7-(5-acetylthiophen-2-yl)-2-oxo-2H-1-benzopyran

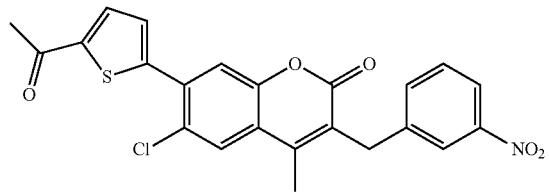

The title compound was synthesized under the same conditions as in the manufacturing example for compound 1g-11-3, except that 5-acetylthiophene-2-boronic acid was used instead of thiophene-3-boronic acid.

¹H-NMR (Bruker (ARX-300), 300 MHz, CDCl₃) δ (ppm): 8.15-8.05 (3H, m), 8.02 (1H, d, J=4.19 Hz), 7.83 (1H, s), 7.72 (2H, dd), 7.60 (1H, t), 4.16 (2H, s), 2.60 (3H, s), 2.54 (3H, s).

Compound 1g-22-1

4-Methyl-3-(3-nitrobenzyl)-7-(3-acetylphenyl)-2-oxo-2H-1-benzopyran

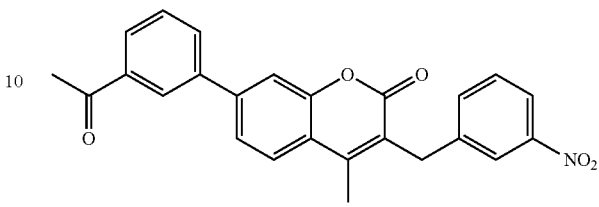

The title compound was synthesized under the same conditions as in the manufacturing example for compound 1g-11-3, except that compound 1g-1e-1 was used instead of compound 1g-1e-3, and that 3-acetylphenylboronic acid was used instead of thiophene-3-boronic acid.

¹H-NMR (Bruker (ARX-300), 300 MHz, CDCl₃) δ (ppm): 8.23 (1H, t), 8.05 (2H, m), 7.88 (1H, d, J=7.63 Hz), 7.82 (1H, d, J=7.63 Hz), 7.75 (1H, d=1.49 Hz), 7.73 (1H, d, J=8.01 Hz), 7.61 (3H, m), 7.45 (1H, t), 4.22 (2H, s), 2.65 (3H, s), 2.46 (3H, s).

MS (Micromass, Quattromicro, ESI+) m/z: 414.08 (M+1).

Compound 1g-23-1

4-Methyl-3-(3-nitrobenzyl)-7-(4-acetylphenyl)-2-oxo-2H-1-benzopyran

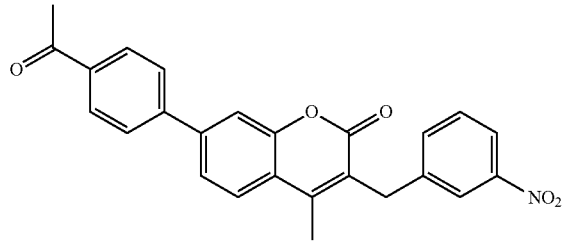

The title compound was synthesized under the same conditions as in the manufacturing example for compound 1g-11-3, except that compound 1g-1e-1 was used instead of compound 1g-1e-3, and that 4-acetylphenylboronic acid was used instead of thiophene-3-boronic acid.

¹H-NMR (Bruker (ARX-300), 300 MHz, CDCl₃) δ (ppm): 8.01 (4H, m), 7.85 (1H, d, J=8.77 Hz), 7.64 (4H, m), 7.45 (1H, t), 6.85 (1H, d, J=8.39 Hz), 4.22 (2H, s), 2.65 (3H, s), 2.46 (3H, s).

MS (Micromass, Quattromicro, ESI+) m/z: 414.08 (M+1).

Compound 1g-28-1

4-Methyl-3-(3-nitrobenzyl)-7-(4-N,N-dimethylaminophenyl)-2-oxo-2H-1-benzopyran

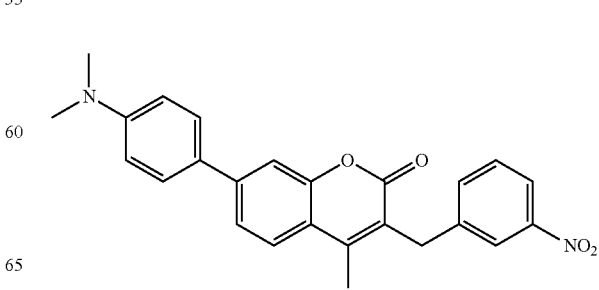

The title compound was synthesized under the same conditions as in the manufacturing example for compound 1g-11-3, except that compound 1g-1e-1 was used instead of compound 1g-1e-3, and that 4-N,N-dimethylaminophenylboronic acid was used instead of thiophene-3-boronic acid.

¹H-NMR (Bruker (ARX-300), 300 MHz, CDCl₃) δ (ppm): 8.11 (2H, t, d, J=8.77 Hz), 7.53 (7H, m), 6.78 (2H, d, J=8.77 Hz), 4.22 (2H, s), 3.10 (6H, s), 2.52 (3H, s).

MS (Micromass, Quattromicro, ESI+) m/z: 415.25 (M+1).

1-Methyl-5-tributylstannyl-1H-imidazole

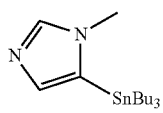

To a dehydrated tetrahydrofuran solution (10 mL) of 1-methylimidazole (1.6 mL, 18.8 mmol), there was added dropwise a mixture of n-BuLi (18 mL, 45 mmol) and TMEDA (6.7 mL, 44.6 mmol) at −20° C. under nitrogen atmosphere. After stirring for 30 minutes, the mixture was raised to room temperature and stirred for another hour. After again cooling to −20° C., a solution of n-Bu₃SnCl (12.5 mL, 46.4 mmol) in tetrahydrofuran (10 mL) was added dropwise thereto, the mixture was raised to room temperature and stirred for 17 hours. The reaction was terminated with water (15 mL), and then extraction was performed twice with ethyl acetate (20 mL). The mixture was then purified by silica gel chromatography (ethyl acetate:methanol=96:4) to yield the title compound (2.2 g, 32%).

¹H-NMR (Bruker (ARX-300), 300 MHz, CDCl₃) δ (ppm): 7.61 (1H, s), 7.02 (1H, s), 3.67 (3H, s), 1.48-1.56 (6H, m), 1.29-1.37 (6H, m), 1.09 (6H, t, J=8.4 Hz), 0.89 (9H, t, J=7.2 Hz).

MS (Micromass, Quattromicro, ESI+) m/z: 372.99 (M+2).

Compound 1g-32-1

4-Methyl-3-(3-nitrobenzyl)-7-(3-methyl-3H-imidazol-4-yl)-2-oxo-2H-1-benzopyran

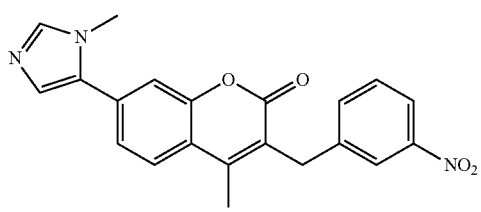

The title compound was synthesized under the same conditions as in the manufacturing example for compound 1g-16-1, except that 1-methyl-5-tributylstannyl-1H-imidazole was used instead of 5-tributylstannylthiazole.

¹H-NMR (Bruker (ARX-300), 300 MHz, CDCl₃) δ (ppm): 8.08 (2H, d, J=6.9 Hz), 7.70 (2H, m), 7.58 (1H, s), 7.47 (1H, t, J=7.8 Hz), 7.38 (2H, m), 7.26 (1H, d, J=3.9 Hz), 4.18 (2H, s), 3.76 (3H, s), 2.53 (3H, s).

Compound 1h-1-5

Dimethylcarbamic acid 2-oxo-2H-3-(2-fluoro-3-aminobenzyl)-4-methyl-6-fluoro-1-benzopyran-7-yl ester

[Chemical Formula 34]

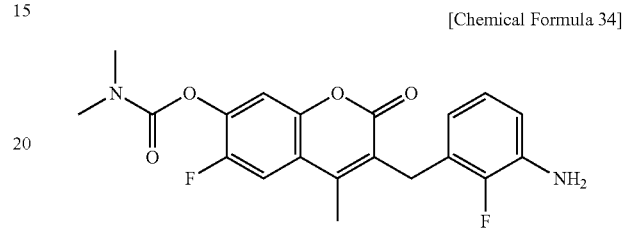

Tin(II) chloride dihydrate (923 mg, 4.09 mmol) was added to an ethanol/ethyl acetate solution (volume ratio 1:1, 50 mL) of compound 1g-1-5 (342.5 mg, 0.819 mmol), and the mixture was stirred at 80° C. for 3 hours. Ethyl acetate was added to the reaction solution, and the organic layer was washed with sodium carbonate solution and saturated saline, and dried over anhydrous magnesium sulfate. The solvent was distilled away under reduced pressure to yield the title compound (311.3 mg, 98%) as a white solid.

¹H NMR (DMSO-d₆, 270 MHz) δ (ppm): 2.41 (3H, s), 2.95 (3H, s), 3.09 (3H, s), 4.08 (2H, s), 6.21-6.26 (1H, m), 6.58-6.75 (2H, m), 7.47 (1H, d, J=6.8 Hz), 7.83 (1H, d, J=11.2 Hz).

ESI (LC/MS positive mode) m/z: 389 (M+H).

Compound 1h-1-1

Dimethylcarbamic acid 2-oxo-2H-3-(3-aminobenzyl)-4-methyl-1-benzopyran-7-yl ester

[Chemical Formula 35]

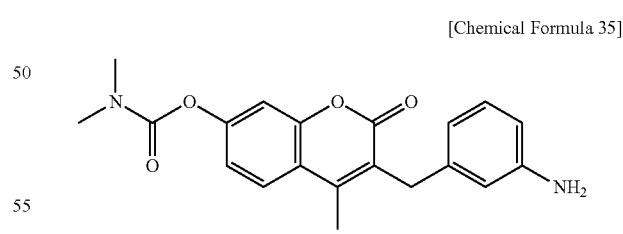

The title compound was synthesized under the same conditions as in the manufacturing example for compound 1h-1-5, except that compound 1g-1-1 was used instead of compound 1g-1-5.

¹H NMR (CDCl₃, 270 MHz) δ (ppm): 2.42 (3H, s), 3.03 (3H, s), 3.13 (3H, s), 3.60 (2H, brs), 3.97 (2H, s), 6.51 (1H, dd, J=2.0, 7.7 Hz), 6.58 (1H, s), 6.64 (1H, d, J=7.7 Hz), 7.02-7.12 (3H, m), 7.59 (1H, d, J=8.9 Hz).

ESI (LC/MS positive mode) m/z: 352 (M+H).

Compound 1h-1-2

Dimethylcarbamic acid 2-oxo-2H-3-(3-aminobenzyl)-4-methyl-6-fluoro-1-benzopyran-7-yl ester

[Chemical Formula 36]

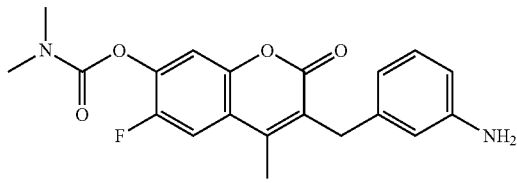

The title compound was synthesized under the same conditions as in the manufacturing example for compound 1h-1-5, except that compound 1g-1-2 was used instead of compound 1g-1-5.

$^1$H NMR (CD$_3$OD, 270 MHz) δ (ppm): 2.44 (3H, s), 3.02 (3H, s), 3.15 (3H, s), 3.95 (2H, s), 6.54-6.60 (2H, m), 7.00 (1H, dd, J=7.6, 7.6 Hz), 7.29 (1H, d, J=6.6 Hz), 7.64 (1H, d, J=11.1 Hz).

ESI (LC/MS positive mode) m/z: 371 (M+H).

Compound 1h-1-3

Dimethylcarbamic acid 2-oxo-2H-3-(3-aminobenzyl)-4-methyl-6-chloro-1-benzopyran-7-yl ester

[Chemical Formula 37]

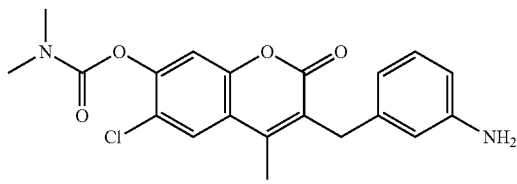

The title compound was synthesized under the same conditions as in the manufacturing example for compound 1h-1-5, except that compound 1g-1-3 was used instead of compound 1g-1-5.

$^1$H NMR (CDCl$_3$, 270 MHz) δ (ppm): 2.40 (3H, s), 3.04 (3H, s), 3.15 (3H, s), 3.96 (2H, s), 6.45-6.65 (3H, m), 7.05 (1H, dd, J=7.7 Hz), 7.25 (1H, s), 7.64 (1H, s).

ESI (LC/MS positive mode) m/z: 387 (M+H).

Compound 1h-1-4

Dimethylcarbamic acid 2-oxo-2H-3-(2-fluoro-3-aminobenzyl)-4-methyl-1-benzopyran-7-yl ester

[Chemical Formula 38]

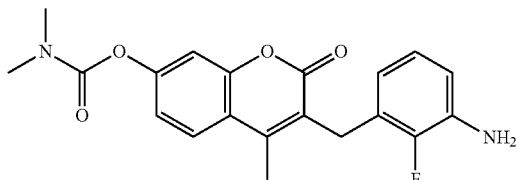

The title compound was synthesized under the same conditions as in the manufacturing example for compound 1h-1-5, except that compound 1g-1-4 was used instead of compound 1g-1-5.

$^1$H NMR (270 MHz, DMSO-d$_6$) δ (ppm): 2.93 (3H, s), 3.06 (3H, s), 3.91 (2H, s), 5.07 (2H, brs), 6.22 (1H, brt, J=7.3 Hz), 6.55-6.75 (2H, m), 7.17 (1H, dd, J=8.7, 2.3 Hz), 7.24 (1H, d, J=2.3 Hz), 7.83 (1H, d, J=8.7 Hz).

ESI (LC/MS positive mode) m/z: 371 (M+1H).

Compound 1h-1-7

Dimethylcarbamic acid 2-oxo-2H-3-(3-aminobenzyl)-4-methyl-6-iodo-1-benzopyran-7-yl ester

[Chemical Formula 39]

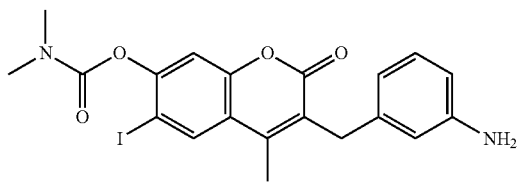

The title compound was synthesized under the same conditions as in the manufacturing example for compound 1h-1-5, except that compound 1g-1-7 was used instead of compound 1g-1-5.

$^1$H NMR (DMSO-d$_6$, 270 MHz) δ (ppm): 2.43 (3H, s), 2.96 (3H, s), 3.13 (3H, s), 3.83 (2H, s), 4.96 (2H, brs), 6.35-6.38 (3H, m), 6.89 (1H, dd, J=7.8, 7.8 Hz), 7.37 (1H, s), 8.22 (1H, s).

ESI (LC/MS positive mode) m/z: 479 (M+H).

Compound 1h-1-8

Dimethylcarbamic acid 2-oxo-2H-3-(3-aminobenzyl)-4-methyl-6-methyl-1-benzopyran-7-yl ester

[Chemical Formula 40]

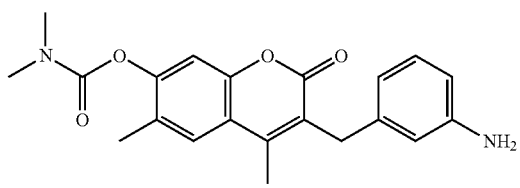

The title compound was synthesized under the same conditions as in the manufacturing example for compound 1h-1-5, except that compound 1g-1-8 was used instead of compound 1g-1-5.

$^1$H NMR (DMSO-d$_6$, 270 MHz) δ (ppm): 2.22 (3H, s), 2.43 (3H, s), 2.94 (3H, s), 3.10 (3H, s), 3.83 (2H, s), 4.96 (2H, brs), 6.35-6.38 (3H, m), 6.90 (1H, dd, J=8.1, 8.1 Hz), 7.21 (1H, s), 7.73 (1H, s).

ESI (LC/MS positive mode) m/z: 367 (M+H).

Compound 1h-1-9

Dimethylcarbamic acid 2-oxo-2H-3-(3-aminobenzyl)-4-methyl-6-cyano-1-benzopyran-7-yl ester

[Chemical Formula 41]

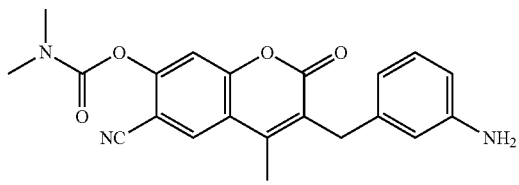

The title compound was synthesized under the same conditions as in the manufacturing example for compound 1h-1-5, except that compound 1g-1-9 was used instead of compound 1g-1-5.

$^1$H NMR (DMSO-$d_6$, 270 MHz) δ (ppm): 2.46 (3H, s), 2.97 (3H, s), 3.12 (3H, s), 3.84 (2H, s), 4.96 (2H, brs), 6.36-6.38 (3H, m), 6.90 (1H, dd, J=7.9, 7.9 Hz), 7.59 (1H, s), 8.44 (1H, s).

ESI (LC/MS positive mode) m/z: 378 (M+H).

Compound 1h-1-10

Dimethylcarbamic acid 2-oxo-2H-3-(2-aminopyridin-4-ylmethyl)-4-methyl-1-benzopyran-7-yl ester

[Chemical Formula 42]

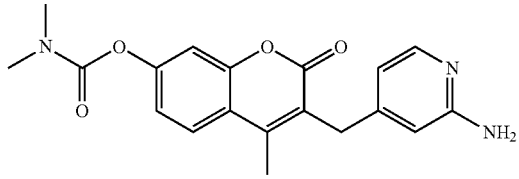

The title compound was synthesized under the same conditions as in the manufacturing example for compound 1g-1-5, except that compound 5d-0-10 was used instead of compound 1e-0-5.

$^1$H NMR (300 MHz) (DMSO-$d_6$) δ (ppm): 2.42 (3H, s), 2.93 (3H, s), 3.06 (3H, s), 3.82 (2H, s), 5.75 (2H, brs), 6.19 (1H, s), 6.37 (1H, dd, J=1.52, 5.34 Hz), 7.18 (1H, dd, J=2.28, 8.77 Hz), 7.25 (1H, d, J=2.28 Hz), 7.76 (1H, d, J=5.34 Hz), 7.84 (1H, d, J=8.77 Hz).

Compound 1h-1-11

Dimethylcarbamic acid 2-oxo-2H-3-(2-aminopyridin-4-ylmethyl)-4-methyl-6-fluoro-1-benzopyran-7-yl ester

[Chemical Formula 43]

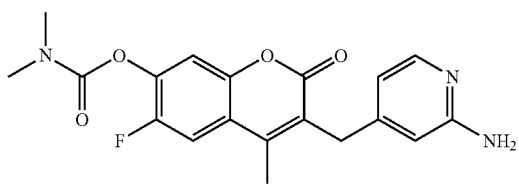

The title compound was synthesized under the same conditions as in the manufacturing example for compound 1g-1-5, except that compound 5d-0-11 was used instead of compound 1e-0-5.

$^1$H NMR (300 MHz) (DMSO-$d_6$) δ (ppm): 2.41 (3H, s), 2.94 (3H, s), 3.08 (3H, s), 3.82 (2H, s), 5.75 (2H, brs), 6.19 (1H, s), 6.37 (1H, d, J=4.95 Hz), 7.48 (1H, d, J=7.24 Hz), 7.76 (1H, d, J=5.72 Hz), 7.85 (1H, d, J=9.53 Hz).

Compound 1h-1-13

Dimethylcarbamic acid 3-(6-aminopyridin-2-ylmethyl)-4-methyl-2-oxo-2H-1-benzopyran-7-yl ester

[Chemical Formula 44]

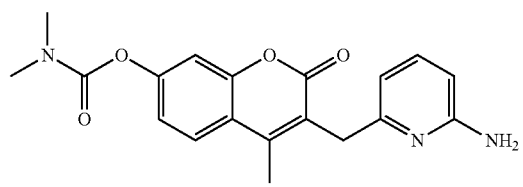

The title compound was synthesized under the same conditions as in the manufacturing example for compound 1g-1-5, except that compound 5d-0-13 was used instead of compound 1e-0-5.

$^1$H NMR (DMSO-$d_6$, 270 MHz) δ (ppm): 2.42 (3H, s), 2.93 (3H, s), 3.07 (2H, d), 3.88 (2H, s), 5.79 (2H, brs), 6.23 (1H, d, J=8.1 Hz), 6.30 (1H, d, J=8.1 Hz), 7.15-7.26 (3H, m), 7.83 (1H, d, J=10.8 Hz).

ESI (LC/MS positive mode) m/z: 354 (M+H).

Compound 1h-1-14

Dimethylcarbamic acid 3-(6-aminopyridin-2-ylmethyl)-6-fluoro-4-methyl-2-oxo-2H-1-benzopyran-7-yl ester

[Chemical Formula 45]

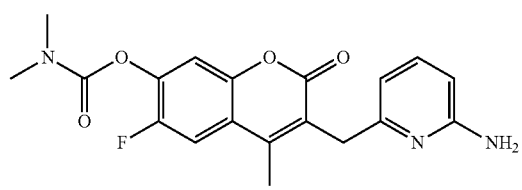

The title compound was synthesized under the same conditions as in the manufacturing example for compound 1g-1-5, except that compound 5d-0-14 was used instead of compound 1e-0-5.

$^1$H NMR (CDCl$_3$, 270 MHz) δ (ppm): 2.45 (3H, s), 3.04 (3H, s), 3.09 (3H, s), 4.04 (2H, s), 6.31 (1H, d, J=7.8 Hz), 6.54 (1H, d, J=7.8 Hz), 7.15-7.40 (3H, m).

ESI (LC/MS positive mode) m/z: 372 (M+H).

Compound 1h-1-15

Dimethylcarbamic acid 3-(6-aminopyridin-2-ylmethyl)-6-chloro-4-methyl-2-oxo-2H-1-benzopyran-7-yl ester

[Chemical Formula 46]

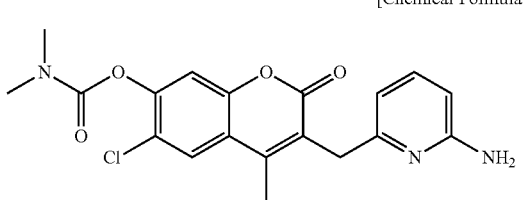

The title compound was synthesized under the same conditions as in the manufacturing example for compound 1g-1-5, except that compound 5d-0-15 was used instead of compound 1e-0-5.

$^1$H NMR (CDCl$_3$, 270 MHz) δ (ppm): 2.46 (3H, s), 3.05 (3H, s), 3.17 (3H, s), 4.04 (2H, s), 6.31 (1H, d, J=7.8 Hz), 6.55 (1H, d, J=7.8 Hz), 7.20-7.35 (2H, m), 7.66 (1H, s).

ESI (LC/MS positive mode) m/z: 388 (M+H).

Compound 1h-1-4F

Dimethylcarbamic acid 3-(3-amino-2-fluorobenzyl)-4-fluoromethyl-2-oxo-2H-1-benzopyran-7-yl ester

[Chemical Formula 47]

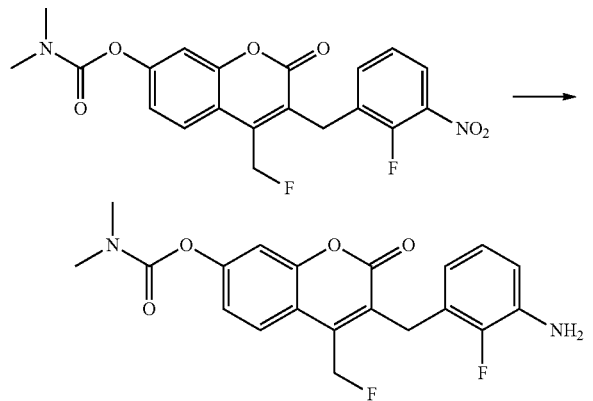

Ethyl acetate (2.0 mL) was added to dimethylcarbamic acid 4-fluoromethyl-3-(2-fluoro-3-nitrobenzyl)-2-oxo-2H-1-benzopyran-7-yl ester (20.5 mg) (6c-1-4), and tin(II) chloride dihydrate (60 mg) was added to the resultant suspension while stirring at room temperature. The suspension was heated under reflux for 1.5 hours, and after cooling to room temperature, saturated sodium hydrogen carbonate was added, and the mixture was extracted with ethyl acetate. The resultant organic layer extraction liquid was washed with saturated saline, and the organic layer was dried over anhydrous magnesium sulfate. The solvent was then distilled away under reduced pressure to yield the title compound (19.5 mg).

$^1$H NMR (270 MHz, CDCl$_3$) δ (ppm): 3.03 (3H, s), 3.13 (3H, s), 4.09 (2H, s), 5.66 (2H, d, J=46.8 Hz), 6.62 (1H, brt, 7.9 Hz), 6.65 (1H, td, J=7.9, 1.0 Hz), 6.83 (1H, dd, J=7.9, 1.0 Hz), 7.12 (1H, dd, J=8.2, 2.3 Hz), 7.15 (1H, d, J=2.3 Hz), 7.76 (1H, dd, J=8.2, 2.3 Hz).

ESI (LC/MS positive mode) m/z: 389 (M+H).

Compound 1h-1-1F

Dimethylcarbamic acid 3-(3-aminobenzyl)-4-fluoromethyl-2-oxo-2H-1-benzopyran-7-yl ester

[Chemical Formula 48]

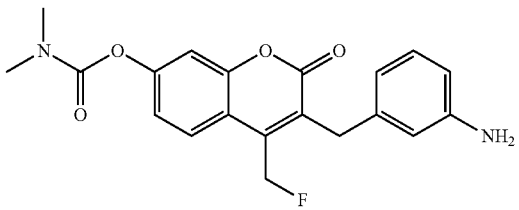

The title compound was synthesized under the same conditions as in the manufacturing example for compound 1h-1-4F, except that compound 6c-1-1 was used instead of compound 6c-1-4.

$^1$H NMR (270 MHz, DMSO-d$_6$) δ (ppm): 2.93 (3H, s), 3.07 (3H, s), 3.91 (2H, s), 4.98 (2H, brs), 5.81 (2H, d, J=46.3 Hz), 6.29-6.43 (3H, m), 6.91 (1H, t, J=8.2 Hz), 7.21 (1H, dd, J=8.7, 2.3 Hz), 7.30 (1H, d, J=2.3 Hz), 7.89 (1H, d, J=8.7, 2.3 Hz).

ESI (LC/MS positive mode) m/z: 371 (M+H).

Compound 1h-1-2F

Dimethylcarbamic acid 3-(3-aminobenzyl)-6-fluoro-4-fluoromethyl-2-oxo-2H-1-benzopyran-7-yl ester

[Chemical Formula 49]

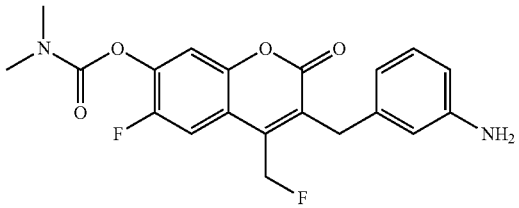

The title compound was synthesized under the same conditions as in the manufacturing example for compound 1h-1-4F, except that compound 6c-1-2 was used instead of compound 6c-1-4.

$^1$H NMR (270 MHz, CDCl$_3$) δ (ppm): 3.04 (3H, s), 3.15 (3H, s), 4.03 (2H, brs), 5.59 (2H, d, J=47.0 Hz), 6.50-6.60 (3H, m), 7.01-7.10 (1H, m), 7.20-7.30 (1H, m), 7.54 (2H, 1H, dd, J=10.5, 1.8 Hz).

ESI (LC/MS positive mode) m/z: 389 (M+H).

Compound 1h-1-3F

Dimethylcarbamic acid 6-chloro-4-fluoromethyl-3-(3-aminobenzyl)-2-oxo-2H-1-benzopyran-7-yl ester

[Chemical Formula 50]

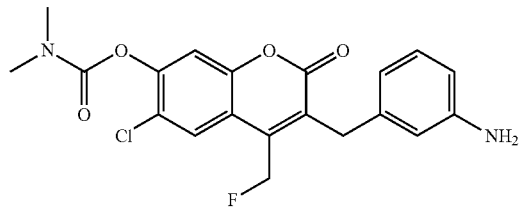

The title compound was synthesized under the same conditions as in the manufacturing example for compound 1h-1-4F, except that compound 6c-1-3 was used instead of compound 6c-1-4.

¹H NMR (DMSO-d₆, 270 MHz) δ (ppm): 8.04 (s, 1H), 7.54 (s, 1H), 6.90 (t, J=7.8 Hz, 1H), 6.36 (m, 3H), 5.84 (d, J=46.0 Hz, 2H), 3.92 (s, 2H), 3.11 (s, 3H), 2.95 (s, 3H).
ESIMS m/z: 405 (M+H).

Compound 1h-1-38

Dimethylcarbamic acid 3-(3-aminobenzyl)-6-carbamoyl-4-methyl-2-oxo-2H-1-benzopyran-7-yl ester

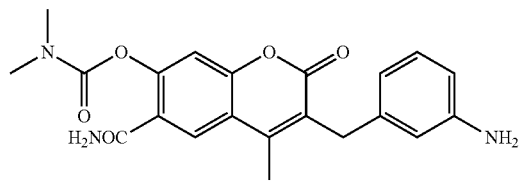

The title compound was synthesized under the same conditions as in the manufacturing example for compound 1h-1-5, except that compound 1g-1-38 was used instead of compound 1g-1-5.

¹H-NMR (DMSO-d₆, 270 MHz) δ (ppm): 2.47 (3H, s), 2.90 (3H, s), 3.05 (3H, s), 3.85 (2H, s), 4.97 (2H, s), 6.35-6.38 (3H, m), 6.90 (1H, t, J=7.8 Hz), 7.28 (1H, s), 7.50 (1H, s), 7.80 (1H, s), 7.98 (1H, s).
ESI (LC/MS positive mode) m/z: 396 (M+H).

Compound 1h-1-39

Dimethylcarbamic acid 3-(3-aminobenzyl)-4-methyl-2-oxo-6-trimethylsilanylethynyl-2H-1-benzopyran-7-yl ester

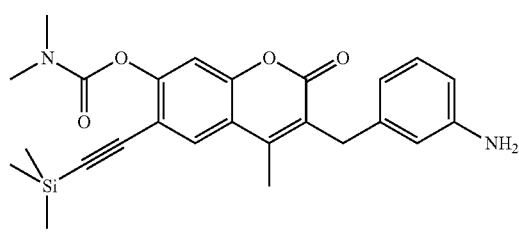

The title compound was synthesized under the same conditions as in the manufacturing example for compound 1h-1-5, except that compound 1g-1-39 was used instead of compound 1g-1-5.

¹H-NMR (DMSO-d₆, 270 MHz) δ (ppm): 0.23 (9H, s), 2.44 (3H, s), 2.94 (3H, s), 3.11 (3H, s), 3.82 (2H, s), 4.96 (2H, s), 6.12-6.15 (3H, m), 6.66 (1H, t, J=8.1 Hz), 7.14 (1H, s), 7.68 (1H, s).
ESI (LC/MS positive mode) m/z: 449 (M+H).

Compound 1h-1-40

Dimethylcarbamic acid 3-(3-aminobenzyl)-6-ethynyl-4-methyl-2-oxo-2H-1-benzopyran-7-yl ester

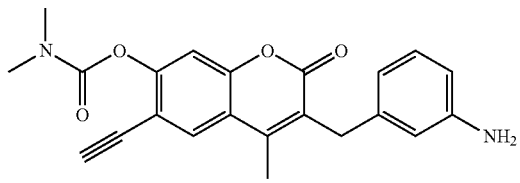

TBAF (1.0 M in 0.245 mL of THF) was added to a solution of compound 1g-1-39 (100 mg, 0.223 mmol) in THF (2 mL), and the mixture was stirred at room temperature for 1 hour. The reaction mixture was then concentrated under reduced pressure to yield a crude product, which was then purified by column chromatography to yield the title compound (77 mg, 92%).

¹H-NMR (DMSO-d₆, 270 MHz) δ (ppm): 2.44 (3H, s), 2.94 (3H, s), 3.09 (3H, s), 3.83 (2H, s), 4.45 (1H, s), 4.97 (1H, brs), 6.35-6.38 (3H, m), 6.96 (1H, t, J=8.0 Hz), 7.38 (1H, s), 7.97 (1H, s).
ESI (LC/MS positive mode) m/z: 377 (M+H).

Compound 1h-1-59

Dimethylcarbamic acid 3-(2-aminobenzoylamino)-4-methyl-2-oxo-2H-1-benzopyran-7-yl ester

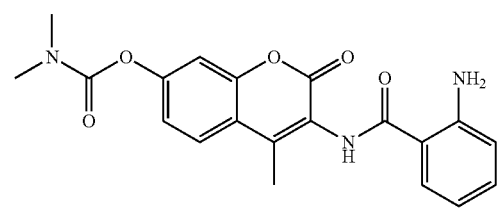

The title compound was synthesized under the same conditions as in the manufacturing example for compound 1h-1-5, except that compound 1g-1-59 was used instead of compound 1g-1-5.

¹H NMR (270 MHz, DMSO-d₆) δ (ppm): 9.63 (s, 1H), 7.86 (d, 1H, J=8.7 Hz), 7.76 (d, 1H, J=6.6 Hz), 7.31 (d, 1H, J=2.3 Hz), 7.25-7.20 (m, 2H), 6.75 (d, 1H. J=8.2 Hz), 6.58 (t, 1H, J=7.3 Hz), 6.50 (s, 2H), 3.08 (s, 3H), 2.94 (s, 3H), 2.36 (s, 3H).
ESIMS m/z: 382 (M+H).

Compound 1h-1d-1

Pyrrolidine-1-carboxylic acid 3-(3-aminobenzyl)-4-methyl-2-oxo-2H-1-benzopyran-7-yl ester

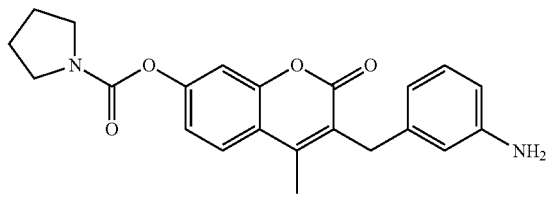

The title compound was synthesized under the same conditions as in the manufacturing example for compound 1h-1-5, except that compound 1g-1d-1 was used instead of compound 1g-1-5.

$^1$H-NMR (CDCl$_3$, 270 MHz) δ (ppm): 1.90-2.04 (4H, m), 2.42 (3H, s), 3.50 (2H, t, J=6.6 Hz), 3.56-3.61 (4H, m), 3.97 (2H, s), 6.49-6.66 (3H, m), 7.05 (1H, t, J=7.8 Hz), 7.09-7.17 (2H, m), 7.59 (1H, d, J=7.4 Hz).

ESI (LC/MS positive mode) m/z: 379 (M+H).

Compound 1h-2-1

4-Methyl-3-(3-aminobenzyl)-7-(pyrimidin-2-yloxy)-2-oxo-2H-1-benzopyran

[Chemical Formula 51]

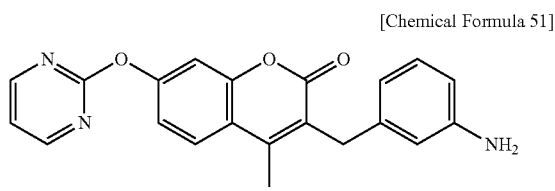

The title compound was synthesized under the same conditions as in the manufacturing example for compound 1h-1-5, except that compound 1g-2-1 was used instead of compound 1g-1-5.

$^1$H NMR (CDCl$_3$, 270 MHz) δ (ppm): 2.45 (3H, s), 3.60 (1H, brs), 3.99 (2H, s), 6.52 (1H, dd, J=2.0, 7.6 Hz), 6.57 (1H, s), 6.64 (1H, d, J=7.6 Hz), 7.06 (1H, dd, J=7.6, 7.6 Hz), 7.11 (1H, t, J=4.8 Hz), 7.16 (1H, dd, J=2.3, 8.7 Hz), 7.23 (1H, d, J=2.3 Hz), 7.68 (1H, d, J=8.7 Hz), 8.59 (2H, d, J=4.8 Hz).

ESI (LC/MS positive mode) m/z: 360 (M+H).

Compound 1h-2-3

4-Methyl-3-(3-aminobenzyl)-7-(pyrimidin-2-yloxy)-6-chloro-2-oxo-2H-1-benzopyran

[Chemical Formula 52]

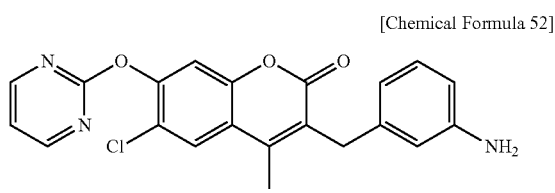

The title compound was synthesized under the same conditions as in the manufacturing example for compound 1h-1-5, except that compound 1g-2-3 was used instead of compound 1g-1-5.

$^1$H NMR (CDCl$_3$, 270 MHz) δ (ppm): 2.42 (3H, s), 4.00 (2H, s), 6.52 (1H, d, J=7.7 Hz), 6.55 (1H, brs), 6.63 (1H, d, J=7.7 Hz), 7.04 (1H, t, J=7.7 Hz), 7.10 (1H, t, J=4.8 Hz), 7.26 (1H, s), 7.72 (1H, s), 8.60 (2H, d, J=4.8 Hz).

ESI (LC/MS positive mode) m/z: 394 (M+H).

Compound 1h-2-4

4-Methyl-3-(2-fluoro-3-aminobenzyl)-7-(pyrimidin-2-yloxy)-2-oxo-2H-1-benzopyran

[Chemical Formula 53]

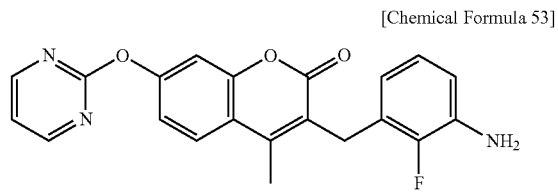

(Synthesis Scheme 1)

The title compound was synthesized under the same conditions as in the manufacturing example for compound 1h-1-5, except that compound 1g-2-4 was used instead of compound 1g-1-5.

$^1$H NMR (270 MHz, DMSO-d$_6$) δ (ppm): 2.45 (3H, s), 3.93 (2H, s), 5.08 (2H, br.s), 6.25 (1H, ddd, J=7.2, 1.7 Hz, J$_{HF}$=7.2 Hz), 6.61 (1H, ddd, J=8.2, 1.7 Hz, J$_{HF}$=8.2 Hz), 6.73 (1H, dd, J=8.2, 7.2 Hz), 7.26 (1H, dd, J=8.8, 2.4 Hz), 7.34 (1H, t, J=4.8 Hz), 7.37 (1H, d, J=2.4 Hz), 7.89 (1H, d, J=8.8 Hz), 8.68 (2H, d, J=4.8 Hz).

ESI (LC/MS positive mode) m/z: 378 (M+H).

Compound 1h-2-4S2

3-{2-Fluoro-3-aminobenzyl}-4-methyl-7-(pyrimidin-2-yloxy)-2-oxo-2H-1-benzothiopyran

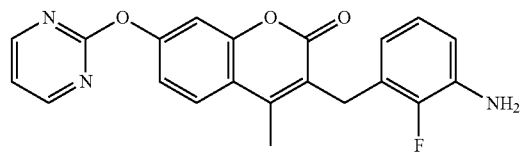

The title compound was synthesized under the same conditions as in the manufacturing example for compound 1h-2-4 (synthesis scheme 2), except that compound 5d-0-4S2 was used instead of compound 4a-0-4.

$^1$H-NMR (270 MHz, DMSO-d$_6$) δ (ppm): 4.02 (2H, s), 5.09 (2H, s), 6.11 (1H, dd, J=7.0 Hz, J$_{HF}$=7.0 Hz), 6.60 (1H, dd, J=8.5 Hz, J$_{HF}$=8.5 Hz), 6.71 (1H, dd, J=7.7, 7.7 Hz), 7.28 (1H, dd, J=8.9, 2.3 Hz), 7.31-7.42 (2H, m), 7.61-7.64 (1H, m), 8.67-8.71 (2H, m).

The CH$_3$ peak was overlapped with the DMSO peak.

ESI (LC-MS positive mode) m/z: 394 (M+H).

Compound 1h-2-5

2-Oxo-2H-3-(2-fluoro-3-aminobenzyl)-4-methyl-6-fluoro-7-(pyrimidin-2-yloxy)-1-benzopyran

[Chemical Formula 54]

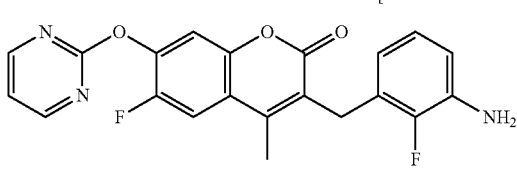

The title compound was synthesized under the same conditions as in the manufacturing example for compound 1g-2-4, except that compound 4a-0-5 was used instead of compound 1e-0-4.

$^1$H-NMR (CD$_3$OD, 270 MHz) δ (ppm): 2.39 (3H, s), 4.03 (2H, s), 6.29-6.43 (1H, m), 6.69-6.78 (2H, m), 7.28-7.39 (3H, m), 7.68-7.72 (1H, m), 7.98 (1H, m).

ESI (LC/MS positive mode) m/z: 396 (M+H).

Compound 1h-2-6

4-Methyl-3-(2-methyl-3-aminobenzyl)-7-(pyrimidin-2-yloxy)-2-oxo-2H-1-benzopyran

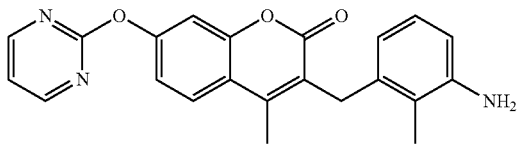

The title compound was synthesized under the same conditions as in the manufacturing example for compound 1h-2-4 (synthesis scheme 2), except that compound 4a-0-6 was used instead of compound 4a-0-4.

$^1$H NMR (Bruker, 300 MHz, CDCl$_3$) δ (ppm): 8.61 (2H, d, J=5.0 Hz), 7.70 (1H, d, J=8.8 Hz), 7.26 (1H, d, J=3.1 Hz), 7.18 (1H, dd, J=2.7, 8.8 Hz), 7.12 (1H, t, J=4.8 Hz), 6.88 (1H, t, J=7.8 Hz), 6.59 (1H, d, J=7.6 Hz), 6.32 (1H, d, J=7.6 Hz), 4.02 (2H, s), 3.73-3.63 (2H, br), 2.35 (3H, s), 2.22 (3H, s).

MS (Micromass, Quattromicro, ESI+) m/z: 373.97 (M+H).

Compound 1h-2-10

4-Methyl-3-(2-aminopyridin-4-ylmethyl)-7-(pyrimidin-2-yloxy)-2-oxo-2H-1-benzopyran

[Chemical Formula 55]

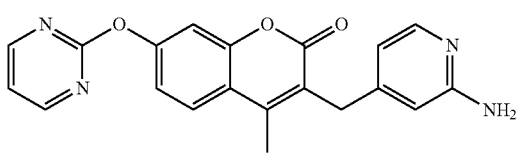

The title compound was synthesized under the same conditions as in the manufacturing example for compound 1g-2-4, except that compound 5d-0-10 was used instead of compound 1e-0-4.

$^1$H NMR (CD$_3$OD, 270 MHz) δ (ppm): 2.36 (3H, s), 3.85 (2H, s), 6.32 (1H, brs), 6.42 (1H, d, J=5.7 Hz), 7.10-7.20 (3H, m), 7.66 (1H, d, J=4.9 Hz), 7.75 (1H, d, J=8.6 Hz), 8.52 (2H, d, J=4.9 Hz).

ESI (LC/MS positive mode) m/z: 361 (M+H).

Compound 1h-2-12

4-Methyl-3-(2-aminopyridin-4-ylmethyl)-7-(pyrimidin-2-yloxy)-6-chloro-2-oxo-2H-1-benzopyran

[Chemical Formula 56]

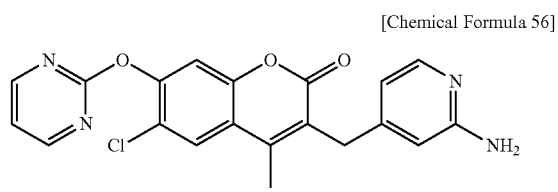

The title compound was synthesized under the same conditions as in the manufacturing example for compound 1g-2-4, except that compound 5d-0-12 was used instead of compound 1e-0-4.

$^1$H NMR (CDCl$_3$, 270 MHz) δ (ppm): 2.42 (3H, s), 3.96 (2H, s), 6.35 (1H, brs), 6.53 (1H, d, J=6.5 Hz), 7.13 (1H, dd, J=4.9 Hz), 7.31 (1H, s), 7.74 (1H, s), 7.96 (1H, d, J=6.5 Hz), 8.59 (2H, d, J=4.9 Hz).

ESI (LC/MS positive mode) m/z: 395 (M+H).

Compound 1h-2-4F 3-(3-Amino-2-fluorobenzyl)-4-fluoromethyl-7-(pyrimidin-2-yloxy)-2-oxo-2H-1-benzopyran

[Chemical Formula 57]

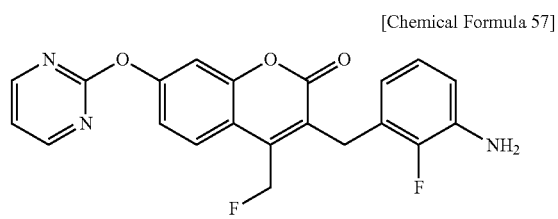

The title compound was synthesized under the same conditions as in the manufacturing example for compound 1h-1-5, except that compound 6c-2-4 was used instead of compound 1g-1-5.

1H NMR (DMSO-d$_6$, 270 MHz) δ (ppm): 8.68 (d, J=4.9 Hz, 2H), 7.94 (dd, J=8.9, 2.4 Hz, 1H), 7.41 (d, J=2.2 Hz, 1H), 7.33 (t, J=4.6 Hz, 1H), 7.29 (dd, J=8.7, 2.2 Hz, 1H), 6.72 (t, J=7.6 Hz, 1H), 6.60 (td, J=8.1, 1.6 Hz, 1H), 6.24 (t, J=6.2 Hz, 1H), 5.83 (d, J=46.2 Hz, 2H), 5.08 (s, 2H), 4.00 (s, 2H).

ESIMS m/z: 396 (M+H).

Compound 1h-2-16

3-(3-Fluoro-2-aminopyridin-4-ylmethyl)-4-methyl-7-(pyrimidin-2-yloxy)-2-oxo-2H-1-benzopyran

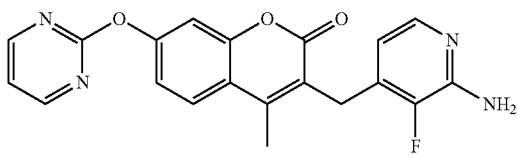

The title compound was synthesized under the same conditions as in the manufacturing example for compound 1h-2-4 (synthesis scheme 2), except that compound 5d-0-16 was used instead of compound 4a-0-4.

$^1$H NMR (DMSO-d$_6$, 270 MHz) δ (ppm): 2.45-2.55 (3H, m), 3.94 (2H, s), 6.12 (2H, brs), 6.28 (1H, dd, J=4.7 Hz), 7.27 (1H, dd, J=8.6 Hz, J=2.1 Hz), 7.34 (1H, dd, J=4.9 Hz), 7.38 (1H, d, J=2.1 Hz), 7.58 (1H, d, J=4.7 Hz), 7.91 (1H, d, J=8.6 Hz), 8.68 (2H, d, J=4.7 Hz).

ESI (LC/MS positive mode) m/z: 479 (M+H).

Compound 1h-2-17

3-(2-Amino-3-fluoropyridin-4-ylmethyl)-6-fluoro-4-methyl-7-(pyrimidin-2-yloxy)-2-oxo-2H-1-benzopyran

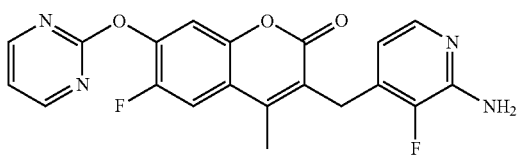

The title compound was synthesized under the same conditions as in the manufacturing example for compound 1h-2-4 (synthesis scheme 2), except that compound 5d-0-17 was used instead of compound 4a-0-4.

$^1$H NMR (DMSO-d$_6$, 270 MHz) δ (ppm): 2.45 (3H, s), 3.94 (2H, s), 6.13 (2H, s), 6.28 (1H, t, J=5.1 Hz), 7.38 (1H, t, J=4.8 Hz), 7.59 (1H, d, J=5.1 Hz), 7.65 (1H, d, J=6.8 Hz), 7.92 (1H, d, J=11.5 Hz), 7.91 (1H, d, J=11.5 Hz), 8.70 (2H, d, J=4.8 Hz).

ESI (LC/MS positive mode) m/z: 397 (M+H).

Compound 1h-2-19

3-(3-Fluoro-2-aminopyridin-4-ylmethyl)-4-methyl-6-methyl-7-(pyrimidin-2-yloxy)-2-oxo-2H-1-benzopyran

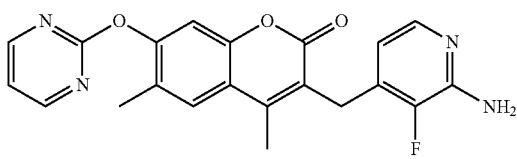

The title compound was synthesized under the same conditions as in the manufacturing example for compound 1h-2-4 (synthesis scheme 2), except that compound 5d-0-19 was used instead of compound 4a-0-4.

$^1$H NMR (DMSO-d$_6$, 270 MHz) δ (ppm): 2.15 (3H, s), 2.46 (3H, s), 3.93 (2H, s), 6.10 (2H, brs), 6.27 (1H, dd, J=5.1 Hz), 7.31 (1H, t, J=4.7 Hz), 7.58 (1H, d, J=5.1 Hz), 7.82 (1H, s), 8.66 (2H, d, J=8.66 Hz).

ESI (LC/MS positive mode) m/z: 393 (M+H).

Compound 1h-2-19Me 3-(2-Amino-3-fluoropyridin-4-ylmethyl)-4-ethyl-6-methyl-7-(pyrimidin-2-yloxy)-2-oxo-2H-1-benzopyran

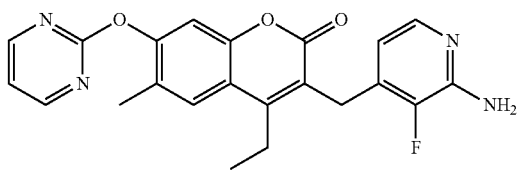

The title compound was synthesized under the same conditions as in the manufacturing example for compound 1h-2-4 (synthesis scheme 2), except that compound 5d-0-19Me was used instead of compound 4a-0-4.

$^1$H NMR (DMSO-d$_6$, 270 MHz) δ (ppm): 1.06 (3H, brt, J=7.4 Hz), 2.16 (3H, s), 2.89 (2H, brq, J=7.4 Hz), 3.91 (2H, s), 6.12 (2H, s), 6.26 (1H, t, J=5.1 Hz), 7.28-7.37 (3H, m), 7.58 (1H, d, J=5.1 Hz), 7.83 (1H, s), 8.67 (2H, d, J=4.8 Hz).

ESI (LC/MS positive mode) m/z: 407 (M+H).

Compound 1h-2-45

4-Methyl-3-(2-aminobenzyl)-7-(pyrimidin-2-yloxy)-2-oxo-2H-1-benzopyran

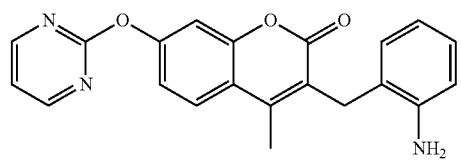

The title compound was synthesized under the same conditions as in the manufacturing example for compound 1h-2-4 (synthesis scheme 2), except that compound 4a-0-45 was used instead of compound 4a-0-4.

$^1$H-NMR (Bruker, 300 MHz, CDCl$_3$) δ (ppm): 8.59 (2H, d, J=4.6 Hz), 7.69 (1H, d, J=8.8 Hz), 7.24 (1H, d, J=2.3 Hz), 7.18 (1H, dd, J=2.3, 8.8 Hz), 7.11 (1H, t, J=4.8 Hz), 7.03 (1H, t, J=7.4 Hz), 6.97 (1H, d, J=7.2 Hz), 6.69 (2H, d, J=7.2 Hz), 3.92 (2H, s), 2.49 (3H, s).

Compound 1h-2-46

4-Methyl-3-(4-aminobenzyl)-7-(pyrimidin-2-yloxy)-2-oxo-2H-1-benzopyran

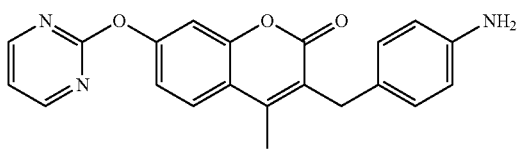

The title compound was synthesized under the same conditions as in the manufacturing example for compound 1h-2-4 (synthesis scheme 2), except that compound 4a-0-46 was used instead of compound 4a-0-4.

$^1$H-NMR (Bruker, 300 MHz, CDCl$_3$) δ (ppm): 8.59 (2H, d, J=5.0 Hz), 7.67 (1H, d, J=8.8 Hz), 7.22 (1H, d, J=2.3 Hz), 7.15 (1H, dd, J=2.3, 8.8 Hz), 7.10 (1H, t, J=5.0 Hz), 7.05 (2H, d, J=8.4 Hz), 6.61 (2H, d, J=8.4 Hz), 5.30 (2H, s), 3.95 (2H, s), 2.45 (3H, s).

MS (Micromass, Quattromicro, ESI+) m/z: 359.99 (M+H).

Compound 1h-2-47

3-(3-Aminobenzyl)-4-hydroxy-7-(pyrimidin-2-yloxy)-2-oxo-2H-1-benzopyran

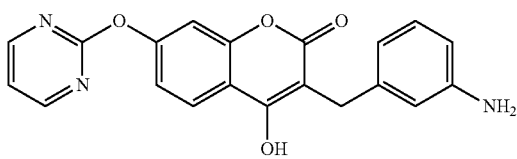

The title compound was synthesized under the same conditions as in the manufacturing example for compound 1h-1-5, except that compound 1g-2-47 was used instead of compound 1g-1-5.

$^1$H NMR (270 MHz, CD$_3$OD) δ (ppm): 8.54 (d, 2H, J=4.9 Hz), 7.94 (d, 1H, J=8.4 Hz), 7.32-7.25 (m, 2H), 7.20-7.10 (m, 4H), 7.02 (m, 1H), 3.89 (s, 2H).

ESIMS m/z: 362 (M+H).

Compound 1h-2-51

3-(3-Aminophenylamino)-4-methyl-7-(pyrimidin-2-yloxy)-2-oxo-2H-1-benzopyran

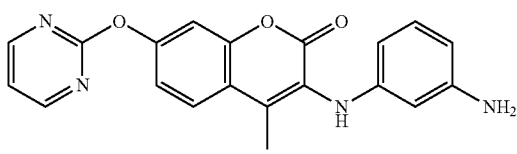

The title compound was synthesized under the same conditions as in the manufacturing example for compound 1h-2-4 (synthesis scheme 2), except that compound 4a-0-51 was used instead of compound 4a-0-4.

$^1$H NMR (270 MHz, DMSO-d$_6$) δ (ppm): 8.69 (d, 2H, J=4.8 Hz), 7.81 (d, 1H, J=8.6 Hz), 7.38 (d, 1H, J=2.1 Hz), 7.33 (t, 1H, J=4.8 Hz), 7.29-7.24 (m, 2H), 6.80 (t, 1H, J=7.7 Hz), 6.00 (m, 2H), 5.86 (s, 1H), 4.86 (s, 2H), 2.26 (s, 3H).

ESIMS m/z: 361 (M+H).

Compound 1h-2-52

3-(3-Aminophenoxy)-4-methyl-7-(pyrimidin-2-yloxy)-2-oxo-2H-1-benzopyran

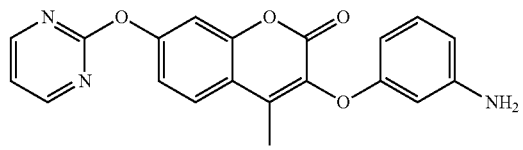

The title compound was synthesized under the same conditions as in the manufacturing example for compound 1h-2-4 (synthesis scheme 2), except that compound 5d-0-52 was used instead of compound 4a-0-4.

$^1$H-NMR (300 MHz, CDCl$_3$) δ (ppm): 8.61 (1H, d, J=5.0 Hz), 7.68 (1H, d, J=8.4 Hz), 7.28 (1H, d, J=2.3 Hz), 7.24 (1H, dd, J=2.3, 8.4 Hz), 7.12 (1H, m), 7.06 (1H, m), 6.38 (1H, m), 6.33 (2H, m), 3.69 (2H, s), 2.40 (3H, s).

MS (ESI+) m/z: 361.99 (M+H).

Compound 1h-2-53

3-(3-Aminophenylthioxy)-4-methyl-7-(pyrimidin-2-yloxy)-2-oxo-2H-1-benzopyran

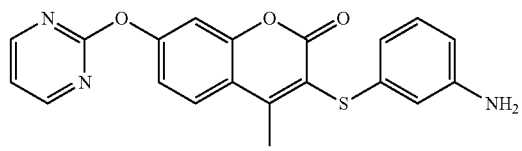

The title compound was synthesized under the same conditions as in the manufacturing example for compound 1h-2-4 (synthesis scheme 2), except that compound 5d-0-53 was used instead of compound 4a-0-4.

$^1$H-NMR (300 MHz, CDCl$_3$) δ (ppm): 8.61 (2H, d, J=4.6 Hz), 7.75 (1H, d, J=8.8 Hz), 7.26 (1H, m), 7.21 (1H, dd, J=2.3, 8.8 Hz), 7.13 (1H, m), 7.04 (1H, m), 6.64 (1H, m), 6.57 (1H, m), 6.50 (1H, m), 3.66 (2H, bs), 2.76 (3H, s).

MS (ESI+) m/z: 377.98 (M+H).

Compound 1h-2-74

3-(2-Aminothiazol-4-ylmethyl)-7-(pyrimidin-2-yloxy)-4-methyl-2-oxo-2H-1-benzopyran

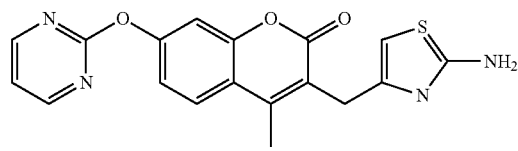

The title compound was synthesized using compound 5d-0-74 under the same conditions as in the manufacturing example for compound 1h-2-4 (synthesis scheme 2).

$^1$H-NMR (Bruker (ARX-300), DMSO-$d_6$) δ (ppm): 8.68 (2H, d, J=4.5 Hz), 7.88 (1H, d, J=8.4 Hz), 7.35-7.31 (2H, m), 7.24 (1H, dd, J=9.0, 2.4 Hz), 6.83 (2H, s), 6.10 (1H, s), 3.79 (2H, s), 2.47 (3H, s).

Compound 1h-3-1

4-Methyl-3-(3-aminobenzyl)-7-(thiazol-2-yloxy)-2-oxo-2H-1-benzopyran

[Chemical Formula 58]

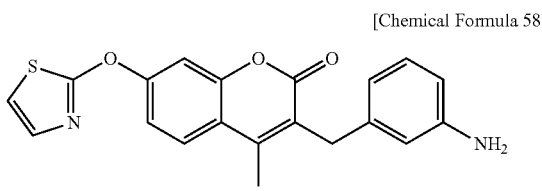

The title compound was synthesized under the same conditions as in the manufacturing example for compound 1h-1-5, except that compound 1g-3-1 was used instead of compound 1g-1-5.

$^1$H NMR (CDCl$_3$, 270 MHz) δ (ppm): 2.46 (3H, s), 4.00 (2H, s), 6.50-6.67 (3H, m), 6.92 (1H, d, J=3.8 Hz), 7.05 (1H, dd, J=7.8, 7.8 Hz), 7.21-7.33 (3H, m), 7.64 (1H, d, J=8.9 Hz).

ESI (LC/MS positive mode) m/z: 365 (M+H).

Compound 1h-3-3

4-Methyl-3-(3-aminobenzyl)-7-(thiazol-2-yloxy)-6-chloro-2-oxo-2H-1-benzopyran

[Chemical Formula 59]

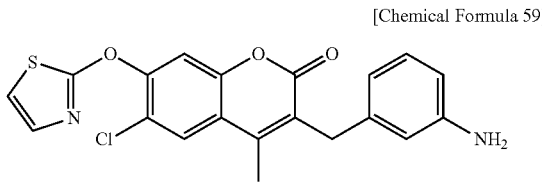

The title compound was synthesized under the same conditions as in the manufacturing example for compound 1h-1-5, except that compound 1g-3-3 was used instead of compound 1g-1-5.

$^1$H NMR (DMSO-$d_6$, 270 MHz) δ (ppm): 2.45 (3H, s), 3.83 (2H, s), 4.96 (2H, brs), 6.35-6.37 (3H, m), 6.86-6.92 (1H, m), 7.28 (1H, d, J=3.6 Hz), 7.32 (1H, d, J=3.6 Hz), 7.73 (1H, s), 8.09 (1H, s).

ESI (LC/MS positive mode) m/z: 399 (M+H).

Compound 1h-3-4

4-Methyl-3-(2-fluoro-3-aminobenzyl)-7-(thiazol-2-yloxy)-2-oxo-2H-1-benzopyran

[Chemical Formula 60]

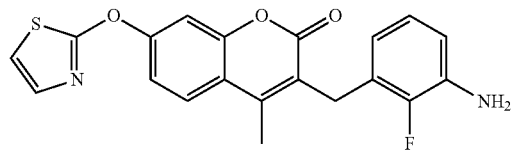

(Synthesis Scheme 1)

The title compound was synthesized under the same conditions as in the manufacturing example for compound 1h-1-5, except that compound 1g-3-4 was used instead of compound 1g-1-5.

$^1$H NMR (DMSO-$d_6$, 270 MHz) δ (ppm): 2.44 (3H, s), 3.92 (2H, s), 6.24 (1H, ddd, J=1.5, 7.0 Hz, $J_{HF}$=7.0 Hz), 6.61 (1H, ddd, J=1.5, 8.3 Hz, $J_{HF}$=8.3 Hz), 6.72 (1H, dd, J=7.0, 8.3 Hz), 7.34-7.38 (4H, m), 7.49 (1H, d, J=2.5 Hz), 7.92 (1H, d, J=8.9 Hz).

ESI (LC/MS positive mode) m/z: 383 (M+H).

Compound 1h-3-8

4-Methyl-3-(3-aminobenzyl)-7-(thiazol-2-yloxy)-6-methyl-2-oxo-2H-1-benzopyran

[Chemical Formula 61]

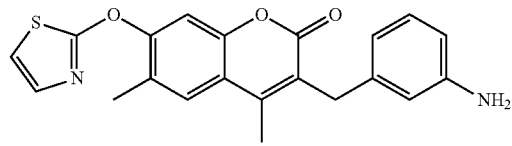

The title compound was synthesized under the same conditions as in the manufacturing example for compound 1h-1-5, except that compound 1g-3-8 was used instead of compound 1g-1-5.

$^1$H NMR (DMSO-$d_6$, 270 MHz) δ (ppm): 2.27 (3H, s), 2.45 (3H, s), 3.84 (2H, s), 4.97 (2H, s), 6.33-6.40 (3H, m), 6.90 (1H, dd, J=8.2, 8.2 Hz), 7.27-7.31 (2H, m), 7.44 (1H, s), 7.84 (1H, s).

ESI (LC/MS positive mode) m/z: 379 (M+H).

Compound 1h-3-19

3-(2-Amino-3-fluoropyridin-4-ylmethyl)-4,6-dimethyl-7-(thiazol-2-yloxy)-2-oxo-2H-1-benzopyran

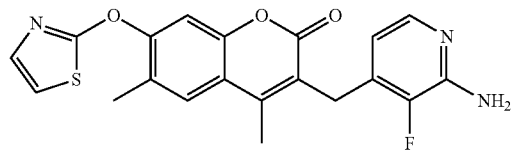

The title compound was synthesized under the same conditions as in the manufacturing example for compound 1h-2-4 (synthesis scheme 2), except that compound 5d-0-19 was used instead of compound 4a-0-4.

¹H NMR (CDCl₃, 270 MHz) δ (ppm): 7.87 (1H, s), 7.58 (1H, d, J=4.8 Hz), 7.45 (1H, s), 7.35-7.25 (2H, m), 6.27 (1H, dd, J=4.8 Hz), 6.10 (2H, brs), 3.93 (2H, s), 2.46 (3H, s), 2.28 (3H, s).

ESI (LC/MS positive mode) m/z: 398 (M+H).

Compound 1h-2a-4

3-{2-Fluoro-3-aminobenzyl}-4-methyl-7-(5-fluoropyrimidin-2-yloxy)-2-oxo-2H-1-benzopyran

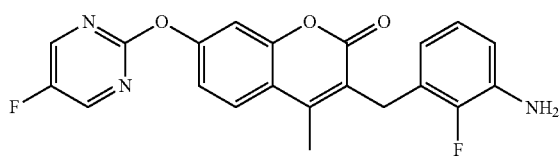

The title compound was synthesized under the same conditions as in the manufacturing example for compound 1h-2-4 (synthesis scheme 2), except that 2-chloro-5-fluoropyrimidine was used instead of 2-bromopyrimidine.

¹H-NMR (Bruker, 300 MHz, CDCl₃) δ (ppm): 8.44 (2H, s), 7.69 (1H, d, J=8.8 Hz), 7.21 (1H, d, J=2.7 Hz), 7.14 (1H, dd, J=2.3, 8.8 Hz), 6.81 (1H, m), 6.63 (1H, m), 6.55 (1H, m), 4.06 (2H, s), 3.70 (2H, s), 2.44 (3H, s).

MS (Micromass, Quattromicro, ESI+) m/z: 395.85 (M+H).

Compound 1h-2b-4

3-{2-Fluoro-3-aminobenzyl}-4-methyl-7-(4-chloropyrimidin-2-yloxy)-2-oxo-2H-1-benzopyran

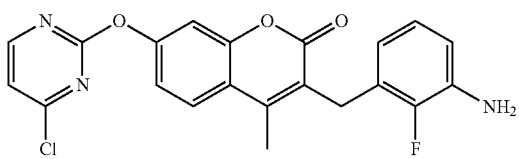

The title compound was synthesized under the same conditions as in the manufacturing example for compound 1h-2-4 (synthesis scheme 2), except that 2,4-dichloropyrimidine was used instead of 2-bromopyrimidine.

¹H-NMR (Bruker, 300 MHz, CDCl₃) δ (ppm): 8.51 (1H, d, J=5.7 Hz), 7.69 (1H, d, J=8.8 Hz), 7.18 (1H, d, J=2.7 Hz), 7.13 (1H, dd, J=2.3, 8.8 Hz), 6.92 (1H, d, J=5.7 Hz), 6.82 (1H, m), 6.64 (1H, m), 6.57 (1H, m), 4.07 (2H, s), 3.71 (2H, s), 2.46 (3H, s).

MS (Micromass, Quattromicro, ESI+) m/z: 411.75 (M), 413.80 (M+2).

Compound 1h-5-4

3-{2-Fluoro-3-aminobenzyl}-4-methyl-7-(2,4-dimethoxypyrimidin-6-yloxy)-2-oxo-2H-1-benzopyran

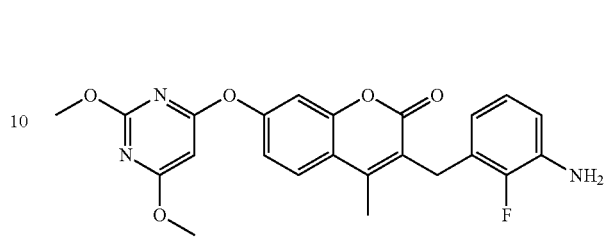

The title compound was synthesized under the same conditions as in the manufacturing example for compound 1h-2-4 (synthesis scheme 2), except that 6-chloro-2,4-dimethoxypyrimidine was used instead of 2-bromopyrimidine.

¹H-NMR (Bruker, 300 MHz, CDCl₃) δ (ppm): 7.64 (1H, d, J=8.8 Hz), 7.15 (1H, d, J=2.7 Hz), 7.09 (1H, dd, J=2.3, 8.8 Hz), 6.81 (1H, m), 6.64 (1H, m), 6.57 (1H, m), 5.86 (1H, s), 4.05 (2H, s), 3.97 (3H, s), 3.89 (3H, s), 3.70 (2H, brs), 2.44 (3H, s).

MS (Micromass, Quattromicro, ESI+) m/z: 438.06 (M+H).

Compound 1h-3a-4

3-(2-Fluoro-3-aminobenzyl)-4-methyl-7-(benzothiazol-2-yloxy)-2-oxo-2H-1-benzopyran

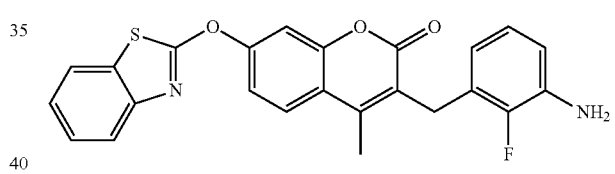

The title compound was synthesized under the same conditions as in the manufacturing example for compound 1h-3-4 (synthesis scheme 2), except that 2-chlorobenzothiazole was used instead of 2-bromothiazole.

¹H NMR (Bruker, 300 MHz) CDCl₃ δ (ppm): 7.72 (3H, m), 7.47 (1H, d, J=2.7 Hz), 7.42 (1H, m), 7.32 (2H, m), 6.82 (1H, m), 6.64 (1H, m), 6.57 (1H, m), 4.07 (2H, s), 3.70 (2H, s), 2.45 (3H, s).

MS (Micromass, Quattromicro, ESI+) m/z: 433.00 (M+H).

Compound 1h-1a-4

Dimethylthiocarbamic acid 4-methyl-3-(2-fluoro-3-aminobenzyl)-2-oxo-2H-1-benzopyran-7-yl ester

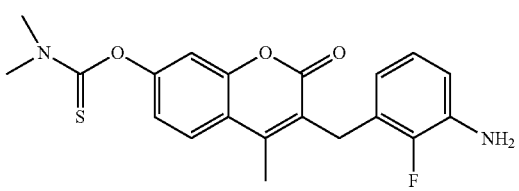

The title compound was synthesized under the same conditions as in the manufacturing example for compound 1h-3-4 (synthesis scheme 2), except that dimethylthiocarbamoyl chloride was used instead of 2-bromothiazole.

¹H-NMR (Bruker, 300 MHz, CDCl₃) δ (ppm): 7.64 (1H, d, J=9.5 Hz), 7.06 (1H, s), 7.04 (1H, dd, J=2.3, 8.0 Hz), 6.81 (1H, m), 6.63 (1H, m), 6.55 (1H, m), 4.05 (2H, s), 3.70 (2H, s), 3.47 (3H, s), 3.38 (3H, s), 2.43 (3H, s).

MS (Micromass, Quattromicro, ESI+) m/z: 387.04 (M+H).

Compound 1h-3b-4

3-(2-Fluoro-3-aminobenzyl)-4-methyl-7-(5-bromothiazol-2-yloxy)-2-oxo-2H-1-benzopyran

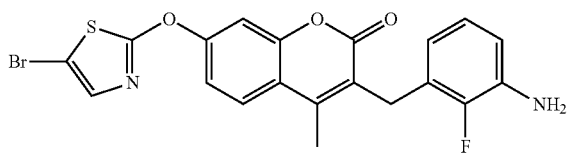

The title compound was synthesized under the same conditions as in the manufacturing example for compound 1h-3-4 (synthesis scheme 2), except that 2,5-dibromothiazole was used instead of 2-bromothiazole.

¹H-NMR (Bruker, 300 MHz, CDCl₃) δ (ppm): 7.66 (1H, d, J=8.8 Hz), 7.29 (1H, d, J=2.7 Hz), 7.21 (1H, dd, J=2.7, 9.7 Hz), 7.19 (1H, s), 6.81 (1H, m), 6.63 (1H, m), 6.55 (1H, m), 4.05 (2H, s), 3.70 (2H, s), 2.43 (3H, s).

MS (Micromass, Quattromicro, ESI+) m/z: 460.67 (M), 462.75 (M+2).

Compound 1h-2a-16

4-Methyl-3-(3-fluoro-2-aminopyridin-4-ylmethyl)-7-(5-fluoropyrimidin-2-yloxy)-2-oxo-2H-1-benzopyran

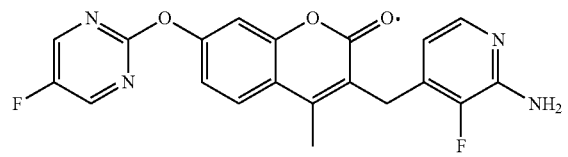

The title compound was synthesized under the same conditions as in the manufacturing example for compound 1h-2-4 (synthesis scheme 2), except that compound 5d-0-16 was used instead of compound 4a-0-4, and that 2-chloro-5-fluoropyrimidine was used instead of 2-bromopyrimidine.

¹H-NMR (Bruker, 300 MHz, CDCl₃) δ (ppm): 8.44 (2H, s), 7.71 (1H, d, J=5.3 Hz), 7.69 (1H, d, J=8.4 Hz), 7.22 (1H, d, J=1.9 Hz), 7.16 (1H, dd, J=1.9, 8.4 Hz), 6.50 (1H, m), 4.55 (2H, brs), 4.05 (2H, s), 2.43 (3H, s).

MS (Micromass, Quattromicro, ESI+) m/z: 396.98 (M+H).

Compound 1h-2b-16

4-Methyl-3-(3-fluoro-2-aminopyridin-4-ylmethyl)-7-(4-chloropyrimidin-2-yloxy)-2-oxo-2H-1-benzopyran

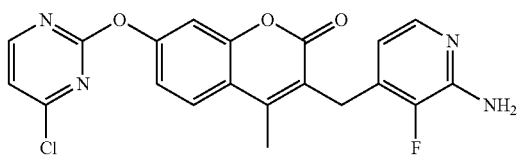

The title compound was synthesized under the same conditions as in the manufacturing example for compound 1h-2-4 (synthesis scheme 2), except that compound 5d-0-16 was used instead of compound 4a-0-4, and that 2,4-dichloropyrimidine was used instead of 2-bromopyrimidine.

¹H-NMR (Bruker, 300 MHz, CDCl₃) δ (ppm): 8.52 (1H, d, J=5.3 Hz), 7.73 (1H, d, J=1.9 Hz), 7.71 (1H, d, J=5.3 Hz), 7.21 (1H, d, J=2.7 Hz), 7.15 (1H, dd, J=1.9, 8.4 Hz), 6.93 (1H, d, J=5.7 Hz), 6.53 (1H, m), 4.57 (2H, brs), 4.06 (2H, s), 2.46 (3H, s).

MS (Micromass, Quattromicro, ESI+) m/z: 412.98 (M), 414.95 (M+2).

Compound 1h-5-16

4-Methyl-3-(3-fluoro-2-aminopyridin-4-ylmethyl)-7-(2,4-dimethoxypyrimidin-6-yloxy)-2-oxo-2H-1-benzopyran

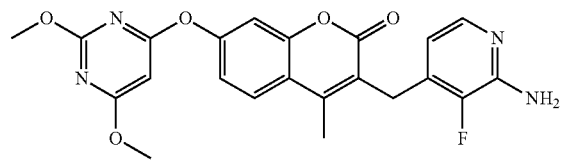

The title compound was synthesized under the same conditions as in the manufacturing example for compound 1h-2-4 (synthesis scheme 2), except that compound 5d-0-16 was used instead of compound 4a-0-4, and that 2,4-dimethoxy-6-chloropyrimidine was used instead of 2-bromopyrimidine.

¹H-NMR (Bruker, 300 MHz, CDCl₃) δ (ppm): 7.72 (1H, d, J=5.3 Hz), 7.65 (1H, d, J=8.8 Hz), 7.17 (1H, d, J=2.3 Hz), 7.12 (1H, dd, J=2.3, 8.8 Hz), 6.52 (1H, m), 5.87 (1H, s), 4.57 (2H, brs), 4.04 (2H, s), 3.98 (3H, s), 3.89 (3H, s), 2.44 (3H, s).

MS (Micromass, Quattromicro, ESI+) m/z: 439.02 (M+H).

Compound 1h-3a-16

4-Methyl-3-(3-fluoro-2-aminopyridin-4-ylmethyl)-7-(benzothiazol-2-yloxy)-2-oxo-2H-1-benzopyran

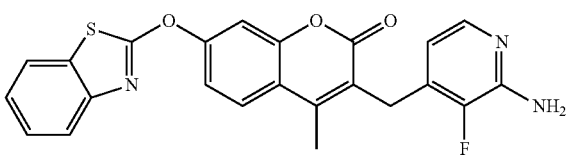

The title compound was synthesized under the same conditions as in the manufacturing example for compound 1h-2-4 (synthesis scheme 2), except that compound 5d-0-16 was used instead of compound 4a-0-4, and that 2-chlorobenzothiazole was used instead of 2-bromopyrimidine.

¹H NMR (Bruker, 300 MHz) CDCl₃ δ (ppm): 7.73 (4H, m), 7.50 (1H, d, J=2.3 Hz), 7.43 (1H, m), 7.36 (1H, dd, J=2.7, 8.8 Hz), 7.33 (1H, m), 6.51 (1H, m), 4.58 (2H, bs), 4.05 (2H, s), 2.46 (3H, s).

MS (Micromass, Quattromicro, ESI+) m/z: 433.96 (M+H).

Compound 1h-3b-16

4-Methyl-3-(3-fluoro-2-aminopyridin-4-ylmethyl)-7-(5-bromothiazol-2-yloxy)-2-oxo-2H-1-benzopyran

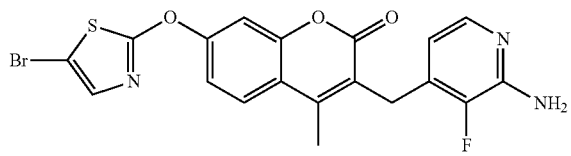

The title compound was synthesized under the same conditions as in the manufacturing example for compound 1h-2-4 (synthesis scheme 2), except that compound 5d-0-16 was used instead of compound 4a-0-4, and that 2,5-dibromothiazole was used instead of 2-bromopyrimidine.

¹H-NMR (Bruker, 300 MHz, CDCl₃) δ (ppm): 7.71 (1H, d, J=5.3 Hz), 7.68 (1H, d, J=8.8 Hz), 7.31 (1H, d, J=2.3 Hz), 7.24 (1H, dd, J=2.7, 8.8 Hz), 7.20 (1H, s), 6.50 (1H, m), 4.56 (2H, s), 4.04 (2H, s), 2.44 (3H, s).

MS (Micromass, Quattromicro, ESI+) m/z: 461.90 (M), 463.90 (M+2).

Compound 1h-1a-16

Dimethylthiocarbamic acid 2-oxo-2H-3-(2-amino-3-fluoropyridin-4-ylmethyl)-4-methyl-1-benzopyran-7-yl ester

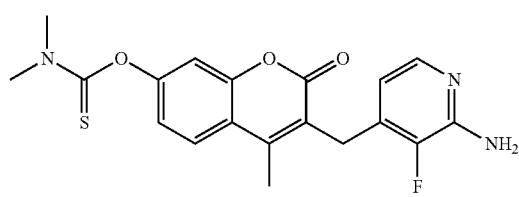

The title compound was synthesized under the same conditions as in the manufacturing example for compound 1h-2-4 (synthesis scheme 2), except that compound 5d-0-16 was used instead of compound 4a-0-4, and that dimethylthiocarbamoyl chloride was used instead of 2-bromopyrimidine.

¹H-NMR (Bruker, 300 MHz, CDCl₃) δ (ppm): 7.71 (1H, d, J=5.3 Hz), 7.65 (1H, d, J=9.2 Hz), 7.08 (1H, s), 7.06 (1H, d, J=4.6 Hz), 6.50 (1H, m), 4.55 (2H, brs), 4.04 (2H, s), 3.47 (3H, s), 3.38 (3H, s), 2.43 (3H, s).

MS (Micromass, Quattromicro, ESI+) m/z: 388.00 (M+H).

Compound 1h-1b-1

3-(3-Aminobenzyl)-7-isobutoxy-4-methyl-2-oxo-2H-1-benzopyran

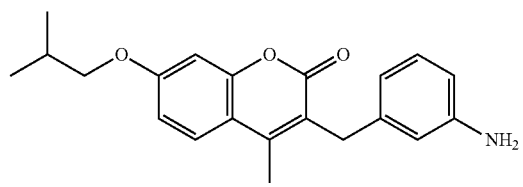

The title compound was synthesized under the same conditions as in the manufacturing example for compound 1h-1-5, except that compound 1g-1b-1 was used instead of compound 1g-1-5.

¹H-NMR (270 MHz, DMSO-d₆) δ (ppm): 0.98 (3H, s), 1.00 (3H, s), 1.95-2.12 (1H, m), 2.39 (3H, s), 3.79 (2H, s), 3.86 (2H, d, J=6.5 Hz), 4.96 (2H, br.s), 6.32-6.41 (3H, m), 6.82-7.00 (3H, m), 7.72 (1H, d, J=9.5 Hz).

ESI (LC-MS positive mode) m/z: 338 (M+H).

Compound 1h-1c-1

3-(3-Aminobenzyl)-7-(2-fluoroethoxy)-4-methyl-2-oxo-2H-1-benzopyran

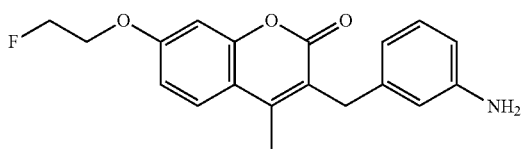

The title compound was synthesized under the same conditions as in the manufacturing example for compound 1h-1-5, except that compound 1g-1c-1 was used instead of compound 1g-1-5.

¹H-NMR (270 MHz, DMSO-d₆) δ (ppm): 2.40 (3H, s), 3.80 (2H, s), 4.27-4.32 (1H, m), 4.37-4.45 (1H, m), 4.66-4.71 (1H, m), 4.84-4.89 (1H, m), 4.96 (2H, br.s), 6.32-6.39 (3H, m), 6.90 (1H, dd, J=8.6, 7.3 Hz), 6.96-7.07 (2H, m), 7.75 (1H, d, J=8.6 Hz).

ESI (LC-MS positive mode) m/z: 328 (M+H).

Compound 1h-1c-3

3-(3-Aminobenzyl)-6-chloro-7-(2-fluoroethoxy)-4-methyl-2-oxo-2H-1-benzopyran

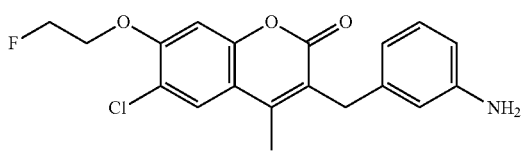

The title compound was synthesized under the same conditions as in the manufacturing example for compound 1h-1-5, except that compound 1g-1c-3 was used instead of compound 1g-1-5.

¹H-NMR (270 MHz, DMSO-d₆) δ (ppm): 2.41 (3H, s), 3.80 (2H, s), 4.36-4.43 (1H, m), 4.46-4.54 (1H, m), 4.68-4.75 (1H, m), 4.86-4.93 (1H, m), 4.96 (2H, br.s), 6.32-6.39 (3H, m), 6.90 (1H, dd, J=8.6, 7.0 Hz), 7.29 (1H, s), 7.90 (1H, s).

ESI (LC-MS positive mode) m/z: 362 (M+H).

Compound 1h-11-3

4-Methyl-3-(3-aminobenzyl)-7-(thiophen-3-yl)-6-chloro-2-oxo-2H-1-benzopyran

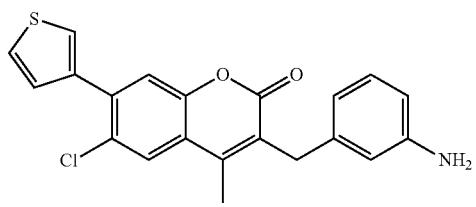

The title compound was synthesized under the same conditions as in the manufacturing example for compound 1h-1-5, except that compound 1g-11-3 was used instead of compound 1g-1-5.

¹H-NMR (Bruker (ARX-300), 300 MHz, CDCl₃) δ (ppm): 7.68 (1H, s), 7.57 ((1H, dd, J=3.05, 1.14 Hz), 7.34-7.39 (2H, m), 7.35 (1H, dd, J=3.82, 1.14 Hz), 7.06 (1H, t, J=8.01 Hz), 6.64 (1H, d, J=8.01 Hz), 6.60 (1H, s), 6.53 (1H, dd, J=7.63, 1.53 Hz), 3.99 (2H, s), 2.44 (3H, s), 2.27 (2H, br).

Compound 1h-12-1

4-Methyl-3-(3-aminobenzyl)-7-(pyridin-4-yl)-2-oxo-2H-1-benzopyran

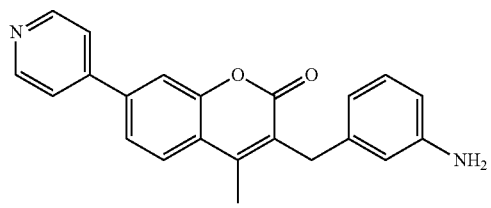

2 mL of a mixture of MeOH and H₂O (9:1), metallic zinc (81 mg, 1.2 mmol) and ammonium chloride (20 mg, 1.6 mmol) were added to compound 1g-12-1 (23 mg, 0.062 mmol), and the obtained mixture was stirred at room temperature for two days. It was then purified by silica gel chromatography (methylene chloride:methanol=30:1) to yield the title compound (15 mg, 73%).

¹H-NMR (Bruker (ARX-300), 300 MHz, CDCl₃) δ (ppm): 8.72 (2H, d, J=6.10 Hz), 7.73 (1H, d, J=8.01 Hz), 7.59-7.53 (4H, m), 7.06 (1H, t, J=7.63 Hz), 6.66 (1H, d, J=7.63 Hz), 6.62 (1H, s), 6.53 (1H, dd, J=7.63, 2.29 Hz), 4.01 (2H, s), 2.49 (3H, s).

MS (Micromass, Quattromicro, ESI+) m/z: 343.40 (M+1).

Compound 1h-16-1

4-Methyl-3-(3-aminobenzyl)-7-(thiazol-5-yl)-2-oxo-2H-1-benzopyran

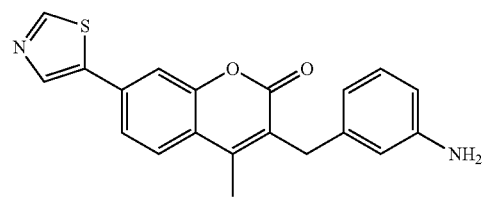

The title compound was synthesized under the same conditions as in the manufacturing example for compound 1h-1-5, except that compound 1g-16-1 was used instead of compound 1g-1-5.

¹H-NMR (Bruker (ARX-300), 300 MHz, CDCl₃) δ (ppm): 8.82 (1H, s), 8.18 (1H, s), 7.64 (1H, d, J=8.01 Hz), 7.52 (1H, s), 7.50 (1H, d, J=8.39 Hz), 7.09 (1H, t, J=7.63 Hz), 6.66 (1H, d, J=7.63 Hz), 6.62 (1H, s), 6.53 (1H, d, J=7.63 Hz), 3.99 (2H, s), 2.46 (3H, s).

Compound 1h-17-1

4-Methyl-3-(3-aminobenzyl)-7-(thiazol-2-yl)-2-oxo-2H-1-benzopyran

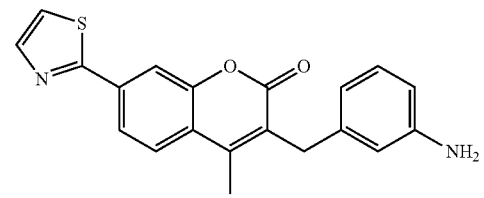

The title compound was synthesized under the same conditions as in the manufacturing example for compound 1h-1-5, except that compound 1g-17-1 was used instead of compound 1g-1-5.

¹H-NMR (Bruker (ARX-300), 300 MHz, DMSO-d₆) δ (ppm): 8.02 (1H, d, J=3.05 Hz), 7.94 (2H, s), 7.91 (1H, d, J=3.43 Hz), 7.90 (1H, s), 6.91 (1H, t, J=8.01 Hz), 6.40-6.36 (3H, m), 4.95 (2H, s), 3.86 (2H, s), 2.47 (3H, s).

Compound 1h-18-1

4-Methyl-3-(3-aminobenzyl)-7-(pyridin-3-yl)-2-oxo-2H-1-benzopyran

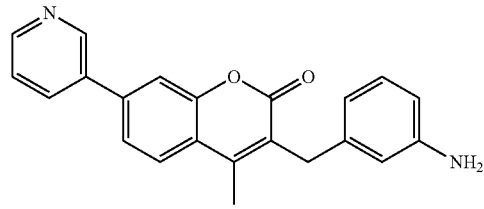

The title compound was synthesized under the same conditions as in the manufacturing example for compound 1h-12-1, except that compound 1g-18-1 was used instead of compound 1g-12-1.

$^1$H-NMR (Bruker (ARX-300), 300 MHz, CDCl$_3$) δ (ppm): 8.89 (1H, d, J=1.91 Hz), 8.66 (1H, dd, J=4.96, 1.53 Hz), 7.92 (1H, dt, J=8.01, 1.91 Hz), 7.72 (1H, d, J=8.01 Hz), 7.54-7.51 (2H, m), 7.42 (1H, dd, J=7.63, 0.30 Hz), 7.06 (1H, t, J=8.01 Hz), 6.66 (1H, d, J=8.01 Hz), 6.62 (1H, s), 6.52 (1H, dd, J=8.01, 1.91 Hz), 4.01 (2H, s), 2.49 (3H, s).

MS (Micromass, Quattromicro, ESI+) m/z: 343.27 (M+1).

Compound 1h-19-3

4-Methyl-3-(3-aminobenzyl)-6-chloro-7-(3-methoxyphenyl)-2-oxo-2H-1-benzopyran

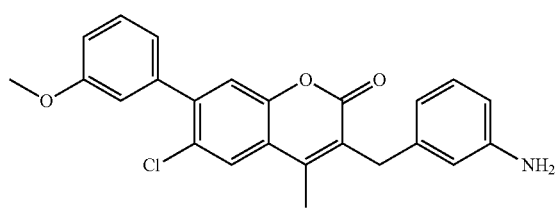

The title compound was synthesized under the same conditions as in the manufacturing example for compound 1h-1-5, except that compound 1g-19-3 was used instead of compound 1g-1-5.

$^1$H-NMR (Bruker (ARX-300), 300 MHz, CDCl$_3$) δ (ppm): 7.69 (1H, s), 7.38 (1H, t, J=7.63 Hz), 7.32 (1H, s), 7.09-6.96 (4H, m), 6.64 (1H, d, J=7.25 Hz), 6.60 (1H, s), 6.52 (1H, dd, J=8.01, 2.29 Hz), 3.99 (2H, s), 3.87 (3H, s), 3.62 (2H, bs), 2.46 (3H, s).

Compound 1h-21-3

4-Methyl-3-(3-aminobenzyl)-6-chloro-7-(5-acetylthiophen-2-yl)-2-oxo-2H-1-benzopyran

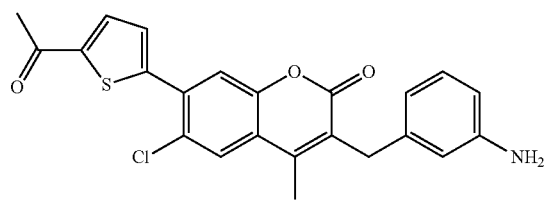

The title compound was synthesized under the same conditions as in the manufacturing example for compound 1h-1-5, except that compound 1g-21-3 was used instead of compound 1g-1-5.

$^1$H-NMR (Bruker (ARX-300), 300 MHz, CDCl$_3$) δ (ppm): 8.79 (2H, d, J=4.96 Hz), 8.17 (1H, s), 7.73 (1H, s), 7.46 (1H, t), 7.13 (2H, m), 6.96 (1H, d, J=7.63 Hz), 4.06 (2H, s), 2.60 (3H, s), 2.41 (3H, s).

MS (Micromass, Quattromicro, ESI+) m/z: 424.09 (M+H).

Compound 1h-22-1

4-Methyl-3-(3-aminobenzyl)-7-(3-acetylphenyl)-2-oxo-2H-1-benzopyran

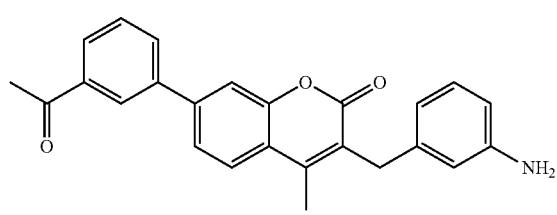

The title compound was synthesized under the same conditions as in the manufacturing example for compound 1h-12-1, except that compound 1g-22-1 was used instead of compound 1g-12-1.

$^1$H-NMR (Bruker (ARX-300), 300 MHz, DMSO-d$_6$) δ (ppm): 8.23 (1H, t), 8.05 (1H, d, J=8.01 Hz), 7.95 (1H, d, J=8.39 Hz), 7.84 (1H, d, J=1.53 Hz), 7.78 (1H, dd, J=8.01 Hz), 7.65 (2H, t), 6.91 (1H, t), 6.43 (3H, m), 4.98 (2H, s), 3.85 (2H, s), 2.71 (3H, s), 2.50 (3H, s).

MS (Micromass, Quattromicro, ESI+) m/z: 384.35 (M+1).

Compound 1h-23-1

4-Methyl-3-(3-aminobenzyl)-7-(4-acetylphenyl)-2-oxo-2H-1-benzopyran

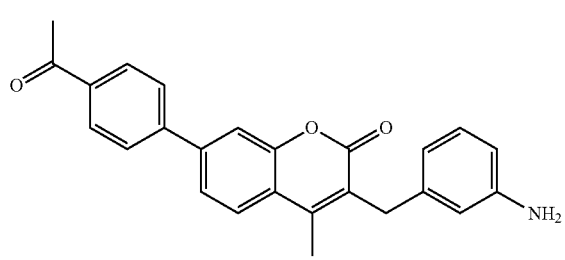

The title compound was synthesized under the same conditions as in the manufacturing example for compound 1h-12-1, except that compound 1g-23-1 was used instead of compound 1g-12-1.

MS (Micromass, Quattromicro, ESI+) m/z: 413.27 (M+Na).

Compound 1h-1e-1

Trifluoromethanesulfonic acid 4-methyl-3-(3-aminobenzyl)-2-oxo-2H-1-benzopyran-7-yl ester

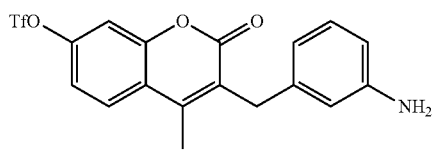

The title compound was synthesized under the same conditions as in the manufacturing example for compound 1h-12-1, except that compound 1g-1e-1 was used instead of compound 1g-12-1.

¹H-NMR (Bruker (ARX-300), 300 MHz, CDCl₃) δ (ppm): 7.67 (1H, d, J=8.77 Hz), 7.22 (2H, m), 7.05 (1H, t), 6.59 (3H, t, d, J=8.39 Hz), 5.29 (1H, s), 4.02 (2H, s), 2.46 (3H, s).

MS (Micromass, Quattromicro, ESI+) m/z: 414.10 (M+1).

Compound 1g-28-1

4-Methyl-3-(3-aminobenzyl)-7-(4-N,N-dimethylaminophenyl)-2-oxo-2H-1-benzopyran

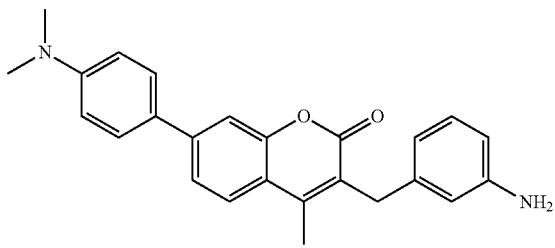

The title compound was synthesized under the same conditions as in the manufacturing example for compound 1h-12-1, except that compound 1g-28-1 was used instead of compound 1g-12-1.

¹H-NMR (Bruker (ARX-300), 300 MHz, CDCl₃) δ (ppm): 7.65 (5H, m), 6.63 (2H, d, J=8.77 Hz), 6.65 (2H, s, d, J=8.39 Hz), 6.53 (2H, dd, J=8.6 Hz), 4.02 (2H, s), 3.64 (2H, bs), 3.15 (6H, s), 2.43 (3H, s).

Compound 1j-1-5-1

Dimethylcarbamic acid 3-{2-fluoro-3-(aminosulfonyl)aminobenzyl}-6-fluoro-4-methyl-2-oxo-2H-1-benzopyran-7-yl ester

[Chemical Formula 62]

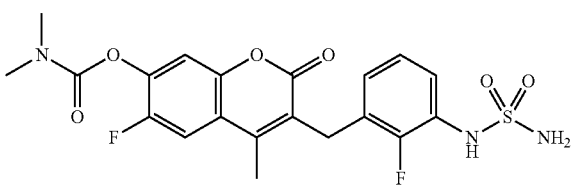

Formic acid (754 μL, 10.0 mmol) was added to chlorosulfonyl isocyanate (1.74 mL, 20.0 mmol) at 0° C., and the mixture was stirred at room temperature for 1 hour. Dichloromethane (10 mL) was then added thereto, and the mixture was further stirred for 2 hours. This solution (3.71 mL) was added to a solution of compound 1h-1-5 (2.88 g, 7.42 mmol) and pyridine (1.21 mL, 15 mmol) in dichloromethane (50 mL), and the mixture was stirred at room temperature for 16 hours. Ethyl acetate was then added to the reaction solution, and the solution was washed with sodium carbonate solution and saturated saline. The organic layer was dried over anhydrous magnesium sulfate, and the solvent was distilled away under reduced pressure. The resultant residue was purified by silica gel column chromatography to yield the title compound (680 mg, 20%).

¹H NMR (DMSO-d₆, 270 MHz) δ (ppm): 2.42 (3H, s), 2.94 (3H, s), 3.08 (3H, s), 3.97 (2H, s), 6.84 (1H, m), 7.00 (1H, dd, J=7.8, 7.8 Hz), 7.10 (2H, brs), 7.33 (1H, m), 7.48 (1H, d, J=6.8 Hz), 7.86 (1H, d, J=11.4 Hz), 9.12 (1H, brs).

ESI (LC/MS positive mode) m/z: 468 (M+2H−Na).

Compound 1j-1-5-1Na

Dimethylcarbamic acid 3-{2-fluoro-3-(aminosulfonyl)aminobenzyl}-6-fluoro-4-methyl-2-oxo-2H-1-benzopyran-7-yl ester sodium salt

[Chemical Formula 63]

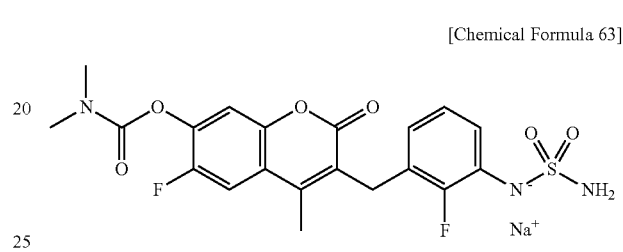

One equivalent of methanol solution of sodium hydroxide was added dropwise at room temperature to a mixture of compound 1j-1-5-1 and methylene chloride. Thirty minutes later, the solvent was distilled away to yield the title compound.

¹H NMR (DMSO-d₆, 270 MHz) δ (ppm): 2.39 (3H, s), 2.94 (3H, s), 3.09 (3H, s), 3.88 (2H, s), 5.43 (1H, brs), 6.21 (1H, m), 6.67 (1H, m), 7.19 (1H, m), 7.43 (1H, J=6.8 Hz), 7.83 (1H, d, J=11.2 Hz).

ESI (LC/MS positive mode) m/z: 468 (M+2H−Na).

Compound 1j-1-5-1K

Dimethylcarbamic acid 3-{2-fluoro-3-aminosulfonyl)aminobenzyl}-6-fluoro-4-methyl-2-oxo-2H-1-benzopyran-7-yl ester potassium salt

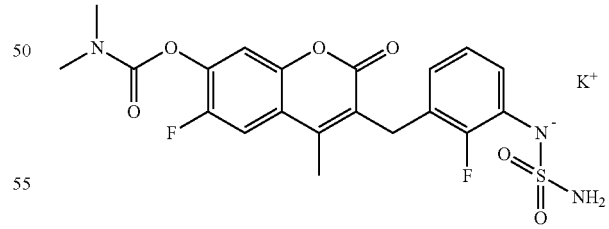

The title compound was synthesized under the same conditions as in the manufacturing example for compound 1j-1-5-1Na, except that KOH was used instead of NaOH.

¹H NMR (CD₃OD) δ (ppm): 7.67 (1.0H, d, J=11.0 Hz), 7.40-7.25 (2H, m), 6.88 (1.0H, t, J=7.9 Hz), 6.64 (1.0H, t, J=7.9 Hz), 4.04 (2.0H, s), 3.15 (3H, s), 3.03 (3H, s), 2.44 (3H, s).

ESI (LC/MS positive mode) m/z: 468 (M+2H−K).

Compound 1j-1-1-1

Dimethylcarbamic acid 3-{3-(aminosulfonyl)aminobenzyl}-4-methyl-2-oxo-2H-1-benzopyran-7-yl ester

[Chemical Formula 64]

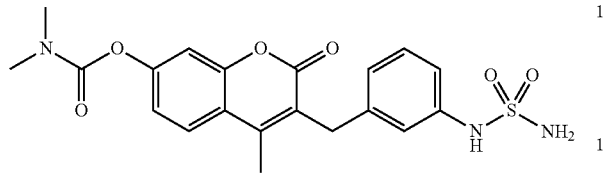

The title compound was synthesized under the same conditions as in the manufacturing example for compound 1j-1-5-1, except that compound 1h-1-1 was used instead of compound 1h-1-5.

$^1$H NMR (CDCl$_3$, 270 MHz) δ (ppm): 2.43 (3H, s), 3.02 (3H, s), 3.12 (3H, s), 3.98 (2H, s), 6.87-7.09 (5H, m), 7.18 (1H, dd, J=8.1 Hz), 7.60 (1H, d, J=8.1 Hz).

ESI (LC/MS positive mode) m/z: 432 (M+H).

Compound 1j-1-2-1

Dimethylcarbamic acid 3-{3-(aminosulfonyl)aminobenzyl}-6-fluoro-4-methyl-2-oxo-2H-1-benzopyran-7-yl ester

[Chemical Formula 65]

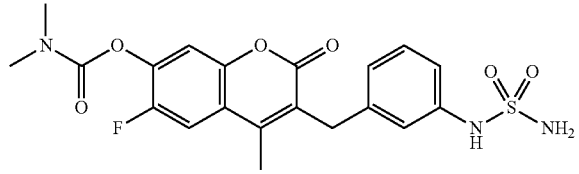

The title compound was synthesized under the same conditions as in the manufacturing example for compound 1j-1-5-1, except that compound 1h-1-2 was used instead of compound 1h-1-5.

$^1$H NMR (CD$_3$OD, 270 MHz) δ (ppm): 2.46 (3H, s), 3.01 (3H, s), 3.15 (3H, s), 4.02 (2H, s), 6.95 (1H, d, J=7.3 Hz), 7.06-7.22 (3H, m), 7.27 (1H, d, J=6.8 Hz), 7.64 (1H, d, J=11.1 Hz).

ESI (LC/MS positive mode) m/z: 450 (M+H).

Compound 1j-1-3-1

Dimethylcarbamic acid 3-{3-(aminosulfonyl)aminobenzyl}-6-chloro-4-methyl-2-oxo-2H-1-benzopyran-7-yl ester

[Chemical Formula 66]

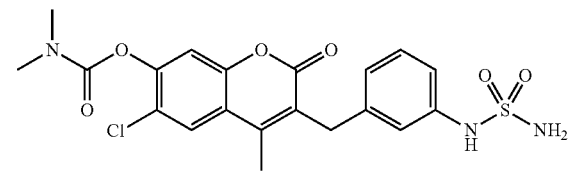

The title compound was synthesized under the same conditions as in the manufacturing example for compound 1j-1-5-1, except that compound 1h-1-3 was used instead of compound 1h-1-5.

$^1$H NMR (CDCl$_3$, 270 MHz) δ (ppm): 2.42 (3H, s), 3.05 (3H, s), 3.22 (3H, s), 3.95 (2H, s), 6.80-7.20 (4H, m), 7.25 (1H, s), 7.60 (1H, s).

ESI (LC/MS positive mode) m/z: 466 (M+H).

Compound 1j-1-4-1

Dimethylcarbamic acid 3-(3-aminosulfonylamino-2-fluoro-benzyl)-4-methyl-2-oxo-2H-1-benzopyran-7-yl ester

[Chemical Formula 67]

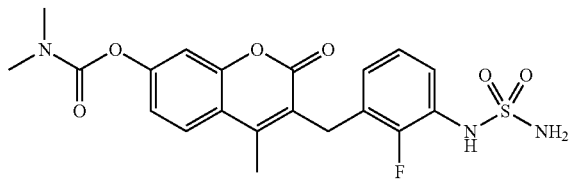

The title compound was synthesized under the same conditions as in the manufacturing example for compound 1j-1-5-1, except that compound 1h-1-4 was used instead of compound 1h-1-5.

$^1$H NMR (270 MHz, DMSO-d$_6$) δ (ppm): 2.44 (3H, s), 2.93 (3H, s), 3.07 (3H, s), 3.97 (2H, s), 6.82 (1H, brt, J=8.6 Hz), 6.99 (1H, brt, J=8.6 Hz), 7.19 (1H, dd, J=8.9, 2.3 Hz), 7.25 (1H, d, J=2.3 Hz), 7.33 (1H, brt, J=8.6 Hz), 7.86 (1H, d, J=8.9 Hz).

ESI (LC/MS positive mode) m/z: 450 (M+H).

Compound 1j-1-4-1Na

Dimethylcarbamic acid 3-{3-(aminosulfonyl)amino-2-fluoro-benzyl}-4-methyl-2-oxo-2H-1-benzopyran-7-yl ester sodium salt

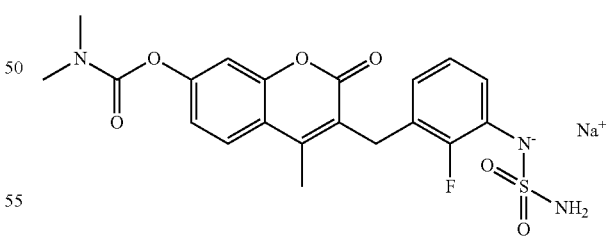

The title compound was synthesized under the same conditions as in the manufacturing example for compound 1j-1-5-1Na, except that compound 1j-1-4-1 was used instead of compound 1j-1-5-1.

$^1$H NMR (DMSO-d$_6$, 270 MHz) δ (ppm): 2.41 (3H, s), 2.93 (3H, s), 3.07 (3H, s), 3.88 (2H, s), 6.18-6.23 (1H, m), 6.67 (1H, dd, J=7.6, 7.9 Hz), 7.14-7.22 (2H, m), 7.24 (1H, d, J=2.3 Hz), 7.83 (1H, d, J=8.6 Hz).

ESI (LC/MS positive mode) m/z: 450 (M+2H−Na).

Compound 1j-1-7-1

Dimethylcarbamic acid 3-{3-(aminosulfonyl)aminobenzyl}-6-iodo-4-methyl-2-oxo-2H-1-benzopyran-7-yl ester

[Chemical Formula 68]

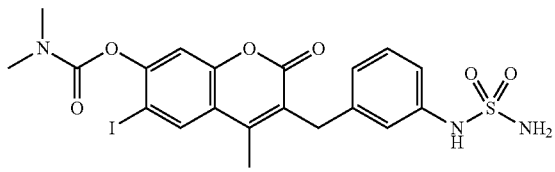

The title compound was synthesized under the same conditions as in the manufacturing example for compound 1j-1-5-1, except that compound 1h-1-7 was used instead of compound 1h-1-5.

$^1$H NMR (DMSO-$d_6$, 270 MHz) δ (ppm): 2.45 (3H, s), 2.96 (3H, s), 3.13 (3H, s), 3.93 (2H, s), 6.83 (1H, d, J=8.1 Hz), 6.94 (1H, s), 7.02-7.05 (2H, m), 7.16 (1H, dd, J=8.1, 8.1 Hz), 7.38 (1H, s), 8.24 (1H, s).

ESI (LC/MS positive mode) m/z: 558 (M+H).

Compound 1j-1-7-1Na

Dimethylcarbamic acid 3-{3-(sulfamoylamino)benzyl}-6-iodo-4-methyl-2-oxo-2H-1-benzopyran-7-yl ester sodium salt

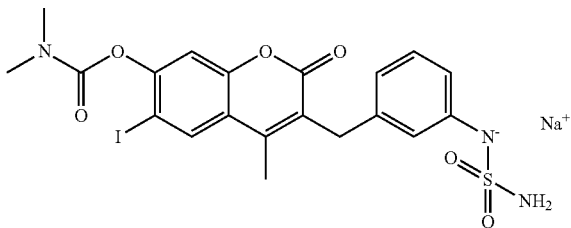

The title compound was synthesized under the same conditions as in the manufacturing example for compound 1j-1-5-1Na, except that compound 1j-1-7-1 was used instead of compound 1j-1-5-1.

$^1$H NMR (DMSO-$d_6$, 270 MHz) δ (ppm): 2.44 (3H, s), 2.96 (3H, s), 3.13 (3H, s), 3.83 (2H, s), 6.36 (1H, d, J=7.6 Hz), 6.68 (1H, s), 6.77 (1H, d, J=7.9 Hz), 6.88 (1H, dd, J=7.6, 7.9 Hz), 7.35 (1H, s), 8.20 (1H, s).

ESI (LC/MS positive mode) m/z: 558 (M+2H−Na).

Compound 1j-1-7-1K

Dimethylcarbamic acid 3-{3-(sulfamoylamino)benzyl}-6-iodo-4-methyl-2-oxo-2H-1-benzopyran-7-yl ester potassium salt

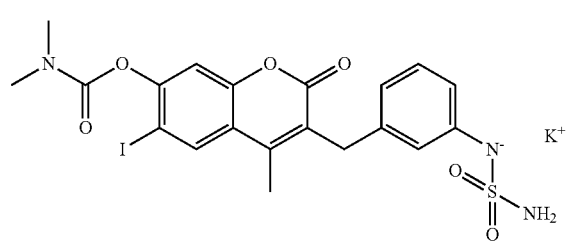

The title compound was synthesized under the same conditions as in the manufacturing example for compound 1j-1-5-1Na, except that compound 1j-1-7-1 was used instead of compound 1j-1-5-1, and that KOH was used instead of NaOH.

$^1$H NMR (DMSO-$d_6$, 270 MHz) δ (ppm): 2.45 (3H, s), 2.96 (3H, s), 3.13 (3H, s), 3.85 (2H, s), 6.48 (1H, d, J=7.8 Hz), 6.74 (1H, s), 6.83 (1H, d, J=7.6 Hz), 6.95 (1H, dd, J=7.6, 7.8 Hz), 7.36 (1H, s), 8.21 (1H, s).

ESI (LC/MS positive mode) m/z: 558 (M+2H−K).

Compound 1j-1-8-1

Dimethylcarbamic acid 3-{3-(aminosulfonyl)aminobenzyl}-6-methyl-4-methyl-2-oxo-2H-1-benzopyran-7-yl ester

[Chemical Formula 69]

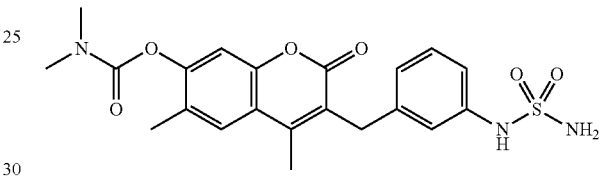

The title compound was synthesized under the same conditions as in the manufacturing example for compound 1j-1-5-1, except that compound 1h-1-8 was used instead of compound 1h-1-5.

$^1$H NMR (DMSO-$d_6$, 270 MHz) δ (ppm): 2.22 (3H, s), 2.45 (3H, s), 2.94 (3H, s), 3.09 (3H, s), 3.93 (2H, s), 6.83 (1H, d, J=8.1 Hz), 6.95 (1H, s), 7.02-7.05 (2H, m), 7.16 (1H, dd, J=8.1, 8.1 Hz), 7.21 (1H, s), 7.75 (1H, s).

ESI (LC/MS positive mode) m/z: 446 (M+H).

Compound 1j-1-9-1

Dimethylcarbamic acid 3-{3-(aminosulfonyl)aminobenzyl}-6-cyano-4-methyl-2-oxo-2H-1-benzopyran-7-yl ester

[Chemical Formula 70]

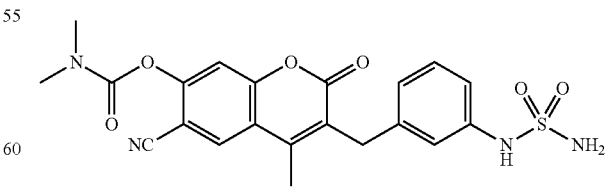

The title compound was synthesized under the same conditions as in the manufacturing example for compound 1j-1-5-1, except that compound 1h-1-9 was used instead of compound 1h-1-5.

¹H NMR (DMSO-d₆, 270 MHz) δ (ppm): 2.97 (3H, s), 3.12 (3H, s), 3.94 (2H, s), 6.84 (1H, d, J=8.1 Hz), 6.97 (1H, s), 7.02-7.05 (2H, m), 7.16 (1H, dd, J=8.1, 8.1 Hz), 7.60 (1H, s), 8.46 (1H, s).

One of the CH₃ peaks was overlapped with the DMSO peak.

ESI (LC/MS positive mode) m/z: 457 (M+H).

Compound 1j-1-4-1F

Dimethylcarbamic acid 3-(3-aminosulfonylamino-2-fluoro-benzyl)-4-fluoromethyl-2-oxo-2H-1-benzopyran-7-yl ester

[Chemical Formula 71]

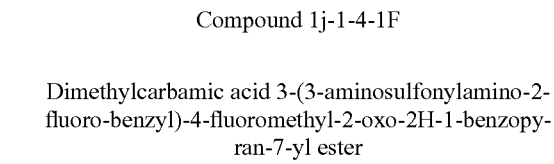

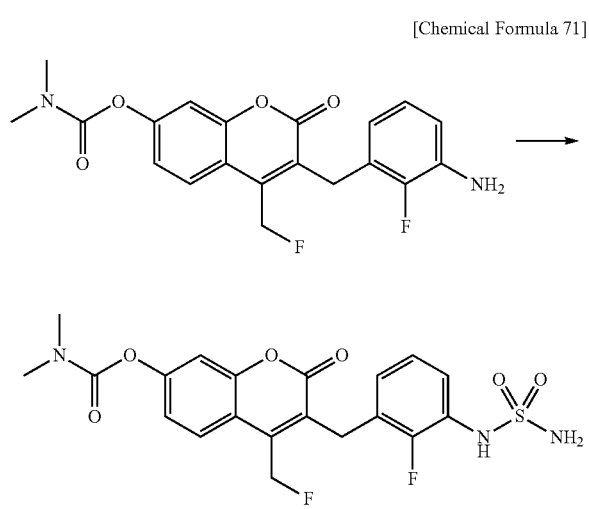

Chlorosulfonyl isocyanate (0.150 mL) and formic acid (0.065 mL) were mixed at 0° C., and the mixture was stirred at room temperature for 1 hour. Dichloromethane (1.2 mL) was added to this mixture and dissolved, and the mixture was further stirred at room temperature for 4 hours. 0.060 mL was taken from the solution, and added at 0° C. to a solution of dimethylcarbamic acid 3-(3-amino-2-fluorobenzyl)-4-fluoromethyl-2-oxo-2H-1-benzopyran-7-yl ester (compound 1h-1-4F) (25.2 mg) in dichloromethane (1.0 mL)/pyridine (0.0065 mL), and the mixture was stirred at room temperature for 3 hours. Saturated sodium hydrogen carbonate was then added to the reaction solution, and the mixture was extracted with ethyl acetate, The extracted liquid was washed with saturated saline, and the organic layer was dried over anhydrous magnesium sulfate. The solvent was distilled away under reduced pressure, and the resultant residue was purified by thin layer silica gel chromatography (aminogel) (dichloromethane:methanol=90:10) to yield the title compound (12.0 mg).

¹H NMR (270 MHz, DMSO-d₆) δ (ppm): 2.93 (3H, s), 3.07 (3H, s), 4.06 (2H, s), 5.84 (2H, d, J=45.8 Hz), 6.84 (1H, brt, J=7.7 Hz), 7.01 (1H, brt, J=7.7 Hz), 7.12 (1H, brs), 7.29-7.40 (2H, m), 7.92 (1H, dd, J=8.9, 2.1 Hz), 9.15 (1H, brs).

ESI (LC/MS positive mode) m/z: 468 (M+H).

Compound 1j-1-3-1F-Other

Dimethylcarbamic acid 3-{3-((tert-butoxycarbonyl) aminosulfonyl)aminobenzyl}-6-chloro-4-fluoromethyl-2-oxo-2H-1-benzopyran-7-yl ester

[Chemical Formula 72]

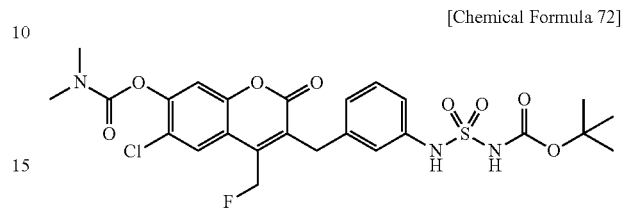

Triethylamine (34 μL, 0.25 mmol) and N-(tert-butoxycarbonyl)-N-{4-(dimethylazaniumylidene)-1,4-dihydropyridin-1-ylsulfonyl}azanide (49 mg, 0.16 mmol) were added in series to a solution of dimethylcarbamic acid 3-(3-aminobenzyl)-6-chloro-4-fluoromethyl-2-oxo-2H-1-benzopyran-7-yl ester (compound 1h-1-3F) (33 mg, 0.082 mmol) in anhydrous dichloromethane (1.0 mL), and the mixture was stirred at room temperature overnight. The reaction mixture was then poured into water and extracted with ethyl acetate. The organic extract was washed with saturated saline and dried over magnesium sulfate. A crude solid was then obtained by vacuum concentration, and purified by preparative TLC (ethyl acetate:hexane=1:2) to yield the title compound (30 mg, 63%) as a white powder.

¹H NMR (DMSO-d₆, 270 MHz) δ (ppm): 8.07 (s, 1H), 7.56 (s, 1H), 7.20-6.80 (m, 6H), 5.86 (d, J=46.2 Hz, 2H), 4.03 (s, 2H), 3.11 (s, 3H), 2.95 (s, 3H), 1.29 (s, 9H).

ESIMS m/z: 528 (M-tBu+2H).

Compound 1j-1-3-1F

Dimethylcarbamic acid 3-{3-(aminosulfonyl)aminobenzyl}-6-chloro-4-fluoromethyl-2-oxo-2H-1-benzopyran-7-yl ester

[Chemical Formula 73]

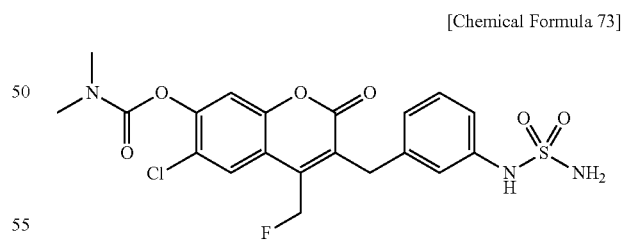

Trifluoroacetic acid (0.1 mL) was added to a solution of dimethylcarbamic acid 3-{3-((tert-butoxycarbonyloxy)aminosulfonyl)aminobenzyl}-6-chloro-4-fluoromethyl-2-oxo-2H-1-benzopyran-7-yl ester (compound 1j-1-3-1F-other) (23 mg, 0.039 mmol) in anhydrous dichloromethane (1.0 mL), and the mixture was stirred at room temperature for 3 hours. The reaction mixture was then poured into saturated sodium hydrogen carbonate and extracted with ethyl acetate. The organic extract was washed with saturated saline and dried over magnesium sulfate. A crude solid was then obtained by vacuum concentration, and purified by preparative TLC (ethyl acetate:hexane=1:1) to yield the title compound (19 mg, 100%) as a pale yellow powder.

¹H NMR (DMSO-d₆, 270 MHz) δ (ppm): 9.40 (brs, 1H), 8.07 (s, 1H), 7.56 (s, 1H), 7.17 (t, J=8.0 Hz, 1H), 7.05 (s+d, 3H), 6.96 (s, 1H), 6.82 (d, J=7.3 Hz, 1H), 5.86 (d, J=46.2 Hz, 2H), 4.03 (s, 2H), 3.11 (s, 3H), 2.95 (s, 3H).

ESIMS m/z: 484 (M+H).

Compound 1j-1-1-1F

Dimethylcarbamic acid 3-{3-(aminosulfonyl)aminobenzyl}-4-fluoromethyl-2-oxo-2H-1-benzopyran-7-yl ester

[Chemical Formula 74]

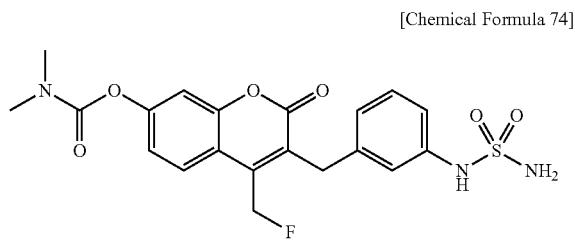

The title compound was synthesized under the same conditions as in the manufacturing example for compound 1j-1-5-1, except that compound 1h-1-1F was used instead of compound 1h-1-5.

¹H NMR (270 MHz, DMSO-d₆) δ (ppm): 2.93 (3H, s), 3.07 (3H, s), 4.02 (2H, s), 5.83 (2H, d, J=46.0 Hz), 6.81 (1H, brd, J=7.4 Hz), 6.96 (1H, brs), 7.05 (3H, m), 7.15 (1H, d, J=7.6 Hz), 7.22 (1H, dd, J=8.7, 2.3 Hz), 7.30 (1H, d, J=2.3 Hz), 7.91 (1H, dd, J=8.7, 2.3 Hz), 9.39 (1H, brs).

ESI (LC/MS positive mode) m/z: 450 (M+H).

Compound 1j-1-2-1F

Dimethylcarbamic acid 3-{3-(aminosulfonyl)aminobenzyl}-6-fluoro-4-fluoromethyl-2-oxo-2H-1-benzopyran-7-yl ester

[Chemical Formula 75]

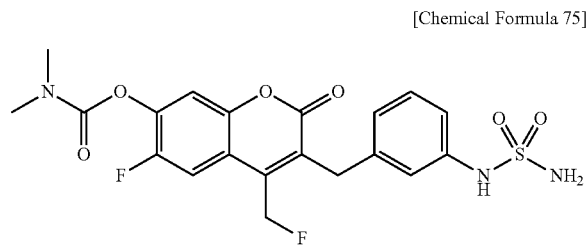

The title compound was synthesized under the same conditions as in the manufacturing example for compound 1j-1-5-1, except that compound 1h-1-2F was used instead of compound 1h-1-5.

¹H NMR (270 MHz, DMSO-d₆) δ (ppm): 2.94 (3H, s), 3.09 (3H, s), 4.03 (2H, s), 5.82 (2H, d, J=46.0 Hz), 6.81 (1H, d, J=8.1 Hz), 6.96 (1H, s), 7.05 (2H, m), 7.17 (1H, t, J=7.7 Hz), 7.54 (1H, d, J=6.9 Hz), 7.89 (1H, d, J=9.7 Hz), 9.36 (1H, brs).

ESI (LC/MS positive mode) m/z: 468 (M+H).

Compound 1j-1-3-1OMe

Dimethylcarbamic acid 3-{3-(aminosulfonyl)aminobenzyl}-6-chloro-4-methoxymethyl-2-oxo-2H-1-benzopyran-7-yl ester

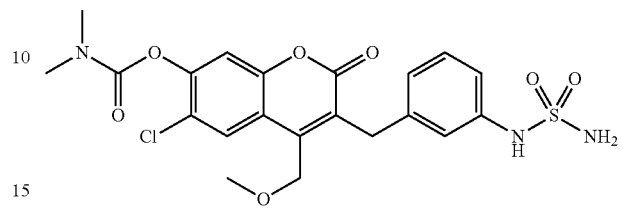

The title compound was synthesized under the same conditions as in the manufacturing example for compound 1j-1-5-1, except that compound 7d-1-3OMe was used instead of compound 1h-1-5.

¹H NMR (270 MHz, DMSO-d₆) δ (ppm): 9.38 (s, 1H), 8.01 (s, 1H), 7.50 (s, 1H), 7.17 (t, 1H, J=8.0 Hz), 7.06-6.95 (m, 4H), 6.82 (d, 1H, J=7.3 Hz), 4.72 (s, 2H), 4.00 (s, 2H), 3.34 (s, 3H), 3.10 (s, 3H), 2.95 (s, 3H).

ESIMS m/z: 496 (M+H).

Compound 1j-1-36-1

Dimethylcarbamic acid 3-{(3-aminosulfonyl)amino-4-fluorobenzyl}-4-methyl-2-oxo-2H-1-benzopyran-7-yl ester

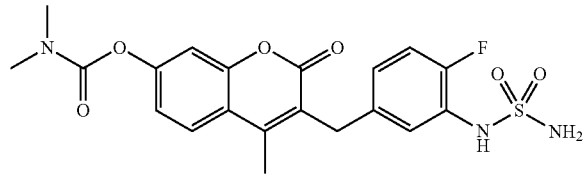

Compound 1j-1-1-1 (300 mg, 0.70 mmol) and N,N-difluoro-2,2'-bipyridinium bis(tetrafluoroborate) (256 mg, 0.70 mmol) were stirred in acetonitrile at 50° C. for 10 hours. The title compound was obtained by silica gel chromatography with a mixed solvent of ethyl acetate and hexane.

¹H-NMR (270 MHz, THF-d₈) δ (ppm): 2.96 (3H, s), 3.08 (3H, s), 4.00 (2H, s), 6.29 (2H, br), 6.96 (2H, m), 7.10 (2H, m), 7.58 (1H, d, J=8.2 Hz), 7.72 (1H, d, J=8.6 Hz), 8.30 (1H, br).

One of the methyl peaks was overlapped with the peak for the solvent.

ESI (LC-MS positive mode) m/z: 450 (M+H).

Compound 1j-1-37-1

Dimethylcarbamic acid 3-{(3-aminosulfonyl)amino-6-fluorobenzyl}-4-methyl-2-oxo-2H-1-benzopyran-7-yl ester

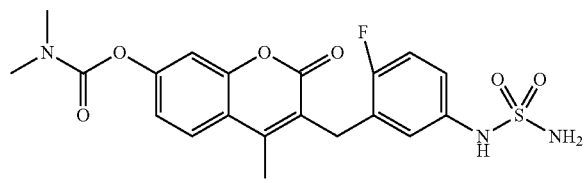

The title compound was obtained as a separate fraction from column chromatography of the reaction mixture for compound 1j-1-36-1.

¹H-NMR (270 MHz, CD₃OD) δ (ppm): 2.50 (3H, s), 3.03 (3H, s), 3.15 (3H, s), 4.06 (2H, s), 6.99 (2H, m), 7.20 (3H, m), 7.83 (1H, dd, J=8.6, 0.7 Hz).

ESI (LC-MS positive mode) m/z: 450 (M+H).

Compound 1j-1-38-1

Dimethylcarbamic acid 3-(3-(aminosulfonyl)aminobenzyl)-6-carbamoyl-4-methyl-2-oxo-2H-1-benzopyran-7-yl ester

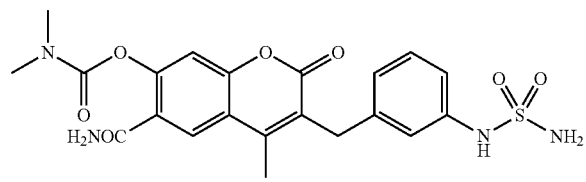

The title compound was synthesized under the same conditions as in the manufacturing example for compound 1j-1-5-1, except that compound 1h-1-38 was used instead of compound 1h-1-5.

¹H-NMR (DMSO-d₆, 270 MHz) δ (ppm): 2.90 (3H, s), 3.05 (3H, s), 3.95 (2H, s), 6.83 (1H, d, J=7.4 Hz), 6.95-7.08 (4H, m), 7.17 (1H, dd, J=7.4, 8.1 Hz), 7.29 (1H, s), 7.50 (1H, brs), 7.81 (1H, brs), 8.00 (1H, s), 9.37 (1H, brs).

The CH₃ peak was overlapped with the DMSO peak.

ESI (LC/MS positive mode) m/z: 475 (M+H).

Compound 1j-1-39-1

Dimethylcarbamic acid 3-(3-(aminosulfonyl)aminobenzyl)-4-methyl-2-oxo-6-trimethylsilanylethynyl-2H-1-benzopyran-7-yl ester

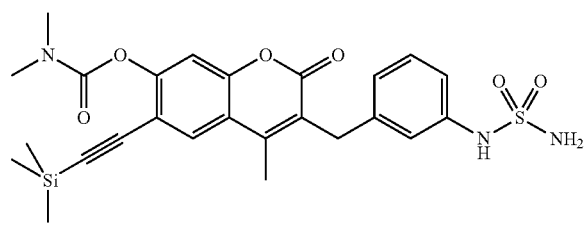

The title compound was synthesized under the same conditions as in the manufacturing example for compound 1j-1-5-1, except that compound 1h-1-39 was used instead of compound 1h-1-5.

¹H-NMR (DMSO-d₆, 270 MHz) δ (ppm): 0.23 (9H, s), 2.46 (3H, s), 2.94 (3H, s), 3.10 (3H, s), 3.93 (2H, s), 6.83 (1H, d, J=7.8 Hz), 6.93-7.09 (4H, m), 7.16 (1H, t, J=7.8 Hz), 7.15 (1H, s), 7.70 (1H, s), 9.13 (1H, brs).

ESI (LC/MS positive mode) m/z: 528 (M+H).

Compound 1j-1-40-1

Dimethylcarbamic acid 3-(3-(aminosulfonyl)aminobenzyl)-6-ethynyl-4-methyl-2-oxo-2H-1-benzopyran-7-yl ester

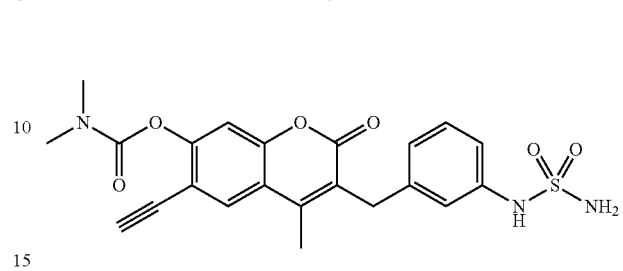

The title compound was synthesized under the same conditions as in the manufacturing example for compound 1j-1-5-1, except that compound 1h-1-40 was used instead of compound 1h-1-5.

¹H-NMR (DMSO-d₆, 270 MHz) δ (ppm): 2.46 (3H, s), 2.94 (3H, s), 3.09 (3H, s), 3.93 (2H, s), 4.45 (1H, s), 6.84 (1H, d, J=7.4 Hz), 6.96 (1H, s), 6.96-7.12 (3H, m), 7.16 (1H, t, J=7.9 Hz), 7.38 (1H, s), 7.99 (1H, s), 9.36 (1H, brs).

ESI (LC/MS positive mode) m/z: 456 (M+H).

Compound 1j-1-72-1

Dimethylcarbamic acid 3-(3-(aminosulfonyl)aminobenzyl)-4-methyl-2-oxo-2H-pyrano[2,3-b]pyridin-7-yl ester

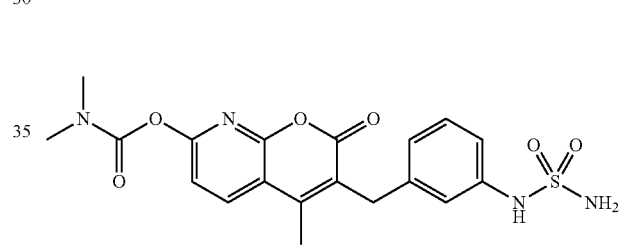

The title compound was synthesized under the same conditions as in the manufacturing example for compound 1j-1-5-1, except that dimethylcarbamic acid 3-(3-aminobenzyl)-4-methyl-2-oxo-2H-pyrano[2,3-b]pyridin-7-yl ester (compound 1h-1-72) was used instead of compound 1h-1-5.

¹H-NMR (DMSO-d₆, 270 MHz) δ (ppm): 2.47 (3H, s), 2.95 (3H, s), 3.06 (3H, s), 6.85 (1H, d, J=7.6 Hz), 6.90-7.22 (1H, brs), 6.97 (1H, s), 7.04 (1H, d, J=7.8 Hz), 7.17 (1H, dd, J=7.6, 7.8 Hz), 7.27 (1H, d, J=8.1 Hz), 8.43 (1H, d, J=8.1 Hz).

ESI (LC/MS positive mode) m/z: 433 (M+H).

Compound 1j-1d-1-1

Pyrrolidine-1-carboxylic acid 3-(3-(aminosulfonyl)aminobenzyl)-4-methyl-4-methyl-2-oxo-2H-1-benzopyran-7-yl ester

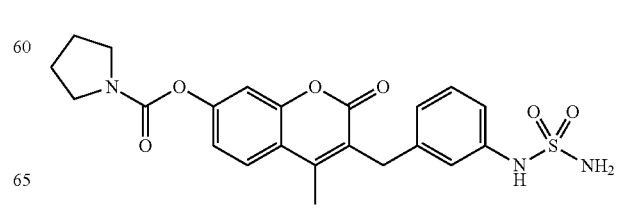

The title compound was synthesized under the same conditions as in the manufacturing example for compound 1j-1-5-1, except that compound 1h-1d-1 was used instead of compound 1h-1-5.

¹H-NMR (DMSO-d₆, 270 MHz) δ (ppm): 1.84-1.94 (4H, m), 2.46 (3H, s), 3.36 (2H, t, J=6.6 Hz), 3.52 (2H, t, J=6.6 Hz), 3.93 (2H, s), 6.84 (1H, d, J=7.3 Hz), 6.94-7.08 (4H, m), 7.13-7.21 (2H, m), 7.26 (1H, d, J=2.2 Hz), 7.86 (1H, d, J=8.7 Hz).

ESI (LC/MS positive mode) m/z: 458 (M+H).

Compound 1j-2-4-1

3-{2-Fluoro-3-(aminosulfonyl)aminobenzyl}-4-methyl-7-(pyrimidin-2-yloxy)-2-oxo-2H-1-benzopyran

[Chemical Formula 76]

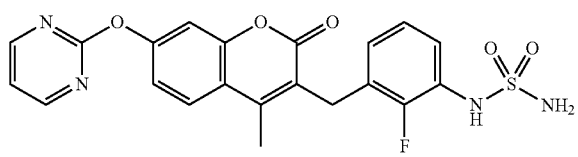

The title compound was synthesized under the same conditions as in the manufacturing example for compound 1j-1-5-1, except that compound 1h-2-4 was used instead of compound 1h-1-5.

¹H NMR (270 MHz, DMSO-d₆) δ (ppm): 2.46 (3H, s), 3.99 (2H, s), 6.80-6.88 (1H, m), 6.97-7.05 (1H, m), 7.06 (2H, br.s), 7.28 (1H, dd, J=8.9, 2.3 Hz), 7.30-7.38 (2H, m), 7.38 (1H, d, J=2.3 Hz), 7.60 (1H, d, J=8.9 Hz), 8.69 (2H, d, J=4.9 Hz), 9.13 (1H, br.s).

ESI (LC/MS positive mode) m/z: 457 (M+H).

Compound 1j-2-4-1Na

3-{2-Fluoro-3-(aminosulfonyl)aminobenzyl}-4-methyl-7-(pyrimidin-2-yloxy)-2-oxo-2H-1-benzopyran sodium salt

[Chemical Formula 77]

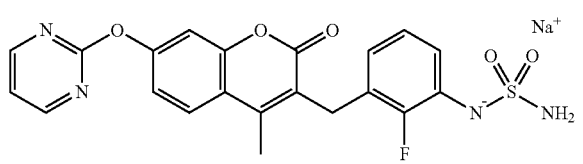

The title compound was synthesized under the same conditions as in the manufacturing example for compound 1j-1-5-1Na, except that compound 1j-2-4-1 was used instead of compound 1j-1-5-1.

¹H NMR (270 MHz, DMSO-d₆) δ (ppm): 2.43 (3H, s), 3.89 (2H, s), 6.12-6.21 (1H, m), 6.60-6.70 (1H, m), 7.13-7.29 (2H, m), 7.33 (1H, t, J=4.8 Hz), 7.36 (1H, d, J=2.3 Hz), 7.88 (1H, d, J=8.9 Hz), 8.69 (2H, d, J=4.8 Hz).

ESI (LC/MS positive mode) m/z: 457 (M+2H−Na).

Compound 1j-2-4-1K 3-(3-Sulfamoylamino-2-fluorobenzyl)-4-methyl-7-(pyrimidin-2-yloxy)-2-oxo-2H-1-benzopyran potassium salt

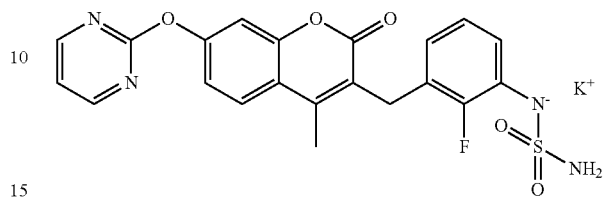

The title compound was synthesized under the same conditions as in the manufacturing example for compound 1j-1-5-1Na, except that compound 1j-2-4-1 was used instead of compound 1j-1-5-1, and that KOH was used instead of NaOH.

¹H NMR (DMSO-d₆, 270 MHz) δ (ppm): 2.44 (3H, s), 3.91 (2H, s), 6.27-6.32 (1H, m), 6.73 (1H, dd, J=7.7, 7.9 Hz), 7.18-7.27 (2H, m), 7.33 (1H, t, J=4.8 Hz), 7.37 (1H, d, J=2.3 Hz), 7.89 (1H, d, J=8.9 Hz), 8.69 (1H, d, J=4.8 Hz).

ESI (LC/MS positive mode) m/z: 457 (M+2H−K).

Compound 1j-3-1-1

3-{3-(Aminosulfonyl)aminobenzyl}-4-methyl-7-(thiazol-2-yloxy)-2-oxo-2H-1-benzopyran

[Chemical Formula 78]

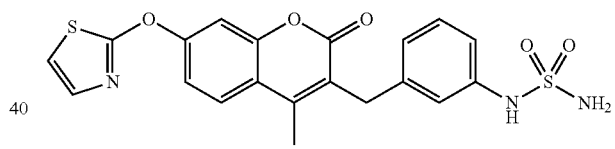

The title compound was synthesized under the same conditions as in the manufacturing example for compound 1j-1-5-1, except that compound 1h-3-1 was used instead of compound 1h-1-5.

¹H NMR (CDCl₃, 270 MHz) δ (ppm): 2.49 (3H, s), 4.04 (2H, s), 6.92 (1H, d, J=3.8 Hz), 7.04-7.09 (3H, m), 7.11-7.14 (1H, m), 7.22-7.31 (3H, m), 7.67 (1H, d, J=8.9 Hz).

ESI (LC/MS positive mode) m/z: 444 (M+H).

Compound 1j-3-3-1

3-{3-(Aminosulfonyl)aminobenzyl}-4-methyl-7-(thiazol-2-yloxy)-6-chloro-2-oxo-2H-1-benzopyran

[Chemical Formula 79]

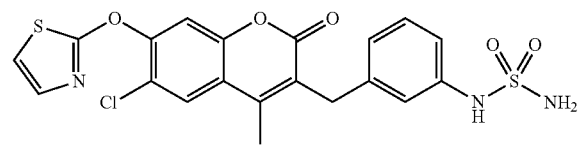

The title compound was synthesized under the same conditions as in the manufacturing example for compound 1j-1-5-1, except that compound 1h-3-3 was used instead of compound 1h-1-5.

$^1$H NMR (DMSO-d$_6$, 270 MHz) δ (ppm): 3.95 (2H, s), 6.84 (1H, d, J=6.9 Hz), 6.97 (1H, s), 7.02-7.05 (2H, m), 7.17 (1H, dd, J=6.9, 6.9 Hz), 7.29 (1H, d, J=3.7 Hz), 7.34 (1H, d, J=3.7 Hz), 7.75 (1H, s), 8.12 (1H, s).

One of the CH$_3$ peaks was overlapped with the DMSO peak.

ESI (LC/MS positive mode) m/z: 478 (M+H).

Compound 1j-3-4-1

3-{2-Fluoro-3-(aminosulfonyl)aminobenzyl}-4-methyl-7-(thiazol-2-yloxy)-2-oxo-2H-1-benzopyran

[Chemical Formula 80]

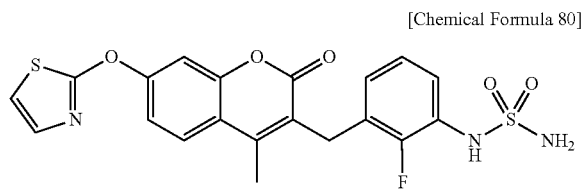

The title compound was synthesized under the same conditions as in the manufacturing example for compound 1j-1-5-1, except that compound 1h-3-4 was used instead of compound 1h-1-5.

$^1$H NMR (DMSO-d$_6$, 270 MHz) δ (ppm): 2.46 (3H, s), 3.98 (2H, s), 6.82-6.87 (1H, m), 6.98-7.04 (1H, m), 7.10 (1H, brs), 7.31-7.39 (4H, m), 7.49 (1H, d, J=2.0 Hz), 7.95 (1H, d, J=8.9 Hz).

ESI (LC/MS positive mode) m/z: 462 (M+H).

Compound 1j-3-4-1Na 3-(3-Sulfamoylamino-2-fluorobenzyl)-4-methyl-7-(thiazol-2-yloxy)-2-oxo-2H-1-benzopyran sodium salt

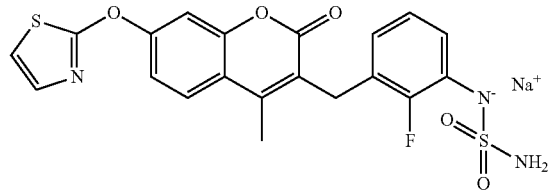

The title compound was synthesized under the same conditions as in the manufacturing example for compound 1j-1-5-1Na, except that compound 1j-3-4-1 was used instead of compound 1j-1-5-1.

$^1$H NMR (DMSO-d$_6$, 270 MHz) δ (ppm): 2.42 (3H, s), 3.89 (2H, s), 6.20-6.25 (1H, m), 6.68 (1H, dd, J=7.9, 8.1 Hz), 7.19 (1H, dd, J=8.2, 8.4 Hz), 7.33-7.37 (3H, m), 7.48 (1H, d, J=2.5 Hz), 7.92 (1H, d, J=8.9 Hz).

ESI (LC/MS positive mode) m/z: 462 (M+2H−Na).

Compound 1j-3-4-1K 3-(3-Sulfamoylamino-2-fluorobenzyl)-4-methyl-7-thiazol-2-oxo-2H-1-benzopyran potassium salt

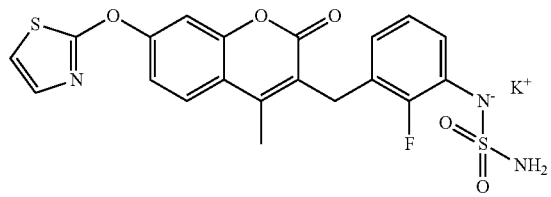

The title compound was synthesized under the same conditions as in the manufacturing example for compound 1j-1-5-1Na, except that compound 1j-3-4-1 was used instead of compound 1j-1-5-1, and that KOH was used instead of NaOH.

$^1$H NMR (DMSO-d$_6$, 270 MHz) δ (ppm): 2.44 (3H, s), 3.92 (2H, s), 6.39-6.45 (1H, m), 6.79 (1H, dd, J=7.1, 8.1 Hz), 7.24 (1H, dd, J=7.9, 8.1 Hz), 7.34-7.38 (3H, m), 7.48 (1H, d, J=2.4 Hz), 7.92 (1H, d, J=8.9 Hz).

ESI (LC/MS positive mode) m/z: 462 (M+2H−K).

Compound 1j-3-8-1

3-{3-(Aminosulfonyl)aminobenzyl}-4-methyl-7-(thiazol-2-yloxy)-6-methyl-2-oxo-2H-1-benzopyran

[Chemical Formula 81]

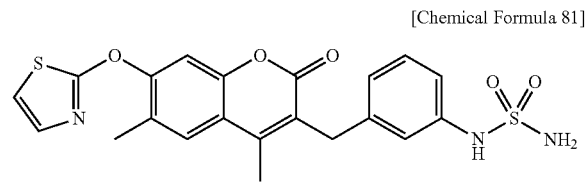

The title compound was synthesized under the same conditions as in the manufacturing example for compound 1j-1-5-1, except that compound 1h-3-8 was used instead of compound 1h-1-5.

$^1$H NMR (DMSO-d$_6$, 270 MHz) δ (ppm): 2.26 (3H, s), 2.46 (3H, s), 3.93 (2H, s), 6.83 (1H, d, J=7.7 Hz), 6.93-7.10 (3H, m), 7.16 (1H, dd, J=7.7, 7.7 Hz), 7.26-7.30 (2H, m), 7.44 (1H, s), 7.85 (1H, s), ESI (LC/MS positive mode) m/z: 458 (M+H).

Compound 1j-3-6-1

3-{2-Chloro-3-(aminosulfonyl)aminobenzyl}-4-methyl-7-(thiazol-2-yloxy)-2-oxo-2H-1-benzopyran

[Chemical Formula 82]

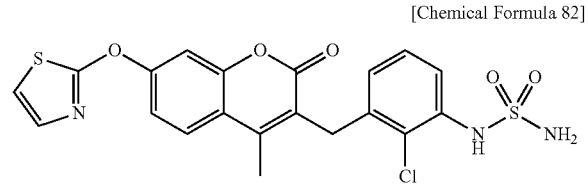

At the synthesis of compound 1j-3-4-1, the title compound was isolated as a byproduct thereof.

$^1$H NMR (DMSO-$d_6$, 270 MHz) δ (ppm): 2.39 (3H, s), 4.03 (2H, s), 6.79 (1H, d, J=6.8 Hz), 7.12-7.20 (3H, m), 7.35-7.44 (4H, m), 7.52 (1H, d, J=2.5 Hz), 7.96 (1H, d, J=9.2 Hz), 8.66 (1H, s).

ESI (LC/MS positive mode) m/z: 478 (M+H).

Compound 1j-16-1-1

4-Methyl-3-(3-(aminosulfonyl)aminobenzyl)-7-(thiazol-5-yl)-2-oxo-2H-1-benzopyran

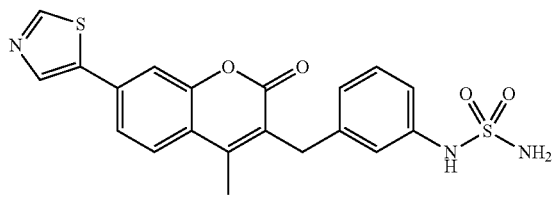

The title compound was synthesized under the same conditions as in the manufacturing example for compound 1j-1-5-1, except that compound 1h-16-1 was used instead of compound 1h-1-5.

$^1$H-NMR (Bruker (ARX-300), 300 MHz, DMSO-d6) δ (ppm): 9.17 (1H, s), 8.53 (1H, s), 7.89 (1H, d, J=8.39 Hz), 7.79 (1H, s), 7.68 (1H, dd, J=8.39, 1.91 Hz), 7.17 (1H, t, J=7.63 Hz), 7.03 (1H, d, J=9.54 Hz), 6.99 (1H, s), 6.84 (1H, d, J=7.63 Hz), 3.95 (2H, s), 2.47 (3H, s).

MS (Micromass, Quattromicro, ESI+) m/z: 450.02 (M+Na).

Compound 1j-17-1-1

4-Methyl-3-(3-(aminosulfonyl)aminobenzyl)-7-(thiazol-2-yl)-2-oxo-2H-1-benzopyran

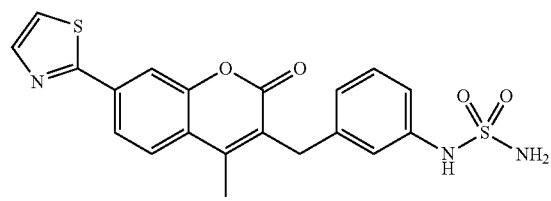

The title compound was synthesized under the same conditions as in the manufacturing example for compound 1j-1-5-1, except that compound 1h-17-1 was used instead of compound 1h-1-5.

$^1$H-NMR (Bruker (ARX-300), 300 MHz, DMSO-$d_6$) δ (ppm): 8.03 (1H, d, J=3.05 Hz), 7.96 (2H, s), 7.92 (2H, s), 7.17 (1H, t, J=6.87 Hz), 7.06-6.99 (3H, m), 6.86 (1H, dd, J=8.39, 1.91 Hz), 3.95 (2H, s), 2.50 (3H, s).

MS (Micromass, Quattromicro, ESI+) m/z: 449.88 (M+Na).

Compound 1j-20-1-1

4-Methyl-3-(3-(aminosulfonyl)aminobenzyl)-7-(1-methyl-1H-imidazol-2-yl)-2-oxo-2H-1-benzopyran

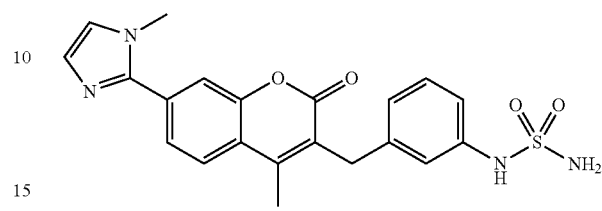

Compound 1h-20-1 (4-methyl-3-(3-aminobenzyl)-7-(1-methyl-1H-imidazol-2-yl)-2-oxo-2H-1-benzopyran) was synthesized under the same conditions as in the manufacturing example for compound 1h-1-5, except that compound 1g-20-1 was used instead of compound 1g-1-5.

The title compound was synthesized under the same conditions as in the manufacturing example for compound 1j-1-5-1, except that compound 1h-20-1 was used instead of compound 1h-1-5.

$^1$H-NMR (Bruker (ARX-300), 300 MHz, DMSO-$d_6$) δ (ppm): 7.93 (1H, d, J=8.39 Hz), 7.75 (1H, d, J=8.39 Hz), 7.70 (1H, s), 7.34 (1H, s), 7.17 (1H, t, J=7.63 Hz), 7.05 (1H, s), 7.03 (1H, d, J=6.10 Hz), 6.99 (1H, s), 6.84 (1H, d, J=7.63 Hz), 3.97 (2H, s), 3.85 (3H, s), 2.50 (3H, s).

MS (Micromass, Quattromicro, ESI+) m/z: 424.95 (M+1).

Compound 1j-32-1-1

4-Methyl-3-(3-(aminosulfonyl)aminobenzyl)-7-(3-methyl-3H-imidazol-4-yl)-2-oxo-2H-1-benzopyran

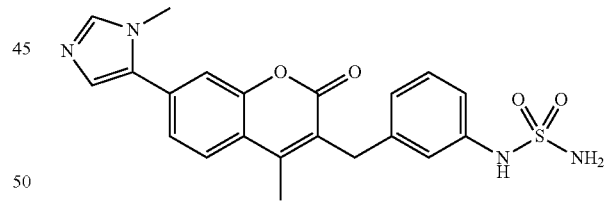

Compound 1h-32-1 (4-methyl-3-(3-aminobenzyl)-7-(3-methyl-3H-imidazol-4-yl)-2-oxo-2H-1-benzopyran) was synthesized under the same conditions as in the manufacturing example for compound 1h-1-5, except that compound 1g-32-1 was used instead of compound 1g-1-5.

The title compound was synthesized under the same conditions as in the manufacturing example for compound 1j-1-5-1, except that compound 1h-32-1 was used instead of compound 1h-1-5.

$^1$H-NMR (Bruker (ARX-300), 300 MHz, DMSO-$d_6$) δ (ppm): 9.34 (1H, s), 7.89 (1H, J=8.7 Hz), 7.78 (1H, s), 7.54 (2H, m), 7.27 (1H, s), 7.17 (1H, t, J=8.1 Hz), 7.02 (4H, m), 6.85 (1H, d, J=7.8 Hz), 3.95 (2H, s), 3.78 (2H, s), 2.48 (3H, s).

MS (Micromass, Quattromicro, ESI+) m/z: 425.01 (M+1).

Compound 1j-1-5-2

Dimethylcarbamic acid 6-fluoro-4-methyl-3-{2-fluoro-3-(methylaminosulfonyl)aminobenzyl}-2-oxo-2H-1-benzopyran-7-yl ester

[Chemical Formula 83]

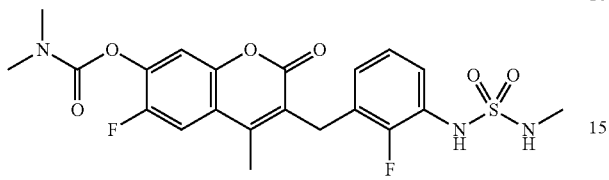

N—(N-methylsulfamoyl)-2-oxazolidinone (27.0 mg, 0.15 mmol) was added to an acetonitrile solution (4 mL) of compound 1h-1-5 (26 mg, 0.07 mmol), and the mixture was stirred at 80° C. for 18 hours. Ethyl acetate was then added to the reaction solution, and the solution was washed with sodium carbonate solution and saturated saline. The organic layer was dried over anhydrous magnesium sulfate, and the solvent was distilled away under reduced pressure. The resultant residue was purified by silica gel column chromatography to yield the title compound (14.7 mg, 45%).

$^1$H NMR (DMSO-d$_6$, 270 MHz) δ (ppm): 2.43 (3H, s), 2.53 (3H, d, J=5.1 Hz), 2.94 (3H, s), 3.09 (3H, s), 3.98 (2H, s), 6.88 (1H, dd, J=6.3, 7.9 Hz), 7.01 (1H, dd, J=7.9, 7.9 Hz), 7.22 (1H, q, J=5.1 Hz), 7.27 (1H, dd, J=9.6, 8.2 Hz), 7.48 (1H, d, J=6.8 Hz), 7.86 (1H, d, J=11.4 Hz), 9.38 (1H, s).

ESI (LC/MS positive mode) m/z: 482 (M+H).

Compound 1j-1-3-2

Dimethylcarbamic acid 3-(3-(N-methylsulfamoyl)aminobenzyl)-6-chloro-4-methyl-2-oxo-2H-1-benzopyran-7-yl ester

[Chemical Formula 84]

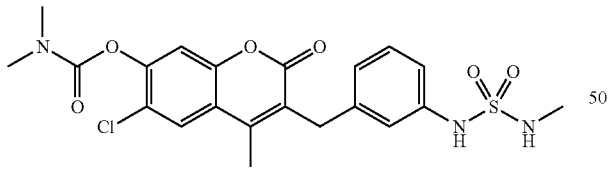

Sulfuryl chloride (2.04 mL, 24.8 mmol) was dissolved in dichloromethane (120 mL), and a methylamine THF solution (11.64 mL, 23.3 mmol) and dimethylaminopyridine (also referred to as "DMAP" herein) (2.84 g, 23.3 mmol) were added thereto at −78° C. The mixture was stirred at room temperature for 2 hours to yield the corresponding sulfamoyl chloride. Dimethylcarbamic acid 3-(3-aminobenzyl)-6-chloro-4-methyl-2-oxo-2H-1-benzopyran-7-yl ester (compound 1h-1-3) (3.0 g, 7.76 mmol), pyridine (3.2 mL) and dichloromethane (60 mL) were added to the reaction solution, and the mixture was stirred at room temperature overnight. Water was then added to the reaction solution, and the solution was extracted with dichloromethane. After washing with sodium hydrogen carbonate solution and saturated saline, the organic layer was dried over anhydrous magnesium sulfate, and the solvent was distilled away under reduced pressure. The resultant residue was purified by silica gel column chromatography to yield the title compound (540 mg).

$^1$H NMR (CDCl$_3$, 270 MHz) δ (ppm): 2.44 (3H, s), 2.68 (3H, d, J=5.1 Hz), 3.05 (3H, s), 3.17 (3H, s), 4.02 (2H, s), 4.57 (1H, m), 6.54 (1H, br), 6.90-7.00 (2H, m), 7.09 (1H, brs), 7.19-7.30 (1H, m), 7.66 (1H, s).

ESI (LC/MS positive mode) m/z: 480 (M+H).

Compound 1j-1-3-2Na

Dimethylcarbamic acid 6-chloro-4-methyl-3-{3-(methylaminosulfonyl)aminobenzyl}-2-oxo-2H-1-benzopyran-7-yl ester sodium salt

[Chemical Formula 85]

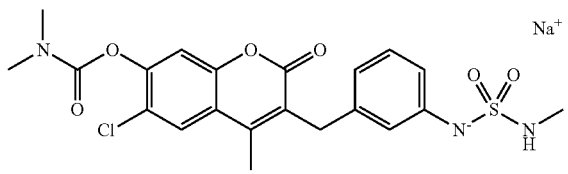

The title compound was synthesized under the same conditions as in the manufacturing example for compound 1j-1-5-1Na, except that compound 1j-1-3-2 was used instead of compound 1j-1-5-1.

$^1$H NMR (DMSO-d$_6$, 270 MHz) δ (ppm): 2.28 (3H, s), 2.43 (3H, s), 2.95 (3H, s), 3.11 (3H, s), 3.80 (2H, s), 4.78 (1H, br), 6.29 (1H, d, J=8.1 Hz), 6.66 (1H, brs), 6.73 (1H, d, J=8.1 Hz), 6.82 (1H, dd, J=8.1, 8.1 Hz), 7.46 (1H, s), 7.97 (1H, s).

ESI (LC/MS positive mode) m/z: 480 (M+2H−Na).

Compound 1j-1-3-2K

Dimethylcarbamic acid 3-(3-(N-methylsulfamoyl)aminobenzyl)-6-chloro-4-methyl-2-oxo-2H-1-benzopyran-7-yl ester potassium salt

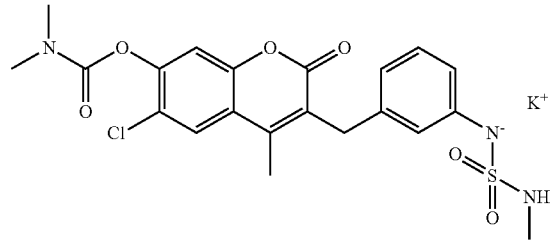

The title compound was synthesized under the same conditions as in the manufacturing example for compound 1j-1-5-1Na, except that compound 1j-1-3-2 was used instead of compound 1j-1-5-1, and that KOH was used instead of NaOH.

$^1$H NMR (CD$_3$OD) δ (ppm): 7.91 (1H, d, J=5.6 Hz), 7.32 (1H, s), 7.14-6.98 (3H, m), 6.77 (1H, d, J=7.4 Hz), 4.02 (2H, s), 3.18 (3H, s), 3.02 (3H, s), 2.53 (3H, s), 2.48 (3H, s).

ESI (LC/MS positive mode) m/z: 480 (M+2H−K).

Compound 1j-1-1-2

Dimethylcarbamic acid 4-methyl-3-{3-(methylaminosulfonyl)aminobenzyl}-2-oxo-2H-1-benzopyran-7-yl ester

[Chemical Formula 86]

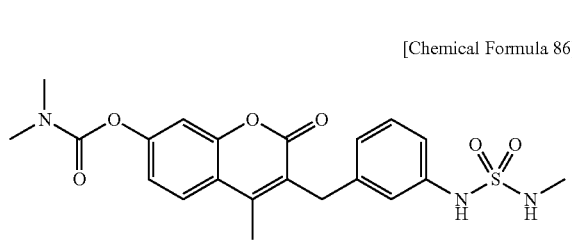

The title compound was synthesized under the same conditions as in the manufacturing example for compound 1j-1-3-2, except that compound 1h-1-1 was used instead of compound 1h-1-3.

$^1$H NMR (CDCl$_3$, 270 MHz) δ (ppm): 2.44 (3H, s), 2.64 (3H, d, J=5.1 Hz), 3.08 (3H, s), 3.17 (3H, s), 4.01 (2H, s), 4.55-4.65 (1H, m), 6.54-7.30 (6H, m), 7.59 (1H, d, J=5.4 Hz).

ESI (LC/MS positive mode) m/z: 446 (M+H).

Compound 1j-1-1S3-2

Dimethylcarbamic acid 4-methyl-3-{3-(methylaminosulfonyl)aminobenzyl}-2-thioxo-2H-1-benzopyran-7-yl ester

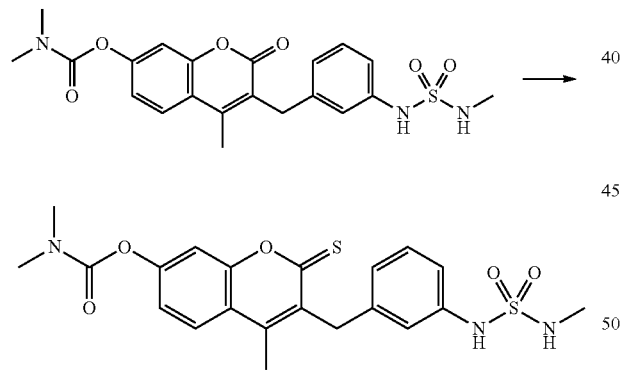

50 mg (0.11 mmol) of compound 1j-1-1-2 was dissolved in 1,4-dioxane, and 30 mg (0.07 mmol) of Lawson's reagent was added thereto. The mixture was heated under reflux under nitrogen atmosphere for 4 hours. The reaction mixture was purified by HPLC to yield 5 mg (10%) of compound 1j-1-1S3-2 as a yellow powder.

$^1$H-NMR (270 MHz, DMSO-d$_6$) δ (ppm): 2.42 (6H, s), 2.95 (3H, s), 3.08 (3H, s), 4.40 (2H, s), 6.83 (1H, d, J=7.6 Hz), 6.96 (1H, s), 7.02 (1H, d, J=7.7 Hz), 7.16 (1H, dd, J=7.7, 7.6 Hz), 7.22 (1H, brs), 7.30 (1H, dd, J=9.0, 2.0 Hz), 7.49 (1H, d, J=2.0 Hz), 7.96 (1H, d, J=9.0 Hz), 9.53 (1H, brs).

ESI (LC-MS positive mode) m/z: 462 (M+H).

Compound 1j-1-2-2

Dimethylcarbamic acid 6-fluoro-4-methyl-3-{3-(methylaminosulfonyl)aminobenzyl}-2-oxo-2H-1-benzopyran-7-yl ester

[Chemical Formula 87]

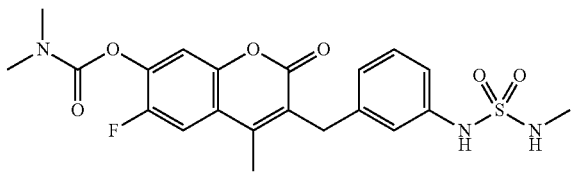

The title compound was synthesized under the same conditions as in the manufacturing example for compound 1j-1-5-2, except that compound 1h-1-2 was used instead of compound 1h-1-5.

$^1$H NMR (CD$_3$OD, 270 MHz) δ (ppm): 2.47 (3H, s), 2.50 (3H, s), 3.02 (3H, s), 3.15 (3H, s), 4.03 (2H, s), 6.93 (1H, d, J=7.8 Hz), 7.03-7.13 (2H, m), 7.19 (1H, dd, J=7.8, 7.8 Hz), 7.29 (1H, d, J=6.8 Hz), 7.66 (1H, d, J=11.0 Hz).

ESI (LC/MS positive mode) m/z: 464 (M+H).

Compound 1j-1-4-2

Dimethylcarbamic acid 3-(3-methylaminosulfonylamino-2-fluorobenzyl)-4-methyl-2-oxo-2H-1-benzopyran-7-yl ester

[Chemical Formula 88]

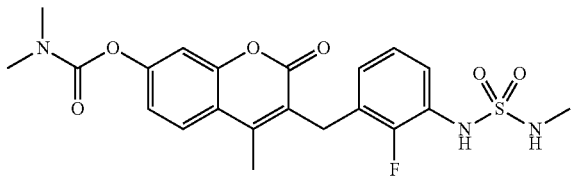

The title compound was synthesized under the same conditions as in the manufacturing example for compound 1j-1-5-2, except that compound 1h-1-4 was used instead of compound 1h-1-5.

$^1$H NMR (270 MHz, DMSO-d$_6$) δ (ppm): 2.44 (3H, s), 2.93 (3H, s), 3.07 (3H, s), 3.98 (2H, s), 6.87 (1H, brt, J=7.6 Hz), 7.01 (1H, t, J=7.6 Hz), 7.15-7.32 (4H, m), 7.86 (1H, d, J=8.7 Hz), 9.37 (1H, brs).

One of the CH$_3$ peaks was overlapped with the DMSO peak.

ESI (LC/MS positive mode) m/z: 464 (M+H).

Compound 1j-1-4-2Na

Dimethylcarbamic acid 3-(3-(N-methylsulfamoyl)amino-2-fluorobenzyl)-4-methyl-2-oxo-2H-1-benzopyran-7-yl ester sodium salt

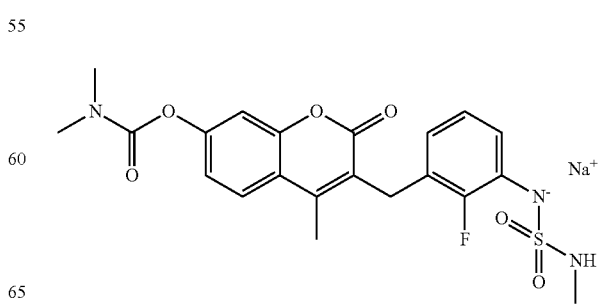

The title compound was synthesized under the same conditions as in the manufacturing example for compound 1j-1-5-1Na, except that compound 1j-1-4-2 was used instead of compound 1j-1-5-1.

¹H NMR (DMSO-d₆, 270 MHz) δ (ppm): 2.35 (3H, s), 2.41 (3H, s), 2.93 (3H, s), 3.07 (3H, s), 3.88 (2H, s), 6.20-6.25 (1H, m), 6.66 (1H, dd, J=7.7, 7.9 Hz), 7.14-7.21 (2H, m), 7.24 (1H, d, J=2.3 Hz), 7.83 (1H, d, J=8.6 Hz).

ESI (LC/MS positive mode) m/z: 464 (M+2H−Na).

Compound 1j-1-7-2

Dimethylcarbamic acid 6-iodo-4-methyl-3-{3-(methylaminosulfonyl)aminobenzyl}-2-oxo-2H-1-benzopyran-7-yl ester

[Chemical Formula 89]

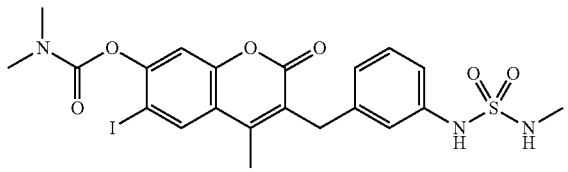

The title compound was synthesized under the same conditions as in the manufacturing example for compound 1j-1-5-2, except that compound 1h-1-7 was used instead of compound 1h-1-5.

¹H NMR (DMSO-d₆, 270 MHz) δ (ppm): 2.43 (3H, d, J=2.7 Hz), 2.45 (3H, s), 2.96 (3H, s), 3.13 (3H, s), 3.93 (2H, s), 6.86 (1H, d, J=8.1 Hz), 6.98-7.03 (2H, m), 7.14-7.23 (2H, m), 7.38 (1H, s), 8.24 (1H, s).

ESI (LC/MS positive mode) m/z: 572 (M+H).

Compound 1j-1-7-2Na

Dimethylcarbamic acid 3-(3-(N-methylsulfamoyl)aminobenzyl)-6-iodo-4-methyl-2-oxo-2H-1-benzopyran-7-yl ester sodium salt

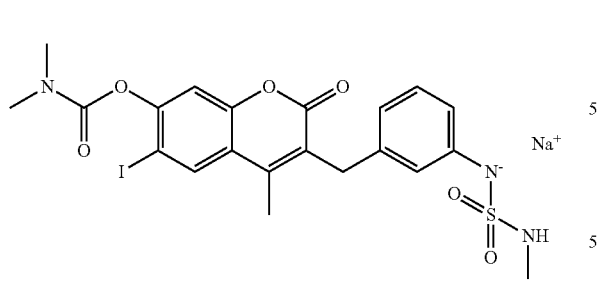

The title compound was synthesized under the same conditions as in the manufacturing example for compound 1j-1-5-1Na, except that compound 1j-1-7-2 was used instead of compound 1j-1-5-1.

¹H NMR (DMSO-d₆, 270 MHz) δ (ppm): 2.34 (3H, s), 2.45 (3H, s), 2.96 (3H, s), 3.13 (3H, s), 3.86 (2H, s), 6.52 (1H, d, J=7.7 Hz), 6.79 (1H, s), 6.85 (1H, d, J=7.8 Hz), 6.96 (1H, dd, J=7.7, 7.8 Hz), 7.36 (1H, s), 8.22 (1H, s).

ESI (LC/MS positive mode) m/z: 572 (M+2H−Na).

Compound 1j-1-7-2K

Dimethylcarbamic acid 3-(3-(N-methylsulfamoyl)aminobenzyl)-6-iodo-4-methyl-2-oxo-2H-1-benzopyran-7-yl ester potassium salt

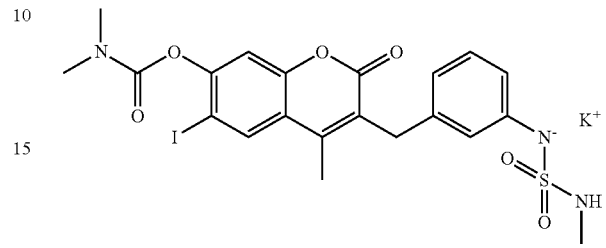

The title compound was synthesized under the same conditions as in the manufacturing example for compound 1j-1-5-1Na, except that compound 1j-1-7-2 was used instead of compound 1j-1-5-1, and that KOH was used instead of NaOH.

¹H NMR (DMSO-d₆, 270 MHz) δ (ppm): 2.36 (3H, s), 2.42 (3H, s), 2.96 (3H, s), 3.14 (3H, s), 3.88 (2H, s), 6.61 (1H, d, J=7.6 Hz), 6.84 (1H, s), 6.89 (1H, d, J=8.1 Hz), 7.02 (1H, dd, J=7.6, 8.1 Hz), 7.37 (1H, s), 8.22 (1H, s).

ESI (LC/MS positive mode) m/z: 572 (M+2H−K).

Compound 1j-1-8-2

Dimethylcarbamic acid 6-methyl-4-methyl-3-{3-(methylaminosulfonyl)aminobenzyl}-2-oxo-2H-1-benzopyran-7-yl ester

[Chemical Formula 90]

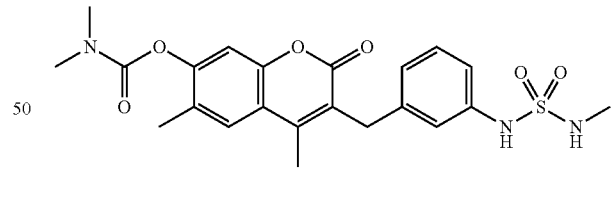

The title compound was synthesized under the same conditions as in the manufacturing example for compound 1j-1-5-2, except that compound 1h-1-8 was used instead of compound 1h-1-5.

¹H NMR (DMSO-d₆, 270 MHz) δ (ppm): 2.23 (3H, s), 2.42 (3H, d, J=5.4 Hz), 2.46 (3H, s), 2.94 (3H, s), 3.10 (3H, s), 3.93 (2H, s), 6.86 (1H, d, J=8.1 Hz), 7.00-7.04 (2H, m), 7.14-7.22 (3H, m), 7.75 (1H, s).

ESI (LC/MS positive mode) m/z: 460 (M+H).

Compound 1j-1-8-2Na

Dimethylcarbamic acid 3-(3-(N-methylsulfamoyl)aminobenzyl)-4,6-dimethyl-2-oxo-2H-1-benzopyran-7-yl ester sodium salt

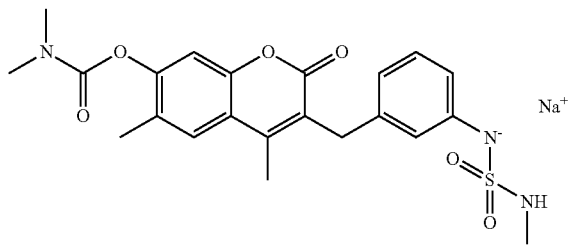

The title compound was synthesized under the same conditions as in the manufacturing example for compound 1j-1-5-1Na, except that compound 1j-1-8-2 was used instead of compound 1j-1-5-1.

$^1$H NMR (DMSO-d$_6$, 270 MHz) δ (ppm): 2.22 (3H, s), 2.32 (3H, s), 2.44 (3H, s), 2.94 (3H, s), 3.09 (3H, s), 3.84 (2H, s), 6.44 (1H, d, 7.4 Hz), 6.75 (1H, s), 6.81 (1H, d, J=8.1 Hz), 6.91 (1H, dd, J=7.4, 8.1 Hz), 7.20 (1H, s), 7.72 (1H, s).

ESI (LC/MS positive mode) m/z: 460 (M+2H−Na).

Compound 1j-1-8-2K

Dimethylcarbamic acid 3-(3-(N-methylsulfamoyl)aminobenzyl)-4,6-dimethyl-2-oxo-2H-1-benzopyran-7-yl ester potassium salt

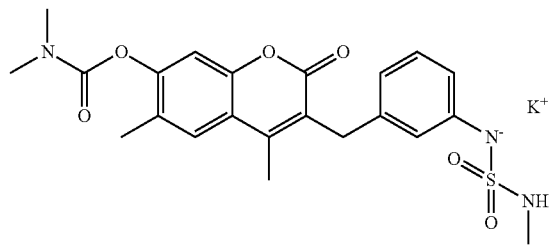

The title compound was synthesized under the same conditions as in the manufacturing example for compound 1j-1-5-1Na, except that compound 1j-1-8-2 was used instead of compound 1j-1-5-1, and that KOH was used instead of NaOH.

$^1$H NMR (DMSO-d$_6$, 270 MHz) δ (ppm): 2.22 (3H, s), 2.33 (3H, s), 2.44 (3H, s), 2.94 (3H, s), 3.09 (3H, s), 3.84 (2H, s), 6.48 (1H, d, J=7.5, 8.3 Hz), 7.19 (1H, s), 7.72 (1H, s).

ESI (LC/MS positive mode) m/z: 460 (M+2H−K).

Compound 1j-1-9-2

Dimethylcarbamic acid 6-cyano-4-methyl-3-{3-methylaminosulfonyl)aminobenzyl}-2-oxo-2H-1-benzopyran-7-yl ester

[Chemical Formula 91]

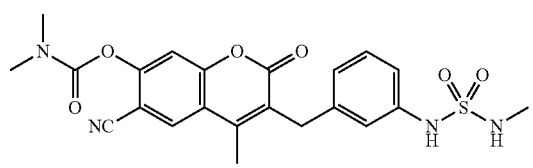

The title compound was synthesized under the same conditions as in the manufacturing example for compound 1j-1-5-2, except that compound 1h-1-9 was used instead of compound 1h-1-5.

$^1$H NMR (DMSO-d$_6$, 270 MHz) δ (ppm): 2.42 (3H, d, J=5.4 Hz), 2.97 (3H, s), 3.12 (3H, s), 3.94 (2H, s), 6.87 (1H, d, J=8.1 Hz), 7.01-7.04 (2H, m), 7.15-7.25 (2H, m), 7.60 (1H, s), 8.46 (1H, s).

One of the CH$_3$ peaks was overlapped with the DMSO peak.

ESI (LC/MS positive mode) m/z: 471 (M+H).

Compound 1j-1-9-2Na

Dimethylcarbamic acid 6-cyano-4-methyl-3-{3-(methylaminosulfonyl)aminobenzyl}-2-oxo-2H-1-benzopyran-7-yl ester sodium salt

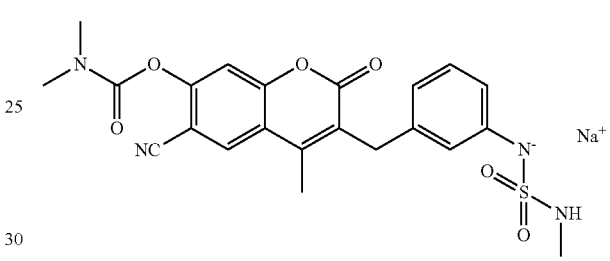

The title compound was synthesized under the same conditions as in the manufacturing example for compound 1j-1-5-1Na, except that compound 1j-1-9-2 was used instead of compound 1j-1-5-1.

$^1$H NMR (270 MHz, DMSO-d$_6$) δ (ppm): 8.42 (s, 1H), 7.57 (s, 1H), 6.82 (t, 1H, J=7.5 Hz), 6.74 (d, 1H, J=7.9 Hz), 6.65 (s, 1H), 6.30 (d, 1H, J=7.4 Hz), 3.81 (s, 2H), 3.11 (s, 3H), 2.96 (s, 3H), 2.45 (s, 3H), 2.28 (s, 3H).

ESIMS m/z: 471 (M+2H−Na).

Compound 1j-1-9-2K

Dimethylcarbamic acid 6-cyano-4-methyl-3-{3-(methylaminosulfonyl)aminobenzyl}-2-oxo-2H-1-benzopyran-7-yl ester potassium salt

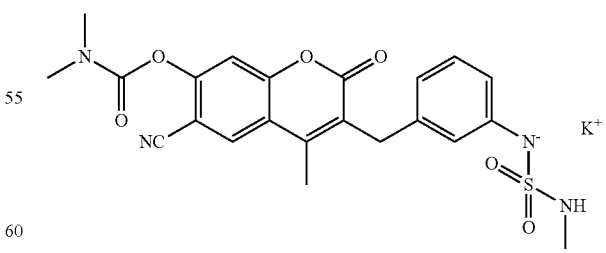

The title compound was synthesized under the same conditions as in the manufacturing example for compound 1j-1-5-1Na, except that compound 1j-1-9-2 was used instead of compound 1j-1-5-1, and that KOH was used instead of NaOH.

¹H NMR (270 MHz, DMSO-d₆) δ (ppm): 8.44 (s, 1H), 7.59 (s, 1H), 6.89 (t, 1H, J=7.5 Hz), 6.78 (d, 1H, J=7.9 Hz), 6.62 (s, 1H), 6.33 (d, 1H, J=7.4 Hz), 3.84 (s, 2H), 3.12 (s, 3H), 2.97 (s, 3H), 2.48 (s, 3H), 2.30 (s, 3H).

ESIMS m/z: 471 (M+2H−K).

Compound 1j-1-10-2

Dimethylcarbamic acid 4-methyl-3-{2-(methylaminosulfonyl)aminopyridin-4-ylmethyl}-2-oxo-2H-1-benzopyran-7-yl ester

[Chemical Formula 92]

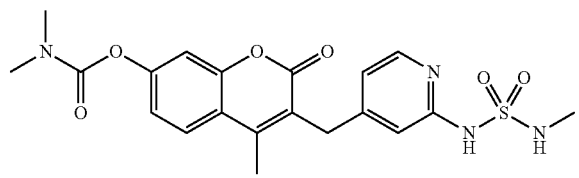

The title compound was synthesized under the same conditions as in the manufacturing example for compound 1j-1-5-2, except that compound 1h-1-10 was used instead of compound 1h-1-5.

¹H NMR (DMSO-d₆, 270 MHz) δ (ppm): 2.40-2.60 (6H, m), 2.93 (3H, s), 3.07 (3H, s), 3.96 (2H, s), 6.75-6.84 (2H, m), 6.85-7.10 (1H, brs), 7.18 (1H, dd, J=8.9, 2.4 Hz), 7.27 (1H, d, J=2.4 Hz), 7.87 (1H, d, J=8.6 Hz), 8.04-8.10 (1H, m).

ESI (LC/MS positive mode) m/z: 447 (M+H).

Compound 1j-1-11-2

Dimethylcarbamic acid 4-methyl-3-{2-(methylaminosulfonyl)aminopyridin-4-ylmethyl}-6-fluoro-2-oxo-2H-1-benzopyran-7-yl ester

[Chemical Formula 93]

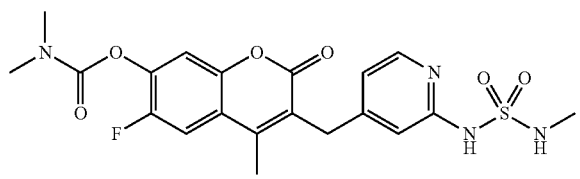

The title compound was synthesized under the same conditions as in the manufacturing example for compound 1j-1-5-2, except that compound 1h-1-11 was used instead of compound 1h-1-5.

¹H NMR (DMSO-d₆, 270 MHz) δ (ppm): 2.40-2.60 (6H, m), 2.92 (3H, s), 3.04 (3H, s), 4.02 (2H, s), 6.75-6.82 (2H, m), 6.82-7.05 (1H, brs), 7.48 (1H, d, J=6.2 Hz), 7.87 (1H, d, J=10.2 Hz), 8.07 (1H, m), 10.00-10.25 (1H, brs).

ESI (LC/MS positive mode) m/z: 465 (M+H).

Compound 1j-1-11-2Na

Dimethylcarbamic acid 3-(2-(N-methylsulfamoyl)aminopyridin-4-ylmethyl)-6-fluoro-4-methyl-2-oxo-2H-1-benzopyran-7-yl ester sodium salt

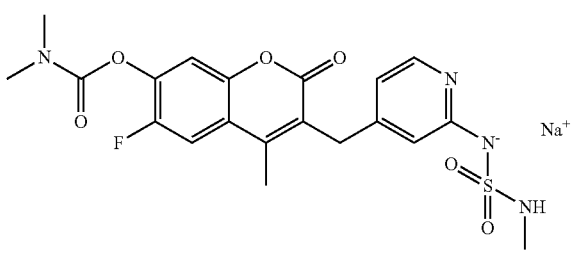

The title compound was synthesized under the same conditions as in the manufacturing example for compound 1j-1-5-1Na, except that compound 1j-1-11-2 was used instead of compound 1j-1-5-1.

¹H NMR (CD₃OD, 270 MHz) δ (ppm): 2.45 (3H, s), 2.50 (3H, s), 2.65 (3H, s), 3.02 (3H, s), 3.95 (2H, s), 6.55 (1H, dd, J=5.1 Hz, J<1.0 Hz), 6.61 (1H, brs), 7.30 (1H, d, J=6.8 Hz), 7.67 (1H, d, J=11.1 Hz), 7.90 (1H, d, J=5.1 Hz).

ESI (LC/MS positive mode) m/z: 465 (M+2H−Na).

Compound 1j-1-11-2K

Dimethylcarbamic acid 3-(2-(N-methylsulfamoyl)aminopyridin-4-ylmethyl)-6-fluoro-4-methyl-2-oxo-2H-1-benzopyran-7-yl ester potassium salt

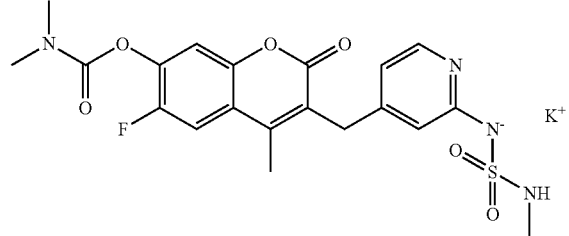

The title compound was synthesized under the same conditions as in the manufacturing example for compound 1j-1-5-1Na, except that compound 1j-1-11-2 was used instead of compound 1j-1-5-1, and that KOH was used instead of NaOH.

¹H NMR (CD₃OD, 270 MHz) δ (ppm): 2.45 (3H, s), 2.50 (3H, s), 2.65 (3H, s), 3.02 (3H, s), 3.95 (2H, s), 6.55 (1H, dd, J=5.1 Hz, J<1.0 Hz), 6.61 (1H, brs), 7.30 (1H, d, J=6.8 Hz), 7.67 (1H, d, J=11.1 Hz), 7.90 (1H, d, J=5.1 Hz).

ESI (LC/MS positive mode) m/z: 465 (M+2H−K).

Compound 1j-1-12-2

Dimethylcarbamic acid 4-methyl-3-{2-(methylaminosulfonyl)aminopyridin-4-ylmethyl}-6-chloro-2-oxo-2H-1-benzopyran-7-yl ester

[Chemical Formula 94]

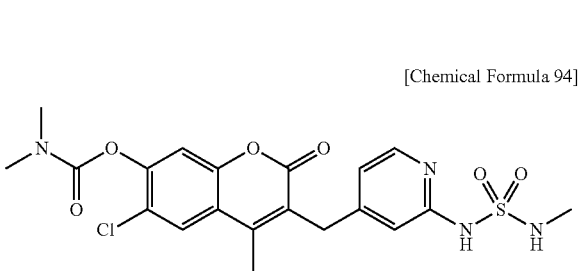

Dimethylcarbamic acid 2-oxo-2H-3-(2-aminopyridin-4-ylmethyl)-4-methyl-6-chloro-1-benzopyran-7-yl ester (compound 1h-1-12) was synthesized under the same conditions as in the manufacturing example for compound 1g-1-5, except that compound 5d-0-12 was used instead of compound 1e-0-5.

The title compound was synthesized under the same conditions as in the manufacturing example for compound 1j-1-5-2, except that compound 1h-1-12 was used instead of compound 1h-1-5.

¹H NMR (CD₃OD, 270 MHz) δ (ppm): 2.51 (3H, s), 2.63 (3H, s), 3.04 (3H, s), 3.18 (3H, s), 4.13 (2H, s), 7.07 (1H, s), 7.08 (1H, d, J=7.8 Hz), 7.35 (1H, s), 7.97 (1H, s), 8.12 (1H, d, J=7.8 Hz).

ESI (LC/MS positive mode) m/z: 481 (M+H).

Compound 1j-1-13-2

Dimethylcarbamic acid 4-methyl-3-{6-(methylaminosulfonyl)aminopyridin-2-ylmethyl}-2-oxo-2H-1-benzopyran-7-yl ester

[Chemical Formula 95]

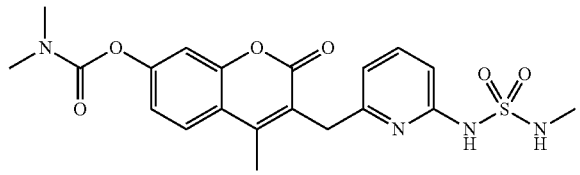

The title compound was synthesized under the same conditions as in the manufacturing example for compound 1j-1-5-2, except that compound 1h-1-13 was used instead of compound 1h-1-5.

¹H NMR (CD₃OD, 270 MHz) δ (ppm): 2.50 (3H, d, J=8.1 Hz), 3.01 (3H, s), 3.13 (3H, s), 4.15 (2H, s), 6.79 (1H, d, J=8.1 Hz), 6.99 (1H, d, J=8.1 Hz), 7.10-7.20 (2H, m), 7.63 (1H, dd, J=8.1 Hz), 7.81 (1H, d, J=8.1 Hz).

ESI (LC/MS positive mode) m/z: 447 (M+H).

Compound 1j-1-14-2

Dimethylcarbamic acid 4-methyl-3-{6-(methylaminosulfonyl)aminopyridin-2-ylmethyl}-6-fluoro-2-oxo-2H-1-benzopyran-7-yl ester

[Chemical Formula 96]

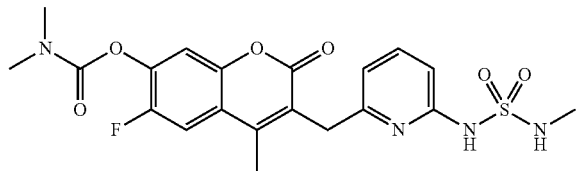

The title compound was synthesized under the same conditions as in the manufacturing example for compound 1j-1-5-2, except that compound 1h-1-14 was used instead of compound 1h-1-5.

¹H NMR (CD₃OD, 270 MHz) δ (ppm): 2.25 (3H, d, J=1.9 Hz), 3.01 (3H, s), 3.15 (3H, s), 4.15 (2H, s), 6.79 (1H, d, J=8.1 Hz), 7.00 (1H, d, J=8.1 Hz), 7.31 (1H, d, J=6.5 Hz), 7.62 (1H, dd, J=8.1 Hz), 7.66 (1H, d, J=11.0 Hz).

ESI (LC/MS positive mode) m/z: 465 (M+H).

Compound 1j-1-15-2

Dimethylcarbamic acid 4-methyl-3-{6-(methylaminosulfonyl)aminopyridin-2-ylmethyl}-6-chloro-2-oxo-2H-1-benzopyran-7-yl ester

[Chemical Formula 97]

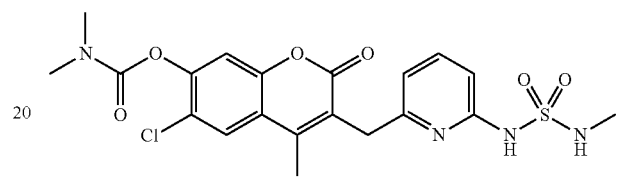

The title compound was synthesized under the same conditions as in the manufacturing example for compound 1j-1-5-2, except that compound 1h-1-15 was used instead of compound 1h-1-5.

¹H NMR (CD₃OD, 270 MHz) δ (ppm): 2.50 (3H, brs), 3.02 (3H, s), 3.17 (3H, s), 4.14 (2H, s), 6.79 (1H, d, J=7.6 Hz), 6.99 (1H, d, J=7.6 Hz), 7.32 (1H, s), 7.62 (1H, dd, J=7.6 Hz), 7.89 (1H, s).

ESI (LC/MS positive mode) m/z: 481 (M+H).

Compound 1j-1-4-2F

Dimethylcarbamic acid 3-(3-methylaminosulfonylamino-2-fluorobenzyl)-4-fluoromethyl-2-oxo-2H-1-benzopyran-7-yl ester

[Chemical Formula 98]

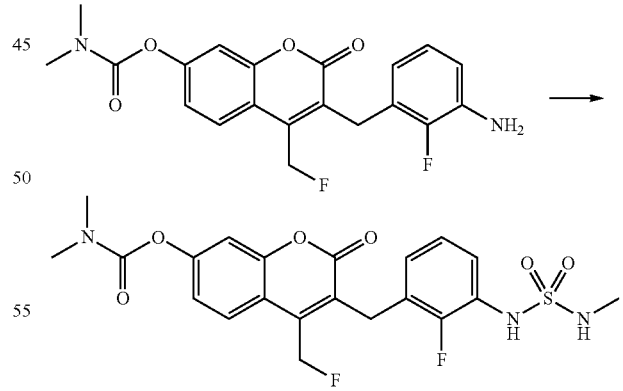

Acetonitrile (1.0 mL) was added to dimethylcarbamic acid 3-(3-amino-2-fluorobenzyl)-4-fluoromethyl-2-oxo-2H-1-benzopyran-7-yl ester (compound 1h-1-4F) (18.5 mg), and triethylamine (0.022 mL) and 2-oxo-oxazolidinone-3-sulfonic acid methylamide (19.0 mg) were added to the resultant suspension while stirring at room temperature. The suspension was heated under reflux for 11 hours, triethylamine (0.022 mL) and 2-oxo-oxazolidinone-3-sulfonic acid methylamide (19.0 mg) were then added thereto, and the mixture was further heated under reflux for 8 hours. After cooling to room temperature, the reaction solution was diluted with a mixed solvent of ethyl acetate and THF (volume ratio 1:1). The organic layer was washed with 0.5 M sodium carbonate solution and saturated saline, and then dried over anhydrous magnesium sulfate. The solvent was distilled away under reduced pressure, and the resultant residue was purified by thin layer silica gel chromatography (amino gel) (dichloromethane:methanol=95:5) to yield the title compound (9.8 mg).

$^1$H NMR (270 MHz, CDCl$_3$) δ (ppm): 2.74 (3H, d, J=5.4 Hz), 3.04 (3H, s), 3.13 (3H, s), 4.11 (2H, s), 5.67 (2H, d, J=46.7 Hz), 6.97-7.05 (2H, m), 7.10-7.30 (2H, m), 7.37-7.45 (1H, m), 7.78 (1H, dt, J=7.2, 1.8 Hz).

ESI (LC/MS positive mode) m/z: 482 (M+H).

Compound 1j-1-1-2F

Dimethylcarbamic acid 3-{3-(methylaminosulfonyl)aminobenzyl}-4-fluoromethyl-2-oxo-2H-1-benzopyran-7-yl ester

[Chemical Formula 99]

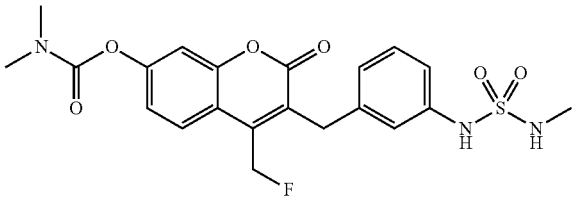

The title compound was synthesized under the same conditions as in the manufacturing example for compound 1j-1-4-2F, except that compound 1h-1-1F was used instead of compound 1h-1-4F.

$^1$H NMR (270 MHz, DMSO-d$_6$) δ (ppm): 2.42 (3H, d, J=5.1 Hz), 2.93 (3H, s), 3.07 (3H, s), 4.02 (2H, brs), 5.84 (2H, d, J=46.2 Hz), 6.84 (1H, brd, J=7.7 Hz), 7.00 (1H, brs), 7.02 (1H, d, J=7.7 Hz), 7.10-7.30 (3H, m), 7.31 (1H, d, J=2.3 Hz), 7.91 (1H, dd, J=8.7, 2.3 Hz), 9.56 (1H, brs).

ESI (LC/MS positive mode) m/z: 464 (M+H).

Compound 1j-1-2-2F

Dimethylcarbamic acid 3-{3-(methylaminosulfonyl)aminobenzyl}-6-fluoro-4-fluoromethyl-2-oxo-2H-1-benzopyran-7-yl ester

[Chemical Formula 100]

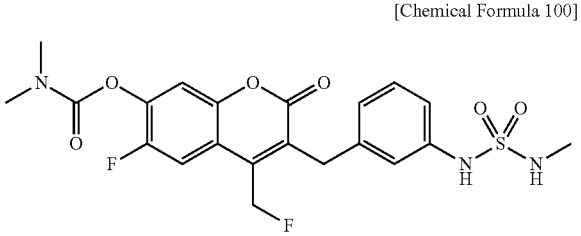

The title compound was synthesized under the same conditions as in the manufacturing example for compound 1j-1-4-2F, except that compound 1h-1-2F was used instead of compound 1h-1-4F.

$^1$H NMR (270 MHz, DMSO-d$_6$) δ (ppm): 2.42 (1H, d, J=5.1 Hz), 2.94 (3H, s), 3.09 (3H, s), 4.03 (2H, brs), 5.83 (2H, d, J=46.3 Hz), 6.84 (1H, d, J=7.7 Hz), 7.00 (1H, s), 7.02 (1H, brd, J=7.7 Hz), 7.18 (1H, t, J=7.7 Hz), 7.23 (1H, q, J=5.1 Hz), 7.54 (1H, d, J=6.8 Hz), 7.89 (1H, dd, J=11.9, 2.3 Hz), 9.55 (1H, brs).

ESI (LC/MS positive mode) m/z: 482 (M+H).

Compound 1j-1-3-2F

Dimethylcarbamic acid 6-chloro-4-fluoromethyl-3-{3-(methylaminosulfonyl)aminobenzyl}-2-oxo-2H-1-benzopyran-7-yl ester

[Chemical Formula 101]

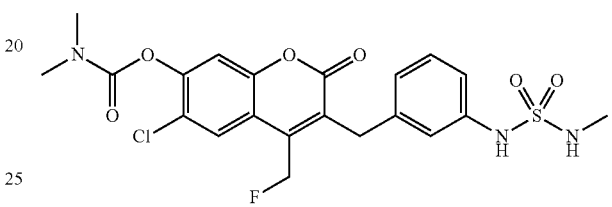

The title compound was synthesized under the same conditions as in the manufacturing example for compound 1j-1-4-2F, except that compound 1h-1-3F was used instead of compound 1h-1-4F.

$^1$H NMR (DMSO-d$_6$, 270 MHz) δ (ppm): 9.57 (brs, 1H), 8.07 (s, 1H), 7.56 (s, 1H), 7.24 (m, 1H), 7.17 (d, J=7.9 Hz, 1H), 7.04 (d, J=9.1 Hz, 1H), 7.00 (s, 1H), 6.84 (d, J=7.3 Hz, 1H), 5.86 (d, J=46.2 Hz, 2H), 4.04 (s, 2H), 3.11 (s, 3H), 2.95 (s, 3H), 2.42 (d, J=4.8 Hz, 3H).

ESIMS m/z: 498 (M+H).

Compound 1j-1-3-2FNa

Dimethylcarbamic acid 3-{3-(methylaminosulfonyl)aminobenzyl}-6-chloro-4-fluoromethyl-2-oxo-2H-1-benzopyran-7-yl ester sodium salt

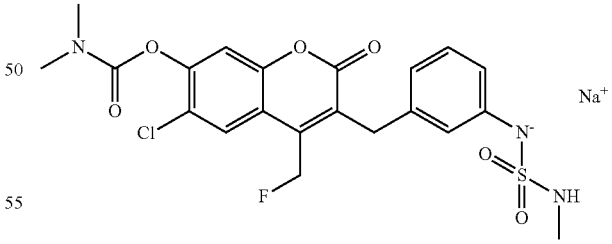

The title compound was synthesized under the same conditions as in the manufacturing example for compound 1j-1-5-1Na, except that compound 1j-1-3-2F was used instead of compound 1j-1-5-1.

$^1$H NMR (DMSO-d$_6$, 270 MHz) δ (ppm): 2.29 (3H, s), 2.95 (3H, s), 3.11 (3H, s), 3.90 (2H, s), 5.84 (1H, d, J=46.2 Hz), 6.31 (1H, brd, J=7.3 Hz), 6.65 (1H, brs), 6.76 (1H, brd, J=7.3 Hz), 6.84 (1H, t, J=7.3 Hz), 7.53 (1H, s), 8.02 (1H, s).

ESI (LC/MS positive mode) m/z: 498 (M+2H−Na).

Compound 1j-1-3-2FK

Dimethylcarbamic acid 3-{3-methylaminosulfonyl)aminobenzyl}-6-chloro-4-fluoromethyl-2-oxo-2H-1-benzopyran-7-yl ester potassium salt

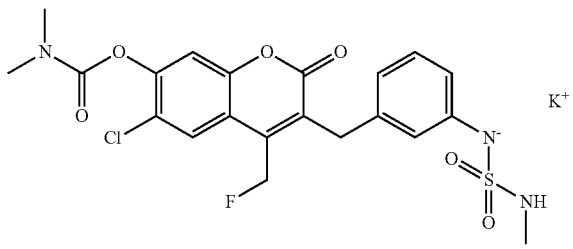

The title compound was synthesized under the same conditions as in the manufacturing example for compound 1j-1-5-1Na, except that compound 1j-1-3-2F was used instead of compound 1j-1-5-1, and that KOH was used instead of NaOH.

$^1$H NMR (DMSO-d$_6$, 270 MHz) δ (ppm): 2.29 (3H, s), 2.95 (3H, s), 3.11 (3H, s), 3.90 (2H, s), 5.84 (1H, d, J=46.2 Hz), 6.31 (1H, brd, J=7.3 Hz), 6.65 (1H, brs), 6.76 (1H, brd, J=7.3 Hz), 6.84 (1H, t, J=7.3 Hz), 7.53 (1H, s), 8.02 (1H, s).

ESI (LC/MS positive mode) m/z: 498 (M+2H−K).

Compound 1j-1-3-2OH

Dimethylcarbamic acid 6-chloro-4-(2-hydroxyethyl)-3-{3-(methylaminosulfonyl)aminobenzyl}-2-oxo-2H-1-benzopyran-7-yl ester

[Chemical Formula 102]

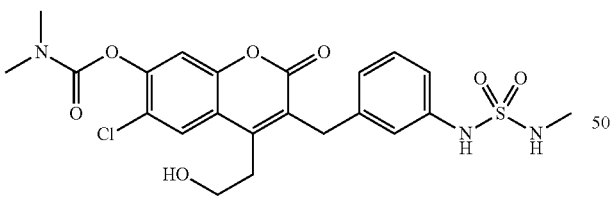

The title compound was synthesized under the same conditions as in the manufacturing example for compound 1j-1-4-2F, except that compound 7d-1-3OH was used instead of compound 1h-1-4F.

$^1$H NMR (DMSO-d$_6$, 270 MHz) δ (ppm): 8.07 (s, 1H), 7.51 (s, 1H), 7.23 (m, 1H), 7.16 (d, J=7.9 Hz, 1H), 7.03 (d, J=9.1 Hz, 1H), 6.98 (s, 1H), 6.84 (d, J=7.3 Hz, 1H), 4.89 (m, 1H), 3.98 (s, 2H), 3.60 (m, 2H), 3.11 (s, 3H), 3.00 (m, 2H), 2.95 (s, 3H), 2.42 (d, J=4.8 Hz, 3H).

ESIMS m/z: 510 (M+H).

Compound 1j-1-1-2OH

Dimethylcarbamic acid 4-(2-hydroxyethyl)-3-{3-(methylaminosulfonyl)aminobenzyl}-2-oxo-2H-1-benzopyran-7-yl ester

[Chemical Formula 103]

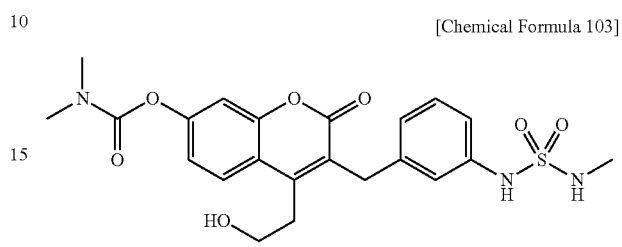

Introduction of hydroxymethyl group was performed for compound 1g-1-1 under the same conditions as in the manufacturing example for compound 7c-1-3OH (to yield compound 7c-1-1OH), and reduction of nitro group was performed under the same conditions as in the manufacturing example for compound 1h-1-5 (to yield compound 7d-1-1OH). Further, sulfamidation was performed under the same conditions as in the manufacturing example for compound 1j-1-4-2F to yield the title compound.

$^1$H NMR (CDCl$_3$, 270 MHz) δ (ppm): 7.62 (d, J=8.4 Hz, 1H), 7.26 (s, 1H), 7.20-6.80 (m, 5H), 5.25 (d, J=5.3 Hz, 1H), 4.00 (s, 2H), 3.58 (m, 2H), 3.10 (s, 3H), 3.05 (m, 2H), 3.02 (s, 3H), 2.60 (d, J=4.9 Hz, 3H), 1.79 (s, 1H).

ESIMS m/z: 476 (M+H).

Compound 1j-1-3-2CO

Dimethylcarbamic acid 6-chloro-3-{3-(methylaminosulfonyl)aminobenzyl}-2-oxo-4-(2-oxopropyl)-2H-1-benzopyran-7-yl ester

[Chemical Formula 104]

The title compound was synthesized under the same conditions as in the manufacturing example for compound 1j-1-4-2F, except that compound 7g-1-3CO was used instead of compound 1h-1-4F.

$^1$H NMR (DMSO-d$_6$, 270 MHz) δ (ppm): 9.56 (s, 1H), 7.91 (s, 1H), 7.51 (s, 1H), 7.22 (q, J=5.1 Hz, 1H), 7.15 (t, J=8.1 Hz, 1H), 7.02 (d, J=8.0 Hz, 1H), 6.97 (s, 1H), 6.80 (d, J=8.0 Hz, 1H), 4.30 (s, 2H), 3.91 (s, 2H), 3.10 (s, 3H), 2.95 (s, 3H), 2.42 (d, J=4.8 Hz, 3H), 2.22 (s, 3H). ESIMS m/z: 522 (M+H).

Compound 1j-1-3-2MeOH

Dimethylcarbamic acid 6-chloro-4-(2-hydroxypropyl)-3-{3-(methylaminosulfonyl)aminobenzyl}-2-oxo-2H-1-benzopyran-7-yl ester

[Chemical Formula 105]

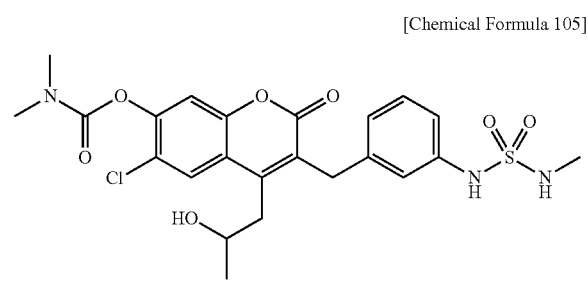

Reduction of nitro group was performed for dimethylcarbamic acid 6-chloro-4-(2-hydroxypropyl)-3-(3-nitrobenzyl)-2-oxo-2H-1-benzopyran-7-yl ester (compound 7c-1-3MeOH) under the same conditions as in the manufacturing example for compound 1h-1-5 (to yield compound 7d-1-3MeOH), and sulfamidation was then performed under the same condition as in the manufacturing example for compound 1j-1-4-2F to yield the title compound.

$^1$H NMR (DMSO-d$_6$, 270 MHz) δ (ppm): 9.54 (s, 1H), 8.07 (s, 1H), 7.49 (s, 1H), 7.24 (q, J=5.1 Hz, 1H), 7.17 (t, J=8.1 Hz, 1H), 7.03 (d, J=8.0 Hz, 1H), 6.97 (s, 1H), 6.82 (d, J=8.0 Hz, 1H), 4.87 (d, J=5.4 Hz, 1H), 4.02 (d, J=14.8 Hz, 1H), 3.98 (d, J=14.8 Hz, 1H), 3.85 (m, 1H), 3.10 (s, 3H), 3.00 (m, 2H), 2.95 (s, 3H), 2.42 (d, J=4.8 Hz, 3H), 1.21 (d, J=5.5 Hz, 3H).

ESIMS m/z: 524 (M+H).

Compound 1j-1-3-2COOMe

{3-(3-(Methylaminosulfonyl)aminobenzyl)-7-dimethylcarbamoyloxy-2-oxo-2H-1-benzopyran-4-yl}acetic acid methyl ester

[Chemical Formula 106]

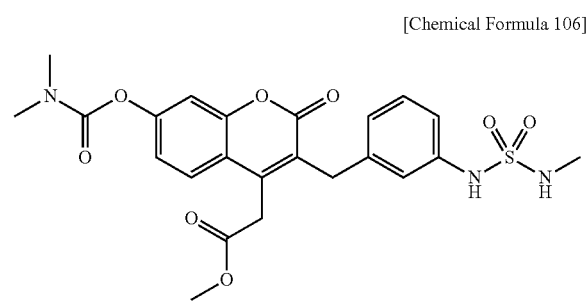

Reduction of nitro group was performed for {3-(3-nitrobenzyl)-7-dimethylcarbamoyloxy-2-oxo-2H-1-benzopyran-4-yl}acetic acid methyl ester (compound 7f-1-1COOMe) under the same conditions as in the manufacturing example for compound 1h-1-5 (to yield compound 7g-1-1COOMe), and sulfamidation was then performed under the same condition as in the manufacturing example for compound 1j-1-4-2F to yield the title compound.

$^1$H NMR (DMSO-d$_6$, 270 MHz) δ (ppm): 7.76 (d, J=8.7 Hz, 1H), 7.29 (d, J=2.5 Hz, 1H), 7.23-7.13 (m, 3H), 7.03 (d, J=8.1 Hz, 1H), 6.98 (s, 1H), 6.81 (d, J=7.6 Hz, 1H), 4.10 (s, 2H), 3.95 (s, 2H), 3.52 (s, 2H), 3.07 (s, 3H), 2.93 (s, 2H), 2.43 (d, J=4.8 Hz, 3H).

ESIMS m/z: 504 (M+H).

Compound 1j-1-3-2CONH2

Dimethylcarbamic acid 4-carbamoylmethyl-6-chloro-3-(3-(methylaminosulfonyl)aminobenzyl)-2-oxo-2H-1-benzopyran-7-yl ester

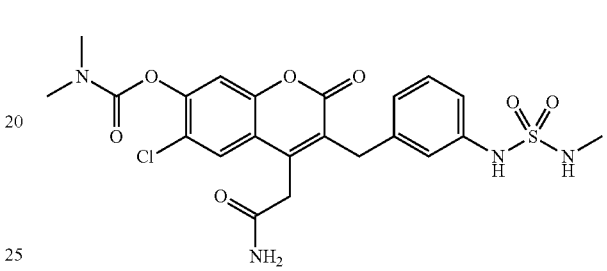

The title compound was synthesized under the same conditions as in the manufacturing example for compound 1j-1-5-2, except that compound 7g-1-3CONH2 was used instead of compound 1h-1-5.

$^1$H NMR (270 MHz, DMSO-d$_6$+CD$_3$OD (1:4)) δ (ppm): 8.57 (s, $^1$H), 8.07 (s, 1H), 7.89 (t, 1H, J=8.1 Hz), 7.76-7.73 (m, 2H), 7.65 (d, 1H, J=5.4 Hz), 4.72 (s, 2H), 4.63 (s, 2H), 3.81 (s, 3H), 3.70 (s, 3H), 3.17 (s, 3H).

ESIMS adz: 523 (M+H).

Compound 1j-1-3-2CONMe2

Dimethylcarbamic acid 6-chloro-4-dimethylcarbamoylmethyl-3-(3-(methylaminosulfonyl)aminobenzyl)-2-oxo-2H-1-benzopyran-7-yl ester

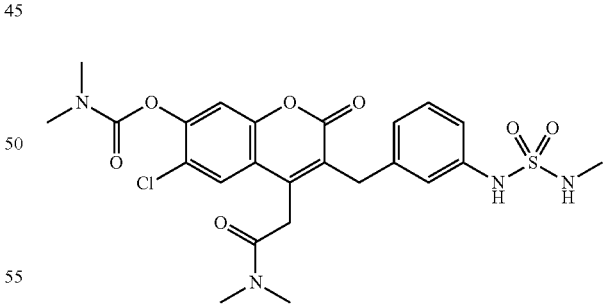

The title compound was synthesized under the same conditions as in the manufacturing example for compound 1j-1-5-2, except that compound 7g-1-3CONMe2 was used instead of compound 1h-1-5.

$^1$H NMR (270 MHz, CDCl$_3$) δ (ppm): 7.32 (s, 1H), 7.30-7.15 (m, 2H), 6.99 (s, 1H), 6.80 (d, 1H, J=7.2 Hz), 6.45 (s, 1H), 6.02 (m, 1H), 3.95 (s, 2H), 3.91 (s, 2H), 3.19 (s, 3H), 3.12 (s, 3H), 3.07 (s, 3H), 2.98 (s, 3H), 2.56 (s, 3H).

ESIMS m/z: 551 (M+H).

Compound 1j-1-37-2

Dimethylcarbamic acid 3-(3-(methylaminosulfonyl)amino-6-fluorobenzyl)-4-methyl-2-oxo-2H-1-benzopyran-7-yl ester

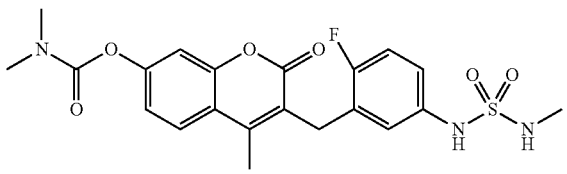

The title compound was synthesized under the same conditions as in the manufacturing example for compound 1j-1-36-1, except that compound 1j-1-1-2 was used instead of compound 1j-1-1-1.

$^1$H-NMR (DMSO-$d_6$, 270 MHz) δ (ppm): 2.37 (3H, s), 2.44 (3H, s), 2.93 (3H, s), 3.02 (3H, s), 3.93 (2H, s), 6.87 (1H, m), 7.04-7.22 (4H, m), 7.27 (1H, br), 7.88 (1H, d, J=10.8 Hz), 9.40 (1H, br).

ESI (LC/MS positive mode) m/z: 464 (M+H).

Compound 1j-1-65-2

Dimethylcarbamic acid 3-(3-(methylaminosulfonyl)amino-6-fluorobenzyl)-4,6-dimethyl-2-oxo-2H-1-benzopyran-7-yl ester

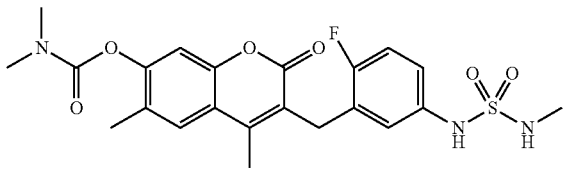

The title compound was synthesized under the same conditions as in the manufacturing example for compound 1j-1-36-1, except that compound 1j-1-8-2 was used instead of compound 1j-1-1-1.

$^1$H-NMR (CD$_3$OD 270 MHz) δ (ppm): 2.30 (3H, s), 2.49 (3H, s), 2.52 (3H, s), 3.02 (3H, s), 3.17 (3H, s), 4.03 (2H, s), 6.99-7.04 (2H, m), 7.22 (1H, m), 7.14 (1H, s), 7.71 (1H, s).

ESI (LC/MS positive mode) m/z: 478 (M+H).

Compound 1j-1-39-2

Dimethylcarbamic acid 3-(3-(methylaminosulfonyl)aminobenzyl)-4-methyl-2-oxo-6-trimethylsilanyl-ethynyl-2H-1-benzopyran-7-yl ester

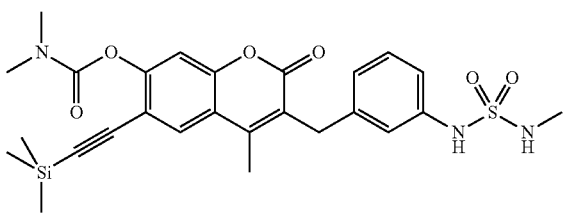

The title compound was synthesized under the same conditions as in the manufacturing example for compound 1j-1-5-2, except that compound 1h-1-39 was used instead of compound 1h-1-5.

$^1$H-NMR (DMSO-$d_6$, 270 MHz) δ (ppm): 0.24 (9H, s), 2.43 (3H, d, J=4.6 Hz), 2.47 (3H, s), 2.95 (3H, s), 3.11 (3H, s), 3.94 (2H, s), 6.63 (1H, d, J=6.9 Hz), 6.74-6.82 (3H, m), 6.89-7.03 (2H, m), 7.15 (1H, s), 7.70 (1H, s).

ESI (LC/MS positive mode) m/z: 542 (M+H).

Compound 1j-1-40-2

Dimethylcarbamic acid 3-(3-(methylaminosulfonyl)aminobenzyl)-6-ethynyl-4-methyl-2-oxo-2H-1-benzopyran-7-yl ester

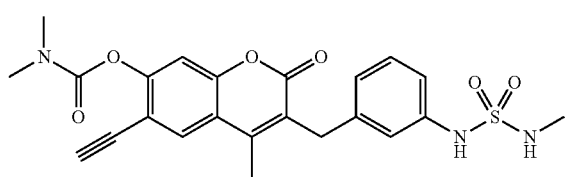

The title compound was synthesized under the same conditions as in the manufacturing example for compound 1j-1-5-2, except that compound 1h-1-40 was used instead of compound 1h-1-5.

$^1$H-NMR (DMSO-$d_6$, 270 MHz) δ (ppm): 2.42 (3H, d, J=4.6 Hz), 2.46 (3H, s), 2.94 (3H, s), 3.09 (3H, s), 3.93 (2H, s), 4.45 (1H, s), 6.86 (1H, d, J=7.6 Hz), 6.93-7.10 (2H, m), 7.07-7.35 (2H, m), 7.38 (1H, s), 7.99 (1H, s), 9.54 (1H, brs).

ESI (LC/MS positive mode) m/z: 470 (M+H).

Compound 1j-1-72-2

Dimethylcarbamic acid 3-(3-(methylaminosulfonyl)aminobenzyl)-4-methyl-2-oxo-2H-pyrano[2,3-b]pyridin-7-yl ester

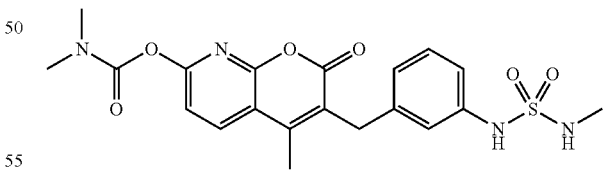

The compound dimethylcarbamic acid 3-(3-aminobenzyl)-4-methyl-2-oxo-2H-pyrano[2,3-b]pyridin-7-yl ester (compound 1h-1-72) was synthesized under the same conditions as in the manufacturing example for compound 1h-1-5, except that compound 1g-1-72 was used instead of compound 1g-1-5.

The title compound was synthesized under the same conditions as in the manufacturing example for compound 1j-1-5-2, except that compound 1h-1-72 was used instead of compound 1h-1-5.

¹H-NMR (DMSO-d₆, 270 MHz) δ (ppm): 2.42 (3H, s), 2.47 (3H, s), 2.95 (3H, s), 3.06 (3H, s), 3.94 (2H, s), 6.87 (1H, d, J=7.3 Hz), 7.01 (1H, s), 7.02 (1H, d, J=7.1 Hz), 7.14-7.20 (2H, m), 7.27 (1H, d, J=8.2 Hz), 8.43 (1H, d, J=8.2 Hz), 9.53 (1H, brs).

ESI (LC/MS positive mode) m/z: 447 (M+H).

Compound 1j-1c-1-2

3-{3-(Methylaminosulfonyl)aminobenzyl}-7-(2-fluoroethoxy)-4-methyl-2-oxo-2H-1-benzopyran

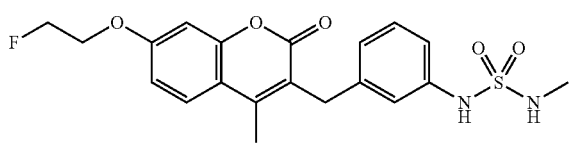

The title compound was synthesized under the same conditions as in the manufacturing example for compound 1j-1-5-2, except that compound 1h-1c-1 was used instead of compound 1h-1-5.

¹H-NMR (270 MHz, DMSO-d₆) δ (ppm): 2.41 (3H, s), 3.90 (2H, s), 4.28-4.33 (1H, m), 4.39-4.44 (1H, m), 4.67-4.71 (1H, m), 4.84-4.88 (1H, m), 6.64 (1H, d, J=7.6 Hz), 6.99-7.06 (4H, m), 7.16 (1H, dd, J=8.1, 7.8 Hz), 7.21 (1H, br.s), 7.77 (1H, d, J=8.6 Hz), 9.51 (1H, br.s).

One of the CH₃ peaks was overlapped with the DMSO peak.

ESI (LC-MS positive mode) m/z: 421 (M+H).

Compound 1j-1d-1-2

Pyrrolidine-1-carboxylic acid 3-(3-(methylaminosulfonyl)aminobenzyl)-4-methyl-2-oxo-2H-1-benzopyran-7-yl ester

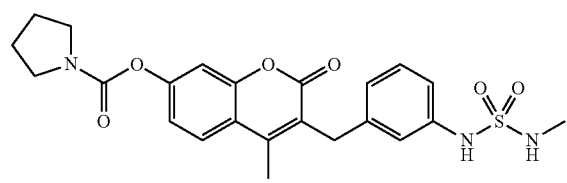

The title compound was synthesized under the same conditions as in the manufacturing example for compound 1j-1-5-2, except that compound 1h-1d-1 was used instead of compound 1h-1-5.

¹H-NMR (DMSO-d₆, 270 MHz) δ (ppm): 1.84-1.94 (4H, m), 2.42 (3H, d, J=3.3 Hz), 2.46 (3H, s), 3.36 (2H, t, J=6.6 Hz), 3.52 (2H, t, J=6.6 Hz), 3.93 (2H, s), 6.86 (1H, d, J=7.8 Hz), 6.98-7.05 (2H, m), 7.13-7.23 (3H, m), 7.26 (1H, d, J=2.3 Hz), 7.86 (1H, d, J=8.9 Hz), 9.53 (1H, brs).

ESI (LC/MS positive mode) m/z: 472 (M+H).

Compound 1j-2-4-2

3-{2-Fluoro-3-(methylaminosulfonyl)aminobenzyl}-4-methyl-7-(pyrimidin-2-yloxy)-2-oxo-2H-1-benzopyran

[Chemical Formula 107]

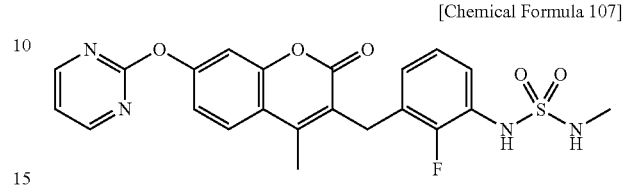

The title compound was synthesized under the same conditions as in the manufacturing example for compound 1j-1-5-2, except that compound 1h-2-4 was used instead of compound 1h-1-5.

¹H NMR (270 MHz, DMSO-d₆) δ (ppm): 2.45 (3H, s), 3.99 (2H, s), 6.83-6.92 (1H, m), 6.97-7.06 (1H, m), 7.17 (1H, br.s), 7.34-7.40 (4H, m), 7.91 (1H, d, J=8.4 Hz), 8.69 (2H, dd, J=4.8, 1.2 Hz), 9.38 (1H, br.s).

One of the CH₃ peaks was overlapped with the DMSO peak.

ESI (LC/MS positive mode) m/z: 471 (M+H).

Compound 1j-2-4-2Na

3-{2-Fluoro-3-(methylaminosulfonyl)aminobenzyl}-4-methyl-7-(pyrimidin-2-yloxy)-2-oxo-2H-1-benzopyran sodium salt

[Chemical Formula 108]

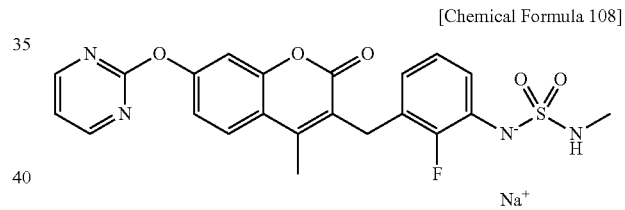

The title compound was synthesized under the same conditions as in the manufacturing example for compound 1j-1-5-1Na, except that compound 1j-2-4-2 was used instead of compound 1j-1-5-1.

¹H NMR (270 MHz, DMSO-d₆) δ (ppm): 2.33 (3H, d, J=3.3 Hz), 2.43 (3H, s), 3.89 (2H, s), 6.10-6.19 (1H, m), 6.58-6.66 (1H, m), 7.17 (1H, ddd, J=8.3, 1.5 Hz, J_{HF}=8.3 Hz), 7.25 (1H, dd, J=8.7, 2.3 Hz), 7.33 (1H, t, J=4.8 Hz), 7.37 (1H, d, J=2.3 Hz), 7.88 (1H, d, J=8.7 Hz), 8.69 (2H, d, J=4.8 Hz).

ESI (LC/MS positive mode) m/z: 471 (M+2H−Na).

Compound 1j-2-4-2K

3-{2-Fluoro-3-(methylaminosulfonyl)aminobenzyl}-4-methyl-7-(pyrimidin-2-yloxy)-2-oxo-2H-1-benzopyran potassium salt

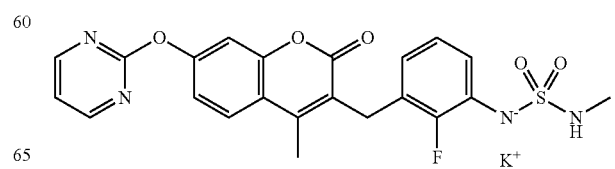

The title compound was synthesized under the same conditions as in the manufacturing example for compound 1j-1-5-1Na, except that compound 1j-2-4-2 was used instead of compound 1j-1-5-1, and that KOH was used instead of NaOH.

$^1$H NMR (270 MHz, DMSO-d$_6$) δ (ppm): 8.69 (d, 2H, J=4.8 Hz), 7.88 (d, 1H, J=8.7 Hz), 7.36 (d, 1H, J=2.3 Hz), 7.33 (t, 1H, J=4.8 Hz), 7.25 (dd, 1H, J=8.7, 2.3 Hz), 7.16 (td, 1H, J=8.5, 1.4 Hz), 6.59 (t, 1H, J=7.8 Hz), 6.10 (t, 1H, J=6.3 Hz), 4.76 (q, 1H, J=5.8 Hz), 3.88 (s, 2H), 2.43 (s, 3H), 2.32 (d, 3H, J=5.6 Hz).

ESI (LC-MS positive mode) m/z: 471 (M+2H−K).

Compound 1j-2-4S1-2

3-{2-Fluoro-3-methylaminosulfonyl)aminobenzyl}-4-methyl-7-(pyrimidin-2-ylthio)-2-oxo-2H-1-benzopyran

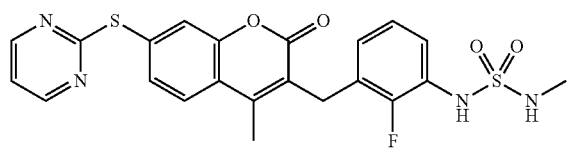

Compound 1h-2-4S1 was synthesized under the same conditions as in the manufacturing example for compound 1h-2-4 (synthesis scheme 2), except that compound 5d-2-4S1 was used instead of compound 4a-0-4.

The title compound was synthesized under the same conditions as in the manufacturing example for compound 1j-2-16-2, except that compound 1h-2-4S1 was used instead of compound 1h-2-16.

$^1$H-NMR (270 MHz, DMSO-d$_6$) δ (ppm): 2.48 (3H, s), 4.01 (2H, s), 6.83-6.92 (1H, m), 6.98-7.05 (1H, m), 7.16 (1H, brs), 7.25-7.35 (2H, m), 7.60 (1H, d, J=8.5 Hz), 7.70-7.74 (1H, m), 7.92 (1H, d, J=8.5 Hz), 8.64 (2H, d, J=4.8 Hz).

ESI (LC-MS positive mode) m/z: 487 (M+H).

Compound 1j-2-4S2-2

3-{2-Fluoro-3-(methylaminosulfonyl)aminobenzyl}-4-methyl-7-(pyrimidin-2-yloxy)-2-oxo-2H-1-benzothiopyran

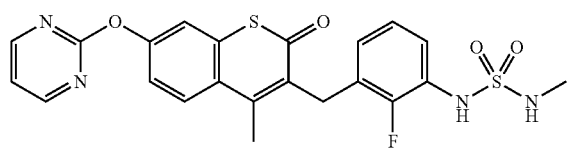

The title compound was synthesized under the same conditions as in the manufacturing example for compound 1j-2-16-2, except that compound 1h-2-4S2 was used instead of compound 1h-2-16.

$^1$H-NMR (270 MHz, DMSO-d$_6$) δ (ppm): 2.54 (3H, s), 4.08 (2H, s), 6.70 (1H, dd, J=7.3 Hz, J$_{HF}$=7.3 Hz), 6.99 (1H, dd, J=7.9 Hz, J$_{HF}$=7.9 Hz), 7.14 (1H, brs), 7.28 (1H, dd, J=8.0, 8.0 Hz), 7.34 (1H, dt, J=4.9, 1.3 Hz), 7.40 (1H, dd, J=8.7, 2.2 Hz), 7.64 (1H, d, J=2.4 Hz), 8.16 (1H, d, J=8.7 Hz), 8.70 (2H, dd, J=4.9, 1.2 Hz), 9.44 (1H, brs).

One of the CH$_3$ peaks was overlapped with the DMSO peak.

ESI (LC-MS positive mode) m/z: 487 (M+H).

Compound 1j-2-5-2

3-{2-Fluoro-3-(methylaminosulfonyl)aminobenzyl}-4-methyl-7-(pyrimidin-2-yloxy)-6-fluoro-2-oxo-2H-1-benzopyran

[Chemical Formula 109]

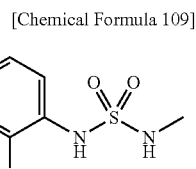

The title compound was synthesized under the same conditions as in the manufacturing example for compound 1j-1-5-2, except that compound 1h-2-5 was used instead of compound 1h-1-5.

$^1$H NMR (CD$_3$OD, 270 MHz) δ (ppm): 2.40 (3H, s), 2.68 (3H, s), 4.09 (2H, s), 6.78-7.04 (3H, m), 7.17-7.39 (4H, m), 7.70-7.89 (1H, m), 8.61-8.63 (2H, m).

ESI (LC/MS positive mode) m/z: 489 (M+H).

Compound 1j-2-6-2

3-{2-Methyl-3-(methylaminosulfonyl)aminobenzyl}-4-methyl-7-(pyrimidin-2-yloxy)-2-oxo-2H-1-benzopyran

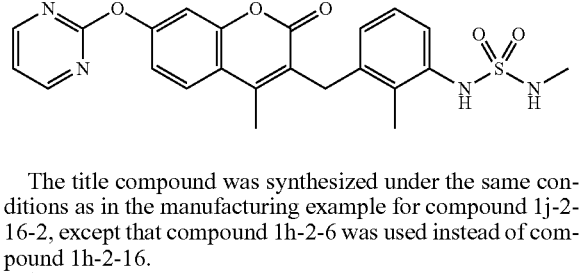

The title compound was synthesized under the same conditions as in the manufacturing example for compound 1j-2-16-2, except that compound 1h-2-6 was used instead of compound 1h-2-16.

$^1$H NMR (Bruker, 300 MHz, CDCl$_3$) δ (ppm): 8.61 (2H, d, J=4.6 Hz), 7.72 (1H, d, J=8.4 Hz), 7.32 (1H, d, J=7.6 Hz), 7.27 (1H, d, J=3.1 Hz), 7.21 (1H, dd, J=2.3, 8.4 Hz), 7.13 (1H, t, J=5.0 Hz), 7.07 (1H, t, J=7.8 Hz), 6.73 (1H, d, J=7.6 Hz), 6.17 (1H, s), 4.36 (1H, q), 4.03 (2H, s), 2.79 (3H, d, J=5.3 Hz), 2.41 (3H, s), 2.38 (3H, s).

MS (Micromass, Quattromicro, ESI−) m/z: 465.08 (M−H).

Compound 1j-2-4-2F

3-{2-Fluoro-3-(methylaminosulfonyl)aminobenzyl}-4-fluoromethyl-7-(pyrimidin-2-yloxy)-2-oxo-2H-1-benzopyran

[Chemical Formula 110]

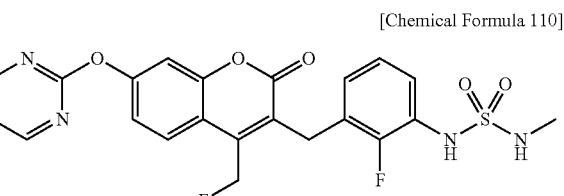

The title compound was synthesized under the same conditions as in the manufacturing example for compound 1j-1-5-2, except that compound 1h-2-4F was used instead of compound 1h-1-5.

$^1$H NMR (DMSO-d$_6$, 270 MHz) δ (ppm): 9.36 (s, 1H), 8.68 (d, J=4.9 Hz, 2H), 7.96 (dd, J=8.9, 2.2 Hz, 1H), 7.42 (d, J=2.4 Hz, 1H), 7.36-7.18 (m, 3H), 7.02 (t, J=7.0 Hz, 1H), 6.88 (t, J=7.0 Hz, 1H), 5.86 (d, J=46.2 Hz, 2H), 4.07 (s, 2H), 2.51 (d, J=5.1 Hz, 3H).

ESIMS m/z: 489 (M+H).

Compound 1j-2-4-2FNa

3-{2-Fluoro-3-(methylaminosulfonyl)aminobenzyl}-4-fluoromethyl-7-(pyrimidin-2-yloxy)-2-oxo-2H-1-benzopyran sodium salt

[Chemical Formula 111]

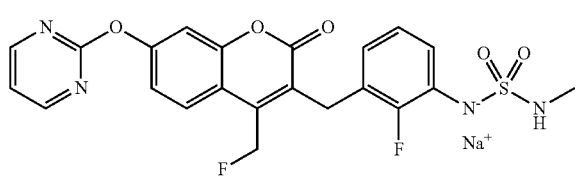

The title compound was synthesized under the same conditions as in the manufacturing example for compound 1j-1-5-1Na, except that compound 1j-2-4-2F was used instead of compound 1j-1-5-1.

$^1$H NMR (DMSO-d$_6$, 270 MHz) δ (ppm): 8.68 (d, J=4.9 Hz, 2H), 7.92 (dd, J=8.9, 2.7 Hz, 1H), 7.40 (d, J=2.2 Hz, 1H), 7.32 (t, J=4.7 Hz, 1H), 7.28 (dd, J=8.8, 2.3 Hz, 1H), 7.15 (t, J=8.9 Hz, 1H), 6.58 (t, J=7.7 Hz, 1H), 6.09 (t, J=7.8 Hz, 1H), 5.81 (d, J=46.2 Hz, 2H), 4.71 (q, J=5.7 Hz, 1H), 3.94 (s, 2H), 2.30 (d, J=5.7 Hz, 3H).

ESIMS m/z: 489 (M+2H−Na).

Compound 1j-2-4-2FK

3-{2-Fluoro-3-(methylaminosulfonyl)aminobenzyl}-4-fluoromethyl-7-(pyrimidin-2-yloxy)-2-oxo-2H-1-benzopyran potassium salt

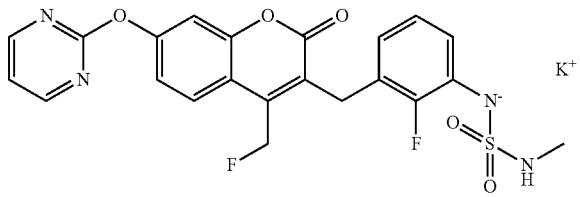

The title compound was synthesized under the same conditions as in the manufacturing example for compound 1j-1-5-1Na, except that compound 1j-2-4-2F was used instead of compound 1j-1-5-1, and that KOH was used instead of NaOH.

$^1$H NMR (270 MHz, DMSO-d$_6$) δ (ppm): 8.69 (d, 2H, J=4.8 Hz), 7.94 (dd, 1H, J=8.8, 2.2 Hz), 7.42 (d, 1H, J=2.3 Hz), 7.34 (t, 1H, J=4.7 Hz), 7.30 (dd, 1H, J=8.8, 2.3 Hz), 7.18 (t, 1H, J=8.9 Hz), 6.62 (t, 1H, J=7.7 Hz), 6.13 (t, 1H, J=7.8 Hz), 5.92 (d, 2H, J=46.2 Hz), 4.80 (q, 1H, J=5.7 Hz), 3.96 (s, 2H), 2.33 (d, 3H, J=5.7 Hz).

Compound 1j-2-10-2

3-{2-(Methylaminosulfonyl)aminopyridin-4-ylmethyl}-4-methyl-7-(pyrimidin-2-yloxy)-2-oxo-2H-1-benzopyran

[Chemical Formula 112]

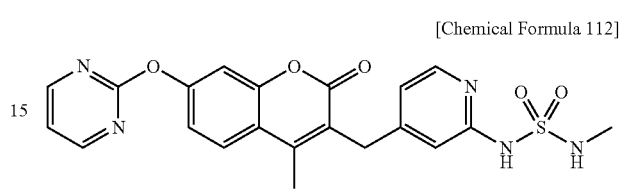

The title compound was synthesized under the same conditions as in the manufacturing example for compound 1j-1-5-2, except that compound 1h-2-10 was used instead of compound 1h-1-5.

$^1$H NMR (CDCl$_3$, 270 MHz) δ (ppm): 2.53 (3H, s), 2.82 (3H, s), 4.18 (2H, s), 7.10-7.35 (4H, m), 7.70-7.80 (2H, m), 8.01 (1H, d, J=6.2 Hz), 8.61 (2H, brs).

ESI (LC/MS positive mode) m/z: 454 (M+H).

Compound 1j-2-12-2

3-{2-(Methylaminosulfonyl)aminopyridin-4-ylmethyl}-4-methyl-7-(pyrimidin-2-yloxy)-6-chloro-2-oxo-2H-1-benzopyran

[Chemical Formula 113]

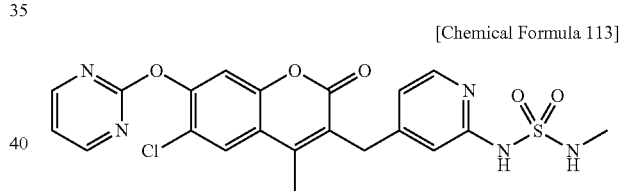

The title compound was synthesized under the same conditions as in the manufacturing example for compound 1j-1-5-2, except that compound 1h-2-12 was used instead of compound 1h-1-5.

$^1$H NMR (CD$_3$OD, 270 MHz) δ (ppm): 2.52 (3H, s), 2.64 (3H, s), 4.11 (2H, s), 7.11 (1H, d, J=6.5 Hz), 7.13 (1H, s), 7.27 (1H, dd, J=4.9 Hz), 7.37 (1H, s), 8.00 (1H, s), 8.12 (1H, d, J=6.5 Hz), 8.62 (2H, d, J=4.9 Hz).

ESI (LC/MS positive mode) m/z: 488 (M+H).

Compound 1j-2-16-2

3-{2-(Methylaminosulfonyl)amino-3-fluoropyridin-4-ylmethyl}-4-methyl-7-(pyrimidin-2-yloxy)-2-oxo-2H-1-benzopyran

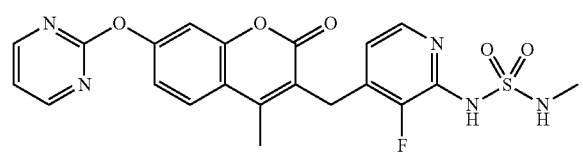

Methylamine (158 μL, 317 μmol) and DMAP (38.7 mg, 317 μmol) were added at −78° C. to a solution of sulfuryl chloride (28 μL, 340 μmol) in dichloromethane (2 mL), and the mixture was then stirred at room temperature for 2 hours to yield the corresponding sulfamoyl chloride. 3-(2-Amino-3-fluoropyridin-4-ylmethyl)-7-(pyrimidin-2-yloxy)-4-methyl-2-oxo-2H-1-benzopyran (compound 1h-2-16) (60 mg, 159 μmol), pyridine (65 μL, 795 μmol) and dichloromethane (2 mL) were added to the reaction solution, and the mixture was stirred at room temperature for 4 hours. After addition of water, the organic layer was extracted with dichloromethane. After washing with sodium hydrogen carbonate solution and saturated saline, the organic layer was dried over anhydrous magnesium sulfate, and the solvent was distilled away under reduced pressure. The resultant residue was purified by silica gel column chromatography to yield the title compound (32 mg, 43%).

$^1$H NMR (CD$_3$OD, 270 MHz) δ (ppm): 2.54 (3H, s), 2.62 (3H, s), 4.22 (2H, s), 6.84 (1H, dd, J=5.4 Hz), 7.20-7.30 (3H, m), 7.80-7.95 (2H, m), 8.63 (2H, d, J=4.9 Hz).

ESI (LC/MS positive mode) m/z: 472 (M+H).

Compound 1j-2-16-2Na 3-(2-(N-Methylsulfamoyl)amino-3-fluoropyridin-4-ylmethyl)-4-methyl-7-(pyrimidin-2-yloxy)-2-oxo-2H-1-benzopyran sodium salt

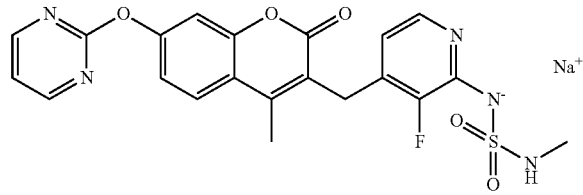

The title compound was synthesized under the same conditions as in the manufacturing example for compound 1j-1-5-1Na, except that compound 1j-2-16-2 was used instead of compound 1j-1-5-1.

$^1$H NMR (DMSO-d$_6$, 270 MHz) δ (ppm): 2.30 (3H, s), 2.46 (3H, s), 3.89 (2H, s), 5.68 (1H, brs), 6.09-6.23 (1H, m), 7.20 (1H, dd, J=2.4, 8.7 Hz), 7.34 (1H, t, J=4.8 Hz), 7.38 (1H, d, J=2.4 Hz), 7.55 (1H, d, J=5.3 Hz), 7.90 (1H, d, J=8.7 Hz), 8.69 (1H, d, J=4.8 Hz).

ESI (LC/MS positive mode) m/z: 472 (M+2H−Na).

Compound 1j-2-16-2K 3-(2-(N-Methylsulfamoyl)amino-3-fluoropyridin-4-ylmethyl)-4-methyl-7-(pyrimidin-2-yloxy)-2-oxo-2H-1-benzopyran potassium salt

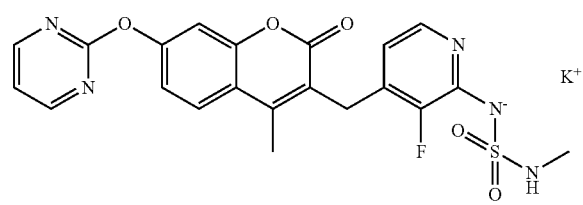

The title compound was synthesized under the same conditions as in the manufacturing example for compound 1j-1-5-1Na, except that compound 1j-2-16-2 was used instead of compound 1j-1-5-1, and that KOH was used instead of NaOH.

$^1$H NMR (DMSO-d$_6$, 270 MHz) δ (ppm): 2.36 (3H, s), 2.47 (3H, s), 3.93 (2H, s), 6.26-6.40 (1H, m), 7.27 (1H, dd, J=2.3, 8.6 Hz), 7.34 (1H, t, J=4.8 Hz), 7.39 (1H, d, =2.3 Hz), 7.64 (1H, d, J=4.8 Hz), 7.91 (1H, d, J=8.6 Hz), 8.69 (1H, d, J=4.8 Hz).

ESI (LC/MS positive mode) m/z: 472 (M+2H−K).

Compound 1j-2-16-2a

3-{2-(Ethylaminosulfonyl)amino-3-fluoropyridin-4-ylmethyl}-4-methyl-7-(pyrimidin-2-yloxy)-2-oxo-2H-1-benzopyran

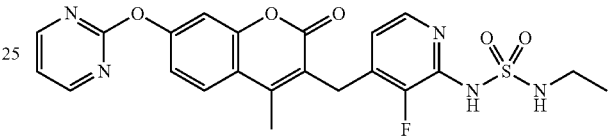

The title compound was synthesized under the same conditions as in the manufacturing example for compound 1j-2-16-2, except that ethylamine was used instead of methylamine.

$^1$H NMR (CD$_3$OD, 270 MHz) δ (ppm): 1.11 (3H, t, J=7.2 Hz), 2.54 (3H, s), 3.03 (2H, q, J=7.2 Hz), 4.12 (2H, s), 6.84 (1H, dd, J=5.4 Hz), 7.20-7.30 (3H, m), 7.80-7.95 (2H, m), 8.63 (2H, d, J=4.6 Hz).

ESI (LC/MS positive mode) m/z: 486 (M+H).

Compound 1j-2-16-2b

3-{2-(Isopropylaminosulfonyl)amino-3-fluoropyridin-4-ylmethyl}-4-methyl-7-(pyrimidin-2-yloxy)-2-oxo-2H-1-benzopyran

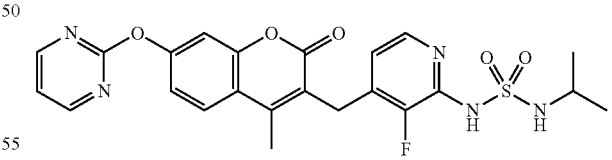

The title compound was synthesized under the same conditions as in the manufacturing example for compound 1j-2-16-2, except that isopropylamine was used instead of methylamine.

$^1$H NMR (CD$_3$OD, 270 MHz) δ (ppm): 0.85-1.30 (6H, m), 2.52 (3H, s), 3.45-4.20 (1H, m), 4.11 (2H, s), 6.82 (1H, dd, J=5.4 Hz), 7.20-7.30 (3H, m), 7.80-7.95 (2H, m), 8.63 (2H, d, J=4.6 Hz).

ESI (LC/MS positive mode) m/z: 500 (M+H).

Compound 1j-2-17-2

3-{2-(methylaminosulfonyl)amino-3-fluoropyridin-4-ylmethyl}-4-methyl-6-fluoro-7-(pyrimidin-2-yloxy)-2-oxo-2H-1-benzopyran

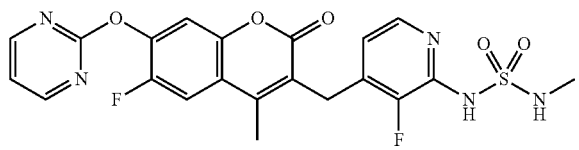

The title compound was synthesized under the same conditions as in the manufacturing example for compound 1j-2-16-2, except that compound 1h-2-17 was used instead of compound 1h-2-16.

$^1$H NMR (DMSO-d$_6$, 270 MHz) δ (ppm): 2.40-2.70 (3H, m), 4.03 (2H, s), 6.75-6.83 (1H, m), 6.97 (1H, brs), 7.38 (1H, dd, J=4.5 Hz), 7.66 (1H, d, J=6.5 Hz), 7.93 (1H, d, J=11.1 Hz), 7.90-7.95 (1H, m), 8.70 (2H, d, J=4.5), 10.36 (1H, brs).

ESI (LC/MS positive mode) m/z: 490 (M+H).

Compound 1j-2-17-2c

3-{2-(Cyclopropylaminosulfonyl)amino-3-fluoropyridin-4-ylmethyl}-4-methyl-6-fluoro-7-(pyrimidin-2-yloxy)-2-oxo-2H-1-benzopyran

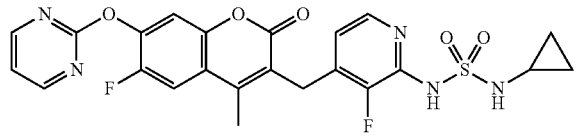

The title compound was synthesized under the same conditions as in the manufacturing example for compound 1j-2-16-2, except that compound 1h-2-17 was used instead of compound 1h-2-16, and that cyclopropylamine was used instead of methylamine.

$^1$H NMR (DMSO-d$_6$, 270 MHz) δ (ppm): 0.40-0.60 (4H, m), 2.24-2.35 (1H, m), 2.40-2.70 (3H, m), 4.02 (2H, s), 6.75-6.85 (1H, m), 7.38 (1H, dd, J=4.5 Hz), 7.66 (1H, d, J=6.5 Hz), 7.93 (1H, d, J=11.1 Hz), 7.90-7.95 (1H, m), 8.70 (2H, d, J=4.5).

ESI (LC/MS positive mode) m/z: 516 (M+H).

Compound 1j-2-18-2

3-{2-(Methylaminosulfonyl)amino-3-fluoropyridin-4-ylmethyl}-4-methyl-6-chloro-7-(pyrimidin-2-yloxy)-2-oxo-2H-1-benzopyran

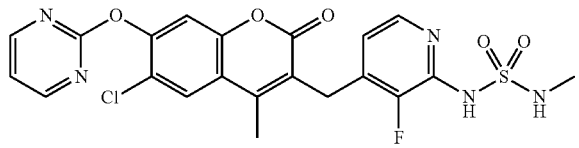

The compound 3-(2-amino-3-fluoropyridin-4-ylmethyl)-4-methyl-6-chloro-7-(pyrimidin-2-yloxy)-2-oxo-2H-1-benzopyran (compound 1h-2-18) was synthesized under the same conditions as in the manufacturing example for compound 1h-2-4 (synthesis scheme 2), except that compound 5d-0-18 was used instead of compound 4a-0-4.

The title compound was synthesized under the same conditions as in the manufacturing example for compound 1j-2-16-2, except that compound 1h-2-18 was used instead of compound 1h-2-16.

$^1$H NMR (CDCl$_3$, 270 MHz) δ (ppm): 2.47 (3H, s), 2.76 (3H, s), 4.08 (2H, s), 6.85 (1H, dd, J=5.1 Hz), 7.13 (1H, dd, J=4.9 Hz), 7.31 (1H, s), 7.73 (1H, s), 7.93 (1H, d, J=5.1 Hz), 8.61 (2H, d, J=4.9 Hz).

ESI (LC/MS positive mode) m/z: 506 (M+H).

Compound 1j-2-19-2

3-{2-(Methylaminosulfonyl)amino-3-fluoropyridin-4-ylmethyl}-4-methyl-6-methyl-7-(pyrimidin-2-yloxy)-2-oxo-2H-1-benzopyran

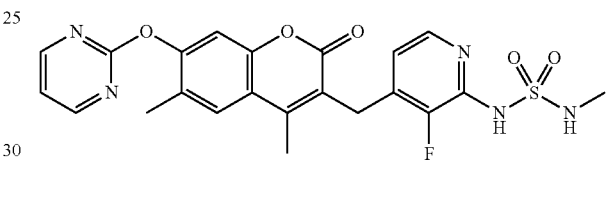

The title compound was synthesized under the same conditions as in the manufacturing example for compound 1j-2-16-2, except that compound 1h-2-19 was used instead of compound 1h-2-16.

$^1$H NMR (CD$_3$OD, 270 MHz) δ (ppm): 2.24 (3H, s), 2.53 (3H, s), 2.62 (3H, s), 4.11 (2H, s), 6.81 (1H, dd, J=5.1 Hz), 7.19 (1H, s), 7.25 (1H, t, J=4.7 Hz), 7.79 (1H, s), 7.92 (1H, d, J=5.1 Hz), 8.61 (2H, d, J=4.9 Hz).

ESI (LC/MS positive mode) m/z: 486 (M+H).

Compound 1j-2-19-2Na 3-(2-(N-Methylsulfamoyl)amino-3-fluoropyridin-4-ylmethyl)-4,6-dimethyl-7-(pyrimidin-2-yloxy)-2-oxo-2H-1-benzopyran sodium salt

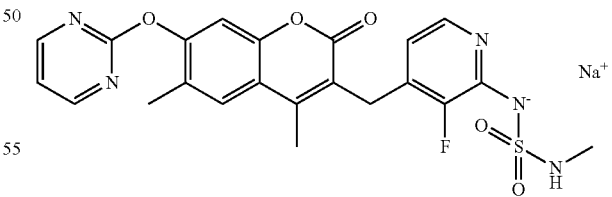

The title compound was synthesized under the same conditions as in the manufacturing example for compound 1j-1-5-1Na, except that compound 1j-2-19-2 was used instead of compound 1j-1-5-1.

$^1$H NMR (DMSO-d$_6$, 270 MHz) δ (ppm): 2.15 (3H, s), 2.30 (3H, s), 2.45 (3H, s), 3.89 (2H, s), 5.66 (1H, brs), 6.07-6.21 (1H, m), 7.29-7.33 (2H, m), 7.54 (1H, d, J=5.3 Hz), 7.82 (1H, s), 8.67 (2H, dd, J=0.9, 4.8 Hz).

ESI (LC/MS positive mode) m/z: 486 (M+2H−Na).

Compound 1j-2-19-2K 3-(2-(N-Methylsulfamoyl)amino-3-fluoropyridin-4-ylmethyl)-4,6-dimethyl-7-(pyrimidin-2-yloxy)-2-oxo-2H-1-benzopyran potassium salt

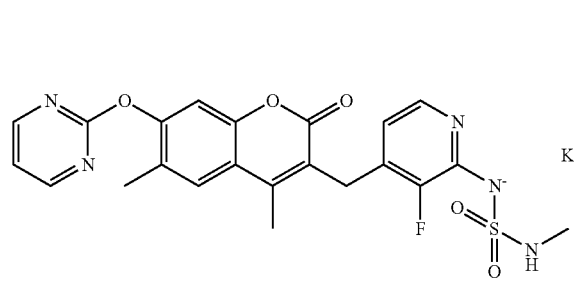

The title compound was synthesized under the same conditions as in the manufacturing example for compound 1j-1-5-1Na, except that compound 1j-2-19-2 was used instead of compound 1j-1-5-1, and that KOH was used instead of NaOH.

$^1$H NMR (DMSO-d$_6$, 270 MHz) δ (ppm): 2.15 (3H, s), 2.37 (3H, s), 2.47 (3H, s), 3.93 (2H, s), 6.30-6.42 (1H, m), 7.29-7.33 (2H, m), 7.67 (1H, d, J=5.3 Hz), 7.83 (1H, s), 8.67 (2H, dd, J=0.8, 4.8 Hz).

ESI (LC/MS positive mode) m/z: 486 (M+2H−K).

Compound 1j-2-19-2Me

3-{2-(Methylaminosulfonyl)amino-3-fluoropyridin-4-ylmethyl}-4-ethyl-6-methyl-7-(pyrimidin-2-yloxy)-2-oxo-2H-1-benzopyran

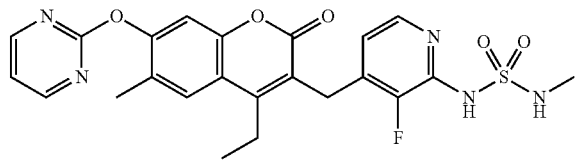

The title compound was synthesized under the same conditions as in the manufacturing example for compound 1j-2-16-2, except that compound 1h-2-19Me was used instead of compound 1h-2-16.

$^1$H NMR (DMSO-d$_6$, 270 MHz) δ (ppm): 1.13 (1H, t, J=7.4 Hz), 2.17 (3H, s), 2.46 (3H, s), 2.92 (1H, brq, J=7.4 Hz), 4.00 (2H), 6.82 (1H, brt, J=4.9 Hz), 7.00 (1H, brq, J=4.8 Hz), 7.32 (1H, t, J=4.8 Hz), 7.34 (1H, s), 7.86 (1H, s), 7.93 (1H, d, J=4.9 Hz), 8.67 (2H, d, J=4.8 Hz), 10.36 (1H, s).

One of the methyl peaks was overlapped with the DMSO peak.

ESI (LC/MS positive mode) m/z: 500 (M+H).

Compound 1j-2-19-2MeNa

3-{2-(Methylaminosulfonyl)amino-3-fluoropyridin-4-ylmethyl}-4-ethyl-6-methyl-7-(pyrimidin-2-yloxy)-2-oxo-2H-1-benzopyran sodium salt

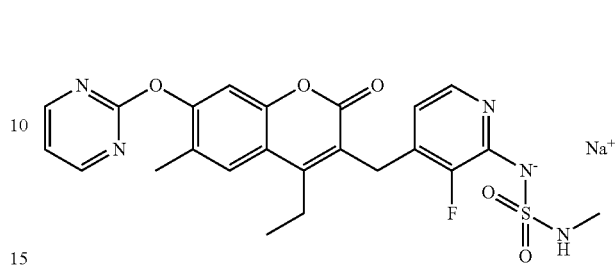

The title compound was synthesized under the same conditions as in the manufacturing example for compound 1j-1-5-1Na, except that compound 1j-2-19-2Me was used instead of compound 1j-1-5-1.

$^1$H NMR (DMSO-d$_6$, 270 MHz) δ (ppm): 1.12 (1H, t, J=7.4 Hz), 2.16 (3H, s), 2.28 (1H, d, J=5.8 Hz), 2.87 (1H, brq, J=7.4 Hz), 3.17 (3H, s), 3.85 (2H, s), 5.50 (1H, q, J=5.8 Hz), 6.04 (1H, t, J=5.1 Hz), 7.32 (1H, s), 7.32 (1H, t, J=4.8 Hz), 7.50 (1H, d, J=5.1 Hz), 7.82 (1H, s), 8.67 (2H, d, J=4.8 Hz).

ESI (LC/MS positive mode) m/z: 500 (M+2H−Na).

Compound 1j-2-19-2MeK

3-{2-(Methylaminosulfonyl)amino-3-fluoropyridin-4-ylmethyl}-4-ethyl-6-methyl-7-(pyrimidin-2-yloxy)-2-oxo-2H-1-benzopyran potassium salt

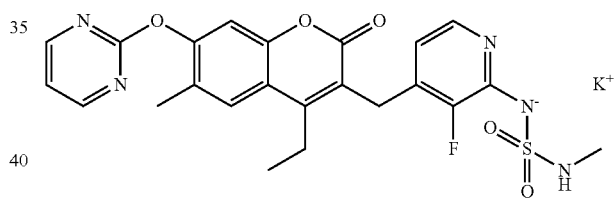

The title compound was synthesized under the same conditions as in the manufacturing example for compound 1j-1-5-1Na, except that compound 1j-2-19-2Me was used instead of compound 1j-1-5-1, and that KOH was used instead of NaOH.

$^1$H NMR (DMSO-d$_6$, 270 MHz) δ (ppm): 1.12 (1H, t, J=7.4 Hz), 2.16 (3H, s), 2.28 (1H, d, J=5.8 Hz), 2.87 (1H, brq, J=7.4 Hz), 3.17 (3H, s), 3.85 (2H, s), 5.50 (1H, q, J=5.8 Hz), 6.04 (1H, t, J=5.1 Hz), 7.32 (1H, s), 7.32 (1H, t, J=4.8 Hz), 7.50 (1H, d, J=5.1 Hz), 7.82 (1H, s), 8.67 (2H, d, J=4.8 Hz).

ESI (LC/MS positive mode) m/z: 500 (M+2H−K).

Compound 1j-2-19-2c

3-{2-(Cyclopropylaminosulfonyl)amino-3-fluoropyridin-4-ylmethyl}-4-methyl-6-methyl-7-(pyrimidin-2-yloxy)-2-oxo-2H-1-benzopyran

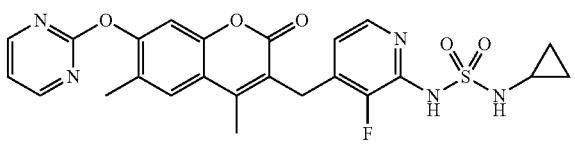

The title compound was synthesized under the same conditions as in the manufacturing example for compound 1j-2-16-2, except that compound 1h-2-19 was used instead of compound 1h-2-16, and that cyclopropylamine was used instead of methylamine.

¹H NMR (DMSO-d₆, 270 MHz) δ (ppm): 0.46-0.55 (4H, m), 2.16 (3H, s), 2.26-2.37 (1H, m), 4.03 (2H, s), 6.76-6.86 (1H, m), 7.30-7.33 (2H, m), 7.54 (1H, brs), 7.85 (1H, s), 7.93 (1H, d, J=5.4 Hz), 8.67 (2H, d, J=4.8 Hz), 10.50 (1H, brs).

One of the CH₃ peaks was overlapped with the DMSO peak.

ESI (LC/MS positive mode) m/z: 512 (M+H).

Compound 1j-2-16-2c

3-{2-(Cyclopropylaminosulfonyl)amino-3-fluoropyridin-4-ylmethyl}-4-methyl-7-(pyrimidin-2-yloxy)-2-oxo-2H-1-benzopyran

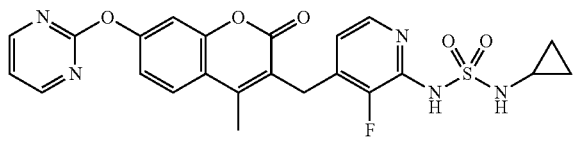

The title compound was synthesized under the same conditions as in the manufacturing example for compound 1j-2-16-2, except that cyclopropylamine was used instead of methylamine.

¹H NMR (DMSO-d₆, 270 MHz) δ (ppm): 0.40-0.60 (4H, m), 2.24-2.35 (1H, m), 2.40-2.70 (3H, m), 4.02 (2H, s), 6.75-6.85 (1H, m), 7.28 (1H, dd, J=1.9, 8.4 Hz), 7.32 (1H, dd, J=4.5 Hz), 7.39 (1H, d, J=2.4 Hz), 7.52 (1H, brs), 7.93 (1H, d, J=8.4 Hz), 7.90-7.95 (1H, m), 8.69 (2H, d, J=4.5), 10.49 (1H, brs).

ESI (LC/MS positive mode) m/z: 498 (M+H).

Compound 1j-2-41-2

3-{2-(Methylaminosulfonyl)amino-3-chloropyridin-4-ylmethyl}-4-methyl-7-(pyrimidin-2-yloxy)-2-oxo-2H-1-benzopyran

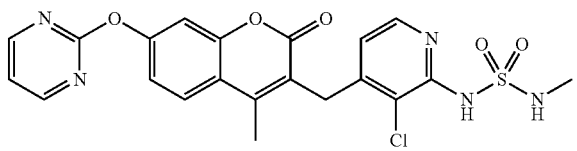

The compound 2-(di-tert-butyloxycarbonyl)amino-3-chloro-4-methylpyridine (compound 5b-0-41) was synthesized using 3-chloro-4-methyl-2-aminopyridine under the same conditions as in the manufacturing example for compound 5b-0-13.

The compound 2-(di-tert-butyloxycarbonyl)amino-3-chloro-4-bromomethylpyridine (compound 5c-0-41) was synthesized using compound 5b-0-41 under the same conditions as in the manufacturing example for compound 5c-0-13.

The compound 2-{2-(di-tert-butyloxycarbonyl)amino-3-chloropyridin-4-ylmethyl}-3-oxobutyric acid ethyl ester (compound 5t-0-41) was synthesized using compound 5c-0-41 under the same conditions as in the manufacturing example for compound 5t-0-10.

The compound 3-(3-chloro-2-aminopyridin-4-ylmethyl)-7-hydroxy-4-methyl-2-oxo-2H-1-benzopyran (compound 5d-0-41) was synthesized using compound 5t-0-41 under the same conditions as in the manufacturing example for compound 5d-0-12.

The compound 3-(3-chloro-2-aminopyridin-4-ylmethyl)-7-(pyrimidin-2-yloxy)-4-methyl-2-oxo-2H-1-benzopyran (compound 1h-2-41) was synthesized under the same conditions as in the manufacturing example for compound 1h-2-4 (synthesis scheme 2), except that compound 5d-0-41 was used instead of compound 4a-0-4.

The title compound was synthesized under the same conditions as in the manufacturing example for compound 1j-2-16-2, except that compound 1h-2-41 was used instead of compound 1h-2-16.

¹H NMR (DMSO-d₆, 270 MHz) δ (ppm): 2.44 (3H, s), 4.04 (2H, s), 6.75 (1H, m), 7.29 (1H, dd, J=2.2, 8.9 Hz), 7.34 (1H, t, J=4.8 Hz), 7.41 (1H, d, J=2.2 Hz), 7.65 (1H, brd, J=4.8 Hz), 7.94 (1H, d, J=8.9 Hz), 8.04 (1H, m), 8.69 (2H, d, J=4.8 Hz).

One of the methyl peaks was overlapped with the DMSO peak.

ESI (LC/MS positive mode) m/z: 488 (M+H).

Compound 1j-2-45-2

3-{2-(Methylaminosulfonyl)aminobenzyl}-4-methyl-7-(pyrimidin-2-yloxy)-2-oxo-2H-1-benzopyran

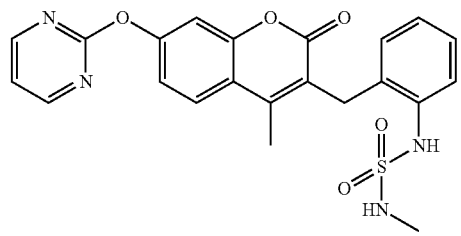

The title compound was synthesized under the same conditions as in the manufacturing example for compound 1j-2-16-2, except that compound 1h-2-45 was used instead of compound 1h-2-16.

¹H-NMR (Bruker, 300 MHz, DMSO-d₆) δ (ppm): 8.94 (1H, s), 8.69 (2H, d, J=5.0 Hz), 7.89 (1H, d, J=8.8 Hz), 7.39 (1H, d, J=2.3 Hz), 7.33 (2H, m), 7.26 (1H, dd, J=2.3, 8.8 Hz), 7.23-7.04 (3H, m), 6.91 (1H, d, J=7.6 Hz), 4.09 (2H, s), 2.61 (3H, d, J=5.0 Hz), 2.37 (3H, s).

MS (Micromass, Quattromicro, ESI+) m/z: 452.97 (M+H).

Compound 1j-2-46-2

3-{4-(Methylaminosulfonyl)aminobenzyl}-4-methyl-7-(pyrimidin-2-yloxy)-2-oxo-2H-1-benzopyran

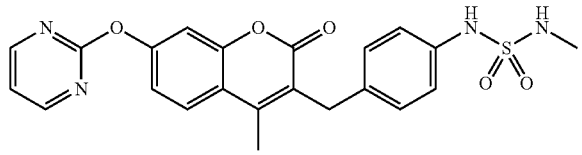

The title compound was synthesized under the same conditions as in the manufacturing example for compound 1j-2-16-2, except that compound 1h-2-46 was used instead of compound 1h-2-16.

$^1$H-NMR (Bruker, 300 MHz, CDCl$_3$) δ (ppm): 8.59 (2H, d, J=5.0 Hz), 7.69 (1H, d, J=8.7 Hz), 7.23 (3H, m), 7.18 (1H, dd, J=2.1, 8.7 Hz), 7.13-7.09 (3H, m), 6.43 (1H, s), 4.40 (1H, m), 4.03 (2H, s), 2.71 (3H, d, J=5.4 Hz), 2.48 (3H, s).

MS (Micromass, Quattromicro, ESI−) m/z: 451.03 (M−H).

Compound 1j-2-52-2

3-(3-(Methylaminosulfonyl)amino-phenoxy)-4-methyl-7-(pyrimidin-2-yloxy)-2-oxo-2H-1-benzopyran

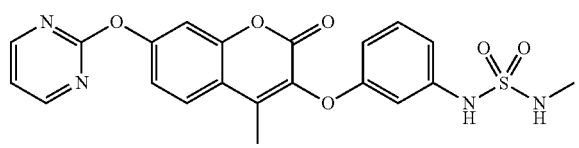

The title compound was synthesized under the same conditions as in the manufacturing example for compound 1j-2-16-2, except that compound 1h-2-52 was used instead of compound 1h-2-16.

$^1$H-NMR (300 MHz, DMSO-d$_6$) δ (ppm): 9.67 (1H, bs), 8.69 (2H, d, J=5.0 Hz), 7.90 (1H, d, =8.8 Hz), 7.46 (1H, d, J=2.3 Hz), 7.34 (3H, m), 7.19 (1H, m), 6.88 (1H, m), 6.82 (1H, m), 6.63 (1H, dd, J=2.3, 8.4 Hz), 2.45 (3H, d, J=4.6 Hz), 2.37 (3H, s).

MS (ESI+) m/z: 455.09 (M+H).

Compound 1j-2-53-2

3-(3-(Methylaminosulfonyl)amino-thiophenoxy)-4-methyl-7-(pyrimidin-2-yloxy)-2-oxo-2H-1-benzopyran

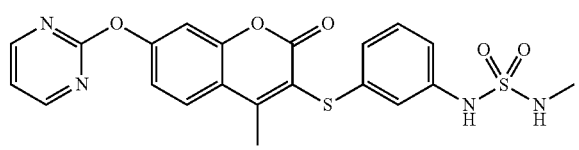

The title compound was synthesized under the same conditions as in the manufacturing example for compound 1j-2-16-2, except that compound 1h-2-53 was used instead of compound 1h-2-16.

$^1$H-NMR (300 MHz, DMSO-d$_6$) δ (ppm): 9.65 (1H, bs), 8.70 (2H, d, J=5.0 Hz), 8.00 (1H, d, J=8.8 Hz), 7.44 (1H, d, J=2.7 Hz), 7.35 (2H, m), 7.32 (1H, dd, J=2.3, 8.8 Hz), 7.20 (1H, m), 7.00 (1H, m), 6.96 (1H, m), 6.85 (1H, m), 2.75 (3H, s), 2.42 (3H, d, J=4.6 Hz).

MS (ESI+) m/z: 471.03 (M+H).

Compound 1j-3-1-2

3-{3-(Methylaminosulfonyl)aminobenzyl}-4-methyl-7-(thiazol-2-yloxy)-2-oxo-2H-1-benzopyran

[Chemical Formula 114]

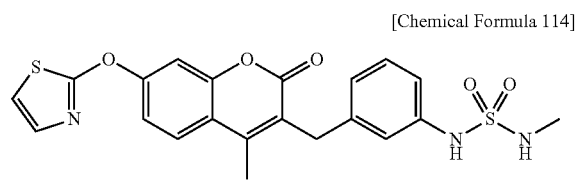

The title compound was synthesized under the same conditions as in the manufacturing example for compound 1j-1-5-2, except that compound 1h-3-1 was used instead of compound 1h-1-5.

$^1$H NMR (DMSO-d$_6$, 270 MHz) δ (ppm): 2.43 (3H, d, J=3.1 Hz), 3.94 (2H, s), 6.87 (1H, d, J=7.3 Hz), 6.99-7.05 (2H, m), 7.13-7.25 (2H, m), 7.32-7.40 (3H, m), 7.49 (1H, d, J=2.5 Hz), 7.94 (1H, d, J=8.9 Hz).

One of the methyl peaks was overlapped with the DMSO peak.

ESI (LC/MS positive mode) m/z: 458 (M+H).

Compound 1j-3-1-2Na 3-(3-(N-Methylsulfamoyl)aminobenzyl)-4-methyl-7-(thiazol-2-yloxy)-2-oxo-2H-1-benzopyran sodium salt

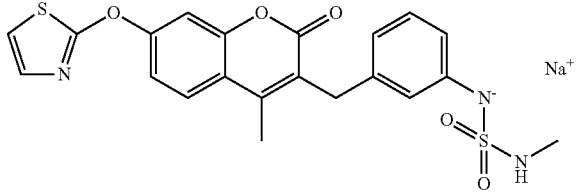

The title compound was synthesized under the same conditions as in the manufacturing example for compound 1j-1-5-1Na, except that compound 1j-3-1-2 was used instead of compound 1j-1-5-1.

$^1$H NMR (DMSO-d$_6$, 270 MHz) δ (ppm): 2.47 (3H, s), 3.91 (2H, s), 6.71 (1H, d, J=7.5 Hz), 6.85-7.04 (2H, m), 7.07 (1H, t, J=7.7 Hz), 7.33-7.38 (3H, m), 7.48 (1H, d, J=2.5 Hz), 7.92 (1H, d, J=8.7 Hz).

One of the CH$_3$ peaks was overlapped with the DMSO peak.

ESI (LC/MS positive mode) m/z: 458 (M+2H−Na).

Compound 1j-3-1-2K

3-{3-(Methylaminosulfonyl)aminobenzyl}-4-methyl-7-(thiazol-2-yloxy)-2-oxo-2H-1-benzopyran potassium salt

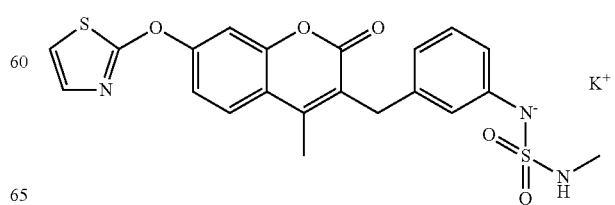

The title compound was synthesized under the same conditions as in the manufacturing example for compound 1j-1-5-1Na, except that compound 1j-3-1-2 was used instead of compound 1j-1-5-1, and that KOH was used instead of NaOH.

¹H NMR (DMSO-d₆, 270 MHz) δ (ppm): 2.47 (3H, s), 3.86 (2H, s), 6.53 (1H, d, J=6.9 Hz), 6.78-6.85 (2H, m), 6.94 (1H, t, J=7.8 Hz), 7.32-7.38 (3H, m), 7.47 (1H, dd, J=1.2, 2.3 Hz), 7.92 (1H, d, J=8.9 Hz).

One of the CH₃ peaks was overlapped with the DMSO peak.

ESI (LC/MS positive mode) m/z: 458 (M+2H−K).

Compound 1j-3-3-2

3-{3-(Methylaminosulfonyl)aminobenzyl}-4-methyl-7-(thiazol-2-yloxy)-6-chloro-2-oxo-2H-1-benzopyran

[Chemical Formula 115]

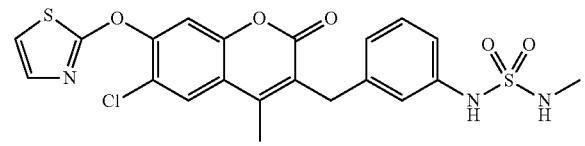

The title compound was synthesized under the same conditions as in the manufacturing example for compound 1j-1-5-2, except that compound 1h-3-3 was used instead of compound 1h-1-5.

¹H NMR (DMSO-d₆, 270 MHz) δ (ppm): 2.42 (3H, d, J=4.9 Hz), 3.95 (2H, s), 6.87 (1H, d, J=7.9 Hz), 7.01-7.04 (2H, m), 7.18 (1H, dd, J=7.9, 7.9 Hz), 7.25 (1H, d, J=4.9 Hz), 7.29 (1H, d, J=3.8 Hz), 7.34 (1H, d, J=3.8 Hz), 7.75 (1H, s), 8.13 (1H, s), 9.56 (1H, s).

One of the CH₃ peaks was overlapped with the DMSO peak.

ESI (LC/MS positive mode) m/z: 492 (M+H).

Compound 1j-3-4-2

3-{2-Fluoro-3-(methylaminosulfonyl)aminobenzyl}-4-methyl-7-(thiazol-2-yloxy)-2-oxo-2H-1-benzopyran

[Chemical Formula 116]

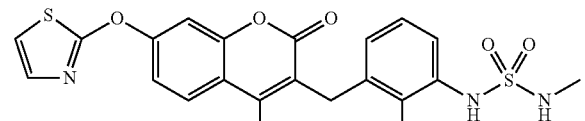

The title compound was synthesized under the same conditions as in the manufacturing example for compound 1j-1-5-2, except that compound 1h-3-4 was used instead of compound 1h-1-5.

¹H NMR (DMSO-d₆, 270 MHz) δ (ppm): 2.46 (3H, s), 3.98 (2H, s), 6.85-6.90 (1H, m), 6.98-7.04 (1H, m), 7.20 (1H, d, J=5.0 Hz), 7.29 (1H, ddd, J=1.5, 7.8 Hz, J_HF=7.8 Hz), 7.34-7.39 (3H, m), 7.49 (1H, d, J=2.5 Hz), 7.95 (1H, d, J=8.9 Hz), 9.39 (1H, brs).

One of the CH₃ peaks was overlapped with the DMSO peak.

ESI (LC/MS positive mode) m/z: 476 (M+H).

Compound 1j-3-4-2Na 3-(3-(N-Methylsulfamoyl)amino-2-fluorobenzyl)-4-methyl-7-(thiazol-2-yloxy)-2-oxo-2H-1-benzopyran sodium salt

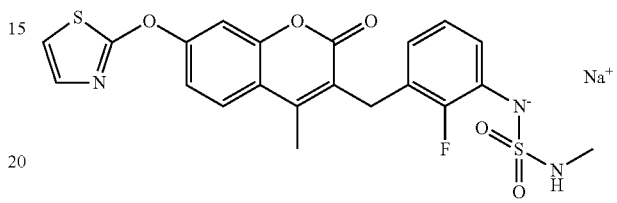

The title compound was synthesized under the same conditions as in the manufacturing example for compound 1j-1-5-1Na, except that compound 1j-3-4-2 was used instead of compound 1j-1-5-1.

¹H NMR (DMSO-d₆, 270 MHz) δ (ppm): 2.37 (3H, s), 2.43 (3H, s), 3.89 (2H, s), 5.36 (1H, brs), 6.28-6.32 (1H, m), 6.69 (1H, dd, J=7.8, 8.1 Hz), 7.19 (1H, dd, J=7.8, 8.6 Hz), 7.31-7.40 (3H, m), 7.47 (1H, m), 7.92 (1H, d, J=8.6 Hz).

ESI (LC/MS positive mode) m/z: 476 (M+2H−Na).

Compound 1j-3-4-2K 3-(3-(N-Methylsulfamoyl)amino-2-fluorobenzyl)-4-methyl-7-(thiazol-2-yloxy)-2-oxo-2H-1-benzopyran potassium salt

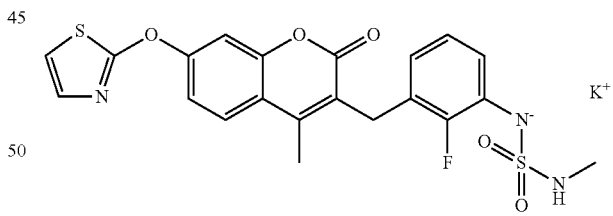

The title compound was synthesized under the same conditions as in the manufacturing example for compound 1j-1-5-1Na, except that compound 1j-3-4-2 was used instead of compound 1j-1-5-1, and that KOH was used instead of NaOH.

¹H NMR (DMSO-d₆, 270 MHz) δ (ppm): 2.40 (3H, s), 2.44 (3H, s), 3.91 (2H, s), 5.66 (1H, brs), 6.37-6.42 (1H, m), 6.75 (1H, dd, J=7.9, 8.0 Hz), 7.24 (1H, dd, J=8.0, 8.4 Hz), 7.34-7.38 (3H, m), 7.48 (1H, dd, J=1.3, 2.3 Hz), 7.92 (1H, d, J=8.9 Hz).

ESI (LC/MS positive mode) m/z: 476 (M+2H−K).

Compound 1j-3-8-2

3-{3-(Methylaminosulfonyl)aminobenzyl}-4-methyl-7-(thiazol-2-yloxy)-6-methyl-2-oxo-2H-1-benzopyran

[Chemical Formula 117]

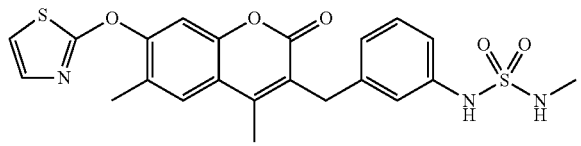

The title compound was synthesized under the same conditions as in the manufacturing example for compound 1j-1-5-2, except that compound 1h-3-8 was used instead of compound 1h-1-5.

$^1$H NMR (DMSO-d$_6$, 270 MHz) δ (ppm): 2.26 (3H, s), 2.41 (3H, d, J=4.1 Hz), 2.46 (3H, s), 3.93 (2H, s), 6.85 (1H, d, J=7.4 Hz), 6.97-7.04 (2H, m), 7.13-7.24 (2H, m), 7.26-7.30 (2H, m), 7.44 (1H, s), 7.85 (1H, s).

ESI (LC/MS positive mode) m/z: 472 (M+H).

Compound 1j-3-8-2Na 3-(3-(N-Methylsulfamoyl)aminobenzyl)-4,6-dimethyl-7-(thiazol-2-yloxy)-2-oxo-2H-1-benzopyran sodium salt

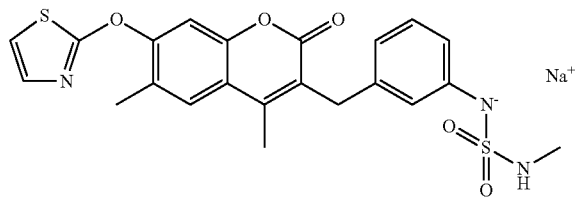

The title compound was synthesized under the same conditions as in the manufacturing example for compound 1j-1-5-1Na, except that compound 1j-3-8-2 was used instead of compound 1j-1-5-1.

$^1$H NMR (DMSO-d$_6$, 270 MHz) δ (ppm): 2.27 (3H, s), 2.34 (3H, s), 2.46 (3H, s), 3.87 (2H, s), 6.53 (1H, d, J=7.1 Hz), 6.80-6.99 (4H, m), 7.27-7.31 (2H, m), 7.44 (1H, s), 7.84 (1H, s).

ESI (LC/MS positive mode) m/z: 472 (M+2H−Na).

Compound 1j-3-8-2K 3-(3-(N-Methylsulfamoyl)aminobenzyl)-4,6-dimethyl-7-(thiazol-2-yloxy)-2-oxo-2H-1-benzopyran potassium salt

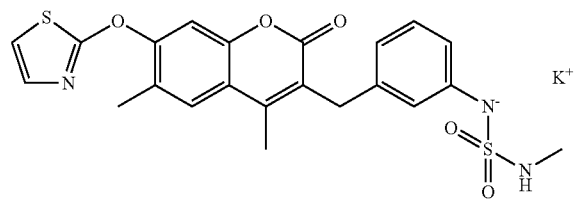

The title compound was synthesized under the same conditions as in the manufacturing example for compound 1j-1-5-1Na, except that compound 1j-3-8-2 was used instead of compound 1j-1-5-1, and that KOH was used instead of NaOH.

$^1$H NMR (DMSO-d$_6$, 270 MHz) δ (ppm): 2.27 (3H, s), 2.34 (3H, s), 2.46 (3H, s), 3.87 (2H, s), 6.53 (1H, d, J=6.9 Hz), 6.79-6.99 (4H, m), 7.27-7.31 (2H, m), 7.44 (1H, s), 7.84 (1H, s).

ESI (LC/MS positive mode) m/z: 472 (M+2H−K).

Compound 1j-3-12-2

3-{2-(Methylaminosulfonyl)aminopyridin-4-ylmethyl}-4-methyl-6-chloro-7-(thiazol-2-yloxy)-2-oxo-2H-1-benzopyran

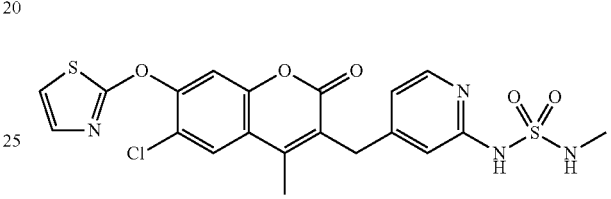

The compound 3-(2-aminopyridin-4-ylmethyl)-4-methyl-6-chloro-7-(thiazol-2-yloxy)-2-oxo-2H-1-benzopyran (compound 1h-3-12) was synthesized under the same conditions as in the manufacturing example for compound 1h-2-4 (synthesis scheme 2), except that compound 5d-0-12 was used instead of compound 4a-0-4.

The title compound was synthesized under the same conditions as in the manufacturing example for compound 1j-2-16-2, except that compound 1h-3-12 was used instead of compound 1h-2-16.

$^1$H NMR (DMSO-d$_6$, 270 MHz) δ (ppm): 2.42 (3H, s), 2.48 (3H, s), 3.95 (2H, s), 6.74-6.77 (2H, m), 7.25-7.35 (2H, m), 7.75 (1H, s), 8.03 (1H, d, J=4.9 Hz), 8.13 (s, 1H).

ESI (LC/MS positive mode) m/z: 493 (M+H).

Compound 1j-3-19-2

3-{2-(Methylaminosulfonyl)amino-3-fluoropyridin-4-ylmethyl}-4-methyl-6-methyl-7-(thiazol-2-yloxy)-2-oxo-2H-1-benzopyran

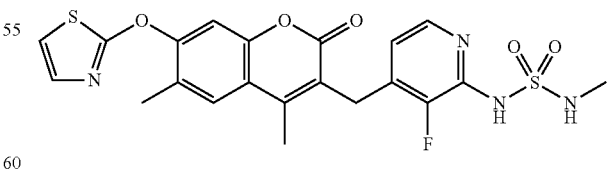

The compound 3-{2-amino-3-fluoropyridin-4-ylmethyl}-4-methyl-6-methyl-7-(thiazol-2-yloxy)-2-oxo-2H-1-benzopyran (compound 1h-3-19) was synthesized under the same conditions as in the manufacturing example for compound 1h-2-4 (synthesis scheme 2), except that compound 5d-0-18 was used instead of compound 4a-0-4.

The title compound was synthesized under the same conditions as in the manufacturing example for compound 1j-2-16-2, except that compound 1h-3-19 was used instead of compound 1h-2-16.

¹H NMR (CD₃OD, 270 MHz) δ (ppm): 2.34 (3H, s), 2.51 (3H, s), 2.62 (3H, s), 4.10 (2H, s), 6.81 (1H, dd, J=5.1 Hz), 7.13 (1H, d, J=3.8 Hz), 7.20-7.30 (2H, m), 7.80 (1H, s), 7.92 (1H, d, J=5.1 Hz).

ESI (LC/MS positive mode) m/z: 491 (M+H).

Compound 1j-3-19-2Na 3-(2-(N-Methylsulfamoyl)amino-3-fluoropyridin-4-ylmethyl)-4,6-dimethyl-7-(thiazol-2-yloxy)-2-oxo-2H-1-benzopyran sodium salt

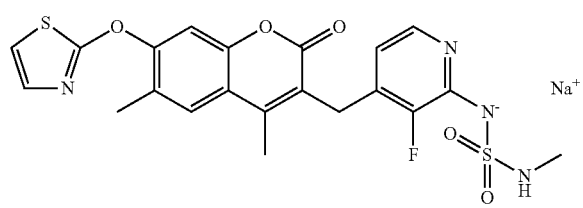

The title compound was synthesized under the same conditions as in the manufacturing example for compound 1j-1-5-1Na, except that compound 1j-3-19-2 was used instead of compound 1j-1-5-1.

¹H NMR (DMSO-d₆) δ (ppm): 7.86 (1H, s), 7.50 (1H, d, J=5.2 Hz), 7.45 (1H, s), 7.35-7.25 (2H, m), 6.09 (1H, br), 3.87 (2H, s), 2.45 (3H, s), 2.28 (3H, s), 2.27 (3H, s).

ESI (LC/MS positive mode) m/z: 491 (M+2H−Na).

Compound 1j-3-19-2c

3-{2-(Cyclopropylaminosulfonyl)amino-3-fluoropyridin-4-ylmethyl}-4-methyl-6-methyl-7-(thiazol-2-yloxy)-2-oxo-2H-1-benzopyran

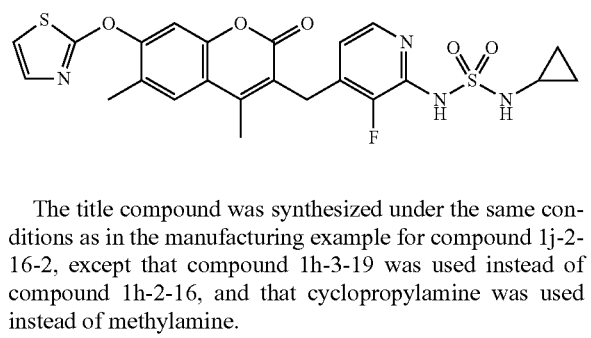

The title compound was synthesized under the same conditions as in the manufacturing example for compound 1j-2-16-2, except that compound 1h-3-19 was used instead of compound 1h-2-16, and that cyclopropylamine was used instead of methylamine.

¹H NMR (DMSO-d₆, 270 MHz) δ (ppm): 0.47-0.55 (4H, m), 2.23-2.37 (1H, m), 2.28 (3H, s), 2.49 (3H, s), 4.02 (2H, s), 6.76-6.87 (1H, m), 7.29 (2H, s), 7.47 (1H, s), 7.55 (1H, brs), 7.89 (1H, s), 7.89-7.94 (1H, m), 10.48 (1H, brs).

ESI (LC/MS positive mode) m/z: 517 (M+H).

Compound 1j-3-20-2

3-{2-(Methylaminosulfonyl)aminopyridin-4-ylmethyl}-4-methyl-6-methyl-7-(thiazol-2-yloxy)-2-oxo-2H-1-benzopyran

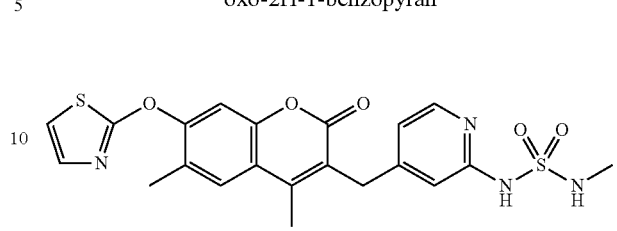

The compound 3-(2-aminopyridin-4-ylmethyl)-7-hydroxy-6-methyl-4-methyl-2-oxo-2H-1-benzopyran (compound 5d-0-20) was synthesized using compound 5t-0-10 and 4-methylresorcinol under the same conditions as in the manufacturing example for compound 5d-0-12.

The compound 3-(2-aminopyridin-4-ylmethyl)-7-(thiazol-2-ylmethyl)-6-methyl-4-methyl-2-oxo-2H-1-benzopyran (compound 1h-3-20) was synthesized under the same conditions as in the manufacturing example for compound 1h-2-4 (synthesis scheme 2), except that compound 5d-0-20 was used instead of compound 4a-0-4.

The title compound was synthesized under the same conditions as in the manufacturing example for compound 1j-2-16-2, except that compound 1h-3-20 was used instead of compound 1h-2-16.

¹H NMR (DMSO-d₆, 270 MHz) δ (ppm): 2.28 (3H, s), 2.45 (3H, s), 2.47 (3H, s), 3.96 (2H, s), 6.82-6.84 (2H, m), 6.96 (1H, br), 7.27-7.31 (2H, m), 7.45 (1H, s), 7.87 (1H, s), 8.07 (1H, d, J=4.3 Hz), 10.25 (1H, br).

ESI (LC/MS positive mode) m/z: 473 (M+H).

Compound 1j-3-20-4

{4-[4,6-Dimethyl-2-oxo-7-(thiazol-2-yloxy)-2H-1-benzopyran-3-ylmethyl]pyridin-2-yl}sulfamic acid

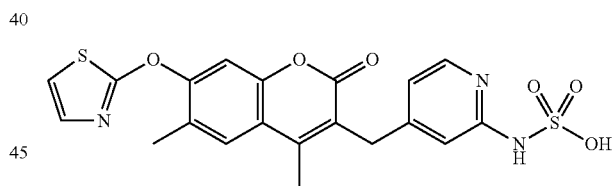

¹H NMR (DMSO-d₆, 270 MHz) δ (ppm): 2.28 (3H, s), 2.46 (3H, s), 3.90 (2H), 6.50-6.55 (1H, m), 7.13 (1H, s), 7.25-7.35 (2H, m), 7.43 (1H, s), 7.80-8.00 (3H, m).

ESI (LC/MS positive mode) m/z: 460 (M+H).

Compound 1j-3-44-2

3-{2-(Methylaminosulfonyl)amino-3-chloropyridin-4-ylmethyl}-4-methyl-6-methyl-7-(thiazol-2-yloxy)-2-oxo-2H-1-benzopyran

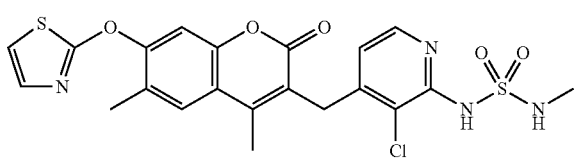

The compound 3-(3-chloro-2-aminopyridin-4-ylmethyl)-7-hydroxy-6-methyl-4-methyl-2-oxo-2H-1-benzopyran (compound 5d-0-44) was synthesized using compound 5t-0-41 and 4-methylresorcinol under the same conditions as in the manufacturing example for compound 5d-0-12.

The compound 3-(3-chloro-2-aminopyridin-4-ylmethyl)-7-(thiazol-yloxy)-6-methyl-4-methyl-2-oxo-2H-1-benzopyran (compound 1h-0-44) was synthesized under the same conditions as in the manufacturing example for compound 1h-2-4 (synthesis scheme 2), except that compound 5d-0-44 was used instead of compound 4a-0-4.

The title compound was synthesized under the same conditions as in the manufacturing example for compound 1j-2-16-2, except that compound 1h-3-44 was used instead of compound 1h-2-16.

$^1$H NMR (DMSO-d$_5$, 270 MHz) δ (ppm): 2.29 (3H, s), 2.43 (3H, s), 3.17 (3H, dd, J=1.3, 5.3 Hz), 4.03 (2H, s), 6.73 (1H, d, J=3.3 Hz), 9.95 (1H, brs).

ESI (LC/MS positive mode) m/z: 507 (M+H).

Compound 1j-2a-4-2

3-{2-Fluoro-3-(methylaminosulfonyl)aminobenzyl}-4-methyl-7-(5-fluoropyrimidin-2-yloxy)-2-oxo-2H-1-benzopyran

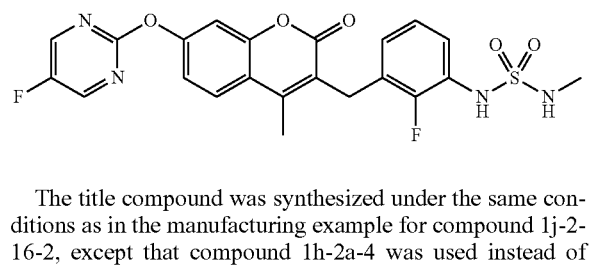

The title compound was synthesized under the same conditions as in the manufacturing example for compound 1j-2-16-2, except that compound 1h-2a-4 was used instead of compound 1h-2-16.

$^1$H-NMR (Bruker, 300 MHz, CDCl$_3$) δ (ppm): 8.44 (2H, s), 7.71 (1H, d, J=8.8 Hz), 7.40 (1H, m), 7.22 (1H, d, J=2.7 Hz), 7.17 (1H, dd, J=2.3, 9.2 Hz), 7.0 (2H, m), 6.58 (1H, brs), 4.38 (1H, m), 4.08 (2H, s), 2.76 (3H, d, J=5.3 Hz), 2.47 (3H, s).

MS (Micromass, Quattromicro, ESI+) m/z: 488.76 (M+H).

Compound 1j-2b-4-2

3-{2-Fluoro-3-(methylaminosulfonyl)aminobenzyl}-4-methyl-7-(4-chloropyrimidin-2-yloxy)-2-oxo-2H-1-benzopyran

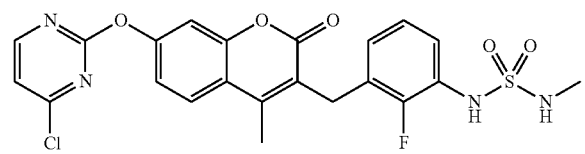

The title compound was synthesized under the same conditions as in the manufacturing example for compound 1j-2-16-2, except that compound 1h-2b-4 was used instead of compound 1h-2-16.

$^1$H-NMR (Bruker, 300 MHz, CDCl$_3$) δ (ppm): 8.51 (1H, d, J=5.7 Hz), 7.72 (1H, d, J=8.8 Hz), 7.41 (1H, m), 7.20 (1H, d, J=2.3 Hz), 7.15 (1H, J=2.3, 8.8 Hz), 7.01 (2H, m), 6.93 (1H, d, J=5.7 Hz), 6.58 (1H, brs), 4.39 (1H, m), 4.09 (2H, s), 2.77 (3H, d, J=5.3 Hz), 2.48 (3H, s).

MS (Micromass, Quattromicro, ESI+) m/z: 504.63 (M+H).

Compound 1j-5-4-2

3-{2-Fluoro-3-(methylaminosulfonyl)aminobenzyl}-4-methyl-7-(2,4-dimethoxypyrimidin-6-yloxy)-2-oxo-2H-1-benzopyran

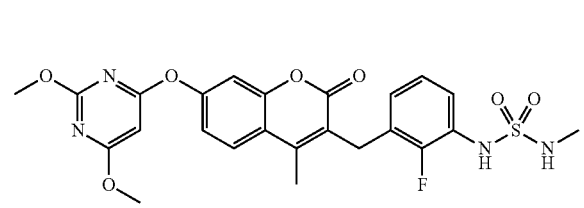

The title compound was synthesized under the same conditions as in the manufacturing example for compound 1j-2-16-2, except that compound 1h-5-4 was used instead of compound 1h-2-16.

$^1$H-NMR (Bruker, 300 MHz, CDCl$_3$) δ (ppm): 7.66 (1H, d, J=8.8 Hz), 7.40 (1H, m), 7.16 (1H, d, J=2.3 Hz), 7.12 (1H, dd, J=2.3, 8.8 Hz), 7.02 (1H, m), 6.97 (1H, m), 6.61 (1H, brs), 5.88 (1H, s), 4.43 (1H, m), 4.08 (2H, s), 3.98 (3H, s), 3.89 (3H, s), 2.76 (3H, d, J=5.3 Hz), 2.46 (3H, s).

MS (Micromass, Quattromicro, ESI+) m/z: 531.07 (M+H).

Compound 1j-3a-4-2

3-{2-Fluoro-3-(methylaminosulfonyl)aminobenzyl}-4-methyl-7-(benzothiazol-2-yloxy)-2-oxo-2H-1-benzopyran

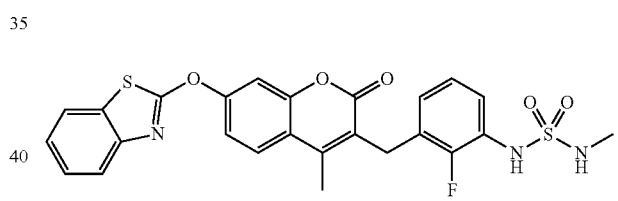

The title compound was synthesized under the same conditions as in the manufacturing example for compound 1j-2-16-2, except that compound 1h-3a-4 was used instead of compound 1h-2-16.

$^1$H NMR (Bruker, 300 MHz, CDCl$_3$) δ (ppm): 7.74 (2H, m), 7.72 (1H, d, J=8.8 Hz), 7.49 (1H, d, J=2.3 Hz), 7.38 (4H, m), 7.02 (1H, m), 6.99 (1H, m), 6.62 (1H, bs), 4.44 (1H, m), 4.09 (2H, s), 2.76 (3H, d, J=5.3 Hz), 2.48 (3H, s).

MS (Micromass, Quattromicro, ESI+) 526.01 (M+H).

Compound 1j-3b-4-2

3-{2-Fluoro-3-(methylaminosulfonyl)aminobenzyl}-4-methyl-7-(5-bromothiazol-2-yloxy)-2-oxo-2H-1-benzopyran

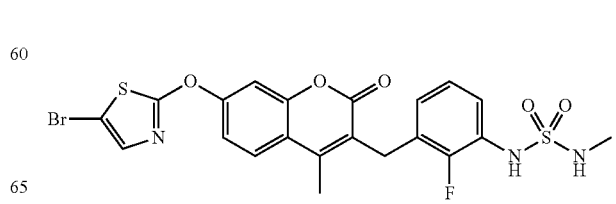

The title compound was synthesized under the same conditions as in the manufacturing example for compound 1j-2-16-2, except that compound 1h-3b-4 was used instead of compound 1h-2-16.

¹H-NMR (Bruker, 300 MHz, CDCl₃) δ (ppm): 7.69 (1H, d, J=8.8 Hz), 7.40 (1H, m), 7.30 (1H, d, J=2.3 Hz), 7.24 (1H, dd, J=2.3, 8.8 Hz), 7.20 (1H, s), 7.01 (1H, m), 6.96 (1H, m), 6.61 (1H, brs), 4.43 (1H, m), 4.07 (2H, s), 2.76 (3H, d, J=5.3 Hz), 2.46 (3H, s).

MS (Micromass, Quattromicro, ESI+) m/z: 553.79 (M), 555.78 (M+2).

Compound 1j-1a-4-2

Dimethylthiocarbamic acid 4-methyl-3-{3-(methylaminosulfonyl)aminobenzyl}-2-oxo-2H-1-benzopyran-7-yl ester

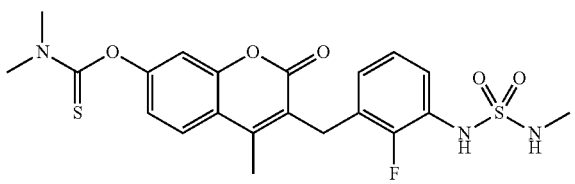

The title compound was synthesized under the same conditions as in the manufacturing example for compound 1j-2-16-2, except that compound 1h-1a-4 was used instead of compound 1h-2-16.

¹H-NMR (Bruker, 300 MHz, CDCl₃) δ (ppm): 7.66 (1H, m), 7.40 (1H, m), 7.06 (2H, m), 7.01 (1H, d, J=8.0 Hz), 6.96 (1H, m), 6.58 (1H, m), 4.40 (1H, m), 4.07 (2H, s), 3.47 (3H, s), 3.38 (3H, s), 2.76 (3H, d, J=5.3 Hz), 2.45 (3H, s).

MS (Micromass, Quattromicro, ESI+) m/z: 480.09 (M+H).

Compound 1j-2a-16-2

3-{2-(Methylaminosulfonyl)amino-3-fluoropyridin-4-ylmethyl}-4-methyl-7-(5-fluoropyrimidin-2-yloxy)-2-oxo-2H-1-benzopyran

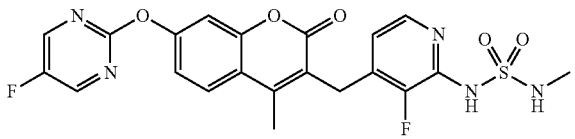

The title compound was synthesized under the same conditions as in the manufacturing example for compound 1j-2-16-2, except that compound 1h-2a-16 was used instead of compound 1h-2-16.

¹H-NMR (Broker, 300 MHz, CDCl₃) δ (ppm): 8.44 (2H, s), 7.71 (1H, d, J=8.8 Hz), 7.40 (1H, m), 7.22 (1H, d, J=2.7 Hz), 7.17 (1H, dd, J=2.3, 9.2 Hz), 7.0 (2H, m), 6.58 (1H, brs), 4.38 (1H, m), 4.08 (2H, s), 2.76 (3H, d, J=5.3 Hz), 2.47 (3H, s).

MS (Micromass, Quattromicro, ESI+) m/z: 488.76 (M+H).

Compound 1j-2b-16-2

3-{2-(Methylaminosulfonyl)amino-3-fluoropyridin-4-ylmethyl}-4-methyl-7-(4-chloropyrimidin-2-yloxy)-2-oxo-2H-1-benzopyran

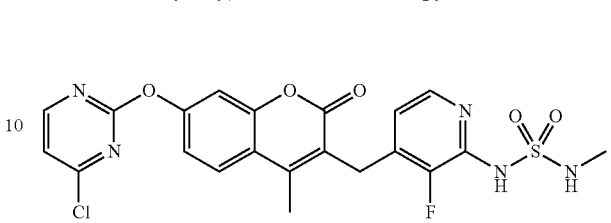

The title compound was synthesized under the same conditions as in the manufacturing example for compound 1j-2-16-2, except that compound 1h-2b-16 was used instead of compound 1h-2-16.

¹H-NMR (Bruker, 300 MHz, CDCl₃) δ (ppm): 8.52 (1H, d, J=5.7 Hz), 7.96 (1H, m), 7.73 (1H, J=8.8 Hz), 7.21 (1H, d, J=2.3 Hz), 7.17 (1H, dd, J=2.7, 8.8 Hz), 7.09 (1H, m), 6.94 (1H, d, J=5.7 Hz), 6.90 (1H, m), 5.47 (1H, m), 4.09 (2H, s), 2.76 (3H, d, J=5.3 Hz), 2.49 (3H, s).

MS (Micromass, Quattromicro, ESI+) m/z: 505.87 (M), 507.86 (M+2).

Compound 1j-5-16-2

3-{2-(Methylaminosulfonyl)amino-3-fluoropyridin-4-ylmethyl}-4-methyl-7-(2,4-dimethoxypyrimidin-6-yloxy)-2-oxo-2H-1-benzopyran

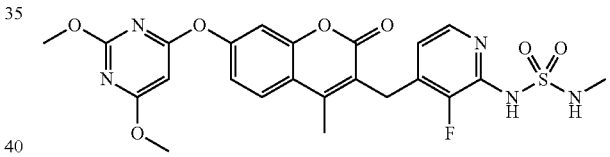

The title compound was synthesized under the same conditions as in the manufacturing example for compound 1j-2-16-2, except that compound 1h-5-16 was used instead of compound 1h-2-16.

¹H-NMR (Broker, 300 MHz, CDCl₃) δ (ppm): 7.94 (1H, m), 7.67 (1H, d, J=8.8 Hz), 7.18 (1H, d, J=2.3 Hz), 7.14 (1H, dd, J=2.3, 8.8 Hz), 7.09 (1H, m), 6.88 (1H, m), 5.89 (1H, s), 5.47 (1H, m), 4.08 (2H, s), 3.98 (3H, s), 3.89 (3H, s), 2.76 (3H, d, J=5.3 Hz), 2.47 (3H, s).

MS (Micromass, Quattromicro, ESI+) m/z: 531.91 (M+H).

Compound 1j-3a-16-2

3-{2-(Methylaminosulfonyl)amino-3-fluoropyridin-4-ylmethyl}-4-methyl-7-(benzothiazol-2-yloxy)-2-oxo-2H-1-benzopyran

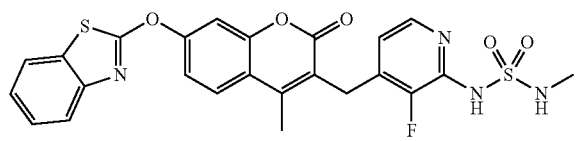

The title compound was synthesized under the same conditions as in the manufacturing example for compound 1j-2-16-2, except that compound 1h-3a-16 was used instead of compound 1h-2-16.

¹H NMR (Broker, 300 MHz, CDCl₃) δ (ppm): 7.94 (1H, d, J=5.3 Hz), 7.73 (3H, m), 7.52 (1H, d, J=2.3 Hz), 7.43 (1H, m), 7.39 (1H, dd, J=2.7, 8.8 Hz), 7.33 (1H, m), 7.15 (1H, m), 6.88 (1H, m), 5.48 (1H, m), 4.09 (2H, s), 2.76 (3H, d, J=5.3 Hz), 2.48 (3H, s).

MS (Micromass, Quattromicro, ESI+) m/z: 526.73 (M+H).

Compound 1j-3b-16-2

3-{2-(Methylaminosulfonyl)amino-3-fluoropyridin-4-ylmethyl}-4-methyl-7-(5-bromothiazol-2-yloxy)-2-oxo-2H-1-benzopyran

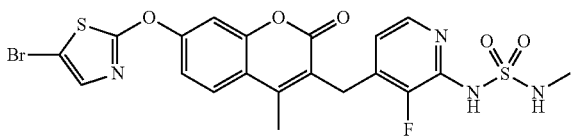

The title compound was synthesized under the same conditions as in the manufacturing example for compound 1j-2-16-2, except that compound 1h-3b-16 was used instead of compound 1h-2-16.

¹H-NMR (Bruker, 300 MHz, CDCl₃) δ (ppm): 7.94 (1H, m), 7.70 (1H, d, J=8.8 Hz), 7.32 (1H, d, J=2.3 Hz), 7.26 (1H, d, J=2.7 Hz), 7.20 (1H, m), 7.09 (1H, m), 6.89 (1H, m), 5.47 (1H, m), 4.07 (2H, s), 2.76 (3H, d, J=5.3 Hz), 2.46 (3H, s).

MS (Micromass, Quattromicro, ESI+) m/z: 554.62 (M), 556.54 (M+2).

Compound 1j-4-16-2

3-{2-(Methylaminosulfonyl)amino-3-fluoropyridin-4-ylmethyl}-4-methyl-7-(pyrazin-2-yloxy)-2-oxo-2H-1-benzopyran

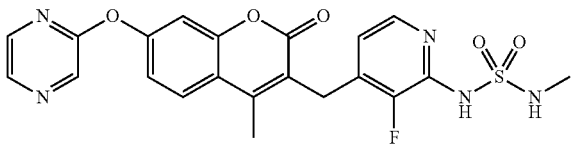

The compound 3-{2-amino-3-fluoropyridin-4-ylmethyl}-4-methyl-7-(pyrazin-2-yloxy)-2-oxo-2H-1-benzopyran (compound 1h-4-16) was synthesized under the same conditions as in the manufacturing example for compound 1h-2-4 (synthesis scheme 2), except that compound 5d-0-16 was used instead of compound 4a-0-4, and that bromopyrazine was used instead of 2-bromopyrimidine.

The title compound was synthesized under the same conditions as in the manufacturing example for compound 1j-2-16-2, except that compound 1h-4-16 was used instead of compound 1h-2-16.

¹H NMR (DMSO-d₆, 270 MHz) δ (ppm): 2.44 (3H, s), 2.52 (3H, s), 4.01 (2H, s), 3.96 (2H, s), 6.72 (1H, d, J=5.0 Hz), 7.10-7.20 (2H, m), 7.78-7.85 (2H, m), 8.09 (1H, dd, J=1.3, 2.5 Hz), 8.27 (1H, d, J=2.5 Hz) 8.42 (1H, brs).

ESI (LC/MS positive mode) m/z: 472 (M+H).

Compound 1j-6-16-2

3-{2-(Methylaminosulfonyl)amino-3-fluoropyridin-4-ylmethyl}-4-methyl-7-(pyridin-2-yloxy)-2-oxo-2H-1-benzopyran

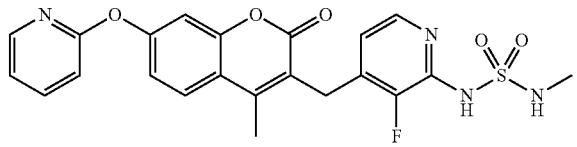

The compound 3-{2-amino-3-fluoropyridin-4-ylmethyl}-4-methyl-7-(pyridin-2-yloxy)-2-oxo-2H-1-benzopyran (compound 1h-6-16) was synthesized under the same conditions as in the manufacturing example for compound 1h-2-4 (synthesis scheme 2), except that compound 5d-0-16 was used instead of compound 4a-0-4, and that 2-bromopyridine was used instead of 2-bromopyrimidine.

The title compound was synthesized under the same conditions as in the manufacturing example for compound 1j-2-16-2, except that compound 1h-6-16 was used instead of compound 1h-2-16.

¹H NMR (CD₃OD, 270 MHz) δ (ppm): 2.52 (3H, s), 2.60 (3H, s), 4.09 (2H), 6.75 (1H, brt, J=5.3 Hz), 7.07-7.28 (4H, m), 7.73 (1H, m), 7.83-7.95 (2H, m), 8.21 (1H, dd, J=1.2, 4.9 Hz).

ESI (LC/MS positive mode) m/z: 471 (M+H).

Compound 1j-2-47-2

3-(3-(Methylaminosulfonyl)aminobenzyl)-4-hydroxy-7-(pyrimidin-2-yloxy)-2-oxo-2H-1-benzopyran

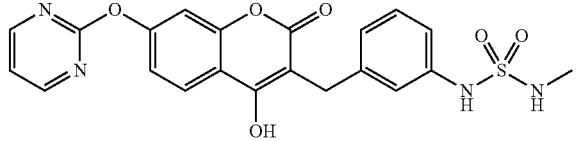

The title compound was synthesized under the same conditions as in the manufacturing example for compound 1j-1-3-2, except that compound 1h-2-47 was used instead of compound 1h-1-3.

¹H NMR (270 MHz, DMSO-d₆) δ (ppm): 9.51 (s, 1H), 8.68 (d, 2H, J=4.8 Hz), 8.00 (d, 1H, J=8.2 Hz), 7.33 (t, 1H, J=4.8 Hz), 7.28 (d, 1H, J=2.1 Hz), 7.19 (dd, 1H, J=8.2, 2.6 Hz), 7.13 (d, 1H, J=7.6 Hz), 7.02-7.00 (m, 2H), 6.87 (d, 1H, J=7.4 Hz), 3.81 (s, 2H), 2.43 (d, 3H, J=4.9 Hz).

ESIMS m/z: 455 (M+H).

Compound 1j-2-51-2

3-(3-(Methylaminosulfonyl)aminophenylamino)-4-methyl-7-(pyrimidin-2-yloxy)-2-oxo-2H-1-benzopyran

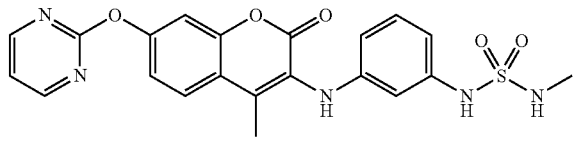

The title compound was synthesized under the same conditions as in the manufacturing example for compound 1j-1-3-2, except that compound 1h-2-51 was used instead of compound 1h-1-3.

¹H NMR (270 MHz, DMSO-d₆) δ (ppm): 9.42 (s, 1H), 8.69 (d, 2H, J=4.8 Hz), 7.83 (d, 1H, J=8.7 Hz), 7.68 (s, 1H), 7.39 (d, 1H, J=2.0 Hz), 7.33 (t, 1H, J=4.8 Hz), 7.28 (d, 1H, J=8.7 Hz), 7.14 (d, 1H, J=5.1 Hz), 7.05 (t, 1H, J=8.4 Hz), 6.61 (d, 1H, J=8.4 Hz), 6.44 (m, 2H), 2.42 (d, 3H, J=5.4 Hz), 2.26 (s, 3H).

ESIMS m/z: 454 (M+H).

Compound 1j-1-59-2

Dimethylcarbamic acid 3-(2-(methylaminosulfonyl)aminobenzoylamino)-methyl-2-oxo-2H-1-benzopyran-7-yl ester

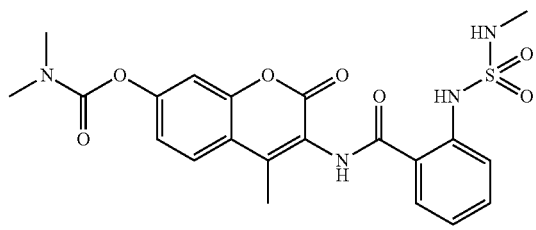

The title compound was synthesized under the same conditions as in the manufacturing example for compound 1j-1-5-2, except that compound 1h-1-59 was used instead of compound 1h-1-5.

¹H NMR (270 MHz, DMSO-d₆) δ (ppm): 10.67 (s, 1H), 10.33 (s, 1H), 8.07 (d, 1H, J=8.1 Hz), 7.89 (d, 1H, J=8.7 Hz), 7.69 (q, 1H, J=4.9 Hz), 7.62-6.59 (m, 2H), 7.34 (d, 1H. J=2.3 Hz), 7.26-7.22 (m, 2H), 3.08 (s, 3H), 2.95 (s, 3H), 2.48 (d, 3H, J=4.9 Hz), 2.42 (s, 3H).

ESIMS m/z: 475 (M+H).

Compound 1j-20-1-2

4-Methyl-3-(3-(methylaminosulfonyl)aminobenzyl)-7-(1-methyl-1H-imidazol-2-yl)-2-oxo-2H-1-benzopyran

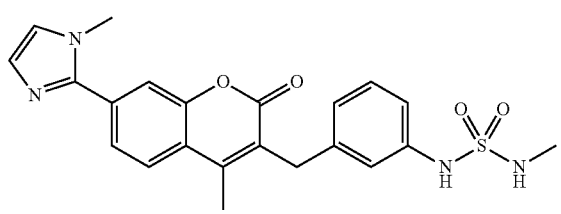

The title compound was synthesized under the same conditions as in the manufacturing example for compound 1j-1-5-2, except that compound 1h-20-1 was used instead of compound 1h-1-5.

¹H-NMR (Bruker (ARX-300), 300 MHz, DMSO-d₆) δ (ppm): 9.57 (1H, s), 7.93 (1H, d, J=8.39 Hz), 7.75 (1H, d, J=8.39 Hz), 7.71 (1H, s), 7.34 (1H, s), 7.21-7.16 (2H, m), 7.05 (3H, s), 6.88 (1H, d, J=7.25 Hz), 3.97 (2H, s), 3.85 (3H, s), 2.50 (3H, s), 2.43 (3H, s).

MS (Micromass, Quattromicro, ESI+) m/z: 439.00 (M+1).

Compound 1j-30-1-2

N-Methyl-N-2-hydroxyethylcarbamic acid 4-methyl-3-(3-(methylaminosulfonyl)aminobenzyl)-2-oxo-2H-1-benzopyran-7-yl ester

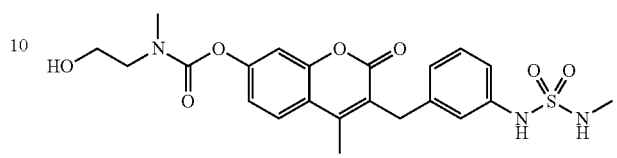

Compound 1j-0-1-2 (7-hydroxy-4-methyl-3-(3-(methylaminosulfonyl)aminobenzyl)-2-oxo-2H-1-benzopyran) was synthesized under the same conditions as in the manufacturing example for compound 1j-1-5-2, except that compound 4a-0-1 was used instead of compound 1h-1-5.

The title compound was synthesized under the same conditions as in the manufacturing example for compound 1j-31-1-2, except that N-methyl-N-2-hydroxyethylamine was used instead of N-methyl-N-carbamoylmethylamine.

¹H-NMR (Broker (ARX-300), 300 MHz, MeOD-d4) δ (ppm): 7.83 (1H, d, J=8.77 Hz), 7.25-7.09 (5H, m), 7.03 (1H, d, J=7.25 Hz), 4.06 (2H, s), 3.78 (2H, t), 3.60 (2H, t), 3.22-3.10 (3H, bs), 2.50 (3H, s), 2.46 (3H, s).

MS (Micromass, Quattromicro, ESI+) m/z: 498.35 (M+Na).

Compound 1j-31-1-2

N-Methyl-N-carbamoylmethylcarbamic acid 4-methyl-3-(3-(methylaminosulfonyl)aminobenzyl)-2-oxo-2H-1-benzopyran-7-yl ester

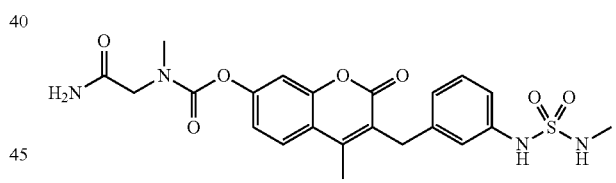

Compound 1j-0-1-2 (7-hydroxy-4-methyl-3-(3-(methylaminosulfonyl)aminobenzyl)-2-oxo-2H-1-benzopyran) was synthesized under the same conditions as in the manufacturing example for compound 1j-1-5-2, except that compound 4a-0-1 was used instead of compound 1h-1-5.

Next, triethylamine (86 μL, 0.62 mmol) and p-NO₂PhCOCl (27 μL, 0.13 mmol) were added to a dimethylformamide solution (1 mL) of compound 1j-0-1-2 (33.4 mg, 0.09 mmol) at room temperature, and after stirring for 30 minutes, N-methyl-N-carbamoylmethylamine (33 uL, 0.27 mmol) was further added, and the mixture was stirred for 10 minutes. Water was then added, and the organic layer was extracted twice with ethyl acetate, and purified by silica gel chromatography (methylene chloride:methanol=20:1) to yield the title compound (18 mg, 41%).

¹H-NMR (Broker (ARX-300), 300 MHz, MeOD-d₄)d (ppm): 7.85 (1H, dd, J=8.39 Hz), 7.27-7.10 (5H, m), 6.97 (1H, d, J=7.63 Hz), 4.09 (1H, s), 4.06 (3H, s), 3.30-3.21 (3H, bs), 2.50 (3H, s), 2.46 (3H, s).

MS (Micromass, Quattromicro, ESI+) m/z: 511.42 (M+1).

Compound 1j-1-3-3

Dimethylcarbamic acid 6-chloro-4-methyl-3-{3-(dimethylaminosulfonyl)aminobenzyl}-2-oxo-2H-1-benzopyran-7-yl ester

[Chemical Formula 118]

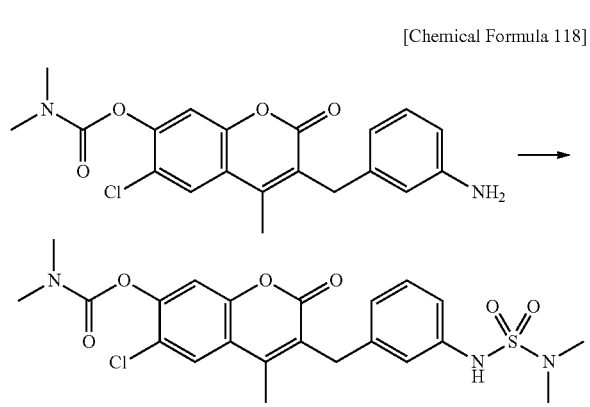

Compound 1h-1-3 (50 mg, 0.129 mmol) was dissolved in dichloromethane (1 mL), and pyridine (42 μL, 0.516 mmol) and dimethylsulfamoyl chloride (41 μL, 0.387 mmol) were added thereto. The mixture was stirred at room temperature for 24 hours. The solvent in the reaction solution was distilled away under reduced pressure, and the resultant residue was purified by amino gel column chromatography (dichloromethane) to yield the title compound (50 mg, 79%) as a white solid.

$^1$H NMR (CDCl$_3$, 270 MHz) δ (ppm): 2.45 (3H, s), 2.76 (6H, s), 3.05 (3H, s), 3.22 (3H, s), 4.05 (2H, s), 6.80-7.60 (5H, m), 7.68 (1H, s).

ESI (LC/MS positive mode) m/z: 494 (M+H).

Compound 1j-1-3-3Na

Dimethylcarbamic acid 3-(3-(N,N-dimethylsulfamoyl)aminobenzyl)-6-chloro-4-methyl-2-oxo-2H-1-benzopyran-7-yl ester sodium salt

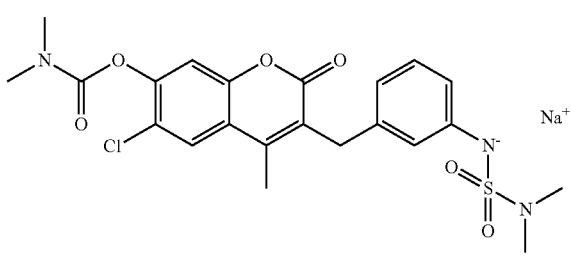

The title compound was synthesized under the same conditions as in the manufacturing example for compound 1j-1-5-1Na, except that compound 1j-1-3-3 was used instead of compound 1j-1-5-1.

$^1$H NMR (CD$_3$OD) δ (ppm): 7.90 (1H, s), 7.31 (1H, s), 7.03-6.90 (3H, m), 6.65 (1H, d, J=7.4 Hz), 4.01 (2H, s), 3.18 (3H, s), 3.02 (3H, s), 2.61 (6H, s), 2.46 (3H, s).

ESI (LC/MS positive mode) m/z: 494 (M+2H−Na).

Compound 1j-1-3-3K

Dimethylcarbamic acid 3-(3-(N,N-dimethylsulfamoyl)aminobenzyl)-6-chloro-4-methyl-2-oxo-2H-1-benzopyran-7-yl ester potassium salt

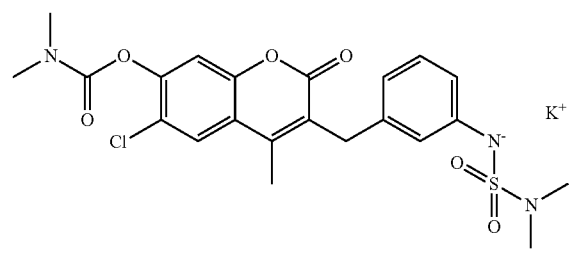

The title compound was synthesized under the same conditions as in the manufacturing example for compound 1j-1-5-1Na, except that compound 1j-1-3-3 was used instead of compound 1j-1-5-1, and that KOH was used instead of NaOH.

$^1$H NMR (CD$_3$OD) δ (ppm): 7.90 (1H, s), 7.31 (1H, s), 7.03-6.90 (3H, m), 6.65 (1H, d, J=7.4 Hz), 4.01 (2H, s), 3.18 (3H, s), 3.02 (3H, s), 2.61 (6H, s), 2.46 (3H, s).

ESI (LC/MS positive mode) m/z: 494 (M+2H−K).

Compound 1j-2-4-3

3-{2-Fluoro-3-(dimethylaminosulfonyl)aminobenzyl}-4-methyl-7-(pyrimidin-2-yloxy)-2-oxo-2H-1-benzopyran

[Chemical Formula 119]

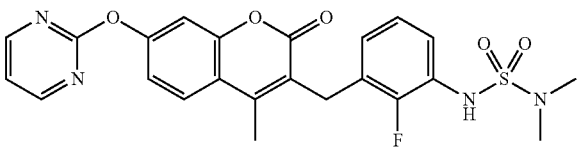

The title compound was synthesized under the same conditions as in the manufacturing example for compound 1j-1-3-3, except that compound 1h-2-4 was used instead of compound 1h-1-3.

$^1$H NMR (270 MHz, DMSO-d$_6$) δ (ppm): 2.48 (3H, s), 2.69 (6H, s), 4.00 (2H, s), 6.88-6.97 (1H, m), 6.97-7.06 (1H, m), 7.24-7.40 (4H, m), 7.91 (1H, J=8.9 Hz), 8.69 (2H, d, J=4.8 Hz), 9.66 (1H, br.s).

ESI (LC/MS positive mode) m/z: 485 (M+H).

Compound 1j-1b-1-3

3-{3-(Dimethylaminosulfonyl)aminobenzyl}-7-isobutoxy-4-methyl-2-oxo-2H-1-benzopyran

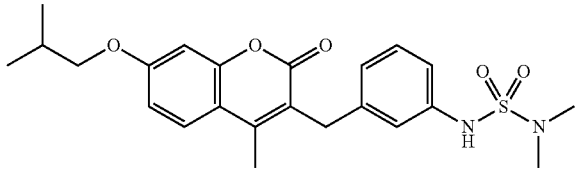

The title compound was synthesized under the same conditions as in the manufacturing example for compound 1j-1-3-3, except that compound 1h-1b-1 was used instead of compound 1h-1-3.

¹H-NMR (270 MHz, DMSO-d₆) δ (ppm): 0.98 (3H, s), 1.00 (3H, s), 1.98-2.10 (1H, m), 2.41 (3H, s), 2.61 (6H, s), 3.86 (2H, d, J=6.6 Hz), 3.90 (2H, s), 6.91 (1H, J=7.8 Hz), 6.94-7.04 (4H, m), 7.18 (1H, dd, J=7.8, 7.6 Hz), 7.75 (1H, d, J=9.6 Hz), 9.79 (1H, br.s).

ESI (LC-MS positive mode) m/z: 445 (M+H).

Compound 1j-1c-1-3

3-{3-(Dimethylaminosulfonyl)aminobenzyl}-7-(2-fluoroethoxy)-4-methyl-2-oxo-2H-1-benzopyran

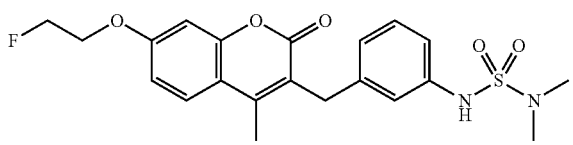

The title compound was synthesized under the same conditions as in the manufacturing example for compound 1j-1-3-3, except that compound 1h-1c-1 was used instead of compound 1h-1-3.

¹H-NMR (270 MHz, DMSO-d₆) δ (ppm): 2.43 (3H, s), 2.61 (6H, s), 3.91 (2H, s), 4.28-4.33 (1H, m), 4.40-4.44 (1H, m), 4.67-4.71 (1H, m), 4.84-4.89 (1H, m), 6.91 (1H, J=7.4 Hz), 6.97-7.06 (4H, m), 7.18 (1H, dd, J=8.0, 7.6 Hz), 7.77 (1H, d, J=8.6 Hz), 9.79 (1H, br.s).

ESI (LC-MS positive mode) m/z: 435 (M+H).

Compound 1j-1c-3-3

3-{3-(Dimethylaminosulfonyl)aminobenzyl}-6-chloro-7-(2-fluoroethoxy)-4-methyl-2-oxo-2H-1-benzopyran

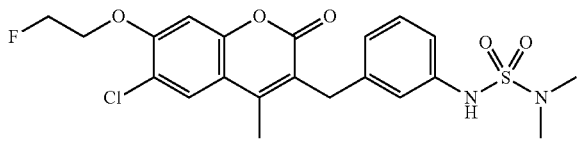

The title compound was synthesized under the same conditions as in the manufacturing example for compound 1j-1-3-3, except that compound 1h-1c-3 was used instead of compound 1h-1-3.

¹H-NMR (270 MHz, DMSO-d₆) δ (ppm): 2.43 (3H, s), 2.62 (6H, s), 3.91 (2H, s), 4.38-4.43 (1H, m), 4.40-4.45 (1H, m), 4.70-4.75 (1H, m), 4.87-4.92 (1H, m), 6.91 (1H, d, J=7.9 Hz), 7.00 (1H, d, J=7.9 Hz), 7.03 (1H, s), 7.18 (1H, dd, J=7.9, 7.9 Hz), 7.30 (1H, s), 7.93 (1H, s), 9.80 (1H, br.s).

ESI (LC-MS positive mode) m/z: 469 (M+H).

Compound 1j-1d-1-3

Pyrrolidine-1-carboxylic acid 3-(3-(dimethylaminosulfonyl)aminobenzyl)-4-methyl-2-oxo-2H-1-benzopyran-7-yl ester

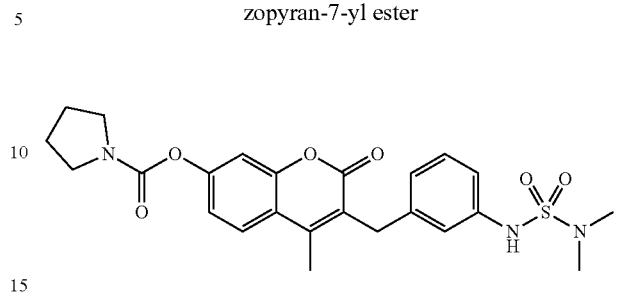

The title compound was synthesized under the same conditions as in the manufacturing example for compound 1j-1-2-3, except that compound 1h-1d-1 was used instead of compound 1h-1-3.

¹H-NMR (CDCl₃, 270 MHz) δ (ppm): 1.92-2.04 (4H, m), 2.45 (3H, s), 2.80 (6H, s), 3.50 (2H, t, J=6.7 Hz), 3.59 (2H, t, J=6.7 Hz), 4.03 (2H, s), 6.37 (1H, brs), 6.97-7.08 (3H, m), 7.12-7.16 (2H, m), 7.19 (1H, d, J=7.4 Hz), 7.61 (1H, d, J=9.4 Hz).

ESI (LC/MS positive mode) m/z: 486 (M+H).

Compound 1j-11-3-3

4-Methyl-3-(3-(dimethylaminosulfonyl)aminobenzyl)-7-(thiophen-3-yl)-6-chloro-2-oxo-2H-1-benzopyran

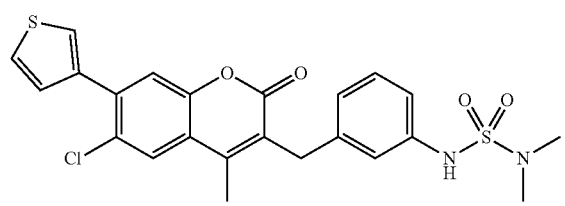

The title compound was synthesized under the same conditions as in the manufacturing example for compound 1j-1-3-3, except that compound 1h-11-3 was used instead of compound 1h-1-3.

¹H-NMR (Bruker (ARX-300), 300 MHz, CDCl₃) δ (ppm): 7.70 (1H, s), 7.58 (1H, dd, J=3.05, 1.53 Hz), 7.42 (1H, dd, J=4.96, 0.60 Hz), 7.38 (1H, s), 7.35 (1H, dd, J=4.96, 1.53 Hz), 7.22 (1H, t, J=7.63 Hz), 7.10 (1H, s), 7.02 (2H, dd, J=8.01, 1.91 Hz), 6.43 (1H, s), 4.05 (2H, s), 2.82 (6H, s), 2.47 (3H, s).

MS (Micromass, Quattromicro, ESI−) m/z: 487.25 (M−1).

Compound 1j-12-1-3

4-Methyl-3-(3-(dimethylaminosulfonyl)aminobenzyl)-7-(pyridin-4-yl)-2-oxo-2H-1-benzopyran

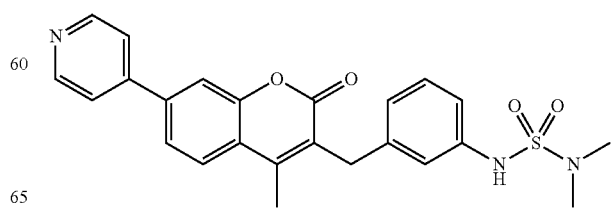

The title compound was synthesized under the same conditions as in the manufacturing example for compound 1j-1-3-3, except that compound 1h-12-1 was used instead of compound 1h-1-3.

$^1$H-NMR (Bruker (ARX-300), 300 MHz, CDCl$_3$) δ (ppm): 8.72 (2H, d, J=4.58 Hz), 7.75 (1H, d, J=8.77 Hz), 7.59 (1H, s), 7.56 (1H, dd, J=6.87, 1.91 Hz), 7.53 (2H, d, J=5.72 Hz), 7.22 (1H, d, J=8.01 Hz), 7.10 (1H, s), 7.05 (1H, d, 8.39 Hz), 7.02 (1H, d, J=7.25 Hz), 6.43 (1H, s), 4.08 (2H, s), 2.82 (6H, s), 2.52 (3H, s).

MS (Micromass, Quattromicro, ESI+) m/z: 450.42 (M+1).

Compound 1j-17-1-2

4-Methyl-3-(3-(methylaminosulfonyl)aminobenzyl)-7-(thiazol-2-yl)-2-oxo-2H-1-benzopyran

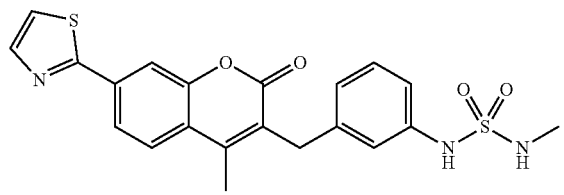

The title compound was synthesized under the same conditions as in the manufacturing example for compound 1j-1-5-2, except that compound 1h-17-1 was used instead of compound 1h-1-5.

$^1$H-NMR (Bruker (ARX-300), 300 MHz, DMSO-d$_6$) δ (ppm): 9.53 (1H, s), 8.02 (1H, d, J=3.05 Hz), 7.96 (2H, s), 7.92 (2H, d, J=3.43 Hz), 7.17 (2H, t, J=8.01 Hz), 7.02 (2H, s), 6.87 (1H, d, J=7.63 Hz), 3.96 (2H, s), 2.50 (3H, s), 2.42 (3H, s).

MS (Micromass, Quattromicro, ESI+) m/z: 463.98 (M+Na).

Compound 1j-18-1-3

4-Methyl-3-(3-(dimethylaminosulfonyl)aminobenzyl)-7-(pyridin-3-yl)-2-oxo-2H-1-benzopyran

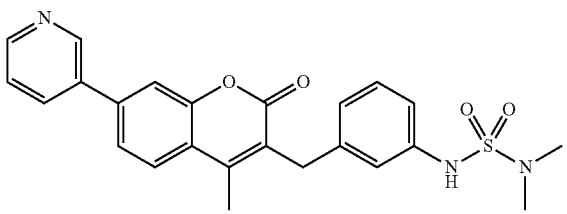

The title compound was synthesized under the same conditions as in the manufacturing example for compound 1j-1-3-3, except that compound 1h-18-1 was used instead of compound 1h-1-3.

$^1$H-NMR (Broker (ARX-300), 300 MHz, CDCl$_3$) δ (ppm): 8.91 (1H, s), 8.67 (1H, s), 7.92 (1H, d, J=8.01 Hz), 7.74 (1H, d, J=8.77 Hz), 7.55 (1H, s), 7.53 (1H, dd, J=6.10, 1.53 Hz), 7.43 (1H, dd, J=7.25, 0.90 Hz), 7.22 (1H, d, J=8.01 Hz), 7.11 (1H, s), 7.05 (1H, d, J=8.01 Hz), 7.02 (1H, dd, J=8.77, 1.91 Hz), 6.40 (1H, s), 4.07 (2H, s), 2.82 (6H, s), 2.52 (3H, s).

MS (Micromass, Quattromicro, ESI+) m/z: 450.44 (M+1).

Compound 1h-19-3-3

4-Methyl-3-(3-(dimethylaminosulfonyl)aminobenzyl)-6-chloro-7-(3-methoxyphenyl)-2-oxo-2H-1-benzopyran

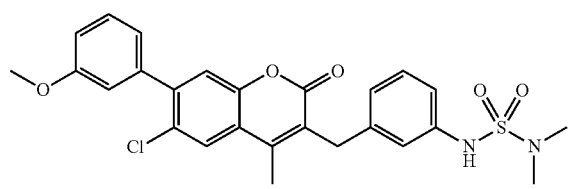

The title compound was synthesized under the same conditions as in the manufacturing example for compound 1j-1-3-3, except that compound 1h-19-3 was used instead of compound 1h-1-3.

$^1$H-NMR (Bruker (ARX-300), 300 MHz, CDCl$_3$) δ (ppm): 7.71 (1H, s), 7.39 (1H, td, J=9.16, 1.14 Hz), 7.32 (1H, s), 7.22 (1H, t, J=8.01 Hz), 7.10 (1H, t, J=1.53 Hz), 7.04-6.96 (5H, m), 6.40 (1H, s), 4.06 (2H, s), 3.86 (3H, s), 2.82 (6H, s), 2.49 (3H, s).

MS (Micromass, Quattromicro, ESI−) m/z: 511.03 (M−1).

Compound 1h-21-3-3

4-Methyl-3-(3-(dimethylaminosulfonyl)aminobenzyl)-6-chloro-7-(5-acetylthiophen-2-yl)-2-oxo-2H-1-benzopyran

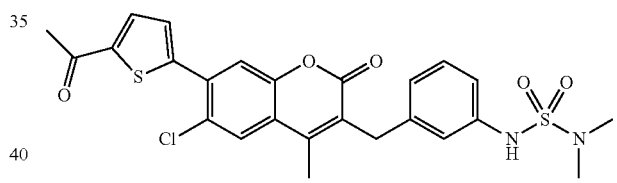

The title compound was synthesized under the same conditions as in the manufacturing example for compound 1j-1-3-3, except that compound 1h-21-3 was used instead of compound 1h-1-3.

$^1$H-NMR (Bruker (ARX-300), 300 MHz, CDCl$_3$) δ (ppm): 7.77 (2H, m), 7.44 (2H, m), 7.26 (1H, t), 7.02-7.00 (3H, m), 6.76 (1H, s), 4.04 (2H, s), 2.81 (6H, s), 2.59 (3H, s), 2.46 (3H, s).

MS (Micromass, Quattromicro, ESI−) m/z: 529.15 (M−H).

Compound 1j-22-1-3

4-Methyl-3-(3-(dimethylaminosulfonyl)aminobenzyl)-7-(3-acetylphenyl)-2-oxo-2H-1-benzopyran

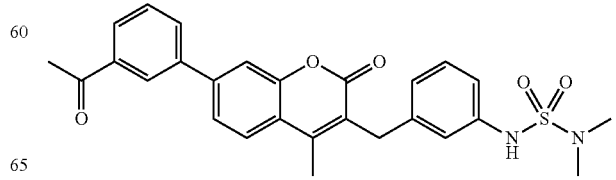

The title compound was synthesized under the same conditions as in the manufacturing example for compound 1j-1-3-3, except that compound 1h-22-1 was used instead of compound 1h-1-3.

¹H-NMR (Bruker (ARX-300), 300 MHz, CDCl₃) δ (ppm): 8.22 (1H, s), 8.00 (1H, d, J=7.63 Hz), 7.81 (1H, d, J=8.01 Hz), 7.69 (1H, d, J=8.77 Hz), 7.62-7.54 (4H, m), 7.22 (1H, t), 7.14-7.00 (2H, m), 6.48 (1H, bs), 3.95 (2H, s), 2.81 (6H, s), 2.61 (3H, s), 2.51 (3H, s).

MS (Micromass, Quattromicro, ESI+) m/z: 513.14 (M+Na).

Compound 1j-23-1-3

4-Methyl-3-(3-(dimethylaminosulfonyl)aminobenzyl)-7-(4-acetylphenyl)-2-oxo-2H-1-benzopyran

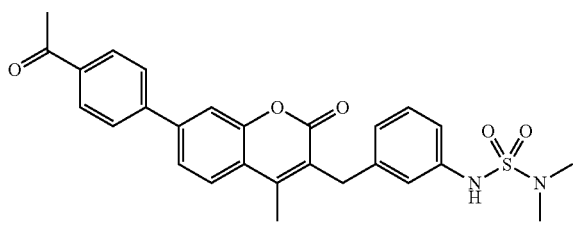

The title compound was synthesized under the same conditions as in the manufacturing example for compound 1j-1-3-3, except that compound 1h-23-1 was used instead of compound 1h-1-3.

¹H-NMR (Bruker (ARX-300), 300 MHz, CDCl₃) δ (ppm): 8.08 (2H, d, J=8.77 Hz), 7.73 (4H, d, J=8.77 Hz), 7.56 (2H, m), 7.19 (3H, m), 6.48 (1H, bs), 4.15 (2H, s), 2.81 (6H, s), 2.65 (3H, s), 2.51 (3H, s).

MS (Micromass, Quattromicro, ESI−) m/z: 489.07 (M−1).

Compound 1j-1e-1-3

Trifluoromethanesulfonic acid 4-methyl-3-(3-(dimethylaminosulfonyl)aminobenzyl)-2-oxo-2H-1-benzopyran-7-yl ester

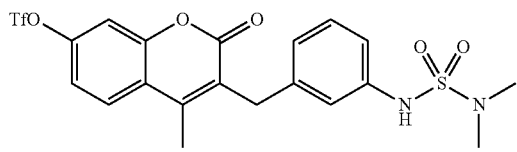

The title compound was synthesized under the same conditions as in the manufacturing example for compound 1j-1-3-3, except that compound 1h-1e-1 was used instead of compound 1h-1-3.

¹H-NMR (Bruker (ARX-300), 300 MHz, CDCl₃) δ (ppm): 7.63 (2H, d, J=8.77 Hz), 7.22 (2H, m), 7.09 (3H, m), 6.23 (1H, bs), 4.02 (2H, s), 2.72 (6H, s), 2.46 (3H, s).

MS (Micromass, Quattromicro, ESI−) m/z: 519.14 (M−1).

Compound 1j-24-1-3

4-Methyl-3-(3-(dimethylaminosulfonyl)aminobenzyl)-7-(3-cyanophenyl)-2-oxo-2H-1-benzopyran

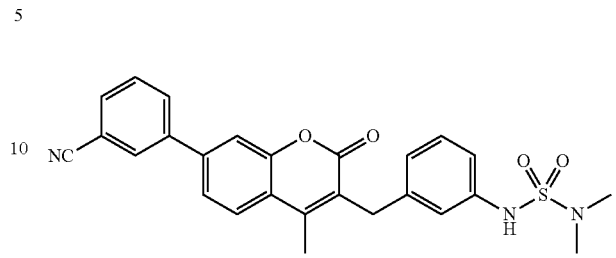

The title compound was synthesized under the same conditions as in the manufacturing example for compound 1g-11-3, except that compound 1j-1e-1-3 was used instead of compound 1g-1e-3, and that 3-cyanophenylboronic acid was used instead of thiophene-3-boronic acid.

¹H-NMR (Bruker (ARX-300), 300 MHz, CDCl₃) δ (ppm): 7.91 (1H, t), 7.82 (1H, d, J=7.63 Hz), 7.78-7.65 (2H, m), 7.60 (1H, t), 7.46 (2H, m), 7.20 (1H, t), 7.06 (1H, s) 7.03 (2H, t), 6.29 (1H, bs), 4.15 (2H, s), 2.81 (6H, s), 2.51 (3H, s).

MS (Micromass, Quattromicro, ESI+) m/z: 474.27 (M+1).

Compound 1j-25-1-3

4-Methyl-3-(3-(dimethylaminosulfonyl)aminobenzyl)-7-(2-methoxyphenyl)-2-oxo-2H-1-benzopyran

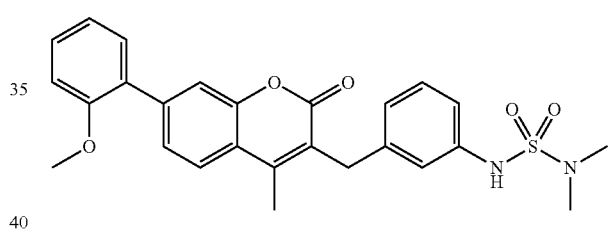

The title compound was synthesized under the same conditions as in the manufacturing example for compound 1g-11-3, except that compound 1j-1e-1-3 was used instead of compound 1g-1e-3, and that 2-methoxyphenylboronic acid was used instead of thiophene-3-boronic acid.

¹H-NMR (Bruker (ARX-300), 300 MHz, CDCl₃) δ (ppm): 7.66 (1H, d, J=8.77 Hz), 7.58 (2H, dd, J=8.77 Hz), 7.51 (2H, m), 7.25 (1H, t), 7.18 (1H, s), 7.05 (4H, m), 6.45 (1H, bs), 4.15 (2H, s), 3.81 (3H, s), 2.81 (6H, s), 2.49 (3H, s).

MS (Micromass, Quattromicro, ESI+) m/z: 479.37 (M+1).

Compound 1j-26-1-3

4-Methyl-3-(3-(dimethylaminosulfonyl)aminobenzyl)-7-(4-cyanophenyl)-2-oxo-2H-1-benzopyran

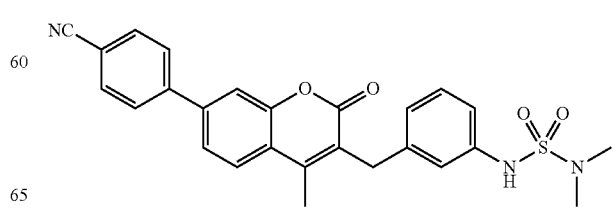

The title compound was synthesized under the same conditions as in the manufacturing example for compound 1g-11-3, except that compound 1j-1e-1-3 was used instead of compound 1g-1e-3, and that 4-cyanophenylboronic acid was used instead of thiophene-3-boronic acid.

¹H-NMR (Bruker (ARX-300), 300 MHz, CDCl₃) δ (ppm): 7.80-7.70 (5H, m), 7.72 (2H, m), 7.22 (1H, t), 7.10 (1H, s) 7.03 (2H, m), 6.29 (1H, bs), 4.15 (2H, s), 2.81 (6H, s), 2.51 (3H, s).

MS (Micromass, Quattromicro, ESI+) m/z: 474.27 (M+1).

Compound 1j-27-1-3

4-Methyl-3-(3-(dimethylaminosulfonyl)aminobenzyl)-7-(4-methoxyphenyl)-2-oxo-2H-1-benzopyran

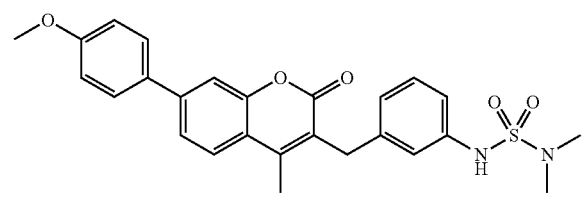

The title compound was synthesized under the same conditions as in the manufacturing example for compound 1g-11-3, except that compound 1j-1e-1-3 was used instead of compound 1g-1e-3, and that 4-methoxyphenylboronic acid was used instead of thiophene-3-boronic acid.

¹H-NMR (Bruker (ARX-300), 300 MHz, CDCl₃) δ (ppm): 8.08 (1H, d, J=8.01 Hz), 7.55 (1H, d, J=1.91 Hz), 7.48 (1H, dd, J=8.39 Hz), 7.41-7.32 (2H, m), 7.22 (1H, t), 7.10-6.99 (5H, m), 6.29 (1H, bs), 4.08 (2H, s), 3.84 (3H, s), 2.81 (6H, s), 2.51 (3H, s).

MS (Micromass, Quattromicro, ESI+) m/z: 474.27 (M+1).

Compound 1j-28-1-3

4-Methyl-3-(3-(dimethylaminosulfonyl)aminobenzyl)-7-(4-N,N-dimethylaminophenyl)-2-oxo-2H-1-benzopyran

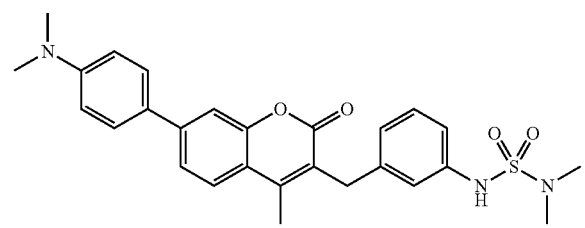

The title compound was synthesized under the same conditions as in the manufacturing example for compound 1j-1-3-3, except that compound 1h-28-1 was used instead of compound 1h-1-3.

¹H-NMR (Bruker (ARX-300), 300 MHz, CDCl₃) δ (ppm): 7.61 (5H, m), 7.25 (1H, t), 7.15-7.08 (3H, s, t), 6.82 (2H, d, J=8.77 Hz), 6.39 (1H, bs), 4.04 (2H, s), 3.02 (6H, s), 2.79 (6H, s), 2.43 (3H, s).

MS (Micromass, Quattromicro, ESI+) m/z: 492.32 (M+1).

Compound 1j-29-1-3

4-Methyl-3-(3-methylaminosulfonyl)aminobenzyl)-7-(benzo[1,3]dioxol-4-yl)-2-oxo-2H-1-benzopyran

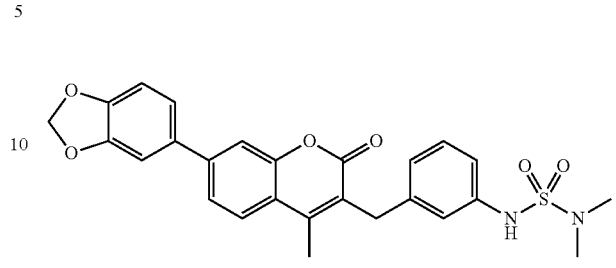

The title compound was synthesized under the same conditions as in the manufacturing example for compound 1g-11-3, except that compound 1j-1e-1-1 was used instead of compound 1g-1e-3, and that benzo[1,3]dioxol-4-boronic acid was used instead of thiophene-3-boronic acid.

¹H-NMR (Bruker (ARX-300), 300 MHz, CDCl₃) δ (ppm): 7.63 (1H, d, J=8.77 Hz), 7.46 (2H, m), 7.23 (1H, t), 7.13 (5H, m), 6.92 (1H, d, J=8.01 Hz), 6.48 (1H, s), 6.02 (2H, s), 4.04 (2H, s), 2.80 (6H, s), 2.47 (3H, s).

MS (Micromass, Quattromicro, ESI−) m/z: 491.34 (M−1).

Compound 1j-1-21-2

Dimethylcarbamic acid 3-(3-(N-(2-cyanoethyl)sulfamoyl)aminobenzyl)-6-chloro-4-methyl-2-oxo-2H-1-benzopyran-7-yl ester

[Chemical Formula 120]

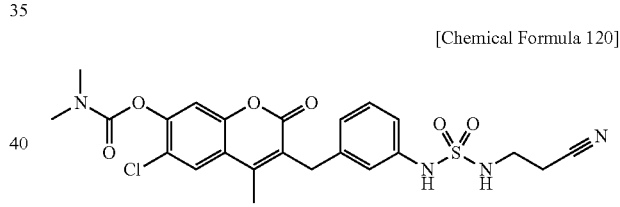

Sulfuryl chloride (66.5 μL, 872 μmol) was dissolved in dichloromethane (4 mL), and 2-cyanoethylamine (57.2 μL, 776 μmol) and DMAP (94.7 mg, 776 μmol) were added thereto at −78° C. The mixture was stirred at room temperature to yield the corresponding sulfamoyl chloride. Dimethylcarbamic acid 3-(3-aminobenzyl)-6-chloro-4-methyl-2-oxo-2H-1-benzopyran-7-yl ester (100 mg, 258.5 μmol), pyridine (0.5 mL) and dichloromethane (2 mL) were added to the reaction solution, and the mixture was stirred at room temperature overnight. Water was then added to the reaction solution, and the mixture was extracted with dichloromethane. After washing with sodium hydrogen carbonate solution and saturated saline, the organic layer was dried over anhydrous magnesium sulfate, and the solvent was distilled away under reduced pressure. The resultant residue was purified by silica gel column chromatography (methanol:methylene chloride=1:20) to yield the title compound (111 mg, 83%).

¹H NMR (CDCl₃, 270 MHz) δ (ppm): 2.44 (3H, s), 2.44-2.55 (2H, m), 3.04 (3H, s), 3.17 (3H, s), 3.15-3.30 (2H, m), 3.99 (2H, s), 6.92-7.15 (3H, m), 7.20 (1H, s), 7.15-7.25 (1H, m), 7.66 (1H, s).

ESI (LC/MS positive mode) m/z: 519 (M+H).

Compound 1j-1-21-2Na

Dimethylcarbamic acid 3-(3-(N-(2-cyanoethyl)sulfamoyl)aminobenzyl)-6-chloro-4-methyl-2-oxo-2H-1-benzopyran-7-yl ester sodium salt

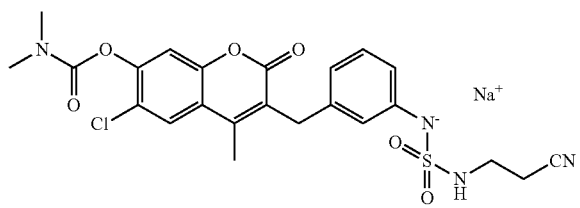

The title compound was synthesized under the same conditions as in the manufacturing example for compound 1j-1-5-1Na, except that compound 1j-1-21-2 was used instead of compound 1j-1-5-1.

$^1$H NMR (CD$_3$OD) δ (ppm): 7.89 (1H, s), 7.30 (1H, s), 7.04-6.98 (3H, m), 6.70 (1H, d, J=7.4 Hz), 3.99 (2H, s), 3.17 (3H, s), 3.02 (3H, s), 2.57-2.52 (2H, m), 2.48 (3H, s).

ESI (LC/MS positive mode) m/z: 519 (M+2H−Na).

Compound 1j-1-21-2K

Dimethylcarbamic acid 3-(3-(N-(2-cyanoethyl)sulfamoyl)aminobenzyl)-6-chloro-4-methyl-2-oxo-2H-1-benzopyran-7-yl ester potassium salt

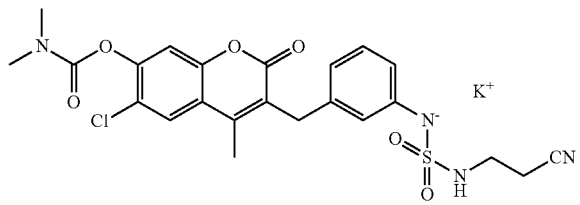

The title compound was synthesized under the same conditions as in the manufacturing example for compound 1j-1-5-1Na, except that compound 1j-1-21-2 was used instead of compound 1j-1-5-1, and that KOH was used instead of NaOH.

$^1$H NMR (CD$_3$OD) δ (ppm): 7.89 (1H, s), 7.30 (1H, s), 7.04-6.98 (3H, m), 6.70 (1H, d, J=7.4 Hz), 3.99 (2H, s), 3.17 (3H, s), 3.02 (3H, s), 2.57-2.52 (2H, m), 2.48 (3H, s).

ESI (LC/MS positive mode) m/z: 519 (M+2H−K).

Compound 1j-1-22-2

Dimethylcarbamic acid 3-(3-(N-(2-hydroxyethyl)sulfamoyl)aminobenzyl)-6-chloro-4-methyl-2-oxo-2H-1-benzopyran-7-yl ester

[Chemical Formula 121]

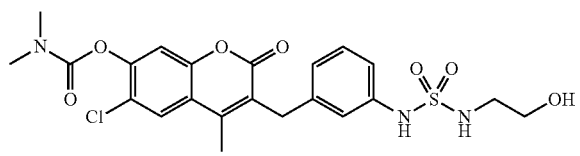

The title compound was synthesized under the same conditions as in the manufacturing example for compound 1j-1-21-2, except that 2-aminoethanol was used instead of 2-cyanoethylamine.

$^1$H NMR (CDCl$_3$, 270 MHz) δ (ppm): 2.44 (3H, s), 3.05 (3H, s), 3.12 (2H, m) 3.17 (3H, s), 3.52 (2H, br), 4.02 (2H, s), 6.92-7.05 (2H, m), 7.09 (1H, brs), 7.19-7.30 (1H, m), 7.66 (1H, s).

ESI (LC/MS positive mode) m/z: 510 (M+H).

Compound 1j-1-23-2

Dimethylcarbamic acid 3-(3-(N-(2-methoxyethyl)sulfamoyl)aminobenzyl)-6-chloro-4-methyl-2-oxo-2H-1-benzopyran-7-yl ester

[Chemical Formula 122]

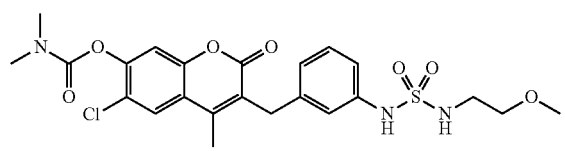

The title compound was synthesized under the same conditions as in the manufacturing example for compound 1j-1-21-2, except that 2-methoxyethylamine was used instead of 2-cyanoethylamine.

$^1$H NMR (CDCl$_3$, 270 MHz) δ (ppm): 2.44 (3H, s), 3.05 (3H, s), 3.17 (3H, s), 3.15-3.25 (2H, s), 3.41 (3H, s), 3.45-3.55 (2H, m), 4.01 (2H, s), 6.95-7.20 (2H, m), 7.09 (1H, s), 7.19-7.30 (1H, in), 7.25 (1H, s), 7.66 (1H, s).

ESI (LC/MS positive mode) m/z: 524 (M+H).

Compound 1j-1-24-2

Dimethylcarbamic acid 3-(3-(N-(2-aminoethyl)sulfamoyl)aminobenzyl)-6-chloro-4-methyl-2-oxo-2H-1-benzopyran-7-yl ester hydrochloride

[Chemical Formula 123]

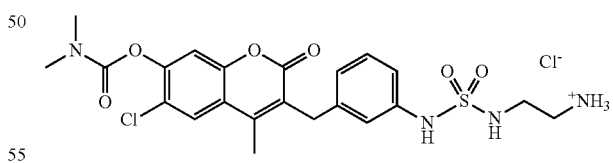

The title compound was synthesized under the same conditions as in the manufacturing example for compound 1j-1-21-2, except that 1,2-ethylenediamine was used instead of 2-cyanoethylamine.

$^1$H NMR (CD$_3$OD, 270 MHz) δ (ppm): 2.51 (3H, s), 2.95-3.05 (2H, m), 3.05 (3H, s), 3.14-3.25 (2H, m), 3.17 (3H, s), 4.05 (2H, s), 6.97 (1H, d, J=8.1 Hz), 7.08 (1H, d, J=8.1 Hz), 7.12 (1H, brs), 7.22 (1H, dd, J=8.1 Hz), 7.32 (1H, s), 7.93 (1H, s).

ESI (LC/MS positive mode) m/z: 509 (M−Cl).

Compound 1j-1-25-2

Dimethylcarbamic acid 3-(3-(N-(2,3-dihydroxypropyl)sulfamoyl)aminobenzyl)-6-chloro-4-methyl-2-oxo-2H-1-benzopyran-7-yl ester

[Chemical Formula 124]

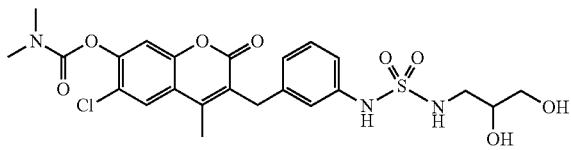

The title compound was synthesized under the same conditions as in the manufacturing example for compound 1j-1-21-2, except that 2,3-dihydroxypropylamine was used instead of 2-cyanoethylamine.

$^1$H NMR (CDCl$_3$, 270 MHz) δ (ppm): 2.38 (3H, s), 3.05 (3H, s), 3.16 (3H, s), 3.30-3.50 (2H, m), 3.52-3.70 (1H, m), 3.89 (2H, s), 6.86 (1H, d, J=7.7 Hz), 6.99 (1H, d, J=7.7 Hz), 7.05 (1H, s), 7.07 (1H, d, J=7.7 Hz), 7.13 (1H, s), 7.60 (1H, s).

ESI (LC/MS positive mode) m/z: 540 (M+H).

Compound 1j-1-26-2

Dimethylcarbamic acid 6-chloro-4-methyl-3-[3-(4-methylpiperazin-1-ylsulfonylamino)benzyl]-2-oxo-2H-1-benzopyran-7-yl ester

[Chemical Formula 125]

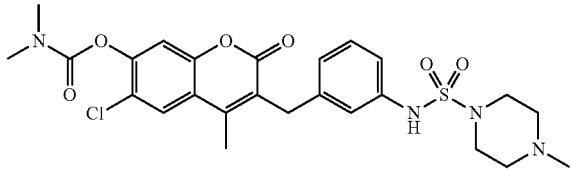

The title compound was synthesized under the same conditions as in the manufacturing example for compound 1j-1-21-2, except that 1-methylpiperazine was used instead of 2-cyanoethylamine.

$^1$H NMR (CDCl$_3$, 270 MHz) δ (ppm): 2.22 (3H, s), 2.25-2.36 (4H, m), 2.43 (3H, s), 3.05 (3H, s), 3.18 (3H, s), 3.20-130 (2H, m), 4.01 (2H, s), 6.95-7.08 (2H, m), 7.15-7.30 (3H, m), 7.65 (1H, s).

ESI (LC/MS positive mode) m/z: 549 (M+H).

Compound 1j-1-28-2

Dimethylcarbamic acid 3-(3-(N—(N'-methyl-2-aminoethyl)-methylsulfamoyl)aminobenzyl)-6-chloro-4-methyl-2-oxo-2H-1-benzopyran-7-yl ester hydrochloride

[Chemical Formula 126]

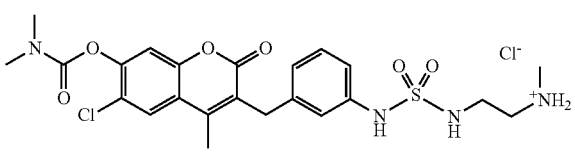

The title compound was synthesized under the same conditions as in the manufacturing example for compound 1j-1-21-2, except that 2-methylaminoethylamine was used instead of 2-cyanoethylamine.

$^1$H NMR (CDCl$_3$, 270 MHz) δ (ppm): 2.41 (3H, brs), 3.00 (6H, s), 3.05 (3H, brs), 3.17 (3H, brs), 3.50-3.65 (2H, m), 3.65-3.75 (2H, m), 3.98 (2H, brs), 6.70-7.60 (5H, m), 7.60 (1H, brs).

ESI (LC/MS positive mode) m/z: 523 (M−Cl).

Compound 1j-1-29-2

Dimethylcarbamic acid 6-chloro-3-[3-(3,4-dihydro-1H-isoquinolin-2-ylsulfonylamino)benzyl]-4-methyl-2-oxo-2H-1-benzopyran-7-yl ester

[Chemical Formula 127]

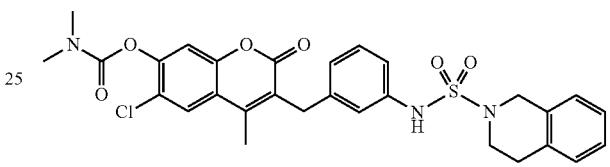

The title compound was synthesized under the same conditions as in the manufacturing example for compound 1j-1-21-2, except that isoquinoline was used instead of 2-cyanoethylamine.

$^1$H NMR (CDCl$_3$, 270 MHz) δ (ppm): 2.30 (3H, s), 2.74 (2H, m), 3.10 (3H, s), 3.17 (3H, s), 3.48 (2H, m), 3.95 (2H, s), 4.42 (2H, s), 6.92-7.27 (9H, m), 7.56 (1H, s).

ESI (LC/MS positive mode) m/z: 582 (M+H).

Compound 1j-1-30-2

Dimethylcarbamic acid 3-(3-(N-2,2,2-trifluoroethylsulfamoyl)aminobenzyl)-6-chloro-4-methyl-2-oxo-2H-1-benzopyran-7-yl ester

[Chemical Formula 128]

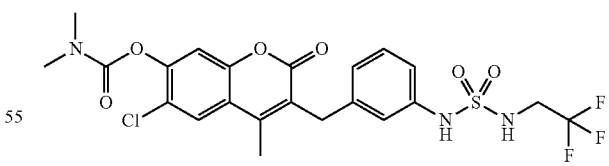

The title compound was synthesized under the same conditions as in the manufacturing example for compound 1j-1-21-2, except that 2,2,2-trifluoroethylamine was used instead of 2-cyanoethylamine.

$^1$H NMR (CDCl$_3$, 270 MHz) δ (ppm): 2.45 (3H, s), 3.04 (3H, s), 3.18 (3H, s), 3.55-3.70 (2H, m), 4.02 (2H, s), 7.00-7.10 (3H, m), 7.20-7.30 (1H, m), 7.62 (1H, s).

ESI (LC/MS positive mode) m/z: 548 (M+H).

Compound 1j-1-31-2

Dimethylcarbamic acid 3-(3-(N-methoxysulfamoyl)aminobenzyl)-6-chloro-4-methyl-2-oxo-2H-1-benzopyran-7-yl ester

[Chemical Formula 129]

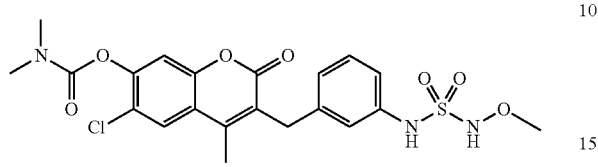

The title compound was synthesized under the same conditions as in the manufacturing example for compound 1j-1-21-2, except that O-methylhydroxylamine was used instead of 2-cyanoethylamine.

$^1$H NMR (CDCl$_3$, 270 MHz) δ (ppm): 2.45 (3H, s), 3.04 (3H, s), 3.18 (3H, s), 3.76 (3H, s), 4.02 (2H, s), 6.78 (1H, brs), 7.00-7.30 (3H, m), 7.65 (1H, s).

ESI (LC/MS positive mode) m/z: 496 (M+H).

Compound 1j-1-32-2

Dimethylcarbamic acid 3-[3-(2-acetylamino-ethanesulfonylamino)benzyl]-6-chloro-4-methyl-2-oxo-2H-1-benzopyran-7-yl ester

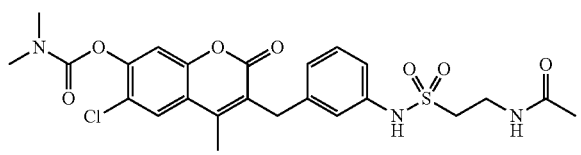

Compound 1h-1-3 (5.8 g, 15 mmol), 2-phthalimidoethanesulfonyl chloride (6.1 g) and triethylamine (10.4 mL) were stirred in dichloromethane at room temperature overnight. Water was then added to the reaction mixture, and extraction was performed with ethyl acetate. The organic extract was washed with hydrochloric acid, sodium bicarbonate water and saturated saline. After drying over magnesium sulfate, the mixture was concentrated under reduced pressure to yield a crude product, which was then purified by column chromatography to yield a compound (9.4 g).

A portion (5.0 g) of the obtained compound and hydrazine monohydrate (0.94 mL) were stirred in an ethanol/THF mixed solvent at room temperature overnight. Water was then added to the reaction mixture, and extraction was performed with ethyl acetate. The organic extract was washed with sodium bicarbonate water and saturated saline. After drying over magnesium sulfate, the mixture was concentrated under reduced pressure to yield a crude product, which was then purified by column chromatography to yield a compound (848 mg).

A portion (50.8 mg) of the obtained compound, acetyl chloride (9.5 μL) and triethylamine (28.5 μL) were stirred in methylene chloride at 0° C. for 2 hours. Water was then added to the reaction mixture, and extraction was performed with ethyl acetate. The organic extract was washed with sodium bicarbonate water and saturated saline. After drying over magnesium sulfate, the mixture was concentrated under reduced pressure to yield a crude product, which was then purified by column chromatography to yield the title compound (56 mg). $^1$H-NMR (CDCl$_3$, 270 MHz) δ (ppm): 1.88 (3H, s), 2.25 (3H, s), 3.04 (3H, s), 3.10-3.30 (5H, m), 3.50-3.70 (2H, m), 4.00 (2H, s), 6.95-8.00 (6H, m).

ESI (LC/MS positive mode) m/z: 536 (M+H).

Compound 1j-1-33-2

Dimethylcarbamic acid 6-chloro-4-methyl-2-oxo-3-[3-(2-oxo-oxazolidine-3-sulfonylamino)benzyl]-2H-1-benzopyran-7-yl ester

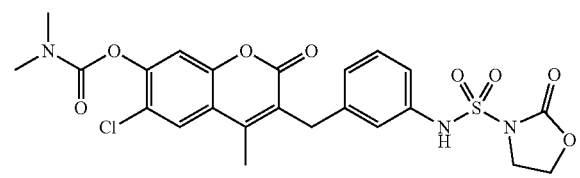

The title compound was synthesized under the same conditions as in the manufacturing example for compound 1j-1-21-2, except that oxazolidinone was used instead of 2-cyanoethylamine.

$^1$H-NMR (CDCl$_3$, 270 MHz) δ (ppm): 2.25 (3H, s), 2.95 (3H, s), 3.10 (3H, s), 3.60-3.80 (2H, m), 3.98 (2H, s), 4.10-4.30 (2H, m), 6.95-7.10 (3H, m), 7.25 (1H, t, J=7.7 Hz), 7.50 (1H, s), 8.05 (1H, s), 10.80 (1H, brs).

ESI (LC/MS positive mode) m/z: 536 (M+H).

Compound 1j-1d-1-2

Pyrrolidine-1-carboxylic acid 3-(3-(N-methylsulfamoyl)aminobenzyl)-4-methyl-2-oxo-2H-1-benzopyran-7-yl ester

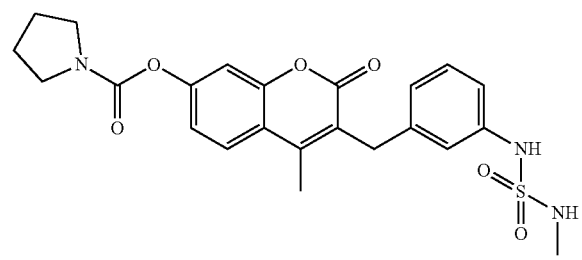

The title compound was synthesized under the same conditions as in the manufacturing example for compound 1j-1-3-2, except that compound 1h-1d-1 was used instead of compound 1h-1-3.

$^1$H-NMR (DMSO-d$_6$, 270 MHz) δ (ppm): 1.84-1.94 (4H, m), 2.42 (3H, d, J=3.3 Hz), 2.46 (3H, s), 3.36 (2H, t, J=6.6 Hz), 3.52 (2H, t, J=6.6 Hz), 3.93 (2H, s), 6.86 (1H, d, J=7.8 Hz), 6.98-7.05 (2H, m), 7.13-7.23 (3H, m), 7.26 (1H, d, J=2.3 Hz), 7.86 (1H, d, J=8.9 Hz), 9.53 (1H, brs).

ESI (LC/MS positive mode) m/z: 472 (M+H).

Compound 1j-1-72-2

Dimethylcarbamic acid 3-(3-(N-methylsulfamoyl)aminobenzyl)-4-methyl-2-oxo-2H-pyrano[2,3-b]pyridin-7-yl ester

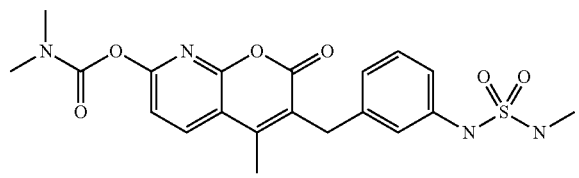

The title compound was synthesized under the same conditions as in the manufacturing example for compound 1j-1-3-2, except that compound 1h-1-72 was used instead of compound 1h-1-3.

$^1$H-NMR (DMSO-$d_6$, 270 MHz) δ (ppm): 2.42 (3H, s), 2.47 (3H, s), 2.95 (3H, s), 3.06 (3H, s), 3.94 (2H, s), 6.87 (1H, d, J=7.3 Hz), 7.01 (1H, s), 7.02 (1H, d, 7.1 Hz), 7.14-7.20 (2H, m), 7.27 (1H, d, J=8.2 Hz), 8.43 (1H, d, J=8.2 Hz), 9.53 (1H, brs).

ESI (LC/MS positive mode) m/z: 447 (M+H).

Compound 1o-2-4-2

2-{2-Fluoro-3-[4-methyl-2-oxo-7-(pyrimidin-2-yloxy)-2H-1-benzopyran-3-ylmethyl]phenylsulfamoyl}-N-methyl-acetamide

Step 1 (Preparation of THF Solution of Compound 1l-1)

2-Propanol (130 μL, 1.69 mmol) was added to a solution of chlorosulfonyl acetyl chloride (1180 μL, 1.69 mmol) in THF (3 mL) at 0° C. under nitrogen atmosphere, and the mixture was stirred at 0° C. for 20 minutes. The mixture was further stirred at room temperature for 2 hours to yield a THF solution of compound 1l-1 quantitatively.

Step 2 (Synthesis of Compound 1m-2-4)

A THF solution of compound 1l-1 obtained in step 1 (1.04 mL, 0.585 mmol) was added dropwise under nitrogen atmosphere to a solution of compound 1h-2-4 (214.4 mg, 0.568 mmol) and diisopropylethylamine (228 μL, 1.306 mmol) in THF (8 mL). After stirring at room temperature for 40 minutes, a solution of sodium hydroxide (46.9 mg, 2.346 mmol) in water (8 mL), and methanol (0.5 mL) were added, and the mixture was stirred for 1 hour. Ethyl acetate (40 mL) was then added to the reaction solution, and the solution was washed twice with 1N hydrochloric acid (20 mL) and once with saturated saline (30 mL). The resultant organic layer was dried over sodium sulfate, and the solvent was distilled away under reduced pressure. The resultant residue was purified by silica gel chromatography (dichloromethane:methanol=10:1) to yield compound 1m-2-4 (65.9 mg, 23%) as a pale yellow solid.

$^1$H NMR (270 MHz, DMSO-$d_6$) δ (ppm): 2.47 (3H, s), 3.67 (2H, s), 4.00 (2H, s), 6.80-6.88 (1H, m), 6.95-7.04 (1H, m), 7.22-7.36 (3H, m), 7.38 (1H, d, J=2.3 Hz), 7.91 (1H, d, J=8.9 Hz), 8.69 (2H, d, J=4.8 Hz).

ESI (LC/MS positive mode) m/z: 500 (M+H).

[Chemical Formula 130]

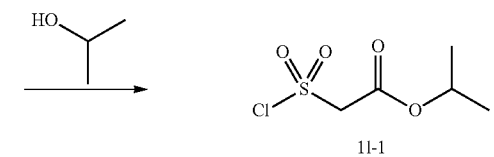

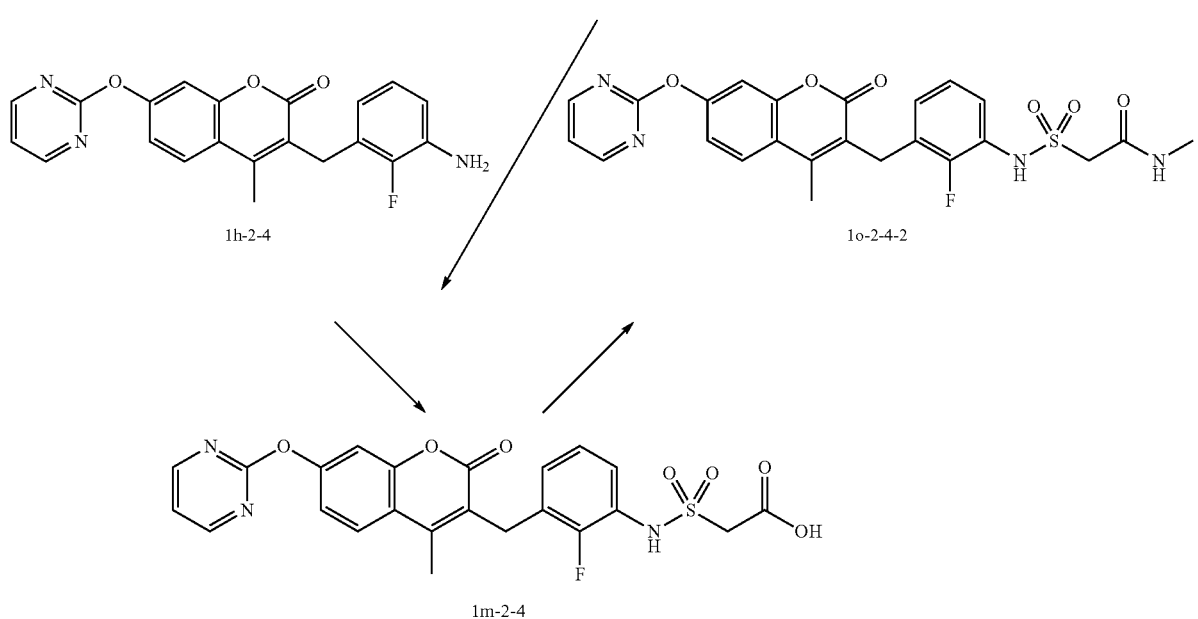

Step 3 (Synthesis of Compound 1o-2-4-2)

N,N-dimethylformamide (1 mL) was added to compound 1m-2-4 (32 mg, 0.064 mmol), 1-ethyl-3-(3-dimethylaminopropyl)carbodiimide hydrochloride (14.5 mg, 0.076 mmol) and 3-hydroxy-3,4-dihydro-4-oxo-1,2,3-benzotriazole (12.4 mg, 0.076 mmol). A 2.0 M methylamine THF solution (96 μL, 0.192 mmol) and diisopropylethylamine (22.3 μL, 0.128 mmol) were added thereto, and the mixture was stirred at room temperature under nitrogen atmosphere for 19 hours. Ethyl acetate (20 mL) was then added to the reaction solution, and the solution was washed twice with 1N hydrochloric acid (20 mL), three times with saturated sodium hydrogen carbonate solution (20 mL) and further once with saturated saline. The resultant organic layer was dried over sodium sulfate, and the solvent was distilled away under reduced pressure. The resultant residue was purified by silica gel column chromatography (methylene chloride:methanol=10:1) and the title compound (9 mg, 28%) was obtained as a white solid.

$^1$H NMR (270 MHz, DMSO-$d_6$) δ (ppm): 2.48 (3H, s), 2.61 (3H, d, J=4.5 Hz), 4.00 (2H, s), 6.95-7.11 (2H, m), 7.25-7.30 (4H, m), 7.92 (1H, d, J=8.9 Hz), 8.15-8.23 (1H, m), 8.69 (2H, d, J=4.8 Hz), 9.71 (1H, s).

ESI (LC/MS positive mode) m/z: 513 (M+H).

Compound 1o-1-3-1

Dimethylcarbamic acid 3-(3-carbamoylmethanesulfonylamino-benzyl)-6-chloro-4-methyl-2-oxo-2H-1-benzopyran-7-yl ester

[Chemical Formula 131]

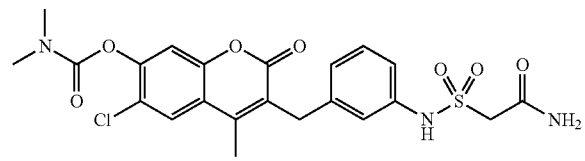

The title compound was synthesized under the same conditions as in the manufacturing example for compound 1o-2-4-2, except that compound 1h-1-3 was used instead of compound 1h-2-4 in step 2, and that ammonia was used instead of methylamine in step 3.

$^1$H NMR (DMSO-$d_6$, 270 MHz) δ (ppm): 2.47 (3H, s), 2.95 (3H, s), 3.11 (3H, s), 3.86 (2H, s), 3.96 (2H, s), 6.96 (1H, d, J=5.4 Hz), 7.03-7.08 (2H, m), 7.21 (1H, m), 7.34 (1H, br), 7.50 (1H, s), 7.60 (1H, br), 8.02 (1H, s), 9.78 (1H, br).

ESI (LC/MS positive mode) m/z: 508 (M+H).

Compound 1o-1-8-1

Dimethylcarbamic acid 3-(3-carbamoylmethanesulfonylamino-benzyl)-4,6-dimethyl-2-oxo-2H-1-benzopyran-7-yl ester

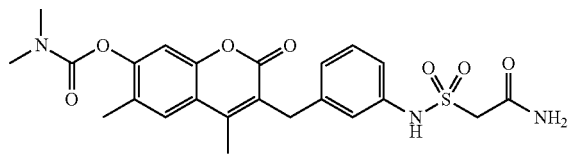

The title compound was synthesized under the same conditions as in the manufacturing example for compound 1o-2-4-2, except that compound 1h-1-8 was used instead of compound 1h-2-4, and that ammonia was used instead of methylamine.

$^1$H-NMR (DMSO-$d_6$, 270 MHz) δ (ppm): 2.18 (3H, s), 2.23 (3H, s), 2.94 (3H, s), 3.09 (3H, s), 3.86 (2H, s), 3.95 (2H, s), 6.43-6.69 (1H, m), 6.76-7.31 (4H, m), 7.74 (1H, s).

ESI (LC/MS positive mode) m/z: 488 (M+H).

Compound 1o-1-3-2

Dimethylcarbamic acid 3-(3-methylcarbamoyl-methanesulfonylamino-benzyl)-6-chloro-4-methyl-2-oxo-2H-1-benzopyran-7-yl ester

[Chemical Formula 132]

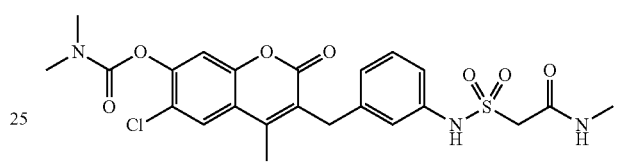

The title compound was synthesized under the same conditions as in the manufacturing example for compound 1o-2-4-2, except that compound 1h-1-3 was used instead of compound 1h-2-4 in step 2.

$^1$H NMR (DMSO-$d_6$, 270 MHz) δ (ppm): 2.47 (3H, s), 2.56 (3H, d, J=5.4 Hz), 2.95 (3H, s), 3.11 (3H, s), 3.87 (2H, s), 3.96 (2H, s), 6.98 (1H, d, J=8.1 Hz), 7.03-7.09 (2H, m), 7.22 (1H, m), 7.50 (1H, s), 8.02 (1H, s), 8.14 (1H, d, J=5.4 Hz), 9.78 (1H, br).

ESI (LC/MS positive mode) m/z: 522 (M+H).

Compound 1o-1-8-2

Dimethylcarbamic acid 4,6-dimethyl-3-(3-methyl-carbamoylmethanesulfonylamino-benzyl)-2-oxo-2H-1-benzopyran-7-yl ester

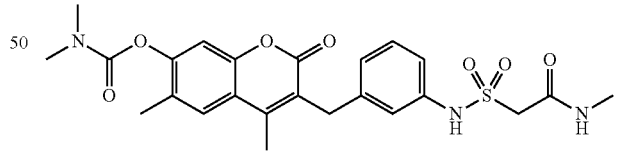

The title compound was synthesized under the same conditions as in the manufacturing example for compound 1o-2-4-2, except that compound 1h-1-8 was used instead of compound 1h-2-4.

$^1$H-NMR (DMSO-$d_6$, 270 MHz) δ (ppm): 2.17 (3H, s), 2.23 (3H, s), 2.94 (3H, s), 3.09 (3H, s), 3.88 (2H, s), 3.95 (2H, s), 6.97 (1H, d, J=8.4 Hz), 7.05-7.12 (2H, m), 7.17-7.27 (2H, m), 7.75 (1H, s).

One of the CH$_3$ peaks was overlapped with the DMSO peak.

ESI (LC/MS positive mode) m/z: 502 (M+H).

Compound 1o-1-40-2

Dimethylcarbamic acid 6-ethynyl-4-methyl-3-(3-methylcarbamoylmethanesulfonylamino-benzyl)-2-oxo-2H-1-benzopyran-7-yl ester

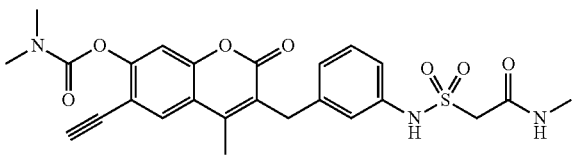

The title compound was synthesized under the same conditions as in the manufacturing example for compound 1o-2-4-2, except that compound 1h-1-40 was used instead of compound 1h-2-4.

$^1$H-NMR (DMSO-$d_6$, 270 MHz) δ (ppm): 2.17 (3H, s), 2.94 (3H, s), 3.09 (3H, s), 3.88 (2H, s), 3.96 (2H, s), 4.43 (1H, s), 6.99 (1H, d, J=6.3 Hz), 7.05-7.13 (2H, m), 7.20-7.26 (2H, m), 7.38 (1H, s), 7.99 (1H, s), 9.77 (1H, s).

One of the CH$_3$ peaks was overlapped with the DMSO peak.

ESI (LC/MS positive mode) m/z: 512 (M+H).

Compound 1o-1-1-3

Dimethylcarbamic acid 3-(3-dimethylcarbamoyl-methanesulfonylamino-benzyl)-4-methyl-2-oxo-2H-1-benzopyran-7-yl ester

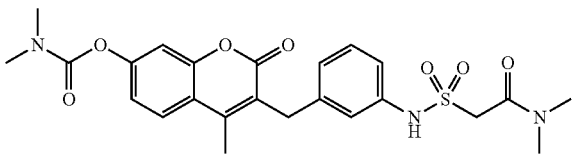

The title compound was synthesized under the same conditions as in the manufacturing example for compound 1o-2-4-2, except that compound 1h-1-1 was used instead of compound 1h-2-4, and that dimethylamine was used instead of methylamine.

$^1$H-NMR (CDCl$_3$, 270 MHz) δ (ppm): 2.46 (3H, s), 2.75 (3H, s), 2.94 (6H, s), 3.06 (3H, s), 3.94 (2H, s), 6.92 (1H, d, J=6.5 Hz), 7.00-7.25 (5H, m), 7.83 (1H, d, J=7.8 Hz).

ESI (LC/MS positive mode) m/z: 502 (M+H).

Compound 1o-1-3-3

Dimethylcarbamic acid 3-(3-dimethylcarbamoyl-methanesulfonylamino-benzyl)-6-chloro-4-methyl-2-oxo-2H-1-benzopyran-7-yl ester

[Chemical Formula 133]

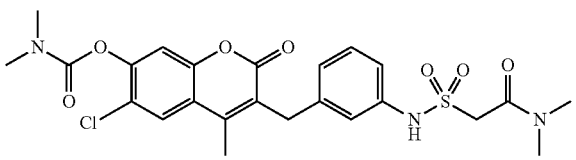

The title compound was synthesized under the same conditions as in the manufacturing example for compound 1o-2-4-2, except that compound 1h-1-3 was used instead of compound 1h-2-4 in step 2, and that dimethylamine was used instead of methylamine in step 3.

$^1$H NMR (DMSO-$d_6$, 270 MHz) δ (ppm): 2.47 (3H, s), 2.76 (3H, s), 2.91 (3H, s), 2.94 (3H, s), 3.10 (3H, s), 3.96 (2H, s), 4.19 (2H, s), 6.98 (1H, d, J=8.1 Hz), 7.03-7.09 (2H, m), 7.23 (1H, m), 7.50 (1H, s), 8.02 (1H, s), 9.85 (1H, br).

ESI (LC/MS positive mode) m/z: 537 (M+H).

Compound 1o-3-1-1

2-{3-[4-Methyl-2-oxo-7-(thiazol-2-yloxy)-2H-1-benzopyran-3-ylmethyl]phenylsulfamoyl}acetamide

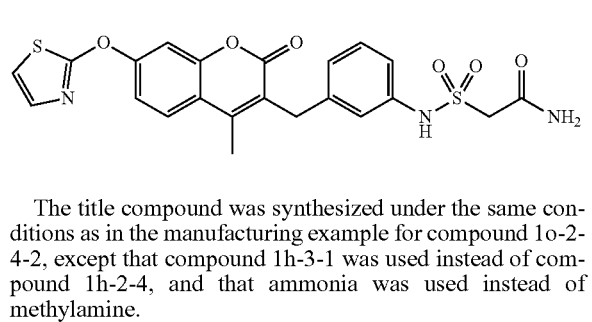

The title compound was synthesized under the same conditions as in the manufacturing example for compound 1o-2-4-2, except that compound 1h-3-1 was used instead of compound 1h-2-4, and that ammonia was used instead of methylamine.

$^1$H-NMR (CDCl$_3$, 270 MHz) δ (ppm): 2.46 (3H, s), 3.88 (2H, s), 4.00 (2H, s), 6.90-7.65 (9H, m).

ESI (LC/MS positive mode) m/z: 486 (M+H).

Compound 1o-3-1-2

N-Methyl-2-{3-[4-methyl-2-oxo-7-(thiazol-2-yloxy)-2H-1-benzopyran-3-ylmethyl]phenylsulfamoyl}acetamide

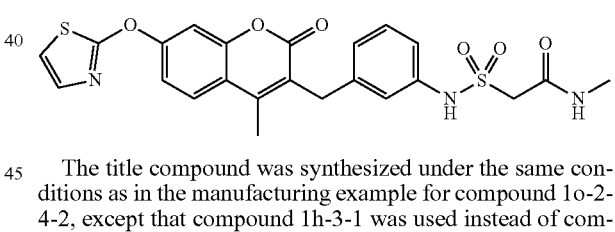

The title compound was synthesized under the same conditions as in the manufacturing example for compound 1o-2-4-2, except that compound 1h-3-1 was used instead of compound 1h-2-4.

$^1$H-NMR (CDCl$_3$, 270 MHz) δ (ppm): 2.46 (3H, s), 2.76-2.78 (1H, m), 3.88 (2H, s), 4.00 (2H, s), 6.90-7.65 (9H, m).

ESI (LC/MS positive mode) m/z: 500 (M+H).

Compound 1o-3-4-2

2-{2-Fluoro-3-[4-methyl-2-oxo-7-(thiazol-2-yloxy)-2H-1-benzopyran-3-ylmethyl]phenylsulfamoyl}-N-methyl-acetamide

[Chemical Formula 134]

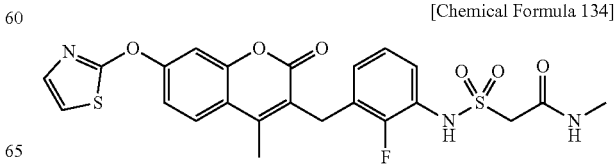

The title compound was synthesized under the same conditions as in the manufacturing example for compound 1o-2-4-2, except that compound 1h-3-4 was used instead of compound 1h-2-4 in step 2.

¹H NMR (DMSO-d₆, 270 MHz) δ (ppm): 2.46 (3H, s), 2.60 (3H, d, J=4.6 Hz), 3.97 (2H, s), 3.99 (2H, s), 6.92-7.07 (2H, m), 7.28-7.39 (4H, m), 7.50 (1H, d, J=2.6 Hz), 7.95 (1H, d, J=8.7 Hz), 8.18 (1H, d, J=4.6 Hz).

ESI (LC/MS positive mode) m/z: 518 (M+H).

Compound 1o-3-1-3

N,N-Dimethyl-2-{3-[4-methyl-2-oxo-7-(thiazol-2-yloxy)-2H-1-benzopyran-3-ylmethyl]phenylsulfamoyl}acetamide

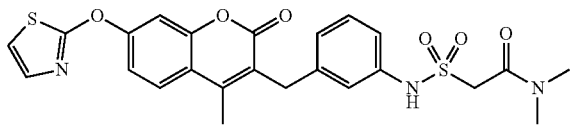

The title compound was synthesized under the same conditions as in the manufacturing example for compound 1o-2-4-2, except that compound 1h-3-1 was used instead of compound 1h-2-4, and that dimethylamine was used instead of methylamine.

¹H-NMR (CDCl₃, 270 MHz) δ (ppm): 2.46 (3H, s), 2.98 (3H, s), 3.04 (3H, s), 3.88 (2H, s), 4.00 (2H, s), 6.90-7.65 (9H, m).

ESI (LC/MS positive mode) m/z: 514 (M+H).

Compound 1j-1-6-4

Dimethylcarbamic acid 3-(3-methanesulfonylaminobenzyl)-4,6-dimethyl-2-oxo-2H-1-benzopyran-7-yl ester

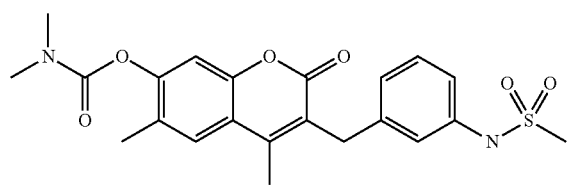

The title compound was synthesized under the same conditions as in the manufacturing example for compound 1j-2-16-2, except that compound 1h-1-6 was used instead of compound 1h-2-16, and that methanesulfonic acid chloride was used instead of N-methylsulfamoyl chloride.

¹H-NMR (DMSO-d₆, 270 MHz) δ (ppm): 2.22 (3H, s), 2.49 (3H, s), 2.89 (6H, s), 3.04 (3H, s), 3.95 (2H, s), 6.96 (1H, d, J=7.6 Hz), 7.00-7.08 (2H, m), 7.18-7.28 (2H, m), 7.75 (1H, s), 9.63 (1H, brs).

ESI (LC/MS positive mode) m/z: 445 (M+H).

Compound 1j-1-10-4

Dimethylcarbamic acid 3-(2-methanesulfonylaminopyridin-4-ylmethyl)-4-methyl-2H-1-benzopyran-7-yl ester

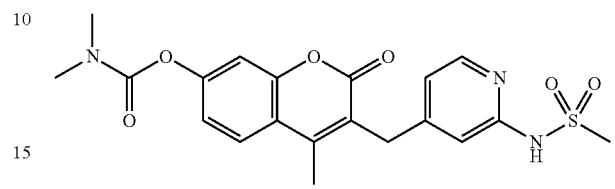

The title compound was synthesized under the same conditions as in the manufacturing example for compound 1j-2-16-2, except that compound 1h-1-10 was used instead of compound 1h-2-16, and that methanesulfonic acid chloride was used instead of N-methylsulfamoyl chloride.

¹H NMR (300 MHz, DMSO-d₆) δ (ppm): 10.73 (brs, 1H), 8.06 (d, 1H, J=5.1 Hz), 7.87 (d, 1H, J=9.0 Hz), 7.26 (d, 1H, J=2.1 Hz), 7.19 (dd, 1H, J=8.7, 6.0 Hz), 6.85 (d, 1H, J=5.4 Hz), 6.78 (s, 1H), 3.96 (s, 2H), 3.20 (s, 3H), 3.07 (s, 3H), 2.93 (s, 3H), 2.46 (s, 3H).

ESIMS m/z: 432 (M+H).

Compound 1j-1-3-4 CONH2

Dimethylcarbamic acid 4-carbamoylmethyl-6-chloro-3-(3-(methanesulfonyl)aminobenzyl)-2-oxo-2H-1-benzopyran-7-yl ester

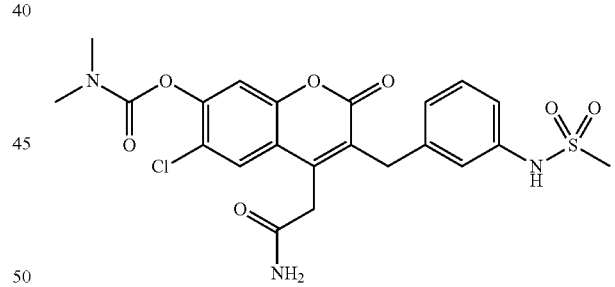

Et₃N (13·L, 0.093 mmol) and methanesulfonyl chloride (3.6·L, 0.050 mmol) were added to a solution of dimethylcarbamic acid 3-(3-aminobenzyl)-4-carbamoylmethyl-6-chloro-2-oxo-2H-1-benzopyran-7-yl ester (20 mg, 0.047 mmol) in methylene chloride (1.0 mL), and the mixture was stirred at room temperature for 2 hours. The solvent was distilled away by concentration under reduced pressure, and the resultant residue was purified by column chromatography to yield the title compound (5.0 mg, 22%) as a white solid.

¹H NMR (270 MHz, DMSO-d₆+CD₃OD (1:4)) δ (ppm): 8.57 (s, 1H), 8.07 (s, 1H), 7.90 (m, 1H), 7.82-7.74 (m, 3H), 4.74 (s, 2H), 4.64 (s, 2H), 3.86 (s, 3H), 3.76 (s, 3H), 3.70 (s, 3H).

ESIMS m/z: 508 (M+H).

Compound 1j-1-3-4CONMe2

Dimethylcarbamic acid 6-chloro-4-dimethylcarbamoylmethyl-3-(3-(methanesulfonyl)aminobenzyl)-2-oxo-2H-1-benzopyran-7-yl ester

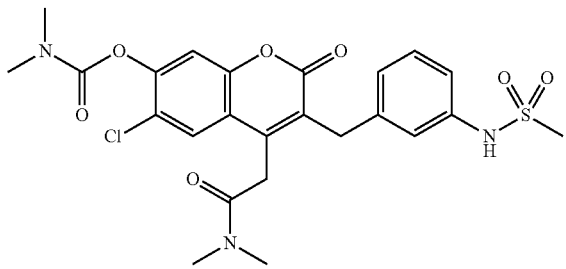

The title compound was synthesized under the same conditions as in the manufacturing example for compound 1j-1-3-4CONH2, except that compound 7d-1-3CONMe2 was used instead of compound 7d-1-3CONH2

$^1$H NMR (270 MHz, CDCl$_3$) δ (ppm): 7.40 (s, 1H), 7.24-7.19 (m, 2H), 7.07-7.00 (m, 3H), 3.97 (s, 2H), 3.80 (s, 2H), 3.16 (s, 3H), 3.12 (s, 3H), 3.04 (s, 3H), 2.95 (s, 3H), 2.92 (s, 3H).

ESIMS m/z: 536 (M+H).

(General Processes-2 and -3)

Next, manufacturing examples associated with General processes-2 and -3 previously mentioned will be explained.

Compound 2a-1

2-Fluoro-1-methyl-3-nitrobenzene

[Chemical Formula 135]

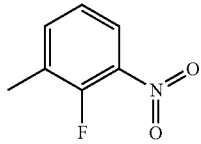

Cesium fluoride (97.5 g, 642 mmol) was added under nitrogen atmosphere to a solution of 2-chloro-1-methyl-3-nitrobenzene (73.4 g, 428 mmol) in DMSO (185 mL), and the mixture was stirred at 140° C. for 10 hours. The reaction mixture was then poured into 0.5N hydrochloric acid and extracted twice with ethyl acetate. The organic extract was washed with saturated saline and dried over magnesium sulfate. A crude product was obtained by vacuum concentration, and then purified by reduced-pressure distillation (boiling point: 118° C. to 122° C./15 mm Hg) to yield the title compound (54.4 g, 82%) as a yellow oil.

$^1$H NMR (DMSO-d$_6$, 270 MHz) δ (ppm): 7.96 (m, 1H), 7.73 (m, 1H), 7.34 (t, J=8.2 Hz, 1H), 2.35 (d, J=2.4 Hz, 3H).

HPLC Rt=2.03 min.

HPLC Conditions:

Column: Combi ODS (ODS, 5 μm, 4.6 mm I.D.×50 mm, Wako Pure Chemical Industries), COSMOSIL (ODS, 5 μm, 4.6 mm I.D.×50 mm, Nacalai Tesque), Intersil C18 (ODS, 5 μm, 4.6 mm I.D.×50 mm, GL Sciences), or SunFire C18 (ODS, 5 μm, 4.6 mm I.D.×50 mm, Waters);

Mobile phase: Water (A) containing 0.05% trifluoroacetic acid, and acetonitrile (B) containing 0.05% trifluoroacetic acid;

Elution method: Stepwise solvent gradient elution (Solvent composition was changed from 10% B to 95% B in 3.5 minutes, then changed to 10% B in 1 minute, and kept at 10% B for 0.5 minute);

Flow rate: 4.0 mL/min.

Compound 1a-1

1-Bromo methyl-2-fluoro-3-nitrobenzene

[Chemical Formula 136]

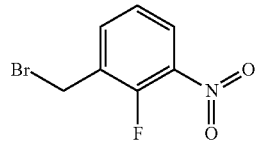

Benzoyl peroxide (10.7 g, 44 mmol) was added under reflux under nitrogen atmosphere to a solution of 2-fluoro-1-methyl-3-nitrobenzene (compound 2a-1) (68.2 g, 440 mmol) and N-bromosuccinimide (95.0 g, 528 mmol) in carbon tetrachloride (1500 mL), and the mixture was stirred under reflux for 5 hours. Impurities were then removed by filtration, and a crude product was obtained by vacuum concentration. It was then purified by column chromatography (hexane), and the title compound (68.7 g, 65%) was obtained as a yellow to light brown oil.

$^1$H NMR (DMSO-d$_6$, 270 MHz) δ (ppm): 8.14 (dd, J=7.0, 1.6 Hz, 1H), 7.97 (dd, J=6.5, 1.6 Hz, 1H), 7.46 (td, J=8.4, 1.4 Hz, 1H), 4.81 (d, J=1.4 Hz, 2H).

HPLC Rt=2.25 min.

HPLC conditions were the same as those for the manufacturing example for compound 2a-1.

Compound 3a-1

2-Chloro-3-nitrobenzoic acid methyl ester

[Chemical Formula 137]

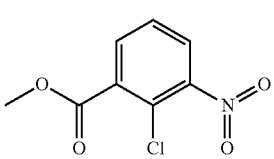

Concentrated sulfuric acid (2.0 mL) was added to a solution of 2-chloro-3-nitrobenzoic acid (10.0 g, 49.6 mmol) in methanol (80 mL), and the mixture was stirred under reflux overnight. After removing methanol by vacuum concentration, water was added, and extraction was performed with ethyl acetate. The organic extract was washed in series with water, saturated sodium hydrogen carbonate and saturated saline, and dried over magnesium sulfate. The title compound (10.6 g, 99%) was obtained by vacuum concentration as a white solid.

$^1$H NMR (CDCl$_3$) δ (ppm): 7.95 (dd, 1H), 7.84 (dd, 1H), 7.48 (t, 1H), 3.98 (s, 3H).

HPLC Rt=11.88 min.

HPLC conditions:
Column: YMC-ODS A (150×6.0 mm);
Eluent: 0-20 min, MeCN/H$_2$O=10/90 to 100/0 (gradient), 20-30 min, MeCN/H$_2$O=100/0 (isocratic);
Flow rate: 1 mL/min.

Compound 2b-1

2-Fluoro-3-nitrobenzoic acid methyl ester

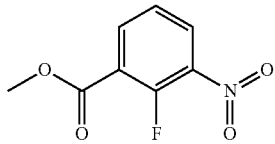

[Chemical Formula 138]

Cesium fluoride (11.2 g) was added to a solution of 2-chloro-3-nitrobenzoic acid methyl ester (10.6 g, 49.0 mmol) in DMSO (49 mL), and the mixture was stirred at 140° C. for 40 minutes. The reaction mixture was then poured into water and extracted with ethyl acetate. The organic extract was washed in series with water and saturated saline, and dried over magnesium sulfate. The title compound (9.23 g, 95%) was then obtained by vacuum concentration as a pale yellow solid.
$^1$H NMR (CDCl$_3$) δ (ppm): 8.24-8.11 (m, 2H), 7.37 (t, 1H), 3.98 (s, 3H).
HPLC Rt=14.62 min.
HPLC conditions were the same as those for the manufacturing example for compound 3a-1.

Compound 2c-1

(2-Fluoro-3-nitrophenyl)methanol

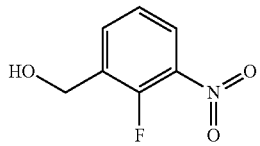

[Chemical Formula 139]

DIBAL (115.7 mL, 1.0 M in toluene) was added at −78° C. to a solution of 2-fluoro-3-nitrobenzoic acid methyl ester (compound 2b-1) (9.22 g, 46.3 mmol) in toluene (92 mL), and the reaction mixture was stirred at −78° C. for 30 minutes and at 0° C. for 30 minutes. The resultant reaction solution was cooled again to −78° C., and methanol, aqueous saturated Rochelle salt solution and ethyl acetate were added thereto. The reaction mixture was then stirred at room temperature for 1 hour, and extracted three times with ethyl acetate. The organic layer was washed with saturated saline and dried over magnesium sulfate. The title compound (7.52 g, 95%) was then obtained by vacuum concentration as a brown oil.
$^1$H NMR (CDCl$_3$) δ (ppm): 7.95 (m, 1H), 7.84 (t, 1H), 7.31 (t, 1H), 4.87 (s, 2H).
HPLC Rt=7.52 min.
HPLC conditions were the same as those for the manufacturing example for compound 3a-1.

Compound 2c-2

4-Fluoro-3-nitrobenzyl alcohol

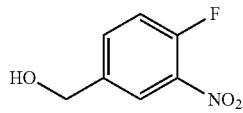

Sodium borohydride (1.36 g, 35.95 mmol) was added to a solution of 4-fluoro-3-nitrobenzaldehyde (2.0 g, 11.83 mmol) in methanol (15 mL) and water (3.0 mL), and the mixture was stirred at room temperature for 3 hours. Water was then added to the reaction mixture, and extraction was performed with ethyl acetate. The organic extract was washed with saturated saline and dried over magnesium sulfate, and then concentrated under reduced pressure to yield the title compound (2.10 g, 95%) as a pale red oil.
$^1$H NMR (270 MHz, CDCl$_3$) δ (ppm): 8.06 (dd, 1H, J=7.1, 2.2 Hz), 7.64 (m, 1H), 7.28 (dd, 1H, J=10.7, 8.6 Hz), 4.76 (s, 2H).

Compound 1a-1

1-Bromomethyl-2-fluoro-3-nitrobenzene

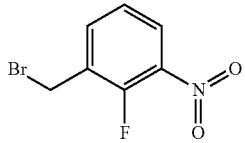

[Chemical Formula 140]

A solution of phosphorus tribromide (4.8 mL) in anhydrous diethylether (100 mL) was added at 0° C. to a solution of (2-fluoro-3-nitrophenyl)methanol (compound 2c-1) (7.52 g, 46.3 mmol) in anhydrous diethylether (130 mL), and the mixture was stirred at 30 minutes at 0° C. The reaction mixture was then poured into ice water and extracted with ethyl acetate. The organic extract was washed in series with saturated sodium hydrogen carbonate solution, water and saturated saline, and dried over magnesium sulfate. The title compound (7.10 g, 70%) was then obtained as a brown oil.
$^1$H NMR (DMSO) δ (ppm): 8.14 (dd, J=7.0, 1.6 Hz, 1H), 7.97 (dd, J=6.5, 1.6 Hz, 1H), 7.46 (td, J=8.4, 1.4 Hz, 1H), 4.81 (d, J=1.4 Hz, 2H).
HPLC Rt=2.25 min.
HPLC conditions were the same as those for the manufacturing example for compound 2a-1.

Compound 1a-2

2-Bromomethyl-4-fluoro-3-nitrobenzene

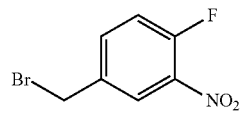

Phosphorus tribromide (1.13 mL) was added to a solution of 4-fluoro-3-nitrobenzyl alcohol (2.1 g, 11.23 mmol) in diethyl ether (40 mL), and the mixture was stirred at room temperature for 1 hour. Water was then added to the reaction mixture, and extraction was performed with ethyl acetate. The organic extract was washed with saturated sodium hydrogen carbonate solution and saturated saline. After drying over magnesium sulfate and concentrating under reduced pressure, the resultant residue was purified by column chromatography to yield the title compound (2.50 mg, 95%) as a pale yellow solid.

$^1$H NMR (270 MHz, CDCl$_3$) δ (ppm): 8.10 (dd, 1H, J=7.1, 2.2 Hz), 7.67 (m, 1H), 7.29 (dd, 1H, J=10.7, 8.6 Hz), 4.49 (s, 2H).

Compound 2c-73

(5-Nitro-thiophen-2-yl)methanol

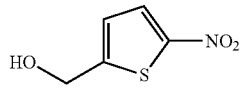

NaBH$_4$ (248 mg, 6.55 mmol) was slowly added to a solution of (5-nitrothiophen-2-yl)aldehyde (1.03 g, 6.55 mmol) in methanol (10 mL) while cooling on ice. The temperature was raised to room temperature, and the mixture was stirred for 4 hours. A 1N HCl solution (20 mL) was then added thereto, and extraction was performed twice with ethyl acetate (40 mL). The organic layer was then purified by silica gel chromatography (hexane:ethyl acetate=3:1) to yield the title compound (917 mg, 88%).

$^1$H-NMR (Bruker (ARX-300), 300 MHz, CDCl$_3$) δ (ppm): 7.82 (1H, d, J=3.82 Hz), 6.93 (1H, d, J=4.20 Hz), 4.88 (2H, s), 2.21 (1H, s).

Compound 1a-73

Methanesulfonic acid (5-nitro-thiophen-2-yl)methanol ester

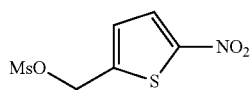

Methylene chloride (8.5 mL), triethylamine (0.90 mL, 6.42 mmol) and methanesulfonic acid chloride (0.43 mL, 5.61 mmol) were mixed with compound 2c-73 (851 mg, 5.35 mmol) at 0° C. The mixture was stirred at 0° C. for 1 hour, and water (10 mL) was added thereto. The organic layer was extracted with methylene chloride (10 mL), and the solvent was distilled away to yield the title compound (1.25 g, 98.5%).

$^1$H-NMR (Bruker (ARX-300), 300 MHz, CDCl$_3$) δ (ppm): 7.84 (1H, d, J=4.20 Hz), 7.13 (1H, d, J=4.20 Hz), 5.36 (2H, s), 3.06 (3H, s).

(General Process-4)

Next, manufacturing examples associated with General process-4 previously mentioned will be explained.

Compound 4a-0-4

2-Oxo-2H-3-(2-fluoro-3-aminobenzyl)-4-methyl-7-hydroxy-1-benzopyran

[Chemical Formula 141]

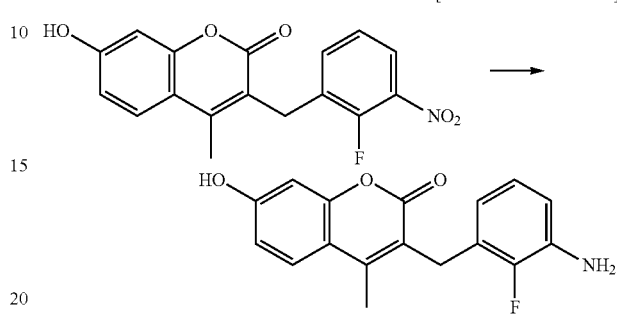

Tin(II) chloride dihydrate (561 mg, 2.49 mmol) was added under nitrogen atmosphere to a solution of the starting material 1e-0-4 (150 mg, 0.46 mmol) in ethyl acetate (4 mL), and heated under reflux for 1 hour. Saturated sodium hydrogen carbonate solution was then added to the reaction solution, and the mixture was extracted with ethyl acetate. The organic layer was washed with saturated saline and dried over anhydrous sodium sulfate, and the solvent was distilled away under reduced pressure. The resultant residue was purified by silica gel column chromatography (dichloromethane:methanol=30:1 to 10:1) to yield the title compound (91.8 mg, 88%) as a white solid.

$^1$H NMR (270 MHz, DMSO-d$_6$) δ (ppm): 2.35 (3H, s), 3.85 (2H, s), 5.06 (2H, br.s), 6.20 (1H, ddd, J=7.6, 1.5 Hz, J$_{HF}$=7.6 Hz), 6.59 (1H, ddd, J=8.2, 1.5 Hz, J$_{HF}$=8.2 Hz), 6.67-6.75 (2H, m), 6.81 (1H, dd, J=8.7, 2.4 Hz), 7.64 (1H, d, J=2.4 Hz), 10.47 (1H, br.s).

ESI (LC/MS positive mode) m/z: 300 (M+H).

Compound 4a-0-5

2-Oxo-2H-3-(2-fluoro-3-aminobenzyl)-4-methyl-6-fluoro-7-hydroxy-1-benzopyran

[Chemical Formula 142]

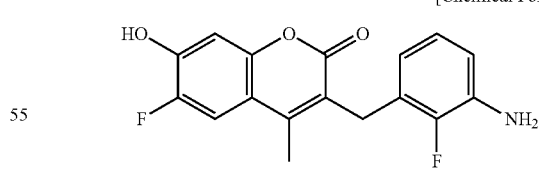

The title compound was synthesized under the same conditions as in the manufacturing example for compound 4a-0-4, except that compound 1e-0-5 was used instead of compound 1e-0-4.

$^1$H NMR (DMSO-d$_6$, 270 MHz) δ (ppm): 2.32 (3H, s), 3.84 (2H, s), 6.20 (1H, dd, J=7.1, 7.1 Hz), 6.58-6.87 (3H, m), 7.55 (1H, d, J=11.0 Hz).

ESI (LC/MS positive mode) m/z: 318 (M+H).

Compound 4a-0-1

2-Oxo-2H-3-(3-aminobenzyl)-4-methyl-7-hydroxy-1-benzopyran

[Chemical Formula 143]

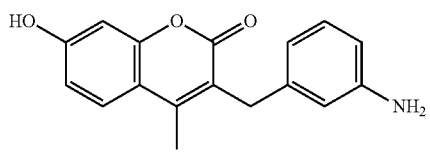

The title compound was synthesized under the same conditions as in the manufacturing example for compound 4a-0-4, except that compound 1e-0-1 was used instead of compound 1e-0-4.

$^1$H NMR (DMSO-$d_6$, 270 MHz) δ (ppm): 2.36 (3H, s), 3.32 (2H, brs), 3.75 (2H, s), 4.96 (1H, brs), 6.32-6.43 (3H, m), 6.71 (1H, d, J=2.4 Hz), 6.81 (1H, dd, J=2.4, 8.7 Hz), 6.89 (1H, ddd, J=2.1, 7.3, 7.3 Hz), 7.64 (1H, d, J=8.7 Hz).

ESI (LC/MS positive mode) m/z: 282 (M+H).

Compound 4a-0-3

2-Oxo-2H-3-(3-aminobenzyl)-4-methyl-6-chloro-7-hydroxy-1-benzopyran

[Chemical Formula 144]

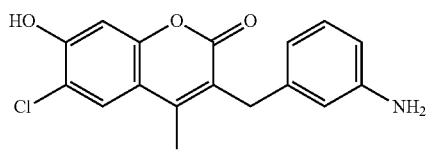

The title compound was synthesized under the same conditions as in the manufacturing example for compound 4a-0-4, except that compound 1e-0-3 was used instead of compound 1e-0-4.

$^1$H NMR (DMSO-$d_6$, 270 MHz) δ (ppm): 2.36 (3H, s), 3.32 (2H, brs), 3.79 (2H, s), 4.93 (1H, brs), 6.29-6.43 (3H, m), 6.82-6.93 (2H, m), 7.79 (1H, s).

ESI (LC/MS positive mode) m/z: 316 (M+H).

Compound 4a-0-6

3-(2-Methyl-3-aminobenzyl)-7-hydroxy-4-methyl-2-oxo-2H-1-benzopyran

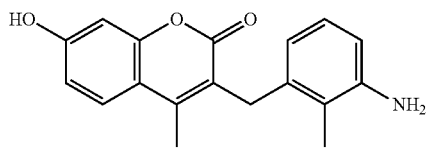

The title compound was synthesized under the same conditions as in the manufacturing example for compound 4a-0-4, except that compound 1e-0-6 was used instead of compound 1e-0-4.

$^1$H NMR (Bruker, 300 MHz, DMSO-$d_5$) δ (ppm): 10.49 (1H, s), 7.63 (1H, d, J=8.8 Hz), 6.82 (1H, dd, J=2.3, 8.8 Hz), 6.72-6.68 (2H, m), 6.48 (1H, d, J=7.6 Hz), 5.99 (1H, d, J=7.6 Hz), 4.77 (2H, s), 3.79 (2H, s), 2.25 (3H, s), 2.07 (3H, s).

MS (Micromass, Quattromicro, ESI+) m/z: 295.95 (M+H).

Compound 4a-0-45

3-(2-Aminobenzyl)-7-hydroxy-4-methyl-2-oxo-2H-1-benzopyran

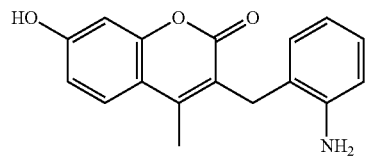

10% Pd/C (15 mg, 20 w/w %) was added to a methanol solution (1 mL) of compound 1e-0-45 (75 mg, 2.4 mmol), and the mixture was stirred for 1 hour under molecular hydrogen atmosphere at 1 atmosphere. The Pd/C was removed by filtration, and the filtrate was purified by silica gel chromatography (methylene chloride:methanol=10:1) to yield the title compound (25 mg, 37%).

$^1$H-NMR (Bruker, 300 MHz, DMSO-$d_6$) δ (ppm): 10.44 (1H, s), 7.64 (1H, d, J=8.8 Hz), 6.88 (1H, t, J=7.4 Hz), 6.82 (1H, dd, J=2.3, 8.8 Hz), 6.73 (1H, d, J=1.9 Hz), 6.65 (1H, d, J=8.0 Hz), 6.58 (1H, d, J=7.6 Hz), 6.41 (1H, t, 7.6 Hz), 5.00 (2H, s), 3.65 (2H, s), 2.36 (3H, s).

MS (Micromass, Quattromicro, ESI+) m/z: 281.84 (M+H).

Compound 4a-0-46

3-(4-Aminobenzyl)-7-hydroxy-4-methyl-2-oxo-2H-1-benzopyran

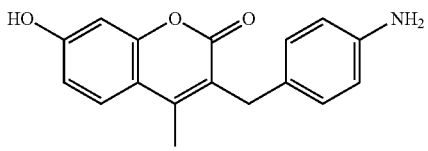

The title compound was synthesized under the same conditions as in the manufacturing example for compound 4a-0-4, except that compound 1e-0-46 was used instead of compound 1e-0-4.

$^1$H-NMR (Bruker, 300 MHz, DMSO-$d_6$) δ (ppm): 10.44 (1H, s), 7.61 (1H, d, J=8.8 Hz), 6.85 (2H, d, J=8.4 Hz), 6.79 (1H, dd, J=2.3, 8.8 Hz), 6.68 (1H, d, J=2.3 Hz), 6.45 (2H, d, J=8.4 Hz), 4.84 (2H, s), 3.72 (2H, s), 2.37 (3H, s).

MS (Micromass, Quattromicro, ESI+) m/z: 281.65 (M+H).

Compound 4a-0-51

3-(3-Aminophenylamino)-7-hydroxy-4-methyl-2-oxo-2H-1-benzopyran

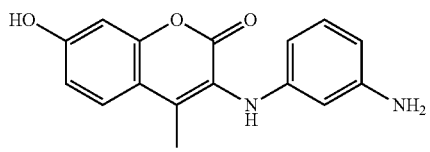

The title compound was synthesized under the same conditions as in the manufacturing example for compound 4a-0-4, except that compound 4a-0-51 was used instead of compound 1e-0-4.

$^1$H NMR (270 MHz, DMSO-d$_6$) δ (ppm): 10.37 (s, 1H), 7.59 (d, 1H, J=8.9 Hz), 7.02 (s, 1H), 6.84 (dd, 1H, J=8.6, 2.3 Hz), 6.80-6.73 (m, 3H), 5.98-5.88 (m, 2H), 5.80 (m, 1H), 5.05 (brs, 1H), 2.22 (s, 3H).

ESIMS m/z: 283 (M+H).

Compound 4a-0-73

3-(5-Nitro-thiophen-2-ylmethyl)-7-hydroxy-4-methyl-2-oxo-2H-1-benzopyran

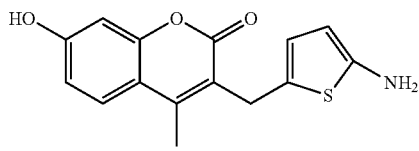

A mixture of compound 1e-0-73 (30 mg, 0.095 mmol) with acetic acid (0.15 mL) was then combined with a mixture of tin(II) chloride dihydrate (129 mg, 0.57 mmol) and concentrated hydrochloric acid (0.25 mL) at room temperature, and the obtained mixture was stirred for 2 hours. Water (10 mL) was added, the mixture was stirred for 10 minutes, and then a saturated NaHCO$_4$ solution was added to adjust the pH of the reaction mixture to 10. The organic layer was extracted twice with a mixed solvent of methylene chloride and methanol (5:1) (20 mL). It was then purified by silica gel chromatography (hexane:ethyl acetate=1:3) to yield the title compound (5 mg, 18%).

$^1$H-NMR (Bruker (ARX-300), 300 MHz, DMSO-d$_6$) δ (ppm): 10.36 (1H, s), 7.63 (1H, d, J=8.77 Hz), 6.97 (1H, dd, J=8.77, 2.30 Hz), 6.69 (1H, d, J=2.30 Hz), 6.30 (1H, d, J=3.43 Hz), 5.63 (1H, d, J=3.43 Hz), 5.17 (2H, s), 3.82 (2H, s), 2.40 (3H, s).

MS (Micromass, Quattromicro, ESI+) m/z: 288.03 (M+1).

Compound 1h-2-4

4-Methyl-3-(2-fluoro-3-aminobenzyl)-7-(pyrimidin-2-yloxy)-2-oxo-2H-1-benzopyran

[Chemical Formula 145]

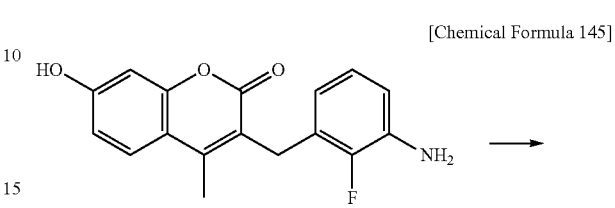

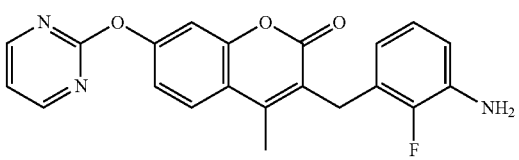

(Synthesis Scheme 2)

60% sodium hydride (11.5 mg, 0.28 mmol) was added under nitrogen atmosphere to a solution of the starting material 4a-0-4 (90.6 mg, 0.30 mmol) in N,N-dimethylformamide (2 mL), and the mixture was stirred at room temperature for 1 hour. 2-Bromopyrimidine (48 mg, 0.30 mmol) was then added thereto, and the mixture was stirred at 100° C. for 5 hours. Ethyl acetate was then added to the reaction solution, and the solution was washed with sodium hydrogen carbonate solution, water and saturated saline. The organic layer was dried over anhydrous sodium sulfate, and the solvent was distilled away under reduced pressure. The resultant residue was purified by silica gel column chromatography (dichloromethane:methanol=1:0 to 40:1) to yield the title compound (60.5 mg, 56%) as a white solid.

$^1$H NMR (270 MHz, DMSO-d$_6$) δ (ppm): 2.45 (3H, s), 3.93 (2H, s), 5.08 (2H, br.s), 6.25 (1H, ddd, J=7.2, 1.7 Hz, J$_{HF}$=7.2 Hz), 6.61 (1H, ddd, J=8.2, 1.7 Hz, J$_{HF}$=8.2 Hz), 6.73 (1H, dd, J=8.2, 7.2 Hz), 7.26 (1H, dd, J=8.8, 2.4 Hz), 7.34 (1H, t, J=4.8 Hz), 7.37 (1H, d, J=2.4 Hz), 7.89 (1H, d, J=8.8 Hz), 8.68 (2H, d, J=4.8 Hz).

ESI (LC/MS positive mode) m/z: 378 (M+H).

Compound 1h-3-4

4-Methyl-3-(2-fluoro-3-aminobenzyl)-7-(thiazol-2-yloxy)-2-oxo-2H-1-benzopyran

[Chemical Formula 146]

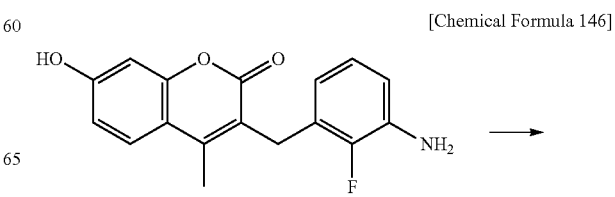

-continued

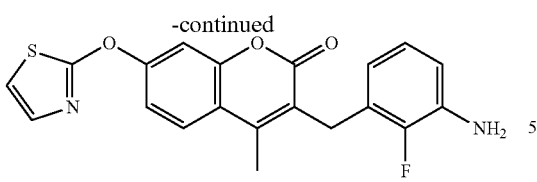

(Synthesis Scheme 2)

The starting material 4a-0-4 (5.0 g, 16.9 mmol) was dissolved in N,N-dimethylformamide (75 mL), and 2-bromothiazole (6.0 mL, 67.6 mmol) and cesium carbonate (11.0 g, 33.8 mmol) were added thereto. The mixture was stirred at 100° C. for 19 hours. Ethyl acetate was then added to the reaction solution, and the solution was washed with water and saturated saline. The organic layer was dried over anhydrous magnesium sulfate, and the solvent was distilled away under reduced pressure. The resultant residue was purified by silica gel column chromatography (dichloromethane:methanol=50:1) to yield the title compound (2.4 g, 38%) as a pale yellow powder.

$^1$H NMR (DMSO-$d_6$, 270 MHz) δ (ppm): 2.44 (3H, s), 3.92 (2H, s), 6.24 (1H, ddd, J=1.5, 7.0 Hz, $J_{HF}$=7.0 Hz), 6.61 (1H, ddd, J=1.5, 8.3 Hz, $J_{HF}$=8.3 Hz), 6.72 (1H, dd, J=7.0, 8.3 Hz), 7.34-7.38 (4H, m), 7.49 (1H, d, J=2.5 Hz), 7.92 (1H, d, J=8.9 Hz).

ESI (LC/MS positive mode) m/z: 383 (M+H).

(General Process-5)

Next, manufacturing examples associated with General process-5 previously mentioned will be explained.

Compound 5b-0-13

2-(Di-tert-butyloxycarbonyl)amino-6-methylpyridine

[Chemical Formula 147]

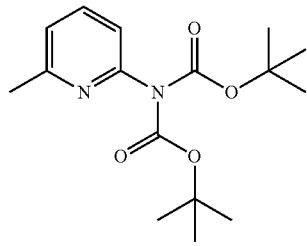

2-Amino-6-methylpyridine (15 g, 138.7 mmol) and $Boc_2O$ (41.4 mL, 180.3 mmol) were stirred at 60° C. overnight, and 100 mL of THF was then added thereto at room temperature. The reaction solution was added dropwise to a mixed solution of $Boc_2O$ (95.6 mL, 416.1 mmol) and DMAP (59.3 g, 485.5 mmol), and the mixture was stirred at room temperature for 4 hours. Ethyl acetate was then added to the reaction solution, and the solution was washed with ammonium chloride solution, sodium hydrogen carbonate solution and saturated saline. The organic layer was dried over anhydrous magnesium sulfate, and the solvent was distilled away under reduced pressure. The resultant residue was purified by silica gel column chromatography to yield the title compound (34.8 g, 82%) as a white solid.

$^1$H NMR (CDCl$_3$, 270 MHz) δ (ppm): 1.31-1.39 (18H, m), 2.42 (3H, s), 7.14 (1H, d, J=7.6 Hz), 7.17 (1H, d, J=7.6 Hz), 7.74 (1H, dd, J=7.6 Hz).

ESI (LC/MS positive mode) m/z: 309 (M+H).

Compound 5c-0-13

2-(Di-tert-butyloxycarbonyl)amino-6-(bromomethyl)pyridine

[Chemical Formula 148]

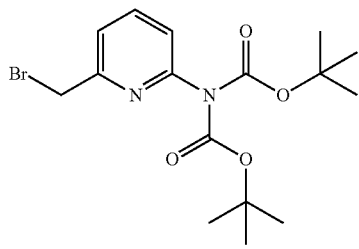

Under nitrogen atmosphere, 6-(di-t-butoxycarbonyl)amino-2-methylpyridine (compound 5b-0-13) (6.0 g, 19.5 mmol), N-bromosuccinimide (4.5 g, 25.3 mmol) and benzoyl peroxide (675 mg, 1.95 mmol) were stirred at 80° C. for 4 hours. The reaction solution was then filtered, and the solvent was distilled away under reduced pressure. The resultant residue was purified by silica gel column chromatography to yield the title compound (4.34 g).

$^1$H NMR (CDCl$_3$, 270 MHz) δ (ppm): 1.31-1.39 (18H, m), 4.51 (2H, s), 7.20 (1H, d, J=8.1 Hz), 7.31 (1H, d, J=8.1 Hz), 7.73 (1H, dd, J=8.1 Hz).

ESI (LC/MS positive mode) m/z: 388 (M+H).

Compound 5t-0-10

2-(2-(Di-tert-butyloxycarbonyl)aminopyridin-4-ylmethyl)-3-oxobutyric acid ethyl ester

[Chemical Formula 149]

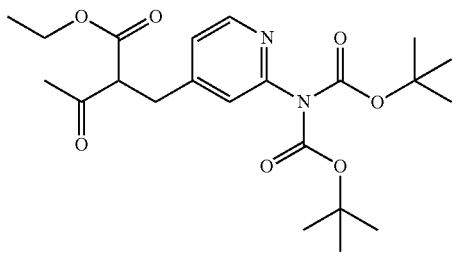

Ethyl acetoacetate (109.6 μL, 0.86 mmol) was dissolved in THF (2.0 mL), and 2-(di-t-butoxycarbonyl)amino-4-(bromomethyl)pyridine (which had been obtained by the method described in Bioorganic & Medicinal Chemistry Letters 2004, 14, 2227-2231) and NaH (39.0 mg, 0.97 mmol) were added thereto. The mixture was stirred at room temperature for 12 hours. Water was then added to the reaction solution, and the solution was extracted with ethyl acetate. After washing with sodium hydrogen carbonate solution and saturated saline, the organic layer was dried over anhydrous magnesium sulfate, and the solvent was distilled away under reduced pressure. The resultant residue was purified by silica gel column chromatography to yield the title compound (206.2 mg, 83%).

¹H NMR (CDCl₃, 270 MHz) δ (ppm): 1.22 (3H, t, J=6.7 Hz), 1.31-1.39 (18H, m), 2.23 (3H, s), 3.17 (1H, dd, J=8.1, 5.4 Hz), 3.78 (1H, dd, J=8.1 Hz), 4.10-4.22 (2H, m), 7.02 (1H, d, J=5.4 Hz), 7.05 (1H, brs), 8.37 (1H, d, J=5.4 Hz).
ESI (LC/MS positive mode) m/z: 437 (M+H).

Compound 5t-0-13

2-(2-(Di-tert-butyloxycarbonyl)aminopyridin-6-ylmethyl)-3-oxobutyric acid ethyl ester

[Chemical Formula 150]

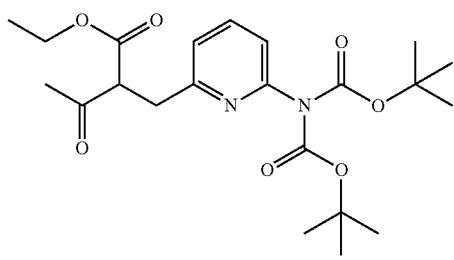

The title compound was obtained under the same conditions as in the manufacturing example for compound 5t-0-10, except that compound 5c-0-13 was used instead of 2-(di-t-butoxycarbonyl)amino-4-(bromomethyl)pyridine.
¹H NMR (CDCl₃, 270 MHz) δ (ppm): 1.22 (3H, t, J=6.7 Hz), 1.31-1.39 (18H, m), 3.20-3.44 (2H, m), 4.11-4.28 (3H, m), 7.06 (1H, d, J=8.1 Hz), 7.10 (1H, d, J=8.1 Hz), 7.63 (1H, dd, J=8.1 Hz).
ESI (LC/MS positive mode) m/z: 437 (M+H).

Compound 5d-0-12

3-(2-Aminopyridin-4-ylmethyl)-6-chloro-7-hydroxy-4-methyl-2-oxo-2H-1-benzopyran

[Chemical Formula 151]

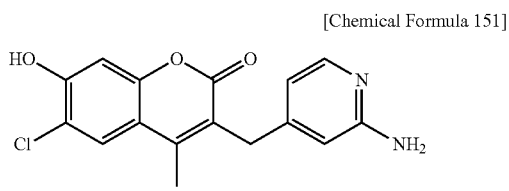

Compound 5t-0-10 (180.9 mg, 414 μmol) and 4-chlororesorcinol (71.9 mg, 497.3 μmol) were stirred in concentrated sulfuric acid (66.3 μL, 1.24 mmol) at room temperature for 24 hours. Ethyl acetate was then added to the reaction solution, and the solution was washed with sodium hydrogen carbonate solution and saturated saline. The organic layer was dried over anhydrous magnesium sulfate, and the solvent was distilled away under reduced pressure. The resultant residue was purified by silica gel column chromatography (methylene chloride:methanol=5:1) to yield the title compound (28.0 mg).
¹H NMR (CD₃OD, 270 MHz) δ (ppm): 2.36 (3H, s), 3.87 (2H, s), 6.41 (1H, brs), 6.51 (1H, d, J=5.4 Hz), 6.69 (1H, s), 7.66 (1H, s), 7.75 (1H, d, J=5.4 Hz).
ESI (LC/MS positive mode) m/z: 317 (M+H).

Compound 5d-0-10

3-(2-Aminopyridin-4-ylmethyl)-7-hydroxy-4-methyl-2-oxo-2H-1-benzopyran

[Chemical Formula 152]

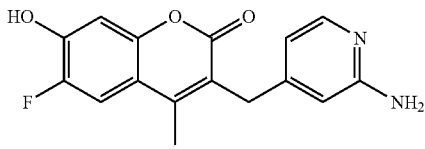

The title compound was obtained from compound 5t-0-10 and resorcinol under the same conditions as in the manufacturing example for compound 5d-0-12.
¹H NMR (300 MHz) (DMSO-d₆) δ (ppm): 2.35 (3H, s), 3.76 (2H, s), 5.76 (2H, brs), 6.20 (1H, s), 6.35 (1H, d, J=5.34 Hz), 6.72 (1H, d, J=2.29 Hz), 6.82 (1H, dd, J=2.67, 8.77 Hz), 7.65 (1H, d, J=8.77 Hz), 7.75 (1H, d, J=5.34 Hz), 10.46 (1H, brs).
Mass (Micromass, Quattromicro) (ESI+) m/z: 282.87 (M+H).

Compound 5d-0-11

3-(2-Aminopyridin-4-ylmethyl)-6-fluoro-7-hydroxy-4-methyl-2-oxo-2H-1-benzopyran

[Chemical Formula 153]

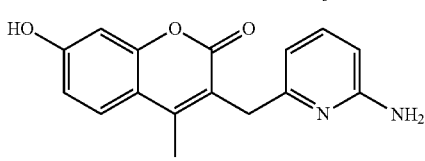

The title compound was obtained from compound 5t-0-10 and 4-fluororesorcinol under the same conditions as in the manufacturing example for compound 5d-0-12.
¹H NMR (300 MHz) (DMSO-d₆) δ (ppm): 2.35 (3H, s), 3.76 (2H, s), 5.74 (2H, brs), 6.19 (1H, s), 6.34 (1H, d, J=5.72 Hz), 6.90 (1H, d, J=7.63 Hz), 6.64 (1H, d, J=11.83 Hz), 7.75 (1H, d, J=5.34 Hz), 11.02 (1H, brs).

Compound 5d-0-13

3-(2-Aminopyridin-6-ylmethyl)-7-hydroxy-4-methyl-2-oxo-2H-1-benzopyran

[Chemical Formula 154]

The title compound was obtained from compound 5t-0-13 and resorcinol under the same conditions as in the manufacturing example for compound 5d-0-12.
$^1$H NMR (DMSO-$d_6$, 270 MHz) δ (ppm): 2.42 (3H, s), 3.82 (2H, s), 5.75-5.85 (2H, m), 6.10-6.20 (2H, m), 6.70 (1H, brs), 6.78 (1H, d, J=8.1 Hz), 7.23 (1H, dd, J=8.1 Hz), 7.64 (1H, d, J=8.1 Hz).
ESI (LC/MS positive mode) m/z: 283 (M+H).

Compound 5d-0-14

3-(2-Aminopyridin-6-ylmethyl)-6-fluoro-7-hydroxy-4-methyl-2-oxo-2H-1-benzopyran

[Chemical Formula 155]

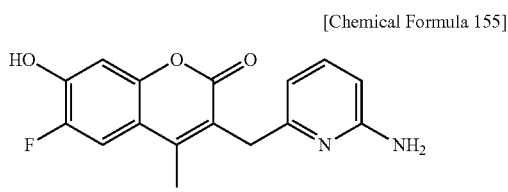

The title compound was obtained from compound 5t-0-13 and 4-fluororesorcinol under the same conditions as in the manufacturing example for compound 5d-0-12.
$^1$H NMR (DMSO-$d_6$, 270 MHz) δ (ppm): 2.38 (3H, s), 3.82 (2H, s), 5.78 (2H, brs), 6.22 (1H, d, J=7.6 Hz), 6.25 (1H, d, J=7.6 Hz), 6.89 (1H, d, J=7.5 Hz), 7.23 (1H, t, J=7.6 Hz), 7.62 (1H, d, J=11.9 Hz), 11.0 (1H, brs).
ESI (LC/MS positive mode) m/z: 301 (M+H).

Compound 5d-0-15

3-(2-Aminopyridin-6-ylmethyl)-6-chloro-7-hydroxy-4-methyl-2-oxo-2H-1-benzopyran

[Chemical Formula 156]

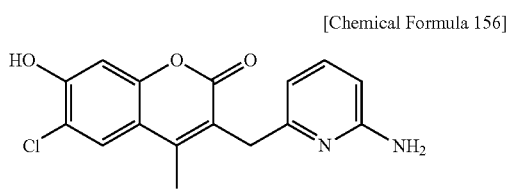

The title compound was obtained from compound 5t-0-13 and 4-chlororesorcinol under the same conditions as in the manufacturing example for compound 5d-0-12.
$^1$H NMR (DMSO-$d_6$, 270 MHz) δ (ppm): 2.38 (3H, s), 3.82 (2H, s), 5.80 (2H, brs), 6.24 (1H, d, J=7.6 Hz), 6.27 (1H, d, J=7.6 Hz), 6.89 (1H, s), 7.23 (1H, t, J=7.6 Hz), 7.78 (1H, s).
ESI (LC/MS positive mode) m/z: 317 (M+H).

Compound 5d-0-16

3-(3-Fluoro-2-aminopyridin-4-ylmethyl)-7-hydroxy-4-methyl-2-oxo-2H-1-benzopyran

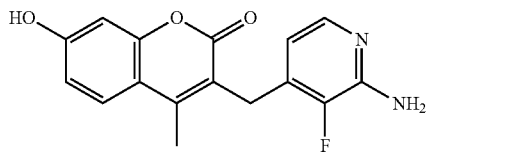

The title compound was synthesized using compound 5t-0-16a and resorsinol under the same conditions as in the manufacturing example for compound 5d-0-12.
$^1$H NMR (DMSO-$d_6$, 270 MHz) δ (ppm): 2.37 (3H, s), 3.86 (2H, s), 6.16 (2H, brs), 6.23 (1H, dd, J=5.1 Hz), 6.91 (1H, s), 7.60 (1H, d, J=5.1 Hz), 7.85 (1H, s).
ESI (LC/MS positive mode) m/z: 301 (M+H).

Compound 5d-0-17

3-(3-Fluoro-2-aminopyridin-4-ylmethyl)-7-hydroxy-6-fluoro-4-methyl-2-oxo-2H-1-benzopyran

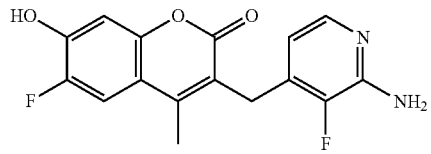

The title compound was synthesized using compound 5t-0-16a and 4-fluororesorsinol under the same conditions as in the manufacturing example for compound 5d-0-12.
$^1$H NMR (DMSO-$d_6$, 270 MHz) δ (ppm): 2.36 (3H, s), 3.86 (2H, s), 6.10 (2H, br), 6.23 (1H, dd, 5.1 Hz), 6.89 (1H, d, J=6.6 Hz), 7.57 (1H, d, J=5.1 Hz), 7.65 (1H, d, J=12 Hz).
ESI (LC/MS positive mode) m/z: 319 (M+H).

Compound 5d-0-18

3-(3-Fluoro-2-aminopyridin-4-ylmethyl)-7-hydroxy-6-chloro-4-methyl-2-oxo-2H-1-benzopyran

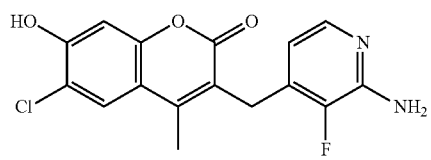

The title compound was synthesized using compound 5t-0-16a and 4-chlororesorsinol under the same conditions as in the manufacturing example for compound 5d-0-12.
$^1$H NMR (DMSO-$d_6$, 270 MHz) δ (ppm): 2.40 (3H, s), 3.86 (2H, s), 6.36 (1H, dd, J=5.1 Hz), 6.91 (1H, s), 7.60 (1H, d, J=5.1 Hz), 7.85 (1H, s).
ESI (LC/MS positive mode) m/z: 335 (M+H).

Compound 5d-0-19

3-(3-Fluoro-2-aminopyridin-4-ylmethyl)-7-hydroxy-6-methyl-4-methyl-2-oxo-2H-1-benzopyran

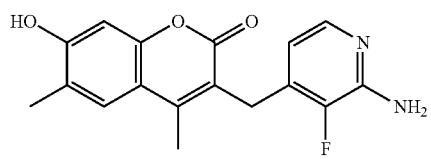

The title compound was synthesized using compound 5t-0-16a and 4-methylresorsinol under the same conditions as in the manufacturing example for compound 5d-0-12.

$^1$H NMR (DMSO-d$_6$, 270 MHz) δ (ppm): 2.19 (3H, s), 2.37 (3H, s), 3.85 (2H, s), 6.09 (2H, brs), 6.21 (1H, dd, J=5.1 Hz), 6.71 (1H, s), 7.54 (1H, s), 7.56 (1H, d, J=5.1 Hz).

ESI (LC/MS positive mode) m/z: 315 (M+H).

Compound 5d-0-19Me 3-(2-Amino-3-fluoropyridin-4-ylmethyl)-4-ethyl-7-hydroxy-6-methyl-2-oxo-2H-1-benzopyran

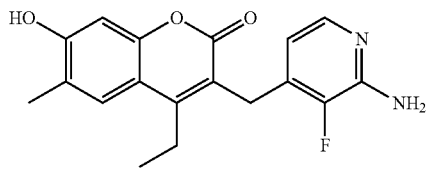

The title compound was synthesized using compound 5t-0-16Meb and 4-methylresorsinol under the same conditions as in the manufacturing example for compound 5d-0-12.

$^1$H NMR (DMSO-d$_6$, 270 MHz) δ (ppm): 1.06 (2H, t, J=7.4 Hz), 2.20 (3H, s), 2.79 (2H, brq, J=7.4 Hz), 3.83 (2H, s), 6.10 (2H, s), 6.20 (1H, t, J=5.1 Hz), 6.75 (1H, s), 7.55 (1H, s), 7.57 (1H, d, J=5.1 Hz), 10.50 (1H, s).

ESI (LC/MS positive mode) m/z: 329 (M+H).

Compound 5d-0-4S1

3-(2-Fluoro-3-aminobenzyl)-7-mercapto-4-methyl-2-oxo-2H-1-benzopyran

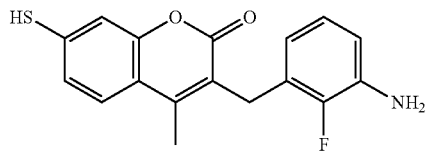

152 mg (1.21 mmol) of 3-hydroxy-benzenethiol and 153 mg (0.60 mmol) of 2-(2-fluoro-3-aminobenzyl)-3-oxobutanoic acid ethyl ester were added to polyphosphoric acid (6 g), and the mixture was stirred and heated at 70° C. for 2.5 hours. Water was then added to the reaction mixture, and the precipitated solid was filtered out. The obtained solid was purified by silica gel column chromatography (dichloromethane:methanol=50:1 to 20:1) to yield 12 mg (1%) of compound 5d-0-4S1 as a pale yellow powder.

ESI (LC/MS positive mode) m/z: 316 (M+H).

Compound 5d-7-4S2

3-(2-Fluoro-3-aminobenzyl)-7-methyloxy-4-methyl-2-oxo-2H-1-benzothiopyran

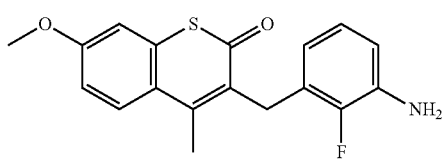

The title compound was synthesized using 3-methyloxy-benzenethiol and 2-(2-fluoro-3-aminobenzyl)-3-oxobutanoic acid ethyl ester under the same conditions as in the manufacturing example for compound 5d-0-4S1.

$^1$H-NMR (270 MHz, CDCl$_3$) δ (ppm): 2.46 (3H, s), 3.70 (2H, brs), 3.88 (3H, s), 4.12 (2H, s), 6.39 (1H, ddd, J=8.1, 1.3 Hz, J$_{HF}$=8.1 Hz), 6.61 (1H, ddd, J=8.2, 1.4 Hz, J$_{HF}$=8.2 Hz), 6.77 (1H, dd, J=7.9, 7.9 Hz), 6.91 (1H, d, J=2.6 Hz), 6.96 (1H, dd, J=9.1, 2.6 Hz), 7.80 (1H, d, J=9.1 Hz).

ESI (LC-MS positive mode) m/z: 330 (M+H).

Compound 5d-0-4S2

3-(2-Fluoro-3-aminobenzyl)-7-hydroxy-4-methyl-2-oxo-2H-1-benzothiopyran

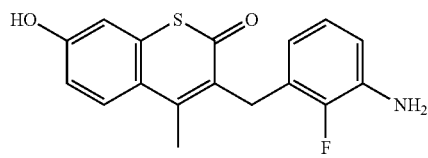

13.5 mg (0.041 mmol) of compound 5d-7-4S2 was dissolved in dichloromethane (1 mL), and 410 µL (0.41 mmol) of a 1 mol/L boron tribromide dichloromethane solution was added thereto. The mixture was stirred under nitrogen atmosphere for 18 hours. Water was then added to the reaction mixture, and the precipitated solid was filtered of to yield 7.6 mg (59%) of compound 5d-0-4S2 as a white powder.

$^1$H-NMR (270 MHz, DMSO-d$_6$) δ (ppm): 2.42 (3H, s), 3.95 (2H, s), 5.61 (2H, brs), 6.07 (1H, ddd, J=7.2, 1.1 Hz, J$_{HF}$=7.2 Hz), 6.58 (1H, ddd, J=8.2, 1.2 Hz, J$_{HF}$=8.2 Hz), 6.69 (1H, dd, J=8.2, 7.2 Hz), 6.80-6.62 (2H, m), 7.91 (1H, d, J=9.7 Hz).

ESI (LC-MS positive mode) m/z: 316 (M+H).

Compound 5c-0-53

N-(3-Mercaptophenyl)acetamide

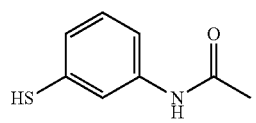

3-Aminothiophenol (1.0 g, 7.99 mmol), acetic anhydride (0.83 mL) and triethyl amine (1.7 mL) were dissolved in methylene chloride, and the solution was stirred at room temperature for 2 hours. It was then purified by silica gel chromatography (hexane:ethyl acetate=3:1) to yield the title compound (1.16 g, 87%).

$^1$H-NMR (300 MHz, CDCl$_3$) δ (ppm): 7.18 (1H, t, J=7.6 Hz), 6.80 (1H, d, J=7.6 Hz), 6.75 (1H, m), 6.71 (1H, dd, J=2.3, 8.0 Hz), 3.72 (2H, bs), 2.40 (3H, s).

MS (ESI+) m/z: 167.91 (M+H).

Compound 5t-0-53

2-(3-Acetoamino-thiophenoxy)-3-oxobutyric acid ethyl ester

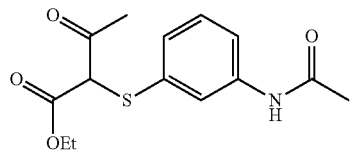

Compound 5c-0-53 (600 mg, 3.59 mmol) and 2-chloro-3-oxobutyric acid ethyl ester (0.50 mL) were dissolved in methylene chloride (6 mL), and triethylamine (0.52 mL) was slowly added dropwise thereto at 0° C. The mixture was raised to room temperature and stirred overnight. It was then purified by silica gel chromatography (hexane:ethyl acetate=5:1) to yield the title compound (181 mg, 17%).

$^1$H-NMR (300 MHz, CDCl$_3$) δ (ppm): 11.8 (1H, s), 7.24 (1H, m), 7.01 (1H, m), 6.87 (2H, m), 4.1 (3H, m), 2.27 (6H, s), 1.18 (3H, m).

MS (ESI+) m/z: 294.99 (M).

Compound 5d-0-53

3-(3-Amino-thiophenoxy)-7-hydroxy-4-methyl-2-oxo-2H-1-benzopyran

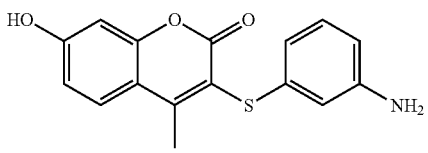

Compound 5t-0-53 (163 mg, 0.552 mmol) and resorcinol (61 mg) were mixed with 70% sulfuric acid (0.5 mL) while cooling on ice, and the mixture was raised to room temperature and stirred overnight. The reaction mixture was added to ice water, and the obtained solid was filtered out to yield the title compound (149 mg, 90%).

$^1$H-NMR (300 MHz, DMSO-d$_6$) δ (ppm): 10.7 (1H, s), 7.74 (1H, d, J=8.8 Hz), 6.93 (1H, t, J=8.0 Hz), 6.86 (1H, dd, J=2.3, 8.4 Hz), 6.74 (1H, d, J=2.3 Hz), 6.37 (3H, m), 5.59 (2H, bs), 2.66 (3H, s).

MS (ESI+) m/z: 300.08 (M+H).

Compound 5t-0-52

2-(3-Acetoaminophenoxy)-3-oxobutyric acid ethyl ester

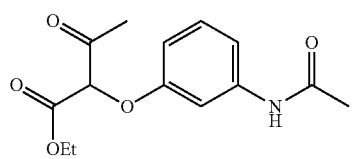

A solution of 3-acetylaminophenol (1 g, 6.61 mmol) in tetrahydrofuran (3.3 mL) was added to a mixture of NaH (264 mg) with tetrahydrofuran (2.6 mL) at 0° C. The mixture was stirred at room temperature for 1 hour, and tetramethylenediamine (1.0 mL) and 2-chloro-3-oxobutyric acid ethyl ester (1.0 mL) were then added thereto. The mixture was heated under reflux for 8 hours, and purified by silica gel chromatography (methylene chloride:methanol=50:1) to yield the title compound (210 mg, 11%).

$^1$H-NMR (300 MHz, CDCl$_3$) δ (ppm): 7.34 (1H, s), 7.29 (1H, s), 7.21 (2H, m), 7.04 (1H, d, J=7.6 Hz), 6.65 (1H, dd, J=2.3, 8.4 Hz), 5.09 (1H, s), 4.29 (2H, q, J=7.2 Hz), 2.38 (3H, s), 2.16 (3H, s), 1.29 (3H, t, J=6.9 Hz).

MS (ESI+) m/z: 280.05 (M+H).

Compound 5d-0-52P 3-(3-Acetylamino-phenoxy)-7-hydroxy-4-methyl-2-oxo-2H-1-benzopyran

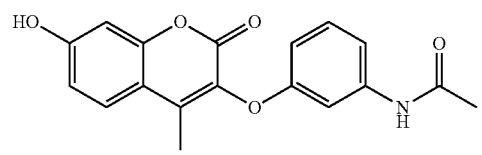

The title compound was synthesized using compound 5t-0-52 and resorcinol under the same conditions as in the manufacturing example for compound 5d-0-53.

$^1$H-NMR (300 MHz, DMSO-d$_6$) δ (ppm): 10.5 (1H, s), 9.91 (1H, s), 7.66 (1H, d, J=8.8 Hz), 7.23 (3H, m), 6.89 (1H, dd, J=2.3, 8.8 Hz), 6.79 (1H, d, J=2.3 Hz), 6.66 (1H, m), 2.29 (3H, s), 1.99 (3H, s).

MS (ESI+) m/z: 326.02 (M+H).

Compound 5d-0-52

3-(3-Aminophenoxy)-7-hydroxy-4-methyl-2-oxo-2H-1-benzopyran

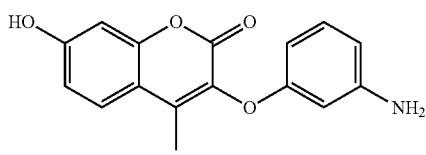

The title compound was synthesized using compound 5t-0-52 and resorcinol under the same conditions as in the manufacturing example for compound 5d-0-53.

$^1$H-NMR (300 MHz, DMSO-d$_6$) δ (ppm): 7.61 (1H, m), 6.91 (1H, m), 6.85 (1H, m), 6.74 (1H, m), 6.21 (1H, J=8.4 Hz), 6.08 (2H, m), 5.12 (2H, bs), 2.26 (3H, s).

MS (ESI+) m/z: 283.97 (M+H).

Compound 5t-0-74

2-(2-Acetylamino-thiazol-4-ylmethyl)-3-oxobutanoic acid ethyl ester

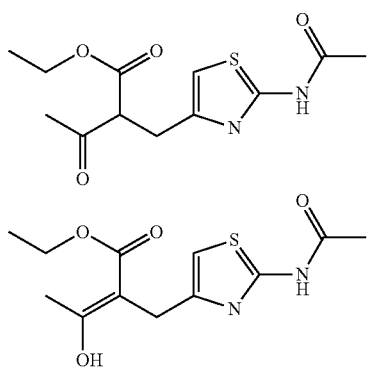

The title compound was synthesized under the same conditions as in the manufacturing example for compound 1c-2, except that 2-acetylamino-4-chloromethyl-thiazole was used instead of 1-bromomethyl-2-fluoro-3-nitrobenzene.

$^1$H-NMR (Bruker (ARX-300), CDCl$_3$) δ (ppm): 9.42 (1H, s), 9.60 (1H, s), 4.21-4.14 (2H, m), 3.94 (1H, t, J=7.4 Hz), 3.19 (2H, q), 2.24 (3H, s), 2.23 (3H, s), 1.23 (3H, t, J=7.1 Hz).

Compound 5d-0-74P 3-(2-Acetylamino-thiazol-4-ylmethyl)-7-hydroxy-4-methyl-2-oxo-2H-1-benzopyran

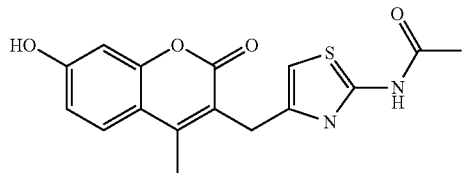

The title compound was synthesized using compound 5t-0-74 under the same conditions as in the manufacturing example for compound 5d-0-12. It was isolated by silica gel chromatography as a separate fraction of compound 5d-0-74.

$^1$H-NMR (Bruker (ARX-300), DMSO-d$_6$) δ (ppm): 11.97 (1H, s), 10.42 (1H, s), 7.42 (1H, d, J=8.4), 6.80 (1H, dd, J=9.0, 2.4 Hz), 6.72 (1H, s), 6.70 (1H, d, J=2.7 Hz), 3.90 (2H, s), 2.38 (3H, s), 2.08 (3H, s).

Compound 5d-0-74

3-(2-Aminothiazol-4-ylmethyl)-7-hydroxy-4-methyl-2-oxo-2H-1-benzopyran

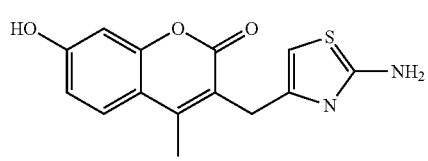

The title compound was synthesized using compound 5t-0-74 under the same conditions as in the manufacturing example for compound 5d-0-12. It was isolated by silica gel chromatography as a separate fraction of compound 5d-0-74P.

$^1$H-NMR (Bruker (ARX-300), CDCl$_3$) δ (ppm): 10.40 (1H, s), 7.63 (1H, d, J=9.0 Hz), 6.81 (2H, s), 6.79 (1H, dd, J=9.3, 2.7 Hz), 6.69 (1H, d, J=2.1 Hz), 6.04 (1H, s), 3.71 (2H, s), 2.38 (3H, s).

(General Process-6)

Next, manufacturing examples associated with General process-6 previously mentioned will be explained.

Compound 6b-1-4

Dimethylcarbamic acid 4-bromomethyl-3-(2-fluoro-3-nitrobenzyl)-2-oxo-2H-1-benzopyran-7-yl ester

[Chemical Formula 157]

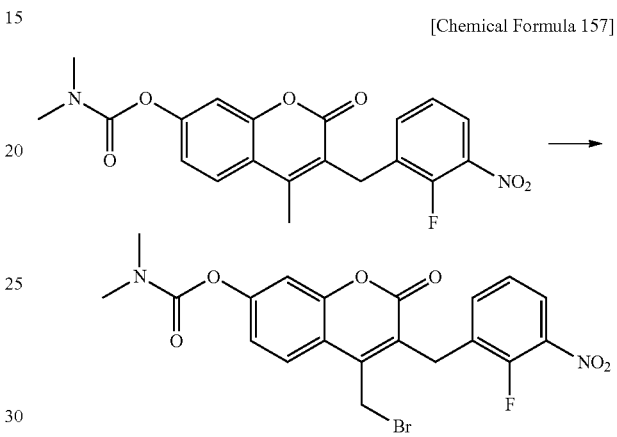

THF (0.9 mL) was added to dimethylcarbamic acid 3-(2-fluoro-3-nitrobenzyl)-4-methyl-2-oxo-2H-1-benzopyran-7-yl ester (compound 1g-1-4) (47.6 mg), and the resultant suspension was stirred at −78° C. for 20 minutes to yield a dark brown solution. This solution was added at 0° C. to a solution of N-bromosuccinimide (28 mg) in THF (0.8 mL) (which had been prepared in advance in a separate container), and the mixture was stirred at 0° C. for 40 minutes. This reaction solution was poured into 1N hydrochloric acid (0.119 mL) diluted with ice water (20 mL), and then extracted with ethyl acetate. The organic layer extraction liquid was washed with saturated saline, and the organic layer was dried over anhydrous magnesium sulfate. The solvent was distilled away under reduced pressure, and the resultant residue was purified by thin layer silica gel chromatography (hexane:ethyl acetate=1:1) to yield the title compound (24.3 mg).

$^1$H NMR (270 MHz, CDCl$_3$) δ (ppm): 3.04 (3H, s), 3.13 (3H, s), 4.15 (2H, s), 4.62 (2H, s), 7.11-7.35 (3H, m), 7.62-7.76 (1H, m), 7.65 (1H, ddd, J=9.0, 8.2, 1.8 Hz), 7.71 (1H, d, J=9.5 Hz), 7.92 (1H, ddd, J=9.0, 8.2, 1.8 Hz).

ESI (LC/MS positive mode) m/z: 479 (M), 481 (M+2H).

Compound 6b-1-1

Dimethylcarbamic acid 4-bromomethyl-3-(3-nitrobenzyl)-2-oxo-2H-1-benzopyran-7-yl ester

[Chemical Formula 158]

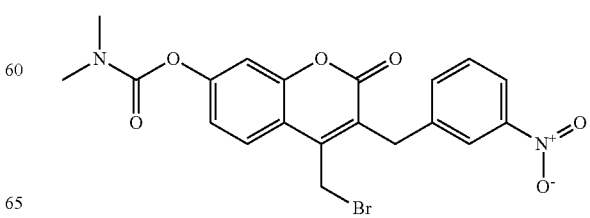

The title compound was synthesized under the same conditions as in the manufacturing example for compound 6b-1-4, except that compound 1g-1-1 was used instead of compound 1g-1-4.

¹H NMR (270 MHz, DMSO-d₆) δ (ppm): 2.94 (3H, s), 3.07 (3H, s), 4.20 (2H, s), 5.07 (2H, s), 7.25 (1H, dd, J=8.7, 2.3 Hz), 7.30 (1H, d, J=2.3 Hz), 7.58 (1H, t, J=8.1 Hz), 7.77 (1H, brd, J=8.1 Hz), 7.96 (1H, d, J=8.7 Hz), 8.05-8.13 (1H, m), 8.22 (1H, t, J=1.9 Hz).

ESI (LC/MS positive mode) m/z: 502 (M+acetonitrile), 504 (M+acetonitrile+2H).

Compound 6b-1-2

Dimethylcarbamic acid 4-bromomethyl-6-fluoro-3-(3-nitrobenzyl)-2-oxo-2H-1-benzopyran-7-yl ester

[Chemical Formula 159]

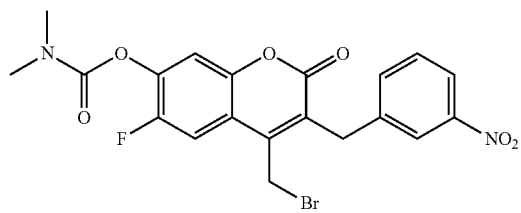

The title compound was synthesized under the same conditions as in the manufacturing example for compound 6b-1-4, except that compound 1g-1-2 was used instead of compound 1g-1-4.

¹H NMR (270 MHz, CDCl₃) δ (ppm): 3.05 (3H, s), 3.15 (3H, s), 4.18 (2H, s), 4.50 (2H, s), 7.45-7.55 (2H, m), 7.66 (1H, d, J=8.1 Hz), 8.05-8.20 (2H, m).

One of the proton peaks of the benzene ring was overlapped with the CDCl₃ peak.

ESI (LC/MS positive mode) m/z: 479 (M), 481 (M+2H).

Compound 6b-1-3

Dimethylcarbamic acid 6-chloro-4-bromomethyl-3-(3-nitrobenzyl)-2-oxo-2H-1-benzopyran-7-yl ester

[Chemical Formula 160]

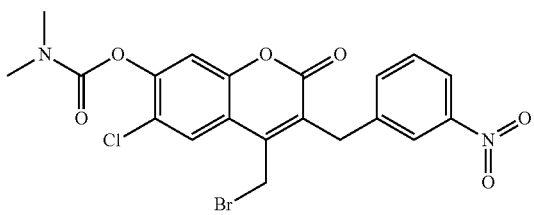

The title compound was synthesized under the same conditions as in the manufacturing example for compound 6b-1-4, except that compound 1g-1-3 was used instead of compound 1g-1-4.

¹H NMR (DMSO-d₅, 270 MHz) δ (ppm): 8.22 (s, 1H), 8.15 (s, 1H), 8.09 (d, J=8.1 Hz, 1H), 7.77 (d, J=8.2 Hz, 1H), 7.58 (t, J=7.9 Hz, 1H), 7.50 (s, 1H), 5.11 (s, 2H), 4.21 (s, 2H), 3.11 (s, 3H), 2.95 (s, 3H).

ESIMS m/z: 497 (M+H).

Compound 6b-2-4

4-Bromomethyl-3-(2-fluoro-3-nitrobenzyl)-7-(pyrimidin-2-yloxy)-2-oxo-2H-1-benzopyran

[Chemical Formula 161]

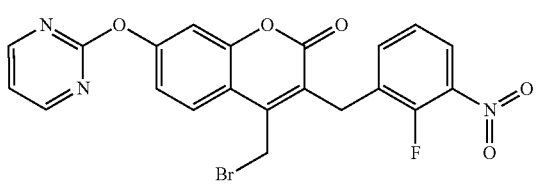

The title compound was synthesized under the same conditions as in the manufacturing example for compound 6b-1-4, except that compound 1g-2-4 was used instead of compound 1g-1-4.

¹H NMR (DMSO-d₆, 270 MHz) δ (ppm): 8.70 (d, J=4.9 Hz, 2H), 8.05-8.00 (m, 2H), 7.63 (t, J=6.4 Hz, 1H), 7.45 (d, J=2.4 Hz, 1H), 7.40-7.30 (m, 3H), 5.03 (s, 2H), 4.16 (s, 2H).

ESIMS m/z: 486 (M+H).

Compound 6c-1-4

Dimethylcarbamic acid 4-fluoromethyl-3-(2-fluoro-3-nitrobenzyl)-2-oxo-2H-1-benzopyran-7-yl ester

[Chemical Formula 162]

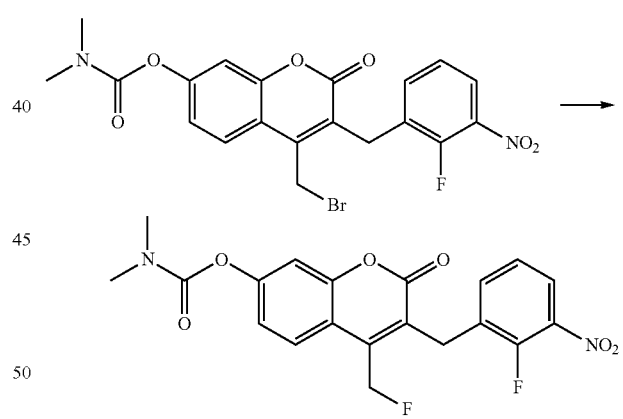

Acetonitrile (1.0 mL) was added to dimethylcarbamic acid 4-bromomethyl-3-(2-fluoro-3-nitrobenzyl)-2-oxo-2H-1-benzopyran-7-yl ester (compound 6b-1-4) (24.0 mg), and potassium fluoride (3.1 mg) and 18-crown-6 (13.2 mg) were added to the resultant suspension while stirring at room temperature. The mixture was stirred at 60° C. for 4 hours, potassium fluoride (3.1 mg) and 18-crown-6 (13.2 mg) were then added to the reaction solution, and the mixture was further stirred at 60° C. for 1.5 hours. This reaction solution was poured into 1N hydrochloric acid (0.110 mL) diluted with ice water (20 mL), and then extracted with ethyl acetate. The resultant organic layer extraction liquid was washed with saturated saline, and the organic layer was dried over anhydrous magnesium sulfate. The solvent was distilled away under reduced pressure, and the resultant residue was purified by thin layer silica gel chromatography (hexane:ethyl acetate=1:1) to yield the title compound (14.7 mg).

$^1$H NMR (270 MHz, CDCl$_3$) δ (ppm): 3.03 (3H, s), 3.13 (3H, s), 4.17 (2H, s), 5.75 (2H, d, J=46.8 Hz), 7.11-7.20 (2H, m), 7.22 (1H, td, J=8.2, 1.3 Hz), 7.70 (1H, td, J=8.2, 1.4 Hz), 7.78 (1H, dt, J=7.4, 1.8 Hz), 7.92 (1H, ddd, J=8.2, 6.8, 1.4 Hz).

ESI (LC/MS positive mode) m/z: 419 (M+H).

Compound 6c-1-1

Dimethylcarbamic acid 4-fluoromethyl-3-(3-nitrobenzyl)-2-oxo-2H-1-benzopyran-7-yl ester

[Chemical Formula 163]

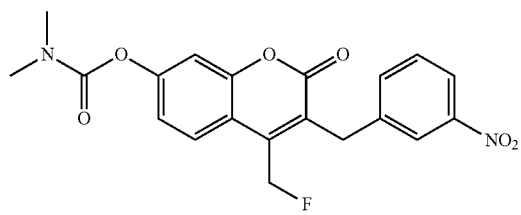

The title compound was synthesized under the same conditions as in the manufacturing example for compound 6c-1-4, except that compound 6b-1-1 was used instead of compound 6b-1-4.

$^1$H NMR (270 MHz, DMSO-d$_6$) δ (ppm): 2.93 (3H, s), 3.07 (3H, s), 4.07 (2H, brs), 5.88 (2H, d, J=46.3 Hz), 7.23 (1H, dd, J=8.7, 2.3 Hz), 7.30 (1H, d, J=2.3 Hz), 7.58 (1H, t, J=8.1 Hz), 7.73 (1H, d, J=8.7 Hz), 7.93 (1H, dd, J=8.1, 1.8 Hz), 8.02-8.12 (1H, m), 8.15 (1H, t, J=1.8 Hz).

ESI (LC/MS positive mode) m/z: 401 (M+H).

Compound 6c-1-2

Dimethylcarbamic acid 6-fluoro-4-fluoromethyl-3-(3-nitrobenzyl)-2-oxo-2H-1-benzopyran-7-yl ester

[Chemical Formula 164]

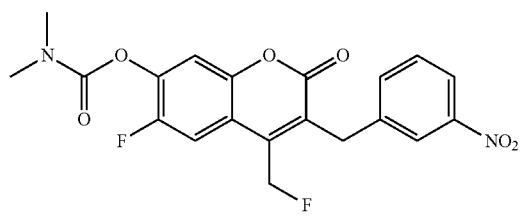

The title compound was synthesized under the same conditions as in the manufacturing example for compound 6c-1-4, except that compound 6b-1-2 was used instead of compound 6b-1-4.

$^1$H NMR (270 MHz, CDCl$_3$) δ (ppm): 3.05 (3H, s), 3.15 (3H, s), 4.21 (2H, brs), 5.65 (2H, d, J=46.8 Hz), 7.45-7.65 (3H, m), 8.05-8.18 (2H, m).

One of the proton peaks of the benzene ring was overlapped with the CDCl$_3$ peak.

ESI (LC/MS positive mode) m/z: 419 (M+H).

Compound 6c-1-3

Dimethylcarbamic acid 6-chloro-4-fluoromethyl-3-(3-nitrobenzyl)-2-oxo-2H-1-benzopyran-7-yl ester

[Chemical Formula 165]

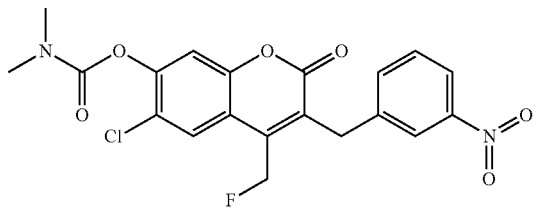

The title compound was synthesized under the same conditions as in the manufacturing example for compound 6c-1-4, except that compound 6b-1-3 was used instead of compound 6b-1-4.

$^1$H NMR (DMSO-d$_6$, 270 MHz) δ (ppm): 8.12 (s, 1H), 8.09 (s+d, 2H), 7.72 (d, J=7.8 Hz, 1H), 7.58 (t, J=7.8 Hz, 1H), 7.56 (s, 1H), 5.95 (d, J=46.0 Hz, 2H), 4.22 (s, 2H), 3.11 (s, 3H), 2.95 (s, 3H).

ESIMS m/z: 435 (M+H).

Compound 6c-2-4

4-Fluoromethyl-3-(2-fluoro-3-nitrobenzyl)-7-(pyrimidin-2-yloxy)-2-oxo-2H-1-benzopyran

[Chemical Formula 166]

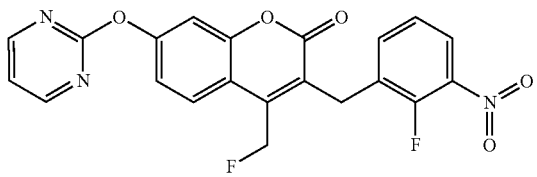

The title compound was synthesized under the same conditions as in the manufacturing example for compound 6c-1-4, except that compound 6b-2-4 was used instead of compound 6b-1-4.

$^1$H NMR (DMSO-d$_6$, 270 MHz) δ (ppm): 8.68 (d, J=4.9 Hz, 2H), 8.02-7.96 (m, 2H), 7.62 (t, J=6.5 Hz, 1H), 7.43 (d, J=2.4 Hz, 1H), 7.35-7.29 (m, 3H), 5.91 (d, J=46.2 Hz, 2H), 4.18 (s, 2H).

ESIMS m/z: 426 (M+H).

Compound 6a-3-4-1P 3-(2-Fluoro-3-{[1-phenyl-meth-(Z)-ylidene]-amino}-benzyl-4-methyl-7-(thiazol-2-yloxy)-2-oxo-2H-1-benzopyran

[Chemical Formula 167]

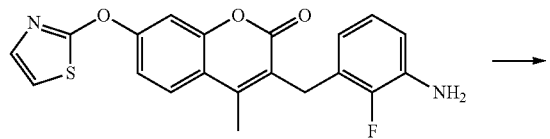

-continued

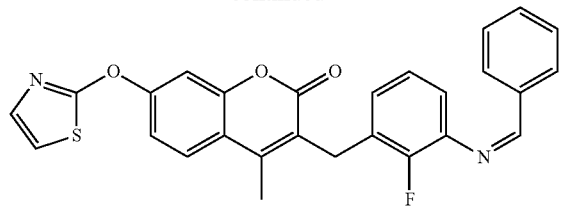

Methanol (4.0 mL) was added to 3-(3-amino-2-fluorobenzyl)-4-methyl-7-(thiazol-2-yloxy)-2-oxo-2H-1-benzopyran (compound 1h-3-4) (200 mg), and benzaldehyde (0.053 mL) was added to the resultant suspension while stirring at room temperature. The suspension was heated under reflux for 3 hours. The reaction solution was then cooled to room temperature, and the solvent was distilled away under reduced pressure. The resultant residue was purified by silica gel chromatography (amino gel) (dichloromethane) to yield the title compound (233 mg).

$^1$H NMR (270 MHz, DMSO-d$_6$) δ (ppm): 4.04 (2H, s), 6.92-7.20 (3H, m), 7.31-7.40 (4H, m), 7.45-7.60 (4H, m), 7.91-8.00 (3H, m), 8.66 (1H, s).

The CH$_3$ peak was overlapped with the DMSO peak.

Compound 6b-3-4-1P

4-Bromomethyl-3-(2-fluoro-3-{[phenyl-meth-(Z)-ylidene]-amino}-benzyl)-7-(thiazol-2-yloxy)-2-oxo-2H-1-benzopyran

[Chemical Formula 168]

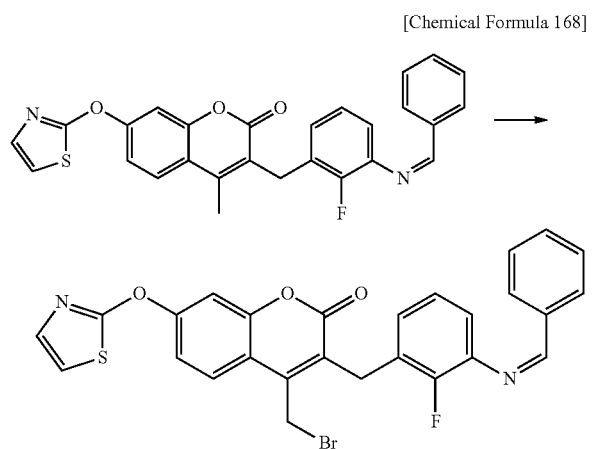

THF (4.5 mL) was added to 3-(2-fluoro-3-{[1-phenyl-meth-(Z)-ylidene]-amino}-benzyl)-4-methyl-7-(thiazol-2-yloxy)-2-oxo-2H-1-benzopyran (compound 6a-3-4-1P) (226 mg), and the mixed solution was stirred at −78° C. for 20 minutes, and further stirred at 0° C. for 1 hour to yield a dark brown solution. This solution was added over 10 minutes to a solution of N-bromosuccinimide (178 mg) in THF (3.0 mL) (which had been prepared in advance in a separate container), and the mixture was further stirred at 0° C. for 1 hour. The reaction solution was added to water (5 mL) to complete the reaction, and the solution was extracted with ethyl acetate. The resultant organic layer extraction liquid was washed with saturated saline, and the organic layer was dried over anhydrous magnesium sulfate. The solvent was then distilled away under reduced pressure, and a residue (320 mg) containing the title compound was obtained.

A peak of the bromomethyl group was observed at around δ 4.9 (ppm) in $^1$H NMR (270 MHz, CD$_3$OD).

Compound 6c-3-4-1P

4-Fluoromethyl-3-(2-fluoro-3-aminobenzyl)-7-(thiazol-2-yloxy)-2-oxo-2H-1-benzopyran

[Chemical Formula 169]

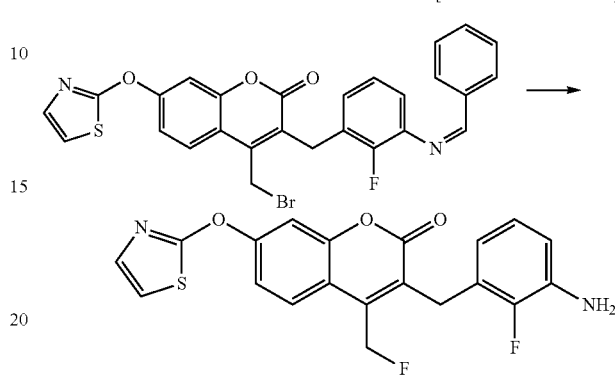

THF (5.0 mL) was added to the residue (315 mg) containing 4-bromomethyl-3-(2-fluoro-3-{[1-phenyl-meth-(Z)-ylidene]-amino}-benzyl)-7-(thiazol-2-yloxy)-2-oxo-2H-1-benzopyran (compound 6b-3-4-1P) obtained in the previous reaction. Potassium fluoride (84.0 mg) and 18-crown-6 (381 mg) were added to the resultant suspension while stirring at room temperature, and the suspension was heated under reflux for 2.5 hours. After cooling to room temperature, ethyl acetate and water were added thereto, and the mixture was extracted. The resultant organic layer extraction liquid was washed with saturated saline, and the organic layer was dried over anhydrous magnesium sulfate. The solvent was distilled away under reduced pressure, ethyl acetate (3.0 mL) and 1N hydrochloric acid (3.0 mL) were added to the resultant residue, and the mixture was stirred at room temperature for 10 minutes. Ethyl acetate and saturated sodium hydrogen carbonate were then added, and the mixture was extracted. The resultant organic layer extraction liquid was washed with saturated saline, and the organic layer was dried over anhydrous magnesium sulfate. The solvent was distilled away under reduced pressure, and the resultant residue was purified by silica gel chromatography (hexane:ethyl acetate=4:1 to 1:1) to yield a mixture (20.6 mg) containing the title compound.

A peak of the fluoromethyl group was observed at around δ 5.5 (ppm) in $^1$H NMR (270 MHz, CDCl$_3$).

(General Process-7)

Next, manufacturing examples associated with General process-7 previously mentioned will be explained.

Compound 7c-1-3OH

Dimethylcarbamic acid 6-chloro-4-(2-hydroxyethyl)-3-(3-nitrobenzyl)-2-oxo-2H-1-benzopyran-7-yl ester

[Chemical Formula 170]

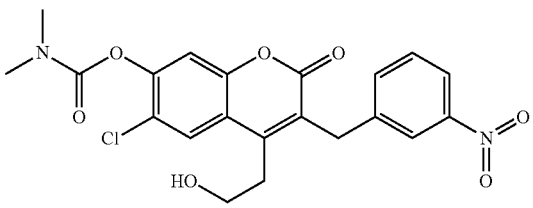

LiHMDS (57.5 mL, 1.0 M in THF) was added under nitrogen atmosphere at −78° C. to a suspension of dimethylcarbamic acid 6-chloro-4-methyl-3-(3-nitrobenzyl)-2-oxo-2H-1-benzopyran-7-yl ester (compound 1g-1-3) (20.0 g, 48.0 mmol) in anhydrous THF (250 mL), and the reaction mixture was stirred at −78° C. for 30 minutes and at 0° C. for 30 minutes. Paraformaldehyde (2.88 g, 96.0 mmol) was then added thereto, and the mixture was stirred at room temperature overnight. The reaction mixture was then poured into water and extracted twice with ethyl acetate. The organic extract was washed with saturated saline and dried over magnesium sulfate. A crude solid was obtained by vacuum concentration, and it was washed with ethyl acetate to yield the title compound (18.5 g, 86%) as a white powder.

$^1$H NMR (DMSO-$d_6$, 270 MHz) δ (ppm): 8.10 (m, 2H), 8.06 (s, 1H), 7.65 (d, J=8.1 Hz, 1H), 7.57 (t, J=8.1 Hz, 1H), 7.52 (s, 1H), 4.91 (t, J=5.4 Hz, 1H), 4.16 (s, 2H), 3.63 (q, J=5.4 Hz, 2H), 3.14 (m, 2H), 3.12 (s, 3H), 2.95 (s, 3H).

ESIMS m/z: 447 (M+H).

Compound 7d-1-3OH

Dimethylcarbamic acid 6-chloro-4-(2-hydroxyethyl)-3-(3-aminobenzyl)-2-oxo-2H-1-benzopyran-7-yl ester

[Chemical Formula 171]

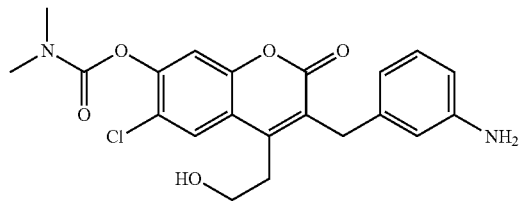

The title compound was synthesized under the same conditions as in the manufacturing example for compound 1h-1-5, except that compound 7c-1-3OH was used instead of compound 1g-1-5.

$^1$H NMR (DMSO-$d_6$, 270 MHz) δ (ppm): 8.04 (s, 1H), 7.49 (s, 1H), 6.90 (t, J=8.0 Hz, 1H), 6.36 (m, 3H), 4.96 (s, 2H), 4.88 (t, J=5.4 Hz, 1H), 3.87 (s, 2H), 3.60 (q, J=5.4 Hz, 2H), 3.11 (s, 3H), 3.04 (t, J=6.0 Hz, 2H), 2.95 (s, 3H).

ESIMS m/z: 417 (M+H).

Compound 7c-1-1OH

Dimethylcarbamic acid 4-(2-hydroxyethyl)-3-(3-nitrobenzyl)-2-oxo-2H-1-benzopyran-7-yl ester

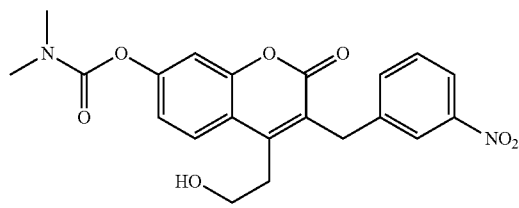

The title compound was synthesized under the same conditions as in the manufacturing example for compound 7c-1-3OH, except that compound 1g-1-1 was used instead of compound 1g-1-3.

$^1$H NMR (270 MHz, DMSO-$d_6$) δ (ppm): 8.13 (d, 1H, J=1.8 Hz), 8.06 (dd, 1H, J=8.1, 1.4 Hz), 7.91 (d, 1H, J=8.7 Hz), 7.73 (d, 1H, J=8.3 Hz), 7.58 (t, 1H, J=8.1 Hz), 7.27 (d, 1H, J=2.3 Hz), 7.20 (dd, 1H, J=8.7, 2.5 Hz), 4.91 (t, 1H, J=5.6 Hz), 4.15 (s, 2H), 3.70 (m, 2H), 3.11 (m, 2H), 3.07 (s, 3H), 2.95 (s, 3H).

ESIMS m/z: 413 (M+H).

Compound 7d-1-1OH

Dimethylcarbamic acid 4-(2-hydroxyethyl)-3-(3-aminobenzyl)-2-oxo-2H-1-benzopyran-7-yl ester

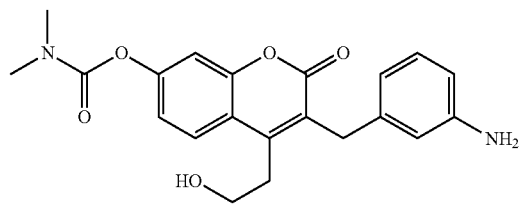

The title compound was synthesized under the same conditions as in the manufacturing example for compound 1h-1-5, except that compound 7c-1-1OH was used instead of compound 1g-1-5.

$^1$H NMR (270 MHz, CDCl$_3$) δ (ppm): 7.62 (d, 1H, J=8.7 Hz), 7.25-7.00 (m, 3H), 6.70-6.42 (m, 3H), 4.00 (s, 2H), 3.71 (t, 2H, J=7.1 Hz), 3.20-3.10 (s+t, 5H), 3.03 (s, 3H).

ESIMS m/z: 383 (M+H).

Compound 7f-1-3CO

Dimethylcarbamic acid 6-chloro-3-(3-nitrobenzyl)-2-oxo-4-(2-oxopropyl)-2H-1-benzopyran-7-yl ester

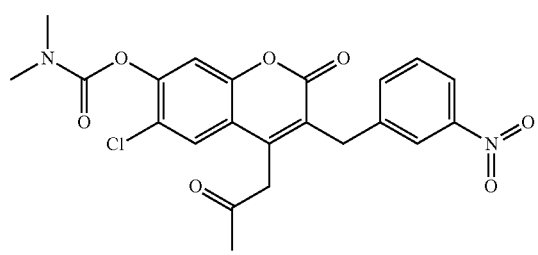

LiHMDS (11.5 mL, 1.0 M in THF) was added under nitrogen atmosphere at −78° C. to a suspension of dimethylcarbamic acid 6-chloro-4-methyl-3-(3-nitrobenzyl)-2-oxo-2H-1-benzopyran-7-yl ester (compound 1g-1-3) (4.0 g, 9.60 mmol) in anhydrous THF (100 mL), and the mixture was stirred at −78° C. for 30 minutes and at 0° C. for 30 minutes. Acetyl chloride (1.36 mL, 19.2 mmol) was then added thereto, and the mixture was stirred at room temperature for 1 hour. The reaction mixture was then poured into water and extracted with ethyl acetate. The organic extract was washed with saturated saline and dried over magnesium sulfate. A crude solid was obtained by vacuum concentration, and purified by column chromatography (ethyl acetate:hexane=1:3) to yield the title compound (1.28 g, 29%) as a white powder.

$^1$H NMR (DMSO-$d_6$, 270 MHz) δ (ppm): 8.12 (s, 1H), 8.05 (d, J=5.4 Hz, 1H), 7.92 (s, 1H), 7.67 (d, J=8.1 Hz, 1H), 7.55

(t, J=8.1 Hz, 1H), 7.51 (s, 1H), 4.44 (s, 2H), 4.07 (s, 2H), 3.10 (s, 3H), 2.95 (s, 3H), 2.27 (s, 3H).
ESIMS m/z: 459 (M+H).

Compound 7g-1-3CO

Dimethylcarbamic acid 6-chloro-3-(3-aminobenzyl)-2-oxo-4-(2-oxopropyl)-2H-1-benzopyran-7-yl ester

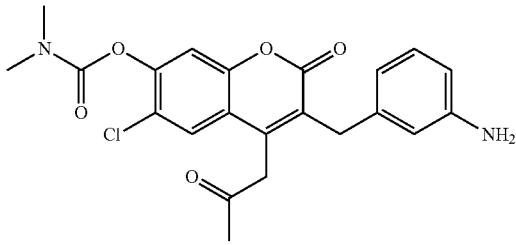

The title compound was synthesized under the same conditions as in the manufacturing example for compound 1h-1-5, except that compound 7f-1-3CO was used instead of compound 1g-1-5.
$^1$H NMR (DMSO-d$_6$, 270 MHz) δ (ppm): 7.89 (s, 1H), 7.53 (s, 1H), 6.88 (t, J=8.1 Hz, 1H), 6.37-6.32 (m, 3H), 5.76 (s, 2H), 4.96 (s, 2H), 3.76 (s, 2H), 3.10 (s, 3H), 2.95 (s, 3H), 2.23 (s, 3H).
ESIMS m/z: 429 (M+H).

Compound 7c-1-3MeOH

Dimethylcarbamic acid 6-chloro-4-(2-hydroxypropyl)-3-(3-nitrobenzyl)-2-oxo-2H-1-benzopyran-7-yl ester

[Chemical Formula 174]

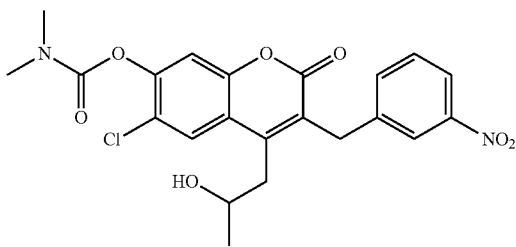

Sodium borohydride (49 mg, 1.30 mmol) was added to a solution of dimethylcarbamic acid 6-chloro-3-(3-nitrobenzyl)-2-oxo-4-(2-oxopropyl)-2H-1-benzopyran-7-yl ester (compound 7f-1-3CO) (300 mg, 0.65 mmol) in anhydrous THF (5.0 mL), and the mixture was stirred at 0° C. for 2 hours. The reaction mixture was then poured into water and extracted with ethyl acetate. The organic extract was washed with saturated saline and dried over magnesium sulfate, and the title compound (280 mg, 93%) was obtained as a pale yellow powder.
$^1$H NMR (DMSO-d$_6$, 270 MHz) δ (ppm): 8.12-8.05 (m, 3H), 7.71 (d, J=8.2 Hz, 1H), 7.60-7.50 (m, 2H), 4.88 (d, J=5.4 Hz, 1H), 4.22 (d, J=14.8 Hz, 1H), 4.11 (d, J=14.8 Hz, 1H), 3.86 (m, 1H), 3.11 (s, 3H), 3.00 (m, 2H), 2.95 (s, 3H), 1.23 (d, J=5.5 Hz, 3H).
ESIMS m/z: 461 (M+H).

Compound 7f-1-1COOH

{3-(3-Nitrobenzyl)-7-dimethylcarbamoyloxy-2-oxo-2H-1-benzopyran-4-yl}acetic acid

[Chemical Formula 175]

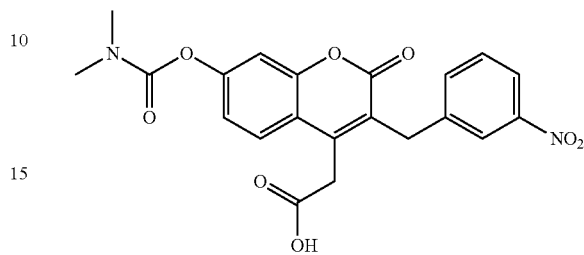

The compound dimethylcarbamic acid 4-(2-hydroxyethyl)-3-(3-nitrobenzyl)-2-oxo-2H-1-benzopyran-7-yl ester (compound 7c-1-1OH) was synthesized under the same conditions as in the manufacturing example for compound 7c-1-3OH, except that compound 1g-1-1 was used instead of compound 1g-1-3.
Jones reagent (3.2 mL, 2.67 M, 8.58 mmol) was added at 0° C. to a solution of compound 7c-1-1OH (1.18 g, 2.86 mmol) in acetone (25 mL), and the mixture was stirred at room temperature for 30 minutes. 2-Propanol was added slowly to the reaction mixture until the red color disappeared, and it was then poured into water and extracted with ethyl acetate. The organic extract was washed with water and dried over magnesium sulfate. The title compound (865 mg, 71%) was obtained by vacuum concentration as a pale yellow powder.
$^1$H NMR (CDCl$_3$, 270 MHz) δ (ppm): 8.12 (s, 1H), 8.07 (d, J=8.2 Hz, 1H), 7.86 (d, J=8.6 Hz, 1H), 7.71 (d, J=8.2 Hz, 1H), 7.58 (t, J=7.6 Hz, 1H), 7.26 (d, J=2.1 Hz, 1H), 7.19 (dd, J=8.7, 2.2 Hz, 1H), 4.14 (s, 2H), 3.29 (s, 2H), 3.07 (s, 3H), 2.93 (s, 3H).
ESIMS m/z: 427 (M+H).

Compound 7f-1-3 COOH (3-(3-Nitrobenzyl)-6-chloro-7-dimethylcarbamoyloxy-2-oxo-2H-1-benzopyran-4-yl)acetic acid

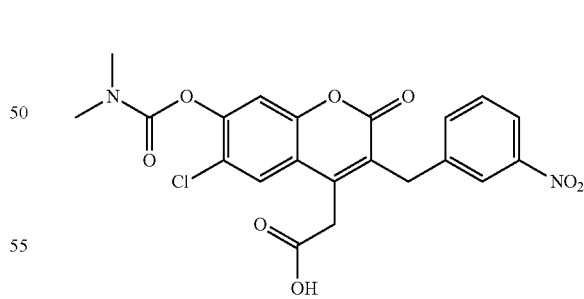

The title compound was synthesized under the same conditions as in the manufacturing example for compound 7i-1-1COOH, except that compound 7c-1-3OH was used instead of compound 7c-1-1OH.
$^1$H NMR (270 MHz, DMSO-d$_6$) δ (ppm): 8.12 (s, 1H), 8.07 (d, 1H, J=5.4 Hz), 8.03 (s, 1H), 7.71 (d, 2H, J=8.1 Hz), 7.57 (t, 1H, J=8.1 Hz), 7.50 (s, 1H), 4.14 (s, 2H), 3.28 (s, 2H), 3.10 (s, 3H), 2.95 (s, 3H).
ESIMS m/z: 461 (M+H).

Compound 7f-1-1COOMe

{3-(3-Nitrobenzyl)-7-dimethylcarbamoyloxy-2-oxo-2H-1-benzopyran-4-yl}acetic acid methyl ester

[Chemical Formula 176]

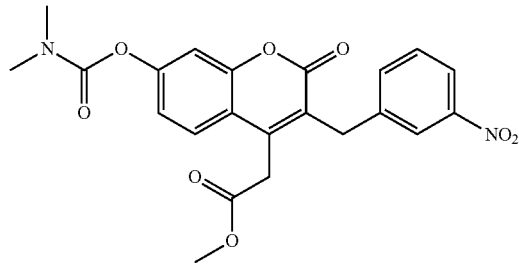

Trimethylsilyl diazomethane (0.82 mL, 2.0 M in hexane) was added to a solution of {3-(3-nitrobenzyl)-7-dimethylcarbamoyloxy-2-oxo-2H-1-benzopyran-4-yl}acetic acid (compound 7f-1-1COOH) (350 mg, 0.82 mmol) in methanol (5.0 mL)/dichloromethane (8.0 mL), and the mixture was stirred at room temperature for 10 minutes. Aacetic acid (2.0 mL) was added to the reaction mixture, and the title compound (338 mg, 94%) was obtained by vacuum concentration as a pale yellow powder.

$^1$H NMR (CDCl$_3$, 270 MHz) δ (ppm): 8.12 (s, 1H), 8.07 (d, J=8.2 Hz, 1H), 7.76 (d, J=8.7 Hz, 1H), 7.70 (d, J=8.1 Hz, 1H), 7.57 (t, J=7.6 Hz, 1H), 7.22 (s, 1H), 7.19 (d, J=8.5 Hz, 1H), 4.24 (s, 2H), 4.16 (s, 2H), 3.50 (s, 3H), 3.06 (s, 3H), 2.93 (s, 3H).

ESIMS m/z: 441 (M+H).

Compound 7f-1-3CONH2

Dimethylcarbamic acid 3-(3-nitrobenzyl)-4-carbamoylmethyl-6-chloro-2-oxo-2H-1-benzopyran-7-yl ester

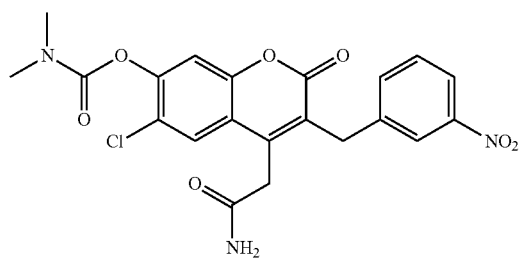

HODhbt (78 mg, 0.50 mmol) and WSC (91 mg, 0.50 mmol) were added to a solution of compound 7f-1-3COOH (185 mg, 0.40 mmol) in DMF (4.0 mL), and the mixture was stirred at room temperature for 2 hours. NH$_3$ (0.33 M in THF, 6.1 mL, 2.00 mmol) was added dropwise to the reaction mixture, and the obtained mixture was stirred at room temperature for a day and a night. Water was then added to the reaction mixture, and extraction was performed with ethyl acetate. The organic extract was washed with saturated saline and dried over magnesium sulfate, and then concentrated under reduced pressure to yield the title compound (170 mg, 93%) as a white solid.

$^1$H NMR (270 MHz, DMSO-d$_6$) δ (ppm): 8.19 (s, 1H), 8.06 (m, 1H), 7.98 (s, 1H), 7.76-7.70 (m, 2H), 7.57 (t, 1H, J=8.1 Hz), 7.52 (s, 1H), 7.26 (s, 1H), 4.13 (s, 2H), 3.96 (s, 2H), 3.10 (s, 3H), 2.95 (s, 3H).

ESIMS m/z: 460 (M+H).

Compound 7g-1-3CONH2

Dimethylcarbamic acid 3-(3-aminobenzyl)-4-carbamoylmethyl-6-chloro-2-oxo-2H-1-benzopyran-7-yl ester

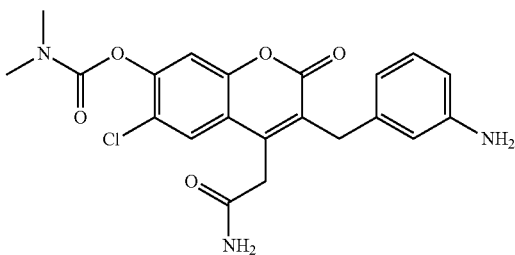

The title compound was synthesized under the same conditions as in the manufacturing example for compound 4a-0-4, except that compound 7f-1-3CONH2 was used instead of compound 1e-0-4.

$^1$H NMR (270 MHz, DMSO-d$_6$) δ (ppm): 8.00 (s, 1H), 7.68 (m, 1H), 7.56 (s, 1H), 7.25 (m, 1H), 6.90 (t, 1H, J=8.1 Hz), 6.36 (m, 3H), 4.96 (s, 2H), 3.83 (s, 2H), 3.83 (s, 2H), 3.10 (s, 3H), 2.95 (s, 3H).

ESIMS m/z: 430 (M+H).

Compound 7 g-1-3CONMe2

Dimethylcarbamic acid 3-(3-aminobenzyl)-4-dimethylcarbamoylmethyl-6-chloro-2-oxo-2H-1-benzopyran-7-yl ester

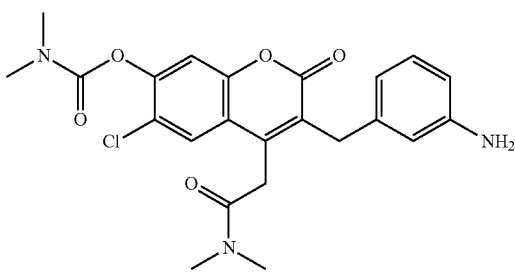

The compound dimethylcarbamic acid 3-(3-nitrobenzyl)-4-dimethylcarbamoylmethyl-6-chloro-2-oxo-2H-1-benzopyran-7-yl ester (compound 7f-1-3CONMe2) was synthesized under the same conditions as in the manufacturing example for compound 7f-1-3CONH2, except that dimethylamine was used instead of ammonia.

The title compound was synthesized under the same conditions as in the manufacturing example for compound 4a-0-4, except that compound 7f-1-3CONMe2 was used instead of compound 1e-0-4.

¹H NMR (270 MHz, DMSO-d₆) δ (ppm): 7.84 (s, 1H), 7.49 (s, 1H), 6.88 (m, 1H), 6.37-6.33 (m, 3H), 4.93 (s, 2H), 4.05 (s, 2H), 3.75 (s, 2H), 3.10 (s, 6H), 2.95 (s, 3H), 2.81 (s, 3H).
ESIMS m/z: 458 (M+H).

Compound 7c-1-3OMe

Dimethylcarbamic acid 6-chloro-4-methoxymethyl-3-(3-nitrobenzyl)-2-oxo-2H-1-benzopyran-7-yl ester

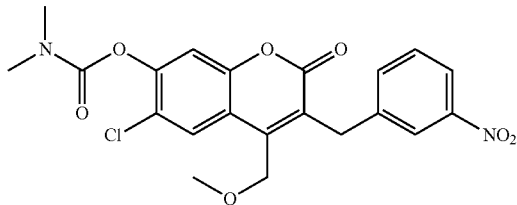

Potassium carbonate (279 mg, 2.01 mmol) was added to a solution of dimethylcarbamic acid 6-chloro-4-bromomethyl-3-(3-nitrobenzyl)-2-oxo-2H-1-benzopyran-7-yl ester (compound 6b-1-3) (500 mg, 1.01 mmol) in THF (7.5 mL)/methanol (5.0 mL), and the mixture was stirred at room temperature for 2 hours. The reaction mixture was then poured into water and extracted with ethyl acetate. The organic extract was washed with saturated saline and dried over magnesium sulfate. The solvent was distilled away by concentration under reduced pressure, and the resultant residue was purified by column chromatography to yield the title compound (40 mg, 10%) as a white solid.
¹H NMR (270 MHz, CDCl₃) δ (ppm): 8.14 (s, 1H), 8.05 (d, 1H, J=8.1 Hz), 7.95 (s, 1H), 7.70 (d, 1H, J=8.0 Hz), 7.47 (t, 1H, J=8.1 Hz), 7.27 (s, 1H), 4.71 (s, 2H), 4.13 (s, 2H), 3.48 (s, 3H), 3.17 (s, 3H), 3.00 (s, 3H).
ESIMS m/z: 447 (M+H).

Compound 7d-1-3OMe

Dimethylcarbamic acid 6-chloro-4-methoxymethyl-3-(3-aminobenzyl)-2-oxo-2H-1-benzopyran-7-yl ester

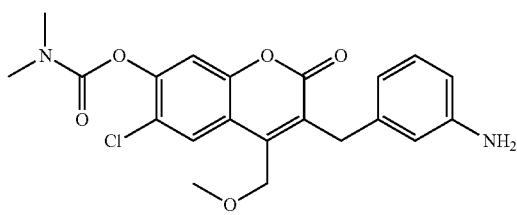

The title compound was synthesized under the same conditions as in the manufacturing example for compound 4a-0-4, except that compound 7c-1-3OMe was used instead of compound 1e-0-4.
¹H NMR (270 MHz, DMSO-d₆) δ (ppm): 8.00 (s, 1H), 7.51 (s, 1H), 6.90 (t, 1H, J=8.0 Hz), 6.38-6.34 (m, 3H), 4.98 (s, 2H), 4.71 (s, 2H), 3.90 (s, 2H), 3.37 (s, 3H), 3.10 (s, 3H), 2.95 (s, 3H).

(General Process-8)

Next, manufacturing examples associated with General process-8 previously mentioned will be explained.

Compound 8c-1

(2-Chloro-3-fluoropyridin-4-yl)-methanol

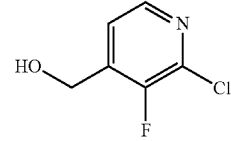

2-Chloro-3-fluoropyridine (1.51 mL, 14.9 mmol) was added under nitrogen atmosphere at −78° C. to a mixture of 2.0 M lithium diisopropylamide (in THF) (7.44 mL, 14.9 mmol) and THY (24 mL), and the mixture was stirred at 0° C. for 2 hours. DMF (11.4 mL, 149 mmol) was added to the mixture, and the obtained mixture was stirred at 0° C. for additional 2 hours. Sodium borohydride (731 mg, 19.3 mmol) was then added thereto, and the mixture was stirred at 0° C. for 1 hour. Water was then added to the reaction solution, which was then extracted with ethyl acetate. The solution was washed with 1N HCl, sodium hydrogen carbonate solution and saturated saline. The organic layer was dried over anhydrous magnesium sulfate, and the solvent was distilled away under reduced pressure. The resultant residue was purified by silica gel column chromatography to yield the title compound (1.4 g, 58%).
¹H NMR (DMSO-d₆, 270 MHz) δ (ppm): 4.65 (2H, d, J=5.8 Hz), 5.70 (1H, t, J=5.8 Hz), 7.56 (1H, dd, J=4.6 Hz), 8.27 (1H, d, J=4.6 Hz).
ESI (LC/MS positive mode) m/z: 162 (M+H).

Compound 8c-2

4-(tert-Butyldimethylsilyloxymethyl)-2-chloro-3-fluoropyridine

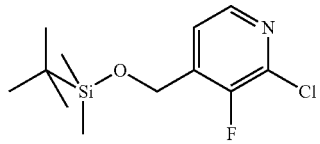

A mixture of (2-chloro-3-fluoropyridin-4-yl)-methanol (200 mg, 1.24 mmol), imidazole (253 mg, 3.72 mmol) and tert-butyldimethylchlorosilane (373 mg, 2.48 mmol) in DMF was stirred at room temperature for 2 hours. Methylene chloride was then added to the reaction solution, and the solution was washed with saturated saline. The organic layer was dried over anhydrous magnesium sulfate, and the solvent was distilled away under reduced pressure. The resultant residue was purified by silica gel column chromatography to yield the title compound (31.9 mg, 93%).
¹H NMR (DMSO-d₆, 270 MHz) δ (ppm): 0.12 (6H, s), 0.86 (9H, s), 4.87 (2H, s), 7.51 (1H, dd, J=4.9 Hz), 8.30 (1H, d, J=4.9 Hz).
ESI (LC/MS positive mode) m/z: 276 (M+H).

Compound 8c-3

Benzhydrylidene-[4-(tert-butyldimethylsilyloxymethyl)-3-fluoropyridin-2-yl]-amine

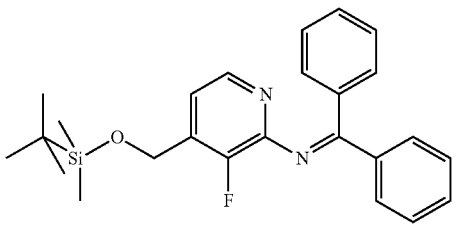

A mixture of 4-(tert-butyldimethylsilyloxymethyl)-2-chloro-3-fluoropyridine (30 mg, 108 μmol), benzophenone imine (14 μL, 84 μmol), tris(dibenzylideneacetone)dipalladium(0) (7.7 mg, 8.4 μmol), (S)-(−)-2,2′-bis(diphenylphosphino)-1,1′-binaphtyl (15.7 mg, 25.3 μmol) and sodium tert-butoxide (10.4 mg, 108 μmol) in toluene (0.5 mL) was stirred at 60° C. overnight. Ethyl acetate was then added to the reaction solution, and the solution was washed with sodium hydrogen carbonate solution and saturated saline. The organic layer was dried over anhydrous magnesium sulfate, and the solvent was distilled away under reduced pressure. The resultant residue was purified by silica gel column chromatography to yield the title compound (27 mg, 60%).

$^1$H NMR (CD$_3$OD, 270 MHz) δ (ppm): 0.00 (6H, s), 0.86 (9H, s), 4.60 (2H, s), 5.42 (1H, s), 7.00-7.80 (11H, m), 7.97 (1H, d, J=5.1 Hz).

ESI (LC/MS positive mode) m/z: 421 (M+H).

Compound 8c-4

[2-(Benzhydrylidene-amino)-3-fluoropyridin-4-yl]-methanol

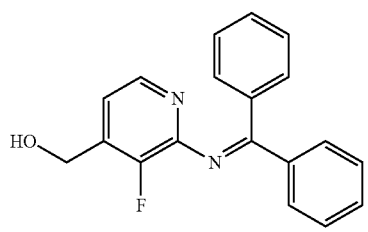

A mixture of benzhydrylidene-[4-(tert-butyldimethylsilyloxymethyl)-3-fluoropyridin-2-yl]-amine (14 mg, 32 μmol) and tetrabutylammonium fluoride (1 mol/L in THF) (65 μL, 65 μmol) in THF (0.5 mL) was stirred at room temperature for 30 minutes. Ethyl acetate was then added to the reaction solution, and the solution was washed with sodium hydrogen carbonate solution and saturated saline. The organic layer was dried over anhydrous magnesium sulfate, and the solvent was distilled away under reduced pressure. The resultant residue was purified by silica gel column chromatography to yield the title compound.

$^1$H NMR (DMSO-d$_6$, 270 MHz) δ (ppm): 4.47 (2H, d, J=5.6 Hz), 5.47 (1H, t, J=5.6 Hz), 7.04-7.20 (3H, m), 7.25-7.40 (3H, m), 7.45-7.75 (5H, m), 8.04 (1H, d, J=5.0 Hz).

ESI (LC/MS positive mode) m/z: 307 (M+H).

Compound 5t-0-16a

2-[2-(Benzhydrylidene-amino)-3-fluoropyridin-4-ylmethyl]-3-oxobutanoic acid ethyl ester

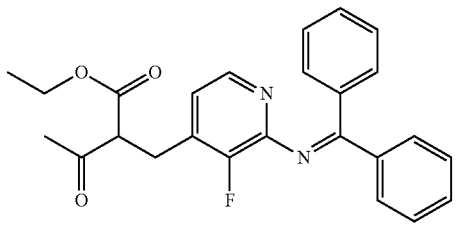

A mixture of [2-(benzhydrylidene-amino)-3-fluoropyridin-4-yl]-methanol (compound 8c-4) (5 g, 16.3 mmol), methanesulfonyl chloride (1.52 mL, 19.6 mmol) and lithium tert-butoxide (in THF) (18 mL, 18 mmol) in THF (40 mL) was stirred at 0° C. for 1 hour. The mixture was added to a solution of acetoacetic acid ethyl ester (4.16 mL, 32.7 mmol), lithium tert-butoxide (in THF) (19.6 mL, 19.6 mmol) and NaI (2.5 g, 16.3 mmol) in THF (18 mL). The solution was stirred at 50° C. for 3 hours, 0.2N LiOH (in water) and ethyl acetate were added thereto, and the solution was washed with 0.2N LiOH (in water) and saturated saline. After drying over anhydrous magnesium sulfate, the solvent was distilled away under reduced pressure to yield the title compound (6.98 g, quant.).

$^1$H NMR (DMSO-d$_6$, 270 MHz) δ (ppm): 1.10 (3H, t, J=7.0 Hz), 2.13 (3H, s), 2.90-3.05 (2H, m), 3.94 (1H, t, J=7.7 Hz), 4.05 (2H, q, J=7.0 Hz), 6.91 (1H, dd, J=4.3 Hz), 7.05-7.15 (2H, m), 7.30-7.75 (8H, m), 7.93 (1H, d, J=4.3 Hz).

ESI (LC/MS positive mode) m/z: 419 (M+H).

Compound 5t-0-16Meb 2-(2-Amino-3-fluoropyridin-4-ylmethyl)-3-oxopentanoic acid ethyl ester

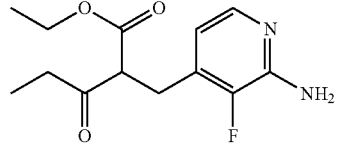

The title compound was synthesized, by performing reaction under the same conditions as in the manufacturing example for compound 5t-0-16a, except that ethylpropionyl acetate was used instead of acetoacetic acid ethyl ester, and then performing deprotection using 3N HCl.

$^1$H NMR (DMSO-d$_6$, 270 MHz) δ (ppm): 0.91 (3H, t, J=7.3 Hz), 1.11 (3H, t, J=7.1 Hz), 2.50-2.61 (2H, m), 2.94-3.02 (2H, m), 3.98-4.12 (3H, m), 6.10 (2H, s), 6.39 (1H, t, J=5.1 Hz), 7.61 (1H, d, J=5.1 Hz).

ESI (LC/MS positive mode) m/z: 269 (M+H).

Compound 5d-0-Me

7-Hydroxy-3,4-dimethyl-2-oxo-2H-1-benzopyran

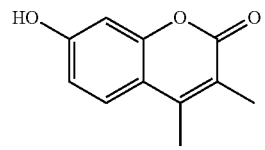

The title compound was synthesized under the same conditions as in the manufacturing example for compound 1e-0-4, except that ethyl 2-methyl acetoacetate was used instead of compound 1c-2.

$^1$H NMR (270 MHz, DMSO-d$_6$) δ (ppm): 10.36 (s, 1H), 7.61 (d, 1H, J=8.7 Hz), 6.79 (dd, 1H, J=8.7, 2.5 Hz), 6.68 (d, 1H, J=2.5 Hz), 2.34 (s, 3H), 2.05 (s, 3H).

ESIMS m/z: 191 (M+H).

Compound 1h-3-Me 3,4-Dimethyl-7-(thiazol-2-yloxy)-2-oxo-2H-1-benzopyran

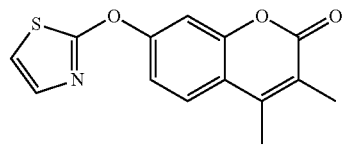

The title compound was synthesized under the same conditions as in the manufacturing example for compound 1g-3-3, except that 7-hydroxy-3,4-dimethyl-2-oxo-2H-1-benzopyran (compound 5d-0-Me) was used instead of compound 1e-0-3.

$^1$H NMR (270 MHz, DMSO-d$_6$) δ: 7.89 (d, 1H, J=9.1 Hz), 7.45 (d, 1H, J=2.5 Hz), 7.36-7.32 (m, 3H), 2.42 (s, 3H), 2.13 (s, 3H).

ESIMS m/z: 274 (M+H).

Compound 1h-3-CH2Br

3-Bromomethyl-4-methyl-7-(thiazol-2-yloxy)-2-oxo-2H-1-benzopyran

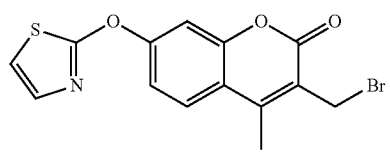

N-Bromosuccinimide (1.17 g, 6.59 mmol) and AIBN (45 mg, 0.27 mmol) were added to a solution of compound 1h-3-Me (1.50 g, 5.49 mmol) in carbon tetrachloride (80 mL), and the mixture was stirred at 75° C. for 2 hours. The solvent was distilled away by concentration under reduced pressure, and the resultant residue was purified by column chromatography (ethyl acetate:hexane=1:2) to yield the title compound (1.25 g, 65%) as a white solid.

$^1$H NMR (270 MHz, DMSO-d$_6$) δ (ppm): 7.99 (d, 1H, J=8.7 Hz), 7.51 (d, 1H, J=2.5 Hz), 7.41 (d, 1H, J=2.5 Hz), 7.38 (m, 2H), 4.68 (s, 2H), 2.54 (s, 3H).

ESIMS m/z: 354 (M+H).

Compound 1h-3-57P

N-(2-(4-Methyl-7-(thiazol-2-yloxy)-2-oxo-2H-1-benzopyran-3-ylmethoxy)phenyl)acetamide

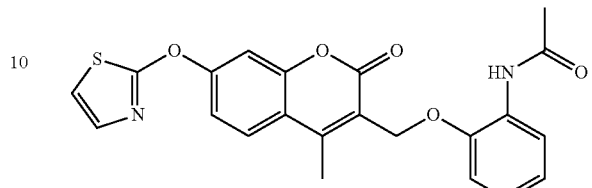

o-Acetamidophenol (118 mg, 0.78 mmol) and potassium carbonate (118 mg, 0.85 mmol) were added to a solution of compound 1h-3-CH2Br (250 mg, 0.71 mmol) in THF (5.0 mL), and the mixture was stirred at 40° C. for 2 hours. The reaction mixture was then poured into water, and extraction was performed with ethyl acetate. The organic extract was washed with saturated saline and dried over magnesium sulfate, and then concentrated under reduced pressure to yield a crude product. The residue was purified by column chromatography (ethyl acetate:hexane=1:2) to yield the title compound (100 mg, 33%) as a white solid.

$^1$H NMR (270 MHz, DMSO-d$_6$) δ (ppm): 8.97 (s, 1H), 8.02 (d, 1H, J=8.7 Hz), 7.97 (d, 1H, J=9.6 Hz), 7.53 (d, 1H, J=2.5 Hz), 7.40 (dd, 1H, J=8.9, 2.5 Hz), 7.37 (s, 2H), 7.25 (d, 1H, J=6.8 Hz), 7.08 (t, 1H, J=8.2 Hz), 6.95 (t, 1H, J=7.3 Hz), 5.10 (s, 2H), 2.56 (s, 3H), 2.04 (s, 3H).

ESIMS m/z: 423 (M+H).

Compound 1h-3-57

3-(2-Aminophenoxymethyl)-4-methyl-7-(thiazol-2-yloxy)-2-oxo-2H-1-benzopyran

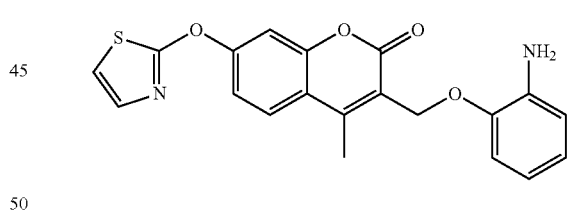

Concentrated sulfuric acid was added to a solution of compound 1h-3-57P (85 mg, 0.20 mmol) in ethanol (3.0 mL), THF (3.0 mL) and water (0.5 mL), and the mixture was stirred at 75° C. for 3 hours. The reaction mixture was then neutralized with saturated sodium hydrogen carbonate solution and extracted with ethyl acetate. The organic extract was washed with saturated saline and dried over magnesium sulfate, and then concentrated under reduced pressure to yield a crude product. The residue was purified by preparative LCMS to yield the title compound (30 mg, 39%) as a pale yellow solid.

$^1$H NMR (270 MHz, DMSO-d$_6$) δ (ppm): 7.99 (d, 1H, J=8.9 Hz), 7.52 (m, 1H), 7.41 (m, 1H), 7.38-7.35 (m, 3H), 6.96 (d, 1H, J=8.1 Hz), 6.70 (d, 1H, J=7.4 Hz), 6.63 (d, 1H, J=7.6 Hz), 6.52 (t, 1H, J=7.6 Hz), 5.02 (s, 2H), 4.71 (s, 2H), 2.55 (s, 3H).

ESIMS m/z: 381 (M+H).

Compound 1j-3-57-2

3-(2-(Methylaminosulfonyl)aminophenoxymethyl)-4-methyl-7-(thiazol-2-yloxy)-2-oxo-2H-1-benzopyran

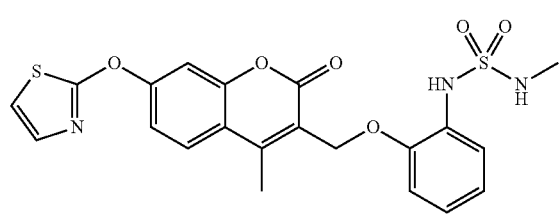

The title compound was synthesized under the same conditions as in the manufacturing example for compound 1j-1-3-2, except that compound 1h-3-57 was used instead of compound 1h-1-3.

$^1$H NMR (270 MHz, DMSO-$d_6$) δ (ppm): 8.41 (s, 1H), 8.02 (d, 1H, J=8.9 Hz), 7.53 (d, 1H, J=2.3 Hz), 7.39 (m, 4H), 7.22 (dd, 1H, J=8.2, 1.2 Hz), 7.10 (m, 2H), 6.94 (td, 1H, J=7.7, 1.3 Hz), 5.08 (s, 2H), 2.56 (s, 3H), 2.41 (d, 3H, J=4.9 Hz).

ESIMS m/z: 474 (M+H).

Compound 1h-3-58P

N-(3-((4-Methyl-7-(thiazol-2-yloxy)-2-oxo-2H-1-benzopyran-3-ylmethyl)amino)phenyl)acetamide

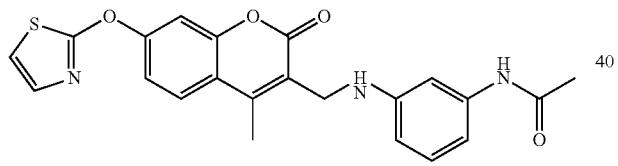

m-Acetylaminoaniline (118 mg, 0.78 mmol) and potassium carbonate (118 mg, 0.85 mmol) were added to a solution of compound 1h-3-CH2Br (250 mg, 0.71 mmol) in THF (5.0 mL), and the mixture was stirred at 75° C. for 3 hours. The reaction mixture was then poured into water, and extraction was performed with ethyl acetate. The organic extract was washed with saturated saline and dried over magnesium sulfate, and then concentrated under reduced pressure to yield a crude product. The residue was purified by column chromatography (ethyl acetate:hexane=1:2) to yield the title compound (110 mg, 37%) as a white solid.

$^1$H NMR (270 MHz, DMSO-$d_6$) δ (ppm): 9.68 (s, 1H), 7.95 (d, 1H, J=8.9 Hz), 7.49 (d, 1H, J=2.5 Hz), 7.39-7.34 (m, 3H), 7.02 (s, 1H), 6.97 (d, 1H, J=7.9 Hz), 6.73 (d, 1H, J=7.6 Hz), 6.33 (d, 1H, J=8.2 Hz), 5.72 (t, 1H, J=4.9 Hz), 4.12 (d, 2H, J=4.9 Hz), 2.51 (s, 3H).

ESIMS m/z: 422 (M+H).

Compound 1h-3-58

3-((3-Aminophenylamino)methyl)-4-methyl-7-(thiazol-2-yloxy)-2-oxo-2H-1-benzopyran

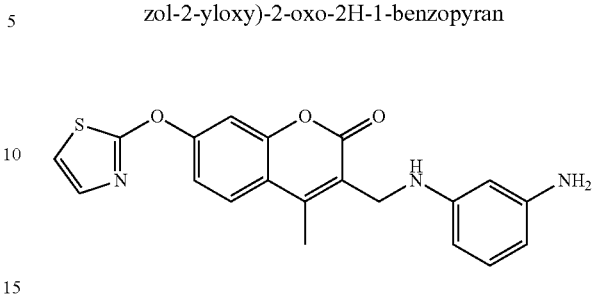

Concentrated sulfuric acid (0.5 mL) was added to a solution of compound 1h-3-58P (92 mg, 0.218 mmol) in ethanol (4.0 mL), THF (4.0 mL) and water (1.0 mL), and the mixture was stirred at 75° C. for 2 hours. The reaction mixture was then neutralized with saturated sodium hydrogen carbonate solution and extracted with ethyl acetate. The organic extract was washed with saturated saline and dried over magnesium sulfate, and then concentrated under reduced pressure to yield a crude product. The residue was purified by preparative LCMS to yield the title compound (38 mg, 46%) as a pale yellow solid.

$^1$H NMR (270 MHz, DMSO-$d_6$) δ (ppm): 7.94 (d, 1H, J=8.9 Hz), 7.49 (d, 1H, J=2.6 Hz), 7.38-7.34 (m, 3H), 6.73 (t, 1H, J=7.4 Hz), 5.88-5.84 (m, 3H), 5.29 (t, 1H, J=5.3 Hz), 4.74 (s, 2H), 4.08 (d, 2H, J=5.3 Hz), 2.50 (s, 3H).

ESIMS m/z: 380 (M+H).

Compound 1j-3-58-2

3-((3-(Methylaminosulfonyl)aminophenylamino)methyl)-4-methyl-7-(thiazol-2-yloxy)-2-oxo-2H-1-benzopyran

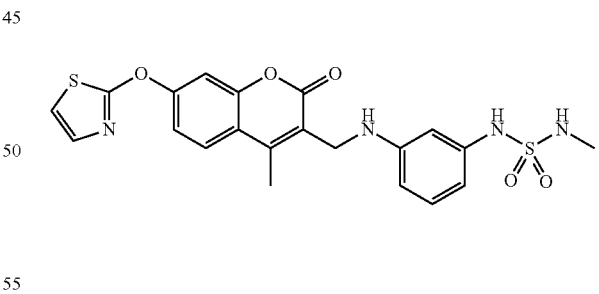

The title compound was synthesized under the same conditions as in the manufacturing example for compound 1j-1-3-2, except that compound 1h-3-58 was used instead of compound 1h-1-3.

$^1$H NMR (270 MHz, DMSO-$d_6$) δ (ppm): 9.40 (s, 1H), 7.95 (d, 1H, J=8.7 Hz), 7.50 (d, 1H, J=2.5 Hz), 7.38-7.35 (m, 3H), 7.11 (q, 1H, J=4.9 Hz), 6.98 (5, 1H, J=7.9 Hz), 6.48-6.42 (m, 2H), 6.33 (d, 1H, J=7.1 Hz), 5.71 (d, 1H, J=4.5 Hz), 4.12 (d, 2H, J=4.8 Hz), 2.51 (s, 3H), 2.45 (d, 3H, J=4.8 Hz).

ESIMS m/z: 473 (M+H).

Compound 1e-0-NAc

N-(7-Hydroxy-4-methyl-2-oxo-2H-1-benzopyran-3-yl)acetamide

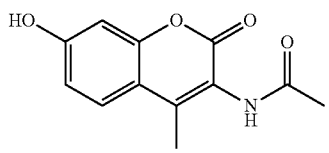

The title compound was synthesized under the same conditions as in the manufacturing example for compound 1e-0-4, except that 2-acetylamino-3-oxobutyric acid ethyl ester (which is known in the literature) was used instead of compound 1c-2.

$^1$H NMR (270 MHz, DMSO-$d_6$) δ (ppm): 10.52 (s, 1H), 9.39 (s, 1H), 7.63 (d, 1H, J=8.6 Hz), 6.84 (dd, 1H, J=8.5, 2.2 Hz), 6.73 (d, 1H, J=2.3 Hz), 2.21 (s, 3H), 2.03 (s, 3H).

ESIMS m/z: 234 (M+H).

Compound 1e-0-NH2

7-Hydroxy-4-methyl-2-oxo-2H-1-benzopyran-3-ylammonium chloride

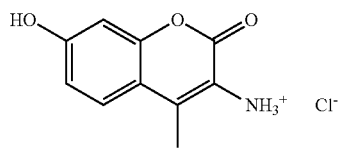

A 5 to 6N isopropanol hydrochloride solution (3.0 mL) was added to a solution of compound 1e-0-NAc (600 mg, 2.57 mmol) in THF (6.0 mL) and water (0.6 mL), and the mixture was stirred at 80° C. for a day and a night. The mixture was then cooled to room temperature and concentrated under reduced pressure to ⅓ volume. The precipitated solid was filtered out to yield the title compound (510 mg, 87%) as a faint orange solid.

$^1$H NMR (270 MHz, DMSO-$d_6$) δ (ppm): 7.41 (d, 1H, J=8.7 Hz), 6.78 (dd, 1H, J=8.7, 2.5 Hz), 6.69 (d, 1H, J=2.3 Hz), 5.69 (brs, 3H), 2.19 (s, 3H).

ESIMS m/z: 192 (M−HCl+H).

Compound 1e-0-60

N-(7-Hydroxy-4-methyl-2-oxo-2H-1-benzopyran-3-yl)-2-nitrobenzenesulfonamide

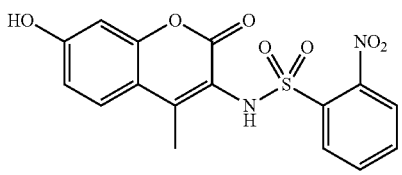

Pyridine (0.18 mL, 2.20 mmol) and o-nitrobenzenesulfonyl chloride (487 mg, 2.20 mmol) were added to a solution of compound 1e-0-NH2 (250 mg, 1.10 mmol) in THF (5.0 mL), and the mixture was stirred at room temperature for a day and a night. Water was then added to the reaction mixture, extraction was performed with ethyl acetate, and the organic extract was washed with water and saturated saline. After drying over magnesium sulfate, it was concentrated under reduced pressure to yield a crude product, which was then purified by column chromatography to yield the title compound (268 mg, 65%) as a yellow solid.

$^1$H NMR (270 MHz, DMSO-$d_6$) δ (ppm): 10.66 (s, 1H), 9.86 (s, 1H), 8.04 (m, 1H), 7.94-7.83 (m, 3H), 7.67 (d, 1H, J=8.7 Hz), 6.86 (dd, 1H, J=8.8, 2.4 Hz), 6.70 (d, 1H, J=2.8 Hz), 2.38 (s, 3H).

ESIMS m/z: 377 (M+H).

Compound 1g-1-60

Dimethylcarbamic acid 3-(2-nitrobenzenesulfonylamino)-4-methyl-2-oxo-2H-1-benzopyran-7-yl ester

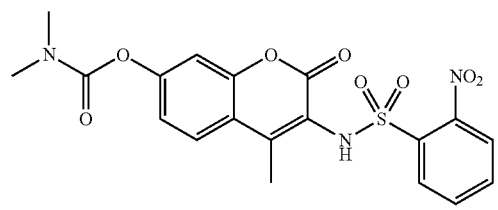

The title compound was synthesized under the same conditions as in the manufacturing example for compound 1g-1-5, except that compound 1e-0-60 was used instead of compound 1e-0-5.

$^1$H NMR (270 MHz, DMSO-$d_6$) δ (ppm): 10.09 (s, 1H), 8.05 (m, 1H), 7.86-7.80 (m, 4H), 7.26-7.20 (m, 2H), 3.06 (s, 3H), 2.93 (s, 3H), 2.43 (s, 3H).

ESIMS m/z: 448 (M+H).

Compound 1h-1-60

Dimethylcarbamic acid 3-(2-aminobenzenesulfonylamino)-4-methyl-2-oxo-2H-1-benzopyran-7-yl ester

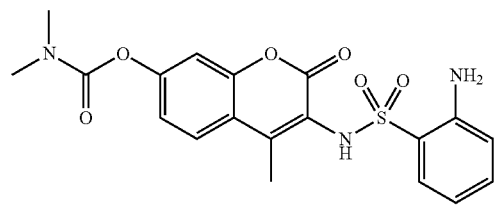

The title compound was synthesized under the same conditions as in the manufacturing example for compound 4a-0-4, except that compound 1g-1-60 was used instead of compound 1e-0-4.

$^1$H NMR (270 MHz, DMSO-$d_6$) δ (ppm): 7.78 (d, 1H, J=8.7 Hz), 7.36 (d, 1H, J=8.4 Hz), 7.27-7.16 (m, 3H), 6.77 (d, 1H, J=8.4 Hz), 6.52 (t, 1H, J=7.5 Hz), 3.06 (s, 3H), 2.93 (s, 3H), 2.32 (s, 3H).

ESIMS m/z: 418 (M+H).

Compound 1j-1-60-2

Dimethylcarbamic acid 3-(2-(methylaminosulfonyl)aminobenzenesulfonylamino)-4-methyl-2-oxo-2H-1-benzopyran-7-yl ester

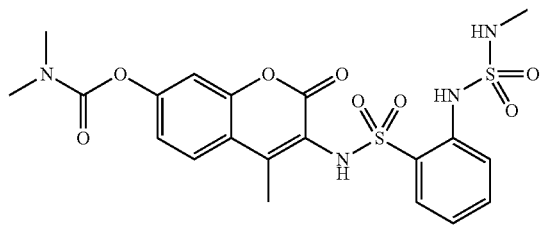

The title compound was synthesized under the same conditions as in the manufacturing example for compound 1j-1-5-2, except that compound 1h-1-60 was used instead of compound 1h-1-5.

$^1$H NMR (270 MHz, DMSO-$d_6$) δ (ppm): 10.18 (s, 1H), 8.99 (s, 1H), 7.79 (m, 2H), 7.62 (d, 1H, J=8.7 Hz), 7.60-6.55 (m, 2H), 7.23-7.15 (m, 2H), 7.08 (m, 1H), 3.06 (s, 3H), 2.93 (s, 3H), 2.47 (d, 3H, J=4.8 Hz), 2.40 (s, 3H).

ESIMS m/z: 511 (M+H).

Compound 5d-0-CO2H

7-Hydroxy-4-methyl-2-oxo-2H-1-benzopyranyl-3-carboxylic acid

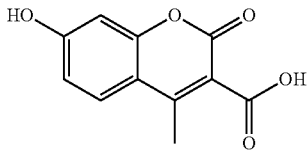

Pyridine (0.1 mL) and a 1N sodium hydroxide aqueous solution (20 mL) were added to 7-hydroxy-4-methyl-3-carbonitrile-2-oxo-2H-1-benzopyran (1.0 g, 4.97 mmol), and the mixture was stirred at room temperature for a day and a night. Water and a 6N hydrochloric acid aqueous solution were added to the reaction mixture (to pH 2), and the deposited precipitate was filtered out. It was then washed with methanol to yield the title compound (577 mg, 53%).

$^1$H NMR (270 MHz, DMSO-$d_6$) δ (ppm): 10.74 (s, 1H), 7.72 (d, 1H, J=8.6 Hz), 6.86 (d, 1H, J=8.6 Hz), 6.75 (s, 1H), 2.41 (s, 3H).

ESIMS m/z: 221 (M+H).

Compound 5d-0-56P

7-Hydroxy-4-methyl-2-oxo-2H-1-benzopyranyl-3-carboxylic acid (3-acetylaminophenyl)amide

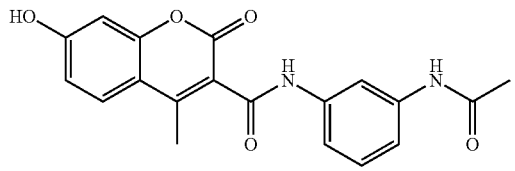

HOBt (221 mg, 1.64 mmol) and WSC (313 mg, 1.64 mmol) were added to a solution of compound 5d-0-CO2H (300 mg, 1.36 mmol) in DMF (10 mL), and the mixture was stirred at room temperature for 30 minutes. 3-Aminoacetamide (225 mg, 1.50 mmol) was then added to the reaction mixture, and it was stirred at room temperature for 1.5 hours. Water was then added to the reaction mixture, and extraction was performed with ethyl acetate. The organic extract was washed with saturated saline and dried over magnesium sulfate, and then concentrated under reduced pressure to yield the title compound (217 mg, 45%) as a pale yellow solid.

$^1$H NMR (270 MHz, DMSO-$d_6$) δ (ppm): 10.73 (s, 1H), 10.45 (s, 1H), 9.99 (s, 1H), 7.98 (s, 1H), 7.73 (d, 1H, J=8.7 Hz), 7.34 (m, 2H), 7.24 (t, 1H, J=7.8 Hz), 6.88 (m, 2H), 6.77 (d, 1H, J=2.3 Hz), 2.39 (s, 3H), 2.04 (s, 3H).

ESIMS m/z: 353 (M+H).

Compound 5d-0-56

7-Hydroxy-4-methyl-2-oxo-2H-1-benzopyranyl-3-carboxylic acid (3-aminophenyl)amide

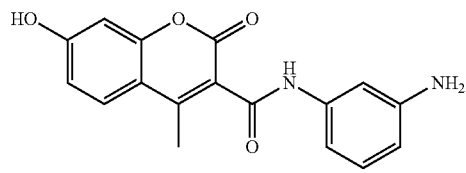

Concentrated sulfuric acid (0.3 mL) was added to a suspension of compound 5d-0-56P (200 mg, 0.57 mmol) in ethanol (5.0 mL), THF (3.0 mL) and water (0.5 mL), and the mixture was stirred under reflux for 4 hours. After cooling to room temperature, saturated sodium hydrogen carbonate solution was added, and extraction was performed with dichloromethane. The organic extract was dried over magnesium sulfate and then concentrated under reduced pressure to yield the title compound (143 mg, 81%) as a pale yellow solid.

$^1$H NMR (270 MHz, DMSO-$d_6$) δ (ppm): 10.70 (s, 1H), 10.11 (s, 1H), 7.72 (d, 1H, J=8.7 Hz), 7.01 (s, 1H), 6.95 (t, 1H, J=7.9 Hz), 6.86 (dd, 1H, J=8.4, 2.1 Hz), 6.77 (d, 1H, J=1.6 Hz), 6.71 (d, 1H, J=7.6 Hz), 6.30 (d, 1H, J=5.8 Hz), 5.13 (brs, 2H), 2.38 (s, 3H).

ESIMS m/z: 311 (M+H).

Compound 1h-1-56

Dimethylcarbamic acid 3-(3-aminophenylcarbamoyl)-4-methyl-2-oxo-2H-1-benzopyran-7-yl ester

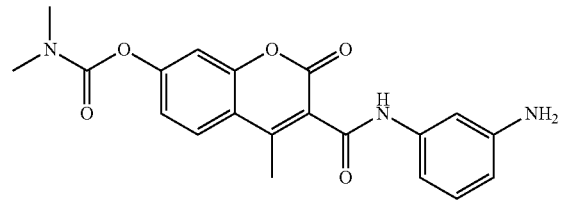

The title compound was synthesized under the same conditions as in the manufacturing example for compound 1g-1-5, except that compound 5d-0-56 was used instead of compound 1e-0-5.

$^1$H NMR (270 MHz, CD$_3$OD) δ (ppm): 8.13 (d, 1H, J=1.8 Hz), 7.92 (d, 1H, J=8.6 Hz), 7.49 (m, 2H), 7.24 m, 2H), 7.14 (dt, 1H, J=5.6, 1.3 Hz), 3.15 (s, 3H), 3.02 (s, 3H), 2.55 (s, 3H).
ESIMS m/z: 382 (M+H).

Compound 1j-1-56-2

Dimethylcarbamic acid 3-(3-(methylaminosulfonyl) aminophenylcarbamoyl)-4-methyl-2-oxo-2H-1-benzopyran-7-yl ester

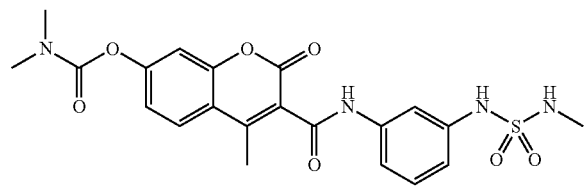

The title compound was synthesized under the same conditions as in the manufacturing example for compound 1j-1-3-2, except that compound 1h-1-56 was used instead of compound 1h-1-3.

$^1$H NMR (270 MHz, DMSO-d$_6$) δ (ppm): 10.52 (s, 1H), 9.74 (s, 1H), 7.92 (d, 1H, J=8.6 Hz), 7.47-7.42 (m, 2H), 7.34 (m, 1H), 7.30-7.22 (m, 3H), 6.97 (d, 1H, J=7.4 Hz), 3.08 (s, 3H), 2.95 (s, 3H), 2.47 (d, 3H, J=4.0 Hz), 2.45 (s, 3H).
ESIMS m/z: 475 (M+H).

2-Hydroxy-4-(pyrimidin-2-yloxy)benzoic acid

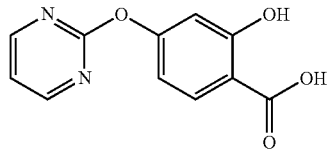

The title compound was synthesized under the same conditions as in the manufacturing example for compound 1g-2-4, except that 2,4-dihydroxybenzoic acid was used instead of compound 1e-0-4.

$^1$H NMR (270 MHz, DMSO-d$_6$) δ (ppm): 8.69 (d, 2H, J=4.8 Hz), 7.85 (d, 1H, J=8.6 Hz), 7.33 (t, 1H, J=4.8 Hz), 6.81 (d, 1H, J=2.3 Hz), 6.77 (dd, 1H, J=8.6, 2.3 Hz).
ESIMS m/z: 233 (M+H).

3-Aminoethyl-2-fluoro-phenylamine

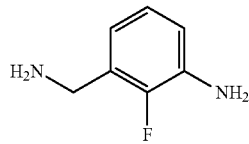

A solution of hexamethyltetramine (595 mg, 4.24 mmol) in chloroform (4.0 mL) was heated under reflux, and a solution of N-(3-bromomethyl-2-fluorophenyl)acetamide (950 mg, 3.86 mmol) in chloroform (8.0 mL) was then added thereto over a period of 40 minutes. The reaction mixture was further heated under reflux for 1 hour, and after returning to room temperature, the white precipitate was filtered out and washed with chloroform. Methanol (24 mL) and concentrated hydrochloric acid (3.0 mL) were added to the white precipitate, and the mixture was stirred at room temperature for 30 hours. After cooling to 0° C., the reaction mixture was rendered alkaline with a 6N sodium hydroxide aqueous solution (16.5 mL). It was then extracted with dichloromethane, and the organic extract was washed with saturated saline and dried over magnesium sulfate, and again washed with saturated saline. After drying over magnesium sulfate, the dried extract was concentrated under reduced pressure to yield a crude product, which was then purified by column chromatography to yield the title compound (337 mg, 48%) as a brown solid.

$^1$H NMR (270 MHz, DMSO-d$_6$) δ (ppm): 6.79 (t, 1H, J=7.6 Hz), 6.52-6.67 (m, 2H), 4.98 (s, 2H).
ESIMS m/z: 141 (M+H).

Compound 1h-1-73

3-(3-Amino-2-fluorobenzyl)-7-(pyrimidin-2-yloxy)-benzo[e][1,3]oxazine-2,4-dione

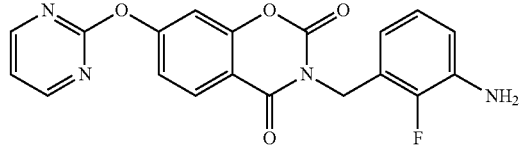

Triethylamine (0.180 mL, 1.29 mmol) was added to a mixture of 2-hydroxy-4-(pyrimidin-2-yloxy)benzoic acid (100 mg, 0.431 mmol) and chloroform (5.0 mL) at room temperature. The dark brown solution was cooled to 4° C., and methyl chloroformate (0.073 mL, 0.945 mmol) was then added thereto. The resulting light purple solution was stirred at room temperature for 2.5 hours and concentrated under reduced pressure. It was then redissolved in chloroform (5.0 mL), and a solution of triethylamine (0.120 mL, 0.861 mmol) and 3-aminoethyl-2-fluoro-phenylamine (60.0 mg, 0.428 mmol) in chloroform (1.0 mL) was added thereto. The obtained mixture was stirred at room temperature for 64 hours. Water was then added to the reaction mixture, and extraction was performed with ethyl acetate. The organic extract was washed with saturated saline and dried over magnesium sulfate, and then again washed with saturated saline. After drying over magnesium sulfate, it was concentrated under reduced pressure to yield a crude product, which was then purified by column chromatography to yield the title compound (25.8 mg, 16%) as a white solid.

$^1$H NMR (270 MHz, DMSO-d$_6$) δ (ppm): 8.72 (d, 2H, J=4.8 Hz), 8.05 (d, 1H, J=8.7 Hz), 7.47 (d, 1H, J=2.1 Hz), 7.38 (t, 1H, J=4.8 Hz), 7.35 (dd, 1H, J=8.7, 2.1 Hz), 6.78 (t, 1H, J=7.8 Hz), 6.67 (m, 1H), 6.45 (m, 1H), 5.15 (s, 2H), 5.06 (s, 2H).
ESIMS m/z: 381 (M+H).

Compound 1j-1-73-2

3-(3-(Methylaminosulfonyl)-2-fluorobenzyl)-7-(pyrimidin-2-yloxy)-benzo[e][1,3]oxazine-2,4-dione

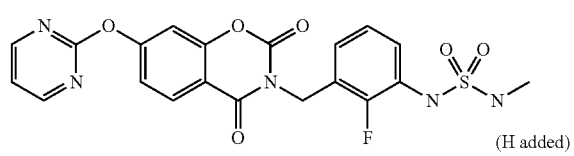

(H added)

The title compound was synthesized under the same conditions as in the manufacturing example for compound 1j-1-3-2, except that 3-(3-amino-2-fluorobenzyl)-7-(pyrimidin-2-yloxy)-benzo[e][1,3]oxazine-2,4-dione (compound 1h-1-73) was used instead of compound 1h-1-3.

$^1$H NMR (270 MHz, DMSO-d$_6$) δ (ppm): 9.44 (s, 1H), 8.71 (d, 2H, J=4.8 Hz), 8.05 (d, 1H, J=8.7 Hz), 7.48 (d, 1H, J=2.2 Hz), 7.38 (t, 1H, J=4.8 Hz), 7.29-7.36 (m, 2H), 7.25 (brq, 1H, J=5.1 Hz), 7.15 (m, 1H), 7.07 (t, 1H, J=7.9 Hz), 5.11 (s, 2H).

One of the methyl peaks was overlapped with the DMSO peak.

ESIMS m/z: 474 (M+H).

2-(3-Methyl-benzo[b]thiophen-6-yloxy)pyrimidine

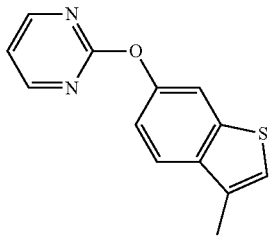

The title compound was synthesized under the same conditions as in the manufacturing example for compound 1g-2-4, except that 4-hydroxyphthalic acid was used instead of compound 1e-0-4.

$^1$H NMR (270 MHz, DMSO-d$_6$) δ (ppm): 8.64 (d, 2H, J=4.5 Hz), 7.85 (d, 1H, J=2.1 Hz), 7.79 (d, 1H, J=8.7 Hz), 7.39 (d, 1H, J=1.1 Hz), 7.27 (t, 1H, J=4.8 Hz), 7.27 (dd, 1H, J=8.7, 2.1 Hz), 2.42 (s, 3H).

ESIMS m/z: 243 (M+H).

Compound 1g-2-74

2-(2-(2-Fluoro-3-nitrobenzyl)-3-methyl-benzo[b]thiophen-6-yloxy)pyrimidine

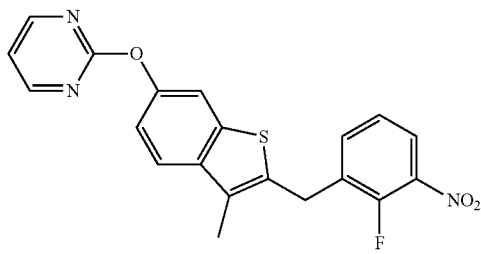

1-Bromomethyl-2-fluoro-3-nitrobenzene (120 mg, 0.513 mmol) and zinc chloride (71 mg, 0.520 mmol) were added to a solution of 2-(3-methyl-benzo[b]thiophen-6-yloxy)pyrimidine (114 mg, 0.470 mmol) in dichloromethane (1.0 mL), and the mixture was heated under reflux for 17.5 hours. After returning to room temperature, 1-bromomethyl-2-fluoro-3-nitrobenzene (120 mg, 0.513 mmol) and zinc chloride (71 mg, 0.520 mmol) were added thereto, and the mixture was heated under reflux for 23 hours. The reaction mixture was then concentrated under reduced pressure, and purified by column chromatography to yield the title compound (67.5 mg, 36%) as a white solid.

$^1$H NMR (270 MHz, DMSO-d$_6$) δ (ppm): 8.63 (d, 2H, J=4.8 Hz), 8.05 (m, 1H), 7.70-7.80 (m, 3H), 7.41 (m 1H), 7.26 (t, 1H, J=4.8 Hz), 7.24 (dd, 1H, J=8.5, 2.1 Hz), 4.40 (s, 2H), 2.41 (s, 3H).

ESIMS m/z: 366 (M+H).

Compound 1h-2-74

2-Fluoro-3-(3-methyl-6-(pyrimidin-2-yloxy)benzo[b]thiophen-2-ylmethyl)-phenylamine

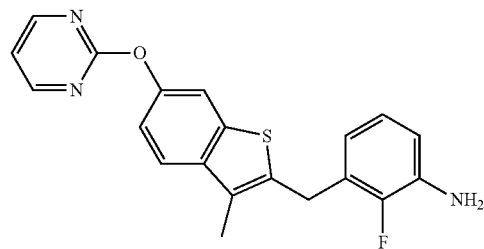

The title compound was synthesized under the same conditions as in the manufacturing example for compound 1h-1-5, except that 2-(2-(2-fluoro-3-nitrobenzyl)-3-methyl-benzo[b]thiophen-6-yloxy)pyrimidine (compound 1g-2-74) was used instead of compound 1e-1-5.

$^1$H NMR (270 MHz, DMSO-d$_6$) δ (ppm): 8.62 (d, 2H, J=4.8 Hz), 7.72 (m, 2H), 7.26 (t, 1H, J=4.8 Hz), 7.33 (dd, 1H, J=8.7, 2.1 Hz), 6.79 (t, 1H, J=7.9 Hz), 6.61 (m, 1H), 6.43 (m, 1H), 5.10 (s, 2H), 4.14 (s, 2H), 2.39 (s, 3H).

ESIMS m/z: 366 (M+H).

Compound 1j-2-74-2

[2-Fluoro-3-(3-methyl-6-(pyrimidin-2-yloxy)benzo[b]thiophen-2-ylmethyl)phenyl]-methylaminosulfonamide

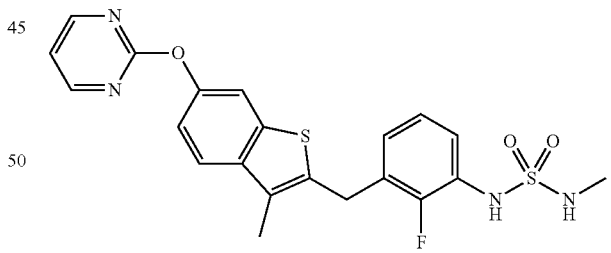

The title compound was synthesized under the same conditions as in the manufacturing example for compound 1j-1-3-2, except that 2-fluoro-3-(3-methyl-6-(pyrimidin-2-yloxy)benzo[b]thiophen-2-ylmethyl)-phenylamine (compound 1h-2-74) was used instead of compound 1h-1-3.

$^1$H NMR (270 MHz, DMSO-d$_6$) δ (ppm): 9.40 (s, 1H), 8.62 (d, 2H, J=4.8 Hz), 7.72 (m, 2H), 7.33 (td, 1H, J=7.8, 2.0 Hz), 7.18-7.28 (m, 4H), 7.00-7.15 (m, 2H), 4.25 (s, 2H), 2.39 (s, 3H).

One of the methyl peaks was overlapped with the DMSO peak.

ESIMS m/z: 459 (M+H).

4-(Pyrimidin-2-yloxy)phthalic acid

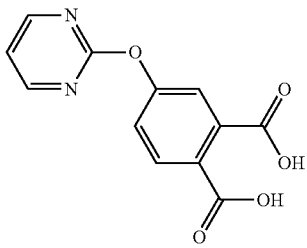

The title compound was synthesized under the same conditions as in the manufacturing example for compound 1g-2-4, except that 4-hydroxyphthalic acid was used instead of compound 1e-0-4.

$^1$H NMR (270 MHz, DMSO-d$_6$) δ (ppm): 8.68 (d, 2H, J=4.8 Hz), 7.78 (d, 1H, J=8.3 Hz), 7.39-7.46 (m, 2H), 7.32 (t, 1H, J=4.8 Hz).

ESIMS m/z: 261 (M+H).

Compound 1h-2-75

2-(3-Amino-2-fluorobenzyl)-5-(pyrimidin-2-yloxy)-isoindole-1,3-dione

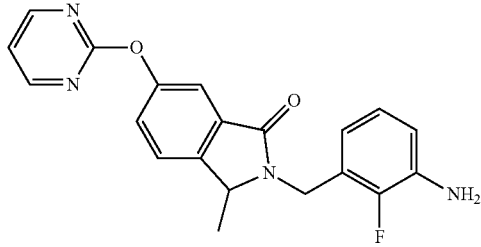

3-Aminomethyl-2-fluoro-phenylamine (50.8 mg, 0.362 mmol) and imidazole (26.0 mg, 0.382 mmol) were added to a solution of 4-(pyrimidin-2-yloxy)phthalic acid (94.1 mg, 0.362 mmol) in DMF (2.0 mL), and the mixture was stirred in a Microwave at 300 W, 150° C. for 5 minutes. Water was then added to the reaction mixture, extraction was performed with ethyl acetate, and the organic extract was washed with saturated saline. After drying over magnesium sulfate, it was concentrated under reduced pressure to yield a crude product, which was then purified by column chromatography to yield the title compound (13.4 mg, 10%) as a white solid.

$^1$H NMR (270 MHz, DMSO-d$_6$) δ (ppm): 8.70 (d, 2H, J=4.8 Hz), 7.97 (d, 1H, J=8.2 Hz), 7.80 (d, 1H, J=2.2 Hz), 7.69 (dd, 1H, J=8.2, 2.2 Hz), 7.36 (t, 1H, J=4.8 Hz), 6.79 (t, 1H, J=7.9 Hz), 6.66 (m, 1H), 6.40 (m, 1H), 5.17 (s, 2H), 4.75 (s, 2H).

ESIMS m/z: 365 (M+H).

Compound 1j-2-75-2

2-(3-Methylaminosulfonyl)-2-fluorobenzyl)-5-(pyrimidin-2-yloxy)-isoindole-1,3-dione

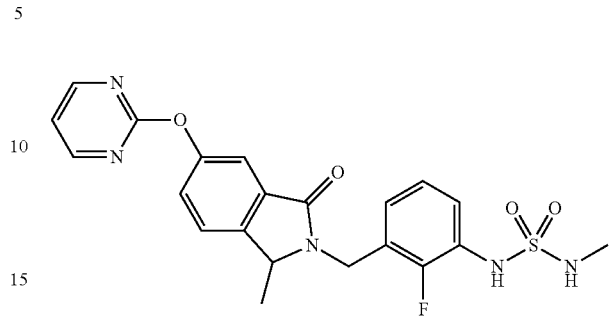

The title compound was synthesized under the same conditions as in the manufacturing example for compound 1j-1-3-2, except that 2-(3-amino-2-fluorobenzyl)-5-(pyrimidin-2-yloxy)-isoindole-1,3-dione (compound 1h-2-75) was used instead of compound 1h-1-3.

$^1$H NMR (270 MHz, DMSO-d$_6$) δ (ppm): 8.70 (d, 2H, J=4.8 Hz), 7.98 (d, 1H, J=7.9 Hz), 7.81 (d, 1H, J=2.0 Hz), 7.69 (dd, 1H, J=7.9, 2.0 Hz), 7.36 (m, 2H), 7.24 (brq, 1H, J=5.1 Hz), 7.09 (m, 2H), 4.82 (s, 2H), 3.17 (d, 1H, J=5.1 Hz).

ESIMS m/z: 458 (M+H).

(3-Acetylaminophenylsulfamoyl)acetic acid ethyl ester

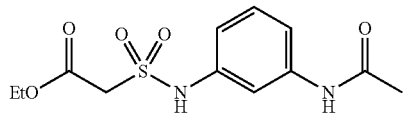

Ethanol was added at 0° C. to a solution of chlorosulfonylacetyl chloride (1.0 g, 5.7 mmol) in ether (6 mL), the mixture was stirred for 2 hours, and the solvent was distilled away. N-(3-Aminophenyl)acetamide (0.89 g), triethylamine (1.2 mL) and tetrahydrofuran (10 mL) were added thereto, and the obtained mixture was stirred at room temperature overnight. It was then purified by silica gel chromatography (methylene chloride:methanol=50:1) to yield the title compound (0.77 g, 46%).

$^1$H-NMR (Bruker (ARX-300), 300 MHz, CDCl$_3$) δ (ppm): 7.49 (1H, bs), 7.44 (1H, bs), 7.31 (1H, t, J=8.0 Hz), 7.19 (1H, bs), 7.06 (1H, d, J=8.0 Hz), 6.94 (1H, bs), 4.28 (2H, q, J=7.2 Hz), 3.95 (2H, s), 2.18 (3H, s), 1.32 (3H, t, J=7.2 Hz).

MS (ESI+) m/z: 301.11 (M+1).

Compound 5d-0-61P

4-Methyl-3-(3-(acetylamino)phenylaminosulfonyl)-7-hydroxy-2-oxo-2H-1-benzopyran

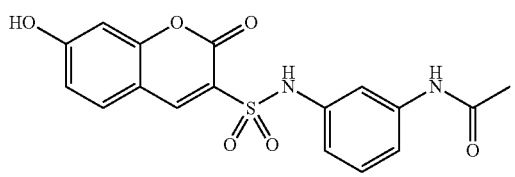

(3-Acetylaminophenylsulfamoyl)acetic acid ethyl ester (280 mg, 0.93 mmol), 2,4-dihydroxybenzaldehyde (516 mg) and piperidine (10 mg) were added to 9 mL of ethanol, and the mixture was heated under reflux overnight. It was then purified by silica gel chromatography (methylene chloride: methanol=30:1) to yield the title compound (304 mg, 87%).

$^1$H-NMR (Broker (ARX-300), 300 MHz, DMSO-d$_6$) δ (ppm): 11.2 (1H, s), 10.4 (1H, s), 9.89 (1H, bs), 8.71 (1H, s), 7.78 (1H, d, J=8.8 Hz), 7.45 (1H, bs), 7.22 (1H, d, J=8.0 Hz), 7.11 (1H, t, J 8.0 Hz), 6.86 (1H, dd, J=2.3, 8.0 Hz), 6.80 (1H, d, J=8.0 Hz), 6.74 (1H, s), 1.98 (3H, s).

MS (ESI+) m/z: 374.80 (M+1).

Compound 5d-0-61

4-Methyl-3-(3-aminophenylaminosulfonyl)-7-hydroxy-2-oxo-2H-1-benzopyran

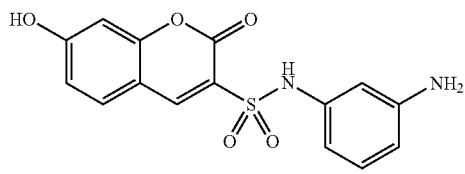

The title compound was obtained using compound 5d-0-61P and 4 equivalents of methanesulfonic acid under heated reflux in an ethanol/water mixed solvent.

$^1$H-NMR (Broker (ARX-300), 300 MHz, DMSO-d$_6$) δ (ppm): 11.2 (1H, bs), 10.0 (1H, s), 8.67 (1H, s), 7.79 (1H, d, J=8.8 Hz), 6.86 (1H, dd, J=2.3, 8.0 Hz), 6.82 (1H, t, J=8.0 Hz), 6.74 (1H, s), 6.36 (1H, m), 6.30 (1H, d, J=8.0 Hz), 6.20 (1H, d, J=8.0 Hz), 5.15 (2H, bs).

MS (ESI+) m/z: 332.92 (M+1).

TESTING EXAMPLES

Testing Example 1

Measurement of Cell Proliferation Inhibitory Activity

The cell proliferation inhibitory activities of the compounds and salts shown in Tables 1-1, 1-2 and Table 2 were measured as follows, using the human colon cancer cell line HCT116 (American Type Culture Collection, VA, USA). 2000 to 3000 cells per well of the human colon cancer cell line HCT116 was placed in a 96-well culture plate, a predetermined concentration (0.00038 μM, 0.00076 μM, 0.0015 μM, 0.0031 μM, 0.0061 μM, 0.012 μM, 0.024 μM, 0.049 μM, 0.098 μM, 0.195 μM, 0.39 μM, 0.78 μM, 1.56 μM, 3.13 μM, 6.25 μM, 12.5 μM, 25 μM or 50 μM) of the test substance was added thereto, and the mixture was then incubated at 37° C. under 5% CO$_2$ environment for 4 days. On day 4 of incubation, the Cell Counting Kit-8 solution (Dojindo Laboratories) was added, the absorbance (measurement wavelength: 450 nm; reference wavelength: 615 nm) was measured following the protocol attached to the kit, and the 50% proliferation inhibitory concentration (IC50) was calculated. The results are shown in Tables 1-1, 1-2 and Table 2.

Testing Example 2

Calculation of AUC Value

The AUC (area under the blood concentration-time curve) values of the compounds and salts shown in Table 2 (only compound 1j-2-16-2 is Na salt; the others are free form) were calculated by administering the test substance to an animal and measuring its concentration in plasma. As the animals, BALB/c (nu/nu) mice (4 to 6 weeks old) procured from Japan Charles River Laboratories were used after a one-week taming period. As for the test substances other than Comp. 1, 5 mg/mL of the substance solution was given at 0.2 mL/10 g body weight (dose of the test substance: 100 mg/kg body weight). As for Comp. 1, 10 mg/mL of the substance solution was given at 0.2 mL/10 g body weight (dose of the test substance: 200 mg/kg body weight). Administration of the substance solution to a mouse was performed forcibly using an oral feeding tube. Blood was collected from the eye pit 15 minutes, 2 hours, 7 hours and 24 hours after administration of the substance solution, using a hematocrit tube treated with heparin. Paraoxon (final concentration: 1 mM) was added to the collected blood as a stabilizer, the mixture was centrifuged at 10000 rpm for 3 minutes, and plasma was separated. The plasma was stored in a freezer set to −80° C. until the time of measurement. The measurement was carried out as follows. 100 μL of distilled water to which the internal standard substance (a structural homolog, concentration adjusted appropriately depending on the compound used) had been added was added to 5 μL of the plasma, and then, a measurement sample was prepared through solid phase extraction processing using an Oasis HLB μElution Plate (Waters), and was analyzed by LC/MS/MS. The plasma concentration was calculated using a calibration curve prepared based on the ratio of standard substance to internal standard substance in control plasma of mice. The AUC was calculated from the data of plasma concentration of the drug by the trapezoidal method using Microsoft Excel 2003 (Microsoft). The results are shown in Table 2.

Compounds or salts according to the present invention are shown in Tables 1-1, 1-2 and Table 2 below using compound numbers as used in this specification. "Comp. 1" denotes a compound of example number 20-44 described in International Publication WO 2002/008217, i.e., a compound represented by formula (A) below. "Comp. 2" denotes a compound of example 2 described in International Publication WO 2002/008217, i.e., a compound represented by formula (B) below (dimethylcarbamic acid 2-oxo-2H-3-benzyl-4-methyl-6-chloro-1-benzopyran-7-yl ester).

[Chemical Formula 177]

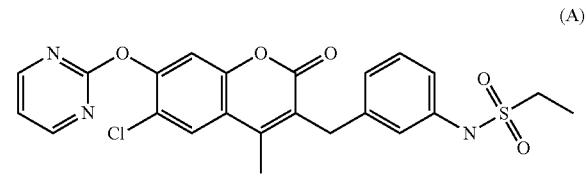

(A)

[Chemical Formula 178]

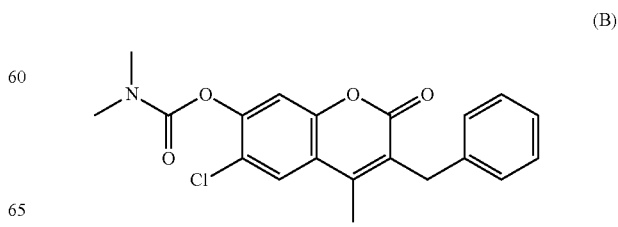

(B)

TABLE 1-1

| Compound | IC50 (μM) |
| --- | --- |
| 1j-1-4-1 | 0.0176 |
| 1j-1-4-2 | 0.0093 |
| 1j-1-4-2F | 0.0106 |
| 1j-1-5-1 | 0.0083 |
| 1j-1-5-2 | 0.0029 |
| 1j-1-3-2 | 0.0041 |
| 1j-1-2-3 | 0.0120 |
| 1j-1-3-2F | 0.0195 |
| 1j-1-7-1 | 0.0114 |
| 1j-1-7-2 | 0.0079 |
| 1j-1-8-2 | 0.0217 |
| 1j-1-9-2 | 0.0242 |
| 1j-1-21-2 | 0.0230 |
| 1j-1-23-2 | 0.0360 |
| 1o-1-3-2 | 0.0210 |
| 1o-1-3-3 | 0.0160 |

TABLE 1-2

| Compound | IC50 (μM) |
| --- | --- |
| 1j-1-10-2 | 0.0319 |
| 1j-1-11-2 | 0.0183 |
| 1j-1-12-2 | 0.0064 |
| 1j-2-17-2 | 0.0211 |
| 1j-2-18-2 | 0.0059 |
| 1j-2-19-2 | 0.0178 |
| 1j-2-19-2Me | 0.0084 |
| 1j-3-4-1 | 0.0225 |
| 1j-3-4-2 | 0.0109 |
| 1j-3-20-2 | 0.0089 |
| 1j-3-12-2 | 0.0122 |
| 1j-3-19-2 | 0.0015 |
| 1j-3-44-2 | 0.0129 |
| Comp. 1 | 0.1600 |
| Comp. 2 | 1.3000 |

TABLE 2

| Compound | AUC (μM · h) | IC50 (μM) |
| --- | --- | --- |
| 1j-1-13-2 | 313.6 | 0.2711 |
| 1j-2-4-1 | 811 | 0.1496 |
| 1j-2-4-2 | 425 | 0.0447 |
| 1j-2-4-2F | 317 | 0.1654 |
| 1j-2-5-2 | 344 | 0.0751 |
| 1j-2-12-2 | 252 | 0.2816 |
| 1j-2-16-2 | 3203 (*) | 0.0408 |
| 1j-3-1-2 | 199.3 | 0.1636 |
| 1j-3-8-2 | 148.9 | 0.0968 |
| 1o-3-4-2 | 367 | 0.3253 |
| Comp. 1 | 97.6 | 0.1600 |

(*) Na salt was used.

As seen in Tables 1-1, 1-2 and Table 2, the compound or salt according to the present invention exhibited a markedly smaller IC50 value than conventional compounds, or exhibited a sufficiently small IC50 value, and a larger AUC value than conventional compounds. This suggests that the compound or salt according to the present invention has markedly high antitumor activity compared to conventional compounds, or that it has sufficiently high antitumor activity that is equivalent to those of conventional compounds, and exhibits higher systemic exposure than conventional compounds.

From Testing examples 1 and 2, it has been revealed that the compound or pharmaceutically acceptable salt thereof according to the present invention is effective as a therapeutic agent for cell proliferative disorders, particularly cancers.

INDUSTRIAL APPLICABILITY

The compound or pharmaceutically acceptable salt thereof, pharmaceutical composition, and therapeutic agent for a cell proliferative disorder according to the present invention can be used for treatment of cell proliferative disorders, particularly cancers.

The invention claimed is:

1. A compound represented by general formula (11) below or a pharmaceutically acceptable salt thereof:

[Chemical Formula 1]

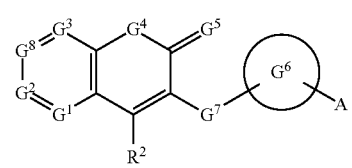

(11)

wherein:
G$^1$, G$^2$, and G$^8$ are each independently —CR$^1$= or —C(-G$^9$-X)=;
G$^3$ is —CR$^1$=;
one from among G$^1$, G$^2$, and G$^8$ is —C(-G$^9$-X)=;
X is a C$_{1-6}$ alkyl group (where the C$_{1-6}$ alkyl group may optionally be substituted with a group selected from a halogen atom, a hydroxy group, a cyano group and —NR$^{56}$R$^{57}$), an aryl group, a heterocyclic group, R$^{31}$CS—, R$^{31}$CO—, R$^{33}$R$^{34}$NCS—, R$^{33}$R$^{34}$NC=NH—, R$^3$R$^4$NCO— or R$^{33}$R$^{34}$NCO$_2$—;
G$^9$ is a single bond, an oxygen atom, a sulfur atom, —(CR$^{35}$R$^{36}$)$_l$— (where l represents an integer of 1 to 3) or —NR$^{37}$—;
Ring G$^6$ is a divalent 6-membered aryl group,
A is a group represented by general formula (2) below or a group represented by general formula (3) below:

[Chemical Formula 2]

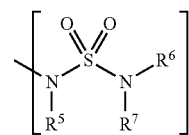

(2)

[Chemical Formula 3]

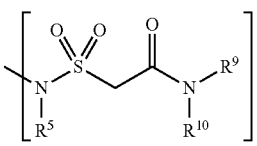

(3)

G$^4$ is an oxygen atom;
G$^5$ is an oxygen atom;
G$^7$ is CH$_2$;
R$^1$ is a hydrogen atom, a halogen atom, a cyano group, a C$_{1-6}$ alkyl group (where the C$_{1-6}$ alkyl group may optionally be substituted with a group selected from a halogen atom, a hydroxy group and —NR$^{46}$R$^{47}$), a C$_{2-7}$ alkenyl group, a carbamoyl group or a C$_{2-7}$ alkynyl group (where the C$_{2-7}$ alkynyl group may optionally be substituted with a C$_{1-4}$ acyl group);

when $G^2$ or $G^3$ is $-CR^1=$, $G^8$ is $-C(-G^9-X)=$, and X is $R^3R^4NCO-$, $R^{33}R^{34}NC=NH-$ or $R^{33}R^{34}NCS-$; when $G^1$ or $G^8$ is $-CR^1=$, $G^2$ is $-C(-G^9-X)=$, and X is $R^3R^4NCO-$, $R^{33}R^{34}NC=NH-$ or $R^{33}R^{34}NCS-$; or when $G^2$ is $-CR^1=$, $G^1$ is $-C(-G^9-X)=$, and X is $R^3R^4NCO-$, $R^{33}R^{34}NC=NH-$ or $R^{33}R^{34}NCS-$, $R^1$ may form a single bond or $-CH_2-$ together with $R^4$ or $R^{34}$;

$R^2$ is a hydroxy group, a $C_{1-6}$ alkoxy group, $-NR^{48}R^{49}$ or a $C_{1-6}$ alkyl group (where the $C_{1-6}$ alkyl group may optionally be substituted with a group selected from a halogen atom, a hydroxy group, a $C_{1-6}$ alkoxy group, a formyl group, $-CO_2R^{50}$ and $-CO_2NR^{51}R^{52}$);

$R^3$, $R^4$, $R^6$, $R^7$, $R^9$, $R^{10}$, $R^{31}$, $R^{46}$ and $R^{47}$ are each independently a hydrogen atom, a $C_{1-6}$ alkoxy group, a $C_{3-8}$ cycloalkyl group or a $C_{1-6}$ alkyl group (where the $C_{1-6}$ alkyl group may optionally be substituted with a group selected from a cyano group, a halogen atom, a hydroxy group, a $C_{1-6}$ alkoxy group, $-NR^{13}R^{14}$, $-CONR^{28}R^{29}$ and an aryl group);

$R^{33}$ and $R^{34}$ are each independently a hydrogen atom, a $C_{1-6}$ alkyl group or an aryl group;

the combination of $R^3$ and $R^4$, combination of $R^6$ and $R^7$, combination of $R^9$ and $R^{10}$, combination of $R^{33}$ and $R^{34}$, and combination of $R^{46}$ and $R^{47}$ may form, together with the nitrogen atom to which they are bonded, a 4- to 6-membered heterocyclic group having at least one nitrogen atom (where the heterocyclic group may optionally be fused with a benzene ring);

one $R^{35}$ group and one $R^{36}$ group are each independently a hydrogen atom, a halogen atom or a $C_{1-6}$ alkyl group;

$R^{13}$, $R^{14}$, $R^{56}$ and $R^{57}$ are each independently a hydrogen atom, a $C_{1-6}$ alkyl group, $-COR^{32}$ or $-CO_2R^{32}$; and $R^5$, $R^8$, $R^{28}$, $R^{29}$, $R^{32}$, $R^{37}$, $R^{38}$, $R^{48}$, $R^{49}$, $R^{50}$, $R^{51}$, and $R^{52}$ are each independently a hydrogen atom or a $C_{1-6}$ alkyl group.

2. The compound or pharmaceutically acceptable salt thereof according to claim 1, wherein the compound represented by general formula (11) is a compound represented by general formula (1) below:

[Chemical Formula 1]

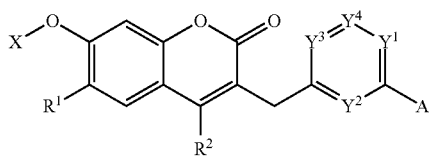

(1)

wherein:
X is a heteroaryl group or $R^3R^4NCO-$;
$Y^1$ and $Y^2$ are each independently $-CR^{11}=$;
$Y^3$ and $Y^4$ may be the same or different, and are each $-CR^{12}=$;
A is a group represented by general formula (2) below or a group represented by general formula (3) below:

[Chemical Formula 2]

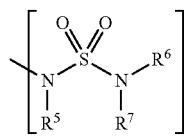

(2)

[Chemical Formula 3]

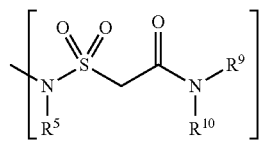

(3)

$R^1$ is a hydrogen atom, a halogen atom, a cyano group, a $C_{1-6}$ alkyl group, a $C_{2-7}$ alkenyl group, a carbamoyl group or a $C_{2-7}$ alkynyl group (where the $C_{2-7}$ alkynyl group may optionally be substituted with a $C_{1-4}$ acyl group);

$R^2$ is a $C_{1-6}$ alkyl group optionally substituted with a halogen atom;

$R^3$, $R^4$, $R^6$, $R^7$, $R^9$ and $R^{10}$ are each independently a hydrogen atom, a $C_{1-6}$ alkoxy group, a $C_{3-8}$ cycloalkyl group or a $C_{1-6}$ alkyl group (where the $C_{1-6}$ alkyl group may optionally be substituted with a group selected from a cyano group, a halogen atom, a hydroxy group, a $C_{1-6}$ alkoxy group and $-NR^{13}R^{14}$);

the combination of $R^3$ and $R^4$, combination of $R^6$ and $R^7$, and combination of $R^9$ and $R^{10}$ may form, together with the nitrogen atom to which they are bonded, a 4- to 6-membered heterocyclic group having at least one nitrogen atom;

$R^5$, $R^8$, $R^{13}$ and $R^{14}$ are each independently a hydrogen atom or a $C_{1-6}$ alkyl group;

$R^{11}$ is a hydrogen atom, a halogen atom, a $C_{1-6}$ alkyl group, a $C_{1-4}$ acyl group, a $C_{1-4}$ acyloxy group or $-NR^{15}R^{16}$;

$R^{12}$ is a hydrogen atom, a halogen atom or a $C_{1-6}$ alkyl group; and $R^{15}$ and $R^{16}$ are each independently a hydrogen atom or a $C_{1-4}$ acyl group.

3. The compound or pharmaceutically acceptable salt thereof according to claim 2, wherein $R^1$ is a hydrogen atom, a halogen atom or a $C_{1-6}$ alkyl group.

4. The compound or pharmaceutically acceptable salt thereof according to claim 2, wherein $R^5$ or $R^8$ is a hydrogen atom.

5. The compound or pharmaceutically acceptable salt thereof according to claim 2, wherein $R^3$, $R^4$, $R^6$, $R^7$, $R^9$ and $R^{10}$ are each independently a hydrogen atom or a $C_{1-6}$ alkyl group.

6. The compound or pharmaceutically acceptable salt thereof according to claim 2, wherein X is a thiazol-2-yl group, a pyrimidin-2-yl group, a 2-pyridyl group or $R^3R^4NCO-$ (where $R^3$ and $R^4$ have the same definitions as above).

7. The compound or pharmaceutically acceptable salt thereof according to claim 2, which is selected from:
dimethylcarbamic acid 3-{3-(aminosulfonyl)aminobenzyl}-4-methyl-2-oxo-2H-1-benzopyran-7-yl ester,
dimethylcarbamic acid 3-{3-(aminosulfonyl)aminobenzyl}-6-fluoro-4-methyl-2-oxo-2H-1-benzopyran-7-yl ester,
dimethylcarbamic acid 3-{3-(aminosulfonyl)aminobenzyl}-6-chloro-4-methyl-2-oxo-2H-1-benzopyran-7-yl ester,
dimethylcarbamic acid 3-(3-aminosulfonylamino-2-fluoro-benzyl)-4-methyl-2-oxo-2H-1-benzopyran-7-yl ester,
dimethylcarbamic acid 3-{2-fluoro-3-(aminosulfonyl) aminobenzyl}-6-fluoro-4-methyl-2-oxo-2H-1-benzopyran-7-yl ester, dimethylcarbamic acid 3-{3-(aminosulfonyl)aminobenzyl}-6-iodo-4-methyl-2-oxo-2H-1-benzopyran-7-yl ester,
dimethylcarbamic acid 3-{3-(aminosulfonyl)aminobenzyl}-6-methyl-4-methyl-2-oxo-2H-1-benzopyran-7-yl ester,
dimethylcarbamic acid 3-{3-(aminosulfonyl)aminobenzyl}-6-cyano-4-methyl-2-oxo-2H-1-benzopyran-7-yl ester,
dimethylcarbamic acid 3-{3-(aminosulfonyl)aminobenzyl}-4-fluoromethyl-2-oxo-2H-1-benzopyran-7-yl ester,
dimethylcarbamic acid 3-{3-(aminosulfonyl)aminobenzyl}-6-fluoro-4-fluoromethyl-2-oxo-2H-1-benzopyran-7-yl ester,
dimethylcarbamic acid 3-{3-(aminosulfonyl)aminobenzyl}-6-chloro-4-fluoromethyl-2-oxo-2H-1-benzopyran-7-yl ester,
dimethylcarbamic acid 3-(3-aminosulfonylamino-2-fluoro-benzyl)-4-fluoromethyl-2-oxo-2H-1-benzopyran-7-yl ester,
3-{2-fluoro-3-(aminosulfonyl)aminobenzyl}-4-methyl-7-(pyrimidin-2-yloxy)-2-oxo-2H-1-benzopyran,
3-{3-(aminosulfonyl)aminobenzyl}-4-methyl-7-(thiazol-2-yloxy)-2-oxo-2H-1-benzopyran,
3-{3-(aminosulfonyl)aminobenzyl}-4-methyl-7-(thiazol-2-yloxy)-6-chloro-2-oxo-2H-1-benzopyran,
3-{2-fluoro-3-(aminosulfonyl)aminobenzyl}-4-methyl-7-(thiazol-2-yloxy)-2-oxo-2H-1-benzopyran,
3-{3-(aminosulfonyl)aminobenzyl}-4-methyl-7-(thiazol-2-yloxy)-6-methyl-2-oxo-2H-1-benzopyran,
3-{2-chloro-3-(aminosulfonyl)aminobenzyl}-4-methyl-7-(thiazol-2-yloxy)-2-oxo-2H-1-benzopyran,
dimethylcarbamic acid 4-methyl-3-{3-(methylaminosulfonyl)aminobenzyl}-2-oxo-2H-1-benzopyran-7-yl ester,
dimethylcarbamic acid 6-fluoro-4-methyl-3-{3-(methylaminosulfonyl)aminobenzyl}-2-oxo-2H-1-benzopyran-7-yl ester,
dimethylcarbamic acid 3-(3-(N-methylsulfamoyl)aminobenzyl)-6-chloro-4-methyl-2-oxo-2H-1-benzopyran-7-yl ester,
dimethylcarbamic acid 3-(3-methylaminosulfonylamino-2-fluoro-benzyl)-4-methyl-2-oxo-2H-1-benzopyran-7-yl ester,
dimethylcarbamic acid 6-iodo-4-methyl-3-{3-(methylaminosulfonyl)aminobenzyl}-2-oxo-2H-1-benzopyran-7-yl ester,
dimethylcarbamic acid 6-methyl-4-methyl-3-{3-(methylaminosulfonyl)aminobenzyl}-2-oxo-2H-1-benzopyran-7-yl ester,
dimethylcarbamic acid 6-cyano-4-methyl-3-{3-(methylaminosulfonyl)aminobenzyl}-2-oxo-2H-1-benzopyran-7-yl ester,
dimethylcarbamic acid 3-(3-methylaminosulfonylamino-2-fluoro-benzyl)-4-fluoromethyl-2-oxo-2H-1-benzopyran-7-yl ester,
dimethylcarbamic acid 3-(3-methylaminosulfonylaminobenzyl)-4-fluoromethyl-2-oxo-2H-1-benzopyran-7-yl ester,
dimethylcarbamic acid 3-(3-methylaminosulfonylaminobenzyl)-6-fluoro-4-fluoromethyl-2-oxo-2H-1-benzopyran-7-yl ester,
dimethylcarbamic acid 6-chloro-4-fluoromethyl-3-{3-(methylaminosulfonyl)aminobenzyl}-2-oxo-2H-1-benzopyran-7-yl ester,
3-{2-fluoro-3-(methylaminosulfonyl)aminobenzyl}-4-methyl-7-(pyrimidin-2-yloxy)-2-oxo-2H-1-benzopyran,
3-{2-fluoro-3-(methylaminosulfonyl)aminobenzyl}-4-methyl-7-(pyrimidin-2-yloxy)-6-fluoro-2-oxo-2H-1-benzopyran,
3-{2-fluoro-3-(methylaminosulfonyl)aminobenzyl}-4-fluoromethyl-7-(pyrimidin-2-yloxy)-2-oxo-2H-1-benzopyran,
3-{3-(methylaminosulfonyl)aminobenzyl}-4-methyl-7-(thiazol-2-yloxy)-2-oxo-2H-1-benzopyran,
3-{3-(methylaminosulfonyl)aminobenzyl}-4-methyl-7-(thiazol-2-yloxy)-6-chloro-2-oxo-2H-1-benzopyran,
3-{2-fluoro-3-(methylaminosulfonyl)aminobenzyl}-4-methyl-7-(thiazol-2-yloxy)-2-oxo-2H-1-benzopyran,
3-{3-(methylaminosulfonyl)aminobenzyl}-4-methyl-7-(thiazol-2-yloxy)-6-methyl-2-oxo-2H-1-benzopyran,
dimethylcarbamic acid 6-chloro-4-methyl-3-{3-(dimethylaminosulfonyl)aminobenzyl}-2-oxo-2H-1-benzopyran-7-yl ester,
3-{2-fluoro-3-(dimethylaminosulfonyl)aminobenzyl}-4-methyl-7-(pyrimidin-2-yloxy)-2-oxo-2H-1-benzopyran,
dimethylcarbamic acid 3-(3-(N-(2-cyanoethyl)sulfamoyl)aminobenzyl)-6-chloro-4-methyl-2-oxo-2H-1-benzopyran-7-yl ester,
dimethylcarbamic acid 3-(3-(N-(2-hydroxyethyl)sulfamoyl)aminobenzyl)-6-chloro-4-methyl-2-oxo-2H-1-benzopyran-7-yl ester,
dimethylcarbamic acid 3-(3-(N-(2-methoxyethyl)sulfamoyl)aminobenzyl)-6-chloro-4-methyl-2-oxo-2H-1-benzopyran-7-yl ester,
dimethylcarbamic acid 3-(3-(N-(2-aminoethyl)sulfamoyl)aminobenzyl)-6-chloro-4-methyl-2-oxo-2H-1-benzopyran-7-yl ester hydrochloride,
dimethylcarbamic acid 3-(3-(N—(N'-methyl-2-aminoethyl)methylsulfamoyl)aminobenzyl)-6-chloro-4-methyl-2-oxo-2H-1-benzopyran-7-yl ester hydrochloride,
dimethylcarbamic acid 3-(3-(N-2,2,2-trifluoroethyl-sulfamoyl)aminobenzyl)-6-chloro-4-methyl-2-oxo-2H-1-benzopyran-7-yl ester,
dimethylcarbamic acid 3-(3-(N-methoxysulfamoyl)aminobenzyl)-6-chloro-4-methyl-2-oxo-2H-1-benzopyran-7-yl ester,
dimethylcarbamic acid 3-(3-carbamoylmethanesulfonylamino-benzyl)-6-chloro-4-methyl-2-oxo-2H-1-benzopyran-7-yl ester,
dimethylcarbamic acid 3-(3-methylcarbamoylmethanesulfonylamino-benzyl)-6-chloro-4-methyl-2-oxo-2H-1-benzopyran-7-yl ester,
2-{2-fluoro-3-[4-methyl-2-oxo-7-(pyrimidin-2-yloxy)-2H-1-benzopyran-3-ylmethyl]phenylsulfamoyl}-N-methyl-acetamide,
dimethylcarbamic acid 3-(3-dimethylcarbamoylmethanesulfonylamino-benzyl)-6-chloro-4-methyl-2-oxo-2H-1-benzopyran-7-yl ester,
2-{2-fluoro-3-[4-methyl-2-oxo-7-(thiazol-2-yloxy)-2H-1-benzopyran-3-ylmethyl]phenylsulfamoyl}-N-methyl-acetamide,
3-{2-methyl-3-(methylaminosulfonyl)aminobenzyl}-4-methyl-7-(pyrimidin-2-yloxy)-2-oxo-2H-1-benzopyran,
3-{2-fluoro-3-(methylaminosulfonyl)aminobenzyl}-4-methyl-7-(5-fluoropyrimidin-2-yloxy)-2-oxo-2H-1-benzopyran, 3-{2-fluoro-3-(methylaminosulfonyl)aminobenzyl}-4-methyl-7-(4-chloropyrimidin-2-yloxy)-2-oxo-2H-1-benzopyran, 3-{2-fluoro-3-(methylaminosulfonyl)aminobenzyl}-4-methyl-7-(2,4-dimethoxypyrimidin-6-yloxy)-2-oxo-2H-1-benzopyran, 3-{2-fluoro-3-(methylaminosulfonyl)aminobenzyl}-4-methyl-7-(benzothiazol-2-yloxy)-2-oxo-2H-1-benzopyran, 3-{2-fluoro-3-(methylaminosulfonyl)aminobenzyl}-4-methyl-7-(5-bromothiazol-2-yloxy)-2-oxo-2H-1-benzopyran, dimethylcarbamic acid 6-fluoro-4-methyl-3-{2-fluoro-3-(methylaminosulfonyl)aminobenzyl}-2-oxo-2H-1-benzopyran-7-yl ester.

8. A pharmaceutical composition comprising the compound or pharmaceutically acceptable salt thereof according to claim 1 as an active ingredient.

9. The compound or pharmaceutically acceptable salt thereof according to claim 2, which is 3-{2-fluoro-3-(methylaminosulfonyl)aminobenzyl}-4-methyl-7-(pyrimidin-2-yloxy)-2-oxo-2H-1-benzopyran.

* * * * *